(12) United States Patent
Dyckman et al.

(10) Patent No.: US 11,058,696 B2
(45) Date of Patent: Jul. 13, 2021

(54) SUBSTITUTED BICYCLIC COMPOUNDS

(71) Applicant: BRISTOL-MYERS SQUIBB COMPANY, Princeton, NJ (US)

(72) Inventors: Alaric J. Dyckman, Lawrenceville, NJ (US); T. G. Murali Dhar, Newtown, PA (US); Hai-Yun Xiao, Belle Mead, NJ (US); John L. Gilmore, Yardley, PA (US); Michael G. Yang, Narbeth, PA (US); Zili Xiao, East Windsor, NJ (US); David Marcoux, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/879,824

(22) Filed: May 21, 2020

(65) Prior Publication Data
US 2020/0281952 A1 Sep. 10, 2020

Related U.S. Application Data

(60) Continuation of application No. 16/188,444, filed on Nov. 13, 2018, now Pat. No. 10,709,719, which is a
(Continued)

(51) Int. Cl.
A61K 31/695 (2006.01)
C07F 7/08 (2006.01)
(Continued)

(52) U.S. Cl.
CPC .......... A61K 31/695 (2013.01); A61K 31/135 (2013.01); A61K 31/137 (2013.01);
(Continued)

(58) Field of Classification Search
CPC ..................................................... A61K 31/695
(Continued)

(56) References Cited

U.S. PATENT DOCUMENTS 6,069,143 A  5/2000 Ali et al.
7,309,721 B2  12/2007 Budhu et al.
(Continued)

FOREIGN PATENT DOCUMENTS

CN  102260177  11/2011
WO  WO 03/062252  7/2003
(Continued)

OTHER PUBLICATIONS

Venkatesh, J. Pharm. Sci. 89, 145-54 (2000).*
(Continued)

Primary Examiner — Nizal S Chandrakumar
(74) Attorney, Agent, or Firm — Gary Greenblatt

(57) ABSTRACT

Disclosed are compounds of Formulas (I), (II), (III), (IV), and (V):

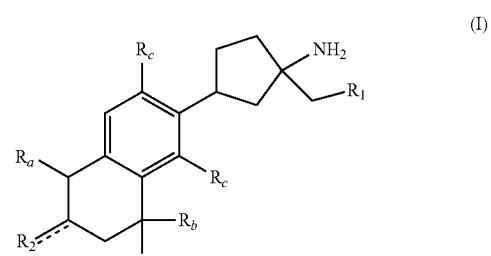

(I)

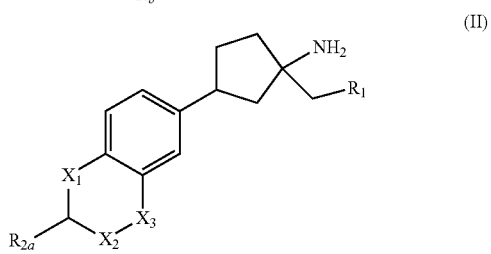

(II)

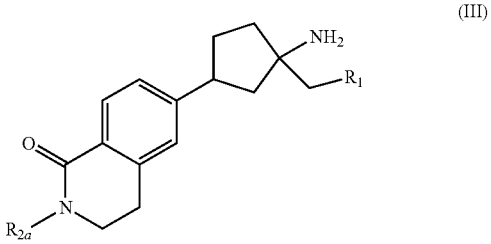

(III)

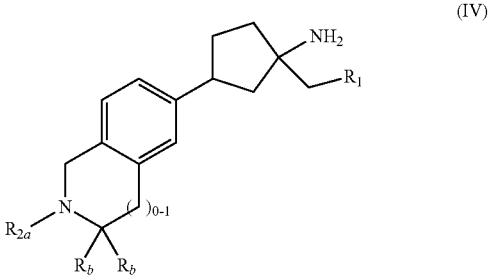

(IV)

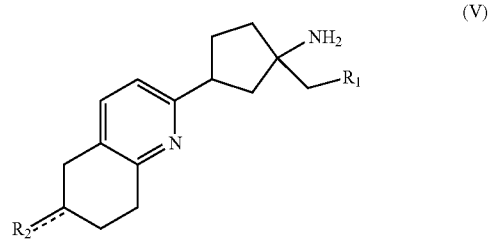

(V)

and/or a salt thereof, wherein $R_1$ is —OH or —OP(O)(OH)$_2$, and $X_1$, $X_2$, $X_3$, $R_2$, $R_{2a}$, $R_a$, $R_b$, and $R_c$ are defined herein. Also disclosed are methods of using such compounds as selective agonists for G protein-coupled receptor S1P$_1$, and pharmaceutical compositions comprising such compounds.

(Continued)

These compounds are useful in treating, preventing, or slowing the progression of diseases or disorders in a variety of therapeutic areas, such as autoimmune diseases and vascular disease.

4 Claims, No Drawings

Related U.S. Application Data continuation of application No. 15/648,250, filed on Jul. 12, 2017, now Pat. No. 10,166,249, which is a continuation of application No. 15/337,843, filed on Oct. 28, 2016, now Pat. No. 9,770,459, which is a division of application No. 14/831,439, filed on Aug. 20, 2015, now Pat. No. 9,522,888.

(60) Provisional application No. 62/039,622, filed on Aug. 20, 2014.

(51) Int. Cl.

| | |
|---|---|
| A61K 31/135 | (2006.01) |
| C07D 215/14 | (2006.01) |
| C07D 241/04 | (2006.01) |
| C07C 323/29 | (2006.01) |
| C07C 251/38 | (2006.01) |
| C07C 251/42 | (2006.01) |
| C07C 251/44 | (2006.01) |
| C07D 209/46 | (2006.01) |
| C07D 213/38 | (2006.01) |
| C07C 275/26 | (2006.01) |
| C07C 217/74 | (2006.01) |
| C07C 323/25 | (2006.01) |
| C07C 235/46 | (2006.01) |
| C07F 9/54 | (2006.01) |
| C07F 9/572 | (2006.01) |
| C07F 9/09 | (2006.01) |
| C07C 215/42 | (2006.01) |
| C07C 217/52 | (2006.01) |
| C07C 217/58 | (2006.01) |
| C07C 219/24 | (2006.01) |
| C07C 233/41 | (2006.01) |
| C07C 233/65 | (2006.01) |
| C07C 251/50 | (2006.01) |
| C07C 251/52 | (2006.01) |
| C07C 251/54 | (2006.01) |
| C07C 271/34 | (2006.01) |
| C07C 317/28 | (2006.01) |
| C07C 317/32 | (2006.01) |
| C07C 321/16 | (2006.01) |
| C07C 321/22 | (2006.01) |
| C07C 321/28 | (2006.01) |
| C07D 213/32 | (2006.01) |
| C07D 213/69 | (2006.01) |
| C07D 213/70 | (2006.01) |
| C07D 215/12 | (2006.01) |
| C07D 217/24 | (2006.01) |
| C07D 231/12 | (2006.01) |
| C07D 231/20 | (2006.01) |
| C07D 239/26 | (2006.01) |
| C07D 241/12 | (2006.01) |
| C07D 277/24 | (2006.01) |
| C07D 305/08 | (2006.01) |
| C07D 309/06 | (2006.01) |
| C07D 309/12 | (2006.01) |
| C07D 311/58 | (2006.01) |
| C07D 311/76 | (2006.01) |
| C07D 319/20 | (2006.01) |
| C07D 333/16 | (2006.01) |
| C07F 9/117 | (2006.01) |
| C07F 9/62 | (2006.01) |
| C07F 9/6503 | (2006.01) |
| C07F 9/6509 | (2006.01) |
| C07F 9/655 | (2006.01) |
| C07F 9/6553 | (2006.01) |
| A61K 31/137 | (2006.01) |
| A61K 31/15 | (2006.01) |
| A61K 31/165 | (2006.01) |
| A61K 31/166 | (2006.01) |
| A61K 31/17 | (2006.01) |
| A61K 31/222 | (2006.01) |
| A61K 31/24 | (2006.01) |
| A61K 31/27 | (2006.01) |
| A61K 31/337 | (2006.01) |
| A61K 31/351 | (2006.01) |
| A61K 31/352 | (2006.01) |
| A61K 31/381 | (2006.01) |
| A61K 31/415 | (2006.01) |
| A61K 31/4174 | (2006.01) |
| A61K 31/426 | (2006.01) |
| A61K 31/44 | (2006.01) |
| A61K 31/4402 | (2006.01) |
| A61K 31/4406 | (2006.01) |
| A61K 31/4409 | (2006.01) |
| A61K 31/47 | (2006.01) |
| A61K 31/4965 | (2006.01) |
| A61K 31/505 | (2006.01) |
| A61K 31/661 | (2006.01) |

(52) U.S. Cl.
CPC ............ *A61K 31/15* (2013.01); *A61K 31/165* (2013.01); *A61K 31/166* (2013.01); *A61K 31/17* (2013.01); *A61K 31/222* (2013.01); *A61K 31/24* (2013.01); *A61K 31/27* (2013.01); *A61K 31/337* (2013.01); *A61K 31/351* (2013.01); *A61K 31/352* (2013.01); *A61K 31/381* (2013.01); *A61K 31/415* (2013.01); *A61K 31/4174* (2013.01); *A61K 31/426* (2013.01); *A61K 31/44* (2013.01); *A61K 31/4402* (2013.01); *A61K 31/4406* (2013.01); *A61K 31/4409* (2013.01); *A61K 31/47* (2013.01); *A61K 31/4965* (2013.01); *A61K 31/505* (2013.01); *A61K 31/661* (2013.01); *C07C 215/42* (2013.01); *C07C 217/52* (2013.01); *C07C 217/58* (2013.01); *C07C 217/74* (2013.01); *C07C 219/24* (2013.01); *C07C 233/41* (2013.01); *C07C 233/65* (2013.01); *C07C 235/46* (2013.01); *C07C 251/38* (2013.01); *C07C 251/42* (2013.01); *C07C 251/44* (2013.01); *C07C 251/50* (2013.01); *C07C 251/52* (2013.01); *C07C 251/54* (2013.01); *C07C 271/34* (2013.01); *C07C 275/26* (2013.01); *C07C 317/28* (2013.01); *C07C 317/32* (2013.01); *C07C 321/16* (2013.01); *C07C 321/22* (2013.01); *C07C 321/28* (2013.01); *C07C 323/25* (2013.01); *C07C 323/29* (2013.01); *C07D 209/46* (2013.01); *C07D 213/32* (2013.01); *C07D 213/38* (2013.01); *C07D 213/69* (2013.01); *C07D 213/70* (2013.01); *C07D 215/12* (2013.01); *C07D 215/14* (2013.01);

C07D 217/24 (2013.01); C07D 231/12 (2013.01); C07D 231/20 (2013.01); C07D 239/26 (2013.01); C07D 241/04 (2013.01); C07D 241/12 (2013.01); C07D 277/24 (2013.01); C07D 305/08 (2013.01); C07D 309/06 (2013.01); C07D 309/12 (2013.01); C07D 311/58 (2013.01); C07D 311/76 (2013.01); C07D 319/20 (2013.01); C07D 333/16 (2013.01); C07F 7/08 (2013.01); C07F 7/081 (2013.01); C07F 9/091 (2013.01); C07F 9/117 (2013.01); C07F 9/5442 (2013.01); C07F 9/5728 (2013.01); C07F 9/62 (2013.01); C07F 9/65031 (2013.01); C07F 9/65522 (2013.01); C07F 9/650952 (2013.01); C07F 9/655345 (2013.01); C07B 2200/05 (2013.01); C07C 2601/02 (2017.05); C07C 2601/04 (2017.05); C07C 2601/08 (2017.05); C07C 2602/10 (2017.05); C07C 2603/74 (2017.05)

(58) Field of Classification Search
USPC .................................................. 546/139
See application file for complete search history.

(56) References Cited

U.S. PATENT DOCUMENTS

| | | | |
|---|---|---|---|
| 7,351,725 | B2 | 4/2008 | Doherty et al. |
| 7,479,504 | B2 | 1/2009 | Bugianesi et al. |
| 7,678,820 | B2 | 3/2010 | Harada et al. |
| 7,687,491 | B2 | 3/2010 | Nishi et al. |
| 8,354,398 | B2 | 1/2013 | Watterson et al. |
| 8,389,509 | B2 | 3/2013 | Dyckman et al. |
| 8,399,451 | B2 | 3/2013 | Gilmore et al. |
| 8,404,672 | B2 | 3/2013 | Pitts et al. |
| 8,629,282 | B2 | 1/2014 | Cherney et al. |
| 9,115,054 | B2 | 8/2015 | Dhar et al. |
| 9,315,492 | B2 | 4/2016 | Zhang et al. |
| 9,359,286 | B2 | 6/2016 | Xiao et al. |
| 2005/0070506 | A1 | 3/2005 | Doherty et al. |
| 2006/0199853 | A1 | 9/2006 | Mioskowski et al. |
| 2008/0200535 | A1 | 8/2008 | Ohmori et al. |
| 2009/0029947 | A1 | 1/2009 | Wallace et al. |
| 2009/0247627 | A1 | 10/2009 | Trapp et al. |
| 2012/0214767 | A1 | 8/2012 | Dhar et al. |
| 2013/0045964 | A1 | 2/2013 | Cherney et al. |
| 2013/0158001 | A1 | 6/2013 | Das et al. |
| 2013/0190361 | A1 | 7/2013 | Das et al. |

FOREIGN PATENT DOCUMENTS

| | | |
|---|---|---|
| WO | WO 03/073986 | 9/2003 |
| WO | WO 03/105771 | 12/2003 |
| WO | WO 2005/000833 | 1/2005 |
| WO | WO 2005/058848 | 6/2005 |
| WO | WO 2005/082089 | 9/2005 |
| WO | WO 2006/047195 | 5/2006 |
| WO | WO 2006/088944 | 8/2006 |
| WO | WO 2006/094347 | 9/2006 |
| WO | WO 2006/100633 | 9/2006 |
| WO | WO 2006/131336 | 12/2006 |
| WO | WO 2007/024922 | 3/2007 |
| WO | WO 2007/081857 | 7/2007 |
| WO | WO 2007/088450 | 8/2007 |
| WO | WO 2007/089715 | 8/2007 |
| WO | WO 2007/109330 | 9/2007 |
| WO | WO 2007/111864 | 10/2007 |
| WO | WO 2008/029370 | 3/2008 |
| WO | WO 2008/074820 | 6/2008 |
| WO | WO 2008/079382 | 7/2008 |
| WO | WO 2008/114157 | 9/2008 |
| WO | WO 2009/043889 | 4/2009 |
| WO | WO 2009/057079 | 5/2009 |
| WO | WO 2009/080728 | 7/2009 |
| WO | WO 2010/042998 | 4/2010 |
| WO | WO 2010/069949 | 6/2010 |
| WO | WO 2010/072352 | 7/2010 |
| WO | WO 2010/081692 | 7/2010 |
| WO | WO 2010/093616 | 8/2010 |
| WO | WO2011096377 | 8/2011 |
| WO | WO2011096377 A1 | 8/2011 |
| WO | WO 2014/018891 | 1/2014 |
| WO | WO 2014/130752 | 8/2014 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802, 784.*
CAS 1036431-06-7—Compound 1.
CAS 1036431-05-6—Compound 1.
Fix-Stenzel, S.R., et al., "A stereoselective and scalable synthesis of a conformationally constrained S1P1 agonist," Tetrahedron Letters 50 (2009), pp. 4081-4083.
Oliveira, Caio C., et al., "Stereoselective Arylation of Substituted Cyclopentenes by Substrate-Directable Heck-Matsuda Reactions: A Concise Total Synthesis of the Sphingosine 1-Phosphate Receptor (S1P1) Agonist VPC01091," J. Org. Chem. (2012), vol. 77, pp. 8182-8190.
Wallace, G.A., et al., "Scalable Synthesis and Isolation of the Four Stereoisomers of Methyl 1-Amino-3-(4-bromophenyl)cyclopentanecarboxylate, Useful Intermediates for the Synthesis of S1P1 Receptor Agonists," J. Org. Chem. (2009), vol. 74, pp. 4886-4889.
Zhu, R., et al., "Asymmetric Synthesis of Conformationally Constrained Fingolimod Analogues—Discovery of an Orally Active Sphingosine 1-Phosphate Receptor Type-1 Agonist and Receptor Type-3 Antagonist," J. Med. Chem. (2007), vol. 50, pp. 6428-6435.
Ung, Alison T., et al., "Synthesis and antagonist activities of 4-Aryl-substituted conformationally restricted cyclopentenyl and cyclopentanyl-glutamate analogues," Tetrahedron 61 (2005), pp. 1803-1812.
Written Opinion of the International Searching Authority for PCT/US2015/046005, dated Feb. 25, 2016.

* cited by examiner

SUBSTITUTED BICYCLIC COMPOUNDS

CROSS-REFERENCE TO RELATED APPLICATIONS

This application is a continuation application, which claims priority to U.S. application Ser. No. 16/188,444, filed Nov. 13, 2018, which is a continuation application of U.S. application Ser. No. 15/648,250, filed Jul. 12, 2017, which is a continuation application of U.S. application Ser. No. 15/337,843, filed Oct. 28, 2016, which is a divisional application of U.S. application Ser. No. 14/831,439, filed Aug. 20, 2015, which claims the benefit of U.S. Application Ser. No. 62/039,622, filed Aug. 20, 2014, each of which is incorporated herein it its entirety.

DESCRIPTION

The present invention generally relates to substituted bicyclic compounds useful as $S1P_1$ agonists. Provided herein are substituted bicyclic compounds, compositions comprising such compounds, and methods of their use. The invention further pertains to pharmaceutical compositions comprising at least one compound according to the invention that are useful for the treatment of conditions related to $S1P_1$ modulation, such as autoimmune diseases and vascular disease.

Sphingosine-1-phosphate (S1P) is a zwitterionic lysophospholipid metabolite of sphingosine (Sph), which in turn is derived from enzymatic cleavage of ceramides. Enzymatic phosphorylation of Sph by two kinases (SphK1 and SphK2) leads to the production of S1P largely from erythrocytes, but also from a radiation resistant source, possibly the lymphatic endothelium (Pappu, R. et al. *Science* 2007, 316, 295-298). Originally thought to operate solely as an intracellular signaling molecule, S1P was subsequently identified as a high affinity ligand for five members of the endothelial differentiation gene (EDG) class of G-protein coupled receptors (GPCRs) named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively) (Chun, J. et al. *Pharmacological Rev.* 2010, 62, 579-587). The interaction of S1P with the S1P receptors plays a fundamental physiological role in a large number of processes including cell proliferation, cell morphology, tumor cell invasion, angiogenesis, tumorigenesis, cytoskeletal rearrangement, vascular development, and lymphocyte trafficking (Olivera, A; Rivera, *J. Adv Exp Med Biol.* 2011, 716, 123-142). S1P receptors are therefore good targets for a wide variety of therapeutic applications such as tumor growth inhibition, vascular disease, and autoimmune diseases.

Among the five S1P receptors, $S1P_1$ has a widespread distribution. It is the predominant family member expressed on lymphocytes and plays an important role in lymphocyte trafficking. S1P interaction with its receptor $S1P_1$ is required for the egress of immune cells from the lymphoid organs (such as thymus and lymph nodes) into the lymphatic vessels. Downregulation of the $S1P_1$ receptor (which can be accomplished through treatment with agonists of $S1P_1$ via receptor internalization) disrupts lymphocyte migration and homing to various tissues. This results in sequestration of the lymphocytes in lymph organs thereby decreasing the number of circulating lymphocytes that are capable of migration to the affected tissues. The development of an $S1P_1$ receptor modulating agent that suppresses lymphocyte migration to the target sites associated with autoimmune and aberrant inflammatory processes could be efficacious in a number of autoimmune and inflammatory disease states.

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109330, WO 07/116866, WO 08/023783 (U.S. Patent Publication No. 2008/0200535), WO 08/029370, WO 08/074820, WO 08/079382, WO 08/114157, WO 09/043889, WO 09/057079, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

SUMMARY OF THE INVENTION

The present invention provides substituted bicyclic compounds, which are useful as modulators of $S1P_1$ activity, including salts thereof.

The present invention also provides pharmaceutical compositions comprising a compound of Formulas (I), (II), (III), (IV), or (V) and/or a pharmaceutically acceptable salt thereof; and a pharmaceutically acceptable carrier.

The present invention also provides a method of treating a disease or disorder associated with the activity of G protein-coupled receptor $S1P_1$, the method comprising administering to a mammalian patient a compound of Formulas (I), (II), (III), (IV), or (V) and/or a pharmaceutically acceptable salt thereof.

The present invention also provides processes and intermediates for making the compounds of Formulas (I), (II), (III), (IV), or (V) and/or salts thereof.

The present invention also provides a compound of Formulas (I), (II), (III), (IV), or (V) and/or a pharmaceutically acceptable salt thereof, for use in therapy.

The present invention also provides the use of the compounds of Formulas (I), (II), (III), (IV), or (V) and/or pharmaceutically acceptable salts thereof, for the manufacture of a medicament for the treatment or prophylaxis of $S1P_1$ receptor-related conditions, such as autoimmune and vascular diseases.

The compounds of Formulas (I), (II), (III), (IV), or (V) and compositions comprising the compounds of Formulas (I), (II), (III), (IV), or (V) may be used in treating, preventing, or curing various $S1P_1$ related conditions. Pharmaceutical compositions comprising these compounds are useful in treating, preventing, or slowing the progression of diseases or disorders in a variety of therapeutic areas, such as autoimmune and vascular diseases.

These and other features of the invention will be set forth in expanded form as the disclosure continues.

DETAILED DESCRIPTION

The first aspect of the present invention provides at least one compound of Formulas (I), (II), (III), (IV), or (V):

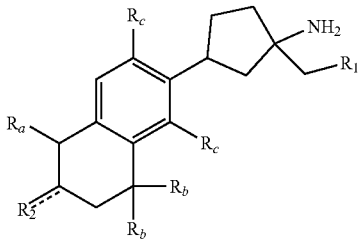
(I)

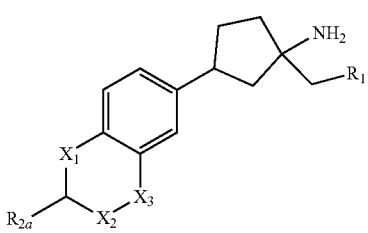
(II)

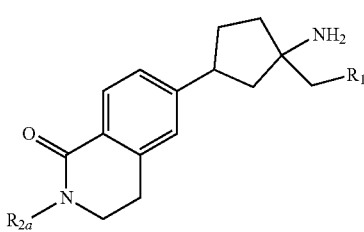
(III)

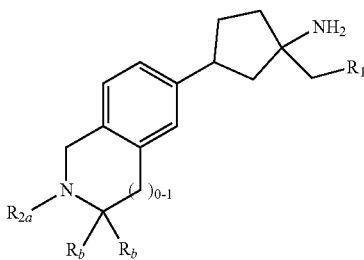
(IV)

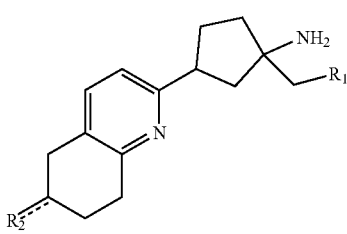
(V)

or a salt thereof, wherein:
$R_1$ is —OH or —OP(O)(OH)$_2$;
$X_1$ is CH$_2$ or O;
$X_2$ is CH$_2$ or O;
$X_3$ is CH$_2$ or O, provided that $X_2$ is O only if both $X_1$ and $X_3$ are each CH$_2$;
$R_2$ is $R_{2a}$ or $R_{2b}$;
---- represents either a single bond to $R_{2a}$ or a double bond to $R_{2b}$;
$R_{2a}$ is —(CH$_2$)$_{3-6}$CH$_3$, —(CH$_2$)$_{1-4}$CH=CR$_x$R$_x$, —(CH$_2$)$_{1-4}$CH=CR$_x$(CH$_2$CH$_3$), —CH=CH(CH$_2$)$_{1-3}$C(R$_x$)$_3$, —CH=CH(CH$_2$)$_{1-3}$OCH$_3$, —(CH$_2$)$_{1-3}$CH=CHCH=CR$_x$R$_x$, —CH=CH(CH$_2$)$_{1-3}$CH=CR$_x$R$_x$, —CH=CHR$_z$, —(CH$_2$)$_{1-3}$R$_z$, —(CH$_2$)$_{1-3}$O(CH$_2$)$_{0-3}$R$_z$, —(CH$_2$)$_{1-3}$S(CH$_2$)$_{0-3}$R$_z$, —CH$_2$S(O)R$_z$, —CH$_2$S(O)$_2$R$_z$, —O(CH$_2$)$_{1-2}$R$_z$, —O(CH$_2$)$_{1-2}$O(CH$_2$)$_{0-2}$R$_z$, —OC(O)R$_z$, —(CH$_2$)$_{1-4}$O(CH$_2$)$_{0-9}$C(R$_x$)$_3$, —(CH$_2$)$_{1-4}$O(CH$_2$)$_{0-9}$CF$_3$, —(CH$_2$)$_{1-4}$CR$_x$R$_x$O(CH$_2$)$_{0-4}$C(R$_x$)$_3$, —(CH$_2$)$_{1-3}$O(CH$_2$)$_{1-4}$CH=CR$_x$(CH$_2$)$_{0-3}$CH$_3$, —(CH$_2$)$_{1-3}$O(CH$_2$)$_{1-4}$CH=CR$_x$R$_x$, —(CH$_2$)$_{1-3}$O(CH$_2$)$_{1-4}$C(OH)R$_x$R$_x$, —(CH$_2$)$_{1-3}$O(CH$_2$)$_{1-4}$O(CH$_2$)$_{0-3}$CH$_3$, —(CH$_2$)$_{1-3}$S(CH$_2$)$_{0-4}$C(R$_x$)$_3$, —(CH$_2$)$_{0-3}$O(CH$_2$)$_{1-4}$S(CH$_2$)$_{0-3}$C(R$_x$)$_3$, —(CH$_2$)$_{1-3}$S(CH$_2$)$_{1-4}$Si(CH$_3$)$_3$, —(CH$_2$)$_{1-3}$S(O)(CH$_2$)$_{0-4}$C(R$_x$)$_3$, —(CH$_2$)$_{1-3}$S(O)$_2$(CH$_2$)$_{0-4}$C(R$_x$)$_3$, —(CH$_2$)$_{1-5}$NR$_x$R$_x$, —O(CH$_2$)$_{1-7}$C(R$_x$)$_3$, —O(CH$_2$)$_{1-4}$O(CH$_2$)$_{0-4}$C(R$_x$)$_3$, —O(CH$_2$)$_{1-4}$CH=CR$_x$(CH$_2$)$_{0-3}$CH$_3$, —O(CH$_2$)$_{1-4}$O(CH$_2$)$_{0-3}$C(R$_x$)$_3$, —O(CH$_2$)$_{1-4}$O(CH$_2$)$_{1-3}$CH=CR$_x$R$_x$, —O(CH$_2$)$_{1-4}$O(CH$_2$)$_{1-3}$C≡CR$_x$, —C(O)(CH$_2$)$_{0-4}$C(R$_x$)$_3$, —OC(O)(CH$_2$)$_{0-4}$C(R$_x$)$_3$, —OC(O)CR$_x$R$_x$(CH$_2$)$_{0-4}$C(R$_x$)$_3$, —OC(O)NR$_x$(CH$_2$)$_{0-5}$C(R$_x$)$_3$, —NR$_x$C(O)NR$_x$(CH$_2$)$_{0-5}$C(R$_x$)$_3$, —C(CH$_3$)=N—O(CH$_2$)$_{0-5}$C(R$_x$)$_3$, —C(CH$_3$)=N—O(CH$_2$)$_{1-2}$(phenyl), —C(CH$_3$)=N—O(CH$_2$)$_{1-2}$(fluorophenyl), —C(CH$_3$)=N—O(CH$_2$)$_{1-2}$(methoxyphenyl), phenyl, or pyridinyl;

$R_{2b}$ is
(i) a 6-membered spiro-ring having one oxygen atom and substituted with zero or 1 substituent selected from —(CH$_2$)$_3$CH$_3$; or
(ii) =N—O—(CH$_2$)$_3$CH$_3$, =N—O—CH$_2$CH(CH$_3$)$_2$, =N—OCH$_2$CH$_2$(phenyl), or =N—O—CH$_2$CH$_2$CH$_2$(phenyl);

$R_a$ is H or —OH;
each $R_b$ is independently H or —CH$_3$;
each $R_c$ is independently H, Cl, I, or —CH$_3$;
each $R_x$ is independently H or —CH$_3$; and
$R_z$ is phenyl, imidazolyl, pyrazolyl, pyridinyl, pyrimidinyl, pyrazinyl, quinolinyl, thiophenyl, thiazolyl, oxetanyl, C$_{3-6}$ cycloalkyl, adamantanyl, or tetrahydropyranyl, each substituted with zero to 4 substituents independently selected from F, Cl, I, C$_{1-4}$ alkyl, —O(C$_{1-3}$ alkyl), —CF$_3$, —OCF$_3$, —(CH$_2$)$_{1-6}$OCH$_3$, —CH$_2$NR$_x$R$_x$, —C(O)NR$_x$R$_x$, —C(O)NR$_x$(C$_{1-4}$ alkyl), and —CH$_2$C(O)NR$_x$R$_x$;

with the provisos that (i) if said compound has the structure of Formula (I) and $R_2$ is —(CH$_2$)$_5$CH$_3$, then at least one of $R_b$ and $R_c$ is not H; and (ii) if said compound has the structure of Formula (II) and $X_1$, $X_2$, and $X_3$ are each CH$_2$, then $R_{2a}$ is not —(CH$_2$)$_5$CH$_3$.

One embodiment provides at least compound of Formulas (I), (II), (III), (IV), or (V) or a salt thereof, wherein $R_1$ is —OH, and $R_2$, $R_{2a}$, $X_1$, $X_2$ $X_3$, $R_a$, $R_b$, and $R_c$ are defined in the first aspect. The compounds of this embodiment have structures of Formulas (Ia), (IIa), (IIIa), (IVa), or (Va):

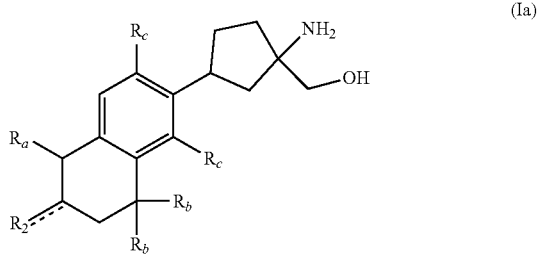
(Ia)

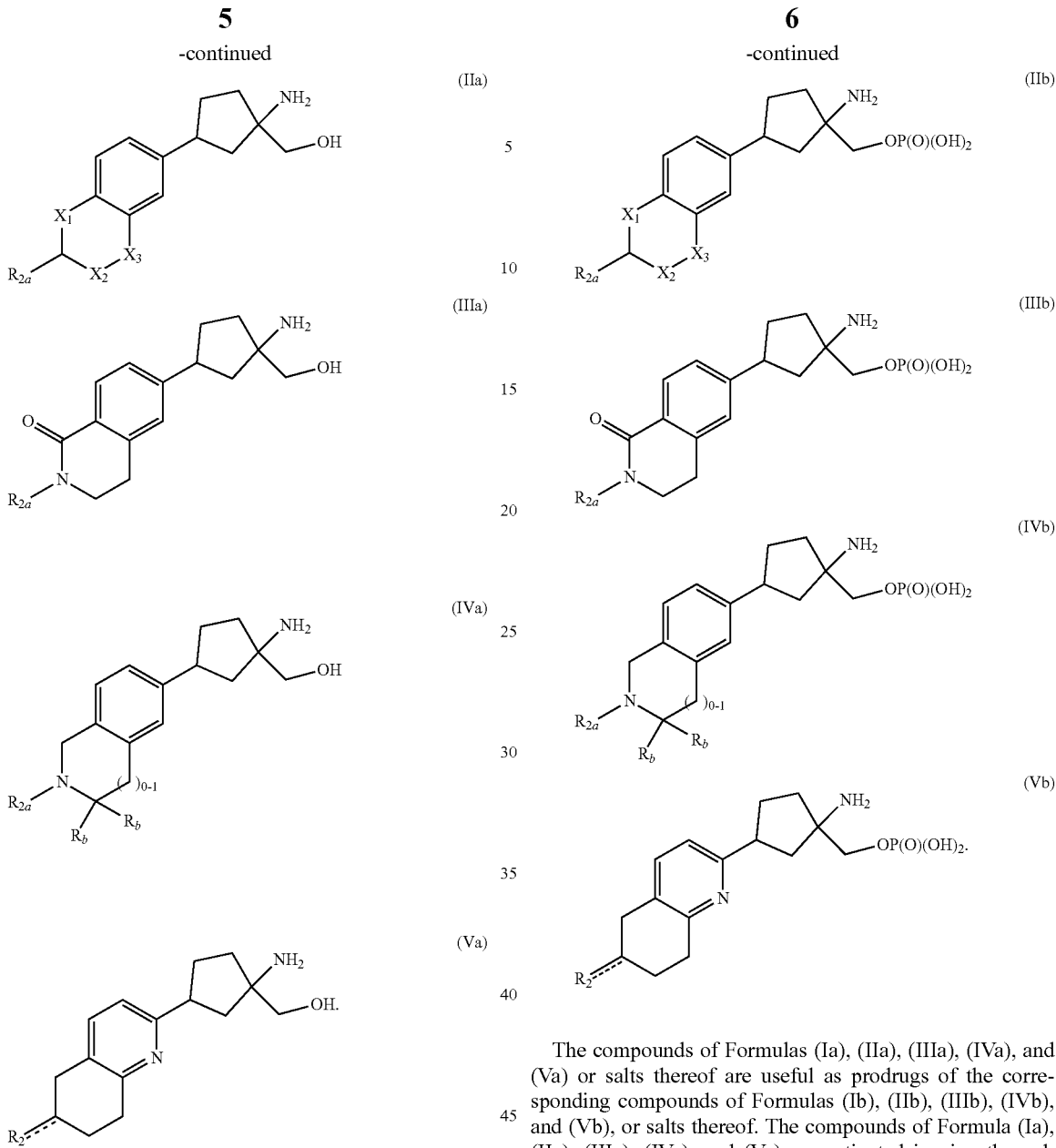

One embodiment provides at least compound of Formulas (I), (II), (III), (IV), or (V) or a salt thereof, wherein $R_1$ is $-OP(O)(OH)_2$, and $R_2$, $R_{2a}$, $X_1$, $X_2$, $X_3$, $R_a$, $R_b$, and $R_c$ are defined in the first aspect. The compounds of this embodiment have structures of Formulas (Ib), (IIb), (IIIb), (IVb), or (Vb):

The compounds of Formulas (Ia), (IIa), (IIIa), (IVa), and (Va) or salts thereof are useful as prodrugs of the corresponding compounds of Formulas (Ib), (IIb), (IIIb), (IVb), and (Vb), or salts thereof. The compounds of Formula (Ia), (IIa), (IIIa), (IVa), and (Va) are activated in vivo through phosphorylation to provide the corresponding phosphorylated compounds. The phosphorylated compounds of Formula (Ib), (IIb), (IIIb), (IVb), and (Vb) or salts thereof are active as selective agonists of $S1P_1$.

One embodiment provides at least one compound of Formulas (I), (II), (III), (IV), or (V), wherein said compound has the structure of Formula (Ic), (IIc), (IIIc), (IVc), or (Vc):

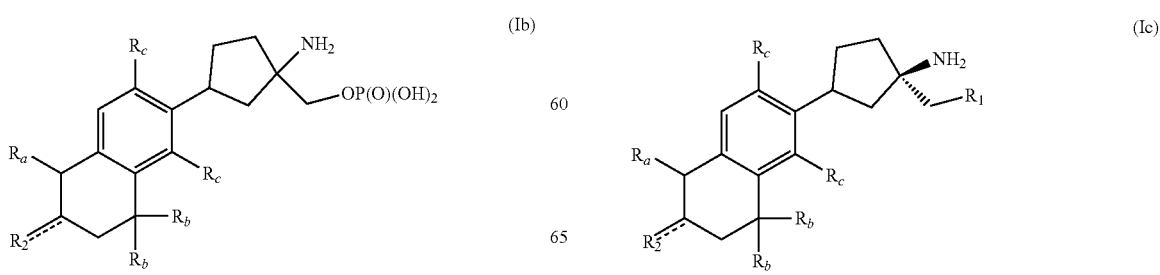

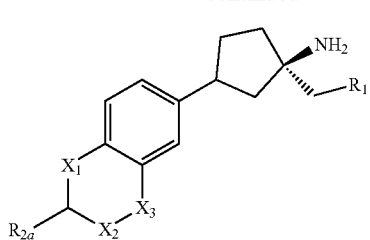

(IIc)

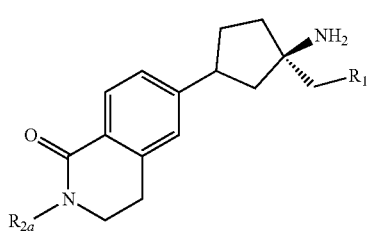

(IIIc)

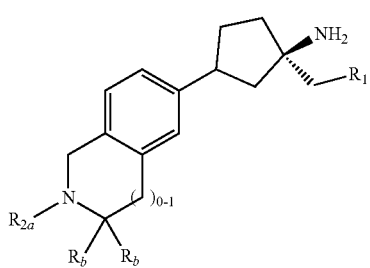

(IVc)

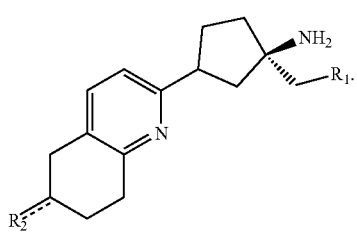

(Vc)

One embodiment provides at least one compound of compound of Formulas (I), (II), (III), (IV), or (V), or a salt thereof, wherein $R_{2a}$ is —(CH$_2$)$_3$CH$_3$, —(CH$_2$)$_{5-6}$CH$_3$, —CH$_2$CH=CHCH$_2$CH$_3$, —CH$_2$CH$_2$CH=CHCH$_2$CH$_3$, —(CH$_2$)$_3$CH=CHCH$_3$, —(CH$_2$)$_3$CH=C(CH$_3$)$_2$, —(CH$_2$)$_4$CH=CH$_2$, —(CH$_2$)$_4$CH=CHCH$_3$, —CH=CH(CH$_2$)$_3$CH$_3$, —CH=CH(CH$_2$)$_3$OCH$_3$, —CH=CHCH$_2$CH$_2$CH(CH$_3$)$_2$, —CH=CHCH$_2$CH$_2$OCH$_3$, —CH$_2$CH=CHCH=CHCH$_3$, —CH=CHCH$_2$CH$_2$CH=CH$_2$, —CH=CH(phenyl) wherein said phenyl is substituted with —CH$_3$ or —OCH$_3$; —CH=CH(tetrahydropyranyl), —(CH$_2$)$_{1-3}$(phenyl) wherein said phenyl is substituted with zero to 2 substituents independently selected from F, I, —CH$_3$, —OCH$_3$, —OCH$_2$CH$_3$, —OCH(CH$_3$)$_2$, and —CH$_2$C(O)N(CH$_3$)$_2$; —(CH$_2$)$_2$(methyl imidazolyl), —(CH$_2$)$_2$(methyl pyrazolyl), —(CH$_2$)$_{1-2}$(pyridinyl) wherein said pyridinyl is substituted with zero to 1 substituent selected from —OCH$_3$; —(CH$_2$)$_2$(pyrimidinyl), —(CH$_2$)$_2$(quinolinyl), —(CH$_2$)$_{2-3}$(tetrahydropyranyl), —CH$_2$O(CH$_2$)$_{3-4}$CH$_3$, —CH$_2$OCH$_2$CH$_2$CH(CH$_3$)$_2$, —CH$_2$OCH$_2$CH$_2$C(CH$_3$)$_3$, —CH$_2$O(CH$_2$)$_9$CH$_3$, —CH$_2$OCH$_2$CH$_2$CH$_2$CF$_3$, —CH$_2$OCH$_2$CH=CHCH$_2$CH$_3$, —CH$_2$OCH$_2$CH=C(CH$_3$)$_2$, —CH$_2$OCH$_2$CH=CHCH$_2$CH$_2$CH$_3$, —CH$_2$OCH$_2$CH$_2$CH=CH$_2$, —CH$_2$OCH$_2$CH$_2$CH$_2$CH=CH$_2$, —CH$_2$OCH$_2$CH$_2$CH=C(CH$_3$)$_2$, —CH$_2$OCH$_2$CH$_2$CH(OH)CH$_3$, —CH$_2$OCH$_2$CH$_2$CH$_2$CH$_2$OH, —CH$_2$OCH$_2$CH$_2$CH$_2$C(CH$_3$)$_2$(OH), —CH$_2$OCH$_2$CH$_2$OCH$_3$, —CH$_2$OCH$_2$CH$_2$CH$_2$OCH$_3$, —CH$_2$OCH$_2$CH$_2$OCH$_2$CH$_2$CH$_3$, —CH$_2$O(phenyl) wherein said phenyl is substituted with zero to 3 substituents independently selected from F, Cl, —CH$_3$, —CH(CH$_3$)$_2$, —C(CH$_3$)$_3$, —OCH$_3$, —OCF$_3$, —(CH$_2$)$_{1-6}$OCH$_3$, —C(O)N(CH$_3$)$_2$, —CH$_2$N(CH$_3$)$_2$, —C(O)N(CH$_2$CH$_3$)(CH$_3$), —C(O)N(CH$_3$)(CH$_2$CH$_2$CH$_2$CH$_3$), and —C(O)N(CH$_3$)(CH$_2$CH(CH$_3$)$_2$); —CH$_2$O(methoxy pyridinyl), —CH$_2$O(tetrahydropyranyl), —CH$_2$O(trifluoromethyl, methyl pyrazolyl), —CH$_2$OCH$_2$(phenyl) wherein said phenyl is substituted with zero to 1 substituent selected from —CH$_3$ and —OCH$_3$; —CH$_2$OCH$_2$(methyl pyrazolyl), —CH$_2$OCH$_2$(tetrahydropyranyl), —CH$_2$OCH$_2$(thiophenyl), —CH$_2$OCH$_2$(trifluoromethyl thiophenyl), —CH$_2$OCH$_2$(ethyl thiophenyl), —CH$_2$OCH$_2$(dimethyl thiophenyl), —CH$_2$CH$_2$OCH$_2$CH$_3$, —CH$_2$CH$_2$OCH$_2$CH(CH$_3$)$_2$, —CH$_2$CH$_2$O(methoxyphenyl), —CH$_2$CH$_2$OCH$_2$(cyclopropyl), —CH$_2$CH$_2$SCH(CH$_3$)$_2$, —(CH$_2$)$_3$OCH$_2$CH$_3$, —(CH$_2$)$_3$OCH(CH$_3$)$_2$, —(CH$_2$)$_3$OCH$_2$CH$_2$CH=CH$_2$, —(CH$_2$)$_3$O(oxetanyl), —(CH$_2$)$_3$O(tetramethyl cyclohexyl), —(CH$_2$)$_3$OCH$_2$SCH$_3$, —CH$_2$S(CH$_2$)$_{2-4}$CH$_3$, —CH$_2$SCH(CH$_3$)$_2$, —CH$_2$SCH$_2$CH(CH$_3$)$_2$, —CH$_2$SCH$_2$C(CH$_3$)$_3$, —CH$_2$SCH$_2$CH$_2$CH(CH$_3$)$_2$, —CH$_2$SCH$_2$CH$_2$C(CH$_3$)$_3$, —CH$_2$SCH$_2$CH$_2$Si(CH$_3$)$_3$, —CH$_2$CH$_2$S(CH$_2$)$_{1-2}$CH$_3$, —CH$_2$CH$_2$SCH$_2$CH(CH$_3$)$_2$, —CH$_2$S(phenyl) wherein said phenyl is substituted with zero to 2 substituents independently selected from —CH$_3$, —CH(CH$_3$)$_2$, and —OCH$_3$; —CH$_2$S(adamantanyl), —CH$_2$S(pyridinyl), —CH$_2$S(methyl pyridinyl), —CH$_2$SCH$_2$CH$_2$(phenyl), —CH$_2$SCH$_2$CH$_2$(pyrazinyl), —CH$_2$SCH$_2$CH$_2$(pyridinyl), —CH$_2$S(O)(CH$_2$)$_3$CH$_3$, —CH$_2$S(O)$_2$(CH$_2$)$_3$CH$_3$, —CH$_2$S(O)(phenyl), —CH$_2$S(O)$_2$(phenyl), —(CH$_2$)$_4$OCH(CH$_3$)$_2$, —(CH$_2$)$_4$CH(CH$_3$)OCH$_3$, —(CH$_2$)$_4$C(CH$_3$)$_2$OCH$_3$, —(CH$_2$)$_5$N(CH$_3$)$_2$, —O(CH$_2$)$_{4-7}$CH$_3$, —OCH$_2$CH$_2$O(CH$_2$)$_{2-4}$CH$_3$, —OCH$_2$CH$_2$OCH$_2$CH(CH$_3$)$_2$, —OCH$_2$CH=CH(CH$_2$)$_{2-3}$CH$_3$, —OCH$_2$CH$_2$OCH$_2$CH=CH$_2$, —OCH$_2$CH$_2$OCH$_2$CH=CH(CH$_3$), —OCH$_2$CH$_2$OCH$_2$CH=C(CH$_3$)$_2$, —OCH$_2$CH$_2$OCH$_2$CH$_2$C≡CH, —OCH$_2$CH$_2$O(CH$_2$)$_{2-3}$CH(CH$_3$)$_2$, —OCH$_2$CH$_2$S(CH$_2$)$_2$CH$_3$, —OCH$_2$(cyclohexyl), —OCH$_2$(tetrahydropyranyl), —OCH$_2$(phenyl) wherein said phenyl is substituted with zero to 1 substituent selected from —CH$_3$, —CH$_2$CH$_3$, —OCH$_3$, —OCF$_3$, and —OCH$_2$CH$_3$; —OCH$_2$CH$_2$O(cyclohexyl), —OCH$_2$CH$_2$O(methyl phenyl), —OCH$_2$CH$_2$OCH$_2$(cyclobutyl), —OCH$_2$CH$_2$OCH$_2$(phenyl), —OCH$_2$CH$_2$OCH$_2$(thiazolyl), —OCH$_2$CH$_2$OCH$_2$(thiophenyl), —C(O)(CH$_2$)$_4$CH$_3$, —OC(O)(CH$_2$)$_4$CH$_3$, —OC(O)C(CH$_3$)$_2$(CH$_2$)$_3$CH$_3$, —OC(O)(phenyl), —OC(O)NH(CH$_2$)$_3$CH$_3$, —OC(O)NH(CH$_2$)$_5$CH$_3$, —OC(O)N(CH$_3$)(CH$_2$)$_3$CH$_3$, —OC(O)N(CH$_3$)(CH$_2$)$_4$CH$_3$, —NHC(O)NH(CH$_2$)$_3$CH$_3$, —C(CH$_3$)=N—O(CH$_2$)$_3$CH$_3$, —C(CH$_3$)=N—OCH$_2$(phenyl), —C(CH$_3$)=N—OCH$_2$(fluorophenyl), —C(CH$_3$)=N—OCH$_2$(methoxyphenyl), —C(CH$_3$)=N—OCH$_2$CH$_2$(phenyl), —OC(O)NH(CH$_2$)$_3$CH$_3$, —OC(O)NH(CH$_2$)$_5$CH$_3$, —OC(O)N(CH$_3$)(CH$_2$)$_{3-4}$CH$_3$, —NHC(O)NH(CH$_2$)$_3$CH$_3$, phenyl, or pyridinyl; and $R_{2b}$ is
(i) a 6-membered spiro-ring having one oxygen atom and substituted with zero or 1 substituent selected from —(CH$_2$)$_3$CH$_3$; or
(ii) =N—O—(CH$_2$)$_3$CH$_3$, =N—O—CH$_2$CH(CH$_3$)$_2$, =N—OCH$_2$CH$_2$(phenyl), or =N—O—CH$_2$CH$_2$CH$_2$ (phenyl); and $R_1$, $X_1$, $X_2$, $X_3$, $R_a$, $R_b$, and $R_c$ are defined in the first aspect. Included in this embodiment are compounds of Formula (Ic), (IIc), (IIIc), (IVc), or (Vc).

One embodiment provides at least one compound of Formula (I) or a salt thereof, wherein: $R_1$ is —OH or —OP(O)(OH)$_2$; $R_2$ is $R_{2a}$ or $R_{2b}$; $R_{2a}$ is —(CH$_2$)$_3$CH$_3$, —(CH$_2$)$_5$CH$_3$, —CH$_2$CH=CHCH$_2$CH$_3$, —CH$_2$CH$_2$CH=CHCH$_2$CH$_3$, —(CH$_2$)$_3$CH=CHCH$_3$, —(CH$_2$)$_3$CH=C(CH$_3$)$_2$, —(CH$_2$)$_4$CH=CH$_2$, —(CH$_2$)$_4$CH=CHCH$_3$, —CH=CH(CH$_2$)$_3$CH$_3$, —CH=CH(CH$_2$)$_3$OCH$_3$, —CH=CHCH$_2$CH$_2$CH(CH$_3$)$_2$, —CH=CHCH$_2$CH$_2$CH$_2$OCH$_3$, —CH$_2$CH=CHCH=CHCH$_3$, —CH=CHCH$_2$CH$_2$CH=CH$_2$, —CH=CH(phenyl) wherein said phenyl is substituted with —CH$_3$ or —OCH$_3$; —CH=CH(tetrahydropyranyl), —(CH$_2$)$_{1-3}$(phenyl) wherein said phenyl is substituted with zero to 2 substituents independently selected from F, I, —CH$_3$, —OCH$_3$, —OCH$_2$CH$_3$, —OCH(CH$_3$)$_2$, and —CH$_2$C(O)N(CH$_3$)$_2$; —(CH$_2$)$_2$(methyl imidazolyl), —(CH$_2$)$_2$(methyl pyrazolyl), —(CH$_2$)$_{1-2}$(pyridinyl) wherein said pyridinyl is substituted with zero to 1 substituent selected from —OCH$_3$; —(CH$_2$)$_2$(pyrimidinyl), —(CH$_2$)$_2$(quinolinyl), —(CH$_2$)$_{2-3}$(tetrahydropyranyl), —CH$_2$O(CH$_2$)$_{3-4}$CH$_3$, —CH$_2$OCH$_2$CH$_2$CH(CH$_3$)$_2$, —CH$_2$OCH$_2$CH$_2$C(CH$_3$)$_3$, —CH$_2$O(CH$_2$)$_9$CH$_3$, —CH$_2$OCH$_2$CH$_2$CF$_3$, —CH$_2$OCH$_2$CH=CHCH$_2$CH$_3$, —CH$_2$OCH$_2$CH=C(CH$_3$)$_2$, —CH$_2$OCH$_2$CH=CHCH$_2$CH$_3$, —CH$_2$OCH$_2$CH$_2$CH=CH$_2$, —CH$_2$OCH$_2$CH$_2$CH$_2$CH=CH$_2$, —CH$_2$OCH$_2$CH$_2$CH=C(CH$_3$)$_2$, —CH$_2$OCH$_2$CH$_2$CH(OH)CH$_3$, —CH$_2$OCH$_2$CH$_2$CH$_2$CH$_2$OH, —CH$_2$OCH$_2$CH$_2$CH$_2$C(CH$_3$)$_2$(OH), —CH$_2$OCH$_2$CH$_2$OCH$_3$, —CH$_2$OCH$_2$CH$_2$CH$_2$OCH$_3$, —CH$_2$OCH$_2$CH$_2$OCH$_2$CH$_2$CH$_3$, —CH$_2$O(phenyl) wherein said phenyl is substituted with zero to 3 substituents independently selected from F, Cl, —CH$_3$, —CH(CH$_3$)$_2$, —C(CH$_3$)$_3$, —OCH$_3$, —OCF$_3$, —(CH$_2$)$_{1-6}$OCH$_3$, —C(O)N(CH$_3$)$_2$, —CH$_2$N(CH$_3$)$_2$, —C(O)N(CH$_2$CH$_3$)(CH$_3$), —C(O)N(CH$_3$)(CH$_2$CH$_2$CH$_2$CH$_3$), and —C(O)N(CH$_3$)(CH$_2$CH(CH$_3$)$_2$); —CH$_2$O(methoxy pyridinyl), —CH$_2$O(tetrahydropyranyl), —CH$_2$O(trifluoromethyl, methyl pyrazolyl), —CH$_2$OCH$_2$(phenyl) wherein said phenyl is substituted with zero to 1 substituent selected from —CH$_3$ and —OCH$_3$; —CH$_2$OCH$_2$(methyl pyrazolyl), —CH$_2$OCH$_2$(tetrahydropyranyl), —CH$_2$OCH$_2$(thiophenyl), —CH$_2$OCH$_2$(trifluoromethyl thiophenyl), —CH$_2$OCH$_2$(ethyl thiophenyl), —CH$_2$OCH$_2$(dimethyl thiophenyl), —CH$_2$CH$_2$OCH$_2$CH$_3$, —CH$_2$CH$_2$OCH$_2$CH(CH$_3$)$_2$, —CH$_2$CH$_2$O(methoxyphenyl), —CH$_2$CH$_2$OCH$_2$(cyclopropyl), —CH$_2$CH$_2$SCH(CH$_3$)$_2$, —(CH$_2$)$_3$OCH$_2$CH$_3$, —(CH$_2$)$_3$OCH(CH$_3$)$_2$, —(CH$_2$)$_3$OCH$_2$CH=CH$_2$, —(CH$_2$)$_3$O(oxetanyl), —(CH$_2$)$_3$O(tetramethyl cyclohexyl), —(CH$_2$)$_3$OCH$_2$SCH$_3$, —CH$_2$S(CH$_2$)$_{2-4}$CH$_3$, —CH$_2$SCH(CH$_3$)$_2$, —CH$_2$SCH$_2$CH(CH$_3$)$_2$, —CH$_2$SCH$_2$C(CH$_3$)$_3$, —CH$_2$SCH$_2$CH$_2$CH(CH$_3$)$_2$, —CH$_2$SCH$_2$CH$_2$C(CH$_3$)$_3$, —CH$_2$SCH$_2$CH$_2$Si(CH$_3$)$_3$, —CH$_2$CH$_2$S(CH$_2$)$_{1-2}$CH$_3$, —CH$_2$CH$_2$SCH$_2$CH(CH$_3$)$_2$, —CH$_2$S(phenyl) wherein said phenyl is substituted with zero to 2 substituents independently selected from —CH$_3$, —CH(CH$_3$)$_2$, and —OCH$_3$; —CH$_2$S(adamantanyl), —CH$_2$S(pyridinyl), —CH$_2$S(methyl pyridinyl), —CH$_2$SCH$_2$CH$_2$(phenyl), —CH$_2$SCH$_2$CH$_2$(pyrazinyl), —CH$_2$SCH$_2$CH$_2$(pyridinyl), —CH$_2$S(O)(CH$_2$)$_3$CH$_3$, —CH$_2$S(O)$_2$(CH$_2$)$_3$CH$_3$, —CH$_2$S(O)(phenyl), —CH$_2$S(O)$_2$(phenyl), —(CH$_2$)$_4$OCH(CH$_3$)$_2$, —(CH$_2$)$_4$CH(CH$_3$)OCH$_3$, —(CH$_2$)$_4$C(CH$_3$)$_2$CH$_3$, —(CH$_2$)$_5$N(CH$_3$)$_2$, —O(CH$_2$)$_{4-7}$CH$_3$, —OCH$_2$CH$_2$O(CH$_2$)$_{2-4}$CH$_3$, —OCH$_2$CH$_2$OCH$_2$CH(CH$_3$)$_2$, —OCH$_2$CH=CH(CH$_2$)$_{2-3}$CH$_3$, —OCH$_2$CH$_2$OCH$_2$CH=CH$_2$, —OCH$_2$CH$_2$OCH$_2$CH=CH(CH$_3$), —OCH$_2$CH$_2$OCH$_2$CH=C(CH$_3$)$_2$, —OCH$_2$CH$_2$OCH$_2$CH$_2$C≡CH, —OCH$_2$CH$_2$O(CH$_2$)$_{2-3}$CH(CH$_3$)$_2$, —OCH$_2$CH$_2$S(CH$_2$)$_2$CH$_3$, —OCH$_2$(cyclohexyl), —OCH$_2$(tetrahydropyranyl), —OCH$_2$(phenyl) wherein said phenyl is substituted with zero to 1 substituent selected from —CH$_3$, —CH$_2$CH$_3$, —OCH$_3$, —OCF$_3$, and —OCH$_2$CH$_3$; —OCH$_2$CH$_2$O(cyclohexyl), —OCH$_2$CH$_2$O(methyl phenyl), —OCH$_2$CH$_2$OCH$_2$(cyclobutyl), —OCH$_2$CH$_2$OCH$_2$(phenyl), —OCH$_2$CH$_2$OCH$_2$(thiazolyl), —OCH$_2$CH$_2$OCH$_2$(thiophenyl), —OC(O)(CH$_2$)$_4$CH$_3$, —OC(O)C(CH$_3$)$_2$(CH$_2$)$_3$CH$_3$, —OC(O)(phenyl), —OC(O)NH(CH$_2$)$_3$CH$_3$, —OC(O)NH(CH$_2$)$_5$CH$_3$, —OC(O)N(CH$_3$)(CH$_2$)$_3$CH$_3$, —OC(O)N(CH$_3$)(CH$_2$)$_4$CH$_3$, —NHC(O)NH(CH$_2$)$_3$CH$_3$, —C(CH$_3$)=N—O(CH$_2$)$_3$CH$_3$, —C(CH$_3$)=N—OCH$_2$(phenyl), —C(CH$_3$)=N—OCH$_2$(fluorophenyl), —C(CH$_3$)=N—OCH$_2$(methoxyphenyl), —C(CH$_3$)=N—OCH$_2$CH$_2$(phenyl), —OC(O)NH(CH$_2$)$_3$CH$_3$, —OC(O)NH(CH$_2$)$_5$CH$_3$, —OC(O)N(CH$_3$)(CH$_2$)$_{3-4}$CH$_3$, —NHC(O)NH(CH$_2$)$_3$CH$_3$, phenyl, or pyridinyl; $R_{2b}$ is: (i) a 6-membered spiro-ring having one oxygen atom and substituted with zero or 1 substituent selected from —(CH$_2$)$_3$CH$_3$; or (ii) =N—O—(CH$_2$)$_3$CH$_3$, =N—O—CH$_2$CH(CH$_3$)$_2$, =N—OCH$_2$CH$_2$(phenyl), or =N—O—CH$_2$CH$_2$CH$_2$(phenyl); $R_a$ is H or —OH; each $R_b$ is independently H or —CH$_3$; and each $R_c$ is independently H, Cl, I, or —CH$_3$; with the proviso that if $R_2$ is —(CH$_2$)$_6$CH$_3$, then at least one of $R_b$ and $R_c$ is not H. Included in this embodiment are compounds of Formula (Ic). Also included in this embodiment are compounds in which $R_1$ is —OH.

One embodiment provides at least one compound of Formula (II) or a salt thereof, wherein $X_1$, $X_2$, $X_3$, and $R_{2a}$ are defined in the first aspect. Included in this embodiment are compounds in which $R_{2a}$ is —(CH$_2$)$_{5-6}$CH$_3$ or —CH$_2$O(CH$_2$)$_{3-4}$CH$_3$. Included in this embodiment are compounds of Formula (IIc). Also included in this embodiment are compounds in which $R_1$ is —OH.

One embodiment provides at least one compound of Formula (III), Formula (IV), or Formula (V) or a salt thereof, wherein $R_1$, $R_2$, $R_{2a}$ and $R_b$ are defined in the first aspect. Included in this embodiment are compounds in which $R_2$ is $R_{2a}$. Included in this embodiment are compounds in which $R_2$ is $R_{2a}$. Also included in this embodiment are compounds in which $R_2$ is $R_{2a}$; $R_{2a}$ is —(CH$_2$)$_3$CH$_3$, —(CH$_2$)$_5$CH$_3$, —(CH$_2$)$_3$(phenyl), or —C(O)(CH$_2$)$_4$CH$_3$; and each $R_b$ is —CH$_3$. Additionally, included in this embodiment are compounds of Formula (IIIc), (IVc), and (Vc). Also included in this embodiment are compounds in which $R_1$ is —OH.

One embodiment provides at least one compound of Formula (I) or a salt thereof, wherein $R_1$ is —OH or —OP(O)(OH)$_2$; $R_2$ is $R_{2a}$; $R_{2a}$ is —(CH$_2$)$_3$CH$_3$, —(CH$_2$)$_5$CH$_3$, —CH$_2$CH=CHCH$_2$CH$_3$, —CH$_2$CH$_2$CH=CHCH$_2$CH$_3$, —(CH$_2$)$_3$CH=CHCH$_3$, —(CH$_2$)$_3$CH=C(CH$_3$)$_2$, —(CH$_2$)$_4$CH=CH$_2$, —(CH$_2$)$_4$CH=CHCH$_3$, —CH=CH(CH$_2$)$_3$CH$_3$, —CH=CH(CH$_2$)$_3$OCH$_3$, —CH=CHCH$_2$CH$_2$CH(CH$_3$)$_2$, —CH=CHCH$_2$CH$_2$CH$_2$OCH$_3$, —CH$_2$CH=CHCH=CHCH$_3$, —CH=CHCH$_2$CH$_2$CH=CH$_2$, —CH=CH(phenyl) wherein said phenyl is substituted with —CH$_3$ or —OCH$_3$; —CH=CH(tetrahydropyranyl), —(CH$_2$)$_{1-3}$(phenyl) wherein said phenyl is substituted with zero to 2 substituents independently selected from F, I, —CH$_3$, —OCH$_3$, —OCH$_2$CH$_3$, —OCH(CH$_3$)$_2$, and —CH$_2$C(O)N(CH$_3$)$_2$; —(CH$_2$)$_2$(methyl imidazolyl), —(CH$_2$)$_2$(methyl pyrazolyl), —(CH$_2$)$_{1-2}$(pyridinyl) wherein said pyridinyl is substituted with zero to 1 substituent selected from —OCH$_3$; —(CH$_2$)$_2$(pyrimidinyl), —(CH$_2$)$_2$(quinolinyl), —(CH$_2$)$_{2-3}$(tetrahydropyranyl), —CH$_2$O(CH$_2$)$_{3-4}$CH$_3$, —CH$_2$OCH$_2$CH$_2$CH(CH$_3$)$_2$, —CH$_2$OCH$_2$CH$_2$C(CH$_3$)$_3$, —CH$_2$O(CH$_2$)$_9$CH$_3$, —CH$_2$OCH$_2$CH$_2$CH$_2$CF$_3$, —CH$_2$OCH$_2$CH=CHCH$_2$CH$_3$, —CH$_2$OCH$_2$CH=C(CH$_3$)$_2$, —CH$_2$OCH$_2$CH=CHCH$_2$CH$_2$CH$_3$, —CH$_2$OCH$_2$CH$_2$CH=CH$_2$, —CH$_2$OCH$_2$CH$_2$CH$_2$CH=CH$_2$, —CH$_2$OCH$_2$CH$_2$CH=C(CH$_3$)$_2$, —CH$_2$OCH$_2$CH$_2$CH(OH)CH$_3$, —CH$_2$OCH$_2$CH$_2$CH$_2$CH$_2$OH, —CH$_2$OCH$_2$CH$_2$CH$_2$C(CH$_3$)$_2$(OH), —CH$_2$OCH$_2$CH$_2$OCH$_3$, —CH$_2$OCH$_2$CH$_2$CH$_2$OCH$_3$, —CH$_2$OCH$_2$CH$_2$OCH$_2$CH$_2$CH$_3$, —CH$_2$O(phenyl) wherein said phenyl is substituted with zero to 3 substituents independently selected from F, Cl, —CH$_3$, —CH(CH$_3$)$_2$, —C(CH$_3$)$_3$, —OCH$_3$, —OCF$_3$, —(CH$_2$)$_{1-6}$OCH$_3$, —C(O)N(CH$_3$)$_2$, —CH$_2$N(CH$_3$)$_2$, —C(O)N(CH$_2$CH$_3$)(CH$_3$), —C(O)N(CH$_3$)(CH$_2$CH$_2$CH$_2$CH$_3$), and —C(O)N(CH$_3$)(CH$_2$CH(CH$_3$)$_2$); —CH$_2$O(methoxy pyridinyl), —CH$_2$O(tetrahydropyranyl), —CH$_2$O(trifluoromethyl, methyl pyrazolyl), —CH$_2$OCH$_2$(phenyl) wherein said phenyl is substituted with zero to 1 substituent selected from —CH$_3$ and —OCH$_3$; —CH$_2$OCH$_2$(methyl pyrazolyl), —CH$_2$OCH$_2$(tetrahydropyranyl), —CH$_2$OCH$_2$(thiophenyl), —CH$_2$OCH$_2$(trifluoromethyl thiophenyl), —CH$_2$OCH$_2$(ethyl thiophenyl), —CH$_2$OCH$_2$(dimethyl thiophenyl), —CH$_2$CH$_2$OCH$_2$CH$_3$, —CH$_2$CH$_2$OCH$_2$CH(CH$_3$)$_2$, —CH$_2$CH$_2$O(methoxyphenyl), —CH$_2$CH$_2$OCH$_2$(cyclopropyl), —CH$_2$CH$_2$SCH(CH$_3$)$_2$, —(CH$_2$)$_3$OCH$_2$CH$_3$, —(CH$_2$)$_3$OCH(CH$_3$)$_2$, —(CH$_2$)$_3$OCH$_2$CH$_2$CH=CH$_2$, —(CH$_2$)$_3$O(oxetanyl), —(CH$_2$)$_3$O(tetramethyl cyclohexyl), —(CH$_2$)$_3$OCH$_2$SCH$_3$, —CH$_2$S(CH$_2$)$_{2-4}$CH$_3$, —CH$_2$SCH(CH$_3$)$_2$, —CH$_2$SCH$_2$CH(CH$_3$)$_2$, —CH$_2$SCH$_2$C(CH$_3$)$_3$, —CH$_2$SCH$_2$CH$_2$CH(CH$_3$)$_2$, —CH$_2$SCH$_2$CH$_2$C(CH$_3$)$_3$, —CH$_2$SCH$_2$CH$_2$Si(CH$_3$)$_3$, —CH$_2$CH$_2$S(CH$_2$)$_{1-2}$CH$_3$, —CH$_2$CH$_2$SCH$_2$CH(CH$_3$)$_2$, —CH$_2$S(phenyl) wherein said phenyl is substituted with zero to 2 substituents independently selected from —CH$_3$, —CH(CH$_3$)$_2$, and —OCH$_3$; —CH$_2$S(adamantanyl), —CH$_2$S(pyridinyl), —CH$_2$S(methyl pyridinyl), —CH$_2$SCH$_2$CH$_2$(phenyl), —CH$_2$SCH$_2$CH$_2$(pyrazinyl), —CH$_2$SCH$_2$CH$_2$(pyridinyl), —CH$_2$S(O)(CH$_2$)$_3$CH$_3$, —CH$_2$S(O)$_2$(CH$_2$)$_3$CH$_3$, —CH$_2$S(O)(phenyl), —CH$_2$S(O)$_2$(phenyl), —(CH$_2$)$_4$OCH(CH$_3$)$_2$, —(CH$_2$)$_4$CH(CH$_3$)OCH$_3$, —(CH$_2$)$_4$C(CH$_3$)$_2$OCH$_3$, —(CH$_2$)$_5$N(CH$_3$)$_2$, —O(CH$_2$)$_{4-7}$CH$_3$, —OCH$_2$CH$_2$O(CH$_2$)$_{2-4}$CH$_3$, —OCH$_2$CH$_2$OCH$_2$CH(CH$_3$)$_2$, —OCH$_2$CH=CH(CH$_2$)$_{2-3}$CH$_3$, —OCH$_2$CH$_2$OCH$_2$CH=CH$_2$, —OCH$_2$CH$_2$OCH$_2$CH=CH(CH$_3$), —OCH$_2$CH$_2$OCH$_2$CH=C(CH$_3$)$_2$, —OCH$_2$CH$_2$OCH$_2$CH$_2$C≡CH, —OCH$_2$CH$_2$O(CH$_2$)$_{2-3}$CH(CH$_3$)$_2$, —OCH$_2$CH$_2$S(CH$_2$)$_3$CH$_3$, —OCH$_2$(cyclohexyl), —OCH$_2$(tetrahydropyranyl), —OCH$_2$(phenyl) wherein said phenyl is substituted with zero to 1 substituent selected from —CH$_3$, —CH$_2$CH$_3$, —OCH$_3$, —OCF$_3$, and —OCH$_2$CH$_3$; —OCH$_2$CH$_2$O(cyclohexyl), —OCH$_2$CH$_2$O(methyl phenyl), —OCH$_2$CH$_2$OCH$_2$(cyclobutyl), —OCH$_2$CH$_2$OCH$_2$(phenyl), —OCH$_2$CH$_2$OCH$_2$(thiazolyl), —OCH$_2$CH$_2$OCH$_2$(thiophenyl), —OC(O)(CH$_2$)$_4$CH$_3$, —OC(O)C(CH$_3$)$_2$(CH$_2$)$_3$CH$_3$, —OC(O)(phenyl), —OC(O)NH(CH$_2$)$_3$CH$_3$, —OC(O)NH(CH$_2$)$_5$CH$_3$, —OC(O)N(CH$_3$)(CH$_2$)$_3$CH$_3$, —OC(O)N(CH$_3$)(CH$_2$)$_4$CH$_3$, —NHC(O)NH(CH$_2$)$_3$CH$_3$, —C(CH$_3$)=N—O(CH$_2$)$_3$CH$_3$, —C(CH$_3$)=N—OCH$_2$(phenyl), —C(CH$_3$)=N—OCH$_2$(fluorophenyl), —C(CH$_3$)=N—OCH$_2$(methoxyphenyl), —C(CH$_3$)=N—OCH$_2$CH$_2$(phenyl), —OC(O)NH(CH$_2$)$_3$CH$_3$, —OC(O)NH(CH$_2$)$_5$CH$_3$, —OC(O)N(CH$_3$)(CH$_2$)$_{3-4}$CH$_3$, —NHC(O)NH(CH$_2$)$_3$CH$_3$, phenyl, or pyridinyl; R$_a$ is H or —OH; each R$_b$ is independently H or —CH$_3$; and each R$_c$ is independently H, Cl, I, or —CH$_3$; with the proviso that if R$_2$ is —(CH$_2$)$_6$CH$_3$, then at least one of R$_b$ and R$_c$ is not H. Included in this embodiment are compounds of Formula (Ic). Also included in this embodiment are compounds in which R$_1$ is —OH.

One embodiment provides at least one compound of Formula (I) or a salt thereof, wherein R$_1$ is —OH or —OP(O)(OH)$_2$; R$_2$ is R$_{2b}$; R$_{2b}$ is: (i) a 6-membered spiro-ring having one oxygen atom and substituted with zero or 1 substituent selected from —(CH$_2$)$_3$CH$_3$; or (ii) =N—O—(CH$_2$)$_3$CH$_3$, =N—O—CH$_2$CH(CH$_3$)$_2$, =N—OCH$_2$CH$_2$(phenyl), or =N—O—CH$_2$CH$_2$CH$_2$(phenyl); R$_a$ is H or —OH; each R$_b$ is independently H or —CH$_3$; and each R$_c$ is independently H, Cl, I, or —CH$_3$. Included in this embodiment are compounds of Formula (Ic). Also included in this embodiment are compounds in which R$_1$ is —OH.

One embodiment provides at least one compound of Formula (I) or a salt thereof, wherein R$_2$ is R$_{2a}$; R$_{2a}$ is —(CH$_2$)$_{3-6}$CH$_3$, —(CH$_2$)$_{1-4}$CH=CR$_x$R$_x$, —(CH$_2$)$_{1-4}$CH=CR$_x$(CH$_2$CH$_3$), —CH=CH(CH$_2$)$_{1-3}$C(R$_x$)$_3$, —CH=CH(CH$_2$)$_{1-3}$OCH$_3$, —(CH$_2$)$_{1-3}$CH=CHCH=CR$_x$R$_x$, —CH=CH(CH$_2$)$_{1-3}$CH=CR$_x$R$_x$, —CH=CHR$_z$, —(CH$_2$)$_{1-3}$R$_z$, —(CH$_2$)$_{1-3}$O(CH$_2$)$_{0-3}$R$_z$, —(CH$_2$)$_{1-3}$S(CH$_2$)$_{0-3}$R$_z$, —CH$_2$S(O)R$_z$, —CH$_2$S(O)$_2$R$_z$, —O(CH$_2$)$_{1-2}$R$_z$, —O(CH$_2$)$_{1-2}$O(CH$_2$)$_{0-2}$R$_z$, —OC(O)R$_z$, —(CH$_2$)$_{1-4}$O(CH$_2$)$_{0-9}$C(R$_x$)$_3$, —(CH$_2$)$_{1-4}$O(CH$_2$)$_{0-9}$CF$_3$, —(CH$_2$)$_{1-4}$CR$_x$R$_x$O(CH$_2$)$_{0-4}$C(R$_x$)$_3$, —(CH$_2$)$_{1-3}$O(CH$_2$)$_{1-4}$CH=CR$_x$(CH$_2$)$_{0-3}$CH$_3$, —(CH$_2$)$_{1-3}$O(CH$_2$)$_{1-4}$CH=CR$_x$R$_x$, —(CH$_2$)$_{1-3}$O(CH$_2$)$_{1-4}$C(OH)R$_x$R$_x$, —(CH$_2$)$_{1-3}$O(CH$_2$)$_{1-4}$O(CH$_2$)$_{0-3}$CH$_3$, —(CH$_2$)$_{1-3}$S(CH$_2$)$_{0-4}$C(R$_x$)$_3$, —(CH$_2$)$_{0-3}$O(CH$_2$)$_{1-4}$S(CH$_2$)$_{0-3}$C(R$_x$)$_3$, —(CH$_2$)$_{1-3}$S(CH$_2$)$_{1-4}$Si(CH$_3$)$_3$, —(CH$_2$)$_{1-3}$S(O)(CH$_2$)$_{0-4}$C(R$_x$)$_3$, —(CH$_2$)$_{1-3}$S(O)$_2$(CH$_2$)$_{1-4}$C(R$_x$)$_3$, —(CH$_2$)$_{1-5}$NR$_x$R$_x$, or —O(CH$_2$)$_{1-7}$C(R$_x$)$_3$; and R$_1$, R$_a$, R$_b$, and R$_c$ are defined in the first aspect. Included in this embodiment are compounds in which R$_{2a}$ is —(CH$_2$)$_3$CH$_3$, —(CH$_2$)$_{5-6}$CH$_3$, —CH$_2$CH=CHCH$_2$CH$_3$, —CH$_2$CH$_2$CH=CHCH$_2$CH$_3$, —(CH$_2$)$_3$CH=CHCH$_3$, —(CH$_2$)$_3$CH=C(CH$_3$)$_2$, —(CH$_2$)$_4$CH=CH$_2$, —(CH$_2$)$_4$CH=CHCH$_3$, —CH=CH(CH$_2$)$_3$CH$_3$, —CH=CH(CH$_2$)$_3$OCH$_3$, —CH=CHCH$_2$CH$_2$CH(CH$_3$)$_2$, —CH=CHCH$_2$CH$_2$CH$_2$OCH$_3$, —CH$_2$CH=CHCH=CHCH$_3$, —CH=CHCH$_2$CH$_2$CH=CH$_2$, —CH=CH(phenyl) wherein said phenyl is substituted with —CH$_3$ or —OCH$_3$; —CH=CH(tetrahydropyranyl), —(CH$_2$)$_{1-3}$(phenyl) wherein said phenyl is substituted with zero to 2 substituents independently selected from F, I, —CH$_3$, —OCH$_3$, —OCH$_2$CH$_3$, —OCH(CH$_3$)$_2$, and —CH$_2$C(O)N(CH$_3$)$_2$; —(CH$_2$)$_2$(methyl imidazolyl), —(CH$_2$)$_2$(methyl pyrazolyl), —(CH$_2$)$_{1-2}$(pyridinyl) wherein said pyridinyl is substituted with zero to 1 substituent selected from —OCH$_3$; —(CH$_2$)$_2$(pyrimidinyl), —(CH$_2$)$_2$(quinolinyl), —(CH$_2$)$_{2-3}$(tetrahydropyranyl), —CH$_2$O(CH$_2$)$_{3-4}$CH$_3$, —CH$_2$OCH$_2$CH$_2$CH(CH$_3$)$_2$, —CH$_2$OCH$_2$CH$_2$C(CH$_3$)$_3$, —CH$_2$O(CH$_2$)$_9$CH$_3$, —CH$_2$OCH$_2$CH$_2$CH$_2$CF$_3$, —CH$_2$OCH$_2$CH=CHCH$_2$CH$_3$, —CH$_2$OCH$_2$CH=C(CH$_3$)$_2$, —CH$_2$OCH$_2$CH=CHCH$_2$CH$_2$CH$_3$, —CH$_2$OCH$_2$CH$_2$CH=CH$_2$, —CH$_2$OCH$_2$CH$_2$CH$_2$CH=CH$_2$, —CH$_2$OCH$_2$CH$_2$CH=C(CH$_3$)$_2$, —CH$_2$OCH$_2$CH$_2$CH(OH)CH$_3$, —CH$_2$OCH$_2$CH$_2$CH$_2$CH$_2$OH, —CH$_2$OCH$_2$CH$_2$CH$_2$C(CH$_3$)$_2$(OH), —CH$_2$OCH$_2$CH$_2$CH$_2$OCH$_3$, —CH$_2$OCH$_2$CH$_2$CH$_2$OCH$_3$, —CH$_2$OCH$_2$CH$_2$OCH$_2$CH$_2$CH$_3$, —CH$_2$O(phenyl) wherein said phenyl is substituted with zero to 3 substituents independently selected from F, Cl, —CH$_3$, —CH(CH$_3$)$_2$, —C(CH$_3$)$_3$, —OCH$_3$, —OCF$_3$, —(CH$_2$)$_{1-6}$OCH$_3$, —C(O)N(CH$_3$)$_2$, —CH$_2$N(CH$_3$)$_2$, —C(O)N(CH$_2$CH$_3$)(CH$_3$), —C(O)N(CH$_3$)(CH$_2$CH$_2$CH$_2$CH$_3$), and —C(O)N(CH$_3$)(CH$_2$CH(CH$_3$)$_2$); —CH$_2$O(methoxy pyridinyl), —CH$_2$O(tetrahydropyranyl), —CH$_2$O(trifluoromethyl, methyl pyrazolyl), —CH$_2$OCH$_2$(phenyl) wherein said phenyl is substituted with zero to 1 substituent selected from —CH$_3$ and —OCH$_3$; —CH$_2$OCH$_2$(methyl pyrazolyl), —CH$_2$OCH$_2$(tetrahydropyranyl), —CH$_2$OCH$_2$(thiophenyl), —CH$_2$OCH$_2$(trifluoromethyl thiophenyl), —CH$_2$OCH$_2$(ethyl thiophenyl), —CH$_2$OCH$_2$(dimethyl thiophenyl), —CH$_2$CH$_2$OCH$_2$CH$_3$, —CH$_2$CH$_2$OCH$_2$CH(CH$_3$)$_2$, —CH$_2$CH$_2$O(methoxyphenyl), —CH$_2$CH$_2$OCH$_2$(cyclopropyl), —CH$_2$CH$_2$SCH(CH$_3$)$_2$, —(CH$_2$)$_3$OCH$_2$CH$_3$, —(CH$_2$)$_3$OCH(CH$_3$)$_2$, —(CH$_2$)$_3$OCH$_2$CH=CH$_2$, —(CH$_2$)$_3$O(oxetanyl), —(CH$_2$)$_3$O(tetramethyl cyclohexyl), —(CH$_2$)$_3$OCH$_2$SCH$_3$, —CH$_2$S(CH$_2$)$_{2-4}$CH$_3$, —CH$_2$SCH(CH$_3$)$_2$, —CH$_2$SCH$_2$CH(CH$_3$)$_2$, —CH$_2$SCH$_2$C(CH$_3$)$_3$, —CH$_2$SCH$_2$CH$_2$CH(CH$_3$)$_2$, —CH$_2$SCH$_2$CH$_2$C(CH$_3$)$_3$, —CH$_2$SCH$_2$CH$_2$Si(CH$_3$)$_3$, —CH$_2$CH$_2$S(CH$_2$)$_{1-2}$CH$_3$, —CH$_2$CH$_2$SCH$_2$CH(CH$_3$)$_2$, —CH$_2$S(phenyl) wherein said phenyl is substituted with zero to 2 substituents independently selected from —CH$_3$, —CH(CH$_3$)$_2$, and —OCH$_3$; —CH$_2$S(adamantanyl), —CH$_2$S(pyridinyl), —CH$_2$S(methyl pyridinyl), —CH$_2$SCH$_2$CH$_2$(phenyl), —CH$_2$SCH$_2$CH$_2$(pyrazinyl), —CH$_2$SCH$_2$CH$_2$(pyridinyl), —CH$_2$S(O)(CH$_2$)$_3$CH$_3$, —CH$_2$S(O)$_2$(CH$_2$)$_3$CH$_3$, —CH$_2$S(O)(phenyl), —CH$_2$S(O)$_2$(phenyl), —(CH$_2$)$_4$OCH(CH$_3$)$_2$, —(CH$_2$)$_4$CH(CH$_3$)OCH$_3$, —(CH$_2$)$_4$C(CH$_3$)$_2$OCH$_3$, or —(CH$_2$)$_5$N(CH$_3$)$_2$.

One embodiment provides at least one compound of Formula (I) or a salt thereof, wherein —O(CH$_2$)$_{1-4}$O(CH$_2$)$_{0-4}$C(R$_x$)$_3$, —O(CH$_2$)$_{1-4}$CH=CR$_x$(CH$_2$)$_{0-3}$CH$_3$, —O(CH$_2$)$_{1-4}$O(CH$_2$) 0-3C(R$_x$)$_3$, —O(CH$_2$)$_{1-4}$O(CH$_2$)$_{1-3}$CH=CR$_x$R$_x$, or —O(CH$_2$)$_{1-4}$O(CH$_2$)$_{1-3}$C≡CR$_x$; and R$_1$, R$_a$, R$_b$, and R$_c$ are defined in the first aspect. Included in this embodiment are compounds in which R$_{2a}$ is —O(CH$_2$)$_{4-7}$CH$_3$, —OCH$_2$CH$_2$O(CH$_2$)$_{2-4}$CH$_3$, —OCH$_2$CH$_2$OCH$_2$CH(CH$_3$)$_2$, —OCH$_2$CH=CH(CH$_2$)$_{2-3}$CH$_3$, —OCH$_2$CH$_2$OCH$_2$CH=CH$_2$, —OCH$_2$CH$_2$OCH$_2$CH=CH(CH$_3$), —OCH$_2$CH$_2$OCH$_2$CH=C(CH$_3$)$_2$, —OCH$_2$CH$_2$OCH$_2$CH$_2$C≡CH, —OCH$_2$CH$_2$O(CH$_2$)$_{2-3}$CH(CH$_3$)$_2$, —OCH$_2$CH$_2$S(CH$_2$)$_2$CH$_3$, —OCH$_2$(cyclohexyl), —OCH$_2$(tetrahydropyranyl), —OCH$_2$(phenyl) wherein said phenyl is substituted with zero to 1 substituent selected from —CH$_3$, —CH$_2$CH$_3$, —OCH$_3$, —OCF$_3$, and —OCH$_2$CH$_3$; —OCH$_2$CH$_2$O(cyclohexyl), —OCH$_2$CH$_2$O(methyl phenyl), —OCH$_2$CH$_2$OCH$_2$(cyclobutyl), —OCH$_2$CH$_2$OCH$_2$(phenyl), —OCH$_2$CH$_2$OCH$_2$(thiazolyl), or —OCH$_2$CH$_2$OCH$_2$(thiophenyl).

One embodiment provides at least one compound of Formula (I) or a salt thereof, —C(O)(CH$_2$)$_{0-4}$C(R$_x$)$_3$, —OC(O)(CH$_2$)$_{0-4}$C(R$_x$)$_3$, —OC(O)CR$_x$R$_x$(CH$_2$)$_{0-4}$C(R$_x$)$_3$, —OC(O)NR$_x$(CH$_2$)$_{0-5}$C(R$_x$)$_3$, —NR$_x$C(O)NR$_x$(CH$_2$)$_{0-5}$C(R$_x$)$_3$, —C(CH$_3$)=N—O(CH$_2$)$_{0-5}$C(R$_x$)$_3$, —C(CH$_3$)=N—O(CH$_2$)$_{1-2}$(phenyl), —C(CH$_3$)=N—O(CH$_2$)$_{1-2}$(fluorophenyl), —C(CH$_3$)=N—O(CH$_2$)$_{1-2}$(methoxyphenyl), phenyl, or pyridinyl; and R$_1$, R$_a$, R$_b$, and R$_c$ are defined in the first aspect. Included in this embodiment are compounds in which R$_{2a}$ is —C(O)(CH$_2$)$_4$CH$_3$, —OC(O)(CH$_2$)$_4$CH$_3$, —OC(O)C(CH$_3$)$_2$(CH$_2$)$_3$CH$_3$, —OC(O)(phenyl), —O C(O)NH(CH$_2$)$_3$CH$_3$, —OC(O)NH(CH$_2$)$_5$CH$_3$, —OC(O)N(CH$_3$)(CH$_2$)$_3$CH$_3$, —OC(O)N(CH$_3$)(CH$_2$)$_4$CH$_3$, —NHC(O)NH(CH$_2$)$_3$CH$_3$, —C(CH$_3$)=N—O(CH$_2$)$_3$CH$_3$, —C(CH$_3$)=N—OCH$_2$(phenyl), —C(CH$_3$)=N—OCH$_2$(fluorophenyl), —C(CH$_3$)=N—OCH$_2$(methoxyphenyl), —C(CH$_3$)=N—OCH$_2$CH$_2$(phenyl), —OC(O)NH(CH$_2$)$_3$CH$_3$, —OC(O)NH(CH$_2$)$_5$CH$_3$, —OC(O)N(CH$_3$)(CH$_2$)$_{3-4}$CH$_3$, —NHC(O)NH(CH$_2$)$_3$CH$_3$, phenyl, or pyridinyl.

One embodiment provides at least one compound of Formula (I) or a salt thereof, wherein R$_1$ is —OH or —OP(O)(OH)$_2$; R$_2$ is R$_{2b}$; R$_{2b}$ is a 6-membered spiro-ring having one oxygen atom and substituted with zero or 1 substituent selected from —(CH$_2$)$_3$CH$_3$; R$_a$ is H or —OH; each R$_b$ is independently H or —CH$_3$; and each R$_c$ is independently H, Cl, I, or —CH$_3$. Included in this embodiment are compounds of Formula (Ic). Also included in this embodiment are compounds in which R$_1$ is —OH. Additionally, included in this embodiment are compounds having the following structures:

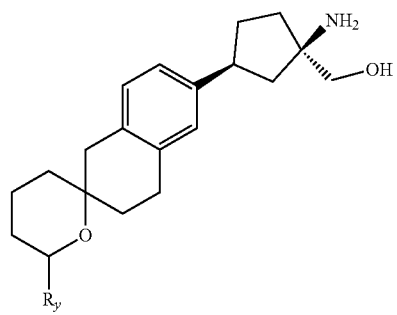

wherein R$_y$ is H or —(CH$_2$)$_3$CH$_3$.

One embodiment provides at least one compound of Formula (I) or a salt thereof, wherein R$_1$ is —OH or —OP(O)(OH)$_2$; R$_2$ is R$_{2b}$; R$_{2b}$ is =N—O—(CH$_2$)$_3$CH$_3$, =N—O—CH$_2$CH(CH$_3$)$_2$, =N—OCH$_2$CH$_2$(phenyl), or =N—O—CH$_2$CH$_2$CH$_2$(phenyl); R$_a$ is H or —OH; each R$_b$ is independently H or —CH$_3$; and each R$_c$ is independently H, Cl, I, or —CH$_3$. Included in this embodiment are compounds of Formula (Ic). Also included in this embodiment are compounds in which R$_1$ is —OH.

One embodiment provides at least one compound of Formula (I) or a salt thereof having the structure:

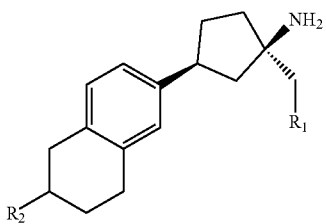

wherein: $R_1$ is —OH or —OP(O)(OH)$_2$; and $R_2$ is —(CH$_2$)$_5$OCH$_3$, —(CH$_2$)$_3$OCH$_2$CH$_3$, —CH$_2$O(methoxyphenyl), or —CH$_2$CH$_2$(methoxyphenyl).

One embodiment provides at least one compound of Formula (I) or a salt thereof having the structure:

wherein $R_1$ is —OH or —OP(O)(OH)$_2$; and $R_2$ is —(CH$_2$)$_5$OCH$_3$ or —(CH$_2$)$_3$OCH$_2$CH$_3$. Included in this embodiment are compounds having the structures:

One embodiment provides at least one compound of Formula (I) or a salt thereof having the structure:

wherein $R_1$ is —OH or —OP(O)(OH)$_2$; and $R_2$ is —CH$_2$O (methoxyphenyl) or —CH$_2$CH$_2$(methoxyphenyl). Included in this embodiment are compounds having the structures:

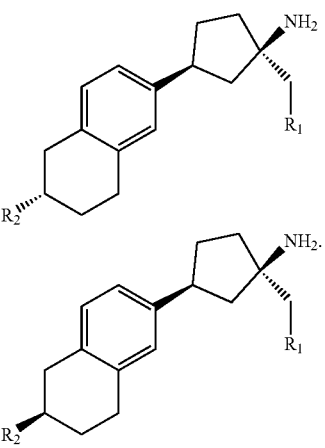

One embodiment provides a compound selected from ((1R,3S)-1-amino-3-((S)-6-(5-methoxypentyl)-5,6,7,8-tetrahydronaphthalen-2-yl)cyclopentyl)methanol (672); ((1R,3S)-1-amino-3-((R)-6-(5-methoxypentyl)-5,6,7,8-tetrahydronaphthalen-2-yl) cyclopentyl)methanol (673); ((1R,3R)-1-amino-3-(6-(5-methoxypentyl)-5,6,7,8-tetrahydronaphthalen-2-yl)cyclopentyl)methanol (674); ((1R,3R)-1-amino-3-((S)-6-(5-methoxypentyl)-5,6,7,8-tetrahydronaphthalen-2-yl)cyclopentyl)methanol; ((1R,3R)-1-amino-3-((R)-6-(5-methoxypentyl)-5,6,7,8-tetrahydronaphthalen-2-yl)cyclopentyl) methanol; ((1R,3S)-1-amino-3-((R)-6-(3-ethoxypropyl)-5,6,7,8-tetrahydronaphthalen-2-yl) cyclopentyl)methanol (678); ((1R,3S)-1-amino-3-((S)-6-(3-ethoxypropyl)-5,6,7,8-tetrahydronaphthalen-2-yl) cyclopentyl)methanol (679); ((1R,3R)-1-amino-3-((S)-6-(3-ethoxypropyl)-5,6,7,8-tetrahydronaphthalen-2-yl) cyclopentyl)methanol; and salts thereof.

One embodiment provides a compound selected from ((1R,3S)-1-amino-3-((R)-6-(5-methoxypentyl)-5,6,7,8-tetrahydronaphthalen-2-yl)cyclopentyl)methyl dihydrogen phosphate; ((1R,3S)-1-amino-3-((S)-6-(5-methoxypentyl)-5,6,7,8-tetrahydronaphthalen-2-yl)cyclopentyl)methyl dihydrogen phosphate; ((1R,3R)-1-amino-3-((R)-6-(5-methoxypentyl)-5,6,7,8-tetrahydronaphthalen-2-yl)cyclopentyl) methyl dihydrogen phosphate; ((1R,3R)-1-amino-3-((S)-6-(5-methoxypentyl)-5,6,7,8-tetrahydronaphthalen-2-yl) cyclopentyl)methyl dihydrogen phosphate; ((1R,3S)-1-amino-3-((R)-6-(3-ethoxypropyl)-5,6,7,8-tetrahydronaphthalen-2-yl)cyclopentyl)methyl dihydrogen phosphate; ((1R,3S)-1-amino-3-((S)-6-(3-ethoxypropyl)-5,6,7,8-tetrahydronaphthalen-2-yl)cyclopentyl)methyl dihydrogen phosphate; and salts thereof.

One embodiment provides a compound selected from ((1R,3S)-1-amino-3-((S)-6-(3-methoxyphenethyl)-5,6,7,8-tetrahydronaphthalen-2-yl)cyclopentyl) methanol (676); ((1R,3S)-1-amino-3-((R)-6-(3-methoxyphenethyl)-5,6,7,8-tetrahydronaphthalen-2-yl)cyclopentyl)methanol (677); ((1R,3S)-1-amino-3-((S)-6-(2-methoxyphenethyl)-5,6,7,8-tetrahydronaphthalen-2-yl)cyclopentyl)methanol (681); ((1R,3S)-1-amino-3-((R)-6-(2-methoxyphenethyl)-5,6,7,8-tetrahydronaphthalen-2-yl)cyclopentyl)methanol (682); ((1R,3R)-1-amino-3-((S)-6-(2-methoxyphenethyl)-5,6,7,8-tetrahydronaphthalen-2-yl) cyclopentyl)methanol (683); ((1R,3S)-1-amino-3-((R)-6-((3-methoxyphenoxy)methyl)-5,6,7,8-tetrahydronaphthalen-2-yl)cyclopentyl)methanol (684); ((1R,3S)-1-amino-3-((S)-6-((3-methoxyphenoxy) methyl)-5,6,7,8-tetrahydronaphthalen-2-yl)cyclopentyl)

methanol (685); ((1R,3R)-1-amino-3-(6-((3-methoxyphenoxy)methyl)-5,6,7,8-tetrahydronaphthalen-2-yl) cyclopentyl)methanol; ((1R,3R)-1-amino-3-((S)-6-((3-methoxyphenoxy)methyl)-5,6,7,8-tetrahydronaphthalen-2-yl)cyclopentyl)methanol; ((1R,3R)-1-amino-3-((R)-6-((3-methoxyphenoxy)methyl)-5,6,7,8-tetrahydronaphthalen-2-yl)cyclopentyl)methanol; and salts thereof.

One embodiment provides a compound selected from ((1R,3R)-1-amino-3-((R)-6-((3-methoxyphenoxy)methyl)-5,6,7,8-tetrahydronaphthalen-2-yl)cyclopentyl)methyl dihydrogen phosphate (688); ((1R,3S)-1-amino-3-((R)-6-(3-methoxyphenethyl)-5,6,7,8-tetrahydronaphthalen-2-yl) cyclopentyl)methyl dihydrogen phosphate; ((1R,3S)-1-amino-3-((S)-6-(3-methoxyphenethyl)-5,6,7,8-tetrahydronaphthalen-2-yl)cyclopentyl)methyl dihydrogen phosphate; ((1R,3S)-1-amino-3-((R)-6-(2-methoxyphenethyl)-5,6,7,8-tetrahydronaphthalen-2-yl)cyclopentyl) methyl dihydrogen phosphate; ((1R,3S)-1-amino-3-((S)-6-(2-methoxyphenethyl)-5,6,7,8-tetrahydronaphthalen-2-yl) cyclopentyl)methyl dihydrogen phosphate; ((1R,3R)-1-amino-3-((S)-6-(2-methoxyphenethyl)-5,6,7,8-tetrahydronaphthalen-2-yl)cyclopentyl)methyl dihydrogen phosphate (698); ((1R,3S)-1-amino-3-((R)-6-((3-methoxyphenoxy)methyl)-5,6,7,8-tetrahydronaphthalen-2-yl)cyclopentyl)methyl dihydrogen phosphate; ((1R,3S)-1-amino-3-((S)-6-((3-methoxyphenoxy)methyl)-5,6,7,8-tetrahydronaphthalen-2-yl)cyclopentyl)methyl dihydrogen phosphate; ((1R,3R)-1-amino-3-((R)-6-((3-methoxyphenoxy)methyl)-5,6,7,8-tetrahydronaphthalen-2-yl)cyclopentyl)methyl dihydrogen phosphate; ((1R,3R)-1-amino-3-((S)-6-((3-methoxyphenoxy)methyl)-5,6,7,8-tetrahydronaphthalen-2-yl)cyclopentyl)methyl dihydrogen phosphate; and salts thereof.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

As used herein, "alkylene" refers to a bivalent alkyl radical having the general formula —$(CH_2)_n$—, where n is the number of methylene units. Non-limiting examples include methylene, dimethylene, trimethylene, tetramethylene, pentamethylene, and hexamethylene. For example, "$(CH_2)_{1-6}$" denotes straight chain alkylene groups with one to six carbon atoms. Further, for example, "$(CH_2)_{0-4}$" denotes a bond and straight chain alkylene groups with one to four carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formulas (I), (II), (III), (IV), and (V) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formulas (I), (II), (III), (IV), or (V) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formulas (I), (II), (III), (IV), or (V) may be formed, for example, by reacting a compound of the Formulas (I), (II), (III), (IV), or (V) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formulas (I), (II), (III), (IV), and (V) can be provided as amorphous solids or crystalline solids. Lyophilization can be employed to provide the compounds as a solid.

It should further be understood that solvates (e.g., hydrates) of the compounds of Formulas (I), (II), (III), (IV), and (V) are also within the scope of the present invention. The term "solvate" means a physical association of a compound of Formulas (I), (II), (III), (IV), or (V) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of Formulas (I), (II), (III), (IV), and (V), subsequent to their preparation, can be isolated and purified to obtain a composition containing an amount by weight equal to or greater than 99% of a compound of Formulas (I), (II), (III), (IV), and (V) ("substantially pure"), which is then used or formulated as described herein. Such "substantially pure" compounds of Formulas (I), (II), (III), (IV), and (V) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formulas (I), (II), (III), (IV), and (V) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formulas (I), (II), (III), (IV), or (V) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formulas (I), (II), (III), (IV), and (V) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formulas (I), (II), (III), (IV), or (V) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formulas (I), (II), (III), (IV), or (V) and/or at least one salt thereof with at least one inert solid diluent, such as, for example, calcium carbonate; calcium phosphate; and kaolin.

Soft gelatin capsules can, for example, be prepared by mixing at least one compound of Formulas (I), (II), (III), (IV), or (V) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formulas (I), (II), (III), (IV), or (V) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethyleneoxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formulas (I), (II), (III), (IV), or (V) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formulas (I), (II), (III), (IV), or (V) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formulas (I), (II), (III), (IV), or (V) and/or at least one pharmaceutically acceptable salt thereof can, for example, be prepared as an oil-in-water emulsion. The oily phase of the emulsions comprising compounds of Formulas (I), (II), (III), (IV), or (V) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formulas (I), (II), (III), (IV), or (V) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formulas (I), (II), (III), (IV), or (V) in an oily phase, such as, for example, a mixture of soybean oil and lecithin; 2) combining the Formulas (I), (II), (III), (IV), or (V) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formulas (I), (II), (III), (IV), or (V) and/or at least one pharmaceutically acceptable salt thereof, and optionally an additional agent selected from any pharmaceutically acceptable carrier, adjuvant, and vehicle. Alternate compositions of this invention comprise a compound of the Formulas (I), (II), (III), (IV), or (V) described herein, and a pharmaceutically acceptable carrier, adjuvant, or vehicle.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, juvenile idiopathic arthritis, systemic lupus erythematosus, cutaneous lupus erythematosus (discoid lupus erythematosus, subacute lupus erythematosus) and lupus nephritis, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis including ANCA-associated vasculitis, giant cell arteritis, Takayasu's arteritis, microscopic poliangiitis, central nervous system vasculitis, Churg-Strauss Syndrome, and rheumatoid vasculitis, erythema, cutaneous eosinophilia, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderrna and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, chronic bacterial infection, thrombocytopenia, IgA nephropathy, mesangioproliferative glomerulonephritis, IgG4-related disease, ankylosing spondylitis, and relapsing polychondritis. Juvenile idiopathic arthritis includes oligoarthritis-onset juvenile idiopathic arthritis, polyarthritis-onset juvenile idiopathic arthritis, systemic-onset juvenile idiopathic arthritis, juvenile psoriatic arthritis, and enthesitis-related juvenile idiopathic arthritis.

One embodiment provides a method for treating autoimmune and/or inflammatory diseases, comprising administering to a mammal in need thereof at least one compound of Formulas (I), (II), (III), (IV), or (V) or a pharmaceutically acceptable salt thereof. Another embodiment provides the compounds of Formulas (I), (II), (III), (IV), or (V) or pharmaceutically acceptable salts thereof, for use in therapy for the treatment of autoimmune and/or inflammatory diseases. In another embodiment, provided is the use of the compounds of Formulas (I), (II), (III), (IV), or (V) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formulas (I), (II), (III), (IV), or (V) or a pharmaceutically effective salt thereof.

In another embodiment, a method for treating vascular disease is provided comprising administering to a mammal in need thereof at least one compound of Formulas (I), (II), (III), (IV), or (V) or a pharmaceutically acceptable salt thereof. Another embodiment provides the compounds of Formulas (I), (II), (III), (IV), or (V) or pharmaceutically acceptable salts thereof, for use in therapy for the treatment of vascular disease. In another embodiment, provided is the use of the compounds of Formulas (I), (II), (III), (IV), or (V) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

In another embodiment, a method for treating inflammatory bowel disease is provided comprising administering to a mammal in need thereof at least one compound of Formulas (I), (II), (III), (IV), or (V) or a pharmaceutically acceptable salt thereof. Another embodiment provides the compounds of Formulas (I), (II), (III), (IV), or (V) or pharmaceutically acceptable salts thereof, for use in therapy for the treatment of inflammatory bowel disease. In another embodiment, provided is the use of the compounds of Formulas (I), (II), (III), (IV), or (V) or pharmaceutically acceptable salts thereof, for the manufacture of a medicament for treatment of inflammatory bowel disease. A therapeutically effective amount may be employed in these embodiments. Preferably, in these embodiments, the inflammatory bowel disease is selected from Crohn's disease, ulcerative colitis, collagenous colitis, lymphocytic colitis, ischaemic colitis, diversion colitis, Behcet's disease, and indeterminate colitis.

In another embodiment, a method for treating lupus is provided comprising administering to a mammal in need thereof at least one compound of Formulas (I), (II), (III), (IV), or (V) or a pharmaceutically acceptable salt thereof. Another embodiment provides the compounds of Formulas (I), (II), (III), (IV), or (V) or pharmaceutically acceptable salts thereof, for use in therapy for the treatment of lupus. In another embodiment, provided is the use of the compounds of Formulas (I), (II), (III), (IV), or (V) or pharmaceutically acceptable salts thereof, for the manufacture of a medicament for treatment of lupus. A therapeutically effective amount may be employed in these embodiments. Lupus includes systemic lupus erythematosus, cutaneous lupus erythematosus, discoid lupus erythematosus, subacute lupus erythematosus and lupus nephritis.

In another embodiment, a method for treating multiple sclerosis is provided comprising administering to a mammal in need thereof at least one compound of Formulas (I), (II), (III), (IV), or (V) or a pharmaceutically acceptable salt thereof. Another embodiment provides the compounds of Formulas (I), (II), (III), (IV), or (V) or pharmaceutically acceptable salts thereof, for use in therapy for the treatment of multiple sclerosis. In another embodiment, provided is the use of the compounds of Formulas (I), (II), (III), (IV), or (V) or pharmaceutically acceptable salts thereof, for the manufacture of a medicament for treatment of multiple sclerosis. A therapeutically effective amount may be employed in these embodiments. Preferably, in these embodiments, multiple sclerosis includes relapsing remitting multiple sclerosis, primary progressive multiple sclerosis, secondary progressive multiple sclerosis, and progressive relapsing multiple sclerosis.

The methods of treating S1P1-associated conditions may comprise administering compounds of Formulas (I), (II), (III), (IV), or (V) alone or in combination with each other and/or other suitable therapeutic agents useful in treating such conditions. Accordingly, "therapeutically effective amount" is also intended to include an amount of the combination of compounds claimed that is effective to act as an agonist at the S1P receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, I1-1 such as anakinra (KINERET®) (an IL-1 receptor antagonist), IL-2, IL-4, IL-5, 11-6, such as CNTO 328 (a chimeric anti-IL-6 antibody), I1-7, I1-8, I1-12, I1-15, I1-16, I1-17, I1-21, I1-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2006).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

SCHEME 1

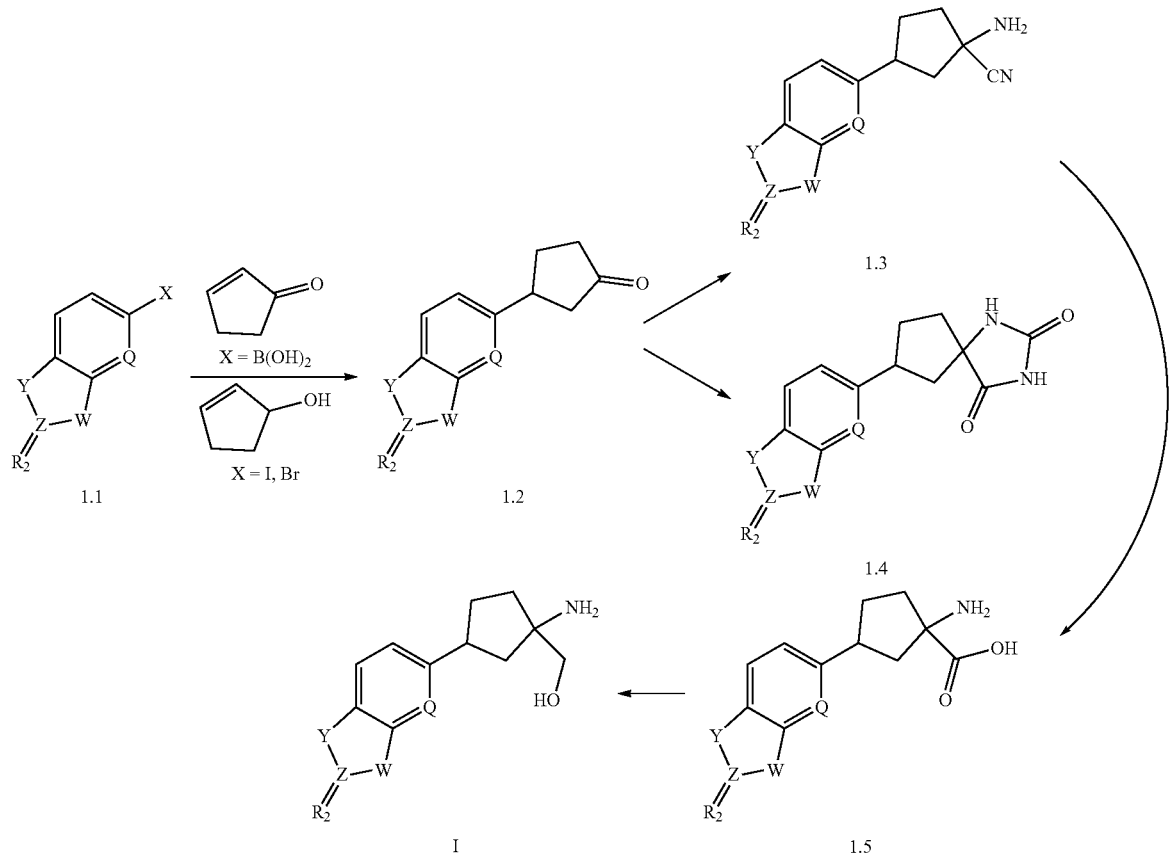

(Z═R$_2$) = NR, CHR, CRR
Q = CH, N
Y = CH$_2$, C═O
W = (—X$_2$—X$_3$—)
W = 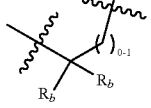

As shown in Scheme 1, compounds of Formula I may be produced, starting with bicyclic compounds 1.1 in which an aryl or heteroaryl boronic acid can be coupled with cyclopentenone in a conjugate addition reaction (catalyzed for example with rhodium or copper complexes) to afford ketone 1.2. This transformation can be done in the presence of chiral ligands (such as BINAP) to provide enantioenriched 1.2. Ketone 1.2 can also be prepared through transition-metal catalyzed coupling of aryl or heteroaryl halogen compounds with cyclopeten-2-enol. Ketone 1.2 can be converted to either amino-nitrile 1.3 or hydantoin 1.4, each of which can be hydrolyzed to provide amino-acid 1.5. Direct reduction of the acid of 1.5, or initial esterification and subsequent reduction of the carbonyl ester, leads to compounds of formula I.

SCHEME 2

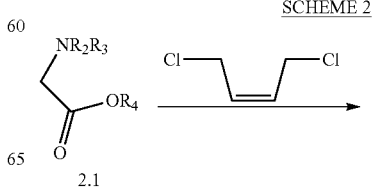

-continued
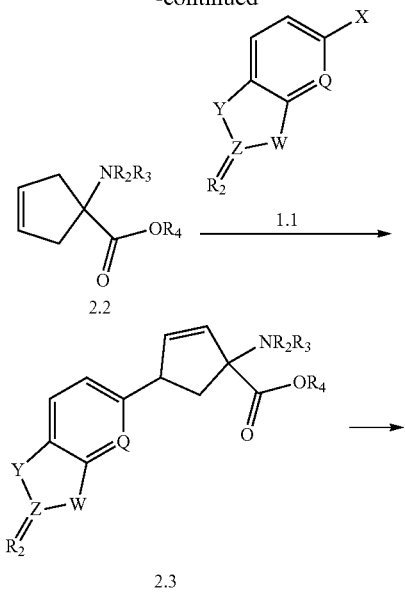
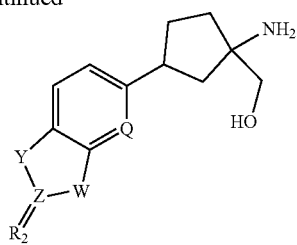
I
Alternatively, I can be obtained from 2.3 through reduction of the olefin and carbonyl. 2.3 can be prepared through the transition-metal mediated coupling of 1.1 and 2.2, with 2.2 coming from the coupling of 2.1 and 1,4-dichlorobut-2-ene under basic conditions.
SCHEME 3
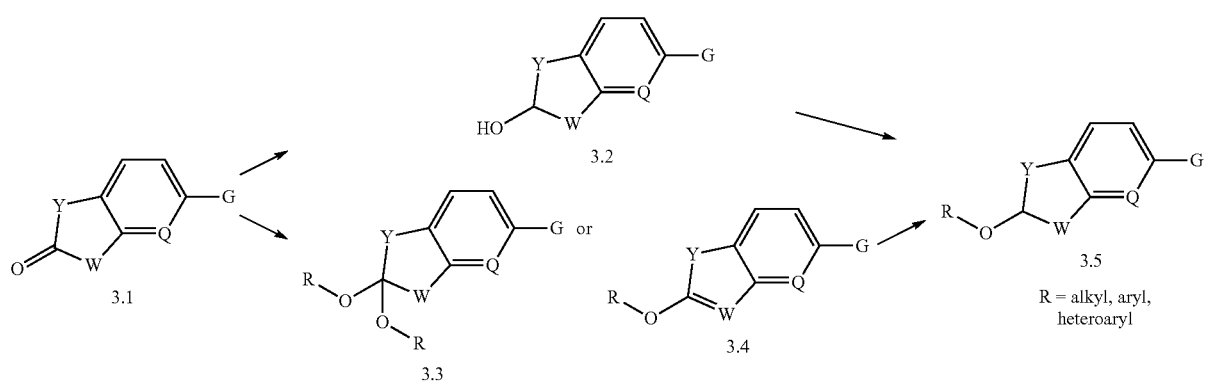
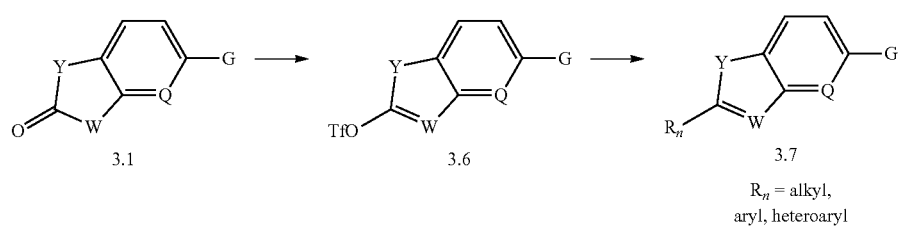

Compounds of formula I can be prepared from carbonyl compounds 3.1 as shown in Scheme 3 by reduction to alcohols 3.2 followed by alkylation to afford ethers 3.5. Alternatively, condensation of 3.1 with alcohols affords ketals 3.3 or enol ethers 3.4, either of which can be reacted under reducing conditions (such as palladium catalyzed hydrogenation) to provide ethers 3.5. Conversion of 3.1 to enol triflate 3.6 can be followed by metal-mediated coupling to afford alkyl, aryl, or heteroaryl derivatives 3.7.

ylic esters 5.2, hydrolysis under acidic or basic conditions to provide acid 5.3, conversion to acid chloride 5.4, followed by cationic cyclization in the presence of a terminal olefin affords ketones 5.3 which can be further modified as described above in Schemes 3 and 4 to for example compounds 5.6. 5.1 can also be coupled with olefins 5.9 under palladium catalysis to afford 5.10, which can undergo reduction of the alkene and then cyclization under acidic condi-

SCHEME 4

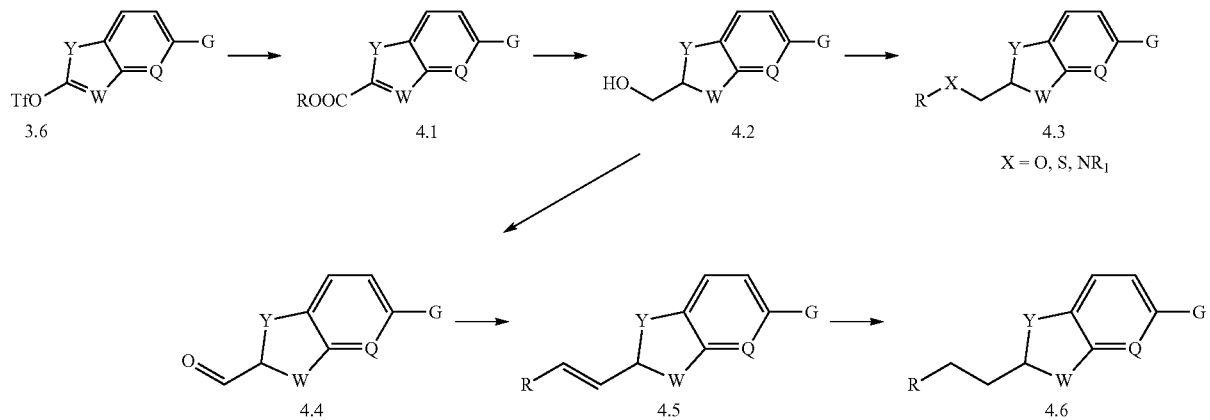

Enol triflate 3.6 can also be converted to carbonyl ester derivatives 4.1 which can be further reduced to alcohols 4.2. Alkylation of 4.2 can provide ethers 4.3 while conversion of the alcohol to a leaving group (e.g. halogen or tosylate) followed by displacement with a nucleophile can lead to 4.3 as ether, amine or thioether derivatives. Oxidation of 4.2 followed by olefination leads to 4.5 which can be further reduced to 4.6.

tions (such as PPA or $H_2SO_4$) to give bicyclic 5.12. Reduction of the ketone of 5.12 affords 5.13.

EXAMPLES

The invention is further defined in the following Examples. It should be understood that the Examples are given by way of illustration only. From the above discussion

SCHEME 5

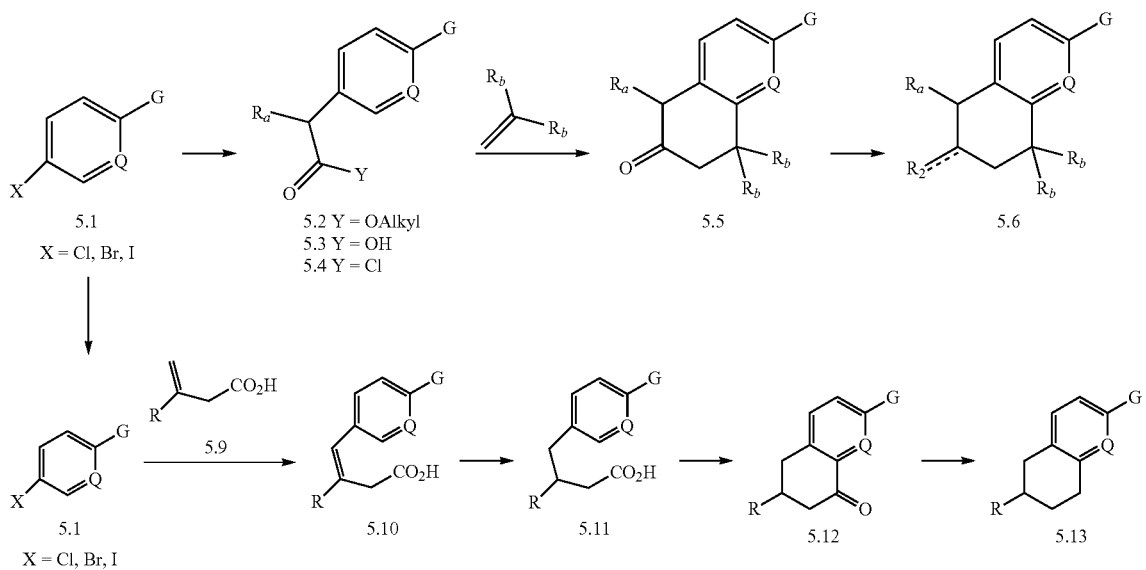

Preparation of bicyclic frameworks useful for the invention are outlined in Scheme 5. Elaboration of 5.1 to carboxand the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

Ac acetyl
AcOH acetic acid
anhyd. anhydrous
aq. aqueous
$BH_3 \cdot DMS$ borane-dimethyl sulfide
$BF_3 \cdot Et_2O$ boron trifluoride diethyl etherate
Bn benzyl
$BOC_2O$ di-tert-butyl dicarbonate
Bu butyl
Boc tert-butoxycarbonyl
CV Column Volumes
DCE dichloroethane
DCM dichloromethane
DEA diethylamine
DIEA diisopropylethylamine
DMA N,N-dimethylacetamide
DMF dimethylformamide
DMPU 1,3-dimethyl-3,4,5,6-tetrahydro-2(1H)-pyrimidinone
DMSO dimethylsulfoxide
EtOAc ethyl acetate
Et ethyl
$Et_3N$ triethyl amine
EtOH ethanol
H or $H_2$ hydrogen
h, hr or hrs hour(s)
hex or Hex hexane
i iso
IPA isopropyl alcohol
HOAc acetic acid
HCl hydrochloric acid
HPLC high pressure liquid chromatography
i-PrOH isopropanol
KHMDS potassium bis(trimethylsilyl) amide
LC liquid chromatography
LCMS liquid chromatography mass spectroscopy
LDA lithium diisopropylamine
LiHMDS lithium bis(trimethylsilyl) amide
m-CPBA meta-chloroperoxybenzoic acid
M molar
mM millimolar
Me methyl
MeCN acetonitrile
MeI methyl iodide
MeOH methanol
MHz megahertz
min. minute(s)
mins minute(s)
$M^{+1}$ $(M+H)^+$
MS mass spectrometry
n or N normal
NIS N-Iodosuccinimide
nm nanometer
nM nanomolar
NMO N-methylmorpholine-N-oxide
NMP N-methylpyrrolidine
Pd/C palladium on carbon
$Pd(OAc)_2$ palladium acetate
$Pd(PPh_3)_4$ tetrakis(triphenylphosphine)palladium
$Pd_2(dba)_3$ tris-(dibenzylideneacetone)dipalladium
Ph phenyl
PPA polyphosphoric acid
PPC pyrophosphoryl chloride
$PPh_3$ triphenylphosphine
Pr propyl
PSI pounds per square inch
Ret Time or Rt retention time
sat. saturated
S-BINAP S)-(−)-2,2'-bis(diphenylphosphino)-1,1'-binaphthyl
SFC supercritical fluid chromatography
t-BuOH tertiary butanol
TFA trifluoroacetic acid
THF tetrahydrofuran
Analytical HPLC Conditions:
Condition A: Column: Waters Acquity UPLC BEH C18, 2.1×50 mm, 1.7-μm particles;
Mobile Phase A: 5:95 acetonitrile:water with 0.05% TFA;
Mobile Phase B: 95:5 acetonitrile:water with 0.05% TFA;
Temperature: 50° C.; Gradient: 0-100% B over 3 minutes, then a 0.75-minute hold at 100% B; Flow: 1.11 mL/min.
Condition B: Column: 1-Waters C18 2.1×30 mm 3.5 um (4 min.); Solvent A=10% MeOH, 90% $H_2O$, 0.1% TFA; Solvent B=90% MeOH, 10% $H_2O$, 0.1% TFA.
Condition C: Column: YMC CombiScreen S5 50×4.6 mm (4 min; Solvent A=Water 90%/MeOH 10%/$H_3PO_4$, 0.2%; Solvent B=MeOH 90%/water 10%/$H_3PO_4$ 0.2%.
Condition G: Column: Waters Acquity BEH C18 2.1×50 mm 1.7 um; Linear gradient of 0-100% solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50 OC; Products detected at 220 nm wavelength w/positive ionization mode.
Condition H: Column: Sunfire C18, (150×3.0 mm), 3.5 μm; Linear gradient of 10 to 100% solvent B over 25 min, then 5 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: Buffer: acetonitrile (5:95); Products detected at 220 nm.
Condition I: Column: Xbridge Phenyl, (150×3.0 mm), 3.5 m; Linear gradient of 10 to 100% solvent B over 25 min, then 5 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: Buffer: acetonitrile (5:95); Products detected at 220 nm.
Condition J: Column: Chromolith SpeedROD (4.6×50 mm); Linear gradient of 0 to 100% solvent B over 4 min, with 1 min hold at 100% B; Solvent A: 10% MeOH, 90% $H_2O$, 0.1% TFA; Solvent B: 90% MeOH, 10% $H_2O$, 0.1% TFA; Flow rate: 4 mL/min; Products detected at 220 nm.
Condition K: Column: YMC ProC18 S5 ODS (50×4.6 mm); Linear gradient of 0 to 100% solvent B over 4 min, with 1 min hold at 100% B Solvent A: 10% MeOH-90% $H_2O$-0.2% $H_3PO_4$; Solvent B: 90% MeOH-10% $H_2O$-0.2% $H_3PO_4$; Flow rate: 4 mL/min; Products detected at 220 nm.
Condition L: Column: Sunfire C18 3.5 um, 3.0×150 mm; Linear gradient of 10 to 100% solvent B over 12 min, with 3 min hold at 100% B; Solvent A=0.05% TFA in $H_2O$:MeCN (95:5); Solvent B=0.05% TFA in $H_2O$:MeCN (5:95). Flow rate: 1 mL/min; Products detected at 220 nm and 256 nm.
Condition M: Waters Acquity BEH C18 2.1×50 mm 1.7 um; Linear gradient of 0-100% solvent B over 1.5 min 100% B; Flow rate: 1 mL/min; Solvent A: 10:90 acetonitrile:water with 0.1% TFA; Solvent B: 90:10 acetonitrile:water with 0.1% TFA; Temperature=40° C.; Products detected at 220 nm wavelength w/positive ionization mode.

Condition Gemini: Column: Phenomenex Gemini C18, 3 μm, 4.6×150 mm; Grad. T: 10 min; Flow R.: 1.0 mL/min.; Solvent Grad.: 30-100% B; Wave: 220 nm. (A=5% MeCN-90% H$_2$O-0.1% TFA; B=95% MeCN-5% H$_2$O-0.1% TFA).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. Compounds of the Examples are identified by the example and step in which they were prepared (e.g., "1-A" denotes the Example 1, step A), or by the example only where the compound was the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations was to further enable the preparation of the examples of this invention. In some instances some functional groups in the outlined examples and claims may be replaced by well known biosteric replacements known in the art, for example, replacement of a carboxylic acid group with a tetrazole or a phosphate moiety.

Those experiments specifying that they were performed in a microwave oven were conducted in a SmithSynthesizer™ oven manufactured by Personal Chemistry or a Discover™ microwave oven manufactured by CEM corporation. The microwave ovens generate a temperature which can be selected to be between 60-250° C. The microwave ovens automatically monitor the pressure which was between 0-300 PSI. Reaction hold times and temperature set points are reported.

INTERMEDIATE 1

(1R,3S)-methyl 1-amino-3-(4-bromophenyl)cyclopentanecarboxylate

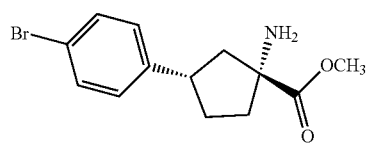

(I-1)

Intermediate 1A:
(S)-3-(4-bromophenyl)cyclopentanone

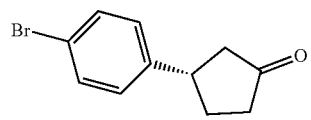

(I-1A)

A solution of 4-bromophenylboronic acid (20 g, 100 mmol) in 1,4-dioxane (120 mL) in a 500 ml flask was purged with nitrogen for 5 mins. S-BINAP (0.992 g, 1.593 mmol) and bis(norbornadiene)rhodium (I) tetrafluoroborate (0.559 g, 1.494 mmol) were added sequentially to the solution under a positive pressure of nitrogen. After 2 hours of agitation at room temperature, water (20 mL) was added followed by cyclopent-2-enone (8.06 mL, 100 mmol) and Et$_3$N (13.88 mL, 100 mmol). The mixture was allowed to stir at room temperature for 16 hours. The resulting dark solids were removed by filtration and the filtrate was poured into 250 ml of ethyl acetate. The solution was washed with water twice and the organic layer was concentrated. The residue was purified by flash column chromatography (split into two batches, each run on a 330 g silica column. 0%-25% ethyl acetate in hexane) to afford 12.1 grams of (S)-3-(4-bromophenyl) cyclopentanone. HPLC purity was >98% and Chiral HPLC analysis indicated approximately 90% ee. The material was further purified by under the Chiral SFC using the following conditions: Instrument: Berger SFC MGIII; Preparation Conditions: Column: ChiralPak AD-H 25×5 cm, 5 μm; Column Temp. 40° C.; Flow rate: 200 ml/min; Mobile Phase: CO$_2$/MeOH=80/20; Detector Wavelength: 225 nm; Analytical Conditions Injection Vol. 1.0 ml; Sample Preparation: 12.1 g in 210 mL MeOH (Conc. 60 mg/ml); Column: ChiralPak AD 25×0.46 cm, 10 μm; Column Temp. 40° C.; Flow rate: 2.0 min; Mobile Phase: CO$_2$/MeOH=70/30; Detector Wavelength: 220 nm; Injection Vol. 5 μL.

The desired enantiomer (major isomer) was isolated and named as "PK2" based on the elution order. The enantiomeric purity of the isolated isomer was determined to be greater than 99.6% on SFC/UV area % at 220 nm. After concentration, 10.5 grams of the desired enantiomer was recovered. HPLC retention time=8.19 min (condition G); LC/MS M$^{+1}$=240.08; $^1$H NMR ((400 MHz, CD3OD) δ ppm 7.43-7.51 (2H, m), 7.10-7.19 (2H, m), 3.32-3.46 (1H, m), 2.67 (1H, dd, J=18.27, 7.48 Hz), 2.39-2.54 (2H, m), 2.23-2.39 (2H, m), 1.97 (1H, ddd, J=12.98, 11.00, 9.02 Hz).

Intermediate 1B: (7S)-7-(4-bromophenyl)-1,3-diaz-aspiro[4.4]nonane-2,4-dione

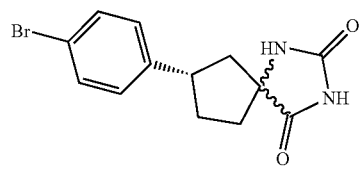

(I-1B)

A total of 9.8 g (S)-3-(4-bromophenyl)cyclopentanone was used, divided into two batches each containing 4.9 g. The two batches were processed under identical conditions as described below.

To a mixture of (S)-3-(4-bromophenyl)cyclopentanone (4.9 g, 20.49 mmol) and potassium cyanide (1.935 g, 29.7 mmol) in EtOH (40 mL) and water (20 mL) in a glass pressure vessel was added ammonium carbonate (4.92 g, 51.2 mmol). The reaction vessel was sealed and placed in an oil bath heated at 80° C. for 24 hours, resulting in the formation of a white solid. After cooling the reaction vessel with an ice bath ice-bath, the vessel was opened and 30 ml of water was add resulting in the formation of additional solids. The solids were collected by filtration, washed twice with 5 ml water, then dried under high vacuum. The two batches were combined (total 13.9 g (7S)-7-(4-bromophenyl)-1,3-diazaspiro[4.4]nonane-2,4-dione) and the material was used without further purification for subsequent steps. HPLC retention time=0.82 min (condition G) LC/MS $M^{+1}$=331.1. $^1$H NMR (400 MHz, MeOD) δ ppm 7.43 (2H, d, J=7.7 Hz), 7.22 (2H, dd, J=8.4, 6.2 Hz), 2.31-2.43 (1H, m), 2.17 (3H, d, J=9.9 Hz), 1.79-2.06 (3H, m).

Intermediate 1C: (3S)-1-amino-3-(4-bromophenyl)cyclopentanecarboxylic acid

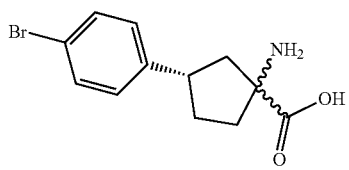

(I-1C)

To (7S)-7-(4-bromophenyl)-1,3-diazaspiro[4.4]nonane-2,4-dione (13.9 g, 45.0 mmol) in 1,4-dioxane (40 mL) in a round bottom flask was added aqueous NaOH (2N, 100 mL, 200 mmol). The mixtures were heated to 95° C. and stirred for 24 hours. Additional NaOH (25 mL, 50 mmol) was added and heating was continued for another two days. The solution was cooled with an ice-bath, neutralized with 5N HCl to approximately pH 7 resulting in the formation of a white precipitate. The solids were collected by filtration and dried under high vacuum for 2 days to provide 14 g of (3S)-1-amino-3-(4-bromophenyl)cyclopentanecarboxylic acid as white solid. The material was used directly in the subsequent step without further purification. HPLC retention time=0.64 min (condition G) LC/MS $M^{+1}$=284.1/286.1.

Intermediate 1D: (3S)-methyl 1-amino-3-(4-bromophenyl)cyclopentanecarboxylate

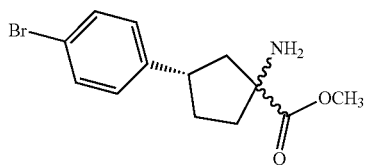

(I-1D)

To a heterogeneous mixture of (3S)-1-amino-3-(4-bromophenyl) cyclopentanecarboxylic acid (14 g, 49.3 mmol) in MeOH (250 mL) was added thionyl chloride (36.0 mL, 493 mmol) dropwise over a period of 20 min. at room temperature via an additional funnel (exothermic). The reaction mixture was placed in an oil bath set to 70° C. for 4 hours. The solvent was removed under vacuum, with the residue being dissolved in ethyl acetate (200 mL) and washed twice with 1N NaOH. The organic layer was then dried over $Na_2SO_4$ and concentrated to give 10.8 g of (3S)-methyl 1-amino-3-(4-bromophenyl)cyclopentanecarboxylate.
HPLC retention time=0.68 min (condition G); LC/MS $M^{+1}$=298/300.

Intermediate 1: (1R,3S)-methyl 1-amino-3-(4-bromophenyl)cyclopentanecarboxylate

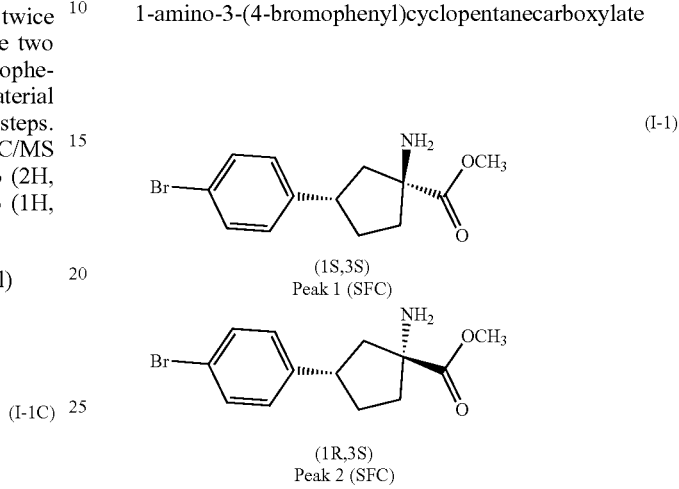

The mixture of diastereomers (I-1D, 9.5 g) was separated by Chiral SFC. The absolute stereochemical assignment of Intermediate 1 and its diastereomer was previously described (Wallace, G. A. et al. *J. Org. Chem.* 2009, 74, 4886-4889). Experimental Details: Instrument: Preparative: Thar SFC350; Analytical: Berger analytical SFC; Preparative Conditions: Column: Lux-Cellulose-4 25×3 cm, 5 μm; Column Temperature: 35° C.; Flow rate: 200 ml/min; Mobile Phase: $CO_2$/(MeOH with 0.1% DEA)=87/13; Detector Wavelength: 220 nm; Injection Vol.: 0.6 ml; Sample Preparation: 9.5 g in 400 ml MeOH (Conc. 23.7 mg/ml). Analytical Conditions: Column: Lux-Cellulose-4 25×0.46 cm, 5 μm; Column Temp. 35° C.; Flow rate: 3 ml/min; Mobile Phase: $CO_2$/(MeOH with 0.1% DEA)=85/15; Detector Wavelength: 220 nm; Injection Vol.: 5 μL. Intermediate 1 was Peak 2: 4.06 g; ret. time=6.64 min on the analytical chiral SFC conditions above. Optical purity: 98.2%; LC/MS $M^{+1}$=298/300; Peak 1: 3.96 g; ret. time=5.47 min on the analytical chiral SFC conditions above. Optical purity: 99.4%. $^1$H NMR (400 MHz, DMSO-$d_6$) δ 8.89 (br. s., 2H), 7.51 (d, J=8.1 Hz, 2H), 7.34 (d, J=8.4 Hz, 2H), 3.80 (s, 3H), 2.59 (dd, J=13.6, 7.5 Hz, 2H), 2.30-1.94 (m, 5H). Peak 1: 3.96 g; ret. time=5.47 min on the analytical chiral SFC conditions above. Optical purity: 99.4%.
Alternative Preparation: HCl Salt of Intermediate 1

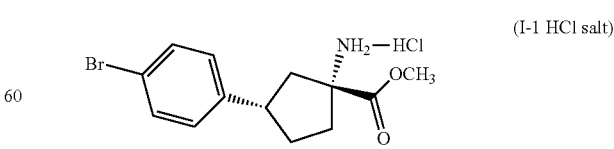

(I-1 HCl salt)

A solution of (3S)-1-amino-3-(4-bromophenyl)cyclopentanecarboxylic acid (10.2 g, 35.9 mmol) in MeOH (100 mL) was cooled in an ice bath, followed by addition of $SOCl_2$ (15.72 mL, 215 mmol) dropwise. After the addition was complete, the solution was refluxed for 3 hrs at which time the reaction was determined to be complete by EA-HPLC. The solution was concentrated to remove the methanol to afford a solid. The solid was taken in 50 ml of 3% $H_2O$ in EtOAc and stirred well for 30 mins. The white solid formed was collected by filtration and the wet white solid was taken in 50 ml of 4% $H_2O$ in 1,2-dimethoxyethane and heated to 50° C. for 3 hrs, then stirred at room temperature overnight. The resulting white solid was collected by filtration and dried to afford product (1R,3S)-methyl 1-amino-3-(4-bromophenyl)cyclopentanecarboxylate hydrochloride (3.5 g, 10.35 mmol). HPLC retention time=6.6 min (condition H) LC/MS $M^{+1}$=298/300. $^1$H NMR (400 MHz, DMSO-$d_6$) δ 8.95 (br. s, 3H) 7.50-7.53 (m, 2H), 7.35-7.37 (m, 2H), 3.81 (s, 3H) 3.17-3.28 (m, 1H), 2.57 (dd, J=14, 7 Hz, 1H), 2.0-2.28 (m, 5H).

INTERMEDIATE 2

(1R,3R)-methyl 1-amino-3-(4-bromophenyl)cyclopentanecarboxylate

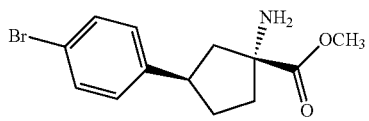

(I-2)

Intermediate 2A: (R)-3-(4-bromophenyl)cyclopentanone

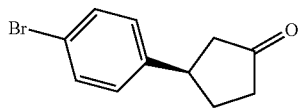

(2A)

A solution of 4-bromophenylboronic acid (20 g, 100 mmol) in 1,4-dioxane (120 mL) was purged with nitrogen for 10 min. (R)-BINAP (0.992 g, 1.593 mmol) and bis(norbornadiene)rhodium (I) tetrafluoroborate (0.559 g, 1.494 mmol) were added sequentially, and the suspension was sonicated for 5 min. The mixture was stirred for 20 min. Water (20 mL) was added, and the reaction mixture became homogeneous. After 10 minutes, cyclopent-2-enone (8.06 mL, 100 mmol) was added, and the reaction mixture was stirred at room temperature overnight. HPLC and LCMS analysis indicated that the reaction had proceeded, but there was more starting material than product. The reaction mixture was filtered through a pad of Celite, and the Celite was washed with ethyl acetate (100 mL). The filtrate was diluted with an additional ethyl acetate (150 mL), washed with water (2×), washed with brine, and dried over anhydrous sodium sulfate. The product mixture was purified by flash silica gel chromatography using a mixture of ethyl acetate and hexane to give (R)-3-(4-bromophenyl)cyclopentanone (6.09 g, 25.5 mmol) as a white solid. The product was 98% pure by HPLC with a ret. time=2.11 min. (Condition J). LC/MS $M^{+1}$=241. $^1$H NMR (400 MHz, CHLOROFORM-d) δ 7.57-7.39 (m, 2H), 7.22-7.06 (m, 2H), 3.39 (ddd, J=10.9, 6.8, 4.1 Hz, 1H), 2.67 (dd, J=18.2, 7.4 Hz, 1H), 2.57-2.38 (m, 2H), 2.38-2.21 (m, 2H), 1.99-1.85 (m, 1H).

Chiral HPLC indicated that the compound was 90-95% enantiomerically pure. The compound (6.03 g) was further purified by Chiral SFC using the conditions listed below. The desired enantiomer was isolated and named as "PK1" in the elution order. The enantiomeric purity of the isolated isomer was determined to be greater than 99.9% on SFC/UV area % at 220 nm. The desired enantiomer (5.45 g) was recovered after concentration. Experimental Details: Instrument: Berger SFC MGIII; Prep. Conditions; Column: ChiralPak AD-H 25×3 cm, 5 μm; Column Temperature: 40° C.; Flow rate: 180 ml/min; Mobile Phase: $CO_2$/MeOH=87/13; Detector Wavelength: 225 nm; Injection Vol.: 0.5 ml; Sample Preparation: 6.03 g in 100 mL MeOH (Conc. 60 mg/ml). Analytical Conditions: Column: ChiralPak AD 25×0.46 cm, 10 μm; Column Temperature: 40° C.; Flow rate: 2.0 min; Mobile Phase: $CO_2$/MeOH=70/30; Detector Wavelength: 220 nm; Injection Vol.: 5 μL.

Intermediate 2B: (7R)-7-(4-bromophenyl)-1,3-diazaspiro[4.4]nonane-2,4-dione

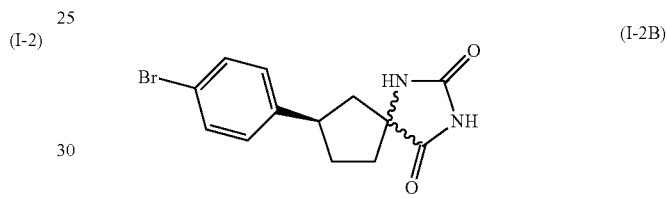

(I-2B)

To a mixture of (R)-3-(4-bromophenyl)cyclopentanone (5.4 g, 22.58 mmol) and potassium cyanide (2.132 g, 32.7 mmol) in EtOH (40 mL) and water (20 mL) in a glass pressure vessel was added ammonium carbonate (5.42 g, 56.5 mmol). The reaction vessel was sealed and placed in an oil bath heated at 80° C. for 20 hours. A large amount of white, free flowing solid formed in the pale yellow solution. Analysis by LCMS indicated remaining starting material so the reaction was continued for an additional 24 hours. As conversion was incomplete, the temperature of the oil bath was raised to 120° C. The white solid completely dissolved at the higher temperature. After 3 hours the solution was cooled down to room temperature. The solution was further cooled in an ice bath, water (30 mL) was added and the resulting white solid was collected by filtration, washed with water, air dried, then placed under high vacuum to afford the target compound (6.9 g, 22.32 mmol) which was used for subsequent reaction without additional purification. HPLC retention time=0.81 min (condition G); LC/MS $M^{+1}$=309/311; $2M^{+H}$=619.

Intermediate 2C: (3R)-1-amino-3-(4-bromophenyl)cyclopentanecarboxylic acid

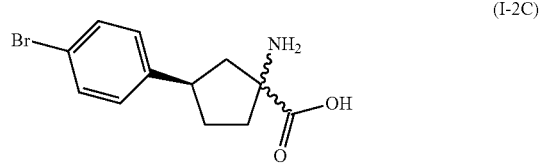

(I-2C)

A solution of (7R)-7-(4-bromophenyl)-1,3-diazaspiro[4.4]nonane-2,4-dione (6.80 g, 22 mmol) in dioxane (20 mL) and NaOH (2N aq) (120 mL, 240 mmol) was heated in an oil bath set to 95° C. The resulting clear, pale yellow solution was left to stir over the weekend. The solution was cooled in an ice bath and neutralized to approximately pH 7 with 6 N HCl resulting in the formation of a precipitate. The solids were collected and left to air dry overnight. The white solid was slurried in hot ethanol (~100 mL) and re-collected by filtration and the solid was air-dried then placed under high vacuum. (5.8 g, 20.41 mmol). HPLC retention time=0.64 min (condition G); LC/MS $M^{+1}$=284/286. $^1$H NMR (500 MHz, METHANOL-$d_4$) δ 7.52-7.38 (m, 2H), 7.31-7.17 (m, 2H), 3.55-3.40 (m, 1H), 2.68 (dd, J=13.3, 6.7 Hz, 1H from single diastereomer), 2.58-2.39 (m, 1H), 2.26-2.15 (m, 1H), 2.10-1.98 (m, 1H), 1.98-1.81 (m, 1H), 1.70 (dd, J=13.2, 11.8 Hz, 1H from single diastereomer).

Intermediate 2D: (3R)-methyl 1-amino-3-(4-bromophenyl)cyclopentanecarboxylate

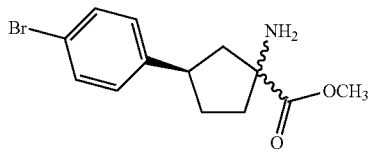

(I-2D)

In a 500 mL round bottom flask containing a stir bar, (3R)-1-amino-3-(4-bromophenyl) cyclopentanecarboxylic acid (5.4 g, 19.00 mmol) was suspended in methanol (100 mL) to afford a white slurry. A dropping funnel was charged with thionyl chloride (13.87 mL, 190 mmol) and the reagent was added dropwise at a rate to keep the mixture from reaching reflux temperature. After the addition was complete, the pale yellow, milky solution was placed in an oil bath set to 70° C. and an air-cooled reflux condenser was attached. The solution was heated for several hours and then allowed to cool to room temperature overnight. The solvent was evaporated under vacuum. The residue was dissolved in ethyl acetate, washed with 1N NaOH (aq), washed with water, then dried over MgSO$_4$ before being filtered and concentrated. The resulting yellow solid was slurried in warm ethyl acetate, with sonication and then filtered. The solid was air-dried and placed under vacuum and the filtrate was evaporated to afford Solid 1: white solid, 4.28 g LCMS shows >98% AP. The filtrate was evaporated to afford a yellow solid (1.89 g). The solid from the filtrate was slurried in a minimal amount of hot ethyl acetate, with sonication, then cooled (ice bath) and filtered cold. The solid was air-dried and placed under vacuum to afford Solid 2: 1.44 g white solid. Combined solids (5.7 g).

Intermediate 2: (1R,3R)-methyl 1-amino-3-(4-bromophenyl)cyclopentanecarboxylate

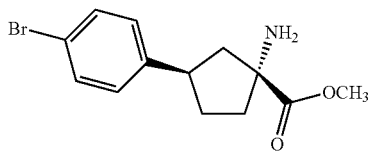

(I-2)

(1R,3R)
Peak 1 (SFC)

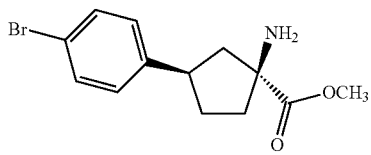

(1S,3R)
Peak 2 (SFC)

The combined solids of (3R)-methyl 1-amino-3-(4-bromophenyl) cyclopentanecarboxylate (4 g) were separated using Chiral SFC separation of the diastereomers. The absolute stereochemical assignment of Intermediate 2 and its diastereomer has been previously described (Wallace, G. A. et al. *J. Organic Chem.* 2009, 74, 4886-4889). Experimental Details: Instrument: Preparative: Thar SFC350; Analytical: Thar analytical MDS. Preparative Conditions: Column: ChiralPak AD-H 25×5 cm, 5 μm; Column Temperature: 35° C.; Flow rate: 300 ml/min; Mobile Phase: CO$_2$/(MeOH with 0.1% DEA)=82/18; Detector Wavelength: 230 nm; Injection Vol.: 0.4-0.5 ml; Sample Preparation: 4 g in 120 ml MeOH (Conc. 33 mg/ml). Analytical Conditions: Column: ChiralPak AD-H 25×0.46 cm, 5 μm; Column Temperature: 35° C.; Flow rate: 3 ml/min; Mobile Phase: CO$_2$/(MeOH with 0.1% DEA)=80/20; Detector Wavelength: 222 nm; Injection Vol.: 5 μL. Intermediate 2 was Peak 1: 1.56 g (99.3% optical purity at 222 nm) Ret. Time=7.18 min on analytical chiral SFC. $^1$H NMR (500 MHz, METHANOL-$d_4$) δ 7.45-7.39 (m, 2H), 7.23-7.17 (m, 2H), 3.78 (s, 3H), 3.40-3.48 (m, 1H), 2.40 (ddd, J=13.0, 8.9, 3.6 Hz, 1H), 2.28-2.21 (m, 1H), 2.18 (dd, J=13.0, 11.7 Hz, 1H), 2.04 (dd, J=13.0, 7.2 Hz, 1H), 1.88-1.79 (m, 1H), 1.79-1.70 (m, 1H). Peak 2: 1.8 g (97.2% optical purity at 222 nm). Ret. Time=7.71 min on analytical chiral SFC. $^1$H NMR (500 MHz, METHANOL-$d_4$) δ 7.45-7.38 (m, 2H), 7.26-7.20 (m, 2H), 3.78 (s, 3H), 3.28-3.20 (m, 1H), 2.66-2.57 (m, 1H), 2.25 (ddd, J=12.8, 11.0, 7.2 Hz, 1H), 2.10 (dt, J=12.2, 6.8 Hz, 1H), 2.03-1.93 (m, 1H), 1.84 (ddd, J=13.0, 7.8, 2.2 Hz, 1H), 1.65 (dd, J=13.3, 11.1 Hz, 1H).

INTERMEDIATES 3-I AND 3-II (1R,3S)-methyl 1-amino-3-(4-iodophenyl)cyclopentanecarboxylate hydrochloride (I-3I) and (1R,3R)-methyl 1-amino-3-(4-iodophenyl)cyclopentanecarboxylate hydrochloride

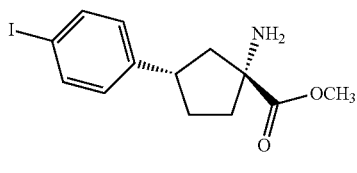

(1R,3S)

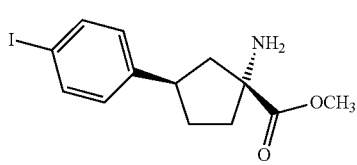

(1R,3R)

Intermediate 3A: 3-(4-iodophenyl)cyclopentanone

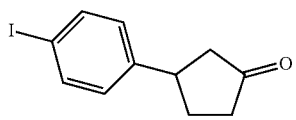

To a solution of cyclopent-2-enone (3.39 g, 0.0407 mol), sodium acetate (6.659 g, 0.0813 mol) and (4-iodophenyl) boronic acid (10 g, 0.0407 mol) in acetic acid (325 mL) was added palladium (II) acetate (0.9728 g, 0.00406 mol) and antimony (III) chloride (0.9279 g, 0.00406 mol) under a nitrogen atmosphere. After being stirred for 2 hours at 25° C., the black precipitation was filtered off and the filtrate was diluted with brine and then extracted twice with dichloromethane. The organic extraction was stirred with saturated sodium bicarbonate for 30 minutes, then washed with brine and dried over sodium sulfate. Removal of the solvent resulted in a yellow oil. Further purification (flash column, chloroform eluent) gave a 6.5 g of 3-(4-iodophenyl)cyclopentanone as a white solid.

Step B: Methyl 1-amino-3-(4-iodophenyl)cyclopentanecarboxylate

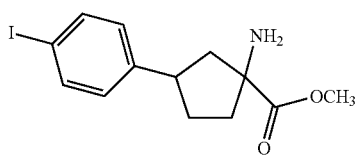 [SMILES: COC(=O)C1(N)CCC(c2ccc(I)cc2)C1]

To a solution of 3-(4-iodophenyl)cyclopentanone (10 g, 0.03496 mol) in methanolic ammonia (7 M, 105 mL) was added sodium cyanide (3.42 g, 0.06993 mmol) and ammonium chloride (3.74 g, 0.06993 mmol). The mixture was allowed to stir at room temperature for 72 hours. Aqueous sodium bicarbonate was added and the reaction mixture was extracted with ethyl acetate. The organic layer was evaporated over sodium sulfate in the presence of vacuum distillation and the obtained crude compound was used as such for the subsequent reaction. The crude mixture of 1-amino-3-(4-iodophenyl) cyclopentanecarbonitrile was dissolved in concentrated hydrochloric acid and refluxed at 70° C. overnight. The reaction mixture was distilled and then co-distilled with water. Acetone was added to the reaction, which was stirred for 30 minutes and the resulting solids (7 g) were filtered off. The solids were used directly in the subsequent step. The solids were dissolved in methanol (140 mL) and thionyl chloride (19.9 g, 0.169184 mol) was added under nitrogen, in the presence of ice water bath cooling. The reaction mixture was then allowed to stir at 70° C. overnight. The methanol was removed by distillation and aqueous sodium bicarbonate was added. The solution was extracted with ethyl acetate. The solution was dried over sodium sulfate and concentrated to provide the product (4.5 g) as a brown oil.

Step C: Intermediates 3I and 3II

Methyl 1-amino-3-(4-iodophenyl)cyclopentanecarboxylate) (approximately 5 g) was purified by Chiral SFC under the conditions described below. The four isomers were isolated and named "Pk1", "Pk2", and "Pk3" and "Pk4" in the elution order. The diastereoisomeric purity of each isolate isomer was determined on the SFC/UV/area % at 220 nm and summarized below. The methanol was evaporated to give the four individual isomers as reddish brown oils. Based on the proton NMR data, Peaks 1 and 4 were enantiomeric and Peaks 2 and 3 were enantiomeric. Absolute configuration was established through correlation to Intermediate 1A and Intermediate 1B after conversion to common products. Instrument: Berger SFC MGIII. Preparative Conditions: Column: ChiralPak AD-H 25×5 cm, 5 μm; Column Temp. 35° C.; Flow rate: 135 mL/min; Mobile Phase: CO$_2$/(MeOH+0.5% DEA)=65/35; Injection Vol. 0.7 mL; Detector Wavelength 220 nm. Sample Conc. (mg/mL) 30 mg/mL.

Diastereoisomeric Purity (Area %) of Each Isomer

|  | Pk1 | Pk2 | Pk3 | Pk4 |
|---|---|---|---|---|
| Diastereoisomeric purity (Area %) | 97.5% | 96.3% | 95.6% | 95.6% |
| Weight | 1.178 g | 1.372 g | 1.312 g | 1.216 g |

Intermediate 3I (Pk1): HPLC retention time=10.62 min (condition I); LC/MS M$^+$=346.0. $^1$H NMR (400 MHz, METHANOL-d$_4$) δ 7.71-7.55 (m, J=8.1 Hz, 2H), 7.16-7.02 (m, J=8.1 Hz, 2H), 3.76 (s, 3H), 3.28-3.10 (m, 1H), 2.61 (dd, J=13.2, 7.9 Hz, 1H), 2.31-2.19 (m, 1H), 2.15-2.05 (m, 1H), 2.03-1.91 (m, 1H), 1.88-1.79 (m, 1H), 1.64 (dd, J=13.1, 11.3 Hz, 1H).

Intermediate 3II (Pk3): HPLC retention time=10.64 min (condition I); LC/MS M$^+$=346.0. $^1$H NMR (400 MHz, METHANOL-d$_4$) δ 7.71-7.56 (m, J=8.4 Hz, 2H), 7.18-7.01 (m, J=8.1 Hz, 2H), 3.75 (s, 3H), 3.49-3.36 (m, 1H), 2.40 (ddd, J=12.7, 8.8, 3.4 Hz, 1H), 2.29-2.13 (m, 2H), 2.10-1.99 (m, 1H), 1.90-1.69 (m, 2H).

INTERMEDIATE 4

(5R,7S)-7-(4-bromophenyl)-3-oxa-1-azaspiro[4.4]nonan-2-one

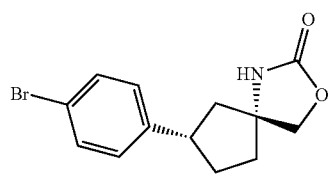
(I-4)

Intermediate 4A: ((1R,3S)-1-amino-3-(4-bromophenyl)cyclopentyl)methanol

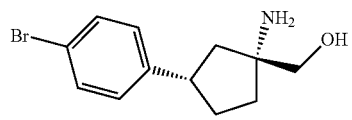
(I-4A)

To a mixture of (1R,3S)-methyl 1-amino-3-(4-bromophenyl) cyclopentanecarboxylate, HCl (15 g, 44.8 mmol) in MeOH (100 mL) at 0° C. was added sodium borohydride (4 g, 106 mmol) portionwise. The reaction mixture was warmed to room temperature and sodium borohydride was added portionwise until the reaction was determined to be complete by HPLC analysis. Water was added to quench the reaction. The reaction mixture was diluted with ethyl acetate and washed with saturated NaCl. The aqueous layer was back extracted several times. The combined organic layers were dried with MgSO$_4$, filtered and concentrated. The product (11 g) was recovered after concentration. HPLC retention time=0.65 min (condition G); LC/MS M$^{+1}$=272: $^1$H NMR (400 MHz, DMSO-d$_6$) δ 7.51-7.40 (m, 2H), 7.27 (d, J=8.4 Hz, 2H), 3.32-3.20 (m, 2H), 3.09-2.92 (m, 1H), 2.11 (dd, J=12.9, 8.7 Hz, 1H), 1.98-1.87 (m, 1H), 1.80 (qd, J=11.1, 7.9 Hz, 1H), 1.69-1.58 (m, 1H), 1.48 (ddd, J=12.4, 7.9, 2.2 Hz, 1H), 1.32 (dd, J=12.8, 10.1 Hz, 1H).

Intermediate 4

To a mixture of ((1R,3S)-1-amino-3-(4-bromophenyl)cyclopentyl)methanol (11 g, 40.7 mmol) and pyridine (3.29 mL, 40.7 mmol) in dioxane (300 mL) was added 1,1'-carbonyldiimidazole (19.81 g, 122 mmol). The reaction mixture was stirred for 4 hours. The reaction mixture was diluted with ethyl acetate and washed with 1M HCl, brine and saturated NaHCO$_3$. The mixture was back extracted several times. The organic layer was dried with MgSO$_4$, filtered and concentrated to afford 10.5 g of desired product as an off-white solid. HPLC retention time=0.87 min (condition G). LC/MS M$^{+1}$=297.9; $^1$H NMR (400 MHz, CHLOROFORM-d) δ 7.45 (d, J=8.6 Hz, 2H), 7.12 (d, J=8.4 Hz, 2H), 6.42 (br. s., 1H), 4.41-4.21 (m, 2H), 3.17-2.91 (m, 1H), 2.34 (dd, J=13.3, 7.4 Hz, 1H), 2.23-2.11 (m, 2H), 2.01-1.90 (m, 2H), 1.88-1.74 (m, 1H).

INTERMEDIATE 5

(5R,7R)-7-(4-bromophenyl)-3-oxa-1-azaspiro[4.4]nonan-2-one

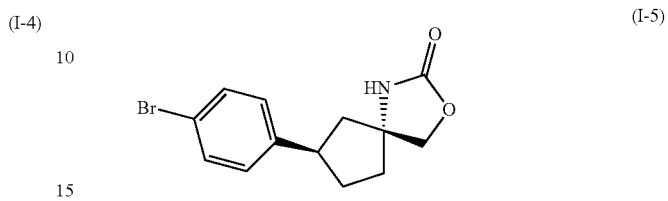
(I-5)

Intermediate 5A: ((1R,3R)-1-amino-3-(4-bromophenyl)cyclopentyl)methanol

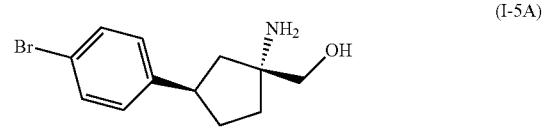 [SMILES: N[C@]1(CO)CC[C@@H](c2ccc(Br)cc2)C1]
(I-5A)

(1R,3R)-methyl 1-amino-3-(4-bromophenyl)cyclopentanecarboxylate (3.88 g, 13.01 mmol) was dissolved in MeOH (65.1 ml) and sodium borohydride (1.477 g, 39.0 mmol) was added portion wise. Additional sodium borohydride was added (0.5 equiv every 1 h) portion wise until the reaction was determined to be complete by HPLC analysis. The reaction was found to be complete after 2 hours. The reaction mixture was quenched with water and diluted with ethyl acetate. The aqueous layer was back extracted three times with EtOAc. The organic layers were combined, washed with saturated NaCl, dried over MgSO$_4$, filtered and concentrated to afford ((1R,3R)-1-amino-3-(4-bromophenyl)cyclopentyl)methanol (3.19 g, 11.81 mmol). HPLC ret time=0.68 min (cond); LC/MS M$^{+1}$=272: $^1$H NMR (400 MHz, CDCl$_3$) δ 7.42 (d, J=8.4 Hz, 2H), 7.13 (d, J=8.4 Hz, 2H), 3.49 (s, 2H), 3.32-3.41 (m, 1H), 2.19-2.25 (m, 1H), 1.98-2.07 (m, 1H), 1.90-1.95 (m, 1H), 1.66-1.74 (m, 2H), 1.52-1.60 (m, 1H).

Intermediate 5

((1R,3R)-1-amino-3-(4-bromophenyl)cyclopentyl)methanol (3.19 g, 11.81 mmol) was dissolved in THF (59.0 ml). Pyridine (0.955 ml, 11.81 mmol) and 1,1'-carbonyldiimidazole (5.74 g, 35.4 mmol) were added portion wise. The reaction mixture was stirred for 4 h and was followed by LCMS. After completion, the mixture was diluted with EtOAc and washed with 1M HCl. The aqueous layer was back extracted twice with EtOAc. The organic layers were combined, washed with saturated NaCl, dried over MgSO$_4$, filtered and concentrated to afford (5R,7R)-7-(4-bromophenyl)-3-oxa-1-azaspiro[4.4]nonan-2-one (2.5 g, 8.44 mmol) after flash chromatography (24 g silica gel column; eluent: hexane 2 CV followed by a gradient to 100% EtOAc over 15 CV) HPLC ret time=0.91 min (cond); LC/MS M$^{+1}$=298. $^1$H NMR (400 MHz, CDCl$_3$) δ 7.46 (d, J=8.5 Hz, 2H), 7.09 (d, J=8.5 Hz, 2H), 5.72-5.81 (m, 1H), 4.35 (dd, J=13 Hz, 8 Hz, 2H), 3.19-3.24 (m, 1H), 2.38-2.44 (m, 1H), 2.15-2.26 (m, 1H), 2.11-2.14 (m, 1H), 1.99-2.05 (m, 1H), 1.79-1.85 (m, 1H), 1.65-1.72 (m, 1H).

INTERMEDIATE 6

Methyl 1-((diphenylmethylene)amino)cyclopent-3-enecarboxylate

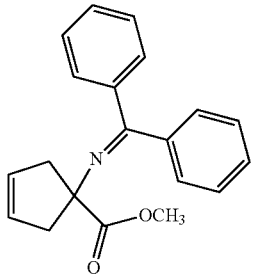

(I-6)

To a mixture of (N,N-diphenylmethylgene)glycine ethyl ester (4 g, 14.96 mmol) in THF (3 mL) at 0° C. was added lithium bis(trimethylsilyl)amide (16.46 mL, 16.46 mmol) dropwise over 30 minutes. After stirring for 30 minutes, the resulting solution was then added dropwise to cis-1,4-dichloro-2-butene (1.823 mL, 16.46 mmol) in THF (1 mL). After 1 hour, lithium bis(trimethylsilyl)amide (14.96 mL, 14.96 mmol) was added at 0° C. The mixture was stirred at room temperature for 8 hours before being quenched by saturated aqueous NH$_4$Cl solution (30 mL) and water (10 mL). The mixture was extracted with ethyl acetate (3×20 mL). The combined ethyl acetate extracts were dried (Na$_2$SO$_4$) and concentrated under reduced pressure. The crude material was filtered through a short plug of silica and purified by silica gel chromatography. HPLC retention time=5.06 min (condition H); LC/MS M$^{+1}$=320. $^1$H NMR (400 MHz, METHANOL-d$_4$) δ 7.23-7.18 (m, 2H), 7.17-7.10 (m, 2H), 3.72-3.56 (m, 2H), 3.24-3.08 (m, 1H), 2.71 (s, 3H), 2.60 (t, J=7.6 Hz, 2H), 2.44 (ddd, J=13.4, 7.1, 1.3 Hz, 1H), 2.18 (t, J=7.6 Hz, 3H), 2.03-1.89 (m, 3H), 1.75 (t, J=12.8 Hz, 1H), 1.69-1.56 (m, 4H), 1.45-1.27 (m, 2H).

INTERMEDIATE 7

(5R,7S)-7-(6-oxo-5,6,7,8-tetrahydronaphthalen-2-yl)-3-oxa-1-azaspiro[4.4]nonan-2-one

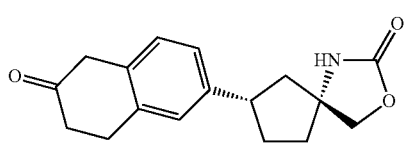

(I-7)

Intermediate 7A: tert-butyl 2-(4-((5R,7S)-2-oxo-3-oxa-1-azaspiro[4.4]nonan-7-yl) phenyl)acetate

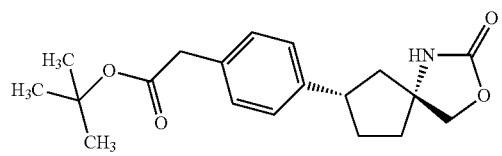

(I-7A)

To a mixture of (5R,7S)-7-(4-bromophenyl)-3-oxa-1-azaspiro[4.4]nonan-2-one (1 g, 3.38 mmol) in dioxane (10 mL) at room temperature was added lithium bis(trimethylsilyl)amide (3.71 mL, 3.71 mmol). The mixture was stirred for 30 minutes, then 1,2,3,4,5-pentaphenyl-1'-(di-t-butylphosphino)ferrocene (0.121 g, 0.169 mmol), Pd$_2$(dba)$_3$ (0.155 g, 0.169 mmol) and (2-(tert-butoxy)-2-oxoethyl)zinc (II) chloride (8.10 mL, 4.05 mmol) were added. The reaction mixture was heated at 80° C. for 2 hours, then cooled to room temperature, diluted with ethyl acetate and washed with 1M HCl. The organic layer was dried with MgSO$_4$, filtered and concentrated. The crude material was purified on a silica gel cartridge (40 g) using an EtOAc/hexane gradient (0-100% EtOAc over 20 minutes) to afford 950 mg of tert-butyl 2-(4-((5R,7S)-2-oxo-3-oxa-1-azaspiro[4.4]nonan-7-yl)phenyl)acetate. HPLC retention time=0.93 min (condition G); LC/MS M$^{+1}$=332.

Intermediate 7B: 2-(4-((5R,7S)-2-oxo-3-oxa-1-azaspiro[4.4]nonan-7-yl)phenyl)acetic acid

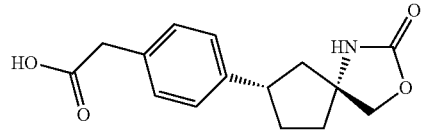

(I-7B)

To a mixture of tert-butyl 2-(4-((5R,7S)-2-oxo-3-oxa-1-azaspiro[4.4]nonan-7-yl) phenyl)acetate (1 g, 3.02 mmol) in DCM (20 mL) was added TFA (10 mL). After 2 h, the solution was concentrated in vacuo and used as such for the subsequent step without further purification. HPLC retention time=0.65 min (condition G); LC/MS M$^{+1}$=276.

Intermediate 7

To a mixture of 2-(4-((5R,7S)-2-oxo-3-oxa-1-azaspiro[4.4]nonan-7-yl)phenyl) acetic acid (800 mg, 2.91 mmol) in DCM (20 mL) was added oxalyl chloride (1 ml, 11.42 mmol) and a few drops of DMF. After one hour, the reaction mixture was concentrated in vacuo. The residue was re-dissolved in DCM (20 mL) in a glass pressure vessel. Granular aluminum chloride (1550 mg, 11.62 mmol) was added and the reaction mixture was cooled to −78° C. Ethylene was bubbled through the solution for 5 minutes and then the reaction vessel was sealed. The reaction mixture was allowed to slowly warm to room temperature and stirred for 4 hours. The mixture was poured onto ice, diluted with dichloromethane and washed with 1M HCl. The organic layer was dried with MgSO$_4$, filtered and concentrated. The crude material was purified on a silica gel cartridge (80 g) using a MeOH/DCM gradient (0-10% MeOH over 13CV). The product containing fractions were collected and dried in vacuo to afford 770 mg of (5R,7S)-7-(6-oxo-5,6,7,8-tetrahydronaphthalen-2-yl)-3-oxa-1-azaspiro[4.4]nonan-2-one. HPLC retention time=0.74 min (condition G); LC/MS $M^{+1}$=286: $^1$H NMR (400 MHz, CHLOROFORM-d) δ 7.20-7.00 (m, 3H), 5.49 (br. s., 1H), 4.45-4.25 (m, 2H), 3.59 (s, 2H), 3.08 (t, J=6.8 Hz, 3H), 2.58 (t, J=6.7 Hz, 2H), 2.38 (dd, J=13.2, 7.3 Hz, 1H), 2.27-2.11 (m, 2H), 2.05-1.92 (m, 2H), 1.92-1.74 (m, 1H).

INTERMEDIATE 8

6-((5R,7S)-2-oxo-3-oxa-1-azaspiro[4.4]nonan-7-yl)-3,4-dihydronaphthalen-2-yl trifluoromethanesulfonate

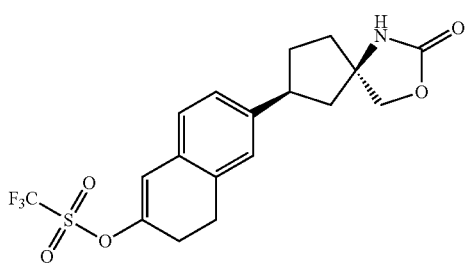

(I-8)

To a mixture of (5R,7S)-7-(6-oxo-5,6,7,8-tetrahydronaphthalen-2-yl)-3-oxa-1-azaspiro[4.4]nonan-2-one (340 mg, 1.192 mmol) and DMPU (0.431 mL, 3.57 mmol) in THF (10 mL) at −78° C. was added LDA (1.456 mL, 2.62 mmol). The reaction mixture was stirred for 30 minutes then 1,1,1-trifluoro-N-phenyl-N-(trifluoromethyl)sulfonyl methanesulfonamide (639 mg, 1.787 mmol) in THF (10 mL) was added. The reaction mixture was warmed to 0° C. After 1 hour, the reaction was quenched with water. The reaction mixture was diluted with ethyl acetate and washed with saturated aqueous NaCl. The organic layer was dried with MgSO$_4$, filtered and concentrated. The crude material was purified on a silica gel cartridge (40 g) using an EtOAc/hexane gradient (0-100% EtOAc over 20 minutes) to afford 400 mg of 6-((5R,7S)-2-oxo-3-oxa-1-azaspiro[4.4]nonan-7-yl)-3,4-dihydronaphthalen-2-yl trifluoromethanesulfonate. HPLC retention time=1.01 min (condition G); LC/MS $M^{+1}$=418. $^1$H NMR (400 MHz, CHLOROFORM-d) δ 7.17-6.95 (m, 3H), 6.74 (s, 1H), 6.48 (s, 1H), 4.48-4.20 (m, 2H), 3.17-2.95 (m, 3H), 2.81-2.60 (m, 2H), 2.33 (dd, J=13.3, 7.2 Hz, 1H), 2.24-2.08 (m, 2H), 2.05-1.74 (m, 3H).

INTERMEDIATE 9

6-((5R,7R)-2-oxo-3-oxa-1-azaspiro[4.4]nonan-7-yl)-3,4-dihydronaphthalen-2-yl trifluoromethanesulfonate

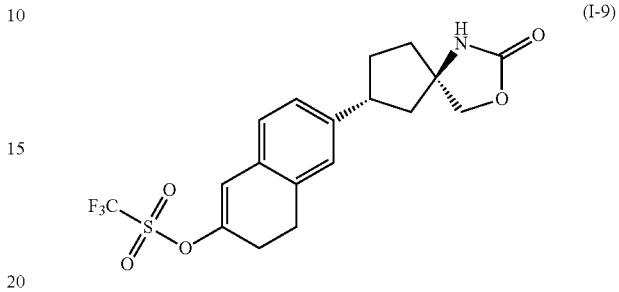

(I-9)

To a mixture of (5R,7R)-7-(6-oxo-5,6,7,8-tetrahydronaphthalen-2-yl)-3-oxa-1-azaspiro[4.4]nonan-2-one (250 mg, 0.876 mmol) and DMPU (317 μl, 2.63 mmol) in THF (10 mL) at −78° C. was added LDA (1071 μl, 1.928 mmol). The reaction mixture was stirred for 30 minutes then 1,1,1-trifluoro-N-phenyl-N-(trifluoromethyl)sulfonyl methanesulfonamide (470 mg, 1.314 mmol) in THF (4381 μl) was added. The reaction mixture was warmed to 0° C. and stirred for 1 hour. LCMS showed conversion to be complete. The reaction was quenched with water. The reaction mixture was diluted with ethyl acetate and washed with saturated NaCl. The organic layer was dried Na$_2$SO$_4$, filtered and concentrated under reduced pressure. The crude material was purified on a silica gel cartridge (80 g) using an EtOAc/Hex gradient (0-100% EtOAc over 12 CV). Product containing fractions were combined, concentrated, and dried in vacuo to afford 6-((5R,7R)-2-oxo-3-oxa-1-azaspiro[4.4]nonan-7-yl)-3,4-dihydronaphthalen-2-yl trifluoromethanesulfonate (200 mg, 0.479 mmol). HPLC retention time=1.12 min (condition G) LC/MS $M^{+1}$=418.3.

INTERMEDIATE 10

(5R,7R)-7-(6-oxo-5,6,7,8-tetrahydronaphthalen-2-yl)-3-oxa-1-azaspiro[4.4]nonan-2-one

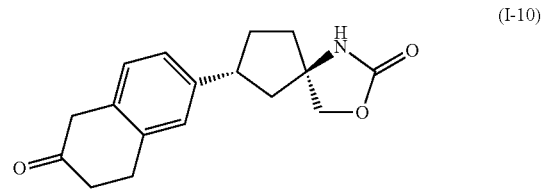 [SMILES: O=C1CCc2cc([C@@H]3CC[C@]4(COC(=O)N4)C3)ccc2C1]

(I-10)

Intermediate 10A: tert-butyl 2-(4-((5R,7R)-2-oxo-3-oxa-1-azaspiro[4.4]nonan-7-yl) phenyl)acetate

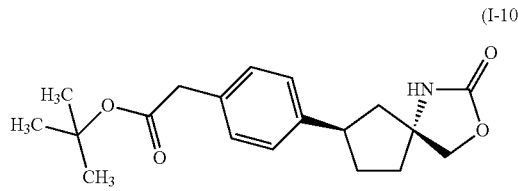

(I-10A)

To a solution of (5R,7R)-7-(4-bromophenyl)-3-oxa-1-azaspiro[4.4]nonan-2-one (Int. 4, 2.1 g, 7.09 mmol) in THF (25.3 ml) at room temperature was added LiHMDS (7.80 ml, 7.80 mmol). The solution was stirred for 15 min. Next, Pd$_2$(dba)$_3$ (0.195 g, 0.213 mmol), 1,2,3,4,5-pentaphenyl-1'-(di-t-butylphosphino)ferrocene (0.151 g, 0.213 mmol), and (2-(tert-butoxy)-2-oxoethyl)zinc(II) bromide, tetrahydrofuran (7.07 g, 21.27 mmol) were sequentially added. The slurry was stirred at 24° C. for 2 h. LCMS analysis showed complete consumption of the starting material. The reaction mixture was diluted with ethyl acetate and washed with 1M HCl. The organic layer was dried over MgSO$_4$, filtered and concentrated. The crude material was purified on a silica gel cartridge (40 g) using hexane:acetone 100:0 to 0:100 over 25 CV. Tert-butyl 2-(4-((5R,7R)-2-oxo-3-oxa-1-azaspiro[4.4]nonan-7-yl)phenyl)acetate (2.35 g, 7.09 mmol) was isolated. HPLC retention time=0.95 min (condition I): LC/MS M$^{+1}$=332: $^1$H NMR (400 MHz, CHLOROFORM-d) δ 7.27-7.21 (m, 2H), 7.21-7.15 (m, 2H), 5.11 (br. s., 1H), 4.40-4.26 (m, 2H), 3.53 (s, 2H), 3.22-3.01 (m, 1H), 2.36 (dd, J=13.2, 7.3 Hz, 1H), 2.25-2.10 (m, 2H), 2.04-1.92 (m, 2H), 1.91-1.76 (m, 1H), 1.47 (s, 9H).

Intermediate 10

The brown liquid tert-butyl 2-(4-((5R,7R)-2-oxo-3-oxa-1-azaspiro[4.4]nonan-7-yl)phenyl)acetate (2.35 g, 7.09 mmol) was dissolved in DCM (60 mL) followed by the addition of trifluoroacetic acid (20 mL, 260 mmol). The reaction mixture was stirred at room temperature for 1 h at which time the solvent was removed under reduced pressure. The resulting material was diluted in DCM (60 mL), purified by acid/base extraction and placed under vacuum for 1 h. The resulting brown gum 2-(4-((5R,7R)-2-oxo-3-oxa-1-azaspiro[4.4]nonan-7-yl)phenyl)acetic acid (1.952 g, 7.09 mmol) was dissolved in DCM (60 mL) followed by the addition of oxalyl chloride (1.862 mL, 21.27 mmol), and DMF (0.027 mL, 0.355 mmol). The resulting solution was stirred until the evolution of gas ceased (about 30 min) at room temperature. LCMS of an aliquot quenched with MeOH showed complete consumption of the acid (RT=0.65 min, Condition I) and appearance of the presumed methyl ester due to methanol quench (RT=0.77 min, condition I) as the only product. The solvent was removed under reduced pressure and the product was placed under vacuum. The brown gum was transfer to a sealed tube with DCM (60 mL) (does not completely dissolve, a brown suspension was obtained). The reaction mixture was cooled to −78° C. followed by the addition of granular aluminum chloride (2.84 g, 21.27 mmol). Ethylene was bubbled through the solution for 7 min and the tube was sealed. A precipitate formed and the reaction mixture was stirred at −78° C. for 15 min and then allowed to reach room temperature. The reaction mixture was stirred for 2 h at room temperature and then depressurized. LCMS analysis showed disappearance of starting material and appearance of the tetralone product. The reaction mixture was poured over ice, diluted with DCM and stirred until the ice melted. The organic layer was washed with brine, dried and concentrated under reduced pressure. Purification on silica gel afforded (5R,7R)-7-(6-oxo-5,6,7,8-tetrahydronaphthalen-2-yl)-3-oxa-1-azaspiro[4.4]nonan-2-one (1.05 g, 3.68 mmol). HPLC retention time=0.74 min (condition I); LC/MS M$^{+1}$=286; $^1$H NMR (400 MHz, CHLOROFORM-d) δ 7.23-7.11 (m, 3H), 5.68 (br. s., 1H), 4.45-4.30 (m, 2H), 3.59 (s, 2H), 3.31-3.18 (m, 1H), 3.08 (t, J=6.8 Hz, 2H), 2.58 (t, J=6.7 Hz, 2H), 2.42-2.39 (m, 1H), 2.32-2.15 (m, 2H), 2.09-1.99 (m, 1H), 1.91-1.83 (m, 1H), 1.82-1.72 (m, 1H).

INTERMEDIATE 12

6-bromo-2-hexyl-3,4-dihydroisoquinolin-1(2H)-one

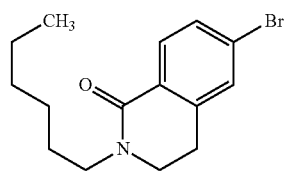

(I-12)

To a stirred cloudy solution of 6-bromo-3,4-dihydro-2H-isoquinolin-1-one (0.6 g, 2.65 mmol) and 1-iodohexane (0.783 mL, 5.31 mmol) in anhydrous tetrahydrofuran (30 mL) was added 60% mineral oil dispersion of sodium hydride (0.212 g, 5.31 mmol) portionwise over 20 min. The reaction mixture was stirred at room temperature under nitrogen for 1 h and 65° C. for 3 h. Additional sodium hydride (0.25 g) and 1-iodohexane (1 mL) were added. The mixture was stirred at 65° C. for 1 h. After anhydrous DMF (3 mL) was added at room temperature, the mixture was stirred at room temperature for 2.5 days. The reaction was quenched with saturated aqueous ammonium chloride solution (6 mL) and water (3 mL). Hexanes (20 mL) were added. The organic solution was separated and washed with water (10 mL). The combined aqueous solutions were extracted with ethyl acetate (3×5 mL). The combined organic solutions were dried over anhydrous sodium sulfate and concentrated. Flash chromatography purification (24 g silica gel column, gradient elution from 0 to 50% ethyl acetate in hexanes) afforded 6-bromo-2-hexyl-3,4-dihydroisoquinolin-1(2H)-one (667 mg, 2.150 mmol) as a yellowish solid. LC/MS M$^{+1}$=310, 312. $^1$H NMR (400 MHz, CHLOROFORM-d) δ 7.94 (d, J=8.1 Hz, 1H), 7.46 (dd, J=8.3, 1.9 Hz, 1H), 7.36-7.30 (m, 1H), 3.60-3.46 (m, 4H), 2.96 (t, J=6.6 Hz, 2H), 1.68-1.57 (m, 2H), 1.32 (br. s., 6H), 0.93-0.83 (m, 3H).

INTERMEDIATE 13

6-bromo-2-(pentyloxy)-1,2,3,4-tetrahydronaphthalene

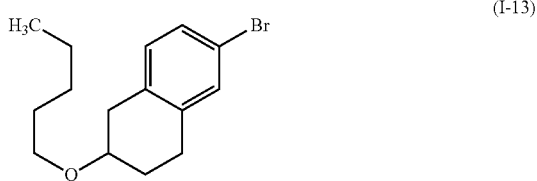 [SMILES: CCCCCOC1CCc2cc(Br)ccc2C1]
(I-13)

Step A: 6-bromo-1,2,3,4-tetrahydronaphthalen-2-ol

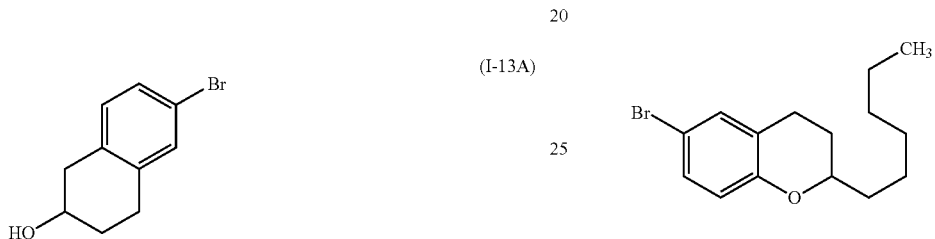
(I-13A)

To a stirred solution of 6-bromo-3,4-dihydronaphthalen-2(1H)-one (2.00 g, 8.89 mmol) in ethanol (15 mL) and dichloromethane (5 mL) was added sodium borohydride (0.336 g, 8.89 mmol) portionwise at room temperature under nitrogen. The mixture was stirred at room temperature overnight. The reaction was quenched with acetone (2 mL). After being stirred at room temperature for 1 h, the mixture was concentrated. The residue was partitioned between saturated aqueous ammonium chloride solution (5 mL), water (3 mL), and ethyl acetate (10 mL). The aqueous layer was separated and extracted with ethyl acetate (3×3 mL). The combined ethyl acetate solutions were dried (anhydrous sodium sulfate) and concentrated under reduced pressure. Flash chromatography purification (40 g silica gel column, gradient elution from 5 to 100% ethyl acetate in hexanes) afforded 6-bromo-1,2,3,4-tetrahydronaphthalen-2-ol (1.55 g, 6.83 mmol) as a liquid. LC/MS [M–H$_2$O]$^{+1}$=209, 211. Chiral SFC separation (AD-H (5×25 cm), 15% MeOH in CO$_2$, 300 ml/min, 220 nm, 35° C.) gave PK1 (560 mg) and PK2 (580 mg) as yellow liquids. Both isomers were converted to their amyl ethers as shown below.

Step B: Intermediate 13

To a stirred solution of 6-bromo-1,2,3,4-tetrahydronaphthalen-2-ol (0.58 g, 2.55 mmol) (PK2) in anhydrous tetrahydrofuran (20 mL) was added 60% mineral oil dispersion of sodium hydride (0.511 g, 12.77 mmol) portionwise. The mixture was stirred at room temperature for 15 min before n-amyl iodide (1.340 mL, 10.22 mmol) was added. The mixture was stirred at room temperature under nitrogen for two days. More 60% mineral oil dispersion of sodium hydride (0.511 g, 12.77 mmol), n-amyl iodide (1.340 mL, 10.22 mmol), and anhydrous tetrahydrofuran (20 mL) were added and the mixture was stirred at room temperature over two days. Saturated aqueous ammonium chloride solution (9 mL) was added slowly. The mixture was concentrated. The aqueous residue was extracted with ethyl acetate (4×5 mL). The combined ethyl acetate extracts were dried (anhydrous sodium sulfate) and concentrated under reduced pressure to give a liquid. Flash chromatography purification (120 g silica gel column, gradient elution from 0 to 5% ethyl acetate in hexanes) afforded 6-bromo-2-(pentyloxy)-1,2,3,4-tetrahydronaphthalene (0.61 g, 2.052 mmol) as a yellow liquid. $^1$H NMR (400 MHz, CHLOROFORM-d) δ 7.24-7.18 (m, 2H), 6.93 (d, J=7.9 Hz, 1H), 3.75-3.66 (m, 1H), 3.57-3.45 (m, 2H), 3.04-2.85 (m, 2H), 2.79-2.66 (m, 2H), 2.08-1.98 (m, 1H), 1.85-1.74 (m, 1H), 1.64-1.55 (m, 2H), 1.39-1.25 (m, 4H), 0.95-0.85 (m, 3H).

INTERMEDIATE 14

6-bromo-2-hexylchroman

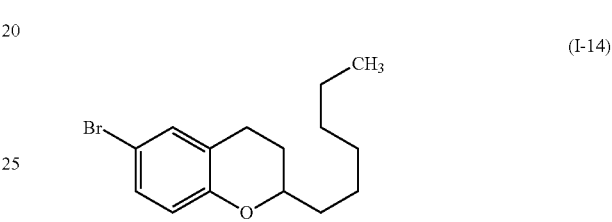
(I-14)

Step A: 6-bromo-2-hexylchroman-4-one

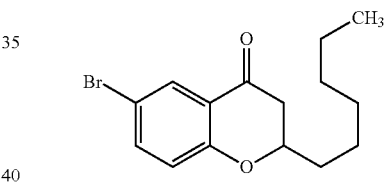

To a stirred solution of 5'-bromo-2'-hydroxyacetophenone (3.2 g, 14.88 mmol) and n-heptaldehyde (2.199 mL, 16.37 mmol) in methanol (50 mL) was added pyrrolidine (2.484 mL, 29.8 mmol) at room temperature under nitrogen. The mixture was stirred at 70° C. for 2 h and at room temperature overnight. The solvent was evaporated. Flash chromatography purification (330 g silica gel column; gradient elution from 0 to 10% ethyl acetate in hexanes) afforded 6-bromo-2-hexylchroman-4-one (3.58 g, 11.50 mmol) as a liquid.

Step B: Intermediate 14

To a stirred solution of 6-bromo-2-hexylchroman-4-one (1.8 g, 5.78 mmol) in ethanol (10 mL) was added sodium borohydride (0.109 g, 2.89 mmol). The resulting mixture was stirred at room temperature under nitrogen for 2 hr before being concentrated. The residue was mixed with saturated aqueous ammonium chloride solution (5 mL), water (3 mL), and ethyl acetate (6 mL). The aqueous layer was separated and extracted with ethyl acetate (3×3 mL). The combined ethyl acetate extracts were dried over Na$_2$SO$_4$ and concentrated under reduced pressure to give a liquid.

The liquid was mixed with triethylsilane (4.62 mL, 28.9 mmol). Trifluoroacetic acid (2.228 mL, 28.9 mmol) was added dropwise at room temperature under nitrogen. The mixture was stirred vigorously at room temperature for 2 hr before water (10 mL) was added. The aqueous layer was separated and extracted with a mixture of ethyl acetate and hexanes (1:1; 3×3 mL). The combined organic solutions were washed water and then with saturated aqueous sodium bicarbonate solution until it was basic, dried (Na$_2$SO$_4$), and concentrated under reduced pressure. Flash chromatography purification using ISCO (40 g silica gel column, 0% to 30% ethyl acetate in hexanes over 15 min) afforded 6-bromo-2-hexylchroman (1.4 g, 4.71 mmol) as a yellow liquid. $^1$H NMR (400 MHz, CHLOROFORM-d) δ 7.18-7.11 (m, 2H), 6.67 (d, J=9.2 Hz, 1H), 3.95 (dddd, J=9.8, 7.3, 5.1, 2.2 Hz, 1H), 2.85-2.66 (m, 2H), 1.97 (dddd, J=13.6, 5.9, 3.5, 2.3 Hz, 1H), 1.79-1.21 (m, 11H), 0.93-0.85 (m, 3H). Chiral SFC separation (Chiralcel OJ-H 3×250 cm, 5 um; CO$_2$/IPA=95/5; 180 mL/min; 220 nm) of the liquid afforded Isomer 1 (0.37 g) and Isomer 2 (0.4 g) as yellow liquids.

INTERMEDIATE 15 methyl 6-((5R,7S)-2-oxo-3-oxa-1-azaspiro[4.4]nonan-7-yl)-1,2,3,4-tetrahydronaphthalene-2-carboxylate

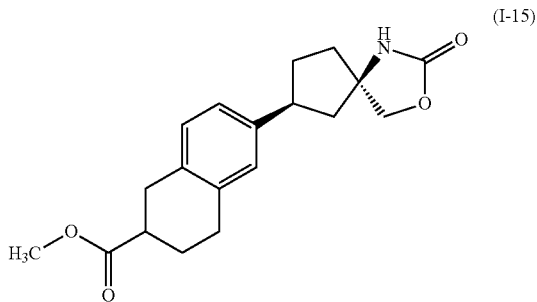 [SMILES: COC(=O)C1CCc2cc([C@H]3CC[C@]4(COC(=O)N4)C3)ccc2C1]

(I-15)

Intermediate 15A: Methyl 4-oxo-6-((5R,7S)-2-oxo-3-oxa-1-azaspiro[4.4]nonan-7-yl)-1,2,3,4-tetrahydronaphthalene-2-carboxylate

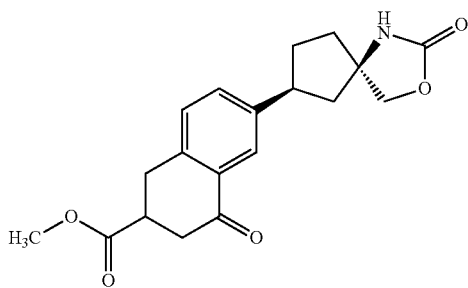

(I-15A)

To a mixture of potassium carbonate (523 mg, 3.78 mmol), (5R,7S)-7-(4-bromophenyl)-3-oxa-1-azaspiro[4.4]nonan-2-one (800 mg, 2.70 mmol), itaconic acid (457 mg, 3.51 mmol), and acetonitrile (8 mL) was added water (2.4 mL). The mixture was stirred till the evolution of carbon dioxide stopped and then bubbled with nitrogen for 3 min. After palladium(II) acetate (30.3 mg, 0.135 mmol) and tri-o-tolylphosphine (82 mg, 0.270 mmol) were added, the mixture was bubbled with nitrogen for an additional 3 min. The mixture was stirred at 80° C. for 20 h and then concentrated. The residue was mixed with water (40 mL), basified with potassium carbonate and filtered. The filtrate was washed with diethyl ether (2×15) then acidified to pH approximately 2 with 6N aqueous hydrochloric acid. The solid was separated and the aqueous solution was extracted with a mixture of THF/EtOAc (3:1) (4×10 mL). The solid and the extracts were combined and concentrated. LC/MS [M–H$_2$O]$^{+1}$=328.

The residue was mixed with THF (5 mL), ethyl acetate (5 mL), methanol (20 mL), and 10% Pd/C (400 mg, 0.376 mmol) and hydrogenated under a hydrogen balloon overnight. The catalyst was filtered off through a membrane filter and washed with methanol. The filtrate was concentrated and lyophilized to give a solid. LC/MS [M–H$_2$O]$^{+1}$=330.

The solid was mixed with 98% sulfuric acid (15 mL, 281 mmol). The clear solution was stirred at room temperature for 4 h. Methanol (8 mL, 198 mmol) was added slowly with water-bath cooling. The mixture was stirred at room temperature for 1 h before being poured onto ice (150 g). The mixture was extracted with ethyl acetate (4×40 mL). The combined ethyl acetate extracts were washed with saturated aqueous sodium bicarbonate solution (20 mL), dried over anhydrous sodium sulfate, and concentrated under reduced pressure. Flash chromatography purification (24 g silica gel column, gradient elution from 10 to 100% ethyl acetate in hexanes) afforded methyl 4-oxo-6-((5R,7S)-2-oxo-3-oxa-1-azaspiro[4.4]nonan-7-yl)-1,2,3,4-tetrahydronaphthalene-2-carboxylate (440 mg, 1.281 mmol). LC/MS M$^{+1}$=344.

Intermediate 15

A mixture of methyl 4-oxo-6-((5R,7S)-2-oxo-3-oxa-1-azaspiro[4.4]nonan-7-yl)-1,2,3,4-tetrahydronaphthalene-2-carboxylate (440 mg, 1.281 mmol), MeOH (15 mL), acetic acid (1.5 mL), and 10% Pd/C (200 mg, 0.188 mmol) was hydrogenated under a hydrogen balloon over a weekend. The mixture was filtered through a membrane filter. The filtrate was concentrated to give methyl 6-((5R,7S)-2-oxo-3-oxa-1-azaspiro[4.4]nonan-7-yl)-1,2,3,4-tetrahydronaphthalene-2-carboxylate (337 mg, 1.023 mmol) as a white solid. LC/MS M$^{+1}$=330.

INTERMEDIATES 16-I AND 16-II (5R,7S)-7-((S)-6-(hydroxymethyl)-5,6,7,8-tetrahydronaphthalen-2-yl)-3-oxa-1-azaspiro[4.4]nonan-2-one (I-16-I) and (5R,7S)-7-((R)-6-(hydroxymethyl)-5,6,7,8-tetrahydronaphthalen-2-yl)-3-oxa-1-azaspiro[4.4]nonan-2-one (I-16-II)

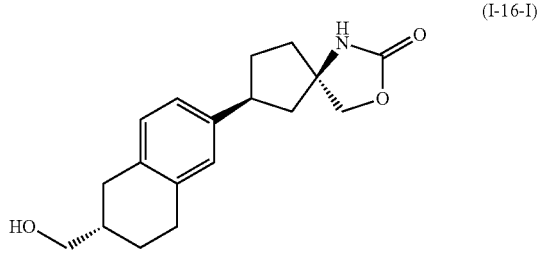

(I-16-I)

-continued (I-16-II)

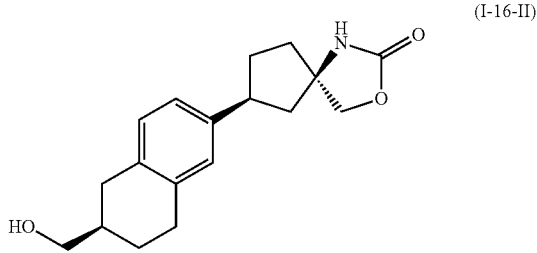

A mixture of methyl 6-((5R,7S)-2-oxo-3-oxa-1-azaspiro[4.4]nonan-7-yl)-1,2,3,4-tetrahydronaphthalene-2-carboxylate (337 mg, 1.023 mmol), anhydrous tetrahydrofuran (3 mL), and 2N THF solution of lithium borohydride (2.56 mL, 5.12 mmol) was stirred at 70° C. for 4 h. Saturated aqueous ammonium chloride solution was added slowly at 0° C. to quench the reaction. Water and ethyl acetate were added. The aqueous solution was extracted with ethyl acetate. The combined ethyl acetate solutions were dried over anhydrous sodium sulfate and concentrated under reduced pressure to give (5R,7S)-7-(6-(hydroxymethyl)-5,6,7,8-tetrahydronaphthalen-2-yl)-3-oxa-1-azaspiro[4.4]nonan-2-one (300 mg, 0.995 mmol). LC/MS $M^{+1}$=302.

Chiral SFC separation (AD-H (0.46×25 cm), 45% MeOH in $CO_2$, 3 ml/min, 220 nm, 35° C.) gave enantiomers 1 and 2 as white solids. Isomer 1: Intermediate 16-I (5R,7S)-7-((S)-6-(hydroxymethyl)-5,6,7,8-tetrahydronaphthalen-2-yl)-3-oxa-1-azaspiro[4.4]nonan-2-one. HPLC retention time=2.87 min (condition C); LC/MS $M^{+1}$=330. $^1$H NMR (400 MHz, CHLOROFORM-d) δ 7.06 (d, J=7.9 Hz, 1H), 6.96 (d, J=7.8 Hz, 1H), 6.92 (s, 1H), 5.22 (br. s., 1H), 4.38-4.18 (m, 2H), 3.73 (s, 3H), 3.07-2.91 (m, 3H), 2.89-2.79 (m, 2H), 2.78-2.68 (m, 1H), 2.31 (dd, J=13.3, 7.3 Hz, 1H), 2.25-2.16 (m, 1H), 2.16-2.07 (m, 2H), 2.01-1.76 (m, 4H). Isomer 2: Intermediate 16-II (5R,7S)-7-((R)-6-(hydroxymethyl)-5,6,7,8-tetrahydronaphthalen-2-yl)-3-oxa-1-azaspiro[4.4]nonan-2-one; HPLC retention time=2.88 min (condition C); LC/MS $M^+$=330; $^1$H NMR (400 MHz, CHLOROFORM-d) δ 7.06 (d, J=7.9 Hz, 1H), 6.96 (d, J=7.9 Hz, 1H), 6.92 (s, 1H), 5.05 (br. s., 1H), 4.35-4.24 (m, 2H), 3.73 (s, 3H), 3.08-2.92 (m, 3H), 2.90-2.79 (m, 2H), 2.78-2.68 (m, 1H), 2.32 (dd, J=13.3, 7.2 Hz, 1H), 2.25-2.06 (m, 3H), 2.01-1.74 (m, 4H).

INTERMEDIATE 17-I AND 17-II ((S)-6-((5R,7S)-2-oxo-3-oxa-1-azaspiro[4.4]nonan-7-yl)-1,2,3,4-tetrahydronaphthalen-2-yl)methyl 4-methylbenzenesulfonate (I-17-I) and ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (I-17-II)

(I-17-1)

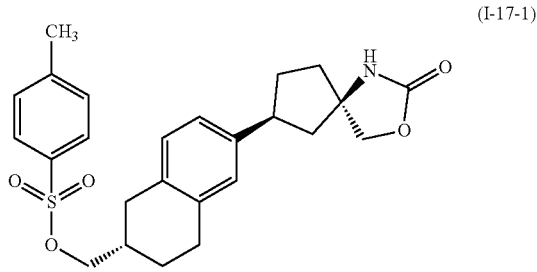

-continued (I-17-II)

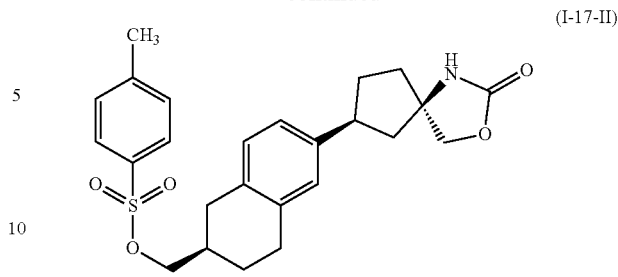

Int-17-II: (5R,7S)-7-((R)-6-(hydroxymethyl)-5,6,7,8-tetrahydronaphthalen-2-yl)-3-oxa-1-azaspiro[4.4]nonan-2-one (enantiomer 2; 690 mg, 2.289 mmol) was dissolved in dry pyridine (5 mL) and p-toluenesulfonyl chloride (1309 mg, 6.87 mmol) was added in one portion. The resulting mixture was reacted at room temperature for 4 h. The solvent was removed in vacuo. The residue was dissolved in methylene chloride and methanol. Flash chromatography purification (40 g silica gel column, gradient elution from 20 to 100% ethyl acetate in hexanes) afforded ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (860 mg, 1.888 mmol) as a white solid. LC/MS $M^{+1}$=456.

Int-17-I was prepared according to the general procedure as Intermediate 17-II using (5R,7S)-7-((S)-6-(hydroxymethyl)-5,6,7,8-tetrahydronaphthalen-2-yl)-3-oxa-1-azaspiro[4.4]nonan-2-one to afford ((S)-6-((5R,7S)-2-oxo-3-oxa-1-azaspiro[4.4]nonan-7-yl)-1,2,3,4-tetrahydronaphthalen-2-yl)methyl 4-methylbenzenesulfonate.

Examples 1 to 4

(1-amino-3-((R)-2-((pentyloxy)methyl)-2,3-dihydrobenzo[b][1,4]dioxin-6-yl)cyclopentyl)methanol (1 to 4)

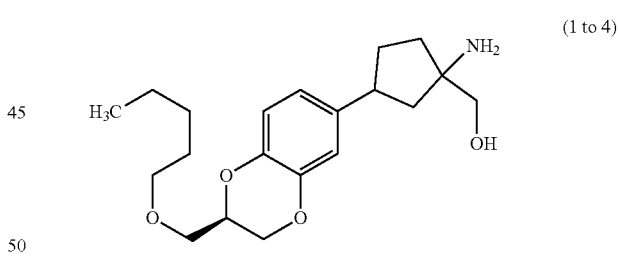

Preparation 1A: (S)-1-(4-bromo-2-(oxiran-2-ylmethoxy)phenyl)ethanone (1A)

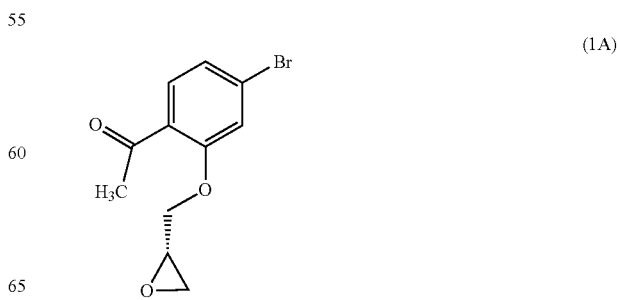

To a stirred solution of 4-bromo-2-hydroxyacetophenone (2.54 g, 11.81 mmol) in anhydrous DMF (10 mL) was added sodium hydride (60% dispersion in mineral oil, 0.520 g, 12.99 mmol). The mixture was stirred at room temperature for 40 min before a solution of (2S)-glycidyl-3-nitrobenzenesulfonate (3.37 g, 12.99 mmol) in anhydrous DMF (5 mL) was added dropwise at room temperature under nitrogen. The mixture was stirred at 70° C. for 3.5 h. The reaction mixture was concentrated to remove DMF and the residue was quenched with 10% aqueous citric acid to pH approximately 3. The mixture was diluted with water (5 mL) and extracted with ethyl acetate (4×10 mL). The combined extracts were dried over anhydrous sodium sulfate and concentrated. Flash chromatography purification (80 g silica gel column, gradient elution from 0 to 40% ethyl acetate in hexanes) afforded (S)-1-(4-bromo-2-(oxiran-2-ylmethoxy)phenyl)ethanone (2.68 g, 9.89 mmol) as a white solid. LC/MS $M^{+23}$=293, 295. $^1$H NMR (400 MHz, CHLOROFORM-d) δ 7.64 (d, J=8.4 Hz, 1H), 7.19 (dd, J=8.3, 1.7 Hz, 1H), 7.12 (d, J=1.8 Hz, 1H), 4.40 (dd, J=10.9, 2.8 Hz, 1H), 4.00 (dd, J=11.0, 6.2 Hz, 1H), 3.45-3.38 (m, 1H), 3.00-2.93 (m, 1H), 2.78 (dd, J=4.8, 2.6 Hz, 1H), 2.65 (s, 3H).

Preparation 1B: (S)-4-bromo-2-(oxiran-2-ylmethoxy)phenyl acetate

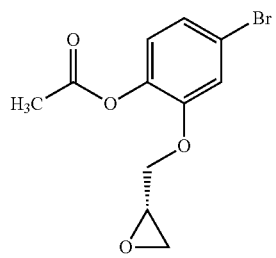

(1B)

To a stirred solution of (S)-1-(4-bromo-2-(oxiran-2-ylmethoxy)phenyl)ethanone (0.76 g, 2.80 mmol) in methylene chloride (30 mL) were added sodium bicarbonate (1.6 g, 19.05 mmol) and m-CPBA (1.257 g, 5.61 mmol). The mixture was stirred at 40° C. for 5 h and room temperature overnight. The solid was filtered off and the filtrate was concentrated. The residue was dissolved in ethyl acetate, washed with a mixture of sodium bicarbonate and thiosulfate aqueous solutions, dried over anhydrous sodium sulfate, and concentrated. Flash chromatography purification (24 g silica gel column, gradient elution from 0 to 40% ethyl acetate in hexanes) afforded (S)-4-bromo-2-(oxiran-2-ylmethoxy)phenyl acetate (0.72 g, 2.508 mmol) as a colorless liquid. LC/MS $M^{+23}$=309, 311.

Preparation 1C: (R)-(6-bromo-2,3-dihydrobenzo[b][1,4]dioxin-2-yl)methanol

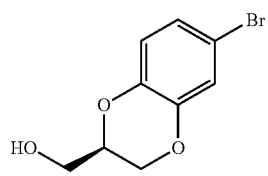

(1C)

(S)-4-bromo-2-(oxiran-2-ylmethoxy)phenyl acetate (0.72 g, 2.508 mmol) was dissolved in tetrahydrofuran (15 mL) and 2M aqueous solution of sodium hydroxide (1.442 mL, 2.88 mmol) was added. The mixture was vigorously stirred at room temperature for 2.5 days. Hexanes (7 mL) was added. The aqueous layer was separated and extracted with ethyl acetate (3×2 mL). The combined organic solutions were dried over anhydrous sodium sulfate and concentrated. Flash chromatography purification (40 g silica gel column, gradient elution from 0 to 40% ethyl acetate in hexanes) afforded (R)-(6-bromo-2,3-dihydrobenzo[b][1,4]dioxin-2-yl)methanol (0.54 g, 2.203 mmol) as a white solid. $^1$H NMR (400 MHz, CHLOROFORM-d) δ 7.04 (d, J=2.4 Hz, 1H), 6.96 (dd, J=8.7, 2.3 Hz, 1H), 6.77 (d, J=8.6 Hz, 1H), 4.30 (dd, J=11.3, 2.3 Hz, 1H), 4.27-4.21 (m, 1H), 4.10 (dd, J=11.3, 7.7 Hz, 1H), 3.95-3.80 (m, 2H).

Preparation 1D: (R)-6-bromo-2-((pentyloxy)methyl)-2,3-dihydrobenzo[b][1,4]dioxine

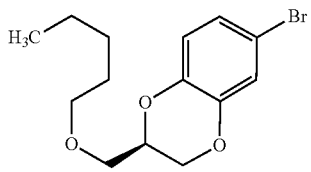

(1D)

To a stirred solution of (R)-(6-bromo-2,3-dihydrobenzo[b][1,4]dioxin-2-yl) methanol (0.38 g, 1.551 mmol) in anhydrous tetrahydrofuran (15 mL) was added sodium hydride (60% mineral oil dispersion, 0.310 g, 7.75 mmol) portionwise at room temperature under nitrogen. The resulting mixture was stirred at room temperature for 15 min before n-amyl iodide (1.017 mL, 7.75 mmol) was added. The mixture was stirred at room temperature for 2 days. Saturated aqueous ammonium chloride solution (4 mL) and hexanes (10 mL) were added. The aqueous layer was separated and extracted with ethyl acetate (2×3 mL). The combined organic solutions were dried over anhydrous sodium sulfate and concentrated. Flash chromatography purification (12 g silica gel column, gradient elution from 0 to 20% ethyl acetate in hexanes) afforded (R)-6-bromo-2-((pentyloxy)methyl)-2,3-dihydrobenzo[b][1,4]dioxine (0.39 g, 1.237 mmol) as a colorless liquid. $^1$H NMR (400 MHz, CHLOROFORM-d) δ 7.01 (d, J=2.4 Hz, 1H), 6.92 (dd, J=8.6, 2.2 Hz, 1H), 6.74 (d, J=8.6 Hz, 1H), 4.31-4.23 (m, 2H), 4.07-3.98 (m, 1H), 3.71-3.63 (m, 1H), 3.58 (dd, J=10.3, 5.9 Hz, 1H), 3.48 (t, J=6.6 Hz, 2H), 1.64-1.51 (m, 2H), 1.37-1.27 (m, 4H), 0.93-0.86 (m, 3H).

Preparation 1E: Ethyl 1-((diphenylmethylene)amino)$_{1-4}$-((R)-2-((pentyloxy)methyl)-2,3-dihydrobenzo[b][1,4]dioxin-6-yl)cyclopent-2-enecarboxylate

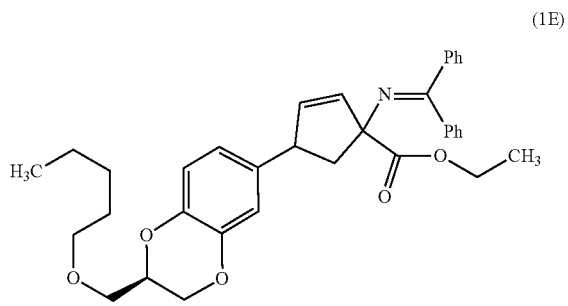 [SMILES: CCCCCOC[C@@H]1COc2cc(C3C=CC(N=C(c4ccccc4)c4ccccc4)(C(=O)OCC)C3)ccc2O1]

(1E)

An oven dried microwave vial with stir bar was charged with (R)-6-bromo-2-((pentyloxy)methyl)-2,3-dihydrobenzo[b][1,4]dioxine (390 mg, 1.237 mmol), ethyl 1-((diphenylmethylene)amino)cyclopent-3-enecarboxylate (593 mg, 1.856 mmol), triphenylphosphine (64.9 mg, 0.247 mmol), palladium(II) acetate (27.8 mg, 0.124 mmol), potassium acetate (243 mg, 2.475 mmol), and DMA (3 mL). The mixture was sparged with nitrogen for 3 minutes. The mixture was processed on a Personal Chemistry microwave (60 minutes at 140° C.). The mixture was mixed with water (60 mL) and extracted with ethyl acetate (5×5 mL). The combined ethyl acetate extracts were dried over anhydrous sodium sulfate and concentrated under reduced pressure. Flash chromatography purification (40 g silica gel column, gradient elution from 5 to 100% ethyl acetate in hexanes) afforded ethyl 1-((diphenylmethylene)amino)$_{1-4}$-((R)-2-((pentyloxy)methyl)-2,3-dihydrobenzo[b][1,4]dioxin-6-yl)cyclopent-2-enecarboxylate (300 mg, 0.542 mmol) as a sticky liquid. LC/MS M+$^1$=554.

Example 1

To a stirred solution of ethyl 1-((diphenylmethylene)amino)$_{1-4}$-((R)-2-((pentyloxy)methyl)-2,3-dihydrobenzo[b][1,4]dioxin-6-yl)cyclopent-2-enecarboxylate (300 mg, 0.542 mmol) and water (0.27 mL) in diethyl ether (8 mL) was added 6 N aqueous hydrochloric acid (0.542 mL, 3.25 mmol). The mixture was stirred at room temperature for 30 min and then basified with potassium carbonate solid and water (1 mL). The mixture was extracted with ethyl acetate (4×4 mL). The combined ethyl acetate extracts were dried over anhydrous sodium sulfate and concentrated under reduced pressure to give a liquid. The liquid was dissolved in EtOH (10 mL). Sodium borohydride (123 mg, 3.25 mmol) was added. The mixture was stirred at room temperature overnight. Next, 6N aqueous hydrochloric acid (2 mL) was added slowly to make pH approximately 2. The mixture was stirred at room temperature for 1 h. The mixture was basified to pH approximately 12 with 2 N aqueous sodium hydroxide solution. After stirring at room temperature for 30 min, the mixture was concentrated. The aqueous residue was extracted with ethyl acetate (4×4 mL). The combined ethyl acetate extracts were dried over anhydrous sodium sulfate and concentrated under reduced pressure to give a solid.

The solid material was dissolved in MeOH (10 mL) and acetic acid (1 mL). Next, 10% Pd/C (100 mg, 0.094 mmol) was added under nitrogen. The mixture was hydrogenated under hydrogen balloon overnight. The catalyst was filtered and washed with methanol. The filtrate was concentrated. The residue was mixed with water (3 mL), basified with potassium carbonate solid, and extracted with ethyl acetate (5×3 mL). The combined ethyl acetate extracts were dried over anhydrous sodium sulfate and concentrated. Flash chromatography purification (4 g silica gel column, gradient elution from 0->20% of 2M ammonia in methanol solution in EtOAc) afforded (1-amino-3-((R)-2-((pentyloxy)methyl)-2,3-dihydrobenzo[b][1,4]dioxin-6-yl)cyclopentyl)methanol (180 mg, 0.515 mmol) as a semisolid. LC/MS M+$^1$=350.

The semisolid was separated into three fractions using chiral SFC (Cell-4 (25×3 cm, 5 μm), CO$_2$/(MeOH+0.5% DEA)=60/40, 130 ml/min, 284 nm, 35° C.). Fractions 1 and 3 were individually concentrated and purified using reverse phase HPLC (Phenomenex Luna 5 u 30×100 mm (Axia), solvent A: 10% MeOH: 90% H$_2$O: 0.1% TFA, solvent B: 90% MeOH, 10% H$_2$O, 0.1% TFA). Concentration, basification with potassium carbonate, and extraction with ethyl acetate gave the corresponding compounds. Fraction 2 was concentrated and separated using chiral SFC (Cell-2-H (3×25 cm), 40% IPA w 0.1% DEA and 0.1% water in CO$_2$, 150 ml/min, 220 nm, 50° C.) to give Fraction 2-A and Fraction 2-B as glassy solids. All four isomers have the same molecular weights. LC/MS M+$^1$=350.

Example 1 (Fraction 1): $^1$H NMR (400 MHz, METHANOL-d$_4$) δ 6.77 (d, J=0.9 Hz, 1H), 6.75-6.73 (m, 2H), 4.30-4.21 (m, 2H), 4.04-3.96 (m, 1H), 3.71-3.57 (m, 2H), 3.53-3.40 (m, 4H), 2.97 (tt, J=11.3, 7.1 Hz, 1H), 2.19 (dd, J=13.1, 7.6 Hz, 1H), 2.04-1.63 (m, 4H), 1.63-1.54 (m, 2H), 1.54-1.43 (m, 1H), 1.40-1.29 (m, 4H), 0.96-0.87 (m, 3H).

Example 2 (Fraction 3): $^1$H NMR (400 MHz, METHANOL-d$_4$) δ 6.77 (d, J=0.9 Hz, 1H), 6.75-6.73 (m, 2H), 4.29-4.21 (m, 2H), 4.03-3.95 (m, 1H), 3.70-3.57 (m, 2H), 3.54-3.40 (m, 4H), 2.97 (tt, J=11.3, 7.1 Hz, 1H), 2.19 (dd, J=12.8, 7.3 Hz, 1H), 2.04-1.63 (m, 4H), 1.63-1.54 (m, 2H), 1.54-1.45 (m, 1H), 1.39-1.30 (m, 4H), 0.95-0.87 (m, 3H).

Example 3 (Fraction 2-A): $^1$H NMR (400 MHz, CHLOROFORM-d) δ 6.77-6.68 (m, 3H), 4.29-4.20 (m, 2H), 4.03-3.96 (m, 1H), 3.71-3.55 (m, 2H), 3.53-3.44 (m, 4H), 3.26-3.17 (m, 1H), 2.16-2.05 (m, 1H), 2.03-1.95 (m, 1H), 1.93-1.85 (m, 1H), 1.74-1.53 (m, 4H), 1.41-1.23 (m, 5H), 0.95-0.88 (m, 3H).

Example 4 (Fraction 2-B): $^1$H NMR (400 MHz, METHANOL-d$_4$) δ 6.78-6.68 (m, 3H), 4.29-4.21 (m, 2H), 4.04-3.96 (m, 1H), 3.71-3.57 (m, 2H), 3.56-3.46 (m, 4H), 3.22 (q, J=7.3 Hz, 1H), 2.17-1.87 (m, 3H), 1.75-1.53 (m, 4H), 1.41-1.23 (m, 5H), 0.97-0.86 (m, 3H).

Using the general procedures for the preparation of Examples 1 to 4, the following compounds were prepared from the corresponding aryl bromide intermediates. The compounds were analyzed using HPLC condition C.

TABLE 1

| Ex. No. | Structure | MW | HPLC ret. time (min.) | MS (M + 1) | Comment |
|---|---|---|---|---|---|
| 5 | 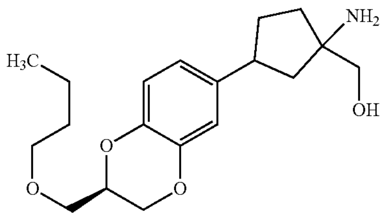 [SMILES: CCCCOC[C@@H]1COc2cc(C3CCC(N)(CO)C3)ccc2O1] | 335.4 | 2.50 | 336 | Cis-cyclopentyl Isomer 1 |
| 6 | | 335.4 | 2.49 | 336 | Cis-cyclopentyl Isomer 2 |
| 7 | 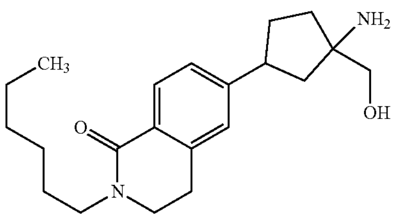 [SMILES: CCCCCCN1CCc2cc(C3CCC(N)(CO)C3)ccc2C1=O] | 344.5 | 2.61 | 345 | Isomer 1 |
| 8 | | 344.5 | 2.63 | 345 | Isomer 2 |
| 9 | | 344.5 | 2.61 | 345 | Isomer 3 |
| 10 | | 344.5 | 2.63 | 345 | Isomer 4 |
| 11 | 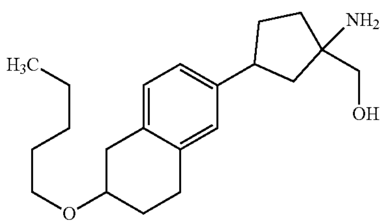 [SMILES: CCCCCOC1CCc2cc(C3CCC(N)(CO)C3)ccc2C1] | 331.5 | 3.09 | 332 | Cyclohexane isomer 1 Mixture of 2 trans cyclopentyl isomers |
| 12 | | 331.5 | 3.08 | 332 | Cyclohexane isomer 1 Mixture of 2 cis cyclopentyl isomers |
| 13 | | 331.5 | 3.05 | 332 | Cyclohexane isomer 2 Mixture of 2 trans cyclopentyl isomers |
| 14 | | 331.5 | 3.05 | 332 | Cyclohexane isomer 2 Mixture of 2 cis cyclopentyl isomers |
| 15 | 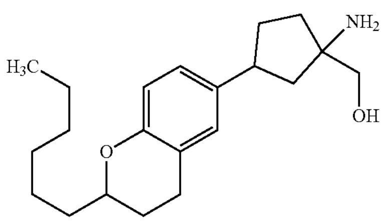 [SMILES: CCCCCCC1CCc2cc(C3CCC(N)(CO)C3)ccc2O1] | 331.5 | 3.38 | 332 | pyran isomer 1 cis-cyclopentyl isomer 1 |
| 16 | | 331.5 | 3.36 | 332 | pyran isomer 1 cis-cyclopentyl isomer 2 |
| 17 | 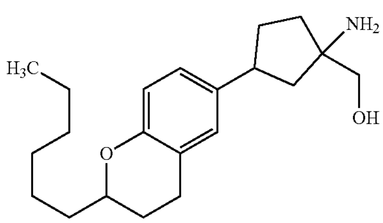 [SMILES: CCCCCCC1CCc2cc(C3CCC(N)(CO)C3)ccc2O1] | 331.5 | 3.35 | 332 | pyran isomer 2 cis-cyclopentyl isomer 1 |
| 18 | | 331.5 | 3.36 | 332 | pyran isomer 2 cis-cyclopentyl isomer 2 |
| 19 | 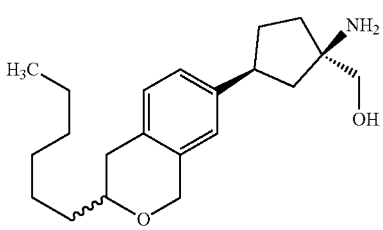 [SMILES: CCCCCCC1Cc2ccc([C@H]3CC[C@](N)(CO)C3)cc2CO1] | 331.5 | 3.31 | 332 | Mixture of 2 diastereomers |
| 20 | 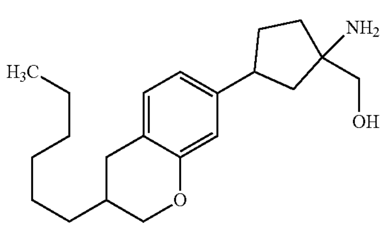 [SMILES: CCCCCCC1COc2cc(C3CCC(N)(CO)C3)ccc2C1] | 331.5 | 3.41 | 332 | pyran isomer 1 cis-cyclopentyl isomer 1 |
| 21 | | 331.5 | 3.51 | 332 | pyran isomer 1 cis-cyclopentyl isomer 2 |
| 22 | | 331.5 | 3.38 | 332 | pyran isomer 2 cis-cyclopentyl isomer 1 |
| 23 | | 331.5 | 3.52 | 332 | pyran isomer 2 cis-cyclopentyl isomer 1 |

TABLE 1-continued

| Ex. No. | Structure | MW | HPLC ret. time (min.) | MS (M + 1) | Comment |
|---|---|---|---|---|---|
| 24 | 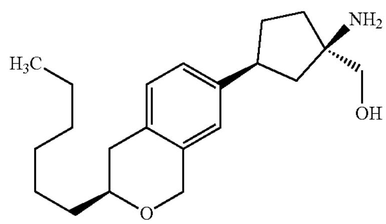 [SMILES: CCCCCC[C@H]1Cc2ccc([C@H]3CC[C@](N)(CO)C3)cc2CO1] | 331.5 | 3.22 | 332 | |
| 25 | 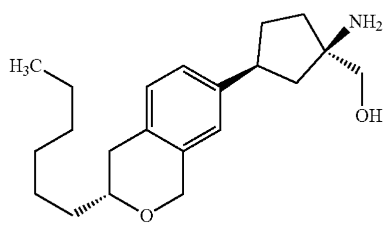 [SMILES: CCCCCC[C@@H]1Cc2ccc([C@H]3CC[C@](N)(CO)C3)cc2CO1] | 331.5 | 3.23 | 332 | |
| 26 | 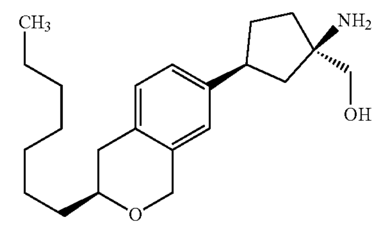 [SMILES: CCCCCCC[C@H]1Cc2ccc([C@H]3CC[C@](N)(CO)C3)cc2CO1] | 345.5 | 3.43 | 346 | |
| 27 | 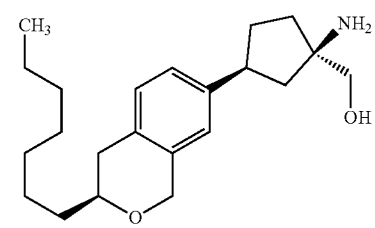 [SMILES: CCCCCCC[C@H]1Cc2ccc([C@H]3CC[C@](N)(CO)C3)cc2CO1] | 345.5 | 3.52 | 346 | |

Examples 28 and 29

((1R,3S)-1-amino-3-(6-(pentyloxy)-5,6,7,8-tetrahydronaphthalen-2-yl) cyclopentyl)methanol

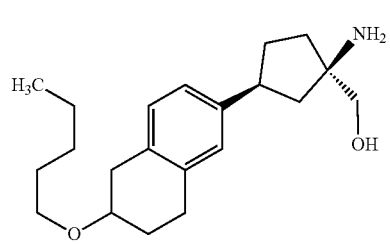

(28 and 29)

Preparation 28A: (5R,7S)-7-(6-(pentyloxy)-5,6,7,8-tetrahydronaphthalen-2-yl)-3-oxa-1-azaspiro[4.4]nonan-2-one (28A)

A mixture of 1-pentanol (10 mL, 92 mmol), p-toluenesulfonic acid monohydrate (8.00 mg, 0.042 mmol), and trimethoxymethane (0.613 mL, 5.61 mmol) was stirred at 100° C. for 2 h with a slow nitrogen stream to remove methanol byproduct. The residual liquid was mixed with (5R,7S)-7-(6-oxo-5,6,7,8-tetrahydronaphthalen-2-yl)-3- oxa-1-azaspiro[4.4]nonan-2-one (400 mg, 1.402 mmol) and stirred at 100° C. under nitrogen for 2.5 h. Next, 10% Pd/C (400 mg) was added at room temperature, followed by ethyl acetate (5 mL). The mixture was vigorously stirred under hydrogen balloon for 4 h. The mixture was filtered through a membrane filter and the filtrate was concentrated. Flash chromatography purification (12 g silica gel column, gradient elution from 0 to 100% ethyl acetate in hexanes) afforded (5R,7S)-7-(6-(pentyloxy)-5,6,7,8-tetrahydronaphthalen-2-yl)-3-oxa-1-azaspiro[4.4]nonan-2-one (350 mg, 0.979 mmol) as a sticky solid. LC/MS M$^{+1}$=358. Chiral separation (Lux-Amy-2 (3×25 cm), 25% MeOH, 120 ml/min, 220 nm, 45° C.) of the solid gave two isomers. Each isomer was hydrolyzed in the following fashion.

Example 28 (Isomer 1)

A mixture of (5R,7S)-7-(6-(pentyloxy)-5,6,7,8-tetrahydronaphthalen-2-yl)-3-oxa-1-azaspiro[4.4]nonan-2-one (110 mg, 0.308 mmol), lithium hydroxide monohydrate (155 mg, 3.69 mmol), dioxane (1 mL), and water (1 mL) was stirred at 90° C. under nitrogen for 15 h. The mixture was cooled and extracted with ethyl acetate (4×1 mL). The combined ethyl acetate extracts were dried over anhydrous sodium sulfate and concentrated under reduced pressure. Purification using reverse phase HPLC (Phenomenex Luna 5 u 30×100 mm (Axia); gradient over 8 min from 30 to 100% of solvent B; solvent A: 10% MeOH: 90% H$_2$O: 0.1% TFA; solvent B: 90% MeOH, 10% H$_2$O, 0.1% TFA), concentration, basification with potassium carbonate, and extraction with ethyl acetate gave ((1R,3S)-1-amino-3-(6-(pentyloxy)-5,6,7,8-tetrahydronaphthalen-2-yl)cyclopentyl)methanol (61 mg, 0.173 mmol) as a white solid. LC/MS M$^{+1}$=332. $^1$H NMR (400 MHz, CHLOROFORM-d) δ 7.03-6.95 (m, 3H), 3.73-3.63 (m, 1H), 3.57-3.42 (m, 4H), 3.09-2.97 (m, 2H), 2.95-2.85 (m, 1H), 2.82-2.68 (m, 2H), 2.27 (dd, J=13.3, 7.8 Hz, 1H), 2.13-2.01 (m, 2H), 1.97-1.46 (m, 7H), 1.37-1.29 (m, 4H), 0.94-0.87 (m, 3H).

Example 29 (Isomer 2)

$^1$H NMR (400 MHz, CHLOROFORM-d) δ 7.03-6.95 (m, 3H), 3.73-3.64 (m, 1H), 3.57-3.49 (m, 2H), 3.48-3.40 (m, 2H), 3.09-2.96 (m, 2H), 2.95-2.86 (m, 1H), 2.81-2.69 (m, 2H), 2.25 (dd, J=13.2, 7.9 Hz, 1H), 2.13-2.00 (m, 2H), 1.95-1.83 (m, 1H), 1.82-1.55 (m, 5H), 1.48 (dd, J=13.2, 11.0 Hz, 1H), 1.37-1.29 (m, 4H), 0.93-0.87 (m, 3H).

Examples 30 and 31

((1R,3S)-1-amino-3-(6-(heptyloxy)-5,6,7,8-tetrahydronaphthalen-2-yl)cyclopentyl)methanol (30 and 31)

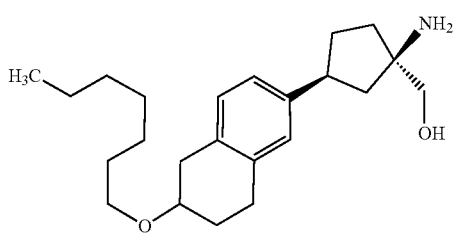

Preparation 30A: (5R,7S)-7-(6-(heptyloxy)-7,8-dihydronaphthalen-2-yl)-3-oxa-1-azaspiro[4.4]nonan-2-one (30A)

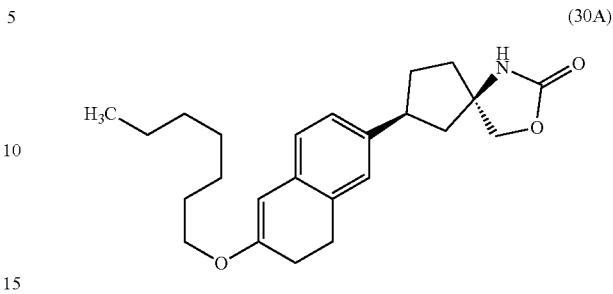

To a mixture of (5R,7S)-7-(6-oxo-5,6,7,8-tetrahydronaphthalen-2-yl)-3-oxa-1-azaspiro[4.4]nonan-2-one (100 mg, 0.350 mmol) and 1-heptanol (500 μL, 3.54 mmol) in toluene (2 mL) was added p-toluenesulfonic acid monohydrate (5 mg, 0.026 mmol). Oven dried 3-angstrom molecular sieves were added and the mixture was heated at reflux overnight. The reaction mixture was diluted with ethyl acetate and washed with saturated NaCl. The organic layer was dried with MgSO$_4$, filtered, and concentrated. The crude material was purified on a silica gel cartridge (40 g) using an EtOAc/Hex gradient (0-100% EtOAc over 20 minutes) to afford 55 mg of (5R,7S)-7-(6-(heptyloxy)-7,8-dihydronaphthalen-2-yl)-3-oxa-1-azaspiro[4.4]nonan-2-one. HPLC retention time=1.26 min (condition G); LC/MS M$^{+1}$=384. $^1$H NMR (400 MHz, CHLOROFORM-d) δ 7.00-6.86 (m, 3H), 5.79 (s, 1H), 5.52 (s, 1H), 4.41-4.24 (m, 2H), 3.86 (t, J=6.6 Hz, 2H), 2.94-2.82 (m, 2H), 2.41 (t, J=8.0 Hz, 2H), 2.36-2.25 (m, 1H), 2.20-2.07 (m, 2H), 2.05-1.90 (m, 2H), 1.79-1.70 (m, 2H), 1.51-1.21 (m, 10H), 0.98-0.83 (m, 3H).

Preparation 30B: (5R,7S)-7-(6-(pentyloxy)-5,6,7,8-tetrahydronaphthalen-2-yl)-3-oxa-1-azaspiro[4.4]nonan-2-one (30B)

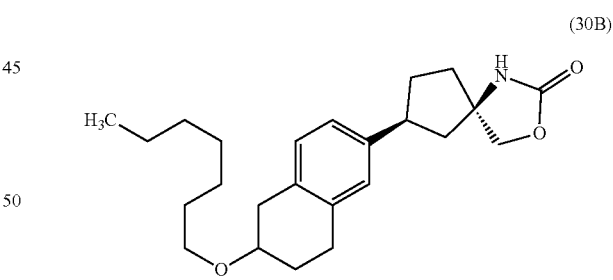

To a mixture of (5R,7S)-7-(6-(heptyloxy)-7,8-dihydronaphthalen-2-yl)-3-oxa-1-azaspiro[4.4]nonan-2-one (53 mg, 0.138 mmol) in MeOH (10 mL) was added Pearlman's Catalyst (19.41 mg, 0.138 mmol). The reaction mixture was hydrogenated under a balloon of H$_2$ for 2 hours. The catalyst was filtered away, and then concentrated in vacuo. The individual isomers were separated using a CHIRALPAK® AS-H column under SFC conditions (30% MeOH in CO$_2$). Isomer 1 (30-B-i, 9 mg) Chiral HPLC retention time=8.55 min; LC/MS M$^{+1}$=386. $^1$H NMR (400 MHz, CHLOROFORM-d) δ 7.10-7.03 (m, 1H), 7.00-6.91 (m, 2H), 5.29 (br. s., 1H), 4.40-4.26 (m, 2H), 3.78-3.67 (m, 1H), 3.55 (qd, J=6.6, 2.4 Hz, 2H), 3.13-2.98 (m, 2H), 2.98-2.88 (m, 1H), 2.84-2.71 (m, 2H), 2.33 (dd, J=13.2, 7.3 Hz, 1H), 2.23-2.04 (m, 3H), 1.96 (dd, J=13.1, 10.9 Hz, 2H), 1.88-1.74 (m, 2H), 1.61 (quin, J=6.9 Hz, 4H), 1.43-1.21 (m, 6H), 0.95-0.85 (m, 3H).

Isomer 2 (30-B-ii, 9 mg) Chiral HPLC retention time=9.81 min; LC/MS M$^{+1}$=386. $^1$H NMR (400 MHz, CHLOROFORM-d) δ 7.09-7.03 (m, 1H), 7.00-6.90 (m, 2H), 5.25 (s, 1H), 4.40-4.24 (m, 2H), 3.80-3.67 (m, 1H), 3.55 (qd, J=6.6, 2.4 Hz, 2H), 3.14-2.99 (m, 2H), 2.98-2.87 (m, 1H), 2.84-2.69 (m, 2H), 2.33 (dd, J=13.2, 7.3 Hz, 1H), 2.22-2.04 (m, 3H), 2.02-1.90 (m, 2H), 1.88-1.74 (m, 2H), 1.60 (q, J=7.0 Hz, 4H), 1.43-1.20 (m, 6H), 0.95-0.85 (m, 3H). The absolute stereochemistry of the isomers was not determined.

Example 30: ((1R,3S)-1-amino-3-(6-(heptyloxy)-5,6,7,8-tetrahydronaphthalen-2-yl) cyclopentyl)methanol

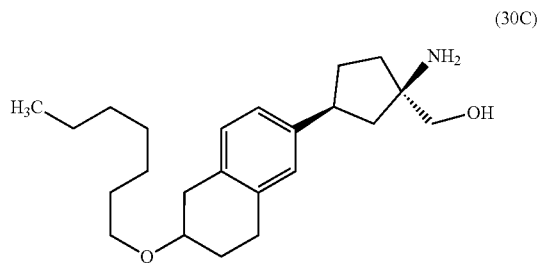 [SMILES: CCCCCCCOC1CCc2cc([C@H]3CC[C@](N)(CO)C3)ccc2C1]

(30C)

To a mixture of (5R,7S)-7-(6-(heptyloxy)-5,6,7,8-tetrahydronaphthalen-2-yl)-3-oxa-1-azaspiro[4.4]nonan-2-one, Isomer 1 (30B-i, 9 mg, 0.023 mmol) in dioxane (4 mL) was added 1N NaOH. The reaction mixture was heated at 100° C. overnight, and then cooled and acidified with TFA. The mixture was concentrated in vacuo, then triturated with MeOH, and filtered. The filtrate was purified filtrate by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Isolated fractions with correct mass and freeze-dried overnight. Recovered 5 mg of ((1R,3S)-1-amino-3-(6-(heptyloxy)-5,6,7,8-tetrahydronaphthalen-2-yl)cyclopentyl) methanol (Example 30): HPLC retention time=9.31 min (condition H); LC/MS M$^{+1}$=360. $^1$H NMR (400 MHz, METHANOL-d$_4$) δ 7.07-6.98 (m, 3H), 3.83-3.73 (m, 1H), 3.71-3.51 (m, 4H), 3.18-3.08 (m, 1H), 3.04 (dd, J=16.6, 5.0 Hz, 1H), 2.96-2.85 (m, 1H), 2.82-2.68 (m, 2H), 2.42 (ddd, J=13.3, 7.1, 1.2 Hz, 1H), 2.17-2.01 (m, 2H), 2.00-1.89 (m, 3H), 1.88-1.77 (m, 1H), 1.73 (t, J=12.8 Hz, 1H), 1.59 (quin, J=6.9 Hz, 2H), 1.45-1.22 (m, 8H), 0.96-0.86 (m, 3H).

Example 31: ((1R,3S)-1-amino-3-(6-(heptyloxy)-5,6,7,8-tetrahydronaphthalen-2-yl) cyclopentyl)methanol To a mixture of (5R,7S)-7-(6-(heptyloxy)-5,6,7,8-tetrahydronaphthalen-2-yl)-3-oxa-1-azaspiro[4.4]nonan-2-one Isomer 2 (30-B-ii, 8 mg, 0.021 mmol) in dioxane (4 mL) was added 1N NaOH. The mixture was heated at 100° C. overnight, and then cooled and acidified with TFA. The mixture was concentrated in vacuo then triturated with MeOH, and filtered. The filtrate was purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Isolated fractions with correct mass and freeze-dried overnight. Recovered 5 mg of ((1R,3S)-1-amino-3-(6-(heptyloxy)-5,6,7,8-tetrahydronaphthalen-2-yl)cyclopentyl)methanol (Example 31). HPLC retention time=9.34 min (condition H); LC/MS M$^{+1}$=360. $^1$H NMR (400 MHz, METHANOL-d$_4$) δ 7.03 (s, 2H), 7.00 (s, 1H), 3.83-3.73 (m, 1H), 3.70-3.61 (m, 2H), 3.61-3.50 (m, 2H), 3.18-3.08 (m, 1H), 3.04 (dd, J=16.4, 4.7 Hz, 1H), 2.97-2.84 (m, 1H), 2.81-2.66 (m, 2H), 2.42 (ddd, J=13.4, 7.1, 1.1 Hz, 1H), 2.19-2.01 (m, 2H), 2.00-1.89 (m, 3H), 1.88-1.77 (m, 1H), 1.73 (t, J=12.8 Hz, 1H), 1.59 (quin, J=6.9 Hz, 2H), 1.44-1.23 (m, 8H), 0.97-0.87 (m, 3H).

The following compounds were prepared according to the general procedures of Examples 28 and 29.

TABLE 2

| Ex. No. | Structure | MW | HPLC ret. time (min.) | HPLC condition | MS (M$^{+1}$) | Comment |
|---|---|---|---|---|---|---|
| 32 | 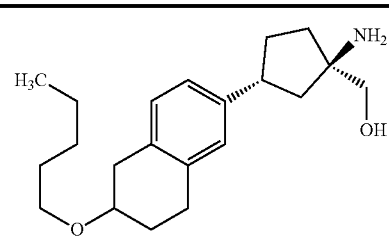 | 331.5 | 3.23 | K | 332 | Isomer 1 |
| 33 | | 331.5 | 3.23 | K | 332 | Isomer 2 |
| 34 | 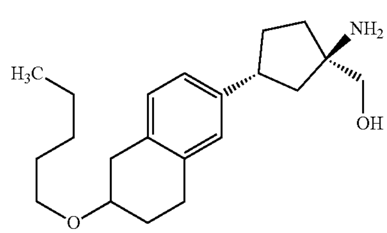 [SMILES: CCCCCOC1CCc2cc([C@@H]3CC[C@](N)(CO)C3)ccc2C1] | 345.5 | 3.29 | C | 346 | Isomer 1 |
| 35 | | 345.5 | 3.26 | C | 346 | Isomer 2 |

TABLE 2-continued

| Ex. No. | Structure | MW | HPLC ret. time (min.) | HPLC condition | MS (M+1) | Comment |
|---|---|---|---|---|---|---|
| 36 | 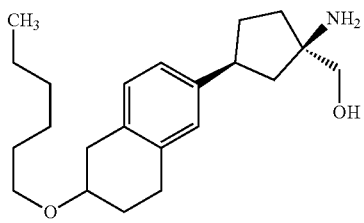 [SMILES: CCCCCCOC1CCc2cc([C@H]3CC[C@](N)(CO)C3)ccc2C1] | 317.5 | 7.59 | H | 318 | Isomer 1 |
| 37 | | 317.5 | 7.59 | H | 318 | Isomer 2 |

Example 38

((1R,3S)-1-amino-3-((S)-6-((Z)-hex-2-en-1-yloxy)-5,6,7,8-tetrahydronaphthalen-2-yl) cyclopentyl) methanol

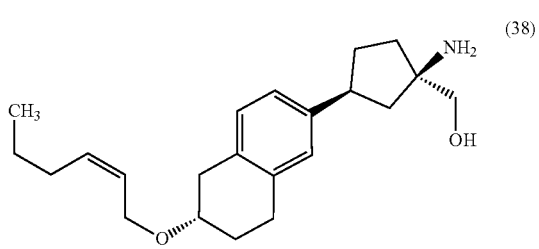 [SMILES: CCC/C=C\CO[C@H]1CCc2cc([C@H]3CC[C@](N)(CO)C3)ccc2C1]

(38)

Preparation 38A: 2-(((S)-6-((5R,7S)-2-oxo-3-oxa-1-azaspiro[4.4]nonan-7-yl)-1,2,3,4-tetrahydronaphthalen-2-yl)oxy)acetaldehyde

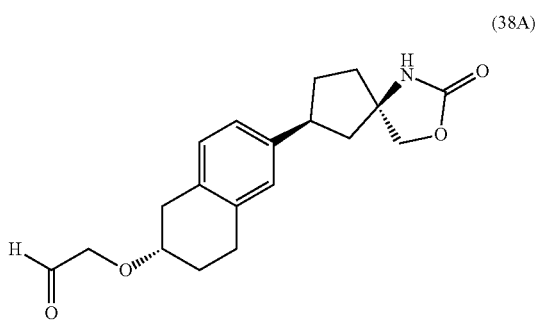 [SMILES: O=CCO[C@H]1CCc2cc([C@H]3CC[C@]4(COC(=O)N4)C3)ccc2C1]

(38A)

A solution of oxalyl dichloride (68.9 mg, 0.543 mmol) in DCM (3 ml) was stirred under $N_2$ and cooled to −78° C. DMSO (64.2 μl, 0.905 mmol) was then added dropwise and stirred for 1 h at the temperature, a solution of (5R,7S)-7-((S)-6-(2-hydroxyethoxy)-5,6,7,8-tetrahydronaphthalen-2-yl)-3-oxa-1-azaspiro[4.4]nonan-2-one (150 mg, 0.453 mmol) in DCM (3 mL) (several drops of DMSO was added to help dissolve the compound) was added dropwise and the mixture was stirred for 30 min. at −78° C. Then TEA (252 μl, 1.810 mmol) was added dropwise and the mixture was stirred for 15 min at −78° C. and warmed to room temperature and stirred for 15 min. The mixture was quenched with water (1 mL) at 0° C., diluted with EtOAc (50 mL), washed with saturated $NH_4Cl$ (2×30 mL), dried ($Na_2SO_4$) and concentrated under vacuo to give 2-(((S)-6-((5R,7S)-2-oxo-3-oxa-1-azaspiro[4.4]nonan-7-yl)-1,2,3,4-tetrahydronaphthalen-2-yl)oxy)acetaldehyde, (150 mg) as a white solid. LC/MS $M^{+1}$=330.

Preparation 38B (Isomer 1) (Condition 1): (5R,7S)-7-((S)-6-((Z)-hex-2-en-1-yloxy)-5,6,7,8-tetrahydronaphthalen-2-yl)-3-oxa-1-azaspiro[4.4]nonan-2-one

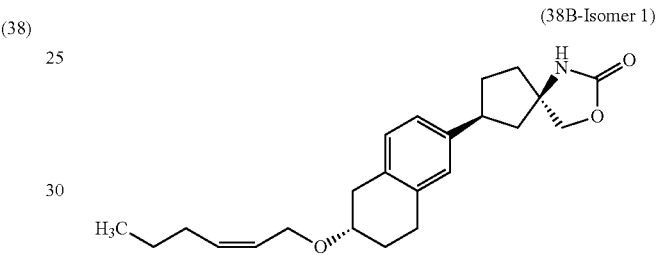

(38B-Isomer 1)

To a solution of butyltriphenylphosphonium bromide (116 mg, 0.364 mmol) in THF (3 mL) at −78° C. and under nitrogen was slowly added n-butyl lithium in hexane (239 μl, 0.383 mmol). The solution was stirred at −78° C. for 15 min, and then stirred at 0° C. for 30 min (light orange color). To the solution was added 2-(((S)-6-((5R,7S)-2-oxo-3-oxa-1-azaspiro[4.4]nonan-7-yl)-1,2,3,4-tetrahydronaphthalen-2-yl)oxy)acetaldehyde (60 mg, 0.182 mmol) in THF (3 mL) at −78° C. The reaction mixture was stirred at −78° C. for 15 min and stirred at room temperature for 2 h. The reaction was quenched with saturated aqueous ammonium chloride and extracted with ethyl acetate. The organic extract was washed with saturated $NH_4Cl$ (3×20 mL), dried over sodium sulfate, filtered, and concentrated in vacuo to give the desired product as white solid, (5R,7S)-7-((S)-6-((Z)-hex-2-en-1-yloxy)-5,6,7,8-tetrahydronaphthalen-2-yl)-3-oxa-1-azaspiro[4.4]nonan-2-one, LC/MS $M^{+1}$=370.

Preparation 38B (Isomer 2) (Condition 2): (5R,7S)-7-((S)-6-((E)-hex-2-en-1-yloxy)-5,6,7,8-tetrahydronaphthalen-2-yl)-3-oxa-1-azaspiro[4.4]nonan-2-one

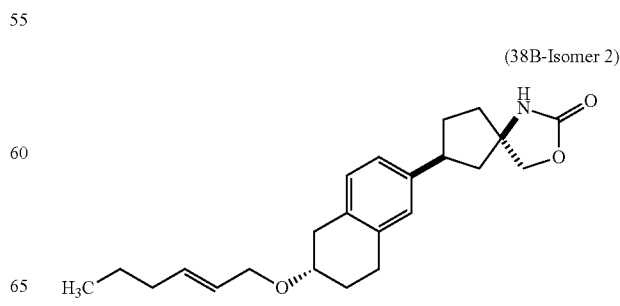

(38B-Isomer 2)

KHMDS (683 μl, 0.683 mmol) was added dropwise to a solution of 5-(butylsulfonyl)-1-phenyl-1H-tetrazole (80 mg, 0.301 mmol) and 2-(((S)-6-((5R,7S)-2-oxo-3-oxa-1-azaspiro[4.4]nonan-7-yl)-1,2,3,4-tetrahydronaphthalen-2-yl)oxy) acetaldehyde (90 mg, 0.273 mmol) in THF (15 ml) at −78° C. The resultant solution was stirred at the temperature for 2 h and warmed to room temperature and stirred for 16 h. Next, water (1 ml) was added with acetone-dry ice cooling, and the mixture was warmed to room temperature, followed by the addition of water (10 ml), extracted with EtOAc (30 ml), washed with saturated NaHCO$_3$(2×15 ml), brine (20 ml), dried (Na$_2$SO$_4$) and concentrated under vacuo to give the desired product which was purified with flash chromatography using ISCO column (12 g, EtOAc/Hexane=0%-40%), to give (5R,7S)-7-((S)-6-((E)-hex-2-en-1-yloxy)-5,6,7,8-tetrahydronaphthalen-2-yl)-3-oxa-1-azaspiro[4.4]nonan-2-one, 15 mg, LC/MS M$^{+1}$=370.

Example 38

To a solution of (5R,7S)-7-((S)-6-((Z)-hex-2-en-1-yloxy)-5,6,7,8-tetrahydronaphthalen-2-yl)-3-oxa-1-azaspiro[4.4] nonan-2-one (90 mg, 0.244 mmol) in dioxane (2 mL) was added lithium hydroxide (58.3 mg, 2.436 mmol) in water (1 mL) and stirred at 100° C. for 16 h. The reaction mixture was diluted with water and extracted with EtOAc. The organic layer was collected, dried over Na$_2$SO$_4$, concentrated on the rotavapor to give the crude product which was purified with preparative HPLC: column Phenomenex Luna C18 5 u 21.2×100 mm. Solvent A: 10% MeOH-90% H$_2$O-0.1% TFA; Solvent B: 90% MeOH-10% H$_2$O-0.1% TFA. Gradient time=15 min. Start B=0%, Final B 100%. Stop time 25 min. to afford ((1R,3S)-1-amino-3-((S)-6-((Z)-hex-2-en-1-yloxy)-5,6,7,8-tetrahydronaphthalen-2-yl)cyclopentyl) methanol, LC/MS M$^{+1}$=344. HPLC retention time=8.20 min. (Condition L), $^1$H NMR (400 MHz, METHANOL-d$_4$) δ 7.10-6.90 (m, 3H), 5.70-5.60 (m, 2H), 4.2 (m, 2H), 3.8 (m, 1H), 3.65 (m, 2H), 3.25-2.72 (m, 5H), 2.40 (m, 1H), 2.15 (m, 3H), 2.10-1.72 (m, 6H), 1.44 (m, 3H), 0.92 (t, J=7.5 Hz, 3H).

Using the general procedure of Example 38, the following compounds were prepared.

TABLE 3

| Ex. No. | Structure | MW | HPLC ret. time (min.) | HPLC condition | MS (M$^{+1}$) | Comment |
|---|---|---|---|---|---|---|
| 39 | 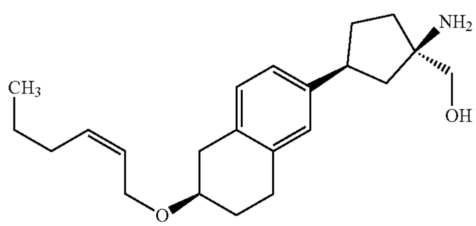 [SMILES: CCC/C=C\CO[C@@H]1CCc2cc([C@H]3CC[C@](N)(CO)C3)ccc2C1] | 343.5 | 8.21 | L | 344 | Step B Condition 1 |
| 40 | 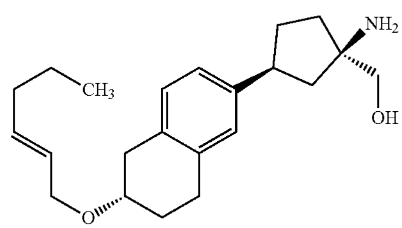 [SMILES: CCC/C=C/CO[C@H]1CCc2cc([C@H]3CC[C@](N)(CO)C3)ccc2C1] | 343.5 | 7.23 | L | 344 | Step B Condition 2 |
| 41 | 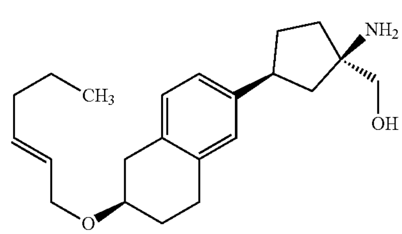 [SMILES: CCC/C=C/CO[C@@H]1CCc2cc([C@H]3CC[C@](N)(CO)C3)ccc2C1] | 343.5 | 7.25 | L | 344 | Step B Condition 2 |
| 42 | 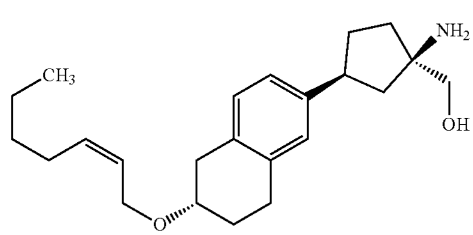 [SMILES: CCCC/C=C\CO[C@H]1CCc2cc([C@H]3CC[C@](N)(CO)C3)ccc2C1] | 357.5 | 7.62 | L | 358 | Step B Condition 1 |

Example 43

((1R,3S)-1-amino-3-((R)-6-((4-ethylbenzyl)oxy)-5,6,7,8-tetrahydronaphthalen-2-yl)cyclopentyl)methanol

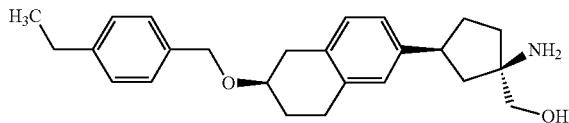
(43)

Preparation 43A: (R)-6-((5R,7S)-2-oxo-3-oxa-1-azaspiro[4.4]nonan-7-yl)-1,2,3,4-tetrahydronaphthalene-2-carbaldehyde

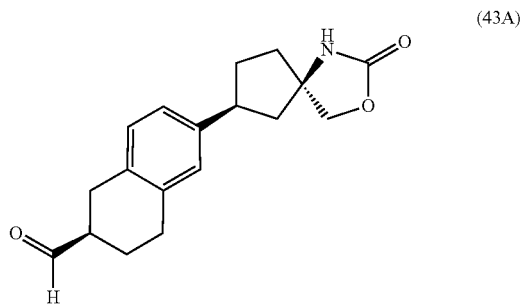 [SMILES: O=C[C@@H]1CCc2cc([C@H]3CC[C@]4(COC(=O)N4)C3)ccc2C1]
(43A)

A solution of oxalyl chloride (261 µl, 2.99 mmol) in DCM (5 ml) was stirred under N₂ and cooled to −78° C. DMSO (424 µl, 5.97 mmol) was then added dropwise and stirred for 1 h at the temperature, a solution of (5R,7S)-7-((R)-6-(hydroxymethyl)-5,6,7,8-tetrahydronaphthalen-2-yl)-3-oxa-1-azaspiro[4.4]nonan-2-one (Preparation 51C, 600 mg, 1.991 mmol) in DCM (3 ml)/1 ml of DMSO was added dropwise and the mixture was stirred for 30 min. at the same temperature. Then TEA (1110 µl, 7.96 mmol) was added dropwise and the mixture was stirred for 15 min and warmed to room temperature and stirred for another 15 min. The mixture was quenched with water (1 ml) at 0° C., diluted with EtOAc (50 ml), washed with saturated NH₄Cl (2×30 ml), dried (Na₂SO₄), and concentrated under vacuo. The residue was purified with flash chromatography (25 g, EtOAc/Hexane=0-100%, gradient time=15 min) to recover 500 mg desired product (R)-6-((5R,7S)-2-oxo-3-oxa-1-azaspiro[4.4]nonan-7-yl)-1,2,3,4-tetrahydronaphthalene-2-carbaldehyde (500 mg). LC/MS M$^{+1}$=300.

Preparation 43B: (5R,7S)-7-((R)-6-((S)-1-hydroxyethyl)-5,6,7,8-tetrahydronaphthalen-2-yl)-3-oxa-1-azaspiro[4.4]nonan-2-one

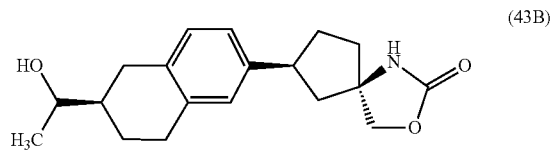 [SMILES: CC(O)[C@@H]1CCc2cc([C@H]3CC[C@]4(COC(=O)N4)C3)ccc2C1]
(43B)

To a stirred mixture of (R)-6-((5R,7S)-2-oxo-3-oxa-1-azaspiro[4.4]nonan-7-yl)-1,2,3,4-tetrahydronaphthalene-2-carbaldehyde (500 mg, 1.670 mmol) and THF (5 mL) was added a solution of methylmagnesium bromide (2227 µl, 6.68 mmol) (3M in diethyl ether) dropwise at −78° C. The solution was gradually warmed up to room temperature and stirred overnight under nitrogen. The reaction was quenched with water at 0° C. The mixture was extracted with EtOAc (30 ml), washed with saturated NH₄Cl (2×30 ml), brine (20 ml), dried (Na₂SO₄) and purified with flash chromatography (25 g, EtOAc/Hexane=0-100%, gradient time=12.5 min) to recover (5R,7S)-7-((R)-6-((S)-1-hydroxyethyl)-5,6,7,8-tetrahydronaphthalen-2-yl)-3-oxa-1-azaspiro[4.4]nonan-2-one (460 mg). LC/MS M$^{+1}$=316.

Preparation 43C: (5R,7S)-7-((R)-6-acetyl-5,6,7,8-tetrahydronaphthalen-2-yl)-3-oxa-1-azaspiro[4.4]nonan-2-one

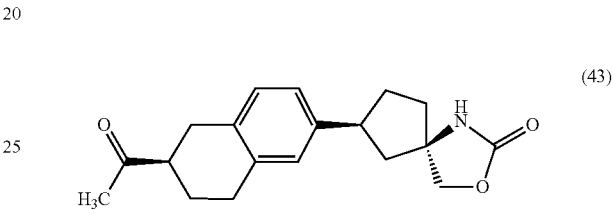
(43)

A solution of oxalyl chloride (511 µl, 5.83 mmol) in DCM (5 ml) was stirred under N₂ and cooled to −78° C. DMSO (621 µl, 8.75 mmol) was then added dropwise and the mixture was stirred for 1 h at −78° C. A solution of (5R,7S)-7-((R)-6-((S)-1-hydroxyethyl)-5,6,7,8-tetrahydronaphthalen-2-yl)-3-oxa-1-azaspiro[4.4]nonan-2-one (460 mg, 1.458 mmol) in DCM (3 ml) was added dropwise and the mixture was stirred for 30 min. at −78° C. Then TEA (1220 µl, 8.75 mmol) was added dropwise and the mixture was stirred for 15 min and warmed to room temperature and stirred for 15 min. The mixture was quenched with water (1 ml) at 0° C., diluted with EtOAc (50 ml), which was washed with saturated NH₄Cl (2×30 ml), dried (Na₂SO₄) and concentrated under vacuo. The residue was purified with flash chromatography (25 g, EtOAc/hexane=0-100%, gradient time=15 min) to recover the desired compound (5R,7S)-7-((R)-6-acetyl-5,6,7,8-tetrahydronaphthalen-2-yl)-3-oxa-1-azaspiro[4.4]nonan-2-one (239 mg). LC/MS M$^{+1}$=314.

Preparation 43D: (R)-6-((5R,7S)-2-oxo-3-oxa-1-azaspiro[4.4]nonan-7-yl)-1,2,3,4-tetrahydronaphthalen-2-yl acetate

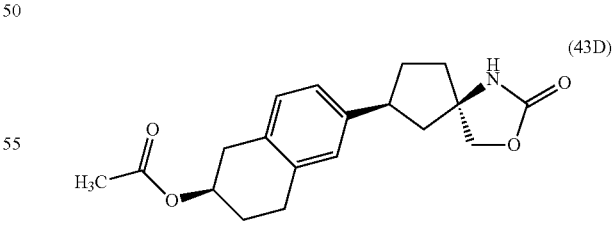
(43D)

To a solution of (5R,7S)-7-((R)-6-acetyl-5,6,7,8-tetrahydronaphthalen-2-yl)-3-oxa-1-azaspiro[4.4]nonan-2-one (220 mg, 0.702 mmol) in DCM (4 ml) was added 77% m-CPBA (315 mg, 1.404 mmol) in portions. The reaction mixture was stirred at room temperature for 60 h before it was washed with 0.2 N aqueous NaOH (10 ml). The wash solution was extracted back with DCM (2×15 ml). The combined organic extracts were dried over Na₂SO₄ and the solvent was removed in vacuo. The residue was purified with flash chromatography (12 g, EtOAc/Hexane=0-60%, gradient time=15 min) to recover the desired product (R)-6-((5R,7S)-2-oxo-3-oxa-1-azaspiro[4.4]nonan-7-yl)-1,2,3,4-tetrahydronaphthalen-2-yl acetate (220 mg). LC/MS M$^{+1}$=330.

Preparation 43E: (5R,7S)-7-((R)-6-hydroxy-5,6,7,8-tetrahydronaphthalen-2-yl)-3-oxa-1-azaspiro[4.4]nonan-2-one

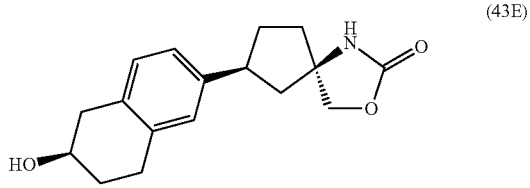 [SMILES: O=C1N[C@@]2(CC[C@H](c3ccc4c(c3)CC[C@@H](O)C4)C2)CO1]
(43E)

To the solution of (R)-6-((5R,7S)-2-oxo-3-oxa-1-azaspiro[4.4]nonan-7-yl)-1,2,3,4-tetrahydronaphthalen-2-yl acetate (200 mg, 0.607 mmol) in MeOH (2 ml), sodium hydroxide (1822 μl, 1.822 mmol) was added and the mixture was stirred at room temperature for 1 h. The mixture was taken in EtOAc (20 ml), washed with saturated NaHCO$_3$ (10 ml) and brine (10 ml), dried (Na$_2$SO$_4$) and concentrated under vacuo to get the desired product which was used to next step as was (5R,7S)-7-((R)-6-hydroxy-5,6,7,8-tetrahydronaphthalen-2-yl)-3-oxa-1-azaspiro[4.4]nonan-2-one (165 mg). LC/MS M$^{+1}$=288.

Preparation 43F: (5R,7S)-7-((R)-6-((4-ethylbenzyl)oxy)-5,6,7,8-tetrahydronaphthalen-2-yl)-3-oxa-1-azaspiro[4.4]nonan-2-one

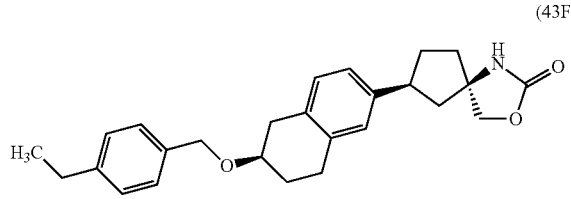 [SMILES: CCc1ccc(CO[C@@H]2CCc3cc([C@H]4CC[C@]5(COC(=O)N5)C4)ccc3C2)cc1]
(43F)

The (5R,7S)-7-((R)-6-hydroxy-5,6,7,8-tetrahydronaphthalen-2-yl)-3-oxa-1-azaspiro[4.4]nonan-2-one (15 mg, 0.052 mmol) was dissolved in anhydrous nitromethane (1.5 ml) in a dry 8 ml tube. Anhydrous iron (III) chloride (2 mg, 0.012 mmol), 4-ethylbenzaldehyde (14.01 mg, 0.104 mmol) and triethylsilane (12.14 mg, 0.104 mmol) were added and the resulting solution was stirred at room temperature for 2 h. Next, 10 ml of water was added and the aqueous layer was extracted with DCM (2×15 ml). The combined organic layers were washed with brine and dried (Na$_2$SO$_4$). The mixture was filtered and concentrated. The residue was purified via gradient flash chromatography (0-60% EtOAc in hexanes, ISCO column 12 g) which provided of the desired product (5R,7S)-7-((R)-6-((4-ethylbenzyl)oxy)-5,6,7,8-tetrahydronaphthalen-2-yl)-3-oxa-1-azaspiro[4.4]nonan-2-one (18 mg). LC/MS M$^{+1}$=406.

Example 43

(5R,7S)-7-((R)-6-((4-ethylbenzyl)oxy)-5,6,7,8-tetrahydronaphthalen-2-yl)-3-oxa-1-azaspiro[4.4]nonan-2-one (20 mg, 0.049 mmol) was mixed with lithium hydroxide hydrate (31.0 mg, 0.740 mmol) in 1,4-dioxane (2 ml) and water (0.5 ml), the mixture was stirred at 100° C. overnight under N$_2$. The solution was concentrated under vacuo and the residue was dissolved in DCM (40 ml), washed with water (15 ml) and brine (10 ml), dried (Na$_2$SO$_4$) and concentrated. The solid was mixed with MeCN (2 ml), the solvent was removed, and the solid was dried under vacuum overnight to give the crude product which was purified with preparative HPLC. Phenomenex Luna C 18 5 u (21.2×150 mm), Solvent A: 10% MeOH-90% H$_2$O-0.1% TFA; Solvent B: 90% MeOH-10% H$_2$O-0.1% TFA, Start B %=0, Final % B=100. Gradient time 15 min, stop time 20 min. to afford ((1R,3S)-1-amino-3-((R)-6-((4-ethylbenzyl)oxy)-5,6,7,8-tetrahydronaphthalen-2-yl) cyclopentyl) methanol (15 mg). LC/MS M$^{+1}$=380. HPLC Rt=7.61 (condition L). $^1$H NMR (400 MHz, METHANOL-d$_4$) δ 7.35-7.25 (m, 2H), 7.23-7.15 (m, 2H), 7.06-6.94 (m, 3H), 4.66-4.55 (m, 2H), 3.94-3.83 (m, 1H), 3.57-3.41 (m, 2H), 3.12-2.88 (m, 3H), 2.84-2.59 (m, 4H), 2.26-1.66 (m, 7H), 1.59-1.46 (m, 1H), 1.29-1.17 (m, 3H).

The examples in Table 4 were prepared according to the general procedure of Example 43.

TABLE 4

| Ex. No. | Structure | MW | HPLC ret. time (min.) | HPLC condition | MS (M$^{+1}$) |
|---|---|---|---|---|---|
| 44 | 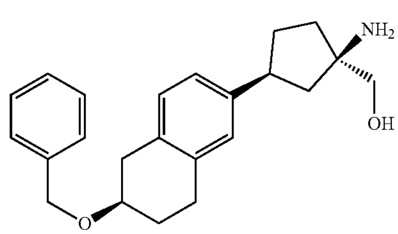 [SMILES: N[C@]1(CO)CC[C@H](c2ccc3c(c2)CC[C@@H](OCc2ccccc2)C3)C1] | 351.49 | 6.70 | L | 352 |

TABLE 4-continued
| Ex. No. | Structure | MW | HPLC ret. time (min.) | HPLC condition | MS (M+1) |
|---|---|---|---|---|---|
| 45 | 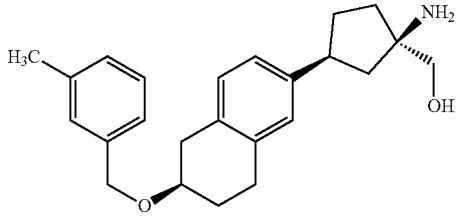 [SMILES: Cc1cccc(CO[C@@H]2CCc3cc([C@H]4CC[C@](N)(CO)C4)ccc3C2)c1] | 365.51 | 8.17 | L | 366 |
| 46 | 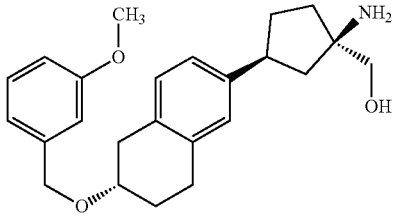 [SMILES: COc1cccc(CO[C@H]2CCc3cc([C@H]4CC[C@](N)(CO)C4)ccc3C2)c1] | 381.51 | 6.82 | L | 382 |
| 47 | 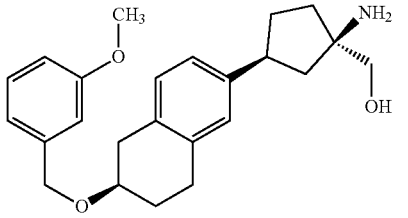 [SMILES: COc1cccc(CO[C@@H]2CCc3cc([C@H]4CC[C@](N)(CO)C4)ccc3C2)c1] | 381.51 | 6.82 | L | 382 |
| 48 | 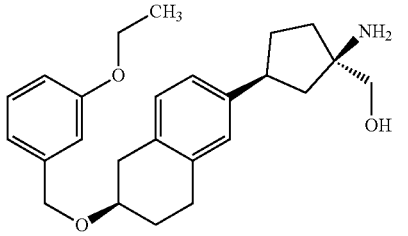 [SMILES: CCOc1cccc(CO[C@@H]2CCc3cc([C@H]4CC[C@](N)(CO)C4)ccc3C2)c1] | 395.54 | 7.10 | L | 396 |
| 49 | 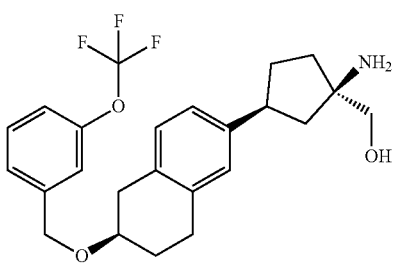 [SMILES: N[C@]1(CO)CC[C@H](c2ccc3c(c2)CC[C@@H](OCc2cccc(OC(F)(F)F)c2)C3)C1] | 435.48 | 8.82 | L | 436 |

Examples 50 and 51

((1R,3S)-1-amino-3-(6-((benzyloxy)methyl)-5,6,7,8-tetrahydronaphthalen-2-yl) cyclopentyl)methanol

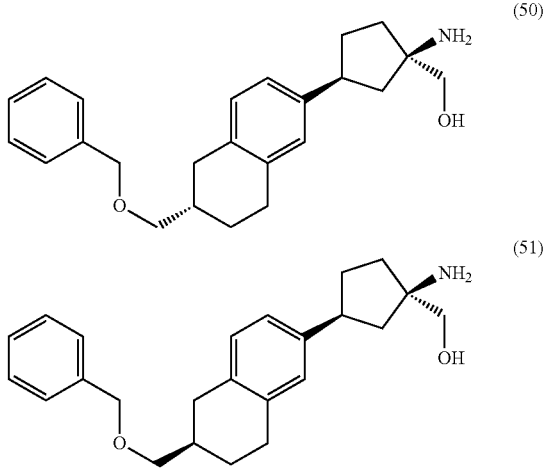

Preparation 50A: Methyl 4-oxo-6-((5R,7S)-2-oxo-3-oxa-1-azaspiro[4.4]nonan-7-yl)-1,2,3,4-tetrahydronaphthalene-2-carboxylate

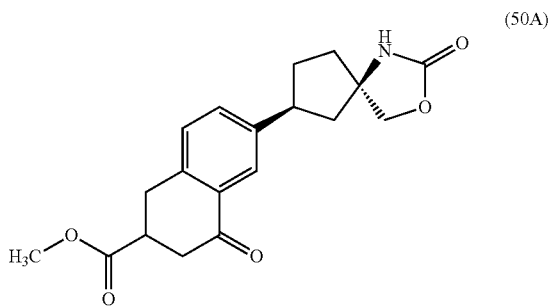 [SMILES: COC(=O)C1CC(=O)c2cc([C@H]3CC[C@]4(COC(=O)N4)C3)ccc2C1]

To a mixture of potassium carbonate (523 mg, 3.78 mmol), (5R,7S)-7-(4-bromophenyl)-3-oxa-1-azaspiro[4.4]nonan-2-one (800 mg, 2.70 mmol), itaconic acid (457 mg, 3.51 mmol), and acetonitrile (8 mL) was added water (2.4 mL). The mixture was stirred till the evolution of carbon dioxide stopped and then bubbled with nitrogen for 3 min. After palladium(II) acetate (30.3 mg, 0.135 mmol) and tri-o-tolylphosphine (82 mg, 0.270 mmol) were added, the mixture was bubbled with nitrogen for an additional 3 min. The mixture was stirred at 80° C. for 20 h and then concentrated. The residue was mixed with water (40 mL), basified with potassium carbonate and filtered. The filtrate was washed with diethyl ether (2×15), acidified to pH approximately 2 with 6N aqueous hydrochloric acid. The solid was separated and the aqueous solution was extracted with a mixture of THF/EtOAc (3:1) (4×10 mL). The solid and the extracts were combined and concentrated. LC/MS $[M-H_2O]^{+1}=328$.

The residue was mixed with THF (5 mL), ethyl acetate (5 mL), methanol (20 mL), and 10% Pd/C (400 mg, 0.376 mmol) and hydrogenated under hydrogen balloon overnight. The catalyst was filtered off through a membrane filter and washed with methanol. The filtrate was concentrated and lyophilized to give a solid. LC/MS $[M-H_2O]^{+1}=330$.

The solid was mixed with 98% sulfuric acid (15 mL, 281 mmol). The clear solution was stirred at room temperature for 4 h. Methanol (8 mL, 198 mmol) was added slowly with water-bath cooling. The mixture was stirred at room temperature for 1 h before being poured onto ice (150 g). The mixture was extracted with ethyl acetate (4×40 mL). The combined ethyl acetate extracts were washed with saturated aqueous sodium bicarbonate solution (20 mL), dried over anhydrous sodium sulfate, and concentrated under reduced pressure. Flash chromatography purification (24 g silica gel column, gradient elution from 10 to 100% ethyl acetate in hexanes) afforded methyl 4-oxo-6-((5R,7S)-2-oxo-3-oxa-1-azaspiro[4.4]nonan-7-yl)-1,2,3,4-tetrahydronaphthalene-2-carboxylate (440 mg, 1.281 mmol). LC/MS $M^{+1}=344$.

Preparation 50B: Methyl 6-((5R,7S)-2-oxo-3-oxa-1-azaspiro[4.4]nonan-7-yl)-1,2,3,4-tetrahydronaphthalene-2-carboxylate

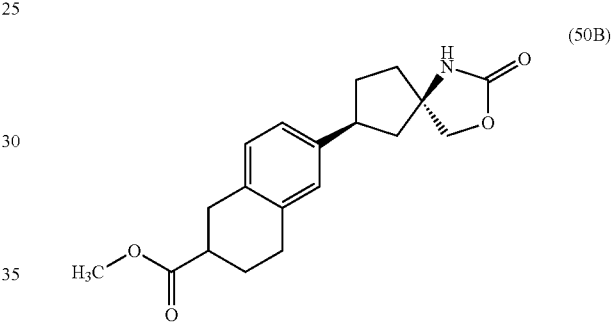

A mixture of methyl 4-oxo-6-((5R,7S)-2-oxo-3-oxa-1-azaspiro[4.4]nonan-7-yl)-1,2,3,4-tetrahydronaphthalene-2-carboxylate (440 mg, 1.281 mmol), MeOH (15 mL), acetic acid (1.5 mL), and 10% Pd/C (200 mg, 0.188 mmol) was hydrogenated under hydrogen balloon over a period of two days. The mixture was filtered through a membrane filter. The filtrate was concentrated to give methyl 6-((5R,7S)-2-oxo-3-oxa-1-azaspiro[4.4]nonan-7-yl)-1,2,3,4-tetrahydronaphthalene-2-carboxylate (337 mg, 1.023 mmol) as a white solid. LC/MS $M^{+1}=330$.

Preparations 50C and 51C: (5R,7S)-7-(6-(hydroxymethyl)-5,6,7,8-tetrahydronaphthalen-2-yl)-3-oxa-1-azaspiro[4.4]nonan-2-one

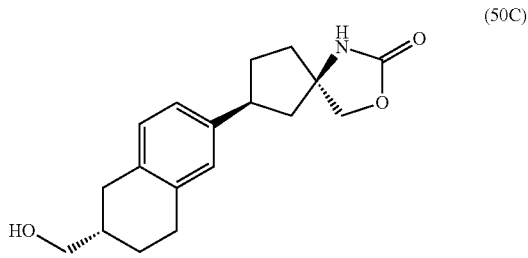

(51C)

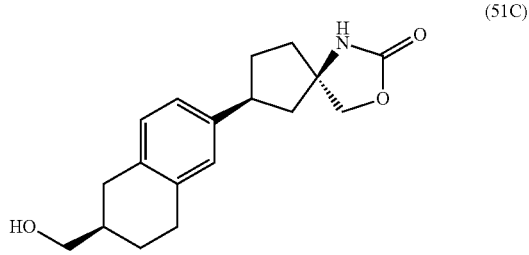

A mixture of methyl 6-((5R,7S)-2-oxo-3-oxa-1-azaspiro[4.4]nonan-7-yl)-1,2,3,4-tetrahydronaphthalene-2-carboxylate (337 mg, 1.023 mmol), anhydrous tetrahydrofuran (3 mL), and 2N THF solution of lithium borohydride (2.56 mL, 5.12 mmol) was stirred at 70° C. for 4 h. Saturated aqueous ammonium chloride solution was added slowly at 0° C. to quench the reaction. Water and ethyl acetate were added. The aqueous solution was extracted with ethyl acetate. The combined ethyl acetate solutions were dried over anhydrous sodium sulfate and concentrated under reduced pressure to give (5R,7S)-7-(6-(hydroxymethyl)-5,6,7,8-tetrahydronaphthalen-2-yl)-3-oxa-1-azaspiro[4.4]nonan-2-one (300 mg, 0.995 mmol). LC/MS M$^{+1}$=302. Chiral SFC separation (AD-H (0.46×25 cm), 45% MeOH in CO$_2$, 3 ml/min, 220 nm, 35° C.) gave enantiomers 50C and 51C as white solids. Isomer 50C: (5R,7S)-7-((S)-6-(hydroxymethyl)-5,6,7,8-tetrahydronaphthalen-2-yl)-3-oxa-1-azaspiro[4.4]nonan-2-one. Isomer 51C: (5R,7S)-7-((R)-6-(hydroxymethyl)-5,6,7,8-tetrahydronaphthalen-2-yl)-3-oxa-1-azaspiro[4.4]nonan-2-one. Each enantiomer was independently converted to derivatives as illustrated below.

Preparation 51D: ((R)-6-((5R,7S)-2-oxo-3-oxa-1-azaspiro[4.4]nonan-7-yl)-1,2,3,4-tetrahydronaphthalen-2-yl)methyl 4-methylbenzene sulfonate (51D)

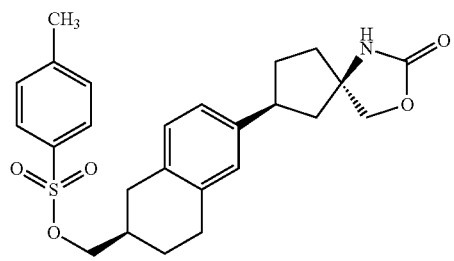

(5R,7S)-7-((R)-6-(hydroxymethyl)-5,6,7,8-tetrahydronaphthalen-2-yl)-3-oxa-1-azaspiro[4.4]nonan-2-one (enantiomer 51C; 690 mg, 2.289 mmol) was dissolved in dry pyridine (5 mL) and p-toluenesulfonyl chloride (1309 mg, 6.87 mmol) was added in one portion. The resulting mixture was reacted at room temperature for 4 h. The solvent was removed in vacuo. The residue was dissolved in methylene chloride and methanol. Flash chromatography purification (40 g silica gel column, gradient elution from 20 to 100% ethyl acetate in hexanes) afforded ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (860 mg, 1.888 mmol) as a white solid. LC/MS M$^{+1}$=456.

Example 51

To a stirred mixture of benzyl alcohol (0.031 mL, 0.296 mmol) and 1N THF solution of potassium tert-butoxide (0.263 mL, 0.263 mmol) was added ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (15 mg, 0.033 mmol). The resulting mixture was stirred at 70° C. under nitrogen overnight. The mixture was concentrated. The residue was mixed with water (0.5 mL), lithium hydroxide monohydrate (28 mg, 0.66 mmol), and dioxane (1 mL). The resulting mixture was stirred at 100° C. under nitrogen for 7 h and room temperature overnight. The mixture was extracted with ethyl acetate (4×1 mL) and the combined ethyl acetate extracts were dried and concentrated. The crude material was purified via preparative LC/MS with the following conditions: Column: Waters XBridge C18, 19×150 mm, 5-μm particles; Guard Column: Waters XBridge C18, 19×10 mm, 5-m particles; Mobile Phase A: 5:95 acetonitrile:water with 10-mM ammonium acetate; Mobile Phase B: 95:5 acetonitrile:water with 10 mM ammonium acetate; Gradient: 15-100% B over 15 minutes, then a 5-minute hold at 100% B; Flow: 20 mL/min. Fractions containing the desired product were combined and dried to give ((1R,3S)-1-amino-3-((R)-6-((benzyloxy)methyl)-5,6,7,8-tetrahydronaphthalen-2-yl)cyclopentyl)methanol (8.0 mg, 0.022 mmol) as a solid. HPLC retention time=1.66 min (condition A) LC/MS M$^{+1}$=366. $^1$H NMR (500 MHz, METHANOL-d$_4$) δ 7.38-7.34 (m, 4H), 7.33-7.27 (m, 1H), 7.03-6.96 (m, 3H), 4.56 (s, 2H), 3.56-3.44 (m, 4H), 3.08-2.97 (m, 1H), 2.87 (dd, J=15.9, 4.5 Hz, 1H), 2.83-2.77 (m, 2H), 2.47 (dd, J=16.3, 10.9 Hz, 1H), 2.26 (dd, J=12.9, 7.4 Hz, 1H), 2.16-1.98 (m, 3H), 1.98-1.86 (m, 1H), 1.84-1.69 (m, 2H), 1.61-1.53 (m, 1H), 1.51-1.40 (m, 1H).

Example 50

Example 50 was prepared from Isomer 50C: (5R,7S)-7-((S)-6-(hydroxymethyl)-5,6,7,8-tetrahydronaphthalen-2-yl)-3-oxa-1-azaspiro[4.4]nonan-2-one using the procedures of Step D and Step E. HPLC retention time=1.65 min (condition A); LC/MS M+1=366. $^1$H NMR (500 MHz, METHANOL-d$_4$) δ 7.62 (s, 1H), 7.34-7.38 (m, 3H), 7.30 (dq, J=8.8, 4.2 Hz, 1H), 7.04-6.96 (m, 3H), 4.56 (s, 2H), 3.61-3.50 (m, 2H), 3.48 (d, J=6.9 Hz, 2H), 3.10-2.98 (m, 1H), 2.88 (dd, J=16.3, 4.5 Hz, 1H), 2.83-2.76 (m, 2H), 2.47 (dd, J=16.3, 10.4 Hz, 1H), 2.33 (dd, J=13.4, 7.4 Hz, 1H), 2.17-1.99 (m, 3H), 1.99-1.79 (m, 3H), 1.66 (t, J=12.4 Hz, 1H), 1.51-1.39 (m, 1H).

The Examples in Table 5 were prepared according to the general procedures of Examples 50 and 51.

TABLE 5

| Ex. No. | Structure | MW | HPLC ret. time (min.) | HPLC condition | MS (M+1) | Comment |
|---|---|---|---|---|---|---|
| 52 | | 331.5 | 1.68 | A | 332 | Isomer 1 |
| 53 | | 331.5 | 3.09 | A | 332 | Isomer 2 |
| 54 | | 345.5 | 1.85 | A | 346 | Isomer 1 |
| 55 | | 345.5 | 1.85 | A | 346 | Isomer 2 |
| 56 | | 369.5 | 1.68 | A | 370 | Isomer 1 |
| 57 | | 369.5 | 3.18 | A | 370 | Isomer 2 |
| 58 | | 347.5 | 1.06 | A | 348 | Isomer 1 |
| 59 | | 361.5 | 1.18 | A | 362 | Isomer 1 |
| 60 | | 347.5 | 1.07 | A | 348 | Isomer 1 |
| 61 | | 347.5 | 1.07 | A | 348 | Isomer 2 |

TABLE 5-continued

| Ex. No. | Structure | MW | HPLC ret. time (min.) | HPLC condition | MS (M$^{+1}$) | Comment |
|---|---|---|---|---|---|---|
| 62 | 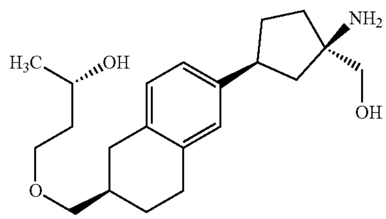 [SMILES: C[C@H](O)CCOC[C@@H]1CCc2cc([C@H]3CC[C@](N)(CO)C3)ccc2C1] | 347.5 | 1.07 | A | 348 | Isomer 1 |
| 63 | 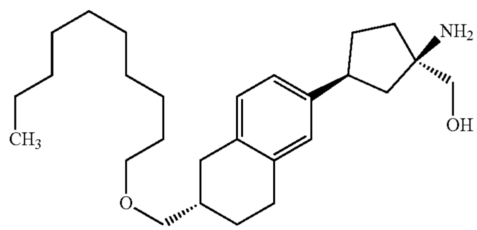 [SMILES: CCCCCCCCCCOC[C@H]1CCc2cc([C@H]3CC[C@](N)(CO)C3)ccc2C1] | 415.7 | 2.51 | A | 416 | |
| 64 | 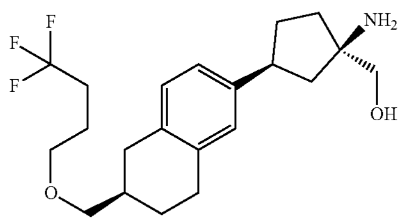 [SMILES: N[C@]1(CO)CC[C@H](c2ccc3c(c2)CC[C@@H](COCCCC(F)(F)F)C3)C1] | 385.5 | 1.39 | A | 386 | |
| 65 | 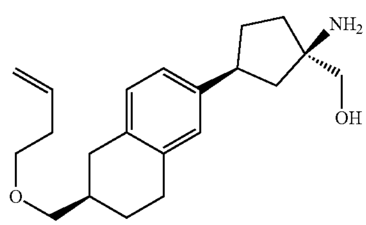 [SMILES: C=CCCOC[C@@H]1CCc2cc([C@H]3CC[C@](N)(CO)C3)ccc2C1] | 329.5 | 6.62 | L | 330 | |
| 66 | 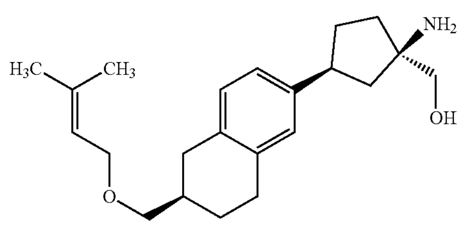 [SMILES: CC(C)=CCOC[C@@H]1CCc2cc([C@H]3CC[C@](N)(CO)C3)ccc2C1] | 343.5 | 6.97 | L | 344 | |
| 67 | 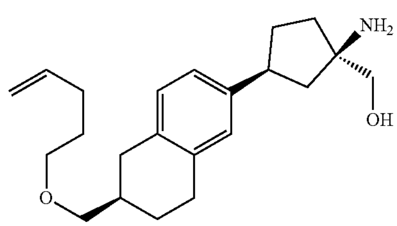 [SMILES: C=CCCCOC[C@@H]1CCc2cc([C@H]3CC[C@](N)(CO)C3)ccc2C1] | 343.5 | 7.15 | L | 344 | |
| 68 | 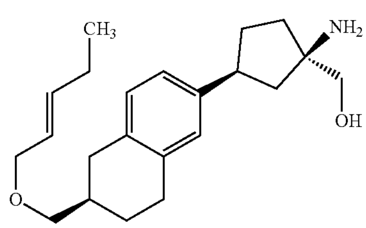 [SMILES: CC/C=C/COC[C@@H]1CCc2cc([C@H]3CC[C@](N)(CO)C3)ccc2C1] | 343.5 | 7.17 | L | 344 | |

TABLE 5-continued

| Ex. No. | Structure | MW | HPLC ret. time (min.) | HPLC condition | MS (M$^{+1}$) | Comment |
|---|---|---|---|---|---|---|
| 69 | 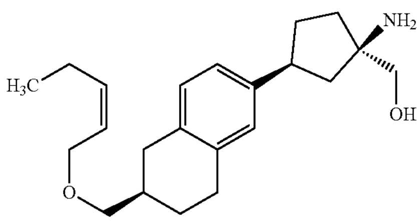 [SMILES: CC/C=C\COC[C@@H]1CCc2cc([C@H]3CC[C@](N)(CO)C3)ccc2C1] | 343.5 | 7.11 | L | 344 | |
| 70 | 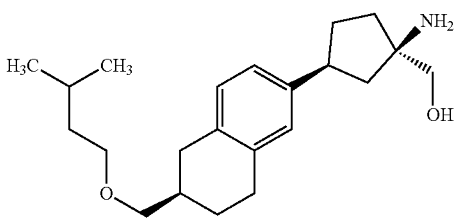 | 345.5 | 3.25 | C | 346 | |
| 71 | 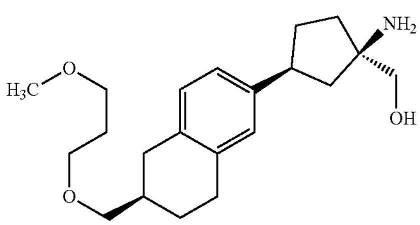 [SMILES: COCCCOC[C@@H]1CCc2cc([C@H]3CC[C@](N)(CO)C3)ccc2C1] | 347.5 | 5.60 | L | 348 | |
| 72 | 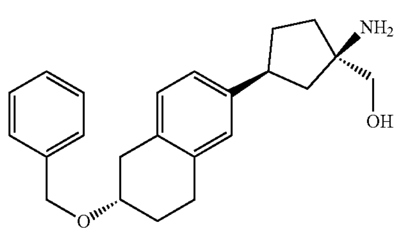 [SMILES: N[C@]1(CO)CC[C@H](c2ccc3c(c2)CC[C@H](OCc2ccccc2)C3)C1] | 351.5 | 8.26 | L | 353 | Preparation (6S)-50D was used |
| 73 | 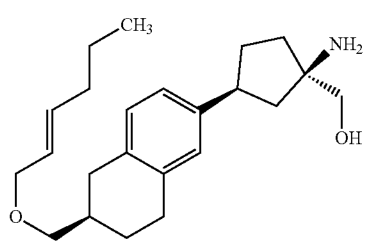 [SMILES: CCC/C=C/COC[C@@H]1CCc2cc([C@H]3CC[C@](N)(CO)C3)ccc2C1] | 357.5 | 7.83 | L | 358 | |
| 74 | 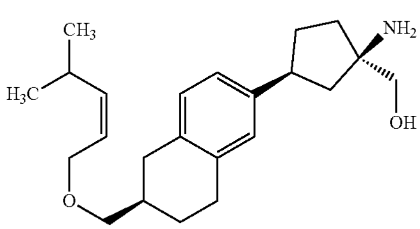 [SMILES: CC(C)/C=C\COC[C@@H]1CCc2cc([C@H]3CC[C@](N)(CO)C3)ccc2C1] | 357.5 | 7.65 | L | 358 | |

TABLE 5-continued
| Ex. No. | Structure | MW | HPLC ret. time (min.) | HPLC condition | MS (M+1) | Comment |
|---|---|---|---|---|---|---|
| 75 | 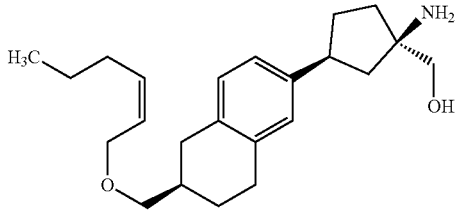 [SMILES: CCC/C=C\COC[C@@H]1CCc2cc([C@H]3CC[C@](N)(CO)C3)ccc2C1] | 357.5 | 7.73 | L | 358 | |
| 76 | 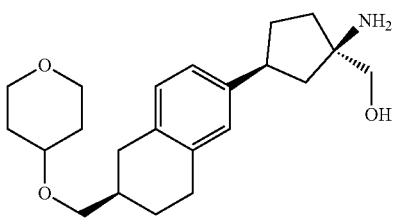 [SMILES: N[C@]1(CO)CC[C@H](c2ccc3c(c2)CC[C@@H](COC2CCOCC2)C3)C1] | 359.5 | 6.50 | L | 360 | |
| 77 | 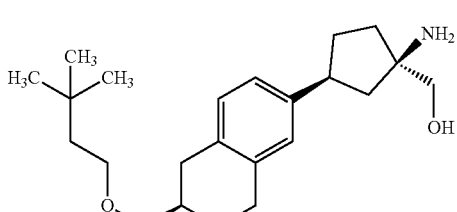 | 359.6 | 3.33 | C | 360 | |
| 78 | 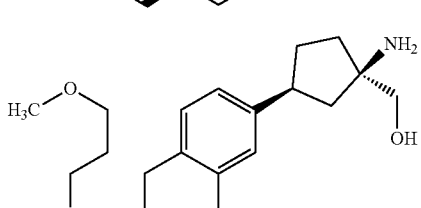 | 361.5 | 5.97 | L | 362 | |
| 79 | 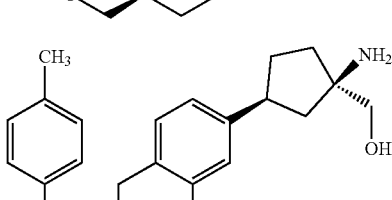 | 365.5 | 7.64 | L | 366 | Preparation (6S)-50D was used |
| 80 | 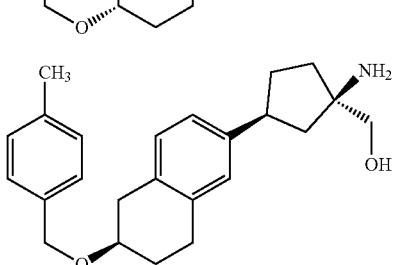 | 365.5 | 8.78 | L | 366 | |
| 81 | 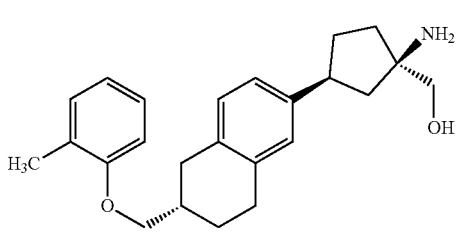 [SMILES: Cc1ccccc1OC[C@H]1CCc2cc([C@H]3CC[C@](N)(CO)C3)ccc2C1] | 365.5 | 7.76 | L | 366 | Preparation (6S)-50D was used |

TABLE 5-continued

| Ex. No. | Structure | MW | HPLC ret. time (min.) | HPLC condition | MS (M$^{+1}$) | Comment |
|---|---|---|---|---|---|---|
| 82 | 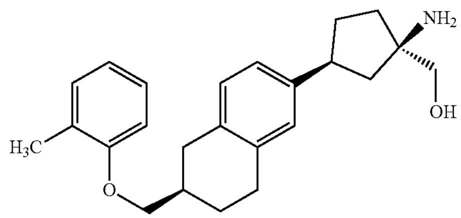 [SMILES: Cc1ccccc1OC[C@@H]1CCc2cc([C@H]3CC[C@](N)(CO)C3)ccc2C1] | 365.5 | 8.84 | L | 366 | |
| 83 | 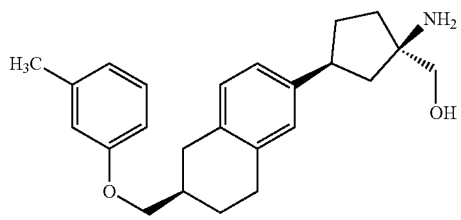 [SMILES: Cc1cccc(OC[C@@H]2CCc3cc([C@H]4CC[C@](N)(CO)C4)ccc3C2)c1] | 365.5 | 8.75 | L | 366 | |
| 84 | 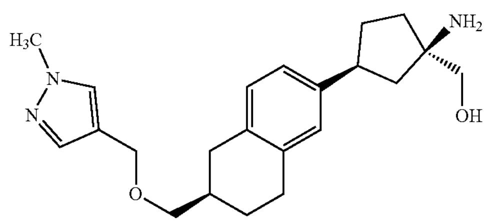 [SMILES: Cn1cc(COC[C@@H]2CCc3cc([C@H]4CC[C@](N)(CO)C4)ccc3C2)cn1] | 369.5 | 5.09 | L | 370 | |
| 85 | 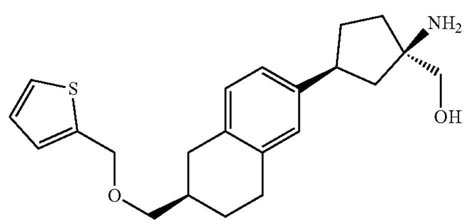 [SMILES: N[C@]1(CO)CC[C@H](c2ccc3c(c2)CC[C@@H](COCc2cccs2)C3)C1] | 371.5 | 6.89 | L | 372 | |
| 86 | 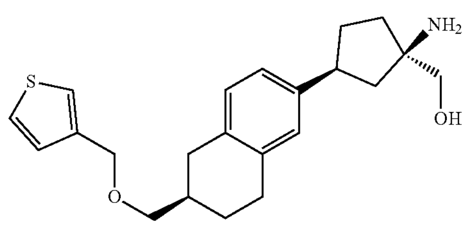 [SMILES: N[C@]1(CO)CC[C@H](c2ccc3c(c2)CC[C@@H](COCc2ccsc2)C3)C1] | 371.5 | 6.80 | L | 372 | |
| 87 | 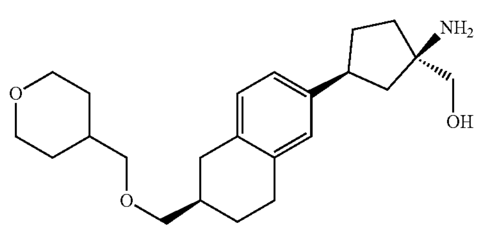 [SMILES: N[C@]1(CO)CC[C@H](c2ccc3c(c2)CC[C@@H](COCC2CCOCC2)C3)C1] | 373.5 | 6.97 | L | 374 | |
| 88 | 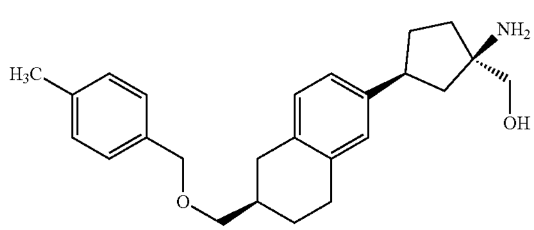 [SMILES: Cc1ccc(COC[C@@H]2CCc3cc([C@H]4CC[C@](N)(CO)C4)ccc3C2)cc1] | 379.5 | 7.51 | L | 380 | |

TABLE 5-continued

| Ex. No. | Structure | MW | HPLC ret. time (min.) | HPLC condition | MS (M+1) | Comment |
|---|---|---|---|---|---|---|
| 89 | 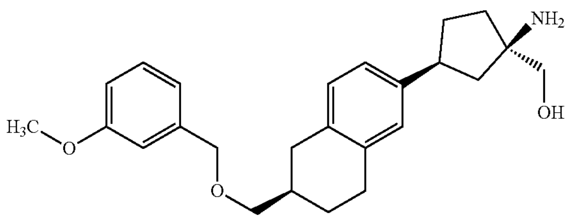 [SMILES: COc1cccc(COC[C@@H]2CCc3cc([C@H]4CC[C@](N)(CO)C4)ccc3C2)c1] | 381.5 | 2.88 | C | 382 | |
| 90 | 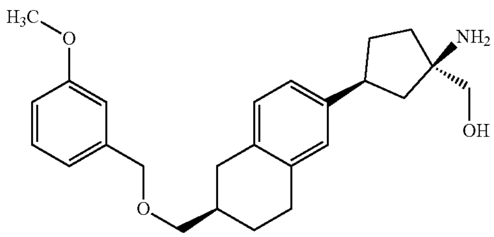 [SMILES: COc1cccc(COC[C@@H]2CCc3cc([C@H]4CC[C@](N)(CO)C4)ccc3C2)c1] | 381.5 | 3.01 | C | 382 | |
| 91 | 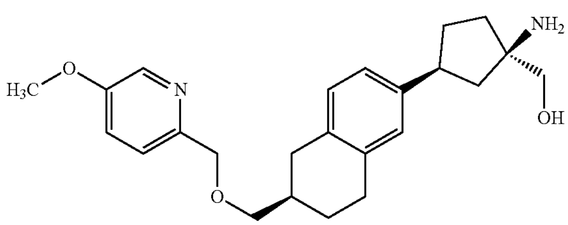 [SMILES: COc1ccc(COC[C@@H]2CCc3cc([C@H]4CC[C@](N)(CO)C4)ccc3C2)nc1] | 382.5 | 4.23 | L | 383 | |
| 92 | 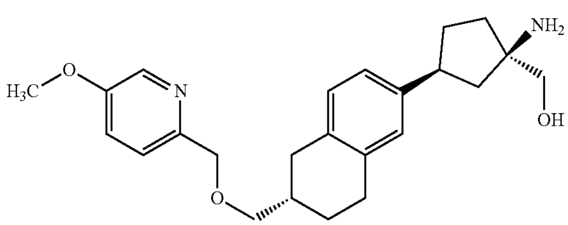 [SMILES: COc1ccc(COC[C@H]2CCc3cc([C@H]4CC[C@](N)(CO)C4)ccc3C2)nc1] | 382.5 | 4.22 | L | 383 | Preparation (6S)-50D was used |
| 93 | 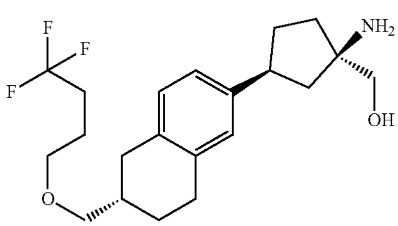 [SMILES: N[C@]1(CO)CC[C@H](c2ccc3c(c2)CC[C@H](COCCCC(F)(F)F)C3)C1] | 385.5 | 2.96 | C | 386 | |
| 94 | 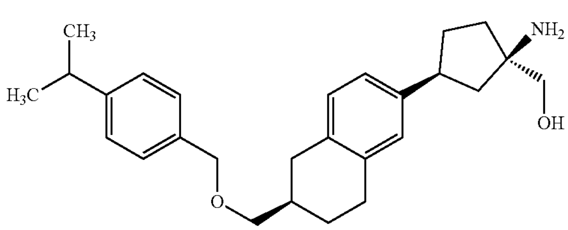 [SMILES: CC(C)c1ccc(COC[C@@H]2CCc3cc([C@H]4CC[C@](N)(CO)C4)ccc3C2)cc1] | 393.6 | 8.49 | L | 394 | |

TABLE 5-continued

| Ex. No. | Structure | MW | HPLC ret. time (min.) | HPLC condition | MS (M+1) | Comment |
|---|---|---|---|---|---|---|
| 95 | 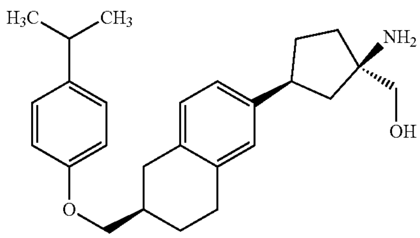 [SMILES: CC(C)c1ccc(OC[C@@H]2CCc3cc([C@H]4CC[C@](N)(CO)C4)ccc3C2)cc1] | 393.6 | 8.58 | L | 394 | |
| 96 | 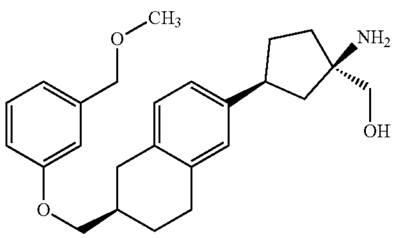 [SMILES: COCc1cccc(OC[C@@H]2CCc3cc([C@H]4CC[C@](N)(CO)C4)ccc3C2)c1] | 395.5 | 6.98 | L | 396 | |
| 97 | 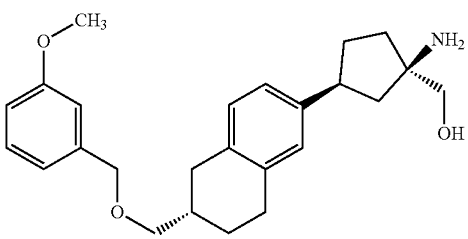 [SMILES: COc1cccc(COC[C@H]2CCc3cc([C@H]4CC[C@](N)(CO)C4)ccc3C2)c1] | 395.5 | 7.11 | L | 396 | Preparation (6S)-50D was used |
| 98 | 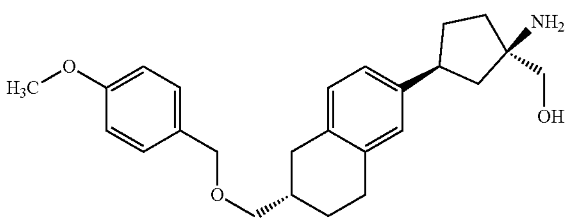 [SMILES: COc1ccc(COC[C@H]2CCc3cc([C@H]4CC[C@](N)(CO)C4)ccc3C2)cc1] | 395.5 | 7.03 | L | 396 | Preparation (6S)-50D was used |
| 99 | 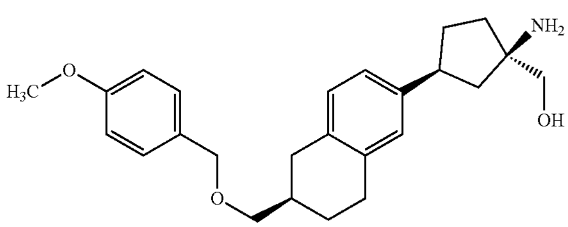 [SMILES: COc1ccc(COC[C@@H]2CCc3cc([C@H]4CC[C@](N)(CO)C4)ccc3C2)cc1] | 395.5 | 6.97 | L | 396 | |
| 100 | 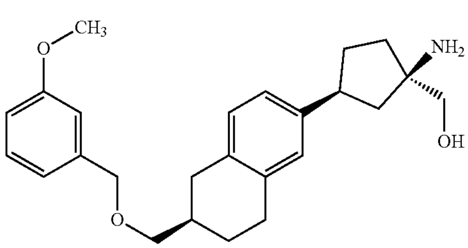 [SMILES: COc1cccc(COC[C@@H]2CCc3cc([C@H]4CC[C@](N)(CO)C4)ccc3C2)c1] | 395.5 | 7.07 | L | 396 | |

TABLE 5-continued

| Ex. No. | Structure | MW | HPLC ret. time (min.) | HPLC condition | MS (M+1) | Comment |
|---|---|---|---|---|---|---|
| 101 | 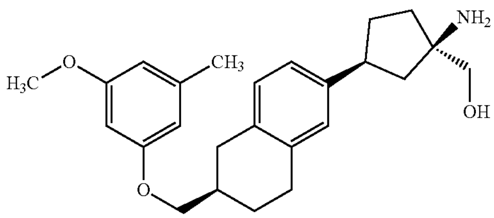 [SMILES: COc1cc(C)cc(OC[C@@H]2CCc3cc([C@H]4CC[C@](N)(CO)C4)ccc3C2)c1] | 395.5 | 7.56 | L | 396 | |
| 102 | 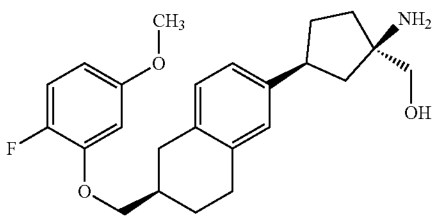 [SMILES: COc1ccc(F)c(OC[C@@H]2CCc3cc([C@H]4CC[C@](N)(CO)C4)ccc3C2)c1] | 399.5 | 6.50 | L | 360 | |
| 103 | 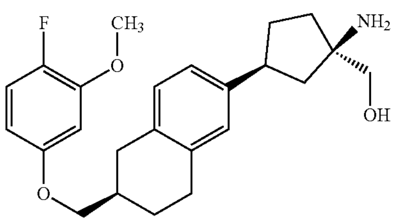 [SMILES: COc1cc(OC[C@@H]2CCc3cc([C@H]4CC[C@](N)(CO)C4)ccc3C2)ccc1F] | 399.5 | 8.21 | L | 400 | |
| 104 | 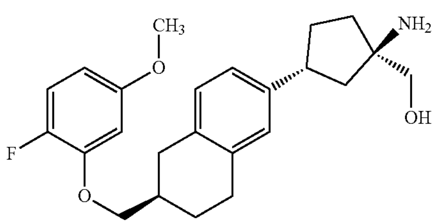 [SMILES: COc1ccc(F)c(OC[C@@H]2CCc3cc([C@@H]4CC[C@](N)(CO)C4)ccc3C2)c1] | 399.5 | 7.12 | L | 400 | |
| 105 | 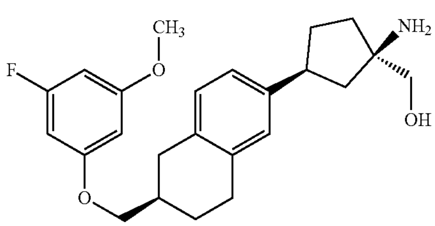 [SMILES: COc1cc(F)cc(OC[C@@H]2CCc3cc([C@H]4CC[C@](N)(CO)C4)ccc3C2)c1] | 399.5 | 7.56 | L | 400 | |
| 106 | 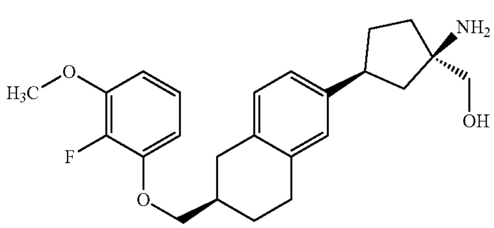 [SMILES: COc1cccc(OC[C@@H]2CCc3cc([C@H]4CC[C@](N)(CO)C4)ccc3C2)c1F] | 399.5 | 7.04 | L | 400 | |
| 107 | 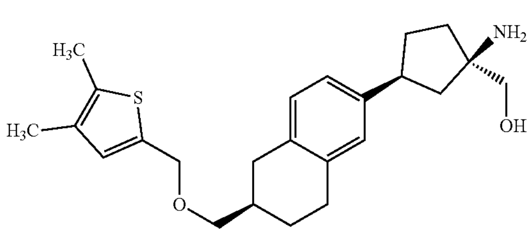 [SMILES: Cc1cc(COC[C@@H]2CCc3cc([C@H]4CC[C@](N)(CO)C4)ccc3C2)sc1C] | 399.6 | 7.72 | L | 400 | |

TABLE 5-continued

| Ex. No. | Structure | MW | HPLC ret. time (min.) | HPLC condition | MS (M+1) | Comment |
|---|---|---|---|---|---|---|
| 108 | 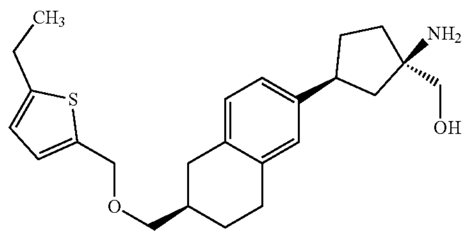 [SMILES: CCc1ccc(COC[C@@H]2CCc3cc([C@H]4CC[C@](N)(CO)C4)ccc3C2)s1] | 399.6 | 7.82 | L | 400 | |
| 109 | 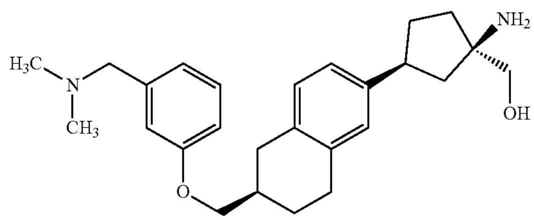 [SMILES: CN(C)Cc1cccc(OC[C@@H]2CCc3cc([C@H]4CC[C@](N)(CO)C4)ccc3C2)c1] | 408.6 | 5.50 | L | 409 | |
| 110 | 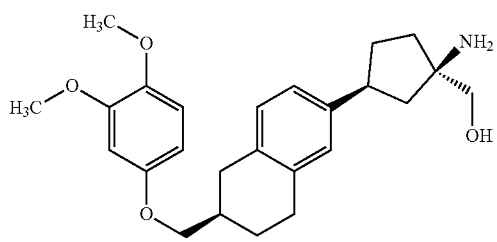 | 411.5 | 2.86 | C | 412 | |
| 111 | 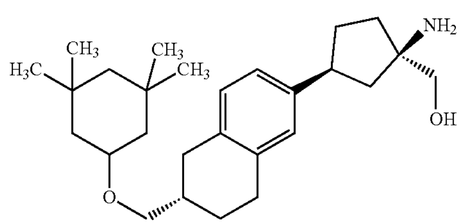 [SMILES: CC1(C)CC(OC[C@H]2CCc3cc([C@H]4CC[C@](N)(CO)C4)ccc3C2)CC(C)(C)C1] | 413.6 | 2.34 | A | 414 | |
| 112 | 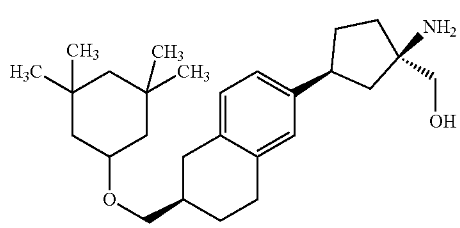 [SMILES: CC1(C)CC(OC[C@@H]2CCc3cc([C@H]4CC[C@](N)(CO)C4)ccc3C2)CC(C)(C)C1] | 413.6 | 2.15 | A | 414 | |
| 113 | 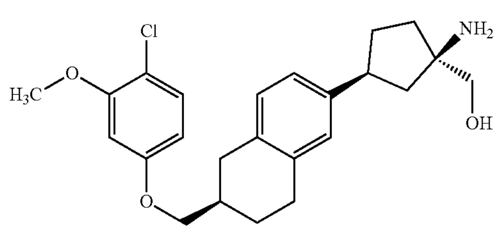 [SMILES: COc1cc(OC[C@@H]2CCc3cc([C@H]4CC[C@](N)(CO)C4)ccc3C2)ccc1Cl] | 416.0 | 8.77 | L | 416 | |

TABLE 5-continued

| Ex. No. | Structure | MW | HPLC ret. time (min.) | HPLC condition | MS (M+1) | Comment |
|---|---|---|---|---|---|---|
| 114 | 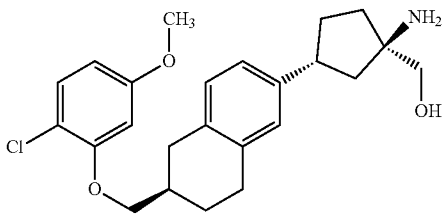 [SMILES: COc1ccc(Cl)c(OC[C@@H]2CCc3cc([C@@H]4CC[C@](N)(CO)C4)ccc3C2)c1] | 416.0 | 7.63 | L | 416 | |
| 115 | 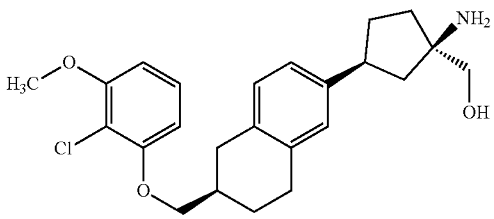 | 416.0 | 7.25 | L | 416 | |
| 116 | 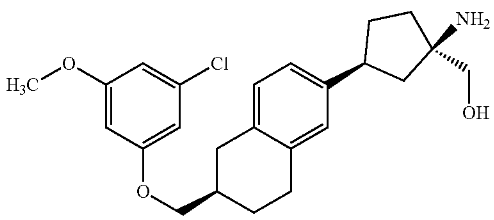 [SMILES: COc1cc(Cl)cc(OC[C@@H]2CCc3cc([C@H]4CC[C@](N)(CO)C4)ccc3C2)c1] | 415.9 | 8.02 | L | 416 | |
| 117 | 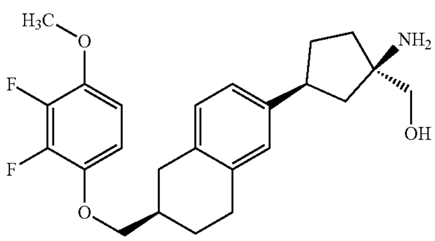 [SMILES: COc1ccc(OC[C@@H]2CCc3cc([C@H]4CC[C@](N)(CO)C4)ccc3C2)c(F)c1F] | 417.5 | 3.11 | C | 418 | |
| 118 | 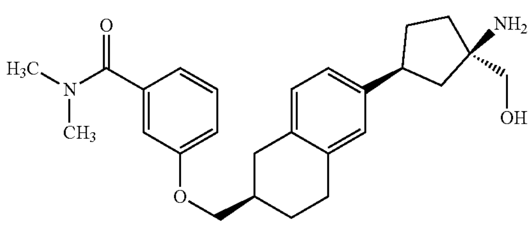 [SMILES: CN(C)C(=O)c1cccc(OC[C@@H]2CCc3cc([C@H]4CC[C@](N)(CO)C4)ccc3C2)c1] | 422.6 | 5.88 | L | 523 | |
| 119 | 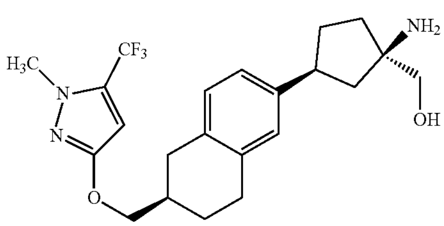 [SMILES: Cn1nc(OC[C@@H]2CCc3cc([C@H]4CC[C@](N)(CO)C4)ccc3C2)cc1C(F)(F)F] | 423.5 | 7.14 | L | 424 | |
| 120 | 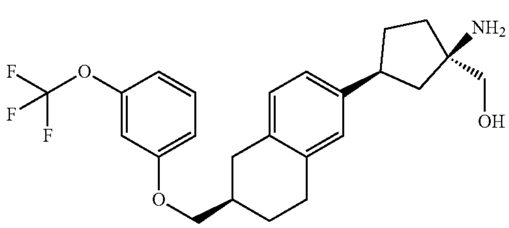 [SMILES: N[C@]1(CO)CC[C@H](c2ccc3c(c2)CC[C@@H](COc2cccc(OC(F)(F)F)c2)C3)C1] | 435.5 | 8.26 | L | 436 | |

TABLE 5-continued

| Ex. No. | Structure | MW | HPLC ret. time (min.) | HPLC condition | MS (M+1) | Comment |
|---|---|---|---|---|---|---|
| 121 | 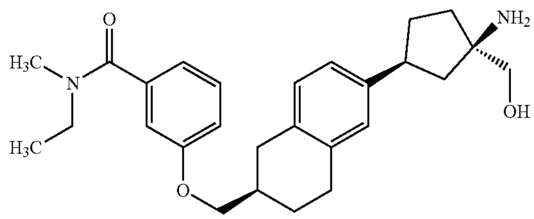 [SMILES: CCN(C)C(=O)c1cccc(OC[C@@H]2CCc3cc([C@H]4CC[C@](N)(CO)C4)ccc3C2)c1] | 436.6 | 6.21 | L | 437 | |
| 122 | 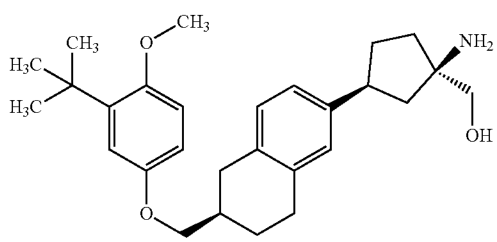 [SMILES: COc1ccc(OC[C@@H]2CCc3cc([C@H]4CC[C@](N)(CO)C4)ccc3C2)cc1C(C)(C)C] | 437.6 | 3.64 | C | 438 | |
| 123 | 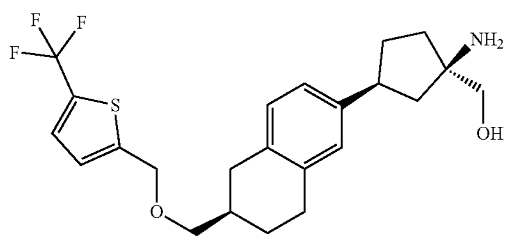 [SMILES: N[C@]1(CO)CC[C@H](c2ccc3c(c2)CC[C@@H](COCc2ccc(C(F)(F)F)s2)C3)C1] | 439.5 | 7.89 | L | 440 | |
| 124 | 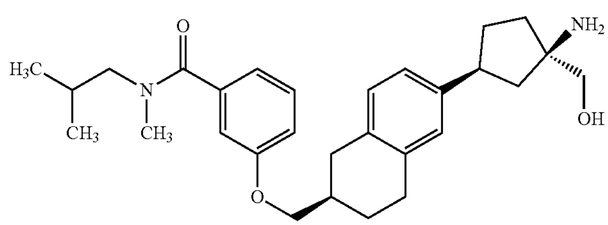 [SMILES: CC(C)CN(C)C(=O)c1cccc(OC[C@@H]2CCc3cc([C@H]4CC[C@](N)(CO)C4)ccc3C2)c1] | 464.7 | 6.93 | L | 465 | |
| 125 | 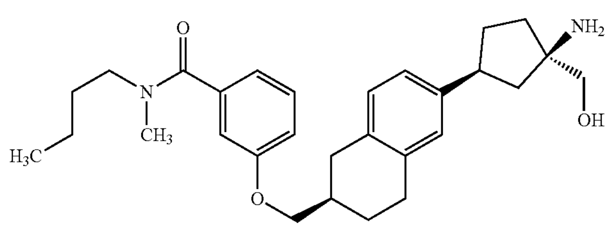 [SMILES: CCCCN(C)C(=O)c1cccc(OC[C@@H]2CCc3cc([C@H]4CC[C@](N)(CO)C4)ccc3C2)c1] | 464.7 | 6.99 | L | 465 | |

The examples in Table 6 were prepared according to the general procedures of Examples 50 and 51.

TABLE 6

| Ex. No. | Structure | MW | HPLC ret. time (min.) | HPLC condition | MS (M$^{+1}$) | Comment |
|---|---|---|---|---|---|---|
| 126 | 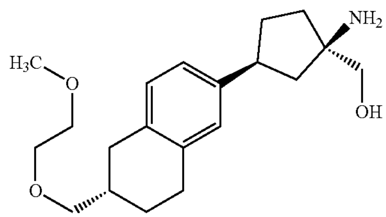 [SMILES: COCCOC[C@H]1CCc2cc([C@H]3CC[C@](N)(CO)C3)ccc2C1] | 333.5 | 0.28 | A | 334 | Isomer 1 |
| 127 | 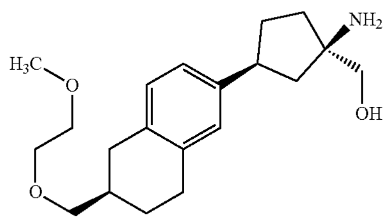 [SMILES: COCCOC[C@@H]1CCc2cc([C@H]3CC[C@](N)(CO)C3)ccc2C1] | 333.5 | 0.25 | A | 334 | Isomer 2 |
| 128 | 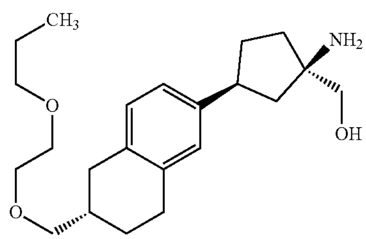 [SMILES: CCCOCCOC[C@H]1CCc2cc([C@H]3CC[C@](N)(CO)C3)ccc2C1] | 361.5 | 0.44 | A | 362 | Isomer 1 |
| 129 | 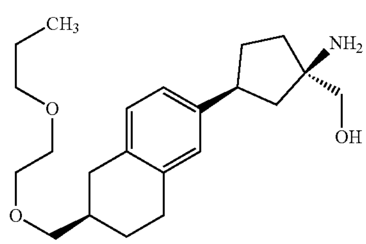 [SMILES: CCCOCCOC[C@@H]1CCc2cc([C@H]3CC[C@](N)(CO)C3)ccc2C1] | 361.5 | 0.66 | A | 362 | Isomer 2 |

The Examples in Table 7 were prepared according to the general procedures of Examples 30 and 31.

TABLE 7

| Ex. No. | Structure | MW | HPLC ret. time (min.) | HPLC condition | MS (M$^{+1}$) | Comment |
|---|---|---|---|---|---|---|
| 130 | | 361.5 | 7.41 | L | 362 | Isomer 1 |
| 131 | | 361.5 | 7.46 | L | 362 | Isomer 2 |

TABLE 7-continued

| Ex. No. | Structure | MW | HPLC ret. time (min.) | HPLC condition | MS (M+1) | Comment |
|---|---|---|---|---|---|---|
| 132 | | 359.2 | 6.18 | L | 360 | Isomer 1 |
| 133 | | 359.2 | 6.20 | L | 360 | Isomer 2 |
| 134 | | 347.5 | 7.14 | L | 348 | Isomer 1 |
| 135 | | 347.5 | 6.80 | L | 348 | Isomer 2 |
| 136 | | 357.5 | 8.07 | L | 358 | Isomer 1 |
| 137 | | 357.5 | 8.97 | L | 358 | Isomer 2 |

The Examples in Table 8 were prepared according to the general procedures of Examples 50 and 51.

TABLE 8

| Ex. No. | Structure | MW | HPLC ret. time (min.) | HPLC condition | MS (M+1) | Comment |
|---|---|---|---|---|---|---|
| 138 | 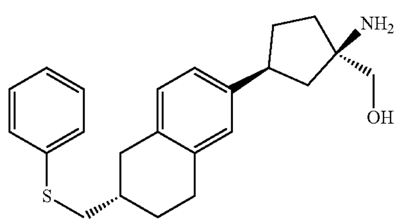 [SMILES: N[C@]1(CO)CC[C@H](c2ccc3c(c2)CC[C@H](CSc2ccccc2)C3)C1] | 367.5 | 1.72 | A | 368 | Isomer 1 |
| 139 | 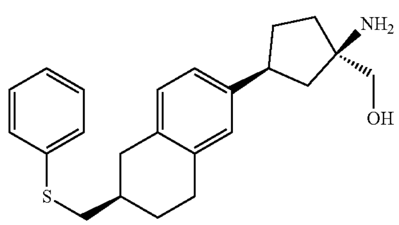 [SMILES: N[C@]1(CO)CC[C@H](c2ccc3c(c2)CC[C@@H](CSc2ccccc2)C3)C1] | 367.5 | 1.73 | A | 368 | Isomer 2 |

TABLE 8-continued

| Ex. No. | Structure | MW | HPLC ret. time (min.) | HPLC condition | MS (M$^{+1}$) | Comment |
|---|---|---|---|---|---|---|
| 140 | 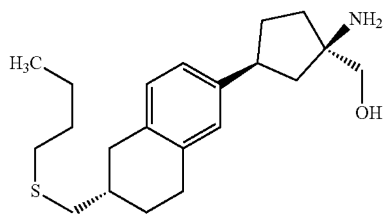 | 347.6 | 1.53 | A | 348 | Isomer 1 |
| 141 | 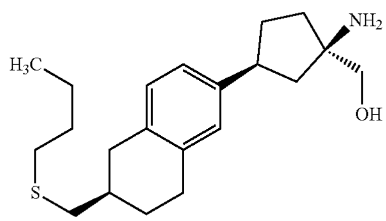 | 347.6 | 1.53 | A | 348 | Isomer 2 |
| 142 | 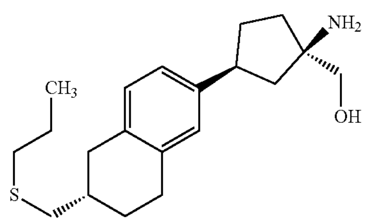 [SMILES: CCCSC[C@H]1CCc2cc([C@H]3CC[C@](N)(CO)C3)ccc2C1] | 333.5 | 3.15 | C | 334 | |
| 143 | 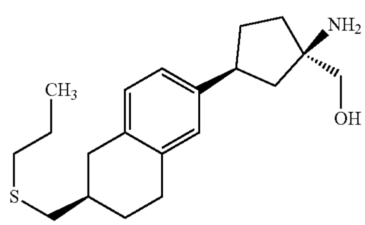 | 333.5 | 3.12 | C | 334 | |
| 144 | 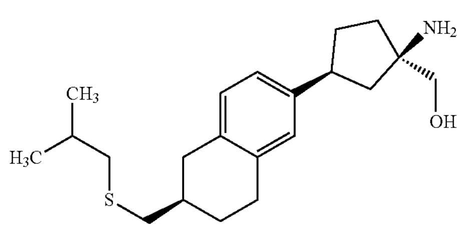 [SMILES: CC(C)CSC[C@@H]1CCc2cc([C@H]3CC[C@](N)(CO)C3)ccc2C1] | 347.6 | 3.30 | C | 348 | |
| 145 | | 347.6 | 8.91 | L | 348.1 | Isomer 1 |
| 146 | | 347.6 | 8.90 | L | 348.1 | Isomer 2 |
| 147 | | 367.6 | 8.56 | L | 368.1 | Isomer 1 |
| 148 | | 367.6 | 8.55 | L | 368.1 | Isomer 2 |

TABLE 8-continued

| Ex. No. | Structure | MW | HPLC ret. time (min.) | HPLC condition | MS (M$^{+1}$) | Comment |
|---|---|---|---|---|---|---|
| 149 | 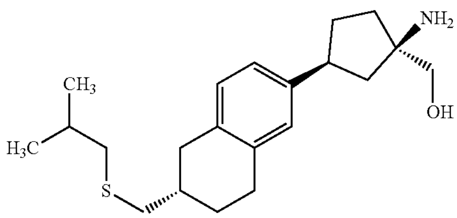 [SMILES: CC(C)CSC[C@H]1CCc2cc([C@H]3CC[C@](N)(CO)C3)ccc2C1] | 347.6 | 3.26 | C | 348 | |
| 150 | 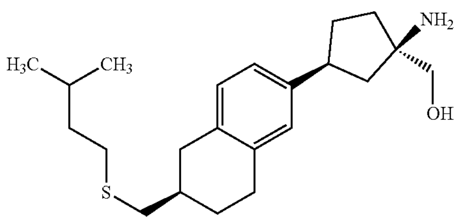 [SMILES: CC(C)CCSC[C@@H]1CCc2cc([C@H]3CC[C@](N)(CO)C3)ccc2C1] | 361.6 | 2.05 | A | 362 | |
| 151 | 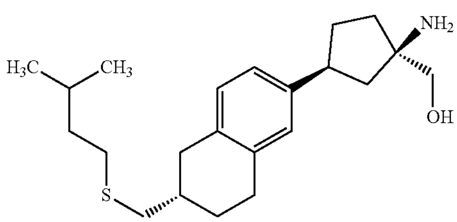 | 361.6 | 3.43 | C | 362 | |
| 152 | 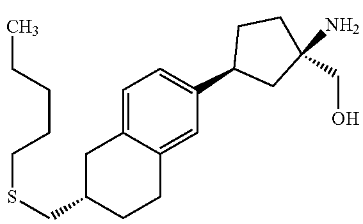 [SMILES: CCCCCSC[C@H]1CCc2cc([C@H]3CC[C@](N)(CO)C3)ccc2C1] | 361.6 | 3.43 | C | 362 | |
| 153 | 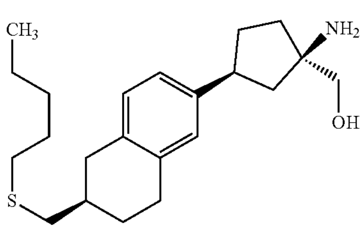 [SMILES: CCCCCSC[C@@H]1CCc2cc([C@H]3CC[C@](N)(CO)C3)ccc2C1] | 361.6 | 3.49 | C | 362 | |
| 154 | 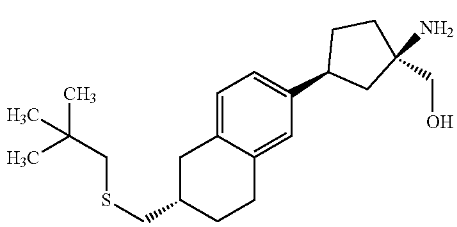 [SMILES: CC(C)(C)CSC[C@H]1CCc2cc([C@H]3CC[C@](N)(CO)C3)ccc2C1] | 361.6 | 3.47 | C | 362 | |

TABLE 8-continued

| Ex. No. | Structure | MW | HPLC ret. time (min.) | HPLC condition | MS (M$^{+1}$) | Comment |
|---|---|---|---|---|---|---|
| 155 | 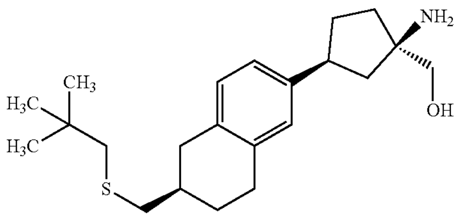 [SMILES: CC(C)(C)CSC[C@@H]1CCc2cc([C@H]3CC[C@](N)(CO)C3)ccc2C1] | 361.6 | 3.40 | C | 362 | |
| 156 | 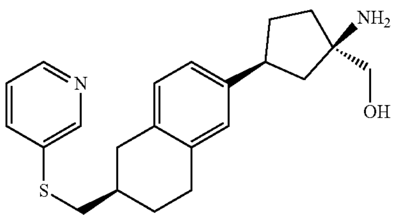 | 368.5 | 2.42 | C | 369 | |
| 157 | 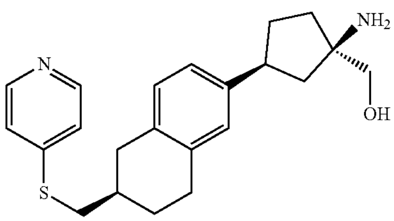 [SMILES: N[C@]1(CO)CC[C@H](c2ccc3c(c2)CC[C@@H](CSc2ccncc2)C3)C1] | 368.5 | 1.66 | C | 369 | |
| 158 | 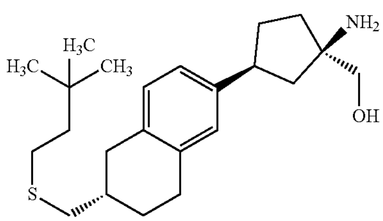 [SMILES: CC(C)(C)CCSC[C@H]1CCc2cc([C@H]3CC[C@](N)(CO)C3)ccc2C1] | 375.6 | 3.59 | C | 376 | |
| 159 | 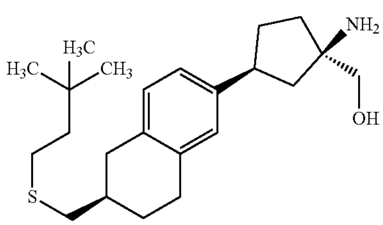 [SMILES: CC(C)(C)CCSC[C@@H]1CCc2cc([C@H]3CC[C@](N)(CO)C3)ccc2C1] | 375.6 | 3.49 | C | 376 | |
| 160 | 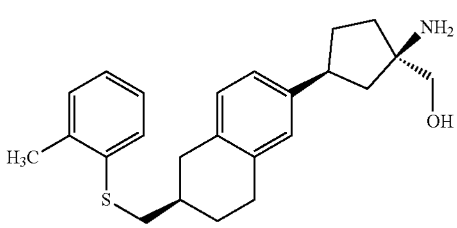 | 381.6 | 3.40 | C | 382 | |
| 161 | 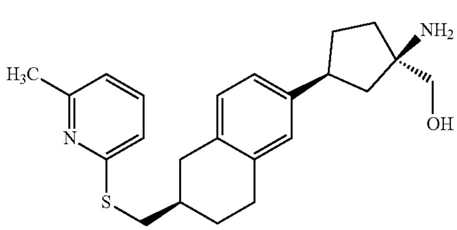 | 382.6 | 2.13 | C | 283 | |

TABLE 8-continued

| Ex. No. | Structure | MW | HPLC ret. time (min.) | HPLC condition | MS (M$^{+1}$) | Comment |
|---|---|---|---|---|---|---|
| 162 | 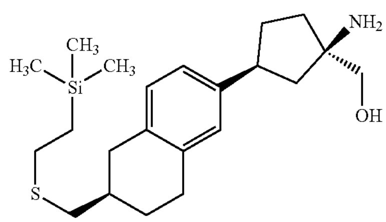 [SMILES: C[Si](C)(C)CCSC[C@@H]1CCc2cc([C@H]3CC[C@](N)(CO)C3)ccc2C1] | 391.7 | 2.03 | A | 392 | |
| 163 | 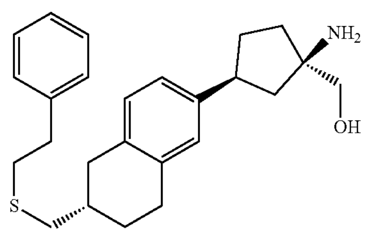 [SMILES: N[C@]1(CO)CC[C@H](c2ccc3c(c2)CC[C@H](CSCCc2ccccc2)C3)C1] | 395.6 | 3.38 | C | 396 | |
| 164 | 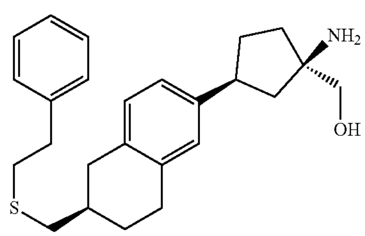 [SMILES: N[C@]1(CO)CC[C@H](c2ccc3c(c2)CC[C@@H](CSCCc2ccccc2)C3)C1] | 395.6 | 3.36 | C | 396 | |
| 165 | 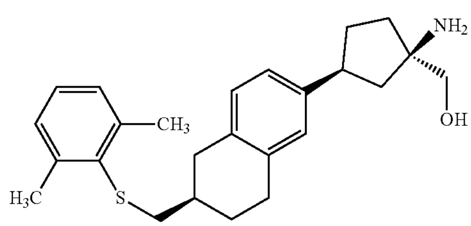 [SMILES: Cc1cccc(C)c1SC[C@@H]1CCc2cc([C@H]3CC[C@](N)(CO)C3)ccc2C1] | 395.6 | 3.63 | C | 396 | |
| 166 | 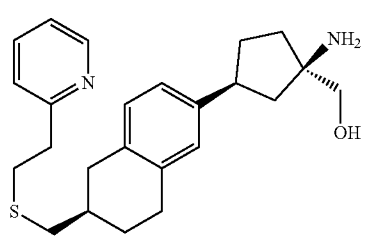 [SMILES: N[C@]1(CO)CC[C@H](c2ccc3c(c2)CC[C@@H](CSCCc2ccccn2)C3)C1] | 396.6 | 0.99 | A | 397 | |
| 167 | 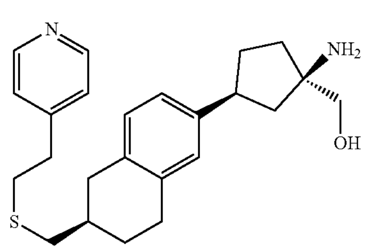 [SMILES: N[C@]1(CO)CC[C@H](c2ccc3c(c2)CC[C@@H](CSCCc2ccncc2)C3)C1] | 396.6 | 1.79 | C | 397 | |

TABLE 8-continued

| Ex. No. | Structure | MW | HPLC ret. time (min.) | HPLC condition | MS (M⁺¹) | Comment |
|---|---|---|---|---|---|---|
| 168 | 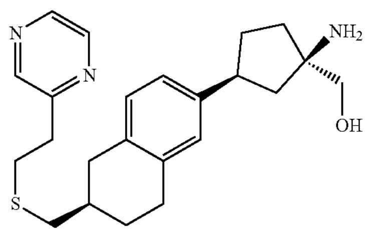 [SMILES: N[C@]1(CO)CC[C@H](c2ccc3c(c2)CC[C@@H](CSCCc2cnccn2)C3)C1] | 397.6 | 1.36 | A | 398 | |
| 169 | 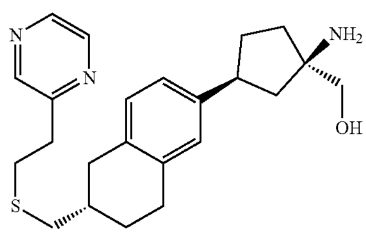 [SMILES: N[C@]1(CO)CC[C@H](c2ccc3c(c2)CC[C@H](CSCCc2cnccn2)C3)C1] | 397.6 | 2.56 | C | 398 | |
| 170 | 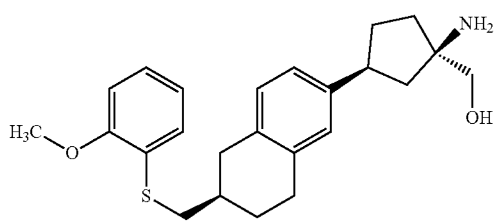 [SMILES: COc1ccccc1SC[C@@H]1CCc2cc([C@H]3CC[C@](N)(CO)C3)ccc2C1] | 397.6 | 3.05 | C | 398 | |
| 171 | 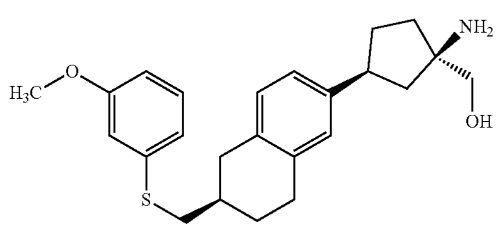 [SMILES: COc1cccc(SC[C@@H]2CCc3cc([C@H]4CC[C@](N)(CO)C4)ccc3C2)c1] | 397.6 | 3.21 | C | 398 | |
| 172 | 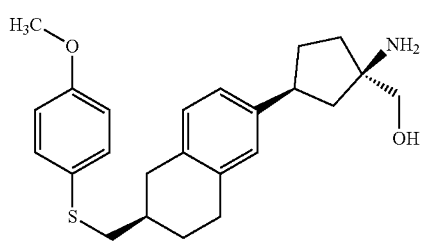 [SMILES: COc1ccc(SC[C@@H]2CCc3cc([C@H]4CC[C@](N)(CO)C4)ccc3C2)cc1] | 397.6 | 3.21 | C | 398 | |
| 173 | 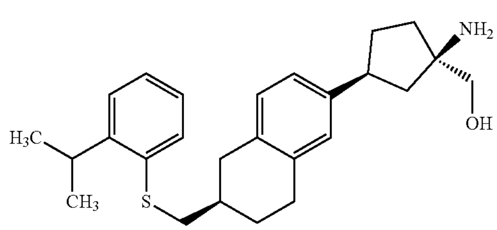 [SMILES: CC(C)c1ccccc1SC[C@@H]1CCc2cc([C@H]3CC[C@](N)(CO)C3)ccc2C1] | 409.6 | 3.58 | C | 410 | |

TABLE 8-continued

| Ex. No. | Structure | MW | HPLC ret. time (min.) | HPLC condition | MS (M+1) | Comment |
|---|---|---|---|---|---|---|
| 174 | 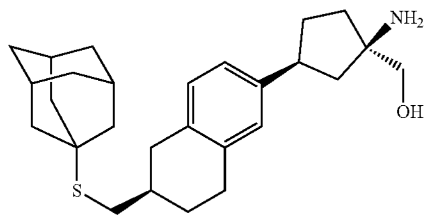 [SMILES: N[C@]1(CO)CC[C@H](c2ccc3c(c2)CC[C@@H](CSC24CC5CC(CC(C5)C2)C4)C3)C1] | 425.7 | 2.16 | A | 426 | |
| 175 | 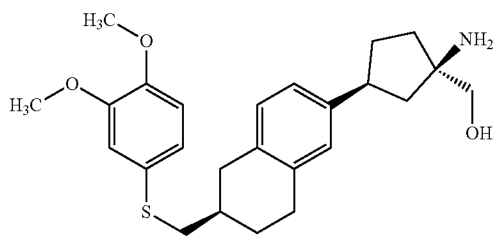 [SMILES: COc1ccc(SC[C@@H]2CCc3cc([C@H]4CC[C@](N)(CO)C4)ccc3C2)cc1OC] | 427.6 | 3.03 | C | 428 | |

Example 176

((1R,3S)-1-amino-3-((S)-6-(2-(isobutylthio)ethyl)-5,6,7,8-tetrahydronaphthalen-2-yl) cyclopentyl)methanol (176)

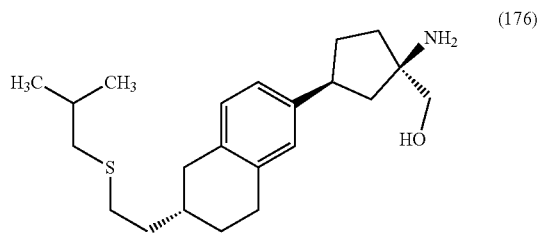 [SMILES: CC(C)CSCC[C@H]1CCc2cc([C@H]3CC[C@](N)(CO)C3)ccc2C1]

Preparation 176A: 2-((S)-6-((5R,7S)-2-oxo-3-oxa-1-azaspiro[4.4]nonan-7-yl)-1,2,3,4-tetrahydronaphthalen-2-yl)ethyl 4-methylbenzenesulfonate (176A)

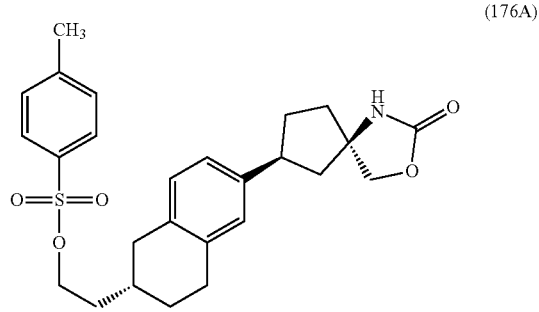 [SMILES: Cc1ccc(S(=O)(=O)OCC[C@H]2CCc3cc([C@H]4CC[C@]5(COC(=O)N5)C4)ccc3C2)cc1]

(5R,7S)-7-((S)-6-(2-hydroxyethyl)-5,6,7,8-tetrahydronaphthalen-2-yl)-3-oxa-1-azaspiro[4.4]nonan-2-one (130 mg, 0.412 mmol) was dissolved in dry pyridine (1 mL) and p-toluenesulfonyl chloride (236 mg, 1.236 mmol) was added in one portion. The resulting mixture was reacted at room temperature for 2 h. The solvent was removed in vacuo. The residue was dissolved in DCM and loaded onto column. Flash chromatography purification (0->100% ethyl acetate in DCM) afforded 2-((S)-6-((5R,7S)-2-oxo-3-oxa-1-azaspiro[4.4]nonan-7-yl)-1,2,3,4-tetrahydronaphthalen-2-yl) ethyl 4-methylbenzenesulfonate (169 mg, 0.360 mmol) as a solid. HPLC retention time=3.46 min (condition C); LC/MS M+1=470.

Example 176

To a stirred mixture of isobutylmercaptan (0.021 mL, 0.192 mmol), 2-((S)-6-((5R,7S)-2-oxo-3-oxa-1-azaspiro[4.4]nonan-7-yl)-1,2,3,4-tetrahydronaphthalen-2-yl)ethyl 4-methylbenzenesulfonate (30 mg, 0.064 mmol), and dioxane (0.5 mL) was added 2N aqueous NaOH (0.096 mL, 0.192 mmol) at 0° C. under nitrogen. The resulting mixture was stirred at the same temperature for 15 min and at 60° C. for 6 h. Next, 2N aqueous NaOH (0.639 mL, 1.278 mmol) was added and the resulting mixture was stirred at 90° C. under nitrogen overnight. The mixture was extracted with ethyl acetate (4×1 mL) and the combined ethyl acetate extracts were dried ($Na_2SO_4$) and concentrated. Purification using reverse phase HPLC (Phenomenex Luna 5μ30×100 mm (Axia); gradient over 8 min from 30 to 100% of solvent B; solvent A: 10% MeOH: 90% $H_2O$: 0.1% TFA; solvent B: 90% MeOH, 10% $H_2O$, 0.1% TFA), concentration, basification with 2N aqueous NaOH and extraction with ethyl acetate gave ((1R,3S)-1-amino-3-((S)-6-(2-(isobutylthio) ethyl)-5,6,7,8-tetrahydronaphthalen-2-yl)cyclopentyl) methanol (22 mg, 0.057 mmol) as a white solid. HPLC retention time=3.39 min (condition C); LC/MS M+=362. $^1$H NMR (400 MHz, CHLOROFORM-d) δ 7.10-6.87 (m, 3H), 3.57-3.38 (m, 2H), 3.15-2.96 (m, 1H), 2.92-2.75 (m, 3H), 2.68-2.58 (m, 2H), 2.48-2.37 (m, 3H), 2.29 (dd, J=13.1, 7.5 Hz, 1H), 2.15-2.02 (m, 1H), 2.00-1.37 (m, 10H), 1.02 (d, J=6.6 Hz, 6H).

The Examples in Table 9 were prepared according to the general procedure of Example 176.

TABLE 9

| Ex. No. | Structure | MW | HPLC ret. time (min.) | HPLC condition | MS (M$^{+1}$) | Comment |
|---|---|---|---|---|---|---|
| 177 | 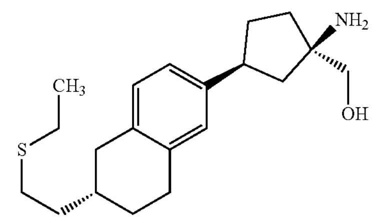 [SMILES: CCSCC[C@H]1CCc2cc([C@H]3CC[C@](N)(CO)C3)ccc2C1] | 333.5 | 3.04 | C | 334 | |
| 178 | 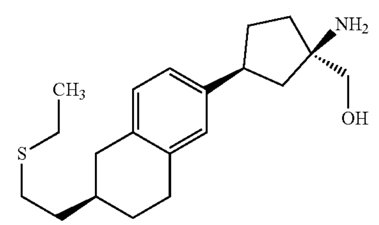 [SMILES: CCSCC[C@@H]1CCc2cc([C@H]3CC[C@](N)(CO)C3)ccc2C1] | 333.5 | 3.12 | C | 334 | |
| 179 | 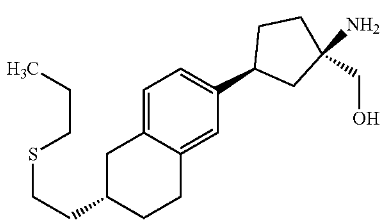 [SMILES: CCCSCC[C@H]1CCc2cc([C@H]3CC[C@](N)(CO)C3)ccc2C1] | 347.6 | 3.24 | C | 348 | |
| 180 | 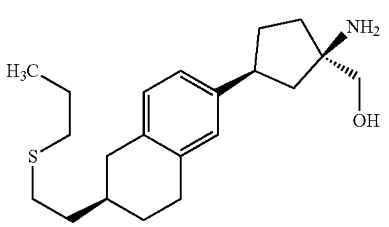 [SMILES: CCCSCC[C@@H]1CCc2cc([C@H]3CC[C@](N)(CO)C3)ccc2C1] | 347.6 | 3.25 | C | 348 | |
| 181 | 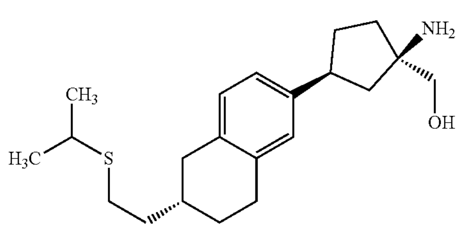 [SMILES: CC(C)SCC[C@H]1CCc2cc([C@H]3CC[C@](N)(CO)C3)ccc2C1] | 347.6 | 3.24 | C | 348 | |
| 182 | 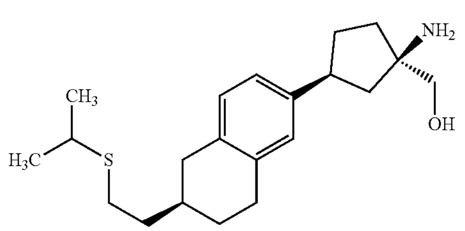 [SMILES: CC(C)SCC[C@@H]1CCc2cc([C@H]3CC[C@](N)(CO)C3)ccc2C1] | 347.6 | 3.29 | C | 348 | |

TABLE 9-continued

| Ex. No. | Structure | MW | HPLC ret. time (min.) | HPLC condition | MS ($M^{+1}$) | Comment |
|---|---|---|---|---|---|---|
| 183 | 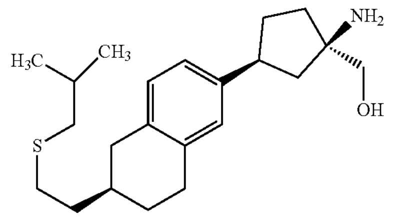 [SMILES: CC(C)CSCC[C@@H]1CCc2cc([C@H]3CC[C@](N)(CO)C3)ccc2C1] | 361.6 | 3.41 | C | 362 | |

Example 184

((1R,3S)-1-amino-3-((S)-6-(2-isobutoxyethyl)-5,6,7,8-tetrahydronaphthalen-2-yl) cyclopentyl)methanol

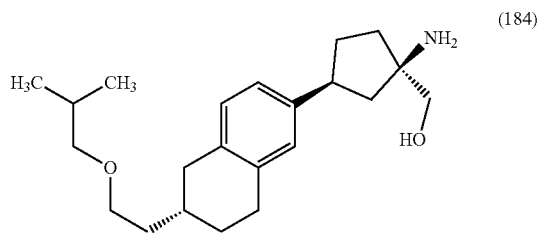 [SMILES: CC(C)COCC[C@H]1CCc2cc([C@H]3CC[C@](N)(CO)C3)ccc2C1]

(184)

To a stirred mixture of 2-methylpropan-1-ol (0.3 mL, 3.25 mmol) and 2-((S)-6-((5R,7S)-2-oxo-3-oxa-1-azaspiro[4.4]nonan-7-yl)-1,2,3,4-tetrahydronaphthalen-2-yl)ethyl 4-methylbenzenesulfonate (40 mg, 0.085 mmol) was added 1N THF solution of potassium tert-butoxide (0.852 mL, 0.852 mmol) at 0° C. under nitrogen. The resulting mixture was at 70° C. for 6 hr before 2 N aqueous NaOH (0.426 mL, 0.852 mmol) was added. The mixture was concentrated to remove THF. Dioxane (0.5 mL) was added and the mixture was stirred at 90° C. under nitrogen overnight. The mixture was extracted with ethyl acetate (4×1 mL). The combined ethyl acetate extracts were dried ($Na_2SO_4$) and concentrated. Purification using reverse phase HPLC (Phenomenex Luna 5 u 30×100 mm (Axia); gradient over 8 min from 30 to 100% of solvent B; solvent A: 10% MeOH: 90% $H_2O$: 0.1% TFA; solvent B: 90% MeOH, 10% $H_2O$, 0.1% TFA), concentration, basification with 2N NaOH, and extraction with ethyl acetate gave ((1R,3S)-1-amino-3-((S)-6-(2-isobutoxyethyl)-5,6,7,8-tetrahydronaphthalen-2-yl)cyclopentyl) methanol (27 mg, 0.076 mmol) as a solid. HPLC retention time=3.41 min (condition C); LC/MS $M^{+1}$=346. $^1$H NMR (400 MHz, CHLOROFORM-d) δ 7.00-6.94 (m, 3H), 3.52 (t, J=6.7 Hz, 2H), 3.45 (br, 2H), 3.18 (d, J=6.8 Hz, 2H), 3.08-2.96 (m, 1H), 2.88-2.75 (m, 3H), 2.41 (dd, J=16.4, 10.5 Hz, 1H), 2.26 (dd, J=13.2, 7.9 Hz, 1H), 2.11-2.00 (m, 1H), 1.99-1.34 (m, 10H), 0.90 (d, J=6.6 Hz, 6H).

The Examples in Table 10 were prepared according to the general procedure of Example 184.

TABLE 10

| Ex. No. | Structure | MW | HPLC ret. time (min.) | HPLC condition | MS ($M^{+1}$) | Comment |
|---|---|---|---|---|---|---|
| 185 | | 303.4 | 5.58 | L | 304 | |
| 186 | | 303.4 | 5.57 | L | 304 | |
| 187 | | 317.5 | 6.28 | L | 318 | |

TABLE 10-continued

| Ex. No. | Structure | MW | HPLC ret. time (min.) | HPLC condition | MS (M$^{+1}$) | Comment |
|---|---|---|---|---|---|---|
| 188 | 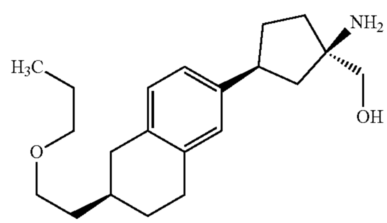 [SMILES: CCCOCC[C@@H]1CCc2cc([C@H]3CC[C@](N)(CO)C3)ccc2C1] | 331.5 | 7.11 | L | 332 | |
| 189 | 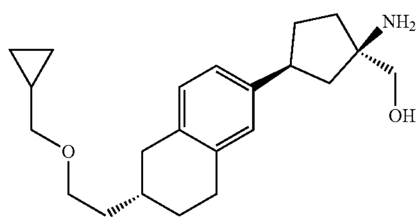 [SMILES: N[C@]1(CO)CC[C@H](c2ccc3c(c2)CC[C@H](CCOCC2CC2)C3)C1] | 343.5 | 2.94 | C | 344 | |
| 190 | 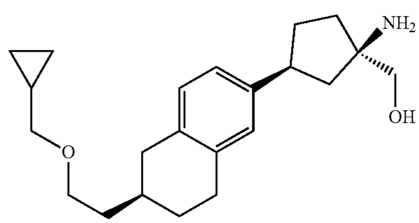 [SMILES: N[C@]1(CO)CC[C@H](c2ccc3c(c2)CC[C@@H](CCOCC2CC2)C3)C1] | 343.5 | 2.83 | C | 344 | |
| 191 | 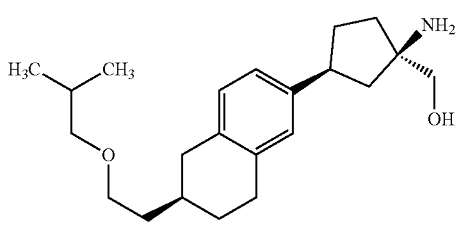 [SMILES: CC(C)COCC[C@@H]1CCc2cc([C@H]3CC[C@](N)(CO)C3)ccc2C1] | 345.5 | 3.22 | C | 346 | |
| 192 | 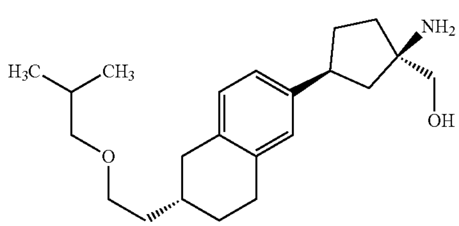 [SMILES: CC(C)COCC[C@H]1CCc2cc([C@H]3CC[C@](N)(CO)C3)ccc2C1] | 345.5 | 3.41 | C | 346 | |
| 193 | 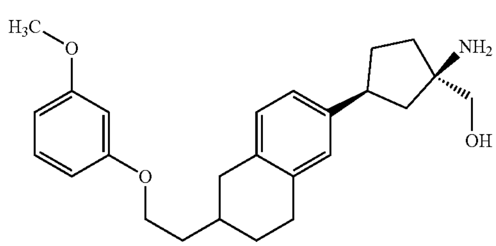 [SMILES: COc1cccc(OCCC2CCc3cc([C@H]4CC[C@](N)(CO)C4)ccc3C2)c1] | 395.5 | 7.50 | L | 396 | Isomer 1 |
| 194 | | 395.5 | 7.50 | L | 396 | Isomer 2 |

Example 195

((1R,3S)-1-amino-3-((S)-6-(4-methoxy-2-methylbenzyl)-5,6,7,8-tetrahydronaphthalen-2-yl)cyclopentyl)methanol (195)

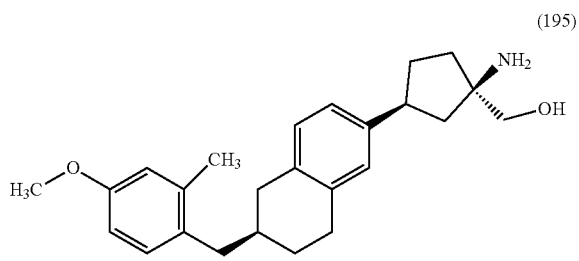 [SMILES: COc1ccc(C[C@@H]2CCc3cc([C@H]4CC[C@](N)(CO)C4)ccc3C2)c(C)c1]

Preparation 195A: (5R,7S)-7-((S)-6-(4-methoxy-2-methylbenzyl)-5,6,7,8-tetrahydronaphthalen-2-yl)-3-oxa-1-azaspiro[4.4]nonan-2-one (195A)

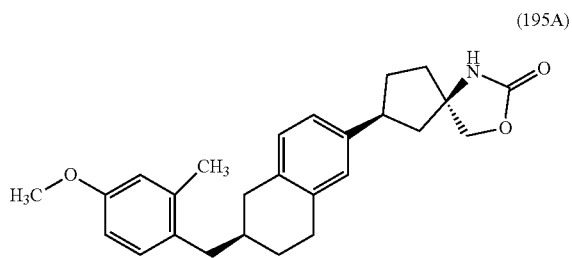 [SMILES: COc1ccc(C[C@@H]2CCc3cc([C@H]4CC[C@]5(COC(=O)N5)C4)ccc3C2)c(C)c1]

To a solution of ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (35 mg, 0.077 mmol) and copper (I) bromide (33.1 mg, 0.230 mmol) in THF (3 mL) was added (4-methoxy-2-methylphenyl)magnesium bromide (4610 µl, 2.305 mmol) at −78° C. The reaction mixture was stirred at −78° C. and allowed to warm to room temperature over 16 h. The reaction mixture was diluted with saturated $NH_4Cl$ and water and extracted with EtOAc. The organic layer was collected, dried over $Na_2SO_4$, concentrated on the rotavapor to give to give (5R,7S)-7-((S)-6-(4-methoxy-2-methylbenzyl)-5,6,7,8-tetrahydronaphthalen-2-yl)-3-oxa-1-azaspiro[4.4]nonan-2-one (20 mg) as a white solid. LC/MS $M^{+1}$=406.

Example 195

To a solution of (5R,7S)-7-((S)-6-(4-methoxy-2-methylbenzyl)-5,6,7,8-tetrahydronaphthalen-2-yl)-3-oxa-1-azaspiro[4.4]nonan-2-one (20 mg, 0.049 mmol) in dioxane (3 mL) and water (1 mL) was added LiOH (11.81 mg, 0.493 mmol). The reaction mixture was stirred at 100° C. for 16 h to give the crude product which was purified on a prep HPLC. HPLC conditions: Phenomenex Luna 5 micron C18 column (21.2×100 mm); MeOH (0.1% TFA)/water (0.1% TFA); 0%-100% gradient over 15 minutes; 20 mL/min. Isolated fractions with correct mass were collected and freeze-dried overnight. Recovered 10 mg of ((1R,3S)-1-amino-3-((S)-6-(4-methoxy-2-methylbenzyl)-5,6,7,8-tetrahydronaphthalen-2-yl)cyclopentyl)methanol TFA. $^1$H NMR (400 MHz, METHANOL-$d_4$) δ 7.20-6.35 (m, 6H), 3.6 (s, 3H), 3.5 (m, 2H), 3.2-2.6 (m, 5H), 2.4 (m, 1H), 2.3 (s, 3H), 2.2 (m, 1H), 2.2-1.5 (m, 7H). LC/MS $M^{+1}$=380.

The Examples in Table 11 were prepared according to the general procedure of Example 195.

TABLE 11

| Ex. No. | Structure | MW | HPLC ret. time (min.) | HPLC method | MS ($M^{+1}$) | Comment |
|---|---|---|---|---|---|---|
| 195 | 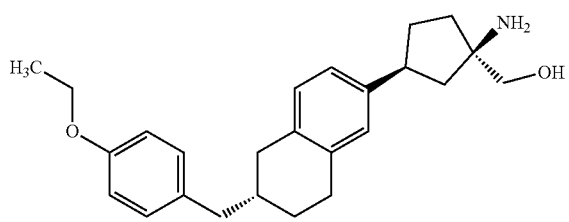 | 379.5 | 7.52 | L | 380 | |
| 196 | 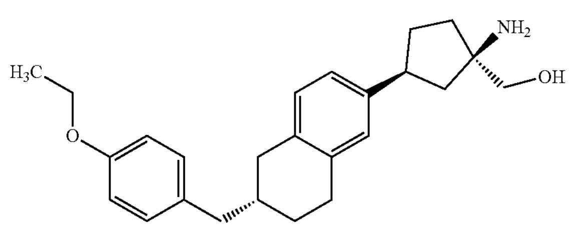 [SMILES: CCOc1ccc(C[C@H]2CCc3cc([C@H]4CC[C@](N)(CO)C4)ccc3C2)cc1] | 379.5 | 7.74 | L | 380 | Preparation (6S)-50D was used |

TABLE 11-continued

| Ex. No. | Structure | MW | HPLC ret. time (min.) | HPLC method | MS ($M^{+1}$) | Comment |
|---|---|---|---|---|---|---|
| 197 | 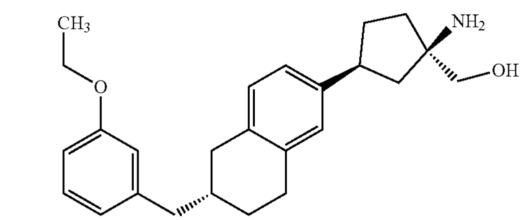 [SMILES: CCOc1cccc(C[C@H]2CCc3cc([C@H]4CC[C@](N)(CO)C4)ccc3C2)c1] | 379.5 | 8.80 | L | 380 | Preparation (6S)-50D was used |
| 198 | 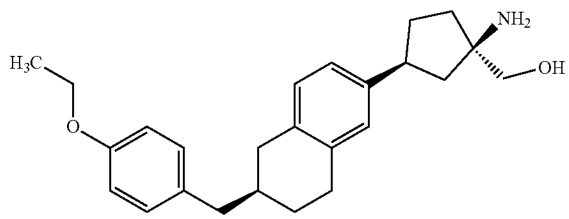 [SMILES: CCOc1ccc(C[C@@H]2CCc3cc([C@H]4CC[C@](N)(CO)C4)ccc3C2)cc1] | 379.5 | 8.81 | L | 380 | |
| 199 | 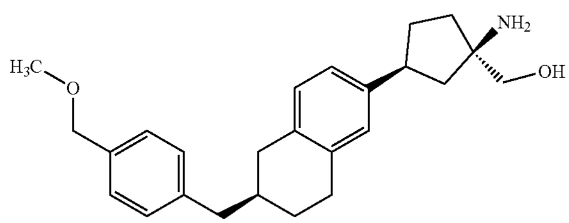 [SMILES: COCc1ccc(C[C@@H]2CCc3cc([C@H]4CC[C@](N)(CO)C4)ccc3C2)cc1] | 379.5 | 7.13 | L | 380 | |
| 200 | 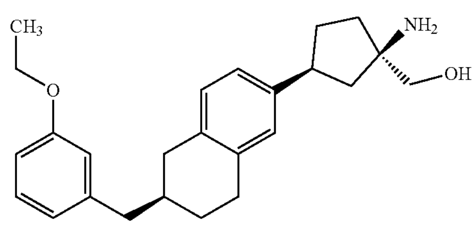 | 379.5 | 8.81 | L | 380 | |
| 201 | 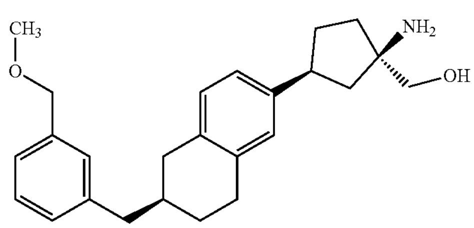 [SMILES: CCOc1cccc(C[C@@H]2CCc3cc([C@H]4CC[C@](N)(CO)C4)ccc3C2)c1] | 379.5 | 7.12 | L | 380 | |
| 202 | 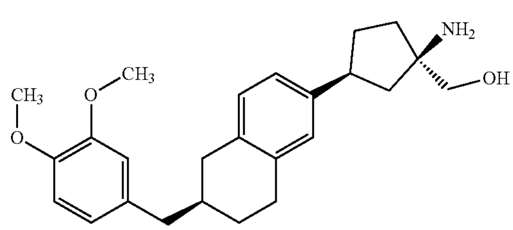 [SMILES: COc1ccc(C[C@@H]2CCc3cc([C@H]4CC[C@](N)(CO)C4)ccc3C2)cc1OC] | 395.5 | 6.64 | L | 380 | |

TABLE 11-continued

| Ex. No. | Structure | MW | HPLC ret. time (min.) | HPLC method | MS (M$^{+1}$) | Comment |
|---|---|---|---|---|---|---|
| 203 | 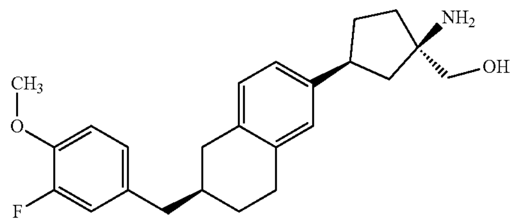 [SMILES: COc1ccc(C[C@@H]2CCc3cc([C@H]4CC[C@](N)(CO)C4)ccc3C2)cc1F] | 383.5 | 7.28 | L | 384 | |
| 204 | 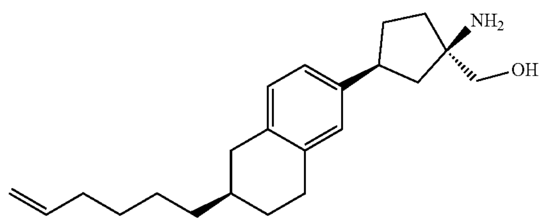 [SMILES: C=CCCCC[C@@H]1CCc2cc([C@H]3CC[C@](N)(CO)C3)ccc2C1] | 327.5 | 8.33 | L | 328 | |
| 205 | 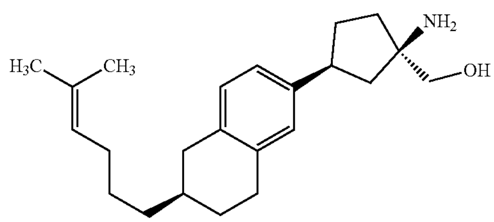 [SMILES: CC(C)=CCCC[C@@H]1CCc2cc([C@H]3CC[C@](N)(CO)C3)ccc2C1] | 341.5 | 8.80 | L | 342 | |
| 206 | 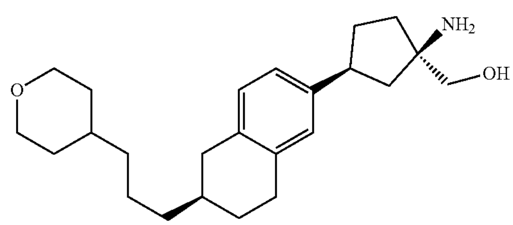 [SMILES: N[C@]1(CO)CC[C@H](c2ccc3c(c2)CC[C@@H](CCCC2CCOCC2)C3)C1] | 371.6 | 7.30 | L | 372 | |
| 207 | 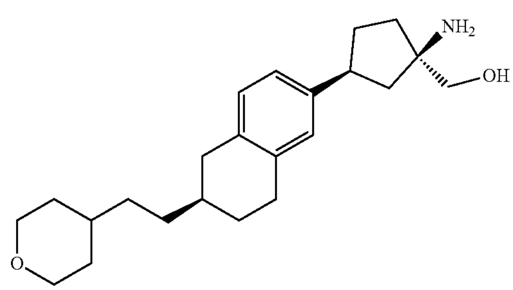 [SMILES: N[C@]1(CO)CC[C@H](c2ccc3c(c2)CC[C@@H](CCC2CCOCC2)C3)C1] | 357.5 | 6.73 | L | 358 | |
| 208 | 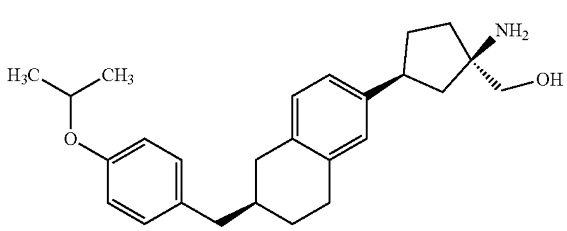 [SMILES: CC(C)Oc1ccc(C[C@@H]2CCc3cc([C@H]4CC[C@](N)(CO)C4)ccc3C2)cc1] | 393.6 | 8.07 | L | 394 | |

TABLE 11-continued

| Ex. No. | Structure | MW | HPLC ret. time (min.) | HPLC method | MS (M$^{+1}$) | Comment |
|---|---|---|---|---|---|---|
| 209 | 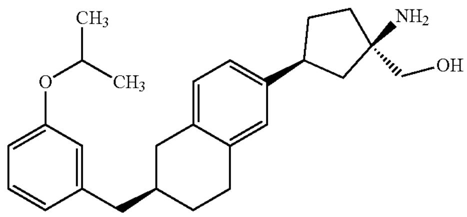 [SMILES: CC(C)Oc1cccc(C[C@@H]2CCc3cc([C@H]4CC[C@](N)(CO)C4)ccc3C2)c1] | 393.6 | 8.01 | L | 394 | |
| 210 | 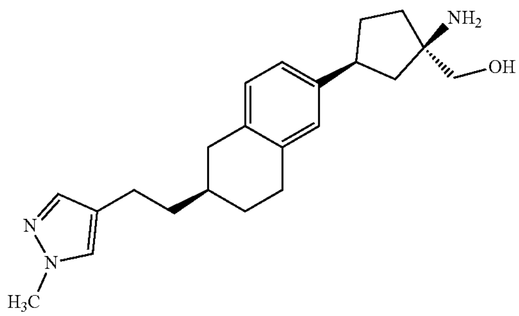 [SMILES: Cn1cc(CC[C@@H]2CCc3cc([C@H]4CC[C@](N)(CO)C4)ccc3C2)cn1] | 353.5 | 5.56 | L | 354 | |
| 211 | 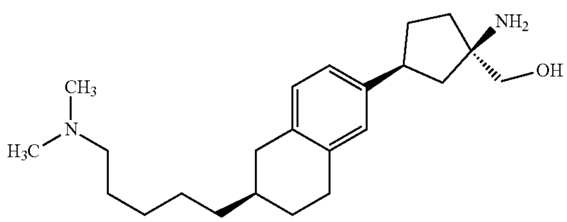 [SMILES: CN(C)CCCCC[C@@H]1CCc2cc([C@H]3CC[C@](N)(CO)C3)ccc2C1] | 358.6 | 4.28 | L | 359 | |
| 212 | 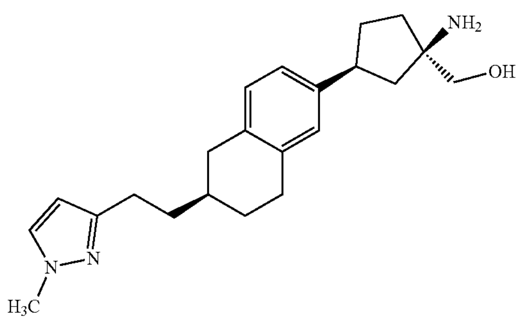 [SMILES: Cn1ccc(CC[C@@H]2CCc3cc([C@H]4CC[C@](N)(CO)C4)ccc3C2)n1] | 353.5 | 5.27 | L | 354 | |
| 213 | 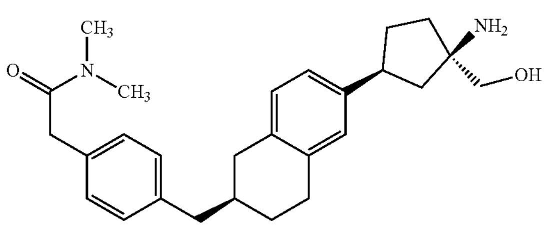 [SMILES: CN(C)C(=O)Cc1ccc(C[C@@H]2CCc3cc([C@H]4CC[C@](N)(CO)C4)ccc3C2)cc1] | 420.6 | 6.12 | L | 421 | |
| 214 | 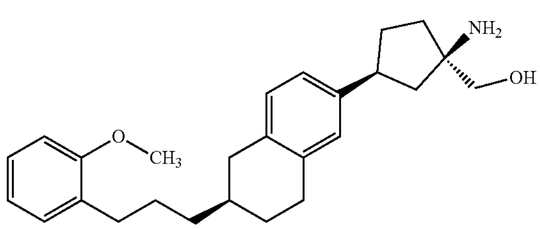 [SMILES: COc1ccccc1CCC[C@@H]1CCc2cc([C@H]3CC[C@](N)(CO)C3)ccc2C1] | 393.6 | 8.39 | L | 394 | |

TABLE 11-continued

| Ex. No. | Structure | MW | HPLC ret. time (min.) | HPLC method | MS (M$^{+1}$) | Comment |
|---|---|---|---|---|---|---|
| 215 | 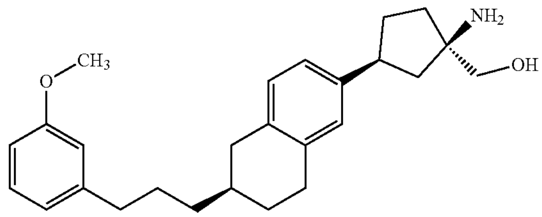 [SMILES: COc1cccc(CCC[C@@H]2CCc3cc([C@H]4CC[C@](N)(CO)C4)ccc3C2)c1] | 393.6 | 8.19 | L | 394 | |
| 216 | 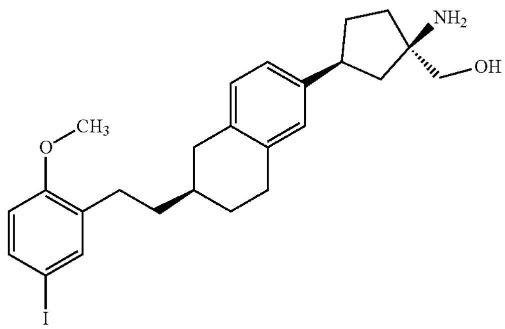 [SMILES: COc1ccc(I)cc1CC[C@@H]1CCc2cc([C@H]3CC[C@](N)(CO)C3)ccc2C1] | 505.4 | 8.87 | L | 506 | |
| 217 | | 353.5 | 3.77 | L | 354 | |
| 218 | | 353.5 | 3.77 | L | 354 | |
| 219 | 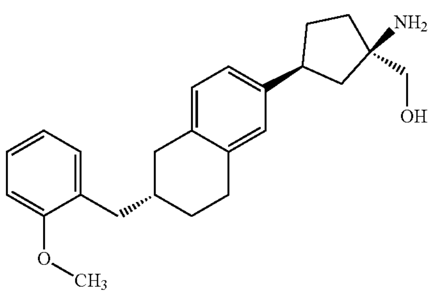 [SMILES: COc1ccccc1C[C@H]1CCc2cc([C@H]3CC[C@](N)(CO)C3)ccc2C1] | 365.5 | 7.45 | L | 366 | |
| 220 | 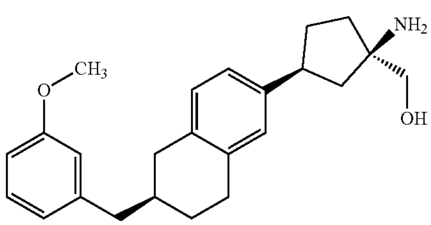 [SMILES: COc1cccc(C[C@@H]2CCc3cc([C@H]4CC[C@](N)(CO)C4)ccc3C2)c1] | 365.5 | 7.26 | L | 366 | |
| 221 | 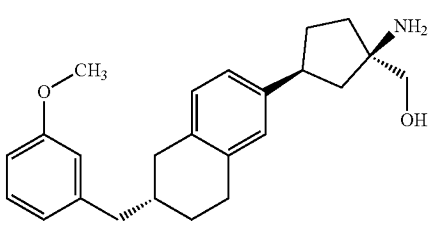 [SMILES: COc1cccc(C[C@H]2CCc3cc([C@H]4CC[C@](N)(CO)C4)ccc3C2)c1] | 365.5 | 7.25 | L | 366 | |

TABLE 11-continued

| Ex. No. | Structure | MW | HPLC ret. time (min.) | HPLC method | MS (M+1) | Comment |
|---|---|---|---|---|---|---|
| 222 | 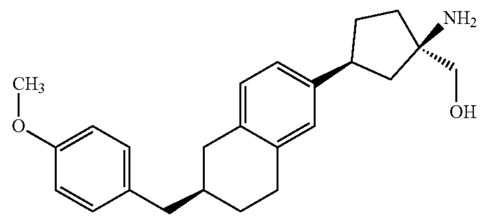 [SMILES: COc1ccc(C[C@@H]2CCc3cc([C@H]4CC[C@](N)(CO)C4)ccc3C2)cc1] | 365.5 | 7.31 | L | 366 | |
| 223 | 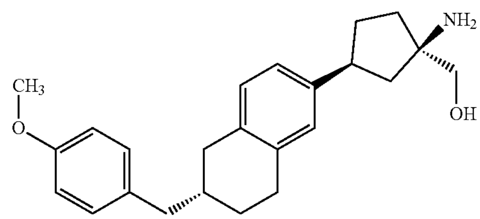 [SMILES: COc1ccc(C[C@H]2CCc3cc([C@H]4CC[C@](N)(CO)C4)ccc3C2)cc1] | 365.5 | 7.24 | L | 366 | |
| 224 | 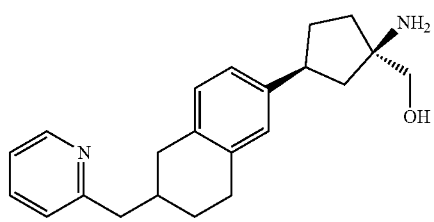 [SMILES: N[C@]1(CO)CC[C@H](c2ccc3c(c2)CCC(Cc2ccccn2)C3)C1] | 336.5 | 3.19 | L | 337 | Isomer 1 |
| 225 | 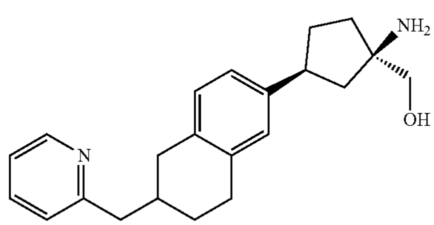 [SMILES: N[C@]1(CO)CC[C@H](c2ccc3c(c2)CCC(Cc2ccccn2)C3)C1] | 336.5 | 3.20 | L | 337 | Isomer 2 |

Examples 226 and 227

((1R,3S)-1-amino-3-(2-hexyl-2,3-dihydro-1H-inden-5-yl)cyclopentyl)methanol

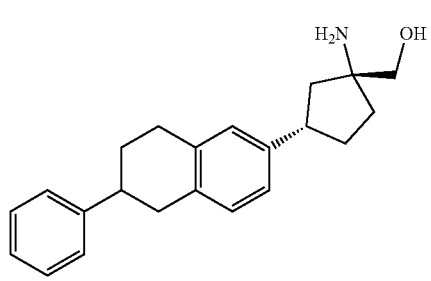

(226 and 227)

Preparation 226A: (5R,7S)-7-(6-phenyl-7,8-dihydronaphthalen-2-yl)-3-oxa-1-azaspiro[4.4]nonan-2-one

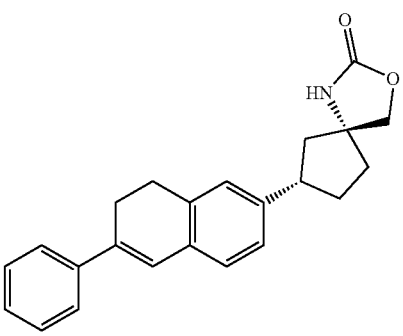

(226A)

To a mixture of 6-((5R,7S)-2-oxo-3-oxa-1-azaspiro[4.4]nonan-7-yl)-3,4-dihydronaphthalen-2-yl trifluoromethanesulfonate (75 mg, 0.180 mmol), triphenylphosphine (10 mg, 0.038 mmol), and acetylacetone cobalt (III) salt (4 mg, 0.011 mmol) in THF (5 mL) was added phenylmagnesium bromide (0.539 mL, 0.539 mmol). The reaction mixture was stirred for 3 hours and during this time was allowed to warm to room temperature. The reaction was quenched with water and the mixture was diluted with ethyl acetate and washed with saturated NaCl. The organic layer was dried with $MgSO_4$, filtered and concentrated. The crude material was purified on a silica gel cartridge (24 g) using an EtOAc/Hex gradient (0-100% EtOAc over 13 CV) to afford 55 mg of (5R,7S)-7-(6-phenyl-7,8-dihydronaphthalen-2-yl)-3-oxa-1-azaspiro[4.4]nonan-2-one. HPLC retention time=1.06 min (condition G); LC/MS $M^{+1}$=346.

Preparation 226B: (5R,7S)-7-(6-phenyl-5,6,7,8-tetrahydronaphthalen-2-yl)-3-oxa-1-azaspiro[4.4]nonan-2-one Isomer 1

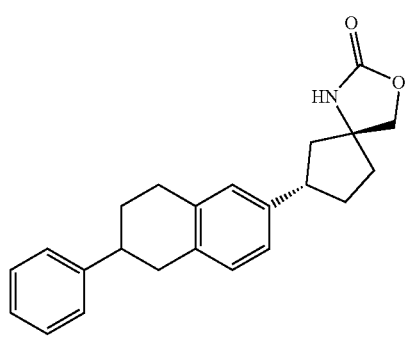

Isomer 2

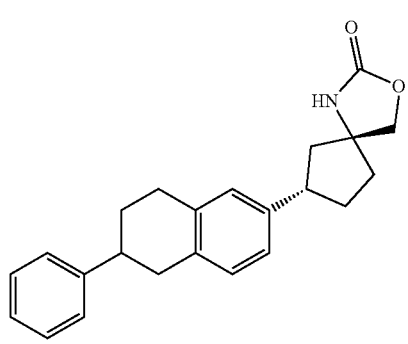

To a mixture of (5R,7S)-7-(6-phenyl-7,8-dihydronaphthalen-2-yl)-3-oxa-1-azaspiro[4.4]nonan-2-one (55 mg, 0.159 mmol) in MeOH (10 mL) was added Pearlman's Catalyst (22.36 mg, 0.159 mmol). The mixture was hydrogenated under a balloon of $H_2$ for one hour. The mixture was filtered to remove the catalyst and concentrated to afford 38 mg of (5R,7S)-7-(6-phenyl-5,6,7,8-tetrahydronaphthalen-2-yl)-3-oxa-1-azaspiro[4.4]nonan-2-one. The individual isomers were separated using a CHIRALPAK® AD-H column under SFC conditions (50% MeOH in $CO_2$). Isomer 1 (226B, 12 mg), retention time on chiral HPLC, 10.3 min; MS (m+1) =348. Isomer 2 (227B, 12 mg), retention time on chiral HPLC, 13.3 min.; MS (m+1)=348. The absolute stereochemistry of the isomers was not determined.

Examples 226 and 227

To a mixture of (5R,7S)-7-(6-phenyl-5,6,7,8-tetrahydronaphthalen-2-yl)-3-oxa-1-azaspiro[4.4]nonan-2-one (12 mg, 0.035 mmol, 226B, isomer 1) in dioxane (2 mL) was added 2N NaOH. The reaction mixture was heated at 100° C. overnight, cooled, and then acidified with TFA. The solvents were removed, MeOH (1.8 mL) was added, and the mixture was filtered to remove solids and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Recovered 8 mg of ((1R,3S)-1-amino-3-(6-phenyl-5,6,7,8-tetrahydronaphthalen-2-yl)cyclopentyl)methanol (Isomer 1, Example 226). HPLC retention time=8.22 min (condition H); LC/MS $M^{+1}$=322; $^1$H NMR (400 MHz, METHANOL-$d_4$) δ 7.40-7.25 (m, 4H), 7.25-7.15 (m, 1H), 7.11-6.97 (m, 3H), 3.81-3.55 (m, 2H), 3.24-3.06 (m, 1H), 3.03-2.79 (m, 5H), 2.45 (ddd, J=13.4, 7.1, 1.1 Hz, 1H), 2.23-2.06 (m, 2H), 2.04-1.86 (m, 4H), 1.75 (t, J=12.7 Hz, 1H); MS (m+1)=322.

To a mixture of (5R,7S)-7-(6-phenyl-5,6,7,8-tetrahydronaphthalen-2-yl)-3-oxa-1-azaspiro[4.4]nonan-2-one (12 mg, 0.035 mmol, 227B, isomer 2) in dioxane (2 mL) was added 2N NaOH. The reaction mixture was heated at 100° C. overnight, cooled, and then acidified with TFA. The solvents were removed, MeOH (1.8 mL) was added, and the mixture was filtered to remove solids and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Recovered 4.5 mg of ((1R,3S)-1-amino-3-(6-phenyl-5,6,7,8-tetrahydronaphthalen-2-yl)cyclopentyl)methanol (Example 227, Isomer 2). HPLC retention time=8.24 min (condition H); LC/MS $M^{+1}$=322; $^1$H NMR (400 MHz, METHANOL-$d_4$) δ 7.36-7.27 (m, 4H), 7.24-7.17 (m, 1H), 7.05 (s, 3H), 3.73-3.58 (m, 2H), 3.21-3.08 (m, 1H), 3.05-2.82 (m, 5H), 2.44 (ddd, J=13.4, 7.1, 1.1 Hz, 1H), 2.21-2.07 (m, 2H), 2.04-1.88 (m, 4H), 1.75 (t, J=12.7 Hz, 1H); MS (m+1)=322.

The Examples in Table 12 were prepared according to the general procedure of Examples 226 and 227.

TABLE 12

| Ex. No. | Structure | MW | HPLC ret. time (min.) | HPLC condition | MS ($M^{+1}$) | Comment |
|---|---|---|---|---|---|---|
| 228 | 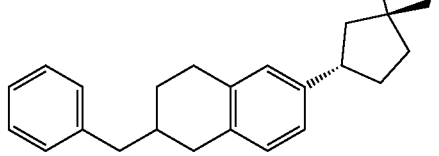 | 335.5 | 8.87 | H | 336 | Isomer 1 |
| 229 | | 335.5 | 8.92 | H | 336 | Isomer 2 |

TABLE 12-continued

| Ex. No. | Structure | MW | HPLC ret. time (min.) | HPLC condition | MS (M+1) | Comment |
|---|---|---|---|---|---|---|
| 230 | 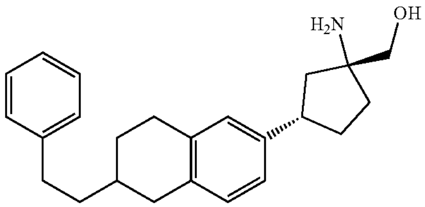 [SMILES: N[C@]1(CO)CC[C@H](c2ccc3c(c2)CCC(CCc2ccccc2)C3)C1] | 349.5 | 9.15 | H | 350 | Isomer 1 |
| 231 | | 349.5 | 9.16 | H | 350 | Isomer 2 |
| 232 | 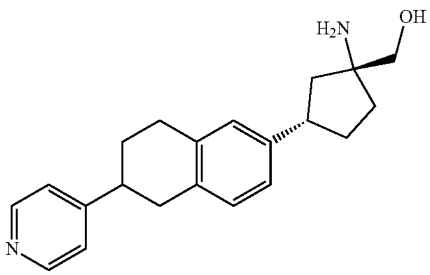 [SMILES: N[C@]1(CO)CC[C@H](c2ccc3c(c2)CCC(c2ccncc2)C3)C1] | 322.5 | 3.78 | H | 323 | Isomer 1 |
| 233 | | 322.5 | 0.5 | G | 323 | Isomer 2 |
| 234 | 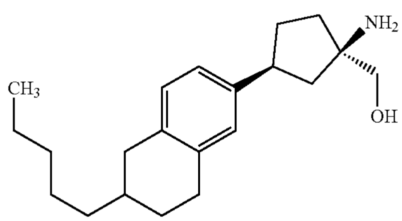 [SMILES: CCCCCC1CCc2cc([C@H]3CC[C@](N)(CO)C3)ccc2C1] | 315.5 | 9.57 | L | 316 | Isomer 1 |
| 235 | | 315.5 | 9.67 | L | 316 | Isomer 2 |
| 236 | 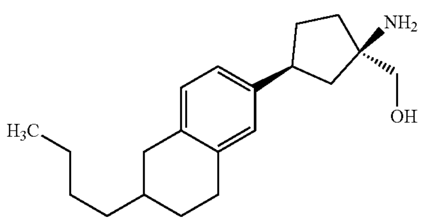 [SMILES: CCCCC1CCc2cc([C@H]3CC[C@](N)(CO)C3)ccc2C1] | 301.5 | 9.05 | L | 302 | Isomer 1 |
| 237 | | 301.5 | 9.02 | L | 302 | Isomer 2 |

Examples 238 and 239

((1R,3S)-3-(6-(2-(allyloxy)ethoxy)-5,6,7,8-tetrahydronaphthalen-2-yl)-1-aminocyclopentyl)methanol (238 and 239)

Preparation 238A: (5R,7S)-7-(3',4'-dihydro-1'H-spiro[[1,3]dioxolane-2,2'-naphthalen]-6'-yl)-3-oxa-1-azaspiro[4.4]nonan-2-one (238A)

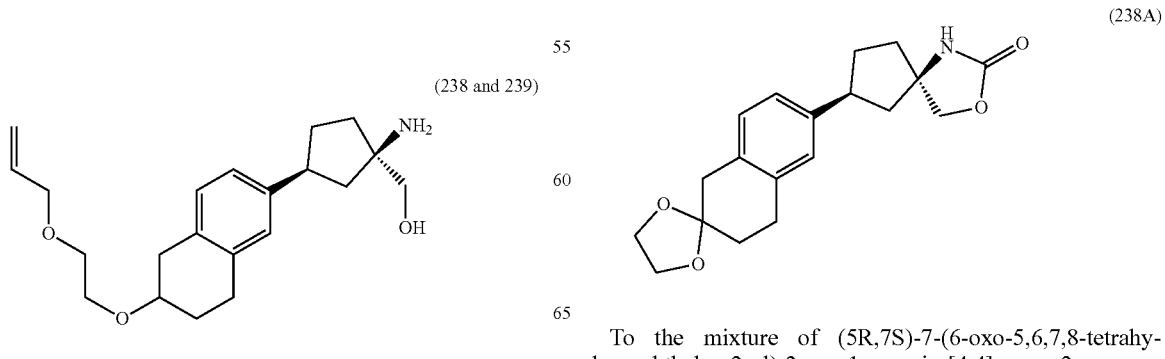

To the mixture of (5R,7S)-7-(6-oxo-5,6,7,8-tetrahydronaphthalen-2-yl)-3-oxa-1-azaspiro[4.4]nonan-2-one (200 mg, 0.701 mmol) and ethane-1,2-diol (870 mg, 14.02 mmol) in MeCN (5 ml), p-toluenesulfonic acid (26.7 mg, 0.140 mmol) was added and the mixture was stirred at room temperature for 16 h. The mixture was diluted with EtOAc (50 ml), the organic layer was washed with saturated NaHCO₃(3×20 ml), dried with Na₂SO₄ and concentrated under reduced pressure to give 205 mg of crude (5R,7S)-7-(3',4'-dihydro-1'H-spiro[[1,3]dioxolane-2,2'-naphthalen]-6'-yl)-3-oxa-1-azaspiro[4.4]nonan-2-one. HPLC retention time=2.58 min (condition B); LC-MS M$^{+1}$=330.

Preparation 238B: (5R,7S)-7-(6-(2-hydroxyethoxy)-5,6,7,8-tetrahydronaphthalen-2-yl)-3-oxa-1-azaspiro[4.4]nonan-2-one

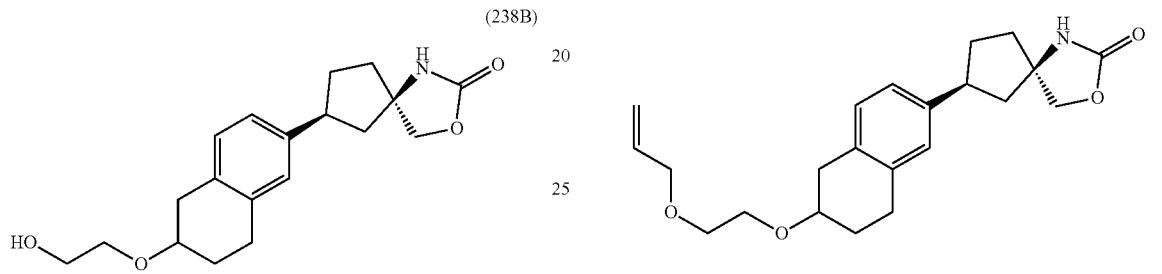

(238B)

To the mixture of (5R,7S)-7-(3',4'-dihydro-1'H-spiro[[1,3]dioxolane-2,2'-naphthalen]-6'-yl)-3-oxa-1-azaspiro[4.4]nonan-2-one (50 mg, 0.152 mmol) and BF₃.OEt₂ (192 μl, 1.52 mmol) in THF (5 ml), NaCNBH₄ (76 mg, 1.21 mmol) was added. The mixture was stirred at room temperature overnight. The reaction was quenched with water (1 ml) at 0° C. The mixture was diluted with EtOAc (40 ml), washed with saturated NaHCO₃(2×20 ml), dried with Na₂SO₄ and concentrated under reduced pressure to give 50 mg of (5R,7S)-7-(6-(2-hydroxyethoxy)-5,6,7,8-tetrahydronaphthalen-2-yl)-3-oxa-1-azaspiro[4.4]nonan-2-one. HPLC retention time=2.42 min (condition B); LC-MS M$^{+1}$=332.

Preparation 238C: 2-((6-((5R,7S)-2-oxo-3-oxa-1-azaspiro[4.4]nonan-7-yl)-1,2,3,4-tetrahydronaphthalen-2-yl)oxy)ethyl 4-methylbenzenesulfonate

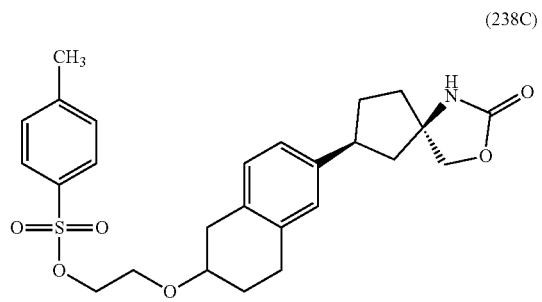 [SMILES: Cc1ccc(S(=O)(=O)OCCOC2CCc3cc([C@H]4CC[C@]5(COC(=O)N5)C4)ccc3C2)cc1]

(238C)

To the mixture of (5R,7S)-7-(6-(2-hydroxyethoxy)-5,6,7,8-tetrahydronaphthalen-2-yl)-3-oxa-1-azaspiro[4.4]nonan-2-one (300 mg, 0.905 mmol) in dry pyridine (5 ml), 4-methylbenzene-1-sulfonyl chloride (518 mg, 2.72 mmol) was added in one portion at 0° C. The resulting mixture was stirred at room temperature for 1 h, the mixture was diluted with EtOAc (80 ml), washed with saturated NaHCO₃(3×30 ml), dried with Na₂SO₄ and concentrated under reduced pressure. The residue was purified with silica gel cartridge (40 g) using an EtOAc/Hex gradient (0-65% EtOAc over 40 minutes) to provide 360 mg 2-((6-((5R,7S)-2-oxo-3-oxa-1-azaspiro[4.4]nonan-7-yl)-1,2,3,4-tetrahydronaphthalen-2-yl)oxy)ethyl 4-methylbenzenesulfonate. HPLC retention time=3.33 min (condition B); LC-MS M$^{+1}$=486. ¹H NMR (400 MHz, METHANOL-d₄) δ 7.77 (d, J=8.1 Hz, 2H), 7.40 (d, J=7.9 Hz, 2H), 7.04-6.94 (m, 3H), 4.42-4.26 (m, 2H), 4.17 (t, J=4.5 Hz, 2H), 3.73 (dt, J=9.5, 4.5 Hz, 3H), 3.08-2.81 (m, 3H), 2.74-2.60 (m, 2H), 2.45 (s, 3H), 2.34-2.27 (m, 1H), 2.09 (s, 2H), 1.95 (s, 3H), 1.82-1.75 (m, 2H).

Preparations 238D and 239D: (5R,7S)-7-(6-(2-(allyloxy)ethoxy)-5,6,7,8-tetrahydronaphthalen-2-yl)-3-oxa-1-azaspiro[4.4]nonan-2-one

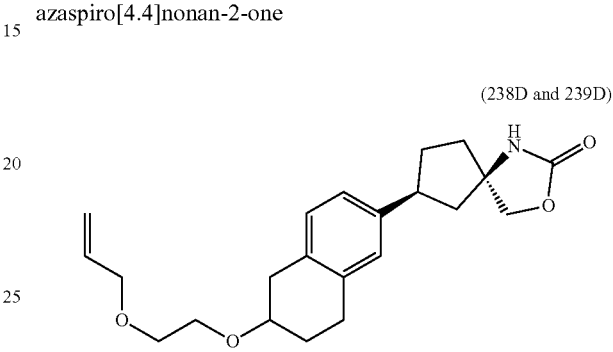

(238D and 239D)

To the mixture of 2-((6-((5R,7S)-2-oxo-3-oxa-1-azaspiro[4.4]nonan-7-yl)-1,2,3,4-tetrahydronaphthalen-2-yl)oxy)ethyl 4-methylbenzenesulfonate (80 mg, 0.165 mmol) and prop-2-en-1-ol (28.7 mg, 0.494 mmol) in 2 ml of THF, KOtBu (92 mg, 0.824 mmol) was added and the mixture was stirred at room temperature for 16 h, then at 65° C. for 1.5 h. The mixture was quenched with water (1 ml) at 0° C., diluted with EtOAc (40 ml), washed with saturated NaHCO₃ (2×20 ml), dried with Na₂SO₄ and concentrated under reduced pressure to give 60 mg (5R,7S)-7-(6-(2-(allyloxy)ethoxy)-5,6,7,8-tetrahydronaphthalen-2-yl)-3-oxa-1-azaspiro[4.4]nonan-2-one. The individual isomers were separated using a Chiral OD-H 25×3 cm ID, 5 um under SFC conditions (20% MeOH in CO₂).

Preparation 238D: Isomer 1 (10 mg), HPLC retention time=3.20 min (condition B); MS (m+1)=372; ¹H NMR (400 MHz, METHANOL-d₄) δ 7.05-6.94 (m, 3H), 6.00-5.82 (m, 1H), 5.33-5.08 (m, 2H), 4.43-4.26 (m, 2H), 4.03 (dt, J=5.6, 1.4 Hz, 2H), 3.89-3.58 (m, 5H), 3.12-2.85 (m, 3H), 2.83-2.69 (m, 2H), 2.29 (dd, J=13.0, 7.0 Hz, 1H), 2.18-2.02 (m, 3H), 2.01-1.74 (m, 4H).

Preparation 239D: Isomer 2 (8 mg), HPLC retention time=3.19 min(condition B); MS (m+1)=372. ¹H NMR (400 MHz, METHANOL-d₄) δ 7.11-6.94 (m, 3H), 6.01-5.84 (m, 1H), 5.35-5.11 (m, 2H), 4.47-4.25 (m, 2H), 4.03 (dt, J=5.6, 1.4 Hz, 2H), 3.88-3.56 (m, 5H), 3.13-2.87 (m, 3H), 2.83-2.67 (m, 2H), 2.29 (dd, J=13.0, 7.0 Hz, 1H), 2.17-1.71 (m, 7H). The absolute stereochemistry of the isomers was not determined.

Examples 238 and 239

To the mixture of (5R,7S)-7-(6-(2-(allyloxy)ethoxy)-5,6,7,8-tetrahydronaphthalen-2-yl)-3-oxa-1-azaspiro[4.4]nonan-2-one (Preparation 238D, 10 mg, 0.027 mmol) and LiOH—H₂O (13.6 mg, 15 eq) in dioxane (1.5 ml) and water (0.5 ml) was heated at 100° C. for 16 h. After cooling, the mixture was diluted with DCM (50 ml) and water (20 ml), the organic layer was separated and the aqueous layer was added saturated NaHCO₃(10 ml) and extracted with DCM (30 ml). The combined DCM mixture was dried with Na₂SO₄, concentrated under vacuo and purified with preparative HPLC: column Phenomenex Luna C18 5 u 21.2× 100 mm. Solvent A: 10% MeOH-90% H₂O-0.1% TFA; Solvent B: 90% MeOH-10% H₂O-0.1% TFA. Gradient time=15 min. Start B=0%, Final B 100%. Stop time 25 min. The desired peak was collected, basified to approximately pH 8 with saturated NaHCO₃, the solvent was removed under reduced pressure and the aqueous layer was extracted with DCM (3×30 ml), which was dried with Na₂SO₄, concentrated under reduced pressure, redissolved in MeCN (2 ml) and water (1 ml) and lyophilized for overnight to give Example 238 (6 mg of isomer 1) ((1R,3S)-3-(6-(2-(allyloxy)ethoxy)-5,6,7,8-tetrahydronaphthalen-2-yl)-1-aminocyclopentyl) methanol. HPLC retention time=8.0 min (condition L); LC-MS M$^{+1}$=346; $^1$H NMR (400 MHz, METHANOL-d₄) δ 7.08-6.94 (m, 3H), 5.92 (ddt, J=17.2, 10.7, 5.4 Hz, 1H), 5.34-5.12 (m, 2H), 4.03 (dt, J=5.6, 1.5 Hz, 2H), 3.89-3.58 (m, 7H), 3.21-2.86 (m, 3H), 2.82-2.71 (m, 2H), 2.48-2.36 (m, 1H), 2.19-2.02 (m, 2H), 2.01-1.81 (m, 4H), 1.72 (t, J=12.7 Hz, 1H).

Example 239 (5 mg of isomer 2) ((1R,3S)-3-(6-(2-(allyloxy)ethoxy)-5,6,7,8-tetrahydronaphthalen-2-yl)-1-aminocyclopentyl)methanol was prepared similarly from 8 mg of Preparation 239D of (5R,7S)-7-(6-(2-(allyloxy)ethoxy)-5,6,7,8-tetrahydronaphthalen-2-yl)-3-oxa-1-azaspiro[4.4]nonan-2-one. HPLC retention time=7.99 min (condition L); LC-MS M$^{+1}$=346; $^1$H NMR (400 MHz, METHANOL-d₄) δ 7.08-6.95 (m, 3H), 6.02-5.82 (m, 1H), 5.33-5.12 (m, 2H), 4.03 (dt, J=5.5, 1.4 Hz, 2H), 3.88-3.54 (m, 7H), 3.14-2.87 (m, 3H), 2.82-2.66 (m, 2H), 2.33 (dd, J=13.2, 6.4 Hz, 1H), 2.15-2.02 (m, 2H), 1.98-1.80 (m, 4H), 1.65 (t, J=12.5 Hz, 1H).

The Examples in Table 13 were prepared according to the general procedure of Examples 238 and 239.

TABLE 13

| Ex. No. | Structure | MW | HPLC ret. time (min.) | HPLC method | MS (M$^{+1}$) | Comment |
|---|---|---|---|---|---|---|
| 240 | | 373.5 | 8.71 | L | 374 | Isomer 1 |
| 241 | | 373.5 | 8.73 | L | 374 | Isomer 2 |
| 242 | 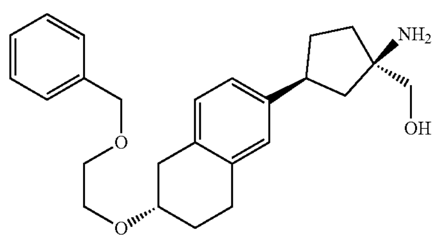 [SMILES: N[C@]1(CO)CC[C@H](c2ccc3c(c2)CC[C@H](OCCOCc2ccccc2)C3)C1] | 395.5 | 8.94 | L | 396 | Isomer 1 |
| 243 | 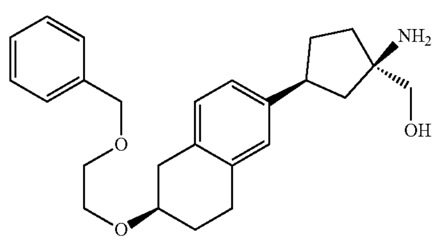 [SMILES: N[C@]1(CO)CC[C@H](c2ccc3c(c2)CC[C@@H](OCCOCc2ccccc2)C3)C1] | 395.5 | 8.95 | L | 396 | Isomer 2 |
| 244 | 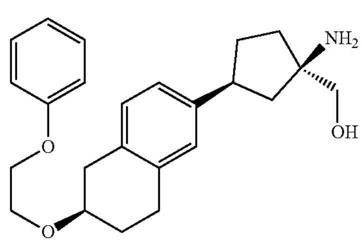 [SMILES: N[C@]1(CO)CC[C@H](c2ccc3c(c2)CC[C@@H](OCCOc2ccccc2)C3)C1] | 395.5 | 8.94 | L | 396 | Isomer 1 |

TABLE 13-continued

| Ex. No. | Structure | MW | HPLC ret. time (min.) | HPLC method | MS (M+1) | Comment |
|---|---|---|---|---|---|---|
| 245 | 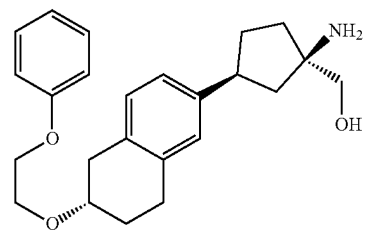 [SMILES: N[C@]1(CO)CC[C@H](c2ccc3c(c2)CC[C@H](OCCOc2ccccc2)C3)C1] | 395.5 | 8.95 | L | 396 | Isomer 2 |
| 246 | 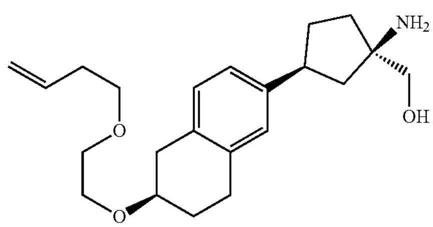 [SMILES: C=CCCOCCO[C@@H]1CCc2cc([C@H]3CC[C@](N)(CO)C3)ccc2C1] | 359.5 | 7.06 | L | 360 | OH-Is#2 |
| 247 | 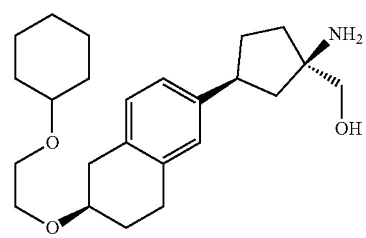 [SMILES: N[C@]1(CO)CC[C@H](c2ccc3c(c2)CC[C@@H](OCCOC2CCCCC2)C3)C1] | 387.6 | 8.03 | L | 388 | |
| 248 | 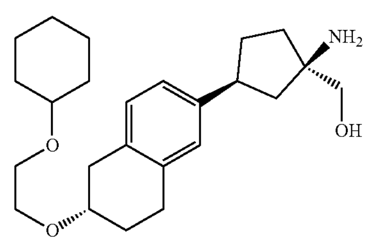 [SMILES: N[C@]1(CO)CC[C@H](c2ccc3c(c2)CC[C@H](OCCOC2CCCCC2)C3)C1] | 387.6 | 6.87 | L | 388 | |
| 249 | 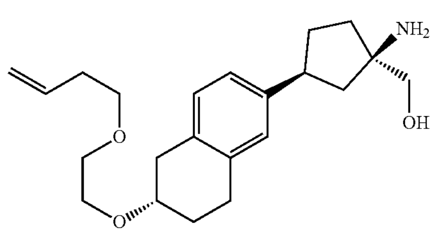 [SMILES: C=CCCOCCO[C@H]1CCc2cc([C@H]3CC[C@](N)(CO)C3)ccc2C1] | 359.5 | 6.05 | L | 360 | |
| 250 | 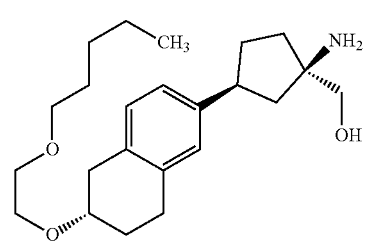 [SMILES: CCCCCOCCO[C@H]1CCc2cc([C@H]3CC[C@](N)(CO)C3)ccc2C1] | 375.6 | 7.00 | L | 376 | |

TABLE 13-continued

| Ex. No. | Structure | MW | HPLC ret. time (min.) | HPLC method | MS (M$^{+1}$) | Comment |
|---|---|---|---|---|---|---|
| 251 | 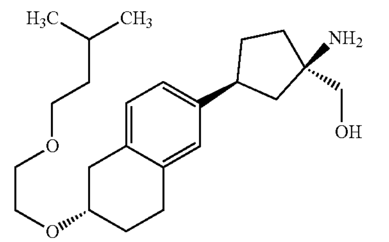 [SMILES: CC(C)CCOCCO[C@H]1CCc2cc([C@H]3CC[C@](N)(CO)C3)ccc2C1] | 375.6 | 6.97 | L | 376 | |
| 252 | 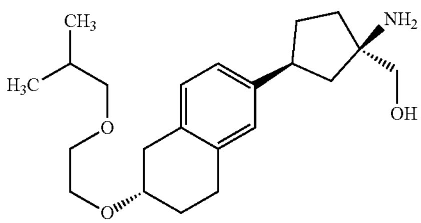 [SMILES: CC(C)COCCO[C@H]1CCc2cc([C@H]3CC[C@](N)(CO)C3)ccc2C1] | 361.5 | 6.51 | L | 362 | |
| 253 | 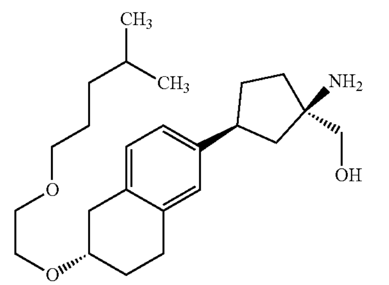 [SMILES: CC(C)CCCOCCO[C@H]1CCc2cc([C@H]3CC[C@](N)(CO)C3)ccc2C1] | 389.6 | 7.50 | L | 390 | |
| 254 | 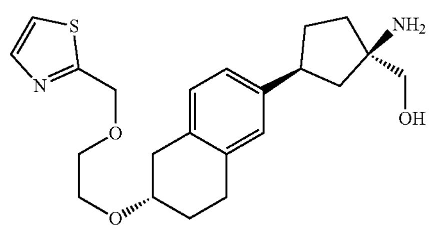 [SMILES: N[C@]1(CO)CC[C@H](c2ccc3c(c2)CC[C@H](OCCOCc2nccs2)C3)C1] | 402.6 | 5.08 | L | 403 | |
| 255 | 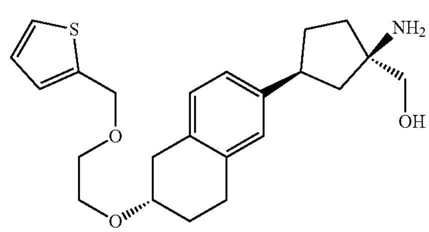 [SMILES: N[C@]1(CO)CC[C@H](c2ccc3c(c2)CC[C@H](OCCOCc2cccs2)C3)C1] | 401.6 | 6.33 | L | 402 | |
| 256 | 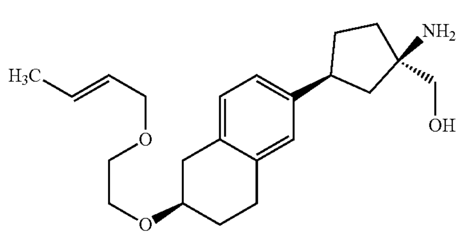 [SMILES: C/C=C/COCCO[C@@H]1CCc2cc([C@H]3CC[C@](N)(CO)C3)ccc2C1] | 359.5 | 5.88 | L | 360 | |

TABLE 13-continued

| Ex. No. | Structure | MW | HPLC ret. time (min.) | HPLC method | MS (M$^{+1}$) | Comment |
|---|---|---|---|---|---|---|
| 257 | 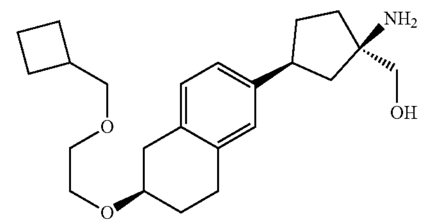 [SMILES: N[C@]1(CO)CC[C@H](c2ccc3c(c2)CC[C@@H](OCCOCC2CCC2)C3)C1] | 373.5 | 7.81 | L | 374 | |
| 258 | 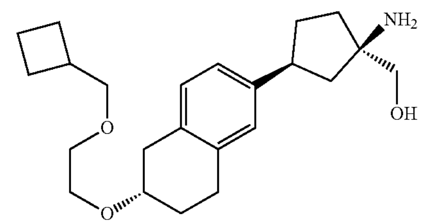 [SMILES: N[C@]1(CO)CC[C@H](c2ccc3c(c2)CC[C@H](OCCOCC2CCC2)C3)C1] | 373.5 | 6.58 | L | 374 | |
| 259 | 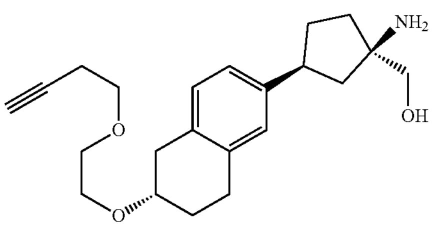 [SMILES: C#CCCOCCO[C@H]1CCc2cc([C@H]3CC[C@](N)(CO)C3)ccc2C1] | 357.4 | 5.75 | L | 358 | |
| 260 | 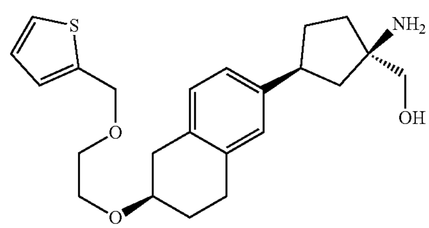 [SMILES: N[C@]1(CO)CC[C@H](c2ccc3c(c2)CC[C@@H](OCCOCc2cccs2)C3)C1] | 401.5 | 6.37 | L | 402 | |
| 261 | 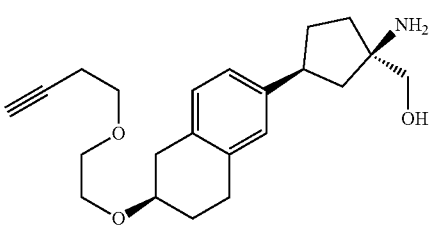 [SMILES: C#CCCOCCO[C@@H]1CCc2cc([C@H]3CC[C@](N)(CO)C3)ccc2C1] | 357.4 | 5.76 | L | 358 | |
| 262 | 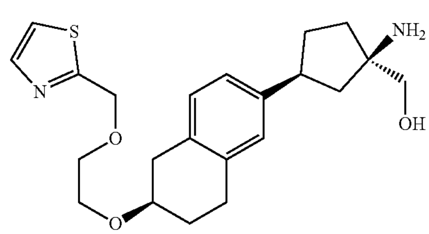 [SMILES: N[C@]1(CO)CC[C@H](c2ccc3c(c2)CC[C@@H](OCCOCc2nccs2)C3)C1] | 402.5 | 5.09 | L | 403 | |

TABLE 13-continued

| Ex. No. | Structure | MW | HPLC ret. time (min.) | HPLC method | MS (M+1) | Comment |
|---|---|---|---|---|---|---|
| 263 | 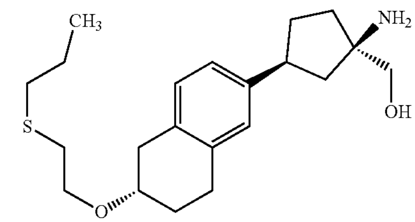 [SMILES: CCCSCCO[C@H]1CCc2cc([C@H]3CC[C@](N)(CO)C3)ccc2C1] | 363.5 | 6.78 | L | 364 | |
| 264 | 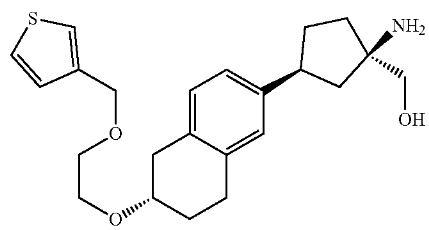 [SMILES: N[C@]1(CO)CC[C@H](c2ccc3c(c2)CC[C@H](OCCOCc2ccsc2)C3)C1] | 401.5 | 6.29 | L | 402 | |
| 265 | 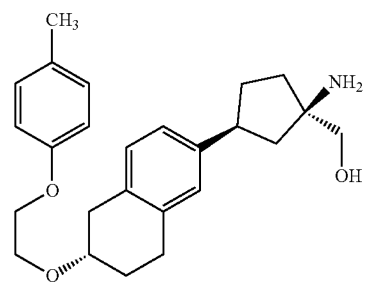 [SMILES: Cc1ccc(OCCO[C@H]2CCc3cc([C@H]4CC[C@](N)(CO)C4)ccc3C2)cc1] | 395.5 | 7.10 | L | 396 | |
| 266 | | 361.5 | 8.73 | L | 362 | Isomer 1 |
| 267 | | 361.5 | 8.74 | L | 362 | Isomer 2 |

Examples 268 and 269

((1R,3S)-1-amino-3-(6-(4-methoxyphenethyl)-5,6,7,8-tetrahydronaphthalen-2-yl) cyclopentyl)methanol (268 and 269)

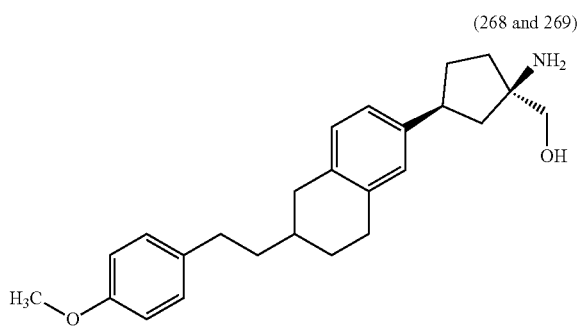 [SMILES: COc1ccc(CCC2CCc3cc([C@H]4CC[C@](N)(CO)C4)ccc3C2)cc1]

To a mixture of 6-((5R,7S)-2-oxo-3-oxa-1-azaspiro[4.4]nonan-7-yl)-3,4-dihydronaphthalen-2-yl trifluoromethanesulfonate (100 mg, 0.240 mmol), copper(I) iodide (4.56 mg, 0.024 mmol), and bis(triphenylphosphine)palladium(II) chloride (16.82 mg, 0.024 mmol) in TEA (3 mL) was added 1-ethynyl-4-methoxybenzene (63.3 mg, 0.479 mmol). The reaction mixture was heated at 60° C. for 1 hour. The reaction mixture was diluted with ethyl acetate and washed with 1M HCl. The organic layer was dried with MgSO$_4$, filtered and concentrated. The crude material was purified on a silica gel cartridge (24 g) using an EtOAc/Hex gradient (0-100% EtOAc over 13 CV) to afford (5R,7S)-7-(6-((4-methoxyphenyl)ethynyl)-7,8-dihydronaphthalen-2-yl)-3-oxa-1-azaspiro[4.4]nonan-2-one (68 mg, 0.170 mmol). LC/MS M$^{+1}$=402.

To a mixture of (5R,7S)-7-(6-((4-methoxyphenyl)ethynyl)-7,8-dihydronaphthalen-2-yl)-3-oxa-1-azaspiro[4.4]nonan-2-one (62 mg, 0.155 mmol) in MeOH (5 mL) was added Pearlman's Catalyst (10.90 mg, 0.078 mmol). The flask was charged with hydrogen and hydrogenated under a balloon for 2 hours. The catalyst was filtered away and the mixture was concentrated in vacuo to afford 45 mg of (5R,7S)-7-(6-(4-methoxyphenethyl)-5,6,7,8-tetrahydronaphthalen-2-yl)-3-oxa-1-azaspiro[4.4]nonan-2-one.
Two diastereomers were separated under SFC conditions on a Chiral AS-H 25×3 cm ID, 5 μm column and eluting with 60/40 CO$_2$/MeOH at 85.0 mL/min. Each isomer was taken to the next step. LC/MS M$^{+1}$=406.

Example 268: To a mixture of (5R,7S)-7-(6-(4-methoxyphenethyl)-5,6,7,8-tetrahydronaphthalen-2-yl)-3-oxa-1-azaspiro[4.4]nonan-2-one (18 mg, 0.044 mmol) in DMSO (1 mL) and MeOH (1 mL) was added 1N NaOH (0.5 mL). The reaction mixture was heated at 90° C. overnight. The mixture was acidified with TFA followed by the removal of most solvent. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight to afford ((1R,3S)-1-amino-3-(6-(4-methoxyphenethyl)-5,6,7,8-tetrahydronaphthalen-2-yl)cyclopentyl)methanol, TFA (14 mg, 0.026 mmol). $^1$H NMR in CD3OD (400 MHz, METHANOL-d$_4$) δ 7.13 (d, J=8.6 Hz, 2H), 7.04-6.96 (m, 3H), 6.84 (d, J=8.8 Hz, 2H), 3.77 (s, 3H), 3.71-3.55 (m, 2H), 3.19-3.01 (m, 1H), 2.95-2.73 (m, 3H), 2.73-2.63 (m, 2H), 2.42 (dd, J=14.2, 7.8 Hz, 2H), 2.21-2.06 (m, 1H), 2.05-1.85 (m, 4H), 1.80-1.59 (m, 4H), 1.43 (dtd, J=12.8, 10.5, 6.1 Hz, 1H). MS (m+1)=380. HPLC Peak RT=10.16 min. (Condition L). Purity=92%.

Example 269: To a mixture of (5R,7S)-7-(6-(4-methoxyphenethyl)-5,6,7,8-tetrahydronaphthalen-2-yl)-3-oxa-1-azaspiro[4.4]nonan-2-one (17 mg, 0.044 mmol) in DMSO (1 mL) and MeOH (1 mL) was added 1N NaOH (0.5 mL). The mixture was heated at 90° C. overnight. The mixture was acidified with TFA followed by the removal of most solvent. The mixture was filtered and purified by HPLC. HPLC conditions: Phenomenex Luna 5 micron C18 column (30× 100 mm); MeCN (0.1% TFA)/water (0.1% TFA); 20%-100% gradient over 15 minutes; 30 mL/min. Fractions with the correct mass were isolated and freeze-dried overnight to afford ((1R,3S)-1-amino-3-(6-(4-methoxyphenethyl)-5,6,7,8-tetrahydronaphthalen-2-yl)cyclopentyl)methanol, TFA (14 mg, 0.026 mmol). $^1$H NMR in CD$_3$OD (400 MHz, METHANOL-d$_4$) δ 7.13 (d, J=8.6 Hz, 2H), 7.04-6.96 (m, 3H), 6.84 (d, J=8.8 Hz, 2H), 3.77 (s, 3H), 3.70-3.55 (m, 2H), 3.19-3.03 (m, 1H), 2.97-2.74 (m, 3H), 2.73-2.62 (m, 2H), 2.42 (dd, J=14.1, 7.7 Hz, 2H), 2.21-2.06 (m, 1H), 2.05-1.87 (m, 4H), 1.81-1.58 (m, 4H), 1.43 (dtd, J=12.7, 10.6, 5.9 Hz, 1H). MS (m+1)=380. HPLC Peak RT=10.16 min. (Condition L) Purity=99%.

The Examples in Table 14 were prepared according to the general procedure of Examples 268 and 269.

TABLE 14

| Ex. No. | Structure | MW | HPLC ret. Time (min.) | HPLC condition | MS (M$^{+1}$) | Comment |
|---|---|---|---|---|---|---|
| 270 | 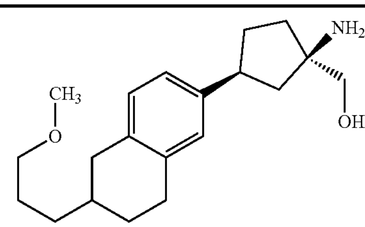 | 317.5 | 7.18 | L | 318 | Isomer 1 |
| 271 | 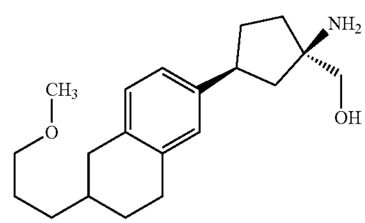 [SMILES: COCCCC1CCc2cc([C@H]3CC[C@](N)(CO)C3)ccc2C1] | 317.5 | 7.16 | L | 318 | Isomer 2 |
| 272 | 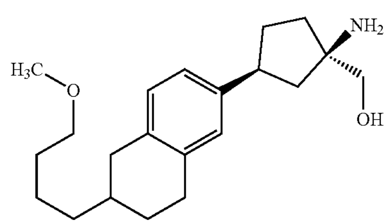 [SMILES: COCCCCC1CCc2cc([C@H]3CC[C@](N)(CO)C3)ccc2C1] | 331.5 | 7.64 | L | 332 | Isomer 1 |
| 273 | 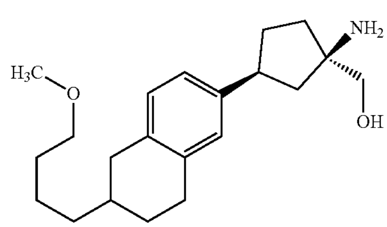 [SMILES: COCCCCC1CCc2cc([C@H]3CC[C@](N)(CO)C3)ccc2C1] | 331.5 | 7.64 | L | 332 | Isomer 2 |

TABLE 14-continued

| Ex. No. | Structure | MW | HPLC ret. Time (min.) | HPLC condition | MS (M+1) | Comment |
|---|---|---|---|---|---|---|
| 274 | 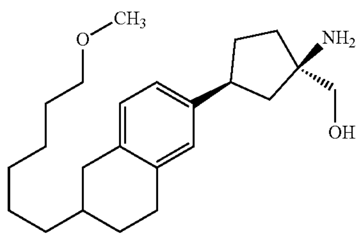 [SMILES: COCCCCCCC1CCc2cc([C@H]3CC[C@](N)(CO)C3)ccc2C1] | 359.6 | 7.58 | L | 360 | Isomer 1 |
| 275 | 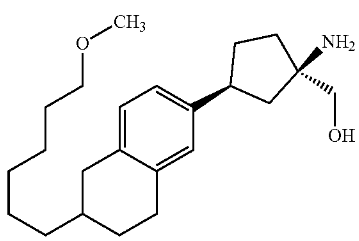 [SMILES: COCCCCCCC1CCc2cc([C@H]3CC[C@](N)(CO)C3)ccc2C1] | 359.6 | 7.58 | L | 360 | Isomer 2 |
| 276 | 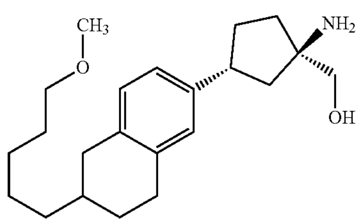 [SMILES: COCCCCCC1CCc2cc([C@@H]3CC[C@](N)(CO)C3)ccc2C1] | 345.5 | 8.18 | L | 346.4 | Isomer 1 |
| 277 | | 345.5 | 8.17 | L | 346.4 | Isomer 2 |

Example 278

((1R,3S)-1-amino-3-((S)-6-(3-isopropoxypropyl)-5,6,7,8-tetrahydronaphthalen-2-yl)cyclopentyl)methanol (278)

Preparation 278A: (5R,7S)-7-((R)-6-(but-3-en-1-yl)-5,6,7,8-tetrahydronaphthalen-2-yl)-3-oxa-1-azaspiro[4.4]nonan-2-one (278A)

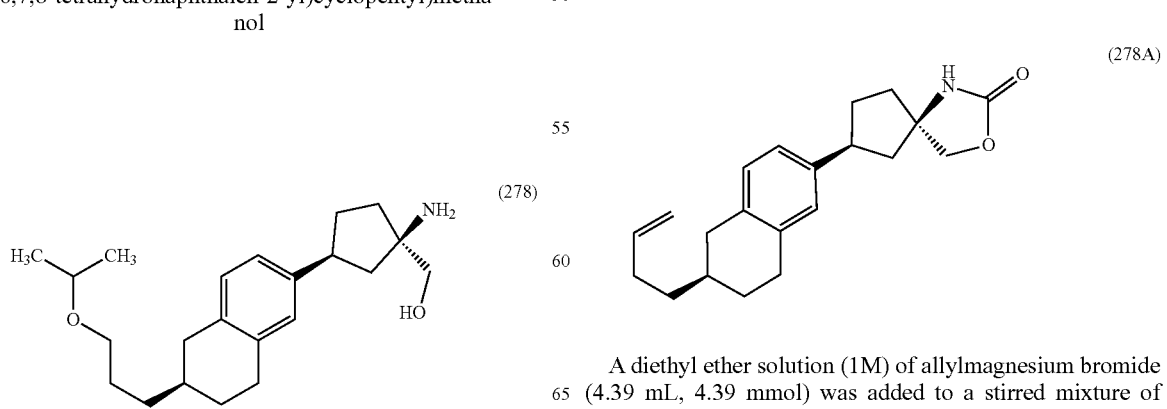

A diethyl ether solution (1M) of allylmagnesium bromide (4.39 mL, 4.39 mmol) was added to a stirred mixture of copper(I) bromide (63.0 mg, 0.439 mmol), ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (100 mg, 0.220 mmol) and anhydrous tetrahydrofuran (2 mL) at −78° C. under nitrogen. The mixture was stirred at −78° C. for 20 min before the temperature was slowly raised to room temperature. The mixture was stirred at room temperature for 16 hr. Saturated aqueous NH$_4$Cl solution (3 mL) was added slowly to quench the reaction. Ethyl acetate (4 mL) and water (1 mL) were added. The aqueous layer was separated and extracted with ethyl acetate (2×3 mL). The combined organic solutions were dried over sodium sulfate and concentrated under reduced pressure to give (5R,7S)-7-((R)-6-(but-3-en-1-yl)-5,6,7,8-tetrahydronaphthalen-2-yl)-3-oxa-1-azaspiro[4.4]nonan-2-one (90 mg, 0.277 mmol). LC/MS M$^{+1}$=326.
Preparation 278B: 3-((S)-6-((5R,7S)-2-oxo-3-oxa-1-azaspiro[4.4]nonan-7-yl)-1,2,3,4-tetrahydronaphthalen-2-yl)propanal

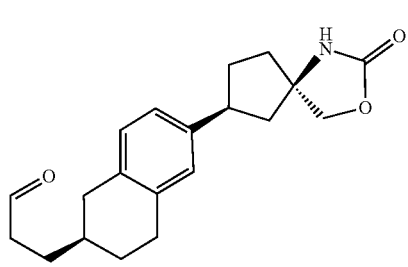

(278B)

To a clear solution of (5R,7S)-7-((R)-6-(but-3-en-1-yl)-5,6,7,8-tetrahydronaphthalen-2-yl)-3-oxa-1-azaspiro[4.4]nonan-2-one (0.09 g, 0.277 mmol) in THF (1.5 mL) were sequentially added 50% NMO in water (0.115 mL, 0.553 mmol) and 4% osmium tetroxide in water (0.051 mL, 8.30 μmol) at room temperature. The solution was vigorously stirred at room temperature overnight. Additional 50% NMO in water (0.06 mL) was added. The solution was vigorously stirred at room temperature for 1 day. Sodium periodate (0.237 g, 1.106 mmol) in H$_2$O (1 mL) was added and the mixture was stirred vigorously at room temperature under nitrogen for 30 min. The mixture was extracted with ethyl acetate (3×2 mL). The combined ethyl acetate extracts were dried (Na$_2$SO$_4$) and concentrated. Flash chromatography purification (4 g silica gel column, gradient elution from 15 to 100% of ethyl acetate in hexanes) afforded 3-((S)-6-((5R,7S)-2-oxo-3-oxa-1-azaspiro[4.4]nonan-7-yl)-1,2,3,4-tetrahydronaphthalen-2-yl)propanal (63 mg, 0.192 mmol) as a solid. HPLC retention time=2.92 min (condition C); LC/MS M$^{+1}$=328.
Preparation 278C: (5R,7S)-7-((S)-6-(3-isopropoxypropyl)-5,6,7,8-tetrahydronaphthalen-2-yl)-3-oxa-1-azaspiro[4.4]nonan-2-one

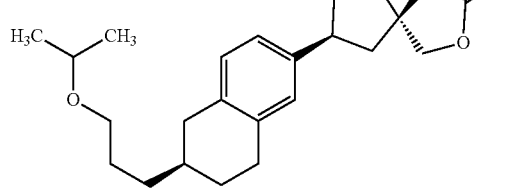

(278C)

To a stirred solution of 3-((S)-6-((5R,7S)-2-oxo-3-oxa-1-azaspiro[4.4]nonan-7-yl)-1,2,3,4-tetrahydronaphthalen-2-yl)propanal (21 mg, 0.064 mmol), isopropoxytrimethylsilane (0.057 mL, 0.321 mmol), and triethylsilane (0.051 mL, 0.321 mmol) in nitromethane (1 mL) was added ferric chloride (1.040 mg, 6.41 μmol) at 0° C. under nitrogen. The mixture was stirred at 0° C. for 15 min and at room temperature for 30 min before being concentrated. The residue was mixed with saturated aqueous sodium bicarbonate solution (1 mL) and extracted with ethyl acetate (3×1 mL). The combined ethyl acetate extracts were dried (Na$_2$SO$_4$) and concentrated under reduced pressure to give (5R,7S)-7-((S)-6-(3-isopropoxypropyl)-5,6,7,8-tetrahydronaphthalen-2-yl)-3-oxa-1-azaspiro[4.4]nonan-2-one (23 mg, 0.062 mmol) as a solid. LC/MS M$^{+1}$=372.

Example 278

A mixture of (5R,7S)-7-((S)-6-(3-isopropoxypropyl)-5,6,7,8-tetrahydronaphthalen-2-yl)-3-oxa-1-azaspiro[4.4]nonan-2-one (23 mg, 0.062 mmol), 2N aqueous NaOH (0.619 mL, 1.238 mmol), and dioxane (0.5 mL) was stirred at 90° C. under nitrogen overnight. The mixture was cooled and extracted with ethyl acetate (4×1 mL). The combined organic solutions were dried over sodium sulfate and concentrated under reduced pressure. Purification using reverse phase HPLC (Phenomenex Luna 5 μ30×100 mm (Axia); gradient over 8 min from 30 to 100% of solvent B; solvent A: 10% MeOH: 90% H$_2$O: 0.1% TFA; solvent B: 90% MeOH, 10% H$_2$O, 0.1% TFA), concentration, basification with 2N aqueous NaOH, and extraction with ethyl acetate gave ((1R,3S)-1-amino-3-((S)-6-(3-isopropoxypropyl)-5,6,7,8-tetrahydronaphthalen-2-yl)cyclopentyl)methanol (21 mg, 0.052 mmol) as a white solid. HPLC retention time=3.04 min (condition C); LC/MS M$^{+1}$=346. $^1$H NMR (400 MHz, CHLOROFORM-d) δ 7.03-6.93 (m, 3H), 3.55 (dt, J=12.2, 6.1 Hz, 1H), 3.51-3.37 (m, 4H), 3.08-2.93 (m, 1H), 2.89-2.71 (m, 3H), 2.38 (dd, J=16.2, 10.7 Hz, 1H), 2.26 (dd, J=13.0, 7.7 Hz, 1H), 2.04 (br. s., 1H), 1.98-1.60 (m, 7H), 1.56-1.45 (m, 1H), 1.45-1.32 (m, 3H), 1.16 (d, J=6.2 Hz, 6H).

Example 279

((1R,3S)-1-amino-3-((R)-6-(3-(oxetan-3-yloxy)propyl)-5,6,7,8-tetrahydronaphthalen-2-yl)cyclopentyl)methanol

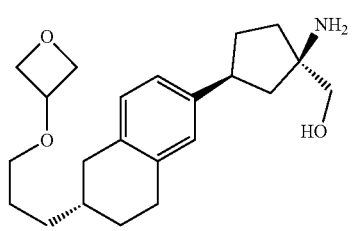

(279)

Preparation 279A: (5R,7S)-7-((R)-6-(3-hydroxypropyl)-5,6,7,8-tetrahydronaphthalen-2-yl)-3-oxa-1-azaspiro[4.4]nonan-2-one Preparation 279B: 3-((R)-6-((5R,7S)-2-oxo-3-oxa-1-azaspiro[4.4]nonan-7-yl)-1,2,3,4-tetrahydronaphthalen-2-yl)propyl 4-methylbenzenesulfonate

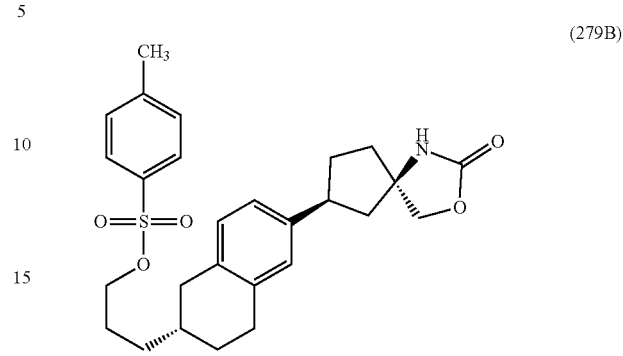
(279B)

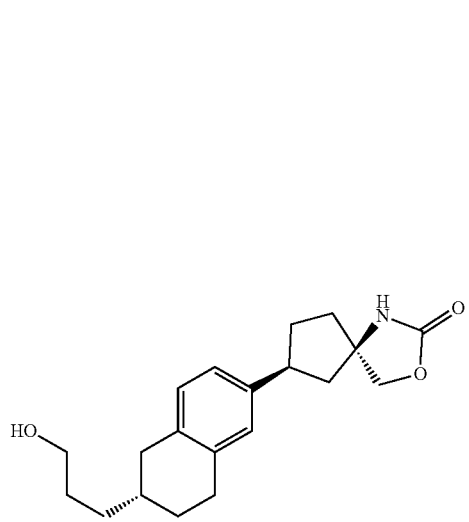
(279A)

The above intermediate was prepared using the same procedure as Preparation 176A Example 279

To a stirred solution of 3-((R)-6-((5R,7S)-2-oxo-3-oxa-1-azaspiro[4.4]nonan-7-yl)-1,2,3,4-tetrahydronaphthalen-2-yl)propanal (162 mg, 0.495 mmol) (Example 278 step B) in 100% ethanol (8 mL) and dichloromethane (2 mL) was added NaBH$_4$ (18.72 mg, 0.495 mmol) at room temperature under nitrogen. The mixture was stirred at room temperature for 1 h. The mixture was concentrated. The reaction was quenched with saturated aqueous NH$_4$Cl solution (1 mL) and water (1 mL) and the mixture was extracted with ethyl acetate (4 mL, 2×1 mL). The combined organic solutions were dried over sodium sulfate and concentrated under reduced pressure to give (5R,7S)-7-((R)-6-(3-hydroxypropyl)-5,6,7,8-tetrahydronaphthalen-2-yl)-3-oxa-1-azaspiro[4.4]nonan-2-one (170 mg, 0.516 mmol) as a white solid. HPLC retention time=3.03 min (condition C); LC/MS M$^{+1}$=330.

To a stirred mixture of 3-((R)-6-((5R,7S)-2-oxo-3-oxa-1-azaspiro[4.4]nonan-7-yl)-1,2,3,4-tetrahydronaphthalen-2-yl)propyl 4-methylbenzenesulfonate (30 mg, 0.062 mmol) and oxetan-3-ol (0.06 mL, 1.016 mmol) was added 1N THF solution of potassium tert-butoxide (0.620 mL, 0.620 mmol) at 0° C. under nitrogen. The resulting mixture was at room temperature for 5 h and 60° C. for 1 hr before 2 N aqueous NaOH (0.310 mL, 0.620 mmol) was added. The mixture was concentrated to remove THF. Dioxane (0.5 mL) was added and the mixture was stirred at 70° C. under nitrogen for 15 hr and at 100° C. for 5 hr. The mixture was cooled and extracted with ethyl acetate (4×1 mL). The combined ethyl acetate extracts were dried (Na$_2$SO$_4$) and concentrated. Purification using reverse phase HPLC (Phenomenex Luna 5 μ30×100 mm (Axia); gradient over 9 min from 20 to 100% of solvent B; solvent A: 10% MeOH: 90% H$_2$O: 0.1% TFA; solvent B: 90% MeOH, 10% H$_2$O, 0.1% TFA), concentration, basification with 2N NaOH, and extraction with ethyl acetate gave ((1R,3S)-1-amino-3-((R)-6-(3-(oxetan-3-yloxy)propyl)-5,6,7,8-tetrahydronaphthalen-2-yl)cyclopentyl)methanol (19 mg, 0.045 mmol) as a solid. HPLC retention time=2.78 min (condition C); LC/MS M$^{+1}$=360. $^1$H NMR (400 MHz, CHLOROFORM-d) δ 7.05-6.87 (m, 3H), 4.81-4.70 (m, 2H), 4.61 (t, J=6.2 Hz, 2H), 4.57-4.48 (m, 1H), 3.37 (t, J=6.6 Hz, 2H), 3.02 (br. s., 1H), 2.90-2.72 (m, 3H), 2.45-2.18 (m, 2H), 2.13-1.61 (m, 10H), 1.56-1.31 (m, 4H).

The Examples in Table 15 were prepared according to the general procedure of Examples 278 and 279.

TABLE 15

| Ex. No. | Structure | MW | HPLC ret. time (min.) | HPLC condition | MS (M$^{+1}$) | Comment |
|---|---|---|---|---|---|---|
| 280 | 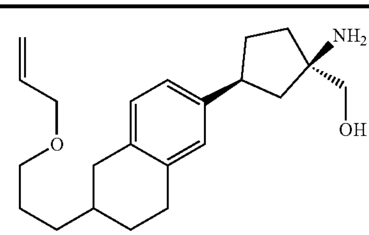 | 343.5 | 6.96 | L | 344 | Isomer 1 |
| 281 |  | 343.5 | 6.93 | L | 344 | Isomer 2 |

TABLE 15-continued
| Ex. No. | Structure | MW | HPLC ret. time (min.) | HPLC condition | MS (M+1) | Comment |
|---|---|---|---|---|---|---|
| 282 | 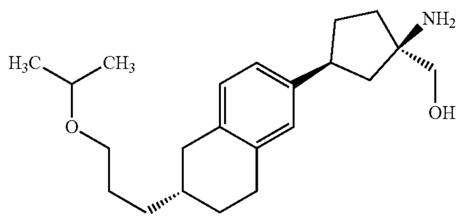 | 345.5 | 3.08 | C | 346 | |
| 283 | 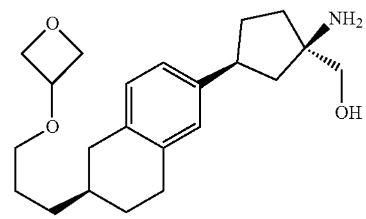 [SMILES: N[C@]1(CO)CC[C@H](c2ccc3c(c2)CC[C@@H](CCCOC2COC2)C3)C1] | 359.5 | 2.80 | C | 360 | |
| 284 | | 363.6 | 7.03 | L | 364 | Isomer 1 |
| 285 | | 363.6 | 7.01 | L | 364 | Isomer 2 |
Example 286
((1R,3S)-1-amino-3-((S)-6-(2-(pyridin-2-yl)ethyl)-5,6,7,8-tetrahydronaphthalen-2-yl) cyclopentyl)methanol
Preparation 286A: 6-((5R,7S)-2-oxo-3-oxa-1-azaspiro[4.4]nonan-7-yl)-1,2,3,4-tetrahydronaphthalene-2-carbaldehyde
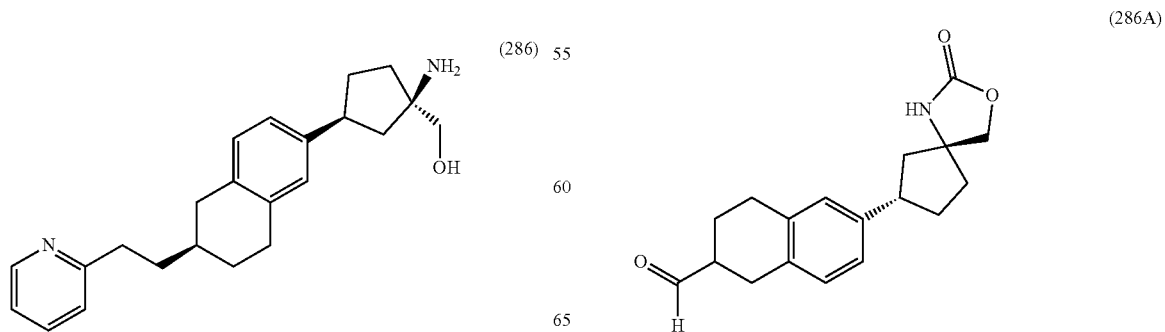

Preparations 286B and 286C: (5R,7S)-7-((S)-6-ethynyl-5,6,7,8-tetrahydronaphthalen-2-yl)-3-oxa-1-azaspiro[4.4]nonan-2-one and (5R,7S)-7-((R)-6-ethynyl-5,6,7,8-tetrahydronaphthalen-2-yl)-3-oxa-1-azaspiro[4.4]nonan-2-one

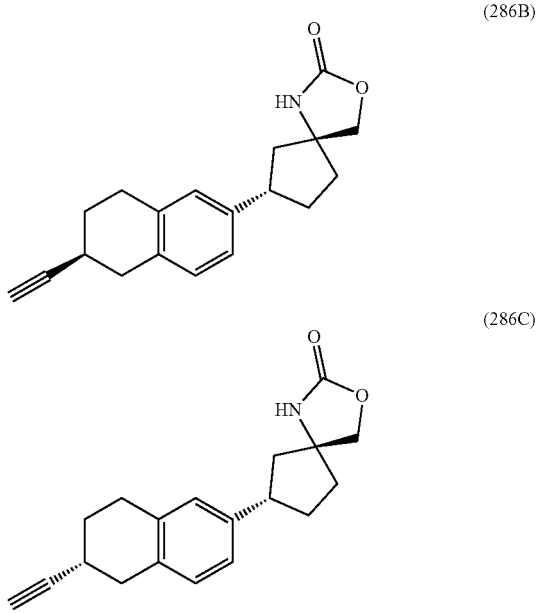

(286B)

(286C)

To a mixture of 6-((5R,7S)-2-oxo-3-oxa-1-azaspiro[4.4]nonan-7-yl)-1,2,3,4-tetrahydronaphthalene-2-carbaldehyde (718 mg, 2.4 mmol) and potassium carbonate (995 mg, 7.20 mmol) in MeOH (3 mL) was added dimethyl (1-diazo-2-oxopropyl) phosphonate (0.540 mL, 3.60 mmol). The reaction mixture was stirred at room temperature for one hour. The reaction mixture was diluted with ethyl acetate and washed with saturated NaCl. The organic layer was dried with MgSO$_4$, filtered and concentrated. The crude material was purified on a silica gel cartridge (40 g) using an EtOAc/Hex gradient (20-100% EtOAc over 12 CV) to afford 580 mg of (5R,7S)-7-6-ethynyl-5,6,7,8-tetrahydronaphthalen-2-yl)-3-oxa-1-azaspiro[4.4]nonan-2-one. The diastereomeric mixture was separated by SFC using a Chiralpak IC, 25×3 cm ID, 5 μm column and eluting with 90/10 CO$_2$/MeOH at 85.0 mL/min. Peak 1 was isolated to afford (5R,7S)-7-((S)-6-ethynyl-5,6,7,8-tetrahydronaphthalen-2-yl)-3-oxa-1-azaspiro[4.4]nonan-2-one (225 mg, 0.762 mmol). Peak 2 was isolated to afford (5R,7S)-7-((R)-6-ethynyl-5,6,7,8-tetrahydronaphthalen-2-yl)-3-oxa-1-azaspiro[4.4]nonan-2-one (245 mg, 0.829 mmol). The absolute stereochemistry was determined by converting Preparation 286B to Preparation 677B. Chiral HPLC analysis indicates compounds were identical and 286B was assigned as the S stereochemistry at the alkynyl center. Preparation 286C was then assigned the R configuration.

Example 286

An oven dried round bottom flask was charged with cesium carbonate (66.2 mg, 0.203 mmol) and bis(di-tert-butyl(4-dimethylaminophenyl)phosphine) dichloropalladium(II) (3 mg, 4.24 μmol) under nitrogen. The mixture was degassed three times under vacuum, followed by the stepwise addition of 2-bromopyridine (10 μl, 0.105 mmol), (5R,7S)-7-((R)-6-ethynyl-5,6,7,8-tetrahydronaphthalen-2-yl)-3-oxa-1-azaspiro[4.4]nonan-2-one (20 mg, 0.068 mmol), and acetonitrile (1 mL). The reaction mixture was heated at 80° C. overnight. Solvent was removed in vacuo and the residue was dissolved in MeOH (2 mL). Pearlman's Catalyst (5 mg, 0.036 mmol) was added and the mixture was hydrogenated under a balloon of H$_2$ for 1 hour. The catalyst was removed by filtration. Next, 1N NaOH (2 mL) was added to the filtrate and the mixture was heated at 95° C. for 6 hours. The mixture was acidfied with TFA then filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions were isolated with the correct mass and freeze-dried overnight to afford ((1R,3S)-1-amino-3-((S)-6-(2-(pyridin-2-yl)ethyl)-5,6,7,8-tetrahydronaphthalen-2-yl) cyclopentyl)methanol (13 mg, 0.033 mmol). HPLC Peak RT=3.66 minutes (Condition L) purity=90%. MS (m+1)=351. $^1$H NMR (400 MHz, METHANOL-d$_4$) δ 8.44 (dd, J=5.1, 0.9 Hz, 1H), 7.77 (td, J=7.7, 1.8 Hz, 1H), 7.37 (d, J=7.9 Hz, 1H), 7.26 (ddd, J=7.5, 5.1, 1.1 Hz, 1H), 6.99 (s, 3H), 3.62-3.46 (m, 2H), 3.14-2.98 (m, 1H), 2.93 (t, J=7.8 Hz, 2H), 2.89-2.69 (m, 2H), 2.45 (dd, J=16.3, 9.7 Hz, 1H), 2.31 (dd, J=13.2, 6.4 Hz, 1H), 2.12-1.98 (m, 2H), 1.97-1.87 (m, 3H), 1.87-1.72 (m, 4H), 1.63 (t, J=12.5 Hz, 1H), 1.46 (dtd, J=12.8, 10.4, 5.9 Hz, 1H).

The Examples in Table 16 were prepared according to the general procedure of Example 286.

TABLE 16

| Ex. No. | Structure | MW | HPLC ret. Time (min.) | HPLC condition | MS (M$^{+1}$) |
| --- | --- | --- | --- | --- | --- |
| 287 | ![structure] | 350.5 | 3.62 | L | 351 |

TABLE 16-continued

| Ex. No. | Structure | MW | HPLC ret. Time (min.) | HPLC condition | MS (M+1) |
|---|---|---|---|---|---|
| 288 | 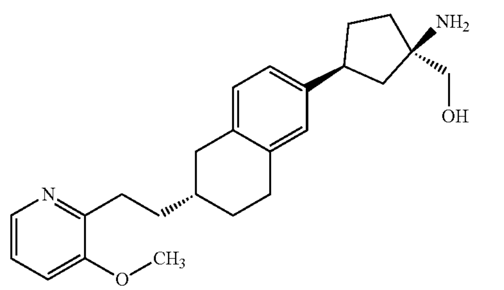 [SMILES: COc1cccnc1CC[C@H]1CCc2cc([C@H]3CC[C@](N)(CO)C3)ccc2C1] | 380.5 | 4.09 | L | 381 |
| 289 | 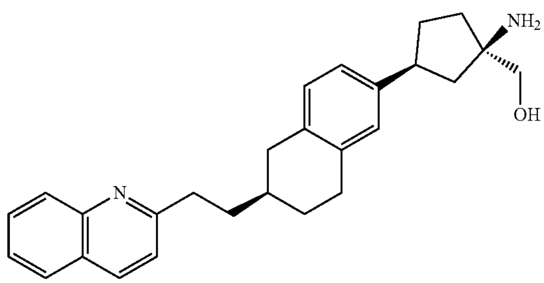 [SMILES: N[C@]1(CO)CC[C@H](c2ccc3c(c2)CC[C@@H](CCc2ccc4ccccc4n2)C3)C1] | 400.6 | 4.37 | L | 401 |
| 290 | 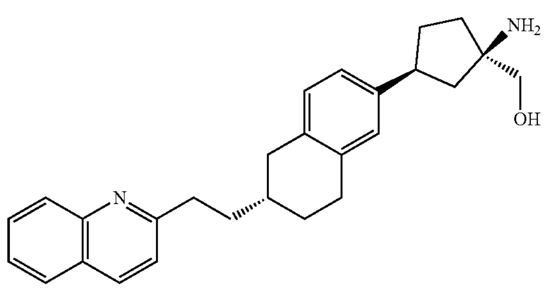 [SMILES: N[C@]1(CO)CC[C@H](c2ccc3c(c2)CC[C@H](CCc2ccc4ccccc4n2)C3)C1] | 400.6 | 4.45 | L | 401 |
| 291 | 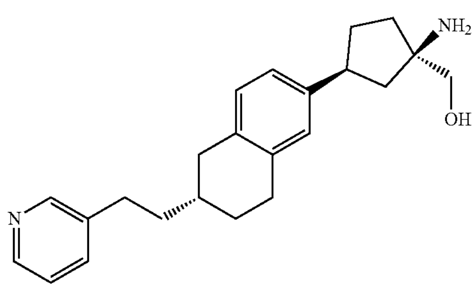 [SMILES: N[C@]1(CO)CC[C@H](c2ccc3c(c2)CC[C@H](CCc2cccnc2)C3)C1] | 350.5 | 3.82 | L | 351 |
| 292 | 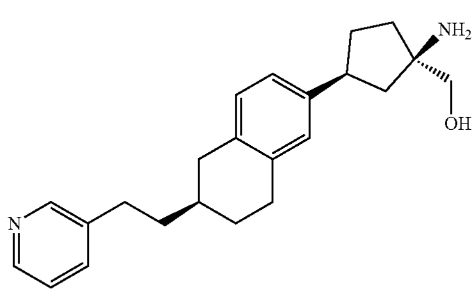 [SMILES: N[C@]1(CO)CC[C@H](c2ccc3c(c2)CC[C@@H](CCc2cccnc2)C3)C1] | 350.1 | 3.86 | L | 351 |

TABLE 16-continued

| Ex. No. | Structure | MW | HPLC ret. Time (min.) | HPLC condition | MS (M+1) |
|---|---|---|---|---|---|
| 293 | 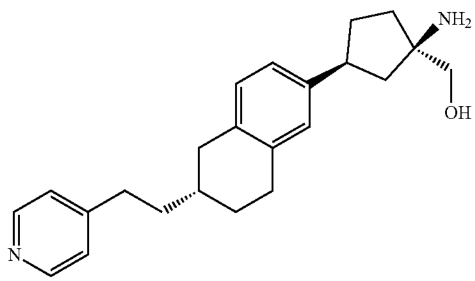 [SMILES: N[C@]1(CO)CC[C@H](c2ccc3c(c2)CC[C@H](CCc2ccncc2)C3)C1] | 350.1 | 3.77 | L | 351 |
| 294 | 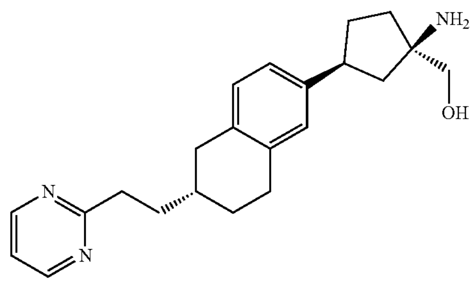 | 351.5 | 4.94 | L | 352 |
| 295 | 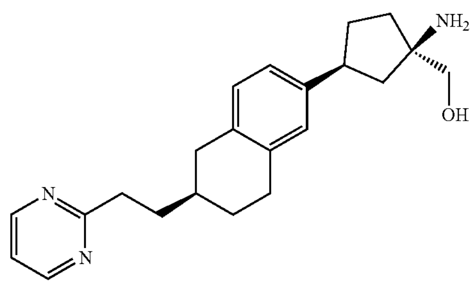 [SMILES: N[C@]1(CO)CC[C@H](c2ccc3c(c2)CC[C@@H](CCc2ncccn2)C3)C1] | 351.5 | 4.95 | L | 352 |
| 296 | 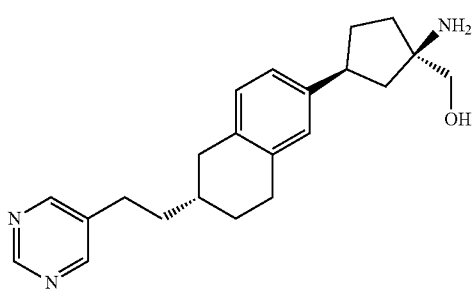 [SMILES: N[C@]1(CO)CC[C@H](c2ccc3c(c2)CC[C@H](CCc2cncnc2)C3)C1] | 351.5 | 5.17 | L | 352 |
| 297 | 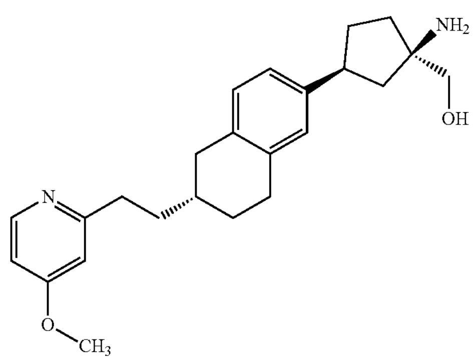 [SMILES: COc1ccnc(CC[C@H]2CCc3cc([C@H]4CC[C@](N)(CO)C4)ccc3C2)c1] | 380.5 | 5.13 | L | 381 |

TABLE 16-continued

| Ex. No. | Structure | MW | HPLC ret. Time (min.) | HPLC condition | MS (M+1) |
|---|---|---|---|---|---|
| 298 | 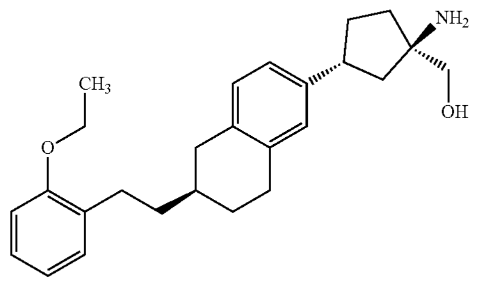 [SMILES: CCOc1ccccc1CC[C@@H]1CCc2cc([C@@H]3CC[C@](N)(CO)C3)ccc2C1] | 393.6 | 8.41 | L | 394 |
| 299 | 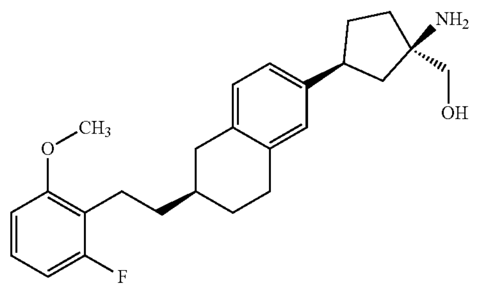 [SMILES: COc1cccc(F)c1CC[C@@H]1CCc2cc([C@H]3CC[C@](N)(CO)C3)ccc2C1] | 397.5 | 7.97 | L | 398 |
| 300 | 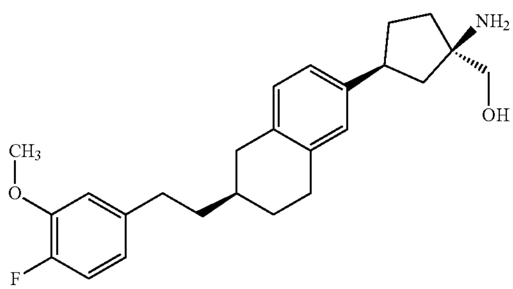 [SMILES: COc1cc(CC[C@@H]2CCc3cc([C@H]4CC[C@](N)(CO)C4)ccc3C2)ccc1F] | 397.5 | 7.89 | L | 398 |
| 301 | 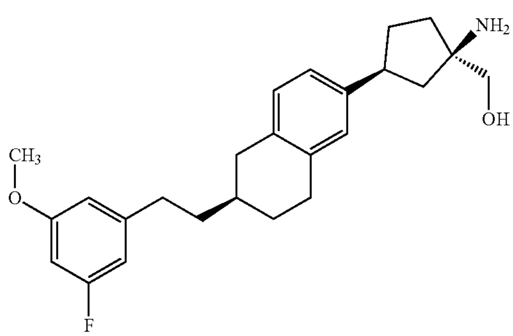 [SMILES: COc1cc(F)cc(CC[C@@H]2CCc3cc([C@H]4CC[C@](N)(CO)C4)ccc3C2)c1] | 397.5 | 9.02 | L | 398 |
| 302 | 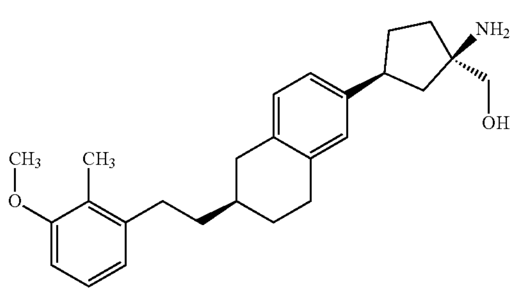 [SMILES: COc1cccc(CC[C@@H]2CCc3cc([C@H]4CC[C@](N)(CO)C4)ccc3C2)c1C] | 393.6 | 8.17 | L | 394 |

TABLE 16-continued

| Ex. No. | Structure | MW | HPLC ret. Time (min.) | HPLC condition | MS (M+1) |
|---|---|---|---|---|---|
| 303 | 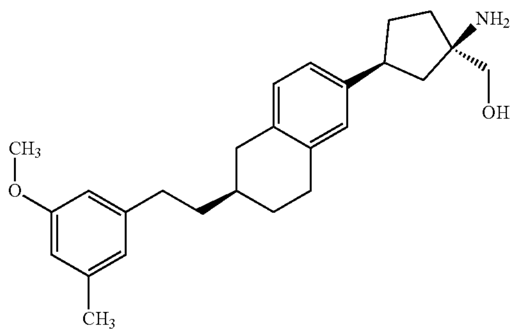 [SMILES: COc1cc(C)cc(CC[C@@H]2CCc3cc([C@H]4CC[C@](N)(CO)C4)ccc3C2)c1] | 393.6 | 8.14 | L | 394 |
| 304 | 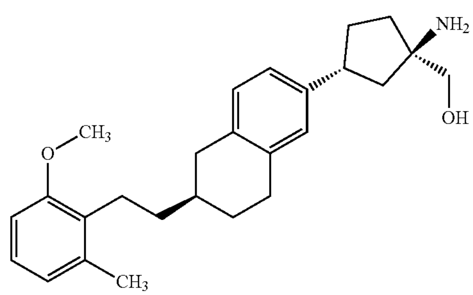 [SMILES: COc1cccc(C)c1CC[C@@H]1CCc2cc([C@@H]3CC[C@](N)(CO)C3)ccc2C1] | 393.6 | 8.26 | L | 394 |

Example 305

((1R,3S)-1-amino-3-((S)-6-(2-(pyridin-2-yl)ethyl)-5,6,7,8-tetrahydronaphthalen-2-yl) cyclopentyl)methanol (305)

Preparation 305A: (5R,7S)-7-((R)-6-(((1-phenyl-1H-tetrazol-5-yl)sulfonyl)methyl)-5,6,7,8-tetrahydronaphthalen-2-yl)-3-oxa-1-azaspiro[4.4]nonan-2-one

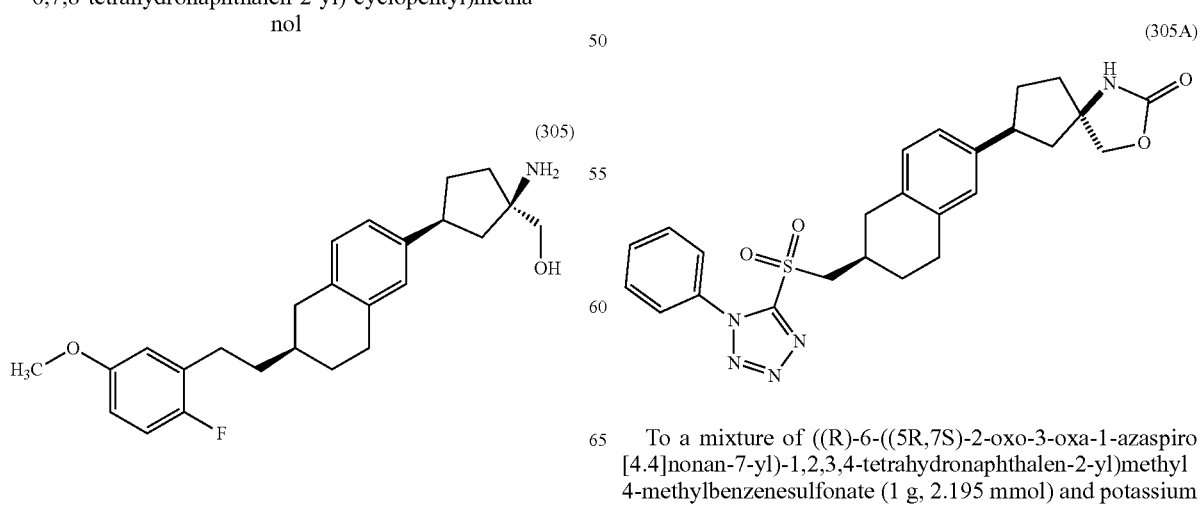

(305A)

To a mixture of ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (1 g, 2.195 mmol) and potassium carbonate (0.910 g, 6.59 mmol) in DMF (10 mL) was added 1-phenyl-1H-tetrazole-5-thiol (0.782 g, 4.39 mmol). The reaction mixture was heated at 80° C. overnight. The reaction mixture was diluted with ethyl acetate and washed with saturated NaCl. The organic layer was dried with MgSO$_4$, filtered and concentrated. The crude material was purified on a silica gel cartridge (40 g) using an EtOAc/Hex gradient (0-100% EtOAc over 13 CV) to afford (5R,7S)-7-((R)-6-(((1-phenyl-1H-tetrazol-5-yl)thio)methyl)-5,6,7,8-tetrahydronaphthalen-2-yl)-3-oxa-1-azaspiro[4.4]nonan-2-one (0.94 g, 2.036 mmol). LC/MS M$^{+1}$=462.

To hydrogen peroxide (8.32 mL, 81 mmol) at 0° C. was added ammonium molybdate tetrahydrate (0.503 g, 0.407 mmol). The resulting solution was added to a mixture of (5R,7S)-7-((R)-6-(((1-phenyl-1H-tetrazol-5-yl)thio)methyl)-5,6,7,8-tetrahydronaphthalen-2-yl)-3-oxa-1-azaspiro[4.4]nonan-2-one (0.94 g, 2.036 mmol) in THF (30 mL) at 0° C. The reaction mixture was stirred overnight at room temperature. The reaction mixture was diluted with ethyl acetate and washed with saturated NaCl. The organic layer was dried with MgSO$_4$, filtered and concentrated to afford (5R,7S)-7-((R)-6-(((1-phenyl-1H-tetrazol-5-yl)sulfonyl)methyl)-5,6,7,8-tetrahydronaphthalen-2-yl)-3-oxa-1-azaspiro[4.4]nonan-2-one one (1 g, 2.026 mmol) which was used without further purification. LC/MS M$^{+1}$=494.

Preparation 305B: (5R,7S)-7-((R)-6-((E)-2-fluoro-5-methoxystyryl)-5,6,7,8-tetrahydronaphthalen-2-yl)-3-oxa-1-azaspiro[4.4]nonan-2-one

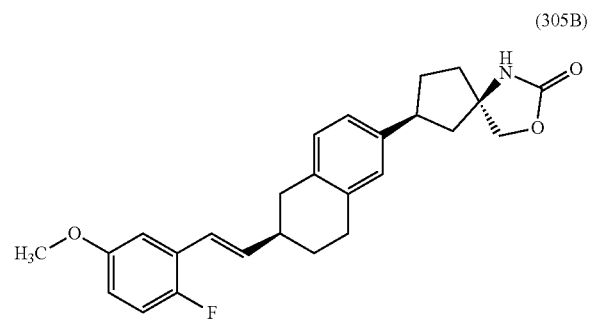 [SMILES: COc1ccc(F)c(/C=C/[C@@H]2CCc3cc([C@H]4CC[C@]5(COC(=O)N5)C4)ccc3C2)c1]

(305B)

To a mixture of 2-fluoro-5-methoxybenzaldehyde (30.0 mg, 0.194 mmol) and (5R,7S)-7-((R)-6-(((1-phenyl-1H-tetrazol-5-yl)sulfonyl)methyl)-5,6,7,8-tetrahydronaphthalen-2-yl)-3-oxa-1-azaspiro[4.4]nonan-2-one (32 mg, 0.065 mmol) in THF was added KHMDS (0.259 mL, 0.259 mmol). After stirring at room temperature for 1 hour, the reaction was quenched with MeOH. The reaction mixture was purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were combined and freeze-dried overnight. Recovered (5R,7S)-7-((R)-6-((E)-2-fluoro-5-methoxystyryl)-5,6,7,8-tetrahydronaphthalen-2-yl)-3-oxa-1-azaspiro[4.4]nonan-2-one (6 mg, 0.014 mmol). LC/MS M$^{+1}$=422.

Example 305

To a mixture of (5R,7S)-7-((R)-6-((E)-2-fluoro-5-methoxystyryl)-5,6,7,8-tetrahydronaphthalen-2-yl)-3-oxa-1-azaspiro[4.4]nonan-2-one (6 mg, 0.014 mmol) in MeOH (2 mL) was added Pearlman's Catalyst (0.5 mg, 3.56 µmol). The mixture was hydrogenated under a balloon of hydrogen for 1 hour. The catalyst was removed by filtration. Next, 1 N NaOH (2 mL) was added and the mixture was heated to reflux overnight. The mixture was cooled and acidified with TFA then purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions were isolated with the correct mass and freeze-dried overnight to afford (1R,3S)-1-amino-3-((S)-6-(2-fluoro-5-methoxyphenethyl)-5,6,7,8-tetrahydronaphthalen-2-yl)cyclopentyl)methanol, TFA (4 mg, 7.66 µmol). $^1$H NMR in CD3OD (400 MHz, METHANOL-d$_4$) δ 7.03-6.98 (m, 3H), 6.95 (t, J=9.2 Hz, 1H), 6.80 (dd, J=6.2, 3.1 Hz, 1H), 6.73 (dt, J=8.8, 3.5 Hz, 1H), 3.77 (s, 3H), 3.71-3.56 (m, 2H), 3.17-3.04 (m, 1H), 2.90 (dd, J=16.6, 4.3 Hz, 1H), 2.85-2.68 (m, 4H), 2.52-2.35 (m, 2H), 2.20-2.08 (m, 1H), 2.07-1.88 (m, 4H), 1.82-1.59 (m, 4H), 1.44 (dtd, J=12.8, 10.4, 6.1 Hz, 1H). MS (m+1)=398. HPLC Peak RT=8.01 min. (Condition L) Purity=98%.

The Examples in Table 17 were prepared according to the general procedure of Example 305.

TABLE 17

| Ex. No. | Structure | MW | HPLC ret. Time (min.) | HPLC condition | MS (M$^{+1}$) |
|---|---|---|---|---|---|
| 306 | 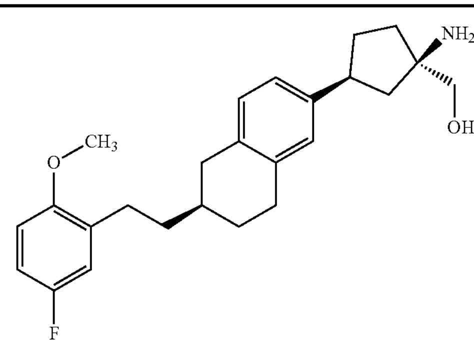 | 397.5 | 7.99 | L | 398 |

TABLE 17-continued

| Ex. No. | Structure | MW | HPLC ret. Time (min.) | HPLC condition | MS (M$^{+1}$) |
|---|---|---|---|---|---|
| 307 | 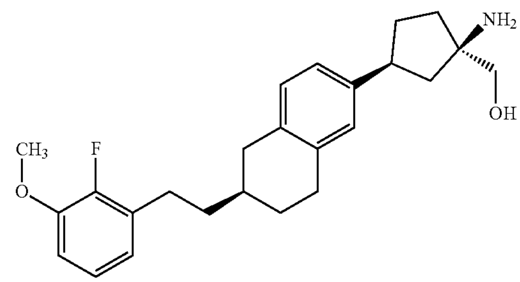 [SMILES: COc1cccc(CC[C@@H]2CCc3cc([C@H]4CC[C@](N)(CO)C4)ccc3C2)c1F] | 397.5 | 7.70 | L | 398 |
| 308 | 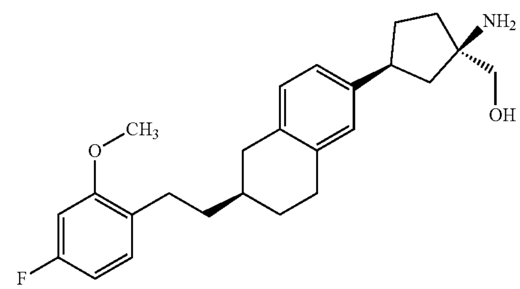 [SMILES: COc1cc(F)ccc1CC[C@@H]1CCc2cc([C@H]3CC[C@](N)(CO)C3)ccc2C1] | 397.5 | 8.07 | L | 398 |
| 309 | 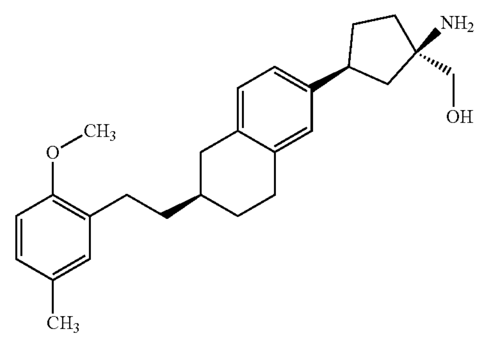 [SMILES: COc1ccc(C)cc1CC[C@@H]1CCc2cc([C@H]3CC[C@](N)(CO)C3)ccc2C1] | 393.6 | 8.36 | L | 394 |
| 310 | 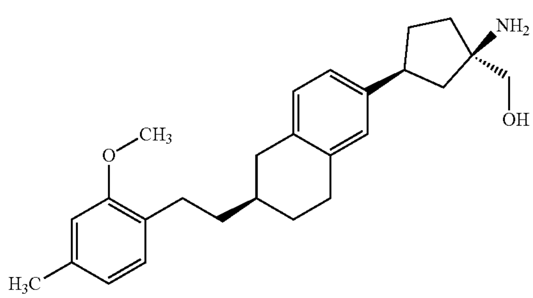 [SMILES: COc1cc(C)ccc1CC[C@@H]1CCc2cc([C@H]3CC[C@](N)(CO)C3)ccc2C1] | 393.6 | 8.38 | L | 394 |
| 311 | 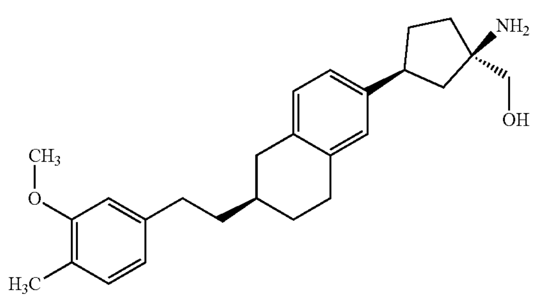 [SMILES: COc1cc(CC[C@@H]2CCc3cc([C@H]4CC[C@](N)(CO)C4)ccc3C2)ccc1C] | 393.6 | 8.33 | L | 394 |

TABLE 17-continued

| Ex. No. | Structure | MW | HPLC ret. Time (min.) | HPLC condition | MS (M$^{+1}$) |
|---|---|---|---|---|---|
| 312 | 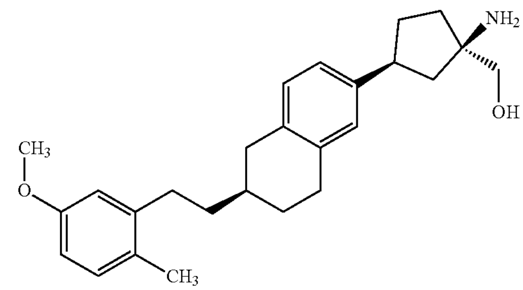 [SMILES: COc1ccc(C)c(CC[C@@H]2CCc3cc([C@H]4CC[C@](N)(CO)C4)ccc3C2)c1] | 393.6 | 1.83 | A | 393 |
| 313 | 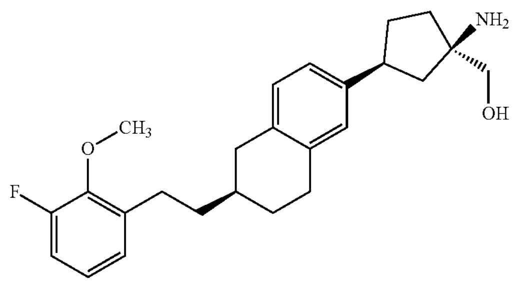 [SMILES: COc1c(F)cccc1CC[C@@H]1CCc2cc([C@H]3CC[C@](N)(CO)C3)ccc2C1] | 397.5 | 9.04 | L | 398 |

Example 314

((1R,3S)-1-amino-3-((S)-6-(5-methoxy-5-methyl-hexyl)-5,6,7,8-tetrahydronaphthalen-2-yl)cyclopentyl)methanol

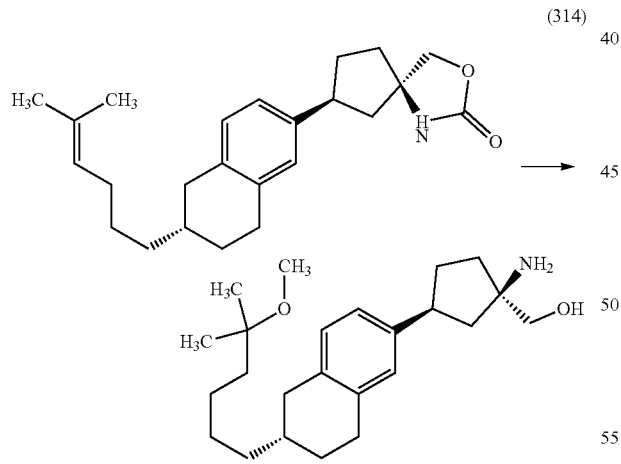

(314)

To a mixture of (5R,7S)-7-((S)-6-(5-methylhex-4-en-1-yl)-5,6,7,8-tetrahydronaphthalen-2-yl)-3-oxa-1-azaspiro[4.4]nonan-2-one (20 mg, 0.054 mmol) in MeOH (10 mL) was added mercuric acetate (26.0 mg, 0.082 mmol). After 1 hour, LCMS showed almost complete conversion to new peak that had the mass of desired product as the Hg adduct. A solution of sodium borohydride (10.29 mg, 0.272 mmol) in sodium hydroxide (0.5 mL, 0.500 mmol) was added to the reaction mixture to remove Hg. The mixture was filtered to remove solids. Next, additional 1N NaOH was added to the filtrate and the mixture was heated to 95° C. overnight. The mixture was cooled and acidified with TFA then purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Isolated fractions with correct mass and freeze-dried overnight to afford ((1R,3S)-1-amino-3-((S)-6-(5-methoxy-5-methylhexyl)-5,6,7,8-tetrahydronaphthalen-2-yl)cyclopentyl)methanol, TFA (10 mg, 0.019 mmol). HPLC Peak RT=7.62 min (Condition L) MS (m+1)=374. $^{1}$H NMR (400 MHz, METHANOL-d$_4$) δ 7.03-6.96 (m, 3H), 3.72-3.55 (m, 2H), 3.20 (s, 3H), 3.15-3.04 (m, 1H), 2.89-2.73 (m, 3H), 2.48-2.31 (m, 2H), 2.19-2.05 (m, 1H), 2.03-1.88 (m, 4H), 1.81-1.62 (m, 2H), 1.59-1.49 (m, 2H), 1.48-1.29 (m, 7H), 1.17 (s, 6H).

Example 315

((1R,3S)-1-amino-3-((R)-6-(4-isopropoxybutyl)-5,6,7,8-tetrahydronaphthalen-2-yl) cyclopentyl)methanol

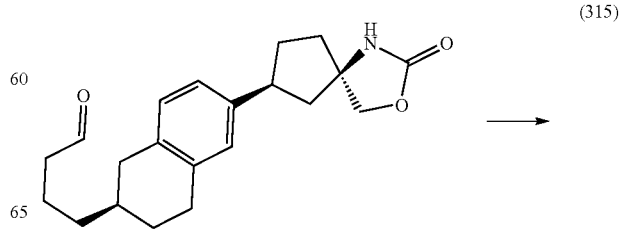

(315)

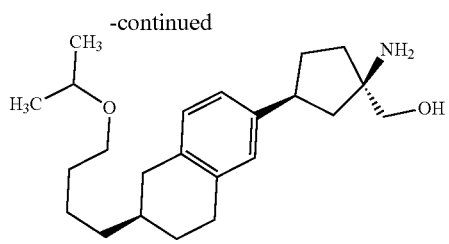

To a stirred solution of 4-((R)-6-((5R,7S)-2-oxo-3-oxa-1-azaspiro[4.4]nonan-7-yl)-1,2,3,4-tetrahydronaphthalen-2-yl)butanal (27 mg, 0.079 mmol), isoproxytrimethylsilane (0.070 mL, 0.395 mmol), and triethylsilane (0.063 mL, 0.395 mmol) in nitromethane (1 mL) was added ferric chloride (1.283 mg, 7.91 μmol) at 0° C. under nitrogen. The mixture was stirred at 0° C. for 15 min and at room temperature for 30 min. The mixture was concentrated. The residue was mixed with saturated aqueous sodium bicarbonate solution (1 mL) and extracted with ethyl acetate (3×1 mL). The combined ethyl acetate extracts were dried ($Na_2SO_4$) and concentrated under reduced pressure. The crude product was dissolved in MeOH/DMSO (1:1) and treated with 1N NaOH at 95° C. overnight. LCMS show complete hydrolysis. The mixture was acidified with TFA then filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with the correct mass were isolated and freeze-dried overnight to afford ((1R,3S)-1-amino-3-((R)-6-(4-isopropoxybutyl)-5,6,7,8-tetrahydronaphthalen-2-yl)cyclopentyl)methanol, TFA (25 mg, 0.048 mmol). MS (m+1)=360. HPLC Peak RT=7.48 min (Condition L). $^1$H NMR (400 MHz, METHANOL-$d_4$) δ 7.03-6.95 (m, 3H), 3.74-3.56 (m, 3H), 3.48 (t, J=6.4 Hz, 2H), 3.18-3.03 (m, 1H), 2.93-2.71 (m, 3H), 2.49-2.31 (m, 2H), 2.20-2.05 (m, 1H), 2.03-1.87 (m, 4H), 1.73 (t, J=12.8 Hz, 2H), 1.58 (q, J=6.5 Hz, 2H), 1.54-1.45 (m, 2H), 1.45-1.30 (m, 3H), 1.17 (d, J=6.2 Hz, 6H).

Example 316

((1R,3S)-1-amino-3-((6S)-6-(5-methoxyhexyl)-5,6,7,8-tetrahydronaphthalen-2-yl) cyclopentyl)methanol

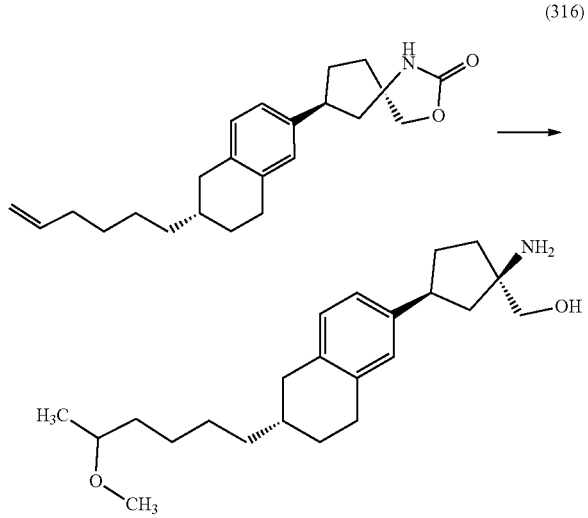

To a mixture of (5R,7S)-7-((S)-6-(hex-5-en-1-yl)-5,6,7,8-tetrahydronaphthalen-2-yl)-3-oxa-1-azaspiro[4.4]nonan-2-one (38 mg, 0.107 mmol) in MeOH (1 mL) was added mercuric acetate (34.3 mg, 0.107 mmol). The reaction mixture was stirred for 2 h then checked by LCMS. LCMS showed desired product mass plus Hg. A solution of sodium borohydride (20.33 mg, 0.537 mmol) in 1M sodium hydroxide (1.075 mL, 1.075 mmol) was added. The mixture was stirred for one hour. The mixture was filtered to remove solids. The filtrate was then heated in 1N NaOH/MeOH at 95° C. overnight, cooled and acidified with TFA, and then purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with the correct mass were isolated and freeze-dried overnight to afford ((1R,3S)-1-amino-3-((6S)-6-(5-methoxyhexyl)-5,6,7,8-tetrahydronaphthalen-2-yl)cyclopentyl) methanol, TFA (18 mg, 0.037 mmol). HPLC Peak RT=7.69/min (Condition L) MS (m+1)=360. $^1$H NMR (400 MHz, METHANOL-$d_4$) δ 7.03-6.96 (m, 3H), 3.72-3.56 (m, 2H), 3.39-3.35 (m, 1H), 3.34 (s, 3H), 3.18-3.03 (m, 1H), 2.91-2.74 (m, 3H), 2.49-2.30 (m, 2H), 2.18-2.05 (m, 1H), 2.03-1.87 (m, 4H), 1.80-1.64 (m, 2H), 1.56 (d, J=3.7 Hz, 1H), 1.50-1.27 (m, 8H), 1.15 (d, J=6.2 Hz, 3H).

Examples 317 to 322

(1-amino-3-(6-hexyl-5,6,7,8-tetrahydroquinolin-2-yl)cyclopentyl)methanol

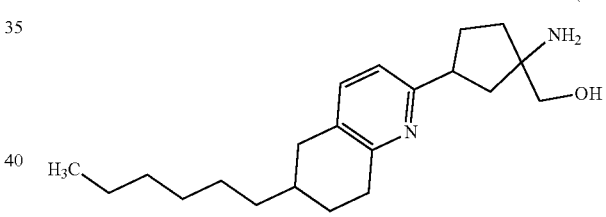

Preparation 317A: 8-hexylidene-1,4-dioxaspiro[4.5]decane

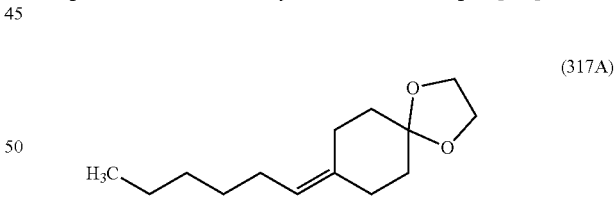

To a mixture of hexyltriphenylphosphonium, iodide salt (25.6 g, 54 mmol) in THF (100 mL) was added LiHMDS (60 mL, 60.0 mmol). The reaction mixture was stirred for 15 minutes, then 1,4-dioxaspiro[4.5]decan-8-one (8.43 g, 54.0 mmol) in THF (100 mL) was added dropwise. The reaction mixture was stirred overnight. The reaction mixture was diluted with ethyl acetate and washed with saturated NaCl. The organic layer was dried with $MgSO_4$, filtered, and concentrated. The crude material was purified on a silica gel cartridge (120 g) using an EtOAc/Hex gradient (100% hexanes for 4 CV then 0-30% EtOAc over 6 CV). Isolated fractions with desired product, concentrated and dried in vacuo. Recovered 3.5 g of 8-hexylidene-1,4-dioxaspiro[4.5]decane.

Preparation 317B: 4-hexylcyclohexanone

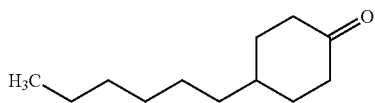
(317B)

To a mixture of 8-hexylidene-1,4-dioxaspiro[4.5]decane (3.5 g, 15.60 mmol) in MeOH (30 mL) was added Pearlman's Catalyst (0.219 g, 1.560 mmol). The reaction mixture was hydrogenated at 50 psi for 2 hours. The mixture was filtered and concentrated. Residue was dissolved in acetone and treated with 1N HCl (20 ml of each). After stirring for 1 hour, the reaction mixture was diluted with ethyl acetate and washed with saturated NaCl. The organic layer was dried with $MgSO_4$, filtered and concentrated to afford 4-hexylcyclohexanone (2.8 g, 15.36 mmol).

Preparation 317C: 6-hexyl-5,6,7,8-tetrahydroquinolin-2-ol

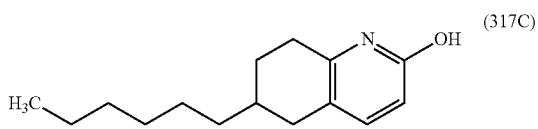 [SMILES: CCCCCCC1CCc2nc(O)ccc2C1]
(317C)

To a mixture of 4-hexylcyclohexanone (2.8 g, 15.36 mmol), pyrrolidine (1.397 mL, 16.89 mmol), and p-toluenesulfonic acid monohydrate (0.088 g, 0.461 mmol) in toluene (100 mL) was added molecular sieves. The reaction mixture was heated at 100° C. overnight. The mixture was filtered and the solvent was removed. This material was dissolved in MeOH (30 mL) in a stainless steel pressure vessel. The vessel was cooled to −78° C. and ammonia was bubbled in for 10 minutes. Methyl propriolate (3.87 mL, 46.1 mmol) was added and the vessel was sealed and heated at 100° C. for 4 hours. The reaction mixture was cooled in an ice bath and then vented and opened. The reaction mixture was diluted with ethyl acetate and washed with water. The organic layer was dried with $MgSO_4$, filtered and concentrated. The crude material was purified on a silica gel cartridge (80 g) using an 20% MeOH/DCM:DCM gradient (0-50% 20% MeOH/DCM over 15 CV). Product containing fractions were combined, concentrated and dried in vacuo to afford 6-hexyl-5,6,7,8-tetrahydroquinolin-2-ol (2.5 g, 10.71 mmol).

Preparation 317D: 2-bromo-6-hexyl-5,6,7,8-tetrahydroquinoline (Isomers 1 and 2)

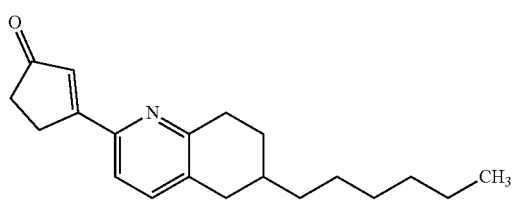
(317D - Isomers 1 and 2)

To a mixture of 6-hexyl-5,6,7,8-tetrahydroquinolin-2-ol (580 mg, 2.486 mmol) and phosphorus tribromide (4.97 mL, 4.97 mmol) in toluene (5 mL) was added phosphorus oxybromide (713 mg, 2.486 mmol). The reaction mixture was heated at 100° C. for 3 days. The mixture was cooled to 0° C. and then poured onto ice. The reaction mixture was diluted with ethyl acetate and washed with saturated $NaHCO_3$. The organic layer was dried with $MgSO_4$, filtered and concentrated. The crude material was purified on a silica gel cartridge (40 g) using an EtOAc/Hex gradient (0-50% EtOAc over 12 CV). Product containing fractions were combined, concentrated and dried in vacuo to afford 2-bromo-6-hexyl-5,6,7,8-tetrahydroquinoline (300 mg, 1.013 mmol).

Preparations 317E1 and 317E2: 3-(6-hexyl-5,6,7,8-tetrahydroquinolin-2-yl)cyclopent-2-enone (Isomers 1 and 2)

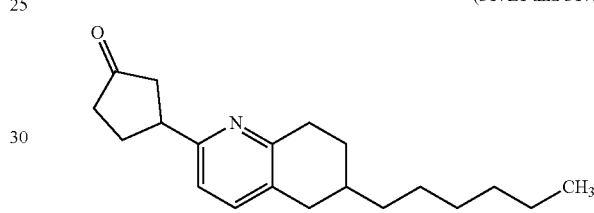
(317E1 and 317E2)

To a mixture of 2-bromo-6-hexyl-5,6,7,8-tetrahydroquinoline (885 mg, 2.99 mmol) in THF (5 mL) was added n-BuLi (2.80 mL, 4.48 mmol) dropwise. The reaction mixture was stirred for 30 minutes. Next, 3-ethoxycyclopent-2-enone (1.774 mL, 14.94 mmol) and lanthanum chloride (1465 mg, 5.97 mmol) were added. The reaction mixture was allowed to warm to 0° C. After 3 hours, the reaction was quenched with water. The reaction mixture was diluted with ethyl acetate and washed with saturated NaCl. The organic layer was dried with $MgSO_4$, filtered, and concentrated. The crude material was purified on a silica gel cartridge (80 g) using an EtOAc/Hex gradient (0-30% EtOAc over 20 CV). The product containing fractions were combined, concentrated and dried in vacuo to afford 440 mg of 3-(6-hexyl-5,6,7,8-tetrahydroquinolin-2-yl)cyclopent-2-enone. $^1$H NMR (400 MHz, CHLOROFORM-d) δ 7.57-7.42 (m, 2H), 6.85 (s, 1H), 3.18 (dd, J=5.0, 2.5 Hz, 3H), 3.07-2.86 (m, 2H), 2.62 (dt, J=5.0, 2.4 Hz, 2H), 2.49 (dd, J=16.9, 10.3 Hz, 1H), 2.16-2.02 (m, 1H), 1.80 (br. s., 1H), 1.54 (dtd, J=13.2, 11.0, 5.5 Hz, 1H), 1.42 (br. s., 4H), 1.33 (br. s., 6H), 1.00-0.82 (m, 3H). The isomers were separated by SFC using a Chiralpak AD-H, 25×3 cm ID, 5 μm column and eluting with 70/30 $CO_2$/MeOH at 85.0 mL/min. Recovered two fractions which were concentrated and dried in vacuo. Isomer 1: Recovered 3-(6-hexyl-5,6,7,8-tetrahydroquinolin-2-yl)cyclopent-2-enone (210 mg, 0.706 mmol). Isomer 2: Recovered 3-(6-hexyl-5,6,7,8-tetrahydroquinolin-2-yl)cyclopent-2-enone (210 mg, 0.706 mmol).

Preparation 317F1 and 317F2

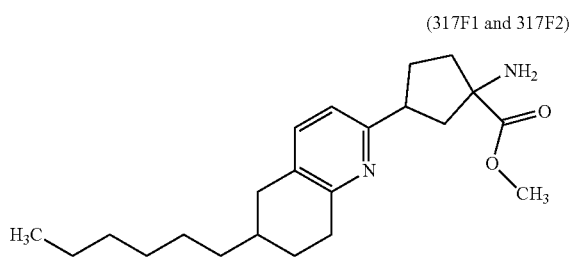 [SMILES: CCCCCCC1CCc2nc(C3CCC(N)(C(=O)OC)C3)ccc2C1]

(317F1 and 317F2)

To a mixture of 3-(6-hexyl-5,6,7,8-tetrahydroquinolin-2-yl)cyclopent-2-enone (210 mg, 0.706 mmol) (Isomer 1; Preparation 317E1) in MeOH (10 mL) and acetic acid (1 mL) was added Pearlman's Catalyst (50 mg, 0.356 mmol). The reaction mixture was hydrogenated under a balloon of $H_2$. After 3 hours, the reaction mixture was filtered and concentrated in vacuo. The isomers were separated by SFC using a Chiralpak IA-H, 25×2.1 cm ID, 5 µm column and eluting with 95/5 $CO_2$/MeOH-ACN 1-1 at 50.0 mL/min. Recovered two fractions which were concentrated and dried in vacuo. Isomer 1A; recovered 45 mg; NMR was consistent with desired product $^1$H NMR (400 MHz, CHLOROFORM-d) δ 7.37-7.25 (m, 1H), 6.94 (d, J=7.7 Hz, 1H), 3.61-3.43 (m, 1H), 3.04-2.76 (m, 3H), 2.74-2.53 (m, 2H), 2.52-2.21 (m, 4H), 2.21-2.08 (m, 1H), 2.08-1.95 (m, 1H), 1.87-1.60 (m, 2H), 1.58-1.44 (m, 1H), 1.44-1.21 (m, 9H), 1.01-0.81 (m, 3H). Isomer 1B; recovered 33 mg; NMR was consistent with desired product. $^1$H NMR (400 MHz, CHLOROFORM-d) δ 7.31 (d, J=7.7 Hz, 1H), 6.94 (d, J=7.9 Hz, 1H), 3.60-3.44 (m, 1H), 3.03-2.75 (m, 3H), 2.71-2.54 (m, 2H), 2.54-2.34 (m, 3H), 2.34-2.22 (m, 1H), 2.22-2.09 (m, 1H), 2.09-1.98 (m, 1H), 1.85-1.66 (m, 2H), 1.60-1.44 (m, 1H), 1.44-1.23 (m, 9H), 0.97-0.86 (m, 3H).

Preparation 317G1 and 317G2: methyl 1-amino-3-(6-hexyl-5,6,7,8-tetrahydroquinolin-2-yl)cyclopentanecarboxylate (Isomers 1 and 2)

To a mixture of 3-(6-hexyl-5,6,7,8-tetrahydroquinolin-2-yl)cyclopentanone (45 mg, 0.150 mmol), ammonium chloride (40.2 mg, 0.751 mmol), and sodium cyanide (36.8 mg, 0.751 mmol) in DCM (5 mL) was added ammonia in MeOH (0.429 mL, 3.01 mmol). The reaction mixture was sealed and stirred for 3 days. The reaction was incomplete as indicated by LCMS analysis. Additional sodium cyanide (36.8 mg, 0.751 mmol) and ammonium chloride (40.2 mg, 0.751 mmol) were added and the reaction mixture was stirred for an additional day. LCMS showed reaction was complete. The reaction mixture was diluted with dichloromethane and washed with water. The organic layer was dried with $MgSO_4$, filtered and concentrated. The crude product was dissolved in dioxane (1 mL), then acetic acid (1 mL) and concentrated HCl (1 mL) were added. The reaction mixture was heated at 100° C. overnight. The reaction mixture was concentrated to dryness then crude material was dissolved in MeOH. HCl (g) was bubbled through for 5 minutes. The mixture was heated at 70° C. for 1 hour. LCMS showed conversion to the desired methyl ester. The mixture was concentrated in vacuo and purified by HPLC. HPLC conditions: Phenomenex Luna 5 micron C18 column (30× 100 mm); MeCN (0.1% TFA)/water (0.1% TFA); 20%-100% gradient over 15 minutes; 30 mL/min. Isolated fractions with correct mass and freeze-dried overnight. Recovered methyl 1-amino-3-(6-hexyl-5,6,7,8-tetrahydroquinolin-2-yl)cyclopentanecarboxylate, TFA (37 mg, 0.078 mmol). $^1$H NMR (400 MHz, METHANOL-$d_4$) δ 8.33-8.06 (m, 1H), 7.91-7.62 (m, 1H), 3.93 (s, 3H), 3.90-3.79 (m, 1H), 3.28-2.98 (m, 3H), 2.90 (dd, J=13.9, 7.7 Hz, 1H), 2.79-2.40 (m, 4H), 2.38-2.08 (m, 3H), 1.85 (br. s., 1H), 1.69-1.51 (m, 1H), 1.52-1.24 (m, 10H), 1.06-0.83 (m, 3H). The isomers were separated by SFC using a Chiralpak OZ-H, 25×3 cm ID, 5 µm column and eluting with 65/35 $CO_2$/MeOH w/0.1% DEA at 85.0 mL/min. Two fractions were recovered which were concentrated and dried in vacuo. Isomer 1: methyl 1-amino-3-(6-hexyl-5,6,7,8-tetrahydroquinolin-2-yl) cyclopentanecarboxylate, TFA (15 mg, 0.032 mmol). Isomer 2: methyl 1-amino-3-(6-hexyl-5,6,7,8-tetrahydroquinolin-2-yl)cyclopentanecarboxylate (18 mg, 0.050 mmol).

Example 317

To a mixture of methyl 1-amino-3-(6-hexyl-5,6,7,8-tetrahydroquinolin-2-yl) cyclopentanecarboxylate, TFA (15 mg, 0.032 mmol) (Isomer 1; Preparation 317G1) in MeOH (3 mL) was added sodium borohydride (7.21 mg, 0.190 mmol). After 2 hour, the reaction was quenched with water. The reaction mixture was concentrated and the residue was triturated in TFA/MeCN, and then filtered. The filtrate was purified by HPLC. HPLC conditions: Phenomenex Luna 5 micron C18 column (30×100 mm); MeCN (0.1% TFA)/water (0.1% TFA); 10%-100% gradient over 15 minutes; 30 mL/min. Isolated fractions with correct mass and freeze-dried overnight to afford (1-amino-3-(6-hexyl-5,6,7,8-tetrahydroquinolin-2-yl)cyclopentyl)methanol, 2 TFA (12.6 mg, 0.021 mmol). $^1$H NMR in $CD_3OD$ was consistent with desired product (400 MHz, METHANOL-$d_4$) δ 8.21 (d, J=8.1 Hz, 1H), 7.73 (d, J=8.1 Hz, 1H), 3.80 (ddd, J=10.7, 7.5, 3.3 Hz, 1H), 3.75-3.63 (m, 2H), 3.28-3.01 (m, 3H), 2.56 (dd, J=17.2, 10.6 Hz, 1H), 2.48-2.25 (m, 3H), 2.22-2.08 (m, 2H), 2.07-1.89 (m, 2H), 1.89-1.77 (m, 1H), 1.59 (dtd, J=13.3, 11.0, 5.8 Hz, 1H), 1.47 (d, J=3.1 Hz, 4H), 1.36 (d, J=3.1 Hz, 6H), 1.00-0.88 (m, 3H); HPLC retention time=6.81 min (condition L); LC/MS $M^{+1}$=331.

The Examples 318-322 in Table 18 were prepared according to the general procedure of Example 317.

TABLE 18

| Ex. No. | Structure | MW | HPLC ret. time (min.) | HPLC condition | MS (M+1) | Comments |
|---|---|---|---|---|---|---|
| 318 | 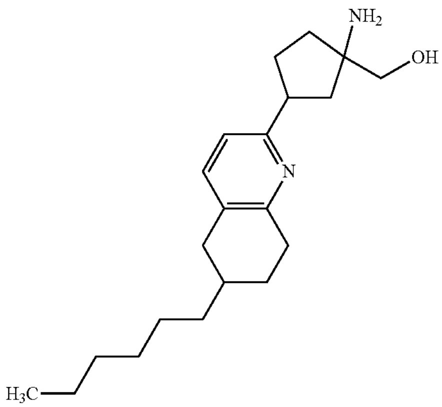 [SMILES: CCCCCCC1CCc2nc(C3CCC(N)(CO)C3)ccc2C1] | 330.5 | 6.73 | L | 331 | Isomer 1A2 |
| 319 | | 330.5 | 6.80 | L | 331 | Isomer 1B1 |
| 320 | | 330.5 | 6.73 | L | 331 | Isomer 1B2 |
| 321 | | 330.5 | 6.95 | L | 331 | Isomer 2A Mixture of 2 diastereomers |
| 322 | | 330.5 | 6.95 | L | 331 | Isomer 2B Mixture of 2 diastereomers |

Examples 326 to 329

5-(3-amino-3-(hydroxymethyl)cyclopentyl)-2-(3-phenylpropyl)isoindolin-1-one

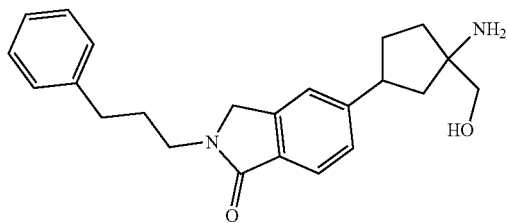

(326)

Preparation 326A: 6-bromo-2-(pentyloxy)quinoline

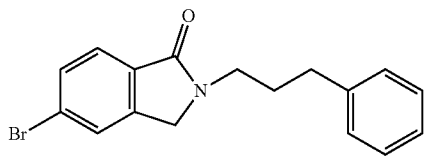

(326A)

To a solution of methyl 4-bromo-2-(bromomethyl)benzoate (2.000 g, 6.49 mmol) and 3-phenyl-1-propylamine (1.016 mL, 7.14 mmol) in EtOH (15 mL) was added potassium carbonate (1.346 g, 9.74 mmol). The reaction mixture was heated at 40° C. for 3 h. The reaction mixture was diluted with ethyl acetate and washed with saturated NaCl. The organic layer was dried with MgSO$_4$, filtered and concentrated. The crude oil was purified on a 80 g silica gel cartridge using 30-60% EtOAc/hexanes gradient to afford 5-bromo-2-(3-phenylpropyl)isoindolin-1-one (1.43 g, 4.33 mmol) as a white solid. $^1$H NMR (400 MHz, CHLOROFORM-d) δ 7.77-7.71 (m, 1H), 7.66-7.59 (m, 2H), 7.35-7.26 (m, 2H), 7.24-7.15 (m, 3H), 4.35 (s, 2H), 3.69 (t, J=7.3 Hz, 2H), 2.79-2.66 (m, 2H), 2.13-1.96 (m, 2H).

Examples 326 to 329

An oven dried microwave vial with a stir bar was charged with 5-bromo-2-(3-phenylpropyl)isoindolin-1-one (750 mg, 2.271 mmol), ethyl 1-((diphenylmethylene) amino)cyclopent-3-enecarboxylate (1233 mg, 3.86 mmol), palladium(II) acetate (102 mg, 0.454 mmol), triphenylphosphine (238 mg, 0.908 mmol), potassium acetate (446 mg, 4.54 mmol) and DMA (20 mL). The mixture was sparged with nitrogen for 10 minutes. The solution was processed on a CEM microwave: 60 minutes at 140° C. The reaction mixture was diluted with ethyl acetate and washed with saturated NaCl. The organic layer was dried with MgSO$_4$, filtered and concentrated. The crude material was purified on a silica gel cartridge (80 g) using an EtOAc/Hex gradient (0-100% EtOAc over 20 minutes) to afford 825 mg of material. This residue was dissolved in ether (20 mL) and treated with 6N HCl for 30 minutes. The reaction mixture was diluted with ethyl acetate and washed with saturated NaHCO$_3$. The organic layer was dried with MgSO$_4$, filtered and concentrated. This residue was dissolved in ethanol (20 mL) and sodium borohydride (859 mg, 22.71 mmol) was added portionwise over several hours until no starting material remained. The reaction was quenched with 1N HCl. The reaction mixture was diluted with ethyl acetate and washed with saturated NaHCO$_3$. The organic layer was dried with MgSO$_4$, filtered and concentrated. This residue was dissolved in MeOH and 10% Pd/C was added. The reaction mixture was hydrogenated under a balloon of H$_2$ for 1 hour. The reaction mixture was filtered and purified by HPLC. HPLC conditions: Phenomenex Luna 5 micron C18 column (30×100 mm); MeCN (0.1% TFA)/water (0.1% TFA); 30%-100% gradient over 10 minutes; 30 mL/min. Fractions with correct mass were isolated, diluted with ethyl acetate, washed with saturated NaHCO$_3$, and back extracted twice with EtOAc. The organic layer was dried with MgSO$_4$, filtered and concentrated to afford 275 mg of 5-(3-amino-3-(hydroxymethyl) cyclopentyl)-2-(3-phenylpropyl)isoindolin-1-one. The individual isomers were separated using a CHIRALPAK® AD-H column under SFC conditions (20% MeOH with 0.5% DEA in CO$_2$).

Example 326 (33 mg) HPLC retention time=5.55 min (condition H); LC/MS M$^{+1}$=X; $^1$H NMR (400 MHz, CHLOROFORM-d) δ 7.78 (d, J=7.9 Hz, 1H), 7.38-7.27 (m, 5H), 7.25-7.16 (m, 3H), 4.34 (s, 2H), 3.68 (t, J=7.3 Hz, 2H), 3.52 (d, J=5.9 Hz, 2H), 2.16-1.87 (m, 8H), 1.83-1.66 (m, 2H), 1.66-1.52 (m, 1H).

Example 327 (105 mg) HPLC retention time=5.61 min (condition H); LC/MS M⁺¹=X; ¹H NMR (400 MHz, CHLOROFORM-d) δ 7.77 (d, J=8.4 Hz, 1H), 7.40-7.34 (m, 2H), 7.33-7.26 (m, 2H), 7.25-7.16 (m, 3H), 4.34 (s, 2H), 3.68 (t, J=7.3 Hz, 2H), 3.56 (br. s., 2H), 3.20 (t, J=7.5 Hz, 1H), 2.77-2.61 (m, 2H), 2.45-2.31 (m, 1H), 2.21-2.08 (m, 1H), 2.08-1.90 (m, 3H), 1.83 (br. s., 2H), 1.65 (t, J=12.0 Hz, 1H).

Example 328 (25 mg) HPLC retention time=5.47 min (condition H); LC/MS M+1=X; ¹H NMR (400 MHz, CHLOROFORM-d) δ 7.78 (d, J=7.9 Hz, 1H), 7.38-7.26 (m, 4H), 7.25-7.17 (m, 3H), 4.34 (s, 2H), 3.68 (t, J=7.3 Hz, 2H), 3.52 (d, J=5.9 Hz, 2H), 3.36 (dd, J=10.1, 4.2 Hz, 1H), 2.80-2.63 (m, 2H), 2.14-1.91 (m, 5H), 1.88-1.67 (m, 2H), 1.62 (dd, J=12.7, 5.2 Hz, 1H).

Example 329 (100 mg) HPLC retention time=5.60 min (condition H); LC/MS M⁺¹=X; 1H NMR (400 MHz, CHLOROFORM-d) δ 7.77 (d, J=7.9 Hz, 1H), 7.39-7.33 (m, 2H), 7.31-7.25 (m, 2H), 7.23-7.14 (m, 3H), 4.33 (s, 2H), 3.67 (t, J=7.3 Hz, 2H), 3.48 (d, J=8.6 Hz, 2H), 3.19 (t, J=7.6 Hz, 1H), 2.34 (dd, J=12.8, 8.1 Hz, 1H), 2.21-1.88 (m, 6H), 1.87-1.64 (m, 2H), 1.54 (t, J=11.8 Hz, 1H).

The absolute stereochemistries of the isomers were not determined.

Examples 330 to 332

5-(3-amino-3-(hydroxymethyl)cyclopentyl)-3,3-dimethyl-2-(3-phenylpropyl)isoindolin-1-one

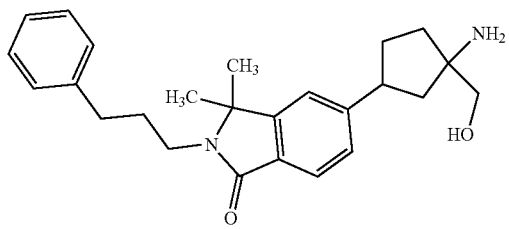 [SMILES: CC1(C)c2cc(C3CCC(N)(CO)C3)ccc2C(=O)N1CCCc1ccccc1]

Preparation 330A: 5-methoxy-3,3-dimethylisoindolin-1-one

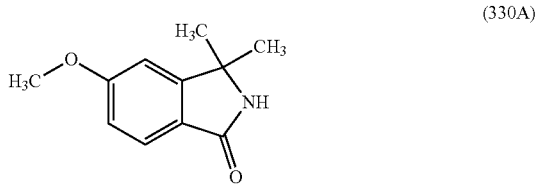

(330A)

To a mixture of 2-(3-methoxyphenyl)-2-methylpropanoic acid (13.01 g, 67 mmol) and Et₃N (9.34 mL, 67.0 mmol) in toluene (200 mL) at 0° C. was added diphenylphosphoryl azide (14.40 mL, 67.0 mmol). After 30 min at 0° C., the reaction mixture was warmed to room temperature then refluxed overnight. The reaction mixture was diluted with ethyl acetate and washed with saturated NaHCO₃ and brine. The organic layer was dried with MgSO₄, filtered and concentrated. This crude residue was dissolved in DCE (100 mL) and added dropwise to a slurry of iron(III) chloride (23.91 g, 147 mmol) in DCE (300 mL) at 0° C. The mixture was stirred for 2 hours and allowed to warm to room temperature. The reaction mixture was diluted with 1M tartaric acid solution and stirred for 30 minutes. The organic layer was separated then dried with MgSO₄, filtered and concentrated. The crude material was purified on a silica gel cartridge (40 g) using an EtOAc/Hex gradient (40-100% EtOAc over 11 CV then held at 100% EtOAc until product completely eluted) to afforded 4.9 g of 5-methoxy-3,3-dimethylisoindolin-1-one. HPLC retention time=0.87 min (condition G); LC/MS M⁺¹=192; ¹H NMR (400 MHz, CHLOROFORM-d) δ ppm 7.74 (1H, d, J=7.70 Hz), 7.40 (1H, br. s.), 6.97 (1H, d, J=7.48 Hz), 6.87 (1H, br. s.), 3.90 (3H, br. s.), 1.55 (6H, br. s.).

Preparation 330B: 5-methoxy-3,3-dimethyl-2-(3-phenylpropyl)isoindolin-1-one

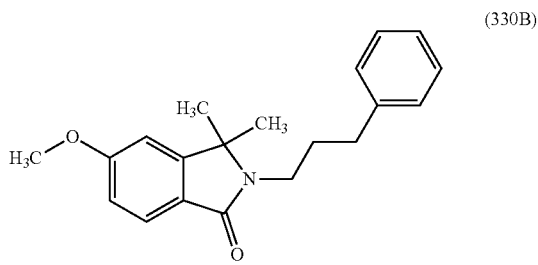 [SMILES: COc1ccc2c(c1)C(C)(C)N(CCCc1ccccc1)C2=O]

(330B)

To a mixture of 5-methoxy-3,3-dimethylisoindolin-1-one (1.8 g, 9.41 mmol) in DMF (50 mL) was added sodium hydride (0.565 g, 14.12 mmol) portionwise. After addition, the reaction mixture was heated to 80° C. for 1 hour followed by the addition of 3-iodopropyl)benzene (3.03 mL, 18.83 mmol). Reaction was incomplete after 2 hours. Additional sodium hydride (0.565 g, 14.12 mmol) was added and the reaction mixture was heated overnight. Reaction was still incomplete. Additional sodium hydride (0.565 g, 14.12 mmol) was added and heating was continued for 4 more hours. The reaction mixture was diluted with ethyl acetate and washed twice with saturated NaCl. The organic layer was dried with MgSO₄, filtered and concentrated. The crude material was purified on a silica gel cartridge (40 g) using an EtOAc/Hex gradient (0-100% EtOAc over 13 CV) to afford 850 mg of 5-methoxy-3,3-dimethyl-2-(3-phenylpropyl) isoindolin-1-one. HPLC retention time=1.00 min (condition G); LC/MS M⁺¹=310; ¹H NMR (400 MHz, CHLOROFORM-d) δ 7.75 (d, J=8.4 Hz, 1H), 7.46-7.14 (m, 5H), 6.96 (dd, J=8.4, 2.2 Hz, 1H), 6.86 (d, J=2.0 Hz, 1H), 3.90 (s, 3H), 2.75 (td, J=7.8, 5.4 Hz, 2H), 2.16-2.02 (m, 2H), 2.00-1.86 (m, 2H), 1.60 (s, 3H), 1.46 (s, 3H). MS (m+1)=310.

Preparation 330C: 5 5-hydroxy-3,3-dimethyl-2-(3-phenylpropyl)isoindolin-1-one

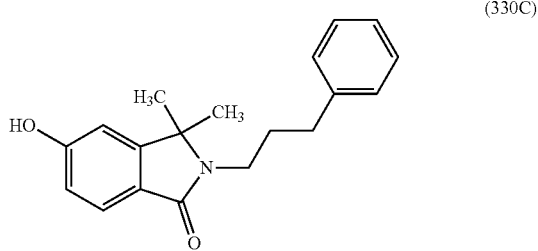 [SMILES: CC1(C)c2cc(O)ccc2C(=O)N1CCCc1ccccc1]

(330C)

To a mixture of 5-methoxy-3,3-dimethyl-2-(3-phenylpropyl)isoindolin-1-one (850 mg, 2.75 mmol) in DCM (Volume: 10 mL) was added BBr₃ in DCM (5.49 mL, 5.49 mmol). The reaction mixture was heated at 50° C. for 5 hours. The reaction mixture was diluted with DCM and washed with saturated NaHCO₃. The organic layer was dried with MgSO₄, filtered and concentrated. DCM was added and solid material precipitated. The mixture was allowed to in a refrigerator for 1 hour. The solid was collected by filtration and dried to afford 450 mg of 5-hydroxy-3,3-dimethyl-2-(3-phenylpropyl)isoindolin-1-one as a tan solid. HPLC retention time=0.87 min (condition G); LC/MS M$^{+1}$=296; $^1$H NMR (400 MHz, DMSO-d₆) δ ppm 10.08 (1H, s), 7.43 (1H, d, J=8.14 Hz), 7.13-7.35 (5H, m), 6.92 (1H, d, J=1.98 Hz), 6.82 (1H, dd, J=8.25, 2.09 Hz), 3.36-3.41 (2H, m), 2.60-2.73 (2H, m), 1.80-1.98 (2H, m), 1.39 (6H, s). MS (m+1)=295.

Preparation 330D: 3,3-dimethyl-1-oxo-2-(3-phenylpropyl)isoindolin-5-yl trifluoromethanesulfonate

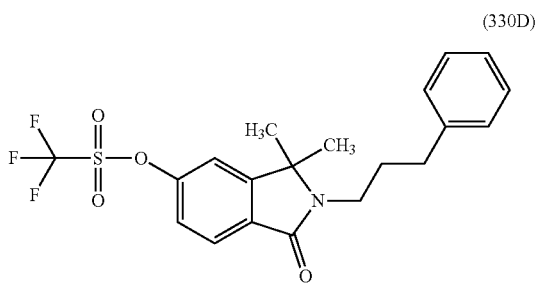 [SMILES: CC1(C)c2cc(OS(=O)(=O)C(F)(F)F)ccc2C(=O)N1CCCc1ccccc1]

(330D)

To a mixture of 5-hydroxy-3,3-dimethyl-2-(3-phenylpropyl)isoindolin-1-one (440 mg, 1.490 mmol) and pyridine (361 μl, 4.47 mmol) in DCM was added triflic anhydride (377 μl, 2.234 mmol). The reaction mixture was stirred for one hour. The reaction mixture was diluted with DCM and washed with saturated NaCl. The organic layer was dried with MgSO₄, filtered and concentrated to afford 600 mg of 3,3-dimethyl-1-oxo-2-(3-phenylpropyl)isoindolin-5-yl trifluoromethanesulfonate which was used immediately in the next step. HPLC retention time=1.09 min (condition G); LC/MS M$^{+1}$=428.

Preparation 330E: Ethyl 4-(3,3-dimethyl-1-oxo-2-(3-phenylpropyl)isoindolin-5-yl)-1-(diphenylmethyleneamino)cyclopent-2-enecarboxylate

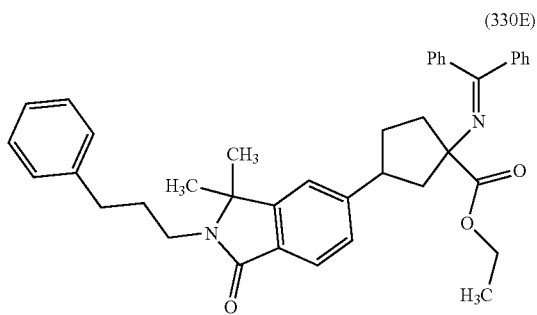 [SMILES: CCOC(=O)C1(N=C(c2ccccc2)c2ccccc2)CCC(c2ccc3c(c2)C(C)(C)N(CCCc2ccccc2)C3=O)C1]

(330E)

An oven dried microwave vial with stir bar was charged with 3,3-dimethyl-1-oxo-2-(3-phenylpropyl)isoindolin-5-yl trifluoromethanesulfonate (662 mg, 1.550 mmol), ethyl 1-((diphenylmethylene)amino)cyclopent-3-enecarboxylate (330 mg, 1.033 mmol), palladium(II) acetate (46.4 mg, 0.207 mmol), triphenylphosphine (108 mg, 0.413 mmol), potassium acetate (203 mg, 2.066 mmol) and DMA (4 mL). The mixture was sparged with nitrogen for 10 minutes. The solution was processed on a CEM microwave: 60 minutes at 140° C. The reaction mixture was diluted with ethyl acetate and washed with saturated NaCl. The organic layer was dried with MgSO₄, filtered and concentrated. The crude material was purified on a silica gel cartridge (80 g) using an EtOAc/Hex gradient (0-100% EtOAc over 20 minutes) to afford 330 mg of ethyl 4-(3,3-dimethyl-1-oxo-2-(3-phenylpropyl)isoindolin-5-yl)-1-(diphenylmethyleneamino)cyclopent-2-enecarboxylate. HPLC retention time=1.05 min (condition G); LC/MS M$^{+1}$=597.

Examples 330 to 332

To a mixture of ethyl 4-(3,3-dimethyl-1-oxo-2-(3-phenylpropyl)isoindolin-5-yl)-1-((diphenylmethylene)amino)cyclopent-2-enecarboxylate (330 mg, 0.553 mmol) in ether (10 mL) was added 6N HCl (5 mL). The reaction mixture was stirred for 30 minutes. The reaction mixture was diluted with ethyl acetate and washed with saturated NaHCO₃. The organic layer was dried with MgSO₄, filtered and concentrated. This residue was dissolved in MeOH (10.00 mL) and sodium borohydride (105 mg, 2.76 mmol) was added. Additional sodium borohydride (105 mg, 2.76 mmol) was added until LCMS showed complete conversion of the starting material. The reaction was quenched with 1N HCl then the reaction mixture was diluted with ethyl acetate and washed with saturated NaHCO₃. The organic layer was dried with MgSO₄, filtered and concentrated. This residue was dissolved in MeOH and Pd/C (58.8 mg, 0.553 mmol) was added. The reaction mixture was hydrogenated under a balloon of H₂ for 1 hour, and then filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Recovered 100 mg of 5-(3-amino-3-(hydroxymethyl) cyclopentyl)-3,3-dimethyl-2-(3-phenylpropyl)isoindolin-1-one. The individual isomers were separated using a CHIRALPAK® AS-H column under SFC conditions (15% MeOH/IPA (1:1) with 0.5% DEA in CO₂).

Example 330: Fraction 1 (4 mg, mixture of two isomers) HPLC retention time=6.98 min (condition H); LC/MS M$^{+1}$=393; $^1$H NMR (400 MHz, METHANOL-d₄) δ 7.77-7.64 (m, 1H), 7.49 (s, 1H), 7.47-7.38 (m, 1H), 7.35-7.23 (m, 4H), 7.22-7.14 (m, 1H), 3.81-3.61 (m, 2H), 3.55-3.45 (m, 3H), 2.74 (t, J=7.8 Hz, 2H), 2.36-2.18 (m, 2H), 2.11-2.00 (m, 3H), 1.99-1.76 (m, 3H), 1.50 (s, 6H).

Example 331: Fraction 2 (13 mg, homochiral) HPLC retention time=7.02 min (condition H); LC/MS M$^{+1}$=393; $^1$H NMR (400 MHz, METHANOL-d₄) δ 7.67 (d, J=7.9 Hz, 1H), 7.51 (s, 1H), 7.48-7.39 (m, 1H), 7.34-7.24 (m, 4H), 7.23-7.11 (m, 1H), 3.60-3.42 (m, 4H), 3.24 (ddd, J=11.2, 7.1, 4.0 Hz, 1H), 2.74 (t, J=7.7 Hz, 2H), 2.31 (dd, J=13.0, 7.7 Hz, 1H), 2.18-1.97 (m, 4H), 1.92-1.71 (m, 2H), 1.68-1.56 (m, 1H), 1.49 (s, 6H), MS (m+1)=393.

Example 332: Fraction 3 (17 mg, homochiral) HPLC retention time=6.99 min (condition H); LC/MS M$^+$=393; $^1$H NMR (400 MHz, METHANOL-d₄) δ 7.67 (d, J=7.7 Hz, 1H), 7.51 (s, 1H), 7.43 (dd, J=7.9, 1.1 Hz, 1H), 7.33-7.23 (m, 4H), 7.22-7.15 (m, 1H), 3.57-3.44 (m, 4H), 3.23 (ddd, J=10.9, 7.4, 3.7 Hz, 1H), 2.74 (t, J=7.8 Hz, 2H), 2.31 (dd, J=13.1, 7.8 Hz, 1H), 2.15-1.97 (m, 4H), 1.89-1.69 (m, 2H), 1.67-1.56 (m, 1H), 1.49 (s, 6H), MS (m+1)=393. The absolute stereochemistry of the isomers was not determined.

Examples 333 to 335

1-(6-(3-amino-3-(hydroxymethyl)cyclopentyl)-3,4-dihydroisoquinolin-2(1H)-yl)hexan-1-one

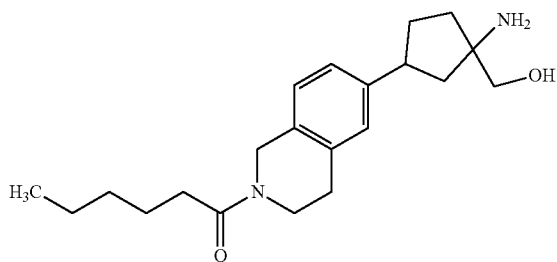 [SMILES: CCCCCC(=O)N1CCc2cc(C3CCC(N)(CO)C3)ccc2C1]

Preparation 333A: 3-(isoquinolin-6-yl)cyclopentanone

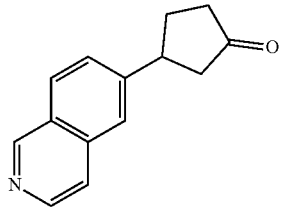

(333A)

To a mixture of 6-bromoisoquinoline (2 g, 9.61 mmol), cyclopent-2-enol (2.021 g, 24.03 mmol), and potassium acetate (2.83 g, 28.8 mmol) in DMF (50 mL) was added tetrabutylammonium chloride (2.67 g, 9.61 mmol) and palladium (II) acetate (0.216 g, 0.961 mmol). The reaction mixture was degassed with nitrogen and then heated at 80° C. overnight. The reaction mixture was diluted with ethyl acetate and washed with saturated NaCl. The organic layer was dried with MgSO$_4$, filtered and concentrated. The crude material was purified on a silica gel cartridge (80 g) using an EtOAc/Hex gradient (20-100% EtOAc over 10 CV) to afford 750 mg of 3-(isoquinolin-6-yl)cyclopentanone. HPLC retention time=0.52 min (condition H); LC/MS M$^{+1}$=212. $^1$H NMR (400 MHz, CHLOROFORM-d) δ 8.92 (dd, J=4.2, 1.8 Hz, 1H), 8.22-8.08 (m, 2H), 7.74-7.61 (m, 2H), 7.43 (dd, J=8.4, 4.2 Hz, 1H), 3.65 (tt, J=10.7, 6.9 Hz, 1H), 2.80 (dd, J=18.3, 7.7 Hz, 1H), 2.66-2.30 (m, 4H), 2.20-2.02 (m, 1H).

Preparation 333B: 7-(isoquinolin-6-yl)-1,3-diazaspiro[4.4]nonane-2,4-dione

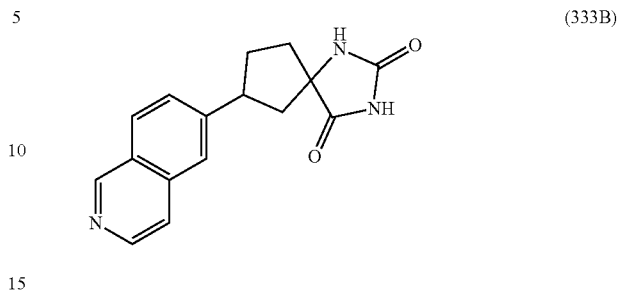

(333B)

To a mixture of 3-(isoquinolin-6-yl)cyclopentanone (820 mg, 3.88 mmol) and potassium cyanide (379 mg, 5.82 mmol) in EtOH (20 mL) and water (10 mL) in a pressure vessel was added potassium cyanide (379 mg, 5.82 mmol). The vessel was sealed and heated at 90° C. overnight. The reaction mixture was cooled and vented. The reaction mixture was diluted with ethyl acetate and washed with saturated NaCl. The organic layer was dried with MgSO$_4$, filtered and concentrated to afford 890 mg of 7-(isoquinolin-6-yl)-1,3-diazaspiro[4.4]nonane-2,4-dione. HPLC retention time=0.65 min (condition G); LC/MS M+$^1$=393. $^1$H NMR (400 MHz, DMSO-d$_6$) δ 10.65 (d, J=12.3 Hz, 1H), 8.86 (dd, J=4.2, 1.5 Hz, 1H), 8.40 (s, 1H), 8.36-8.25 (m, 1H), 7.99 (d, J=8.6 Hz, 1H), 7.84 (d, J=2.2 Hz, 1H), 7.74 (ddd, J=16.5, 8.7, 2.1 Hz, 1H), 7.52 (dd, J=8.4, 4.2 Hz, 1H), 3.65-3.39 (m, 1H), 2.56 (dd, J=13.6, 8.1 Hz, 1H), 2.41-2.08 (m, 3H), 2.03-1.78 (m, 2H).

Preparation 333C: methyl 1-amino-3-(isoquinolin-6-yl)cyclopentanecarboxylate

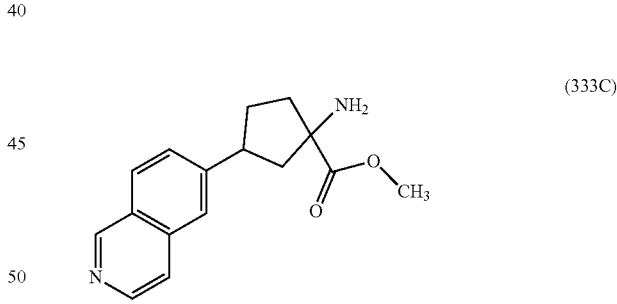

(333C)

To a mixture of 7-(isoquinolin-6-yl)-1,3-diazaspiro[4.4]nonane-2,4-dione (890 mg, 3.16 mmol) in MeOH (20 mL) was added 2N NaOH. After heating for two days, the reaction mixture was concentrated in vacuo and dried. The crude product was suspended in MeOH. HCl (g) was bubbled through for 15 minutes then the reaction mixture was heated at 80° C. The solvent was partially removed in vacuo, then the mixture was filtered and purified by HPLC. HPLC conditions: Phenomenex Luna C18 5 micron column (250×30 mm); 10-100% MeCN/water (0.1% TFA); 25 minute gradient; 30 mL/min. Recovered 750 mg of methyl 1-amino-3-(isoquinolin-6-yl)cyclopentanecarboxylate. HPLC retention time=0.43 min (condition G); LC/MS M$^{+1}$=271.

Preparation 333D: methyl 1-(tert-butoxycarbonylamino)-3-(isoquinolin-6-yl) cyclopentanecarboxylate

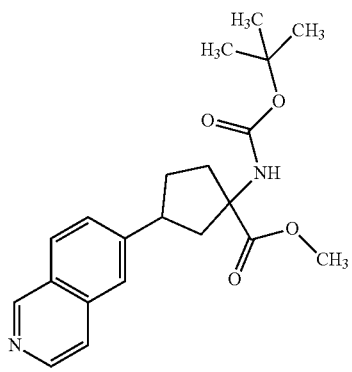

(333D)

To a mixture of methyl 1-amino-3-(isoquinolin-6-yl)cyclopentanecarboxylate and DIEA (1.022 mL, 5.85 mmol) in acetonitrile (10 mL) was added (Boc)$_2$O (1.359 mL, 5.85 mmol). The reaction mixture was stirred at room temperature for 2 hours. The reaction mixture was diluted with ethyl acetate and washed with saturated NaCl. The organic layer was dried with MgSO$_4$, filtered and concentrated. The crude material was purified on a silica gel cartridge (24 g) using an EtOAc/Hex gradient (0-100% EtOAc over 12 CV). Recovered 380 mg of methyl 1-(tert-butoxycarbonylamino)-3-(isoquinolin-6-yl)cyclopentanecarboxylate. HPLC retention time=0.72 min (condition G); LC/MS M$^{+1}$=371. $^1$H NMR (400 MHz, CHLOROFORM-d) δ 8.88 (dd, J=4.2, 1.8 Hz, 1H), 8.09 (dd, J=18.3, 8.8 Hz, 2H), 7.73-7.63 (m, 2H), 7.39 (dd, J=8.3, 4.3 Hz, 1H), 5.36-5.02 (m, 1H), 3.81 (d, J=3.1 Hz, 3H), 3.68-3.43 (m, 1H), 2.67-2.25 (m, 3H), 2.21-1.80 (m, 3H), 1.47 (d, J=5.1 Hz, 9H).

Preparation 333E: methyl 1-(tert-butoxycarbonylamino)-3-(1,2,3,4-tetrahydroisoquinolin-6-yl) cyclopentanecarboxylate

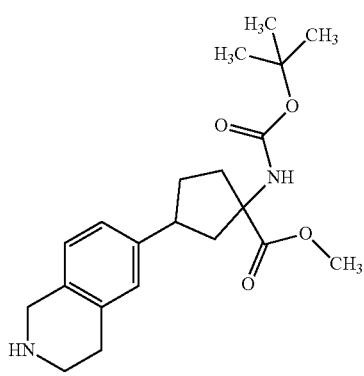

(333E)

To a mixture of methyl 1-((tert-butoxycarbonyl)amino)-3-(isoquinolin-6-yl) cyclopentanecarboxylate (280 mg, 0.756 mmol) in acetic acid (10 mL) was added platinum(IV) oxide (17.16 mg, 0.076 mmol). The reaction mixture was hydrogenated on a Parr shaker for 2 hours at 40 PSI of hydrogen. The catalyst was removed by filtration and the mixture was concentrated to give 200 mg of methyl 1-(tert-butoxycarbonylamino)-3-(1,2,3,4-tetrahydroisoquinolin-6-yl)cyclopentanecarboxylate. HPLC retention time=0.70 min (condition G); LC/MS M$^{+1}$=375.

Preparation 333F: Methyl 1-(tert-butoxycarbonylamino)-3-(2-hexanoyl-1,2,3,4-tetrahydroisoquinolin-6-yl)cyclopentanecarboxylate

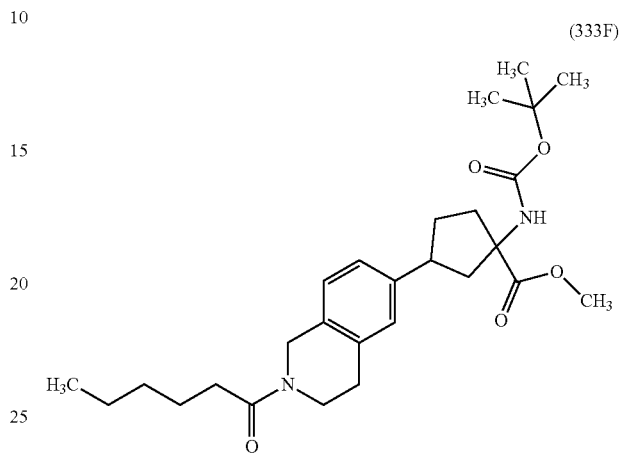

(333F)

To a mixture of methyl 1-((tert-butoxycarbonyl)amino)-3-(1,2,3,4-tetrahydroisoquinolin-6-yl)cyclopentanecarboxylate (200 mg, 0.534 mmol) and DIEA (200 μl, 1.145 mmol) in DCM (5 mL) was added hexanoyl chloride (74.7 μl, 0.534 mmol). The reaction mixture was stirred for 30 minutes. The reaction mixture was diluted with ethyl acetate and washed with saturated NaCl. The organic layer was dried with MgSO$_4$, filtered and concentrated. The crude material was purified on a silica gel cartridge (24 g) using an EtOAc/Hex gradient (0-100% EtOAc over 13CV). Recovered 140 mg of methyl 1-(tert-butoxycarbonylamino)-3-(2-hexanoyl-1,2,3,4-tetrahydroisoquinolin-6-yl)cyclopentanecarboxylate.
HPLC retention time=1.12 min (condition G); LC/MS M$^{+1}$=473.

Examples 333 to 335

To a mixture of methyl 1-((tert-butoxycarbonyl)amino)-3-(2-hexanoyl-1,2,3,4-tetrahydroisoquinolin-6-yl)cyclopentanecarboxylate (140 mg, 0.296 mmol) in DCM (2 mL) was added TFA (2 mL). The reaction mixture was stirred for 1 hour. LCMS shows complete removal of Boc group. The mixture was concentrated in vacuo, and MeOH (5 mL) was added followed by portionwise addition of sodium borohydride (56.0 mg, 1.481 mmol). After one hour, more sodium borohydride (112.0 mg, 3.5 mmol) was added. The reaction was quenched with water. The reaction mixture was diluted with ethyl acetate and washed with saturated NaCl. The organic layer was dried with MgSO$_4$, filtered and concentrated. HPLC conditions: Phenomenex Luna 5 micron C18 column (30×100 mm); MeCN (0.1% TFA)/water (0.1% TFA); 10%-100% gradient over 15 minutes; 30 mL/min. Recovered 44 mg of 1-(6-(3-amino-3-(hydroxymethyl)cyclopentyl)-3,4-dihydroisoquinolin-2(1H)-yl)hexan-1-one.
The individual isomers were separated using a CHIRALPAK® AS-H column under SFC conditions (15% MeOH with 0.1% DEA in CO$_2$).

Example 333: Isomer 1 (9 mg, racemic) HPLC retention time=6.60 min (condition H); LC/MS M+1=393. 1H NMR (400 MHz, METHANOL-d4) δ 7.17 (br. s., 3H), 3.77 (t, J=6.5 Hz, 2H), 3.58-3.43 (m, 2H), 3.10 (tt, J=11.3, 7.2 Hz, 1H), 2.73 (t, J=6.5 Hz, 2H), 2.54 (t, J=7.5 Hz, 2H), 2.29 (dd, J=13.1, 7.6 Hz, 1H), 2.03-1.90 (m, 3H), 1.89-1.70 (m, 2H), 1.69-1.53 (m, 3H), 1.42-1.16 (m, 5H), 0.97-0.81 (m, 3H).

Example 334: Isomer 2 (10 mg, homochiral) HPLC retention time=6.54 min (condition H); LC/MS M+=393. 1H NMR (400 MHz, METHANOL-d4) δ 7.13 (br. s., 3H), 3.76 (t, J=6.6 Hz, 2H), 3.62-3.45 (m, 2H), 3.43-3.36 (m, 1H), 2.85 (q, J=7.3 Hz, 1H), 2.72 (t, J=6.4 Hz, 2H), 2.54 (t, J=7.6 Hz, 2H), 2.28-2.01 (m, 2H), 1.98-1.87 (m, 2H), 1.81-1.51 (m, 5H), 1.45-1.10 (m, 6H), 0.89 (br. s., 3H).

Example 335: Isomer 3 (8.5 mg, homochiral) HPLC retention time=6.54 min (condition H); LC/MS M+1=393. 1H NMR (400 MHz, METHANOL-d4) δ 7.67 (d, J=7.7 Hz, 1H), 7.51 (s, 1H), 7.43 (dd, J=7.9, 1.1 Hz, 1H), 7.33-7.23 (m, 4H), 7.22-7.15 (m, 1H), 3.57-3.44 (m, 4H), 3.23 (ddd, J=10.9, 7.4, 3.7 Hz, 1H), 2.74 (t, J=7.8 Hz, 2H), 2.31 (dd, J=13.1, 7.8 Hz, 1H), 2.15-1.97 (m, 4H), 1.89-1.69 (m, 2H), 1.67-1.56 (m, 1H), 1.49 (s, 6H), MS (m+1)=393. The absolute stereochemistry of the isomers was not determined.

Example 336

(((1R,3S)-1-amino-3-((6S)-6-((phenylsulfinyl) methyl)-5,6,7,8-tetrahydronaphthalen-2-yl) cyclopentyl)methanol

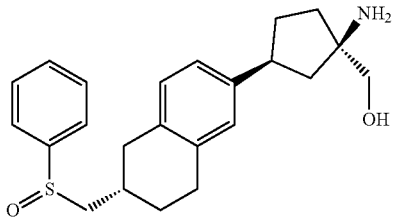

(336)

To a stirred clear solution of ((1R,3S)-1-amino-3-((S)-6-((phenylthio)methyl)-5,6,7,8-tetrahydronaphthalen-2-yl)cyclopentyl)methanol (6 mg, 0.016 mmol), DMSO (0.035 mL, 0.490 mmol), and L-10-(−)-camphor sulfonic acid (18.96 mg, 0.082 mmol) in dichloromethane (0.5 mL) and methanol (0.2 mL) cooled with dry-ice was added 77% m-CPBA (3.66 mg, 0.016 mmol). The temperature was raised to 0° C. over 30 min. The mixture was stirred at 0° C. for 30 min and room temperature for 30 min. The mixture was concentrated and purified using reverse phase HPLC (Waters Xbridge C18 19×100 mm; gradient over 8 min from 20 to 100% of solvent B; solvent A: 10% MeOH: 90% H2O: 0.1% TFA; solvent B: 90% MeOH, 10% H2O, 0.1% TFA), concentration, basification with K2CO3, and extraction with ethyl acetate gave ((1R,3S)-1-amino-3-((6S)-6-((phenylsulfinyl) methyl)-5,6,7,8-tetrahydronaphthalen-2-yl)cyclopentyl) methanol (6 mg, 0.015 mmol) as a glassy solid. LC/MS M+1=384. 1H NMR (500 MHz, CHLOROFORM-d) δ 7.68-7.62 (m, 2H), 7.56-7.47 (m, 3H), 7.03-6.94 (m, 3H), 3.50-3.41 (m, 2H), 3.18-2.90 (m, 3H), 2.87-2.77 (m, 2H), 2.73-2.52 (m, 2H), 2.47-2.36 (m, 1H), 2.26 (dd, J=13.3, 7.8 Hz, 1H), 2.21-1.97 (m, 2H), 1.96-1.82 (m, 1H), 1.79-1.70 (m, 1H), 1.70-1.58 (m, 2H), 1.49 (dd, J=13.3, 11.1 Hz, 1H).

Example 337

((1R,3S)-1-amino-3-((S)-6-((phenylsulfonyl) methyl)-5,6,7,8-tetrahydronaphthalen-2-yl) cyclopentyl)methanol

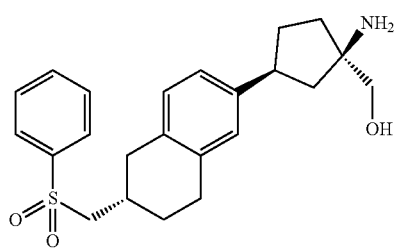

(337)

To a stirred solution of ((1R,3S)-1-amino-3-((S)-6-((phenylthio)methyl)-5,6,7,8-tetrahydronaphthalen-2-yl)cyclopentyl)methanol (2 mg, 5.44 μmol) and L-10-(−)-camphor sulfonic acid (6.32 mg, 0.027 mmol) in dichloromethane (5 mL) was added 77% m-CPBA (3.13 mg, 10.88 μmol). The mixture was stirred at room temperature for 3 h.

Purification using reverse phase HPLC (Waters Xbridge C18 19×100 mm; gradient over 8 min from 30 to 100% of solvent B; solvent A: 10% MeOH: 90% H2O: 0.1% TFA; solvent B: 90% MeOH, 10% H2O, 0.1% TFA), concentration, basification with aqueous K2CO3 solution, and extraction with ethyl acetate gave ((1R,3S)-1-amino-3-((S)-6-((phenylsulfonyl)methyl)-5,6,7,8-tetrahydronaphthalen-2-yl)cyclopentyl)methanol (2 mg, 4.76 μmol) as a solid. LC/MS M+1=400. HPLC Retention time=7.04 min (condition L) 1H NMR (400 MHz, METHANOL-d4) δ 7.99-7.93 (m, 2H), 7.77-7.70 (m, 1H), 7.68-7.61 (m, 2H), 7.01-6.87 (m, 3H), 3.53-3.42 (m, 2H), 3.27 (dd, J=6.3, 5.0 Hz, 2H), 3.07-2.88 (m, 2H), 2.80-2.71 (m, 2H), 2.55 (dd, J=16.3, 9.9 Hz, 1H), 2.40-2.14 (m, 2H), 2.09-1.95 (m, 2H), 1.95-1.67 (m, 3H), 1.64-1.49 (m, 2H).

The examples in Table 19 were prepared according to the general procedures for Examples 336 and 337.

TABLE 19

| Ex. No. | Structure | MW | HPLC ret. time (min.) | HPLC condition | MS (M$^{+1}$) |
|---|---|---|---|---|---|
| 338 | 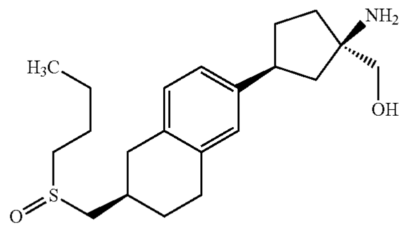 [SMILES: CCCCS(=O)C[C@@H]1CCc2cc([C@H]3CC[C@](N)(CO)C3)ccc2C1] | 363.6 | 2.21 | C | 364 |
| 339 | 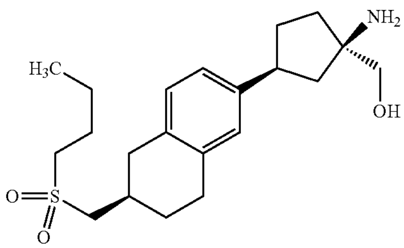 [SMILES: CCCCS(=O)(=O)C[C@@H]1CCc2cc([C@H]3CC[C@](N)(CO)C3)ccc2C1] | 379.6 | 2.17 | C | 380 |

Example 343

((1R,3S)-1-amino-3-((S)-6-hexyl-3-iodo-5,6,7,8-tetrahydronaphthalen-2-yl) cyclopentyl)methanol, TFA

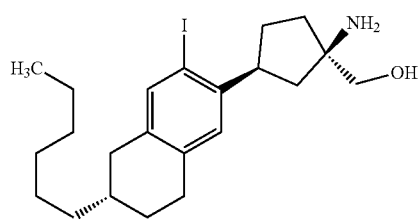

(343)

To a solution of ((1R,3S)-1-amino-3-((S)-6-hexyl-5,6,7,8-tetrahydronaphthalen-2-yl)cyclopentyl)methanol, TFA (see PCT/US2014/017534) (10 mg, 0.023 mmol) in TFA (1 mL) was added NIS (15.22 mg, 0.068 mmol) at room temperature. After 1 h, LCMS showed complete consumption of starting material. The solvent was removed and purification on HPLC prep was performed. HPLC: condition=2 mL injection, gradient time of 5 min, start B=20% to 100%, stop time of 15 min, Solvent A=0.1% TFA in water, Solvent B=0.1% TFA in MeCN, column=LUNA, wavelength of 220 nm. ((1R,3S)-1-amino-3-((S)-6-hexyl-3-iodo-5,6,7,8-tetrahydronaphthalen-2-yl)cyclopentyl) methanol, TFA (3.5 mg, 5.78 μmol) was isolated with >95% purity. HPLC retention time=12.3 min (condition L) LC/MS M+$^1$=456. $^1$H NMR (400 MHz, METHANOL-d$_4$) δ 7.56 (s, 1H), 7.08 (s, 1H), 3.54-3.41 (m, 2H), 3.01 (tt, J=11.1, 7.2 Hz, 1H), 2.87-2.69 (m, 3H), 2.34 (dd, J=16.2, 10.5 Hz, 1H), 2.20 (dd, J=13.0, 7.5 Hz, 1H), 2.07-1.84 (m, 3H), 1.83-1.60 (m, 3H), 1.60-1.48 (m, 1H), 1.47-1.25 (m, 11H), 1.00-0.88 (m, 3H).

The examples in Table 20 were prepared according to the general procedure in Example 343.

TABLE 20

| Ex. No. | Structure | MW | HPLC ret. time (min.) | HPLC condition | MS (M$^{+1}$) |
|---|---|---|---|---|---|
| 344 | 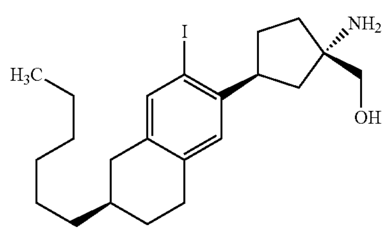 [SMILES: CCCCCC[C@@H]1CCc2cc([C@H]3CC[C@@](N)(CO)C3)c(I)cc2C1] | 455.4 | 12.2 | L | 456 |

TABLE 20-continued

| Ex. No. | Structure | MW | HPLC ret. time (min.) | HPLC condition | MS (M+1) |
|---|---|---|---|---|---|
| 345 | 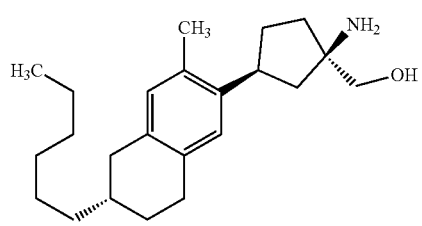 | 363.9 | 10.9 | L | 364/366 |

Example 346

((1R,3S)-1-amino-3-((S)-6-hexyl-3-methyl-5,6,7,8-tetrahydronaphthalen-2-yl) cyclopentyl)methanol, TFA (346)

To a solution of ((1R,3S)-1-amino-3-((S)-6-hexyl-3-iodo-5,6,7,8-tetrahydronaphthalen-2-yl)cyclopentyl)methanol, TFA (90 mg, 0.158 mmol) (dried with toluene evaporation) and ferric acetylacetonate (11.16 mg, 0.032 mmol) in a mixture of THF (1.5 mL) and N-methyl-2-pyrrolidinone (0.3 mL) was added methylmagnesium bromide (0.263 mL, 0.790 mmol) at room temperature. LCMS showed desired product along with SM and desiodo product. The mixture was injected through HPLC. HPLC: condition=2 mL injection, gradient time of 5 min, start B=20% to 100%, stop time of 15 min, Solvent A=0.1% TFA in Water, Solvent B=0.1% TFA in MeCN, column=LUNA, wavelength of 220. ((1R,3S)-1-amino-3-((S)-6-hexyl-3-methyl-5,6,7,8-tetrahydronaphthalen-2-yl)cyclopentyl)methanol, TFA (15 mg, 0.031 mmol) was isolated with >95% purity. HPLC retention time=11.6 min (condition L) LC/MS M+1=344. 1H NMR (400 MHz, METHANOL-d4) δ 7.05-6.99 (m, 1H), 7.08 (s, 1H), 3.54-3.41 (m, 2H), 3.01 (tt, J=11.1, 7.2 Hz, 1H), 2.87-2.69 (m, 3H), 2.34 (dd, J=16.2, 10.5 Hz, 1H), 2.26 (s, 3H), 2.20 (dd, J=13.0, 7.5 Hz, 1H), 2.07-1.84 (m, 3H), 1.83-1.60 (m, 3H), 1.60-1.48 (m, 1H), 1.47-1.25 (m, 11H), 1.00-0.88 (m, 3H).

Example 347

6-((1 S,3R)-3-amino-3-(hydroxymethyl)cyclopentyl)-1,2,3,4-tetrahydronaphthalen-2-yl hexanoate, TFA

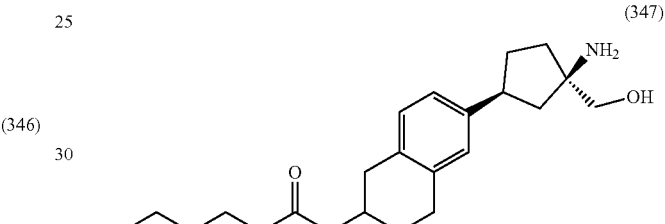
(347)

Preparation 347A: (5R,7S)-7-(6-hydroxy-5,6,7,8-tetrahydronaphthalen-2-yl)-3-oxa-1-azaspiro[4.4]nonan-2-one

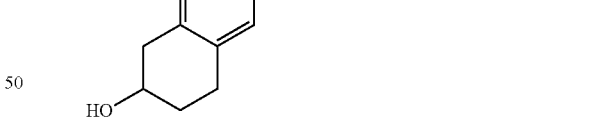
(347A)

To a solution of (5R,7S)-7-(6-oxo-5,6,7,8-tetrahydronaphthalen-2-yl)-3-oxa-1-azaspiro[4.4]nonan-2-one (200 mg, 0.701 mmol) in MeOH (7009 μl) at 0° C. was added sodium borohydride (53.0 mg, 1.402 mmol) in one portion. The reaction mixture was stirred at 0° C. for 30 min and then allowed to warm to room temperature. LCMS showed completion. The solvent was removed, the slurry was diluted with DCM and washed twice with DCM. The organic layer was dried with Na2SO4 and concentrated to afford (5R,7S)-7-(6-hydroxy-5,6,7,8-tetrahydronaphthalen-2-yl)-3-oxa-1-azaspiro[4.4]nonan-2-one (201 mg, 0.699 mmol). The material was used directly for further reaction. HPLC retention time=0.75 min (condition G); LC/MS M+1=288.

Preparation 347B: 6-((1S,3R)-3-amino-3-(hydroxymethyl)cyclopentyl)-1,2,3,4-tetrahydronaphthalen-2-ol

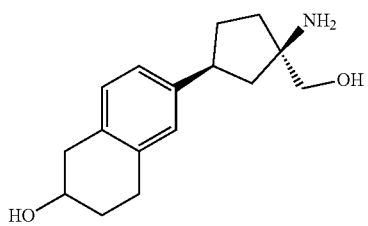
(347B)

To a mixture of (5R,7S)-7-(6-hydroxy-5,6,7,8-tetrahydronaphthalen-2-yl)-3-oxa-1-azaspiro[4.4]nonan-2-one (200 mg, 0.696 mmol) in dioxane (5 mL) was added 1N NaOH (6.96 mL, 6.96 mmol). The reaction mixture was heated at 100° C. for 14 h. LCMS showed complete consumption of starting material. The reaction mixture was diluted with ethyl acetate and washed with H$_2$O. The organic layer was dried with MgSO$_4$, filtered and concentrated. The organic layer was dried with MgSO$_4$, filtered, and concentrated to afford 6-((1S,3R)-3-amino-3-(hydroxymethyl)cyclopentyl)-1,2,3,4-tetrahydronaphthalen-2-ol (180 mg, 0.689 mmol). HPLC retention time=4.9 min (condition L) LC/MS M$^{+1}$=262. $^1$H NMR (400 MHz, METHANOL-d$_4$) δ 7.06-6.95 (m, 3H), 4.10-3.96 (m, 1H), 3.73-3.52 (m, 2H), 3.16-3.07 (m, 1H), 3.02 (dd, J=16.3, 4.6 Hz, 1H), 2.98-2.87 (m, 1H), 2.82 (dd, J=9.5, 5.9 Hz, 1H), 2.68 (dd, J=16.2, 8.0 Hz, 1H), 2.48-2.37 (m, 1H), 2.16-2.08 (m, 1H), 2.08-1.99 (m, 1H), 1.99-1.86 (m, 3H), 1.83-1.67 (m, 2H).

Preparation 347C: ((1R,3S)-3-(6-hydroxy-5,6,7,8-tetrahydronaphthalen-2-yl)-1-(hydroxymethyl)cyclopentyl)carbamate

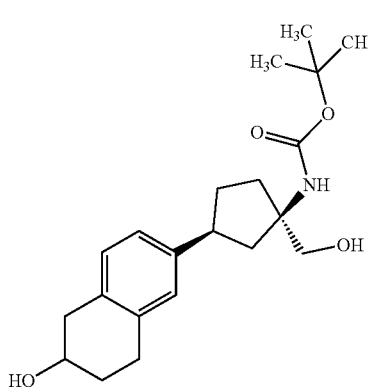
(347C)

To a solution of 6-((1S,3R)-3-amino-3-(hydroxymethyl)cyclopentyl)-1,2,3,4-tetrahydronaphthalen-2-ol (182 mg, 0.696 mmol) in DCM (6964 μl) was added BOC$_2$O (243 μl, 1.045 mmol) and triethylamine (146 μl, 1.045 mmol). The reaction mixture was stirred at room temperature overnight and LCMS showed complete consumption of starting material. The reaction mixture was diluted with ethyl acetate and washed with 1N HCl. The organic layer was dried with MgSO$_4$, filtered, and concentrated to afford tert-butyl ((1R,3S)-3-(6-hydroxy-5,6,7,8-tetrahydronaphthalen-2-yl)-1-(hydroxymethyl) cyclopentyl)carbamate (250 mg, 0.692 mmol) as an oil. HPLC retention time=0.89 min (condition G); LC/MS M$^{+1}$=364.

Preparation 347D: (5R,7S)-tert-butyl 7-(6-hydroxy-5,6,7,8-tetrahydronaphthalen-2-yl)-2,2-dimethyl-3-oxa-1-azaspiro[4.4]nonane-1-carboxylate

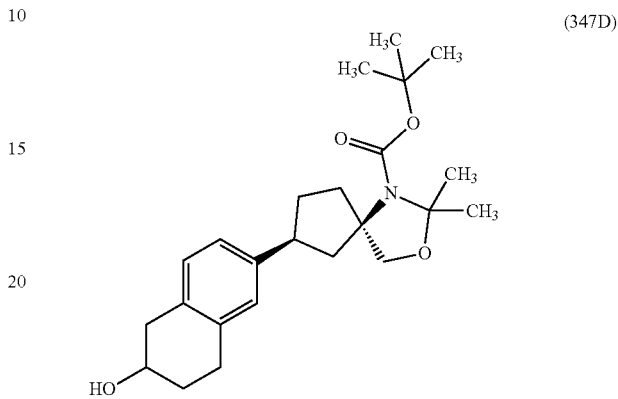
(347D)

To a solution of tert-butyl ((1R,3S)-3-(6-hydroxy-5,6,7,8-tetrahydronaphthalen-2-yl)-1-(hydroxymethyl)cyclopentyl)carbamate (250 mg, 0.692 mmol) in acetone (6916 μl) was added 2,2-dimethoxypropane (170 μl, 1.383 mmol) followed by BF$_3$.OEt$_2$ (175 μl, 1.383 mmol). The reaction was monitored by LCMS and after 1 h a considerable amount of desired product (RT of 1.14 min) was formed. The reaction was quenched with 0.5 mL Et$_3$N to complex BF$_3$. The solvent was removed under reduced pressure and placed under vacuum to afford (5R,7S)-tert-butyl 7-(6-hydroxy-5,6,7,8-tetrahydronaphthalen-2-yl)-2,2-dimethyl-3-oxa-1-azaspiro[4.4]nonane-1-carboxylate (278 mg, 0.692 mmol). HPLC retention time=1.16 min (condition G); LC/MS M$^{+1}$=402.

To a solution a solution of (5R,7S)-tert-butyl 7-(6-hydroxy-5,6,7,8-tetrahydronaphthalen-2-yl)-2,2-dimethyl-3-oxa-1-azaspiro[4.4]nonane-1-carboxylate (0.040 g, 0.1 mmol) in DCM (1.000 ml) was added pyridine (0.024 ml, 0.300 mmol) and hexanoyl chloride (0.028 ml, 0.200 mmol) at room temperature. LCMS showed a rapid conversion to the desired product at 1.41 min. HPLC retention time=1.41 min (condition G); LC/MS M$^{+1}$=500.4. To this solution was added TFA (1 mL) and the reaction was followed by LCMS. LCMS showed rapid conversion to the desired compound. The mixture was concentrated under reduced pressure, dissolved in MeOH and purified by HPLC prep: HPLC: condition=2 mL injection, gradient time of 5 min, start B=20% to 100%, stop time of 15 min, Solvent A=0.1% TFA in Water, Solvent B=0.1% TFA in MeCN, column=LUNA, wavelength of 220. 6-((1S,3R)-3-amino-3-(hydroxymethyl) cyclopentyl)-1,2,3,4-tetrahydronaphthalen-2-yl hexanoate, TFA (16 mg, 0.030 mmol) was isolated as a colorless oil with purity >95%. HPLC retention time=0.89 min (condition G) LC/MS M$^{+1}$=361. $^1$H NMR (400 MHz, METHANOL-d$_4$) δ 7.11-6.92 (m, 3H), 5.24-5.13 (m, 1H), 3.73-3.54 (m, 2H), 3.08 (dd, J=16.6, 4.7 Hz, 2H), 3.01-2.88 (m, 1H), 2.88-2.77 (m, 2H), 2.50-2.38 (m, 1H), 2.36-2.25 (m, 2H), 2.13 (d, J=2.9 Hz, 1H), 2.09-1.87 (m, 4H), 1.74 (t, J=12.8 Hz, 1H), 1.61 (quin, J=7.1 Hz, 3H), 1.43-1.22 (m, 4H), 0.96-0.83 (m, 3H).

The examples in Table 21 were prepared according to the general procedures in Example 347.

TABLE 21

| Ex. No. | Structure | MW | HPLC ret. time (min.) | HPLC method | MS (M$^{+1}$) | Comment |
|---|---|---|---|---|---|---|
| 348 | 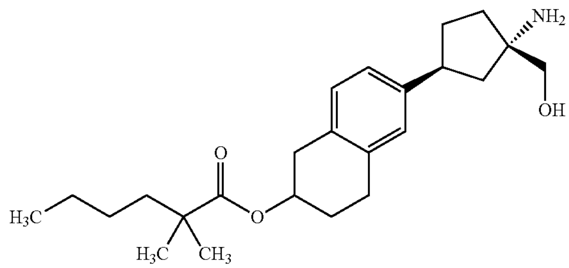 [SMILES: CCCCC(C)(C)C(=O)OC1CCc2cc([C@H]3CC[C@@](N)(CO)C3)ccc2C1] | 387.6 | 0.84 | G | 388 | |
| 349 | 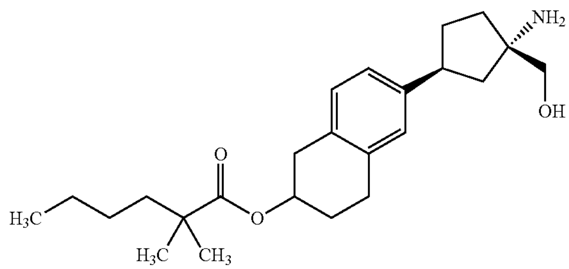 [SMILES: CCCCC(C)(C)C(=O)OC1CCc2cc([C@H]3CC[C@@](N)(CO)C3)ccc2C1] | 387.6 | 9.00 | L | 388 | Isomer 1 |
| 350 | 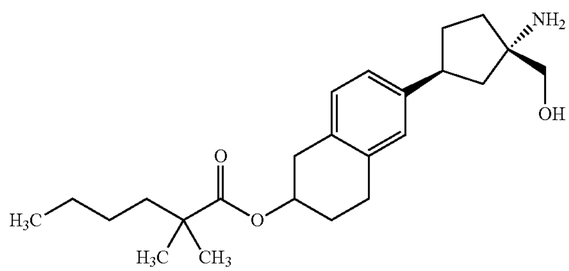 | 387.6 | 9.05 | L | 388 | Isomer 2 |
| 351 | 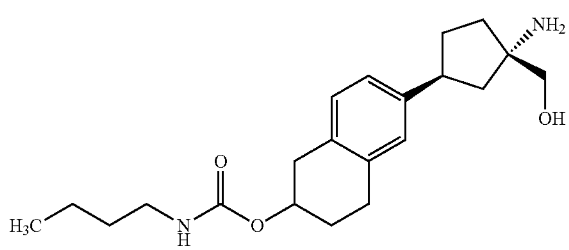 [SMILES: CCCCNC(=O)OC1CCc2cc([C@H]3CC[C@@](N)(CO)C3)ccc2C1] | 360.5 | 6.9 | L | 361 | |
| 352 | 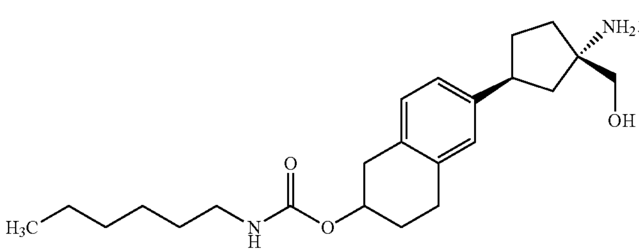 | 388.3 | 7.9 | L | 389 | |

TABLE 21-continued

| Ex. No. | Structure | MW | HPLC ret. time (min.) | HPLC method | MS (M$^{+1}$) | Comment |
|---|---|---|---|---|---|---|
| 353 | 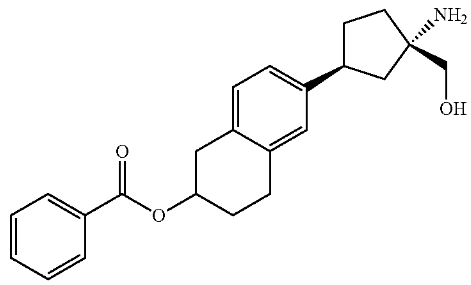 [SMILES: N[C@@]1(CO)CC[C@H](c2ccc3c(c2)CCC(OC(=O)c2ccccc2)C3)C1] | 365.5 | 7.6 | L | 366 | |

Separation procedure for Examples 349 and 350: Preparative Chromatographic Conditions: Instrument: Berger SFC MGII; Column: Chiral AD-H 25×3 cm ID, 5 µm; Flow rate: 85.0 mL/min; Mobile Phase: 85/15 CO$_2$/MeOH w/0.1% DEA; Detector Wavelength: 220 nm; Sample Prep and Inj. Volume: 2500 µL of 20 mg dissolved in 6 mL MeOH/ACN. Analytical Chromatographic Conditions: Instrument: Berger analytical SFC; Column: Chiral AD-H 250×4.6 mm ID, 5 µm; Flow rate: 2.0 mL/min; Mobile Phase: 80/20 CO$_2$/MeOH w/0.1% DEA.

Example 354

6-((1 S,3R)-3-amino-3-(hydroxymethyl)cyclopentyl)-1,2,3,4-tetrahydronaphthalen-2-yl butyl(methyl) carbamate, TFA

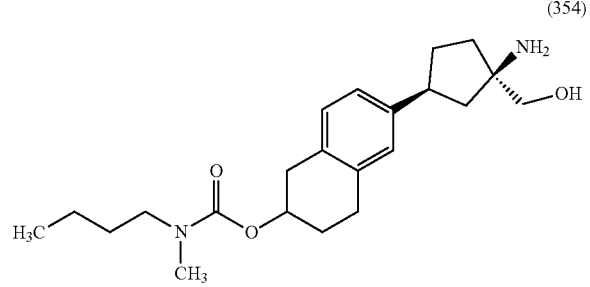 [SMILES: CCCCN(C)C(=O)OC1CCc2cc([C@H]3CC[C@](N)(CO)C3)ccc2C1]

(354)

Preparation 354A: (5R,7S)-tert-butyl 7-(6-((butyl(methyl)carbamoyl)oxy)-5,6,7,8-tetrahydronaphthalen-2-yl)-2,2-dimethyl-3-oxa-1-azaspiro[4.4]nonane-1-carboxylate (354A)

To a solution of (5R,7S)-tert-butyl 7-(6-((butylcarbamoyl)oxy)-5,6,7,8-tetrahydronaphthalen-2-yl)-2,2-dimethyl-3-oxa-1-azaspiro[4.4]nonane-1-carboxylate (0.050 g, 0.1 mmol) in THF (2 mL) was added potassium tert-butoxide (0.045 g, 0.400 mmol) followed by MeI (0.025 mL, 0.400 mmol). The reaction mixture was stirred 1 h at room temperature when LCMS showed complete consumption. The mixture was diluted with EtOAc and washed twice with 1N HCl, dried over MgSO$_4$, filtered and concentrated under reduced pressure. The resulting material was used directly in the next reaction. HPLC retention time=1.95 min (condition G); LC/MS M$^{+1}$=515.

Example 354

To a solution of (5R,7S)-tert-butyl 7-(6-((butyl(methyl)carbamoyl)oxy)-5,6,7,8-tetrahydronaphthalen-2-yl)-2,2-dimethyl-3-oxa-1-azaspiro[4.4]nonane-1-carboxylate (51.5 mg, 0.1 mmol) in DCM (2 mL) was added TFA (1 mL). The solution was stirred for 30 min at room temperature when LCMS showed complete consumption. The solvent was removed under reduced pressure and the resulting oil was dissolved in MeOH. The solution was injected on the HPLC. Condition=2 mL injection, gradient time of 5 min, start B=20% to 100%, stop time of 15 min, Solvent A=0.1% TFA in water, Solvent B=0.1% TFA in MeCN, column=LUNA, wavelength of 220 providing 6-((1S,3R)-3-amino-3-(hydroxymethyl)cyclopentyl)-1,2,3,4-tetrahydronaphthalen-2-yl butyl(methyl)carbamate, TFA (12 mg, 0.023 mmol) with >95% purity. HPLC retention time=7.31 min (condition L); LC/MS $M^{+1}$=375. $^1$H NMR (400 MHz, METHANOL-$d_4$) δ 7.12-6.97 (m, 3H), 5.15-4.99 (m, 1H), 3.64 (dd, J=13.9, 12.5 Hz, 2H), 3.20-3.01 (m, 4H), 3.01-2.75 (m, 6H), 2.43 (dd, J=12.2, 6.9 Hz, 1H), 2.20-2.09 (m, 1H), 2.09-1.89 (m, 5H), 1.73 (t, J=12.8 Hz, 1H), 1.61-1.47 (m, 1H), 1.47-1.25 (m, 2H), 1.25-1.07 (m, 1H), 0.97 (t, J=7.2 Hz, 1.5H), 0.87-0.72 (m, 1.5H) mixture of 1:1 rotamer.

Example 355

N-(6-((1 S,3R)-3-amino-3-(hydroxymethyl)cyclopentyl)-1,2,3,4-tetrahydronaphthalen-2-yl)hexanamide, TFA

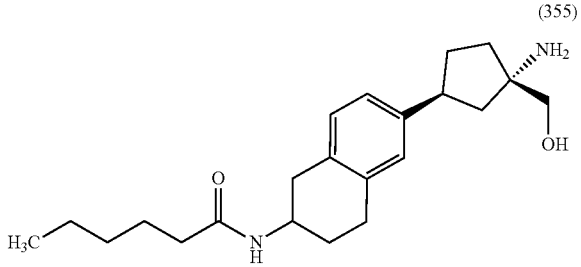 [SMILES: CCCCCC(=O)NC1CCc2cc([C@H]3CC[C@@](N)(CO)C3)ccc2C1]

(355)

Preparation 355A: (5R,7S)-7-(6-amino-5,6,7,8-tetrahydronaphthalen-2-yl)-3-oxa-1-azaspiro[4.4]nonan-2-one

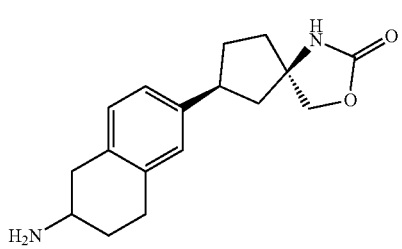

(355A)

To a solution of (5R,7S)-7-(6-oxo-5,6,7,8-tetrahydronaphthalen-2-yl)-3-oxa-1-azaspiro[4.4]nonan-2-one (50 mg, 0.175 mmol) in MeOH (1752 µl) was added ammonium acetate (135 mg, 1.752 mmol) followed by sodium cyanoborohydride (16.52 mg, 0.263 mmol). The reaction mixture was stirred at room temperature overnight. LCMS showed complete consumption of starting material. Next, 4 mL of 1N HCl was added and the solvent was removed under reduced pressure. DCM was added and the organic layer was washed twice with 1N HCl. The aqueous layer was basified with 1N NaOH and extracted 3 times with EtOAc. The organic fractions were combined, dried and concentrated affording (5R,7S)-7-(6-amino-5,6,7,8-tetrahydronaphthalen-2-yl)-3-oxa-1-azaspiro[4.4]nonan-2-one (44 mg, 0.154 mmol) as a brown oil. The material was used directly for further reaction. HPLC retention time=0.55 min (condition G); LC/MS $M^+$=287.

Preparation 355B: ((1R,3S)-1-amino-3-(6-amino-5,6,7,8-tetrahydronaphthalen-2-yl)cyclopentyl)methanol

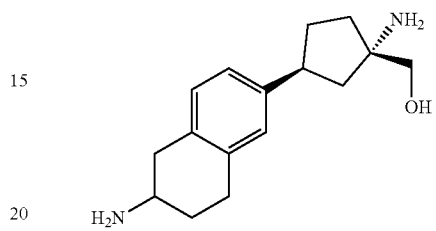

(355B)

To a solution of (5R,7S)-7-(6-amino-5,6,7,8-tetrahydronaphthalen-2-yl)-3-oxa-1-azaspiro[4.4]nonan-2-one (44 mg, 0.154 mmol) in dioxane (1536 µl) in a vial was added NaOH (1536 µl, 1.536 mmol). The vial was sealed and warmed to 100° C. for 1 h. LCMS showed complete conversion. Next, 4 mL NaOH 1N was added and the aqueous layer was washed three times with EtOAc. The organics layers were combined, dried and concentrated affording ((1R,3S)-1-amino-3-(6-amino-5,6,7,8-tetrahydronaphthalen-2-yl) cyclopentyl)methanol (20 mg, 0.077 mmol) as an oil. HPLC retention time=0.42 min (condition G); LC/MS $M^{+1}$=261.

Example 355

To a solution of ((1R,3S)-1-amino-3-(6-amino-5,6,7,8-tetrahydronaphthalen-2-yl)cyclopentyl)methanol (10 mg, 0.038 mmol) in DCM (384 µl) was added hexanoyl chloride (6.44 µl, 0.046 mmol). The reaction mixture was stirred at 25° C. for 15 min and the reaction was quenched with 1N NaOH. The aqueous layer was extracted 3 times with EtOAc. The organic layers were combined, dried and concentrated under reduced pressure. The resulting oil was dissolved in MeOH. The solution was injected on the HPLC prep: condition=2 mL injection, gradient time of 5 min, start B=20% to 100%, stop time of 15 min, Solvent A=0.1% TFA in water, Solvent B=0.1% TFA in MeCN, column=LUNA, wavelength of 220 nm. N-(6-((1S,3R)-3-amino-3-(hydroxymethyl)cyclopentyl)-1,2,3,4-tetrahydronaphthalen-2-yl)hexanamide, TFA (3.7 mg, 7.44 µmol) was obtained with >95% purity. HPLC retention time=6.59 min (condition L) LC/MS $M^{+1}$=359. $^1$H NMR (400 MHz, METHANOL-$d_4$) δ 7.10-6.98 (m, 3H), 4.13-4.00 (m, 1H), 3.64 (dd, J=13.6, 11.0 Hz, 2H), 3.20-3.07 (m, 1H), 3.01 (dd, J=16.0, 4.5 Hz, 1H), 2.90 (dd, J=8.0, 5.0 Hz, 2H), 2.65 (dd, J=16.3, 9.7 Hz, 1H), 2.43 (dd, J=13.3, 6.1 Hz, 1H), 2.21 (t, J=7.5 Hz, 2H), 2.17-2.01 (m, 2H), 2.01-1.87 (m, 3H), 1.79-1.57 (m, 4H), 1.44-1.27 (m, 4H), 0.94 (t, J=7.0 Hz, 3H).

Example 356 in Table 22 was prepared according to the general procedure for Example 355.

TABLE 22

| Ex. No. | Structure | MW | HPLC ret. time (min.) | HPLC method | MS (M+1) |
|---|---|---|---|---|---|
| 356 | 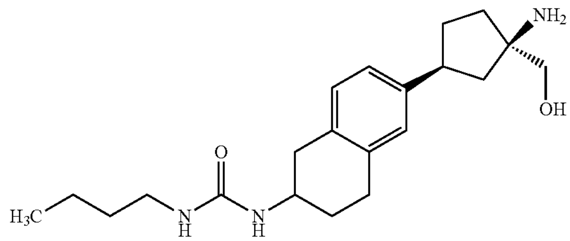 [SMILES: CCCCNC(=O)NC1CCc2cc([C@H]3CC[C@](N)(CO)C3)ccc2C1] | 359.5 | 0.61 | G | 360 |

Example 357

((1R,3S)-1-amino-3-(6'-butyl-3,3',4,4',5',6'-hexahydro-1H-spiro[naphthalene-2,2'-pyran]-6-yl)cyclopentyl)methanol

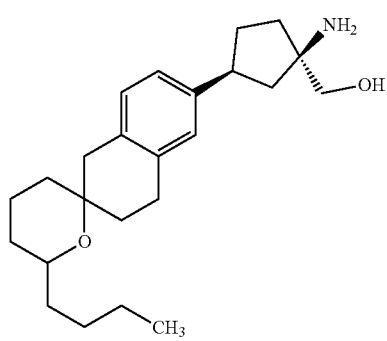

(357)

Preparation 357A: 5R,7S)-7-(6'-butyl-4'-chloro-3,3',4,4',5', 6'-hexahydro-1H-spiro[naphthalene-2,2'-pyran]-6-yl)-3-oxa-1-azaspiro[4.4]nonan-2-one

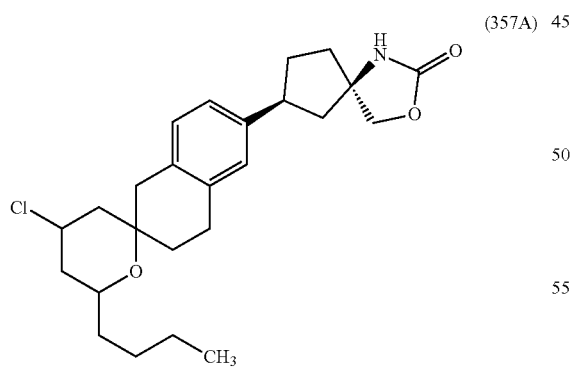

(357A)

To a solution of (5R,7S)-7-(6-oxo-5,6,7,8-tetrahydronaphthalen-2-yl)-3-oxa-1-azaspiro[4.4]nonan-2-one (200 mg, 0.701 mmol) and oct-1-en-4-ol (180 µl, 1.402 mmol) in CH$_2$Cl$_2$ (700 µl) at room temperature was added tin(IV) chloride (841 µl, 0.841 mmol). LCMS showed that the reaction was complete within 2 h. The reaction was quenched by saturated NaHCO$_3$ and the aqueous layer was back extract three times with DCM. The organic layers were combined, dried and concentrated under reduced pressure. The resulting oil was purified by HPLC prep (condition=2 mL injection, gradient time of 5 min, start B=20% to 100%, stop time of 15 min, Solvent A=0.1% TFA in Water, Solvent B=0.1% TFA in MeCN, column=LUNA, wavelength of 220) affording (5R,7S)-7-(6'-butyl-4'-chloro-3,3',4,4',5',6'-hexahydro-1H-spiro[naphthalene-2,2'-pyran]-6-yl)-3-oxa-1-azaspiro[4.4]nonan-2-one (149 mg, 0.345 mmol) as a brown solid which was used directly for further reaction. HPLC retention time=1.18 min (condition G) LC/MS M$^{+1}$=432/434.

Preparation 357B: (5R,7S)-7-(6'-butyl-3,3',4,4',5',6'-hexahydro-1H-spiro[naphthalene-2,2'-pyran]-6-yl)-3-oxa-1-azaspiro[4.4]nonan-2-one

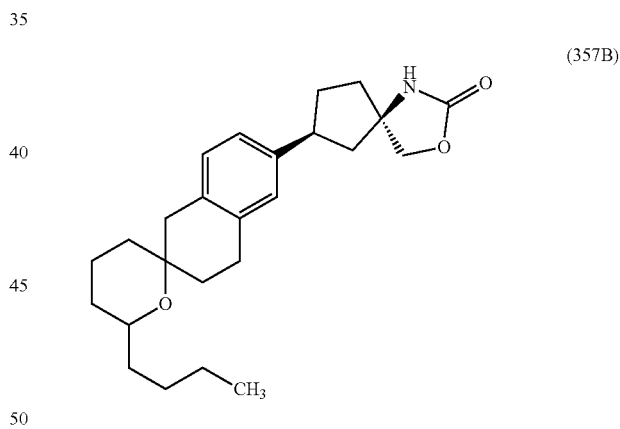

(357B)

To a solution of (5R,7S)-7-(6'-butyl-4'-chloro-3,3',4,4',5', 6'-hexahydro-1H-spiro[naphthalene-2,2'-pyran]-6-yl)-3-oxa-1-azaspiro[4.4]nonan-2-one (300 mg, 0.694 mmol) in i-PrOH (3472 µl) was added HCl (6945 µl, 41.7 mmol) followed by zinc (4540 mg, 69.4 mmol). The reaction mixture was warmed to 80° C. and followed by LCMS. Conversion of >90% after 3 days was measured. The heterogeneous mixture was filtered through Celite eluting with EtOAc. The oil obtained after concentration under reduced pressure was purified by HPLC prep (condition=2 mL injection, gradient time of 5 min, start B=20% to 100%, stop time of 15 min, Solvent A=0.1% TFA in Water, Solvent B=0.1% TFA in MeCN, column=LUNA, wavelength of 220) affording (5R,7S)-7-(6'-butyl-3,3',4,4',5',6'-hexahydro-1H-spiro[naphthalene-2,2'-pyran]-6-yl)-3-oxa-1-azaspiro

[4.4]nonan-2-one (100 mg, 0.252 mmol) as a white solid which was used directly for further reaction. HPLC retention time=1.21 min (condition G) LC/MS M$^{+1}$=398.3. Stereoisomer separation was then performed. Approximately 110 mg sample was resolved. Four isomers were collected. Preparative Chromatographic Conditions: Instrument: Berger SFC MGII; Column: Chiral OJ-H 25×3 cm ID, 5 μm; Flow rate:

85.0 mL/min; Mobile Phase: 85/15 CO$_2$/1:1 MeOH:CAN; Detector Wavelength: 220 nm; Sample Prep and Inj. Volume: 1000 μL of 1100 mg dissolved in 7 mL MeOH/ACN. Analytical Chromatographic Conditions: Instrument: Berger analytical SFC; Column: Chiral OJ-H 250×4.6 mm ID, 5 μm; Flow rate: 2.0 mL/min; Mobile Phase: 87/13 CO$_2$/1:1 MeOH:CAN.

Example 357: ((1R,3S)-1-amino-3-(6'-butyl-3,3',4,4',5',6'-hexahydro-1H-spiro[naphthalene-2,2'-pyran]-6-yl)cyclopentyl)methanol, TFA (Isomer 1)

To a solution of Isomer I of (5R,7S)-7-(6'-butyl-3,3',4,4',5',6'-hexahydro-1H-spiro[naphthalene-2,2'-pyran]-6-yl)-3-oxa-1-azaspiro[4.4]nonan-2-one (17 mg, 0.043 mmol) in dioxane (428 μl) was added NaOH (428 μl, 0.428 mmol). The reaction mixture was warmed to 100° C. LCMS showed complete conversion after 2 h. The reaction mixture was cooled down to room temperature, diluted with EtOAc and 1N NaOH. The aqueous layer was extracted three times with EtOAc. The organic layers were combined, dried, and concentrated under reduced pressure. The resulting oil was diluted in MeOH and injected on HPLC: condition=2 mL injection, gradient time of 5 min, start B=20% to 100%, stop time of 15 min, Solvent A=0.1% TFA in Water, Solvent B=0.1% TFA in MeCN, column=LUNA, wavelength of 220 affording ((1R,3S)-1-amino-3-(6'-butyl-3,3',4,4',5',6'-hexahydro-1H-spiro[naphthalene-2,2'-pyran]-6-yl)cyclopentyl) methanol, TFA isomer 1 (15 mg, 0.031 mmol). HPLC retention time=9.09 min (condition L). LC/MS M$^{+1}$=372. $^1$H NMR (400 MHz, METHANOL-d$_4$) δ 7.08-6.93 (m, 3H), 3.72-3.52 (m, 3H), 3.21-3.04 (m, 1H), 2.92-2.75 (m, 1H), 2.75-2.60 (m, 3H), 2.55-2.37 (m, 2H), 2.20-2.03 (m, 1H), 2.02-1.90 (m, 3H), 1.90-1.78 (m, 1H), 1.73 (t, J=12.8 Hz, 2H), 1.68-1.45 (m, 4H), 1.44-1.32 (m, 2H), 1.32-1.09 (m, 5H), 0.85 (t, J=7.0 Hz, 3H).

The examples in Table 23 were prepared according to the general procedure for Example 357

TABLE 23

| Ex. No. | Structure | MW | HPLC ret. time (min.) | HPLC method | MS (M$^{+1}$) | Comment |
|---|---|---|---|---|---|---|
| 358 | | 371.6 | 8.96 | L | 372 | Isomer 2 |
| 359 | | 371.6 | 8.98 | L | 372 | Isomer 3 |
| 360 | | 371.6 | 8.96 | L | 372 | Isomer 4 |
| 361 | | 315.5 | 6.68 | L | 316 | — |

Examples 362 to 363

6-((1S,3R)-3-amino-3-(hydroxymethyl)cyclopentyl)-2-butyl-1,2,3,4-tetrahydronaphthalen-1-ol, TFA

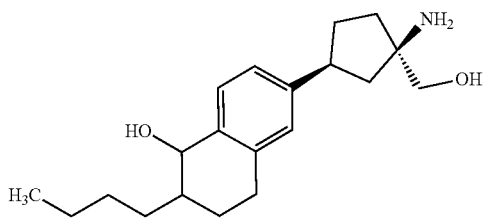 [SMILES: CCCCC1CCc2cc([C@H]3CC[C@](N)(CO)C3)ccc2C1O]

Preparation 362A: (5R,7S)-7-(6-butyl-5-hydroxy-5,6,7,8-tetrahydronaphthalen-2-yl)-3-oxa-1-azaspiro[4.4]nonan-2-one (362A)

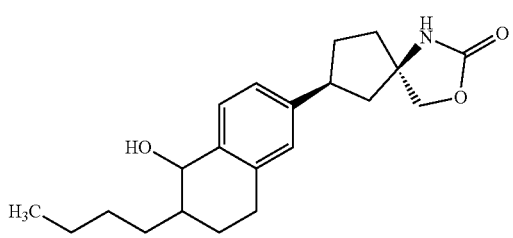

To a solution of (5R,7S)-7-(6-butyl-7,8-dihydronaphthalen-2-yl)-3-oxa-1-azaspiro[4.4]nonan-2-one (0.5 g, 1.536 mmol) in THF (15.36 ml) was added BH$_3$.DMS (0.307 ml, 1.536 mmol) at room temperature. The reaction mixture was stirred for 1.5 h. LCMS showed no starting material. To the reaction mixture was added 1N NaOH (0.5 mL) and H$_2$O$_2$ (1.569 ml, 15.36 mmol) and the reaction mixture was stirred at room temperature for 15 min. The reaction mixture was diluted with water, extracted with EtOAc, and then washed with water (2×). The organic layers were combined, dried over Na$_2$SO$_4$, and concentrated under reduced pressure. The resulting oil was purified on ISCO affording (5R,7S)-7-(6-butyl-5-hydroxy-5,6,7,8-tetrahydronaphthalen-2-yl)-3-oxa-1-azaspiro[4.4]nonan-2-one (0.34 g, 0.990 mmol). $^1$H NMR (400 MHz, CHLOROFORM-d) δ 7.45 (d, J=7.9 Hz, 1H), 7.07 (d, J=7.9 Hz, 1H), 6.95 (s, 1H), 6.22-6.08 (m, 1H), 4.41 (d, J=6.6 Hz, 1H), 4.37-4.23 (m, 2H), 3.11-2.92 (m, 2H), 2.84-2.69 (m, 2H), 2.37-2.24 (m, 1H), 2.21-2.02 (m, 3H), 2.02-1.88 (m, 2H), 1.88-1.60 (m, 4H), 1.57-1.51 (m, 1H), 1.50-1.44 (m, 1H), 1.42-1.25 (m, 4H), 1.03-0.86 (m, 3H).

Examples 362 and 363

To a solution of (5R,7S)-7-(6-butyl-5-hydroxy-5,6,7,8-tetrahydronaphthalen-2-yl)-3-oxa-1-azaspiro[4.4]nonan-2-one (22 mg, 0.064 mmol) in dioxane (320 µl) was added NaOH (641 µl, 0.641 mmol). The reaction mixture was warmed to 90° C. and stirred until full conversion was observed (2 h). The reaction mixture was cooled, diluted with water and EtOAc. The aqueous layer was back extract three times with EtOAc. The organic layers were combined, dried and concentrated under reduced pressure. The resulting oil was solubilized in MeOH and purified by HPLC: condition=2 mL injection, gradient time of 5 min, start B=20% to 100%, stop time of 15 min, Solvent A=0.1% TFA in Water, Solvent B=0.1% TFA in MeCN, column=LUNA, wavelength of 220 nm. 6-((1S,3R)-3-amino-3-(hydroxymethyl)cyclopentyl)-2-butyl-1,2,3,4-tetrahydronaphthalen-1-ol, TFA (9 mg, 0.02 mmol) was obtained with >95% purity. Preparative Chromatographic Conditions: Instrument: Berger SFC MGII; Column: Chiral OD-H 25×3 cm ID, 5 µm; Flow rate: 85.0 mL/min; Mobile Phase: 75/25 CO$_2$/MeOH; Detector Wavelength: 220 nm; Sample Preparation and Inj. Volume: 700 µL-1000 µL of 52 mg dissolved in 2 mL MeOH. Analytical Chromatographic Conditions: Instrument: Berger analytical SFC; Column: Chiral OD-H 250× 4.6 mm ID, 5 µm; Flow rate: 2.0 mL/min; Mobile Phase: 80/20 CO$_2$/MeOH.

Example 362: Isomer 1: HPLC retention time=0.77 min (condition G); LC/MS M$^{+1}$=318; $^1$H NMR (400 MHz, METHANOL-d$_4$) δ 7.41 (d, J=8.1 Hz, 1H), 7.17-7.07 (m, 1H), 7.01 (s, 1H), 4.34 (d, J=6.8 Hz, 1H), 3.64 (dd, J=15.6, 11.7 Hz, 2H), 3.21-3.06 (m, 1H), 2.77 (t, J=6.3 Hz, 2H), 2.43 (dd, J=13.4, 7.0 Hz, 1H), 2.18-2.04 (m, 2H), 2.03-1.88 (m, 3H), 1.81-1.63 (m, 3H), 1.59-1.44 (m, 2H), 1.44-1.30 (m, 3H), 1.30-1.17 (m, 1H), 1.02-0.90 (m, 3H).

Example 363: Isomer 2: HPLC retention time=0.78 min (condition G); LC/MS M$^{+1}$=318; $^1$H NMR (400 MHz, METHANOL-d$_4$) δ 7.41 (d, J=8.1 Hz, 1H), 7.17-7.07 (m, 1H), 7.01 (s, 1H), 4.34 (d, J=6.8 Hz, 1H), 3.64 (dd, J=15.6, 11.7 Hz, 2H), 3.21-3.06 (m, 1H), 2.77 (t, J=6.3 Hz, 2H), 2.43 (dd, J=13.4, 7.0 Hz, 1H), 2.18-2.04 (m, 2H), 2.03-1.88 (m, 3H), 1.81-1.63 (m, 3H), 1.59-1.44 (m, 2H), 1.44-1.30 (m, 3H), 1.30-1.17 (m, 1H), 1.02-0.90 (m, 3H).

Examples 364 to 366

(5R,7S)-7-(6-butyl-5-oxo-5,6,7,8-tetrahydronaphthalen-2-yl)-3-oxa-1-azaspiro[4.4]nonan-2-one

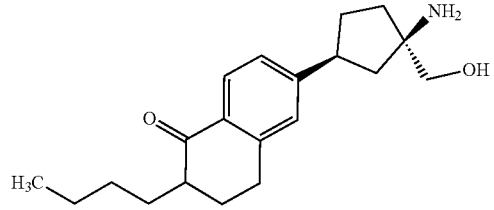 [SMILES: CCCCC1CCc2cc([C@H]3CC[C@](N)(CO)C3)ccc2C1=O]

To a solution of (5R,7S)-7-(6-butyl-5-hydroxy-5,6,7,8-tetrahydronaphthalen-2-yl)-3-oxa-1-azaspiro[4.4]nonan-2-one (150 mg, 0.437 mmol) in DCM (2184 µl) was added DMP (370 mg, 0.873 mmol) at room temperature. LCMS showed complete conversion after 1 h. The reaction mixture was diluted with DCM and extracted with 1N Na$_2$S$_2$O$_3$ and 1N NaOH affording an oily compound after concentration under reduced pressure. The resulting oil was solubilized in MeOH and purified by HPLC: condition=2 mL injection, gradient time of 5 min, start B=20% to 100%, stop time of 15 min, Solvent A=0.1% TFA in Water, Solvent B=0.1% TFA in MeCN, column=LUNA, wavelength of 220. (5R,7S)-7-(6-butyl-5-oxo-5,6,7,8-tetrahydronaphthalen-2-yl)-3-oxa-1-azaspiro[4.4]nonan-2-one (128 mg, 0.375 mmol) was obtained with >95% purity. HPLC retention time=1.24 min (condition G); LC/MS M$^{+1}$=342; $^1$H NMR (400 MHz, CHLOROFORM-d) δ 7.98 (d, J=8.1 Hz, 1H), 7.16 (dd, J=8.1, 1.5 Hz, 1H), 7.10 (s, 1H), 6.59 (s, 1H), 4.33 (dd, J=13.2, 8.1 Hz, 2H), 3.15-3.02 (m, 1H), 3.02-2.91 (m, 2H), 2.52-2.41 (m, 1H), 2.35 (dd, J=13.2, 7.3 Hz, 1H), 2.31-2.09 (m, 3H), 2.07-1.78 (m, 6H), 1.60-1.45 (m, 1H), 1.45-1.31 (m, 4H), 1.02-0.86 (m, 3H). Preparative Chromatographic Conditions: Instrument: Berger SFC MGII; Column: Chiral OD-H 25×3 cm ID, 5 μm; Flow rate: 80.0 mL/min; Mobile Phase: 75/25 CO₂/MeOH; Detector Wavelength: 220 nm; Sample Prep and Inj. Volume: 700 μL-1000 μL of 52 mg dissolved in 2 mL MeOH. Analytical Chromatographic Conditions: Instrument: Berger analytical SFC; Column: Chiral OD-H 250×4.6 mm ID, 5 μm; Flow rate: 2.0 mL/min; Mobile Phase: 75/25 CO₂/MeOH.

Example 365: Isomer 1: HPLC retention time=1.24 min (condition G); LC/MS $M^{+1}$=342; ¹H NMR (400 MHz, METHANOL-$d_4$) δ 7.89 (d, J=8.1 Hz, 1H), 7.35-7.16 (m, 2H), 3.60-3.46 (m, 2H), 3.17 (ddd, J=11.2, 7.0, 3.7 Hz, 1H), 3.10-2.92 (m, 2H), 2.57-2.43 (m, 1H), 2.39-2.18 (m, 2H), 2.17-2.04 (m, 1H), 2.04-1.75 (m, 6H), 1.63 (t, J=12.3 Hz, 1H), 1.58-1.34 (m, 4H), 1.01-0.89 (m, 3H).

Example 366: Isomer 2: HPLC retention time=1.24 min (condition G); LC/MS $M^{+1}$=342; ¹H NMR (400 MHz, METHANOL-$d_4$) δ 7.89 (d, J=8.1 Hz, 1H), 7.35-7.16 (m, 2H), 3.60-3.46 (m, 2H), 3.17 (ddd, J=11.2, 7.0, 3.7 Hz, 1H), 3.10-2.92 (m, 2H), 2.57-2.43 (m, 1H), 2.39-2.18 (m, 2H), 2.17-2.04 (m, 1H), 2.04-1.75 (m, 6H), 1.63 (t, J=12.3 Hz, 1H), 1.58-1.34 (m, 4H), 1.01-0.89 (m, 3H).

Example 367

((1R,3S)-1-amino-3-((R)-6-((E)-hex-1-en-1-yl)-5,6,7,8-tetrahydronaphthalen-2-yl) cyclopentyl)methanol

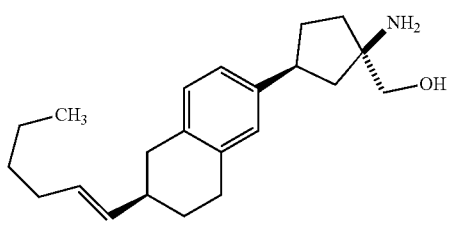

(367)

Preparation 367A: 5-(pentylsulfonyl)-1-phenyl-1H-tetrazole

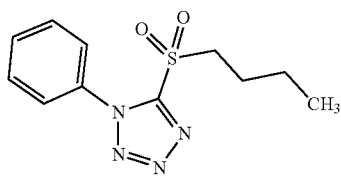

(367A)

DEAD (727 μl, 4.59 mmol) was added dropwise to a solution of pentan-1-ol (300 mg, 3.40 mmol), 1-phenyl-1H-tetrazole-5-thiol (740 mg, 4.15 mmol) and Ph₃P (1089 mg, 4.15 mmol) in THF (20 ml) at 0° C. The mixture was stirred at a temperature range of from 0° C. to room temperature for 16 h. The mixture was diluted with EtOAc (30 ml), which was washed with brine (2×20 ml), water (20 ml) and brine (20 ml), dried (Na₂SO₄) and concentrated under vacuo. The residue was purified with flash chromatography using Isco column (25 g, EtOAc/Hexane=0-50%, gradient time=25 min) to get 5-(pentylthio)-1-phenyl-1H-tetrazole (650 mg). LC/MS $M^{+1}$=249. Ammonium molybdate tetrahydrate (679 mg, 0.550 mmol) was added in 30% H₂O₂ (4064 μl, 39.8 mmol) at 0° C. and the resultant solution was added dropwise to a solution of 5-(pentylthio)-1-phenyl-1H-tetrazole (650 mg, 2.62 mmol) in EtOH (20 ml) at 0° C., the mixture was allowed to warm to room temperature and stirred at room temperature for 16 h. Next, 30 ml of brine was added and the mixture was extracted with EtOAc (80 ml), which was washed with brine and dried (Na₂SO₄), concentrated under vacuo to give the desired product which was used as is. 5-(pentylsulfonyl)-1-phenyl-1H-tetrazole (700 mg). LC/MS $M^{+1}$=281.

Preparation 367B: (5R,7S)-7-((R)-6-((E)-hex-1-en-1-yl)-5,6,7,8-tetrahydronaphthalen-2-yl)-3-oxa-1-azaspiro[4.4]nonan-2-one

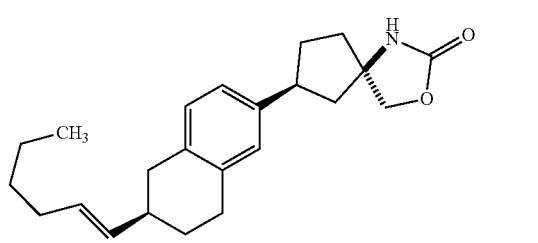

(367B)

KHMDS (418 μl, 0.209 mmol) was added dropwise to a solution of 5-(pentylsulfonyl)-1-phenyl-1H-tetrazole (25.8 mg, 0.092 mmol) and (R)-6-((5R,7S)-2-oxo-3-oxa-1-azaspiro[4.4]nonan-7-yl)-1,2,3,4-tetrahydronaphthalene-2-carbaldehyde (25 mg, 0.084 mmol) in THF (3 ml) at −78° C. and the resultant solution was stirred at the temperature for 1 h. H₂O (1 ml) was added and the mixture was warmed to room temperature and 30 ml of brine was added and the mixture was extracted with EtOAc (80 ml), which was washed with brine and dried (Na₂SO₄), concentrated under vacuo to afford (5R,7S)-7-((R)-6-((E)-hex-1-en-1-yl)-5,6,7,8-tetrahydronaphthalen-2-yl)-3-oxa-1-azaspiro[4.4]nonan-2-one (5 mg). LC/MS $M^{+1}$=354.

Example 367

(5R,7S)-7-((R)-6-((E)-hex-1-en-1-yl)-5,6,7,8-tetrahydronaphthalen-2-yl)-3-oxa-1-azaspiro[4.4]nonan-2-one (5 mg, 0.014 mmol) in 1,4-dioxane (2 ml) was mixed with water (0.5 ml) and lithium hydroxide hydrate (5.94 mg, 0.141 mmol) was added. The mixture was stirred at 100° C. for 16 h under N₂. After cooling, the mixture was filtered and washed with MeOH, the combined solvents were evaporated and the residue was purified with prep HPLC: column Phenomenex Luna C18 5 u 21.2×100 mm. Solvent A: 10% MeOH-90% H₂O-0.1% TFA; Solvent B: 90% MeOH-10% H₂O-0.1% TFA. Gradient time=15 min. Start B=0%, Final B 100%. Stop time 20 min. The collected fraction was basified with saturated NaHCO₃, concentrated under vacuo and the aqueous layer was extracted with DCM (3×20 ml), which was dried (Na₂SO₄) and concentrated under vacuo. The residue was freeze dried to afford ((1R,3S)-1-amino-3-((R)-6-((E)-hex-1-en-1-yl)-5,6,7,8-tetrahydronaphthalen-2-yl)cyclopentyl)methanol (3 mg). LC/MS $M^{+1}$=328. HPLC Rt=8.52 (condition L). ¹H NMR (400 MHz, METHANOL-$d_4$) δ 7.05-6.88 (m, 3H), 5.59-5.30 (m, 2H), 3.60-3.45 (m, 2H), 3.10-2.98 (m, 1H), 2.89-2.74 (m, 3H), 2.64-2.18 (m, 3H), 2.11-1.74 (m, 8H), 1.69-1.46 (m, 3H), 1.02-0.85 (m, 5H).

The examples in Table 24 were prepared according to the general procedure of Example 367.

TABLE 24

| Ex. No. | Structure | MW | HPLC ret. time (min.) | HPLC method | MS (M$^{+1}$) |
|---|---|---|---|---|---|
| 368 | 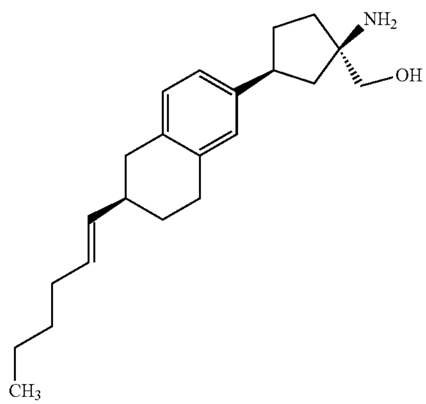 [SMILES: CCCC/C=C/[C@@H]1CCc2cc([C@H]3CC[C@](N)(CO)C3)ccc2C1] | 327.5 | 8.52 | L | 328 |
| 369 | 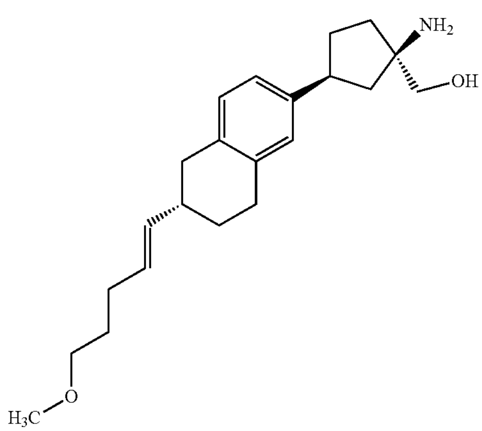 [SMILES: COCCC/C=C/[C@H]1CCc2cc([C@H]3CC[C@](N)(CO)C3)ccc2C1] | 343.5 | 6.87 | L | 344 |
| 370 | 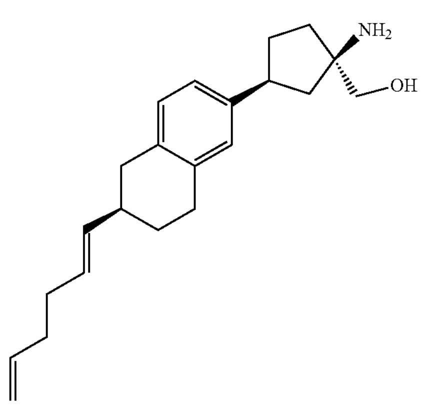 [SMILES: C=CCC/C=C/[C@@H]1CCc2cc([C@H]3CC[C@](N)(CO)C3)ccc2C1] | 325.5 | 7.63 | L | 326 |

TABLE 24-continued

| Ex. No. | Structure | MW | HPLC ret. time (min.) | HPLC method | MS (M+1) |
|---|---|---|---|---|---|
| 371 | 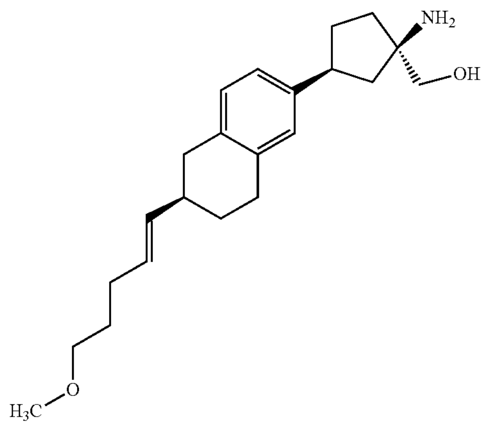 [SMILES: COCCC/C=C/[C@@H]1CCc2cc([C@H]3CC[C@](N)(CO)C3)ccc2C1] | 343.5 | 6.76 | L | 344 |
| 372 | 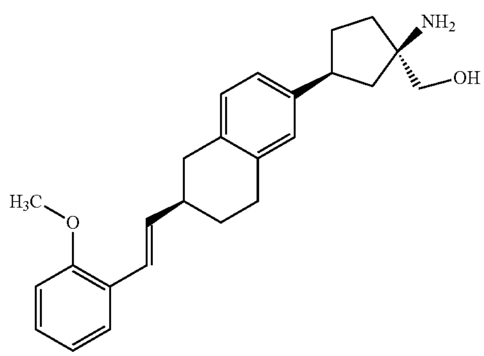 [SMILES: COc1ccccc1/C=C/[C@@H]1CCc2cc([C@H]3CC[C@](N)(CO)C3)ccc2C1] | 377.5 | 7.63 | L | 378 |
| 373 | 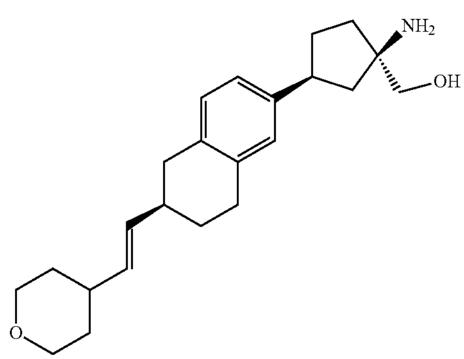 [SMILES: N[C@]1(CO)CC[C@H](c2ccc3c(c2)CC[C@@H](/C=C/C2CCOCC2)C3)C1] | 355.5 | 6.52 | L | 356 |
| 374 | 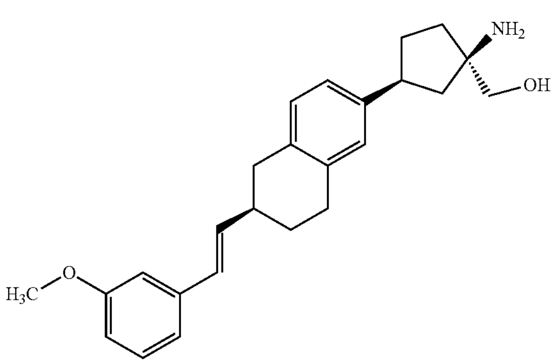 [SMILES: COc1cccc(/C=C/[C@@H]2CCc3cc([C@H]4CC[C@](N)(CO)C4)ccc3C2)c1] | 377.5 | 7.54 | L | 378 |

TABLE 24-continued

| Ex. No. | Structure | MW | HPLC ret. time (min.) | HPLC method | MS (M+1) |
|---|---|---|---|---|---|
| 375 | 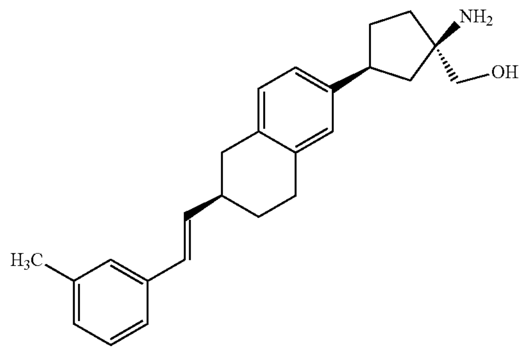 [SMILES: Cc1cccc(/C=C/[C@@H]2CCc3cc([C@H]4CC[C@](N)(CO)C4)ccc3C2)c1] | 361.5 | 8.13 | L | 362 |
| 376 | 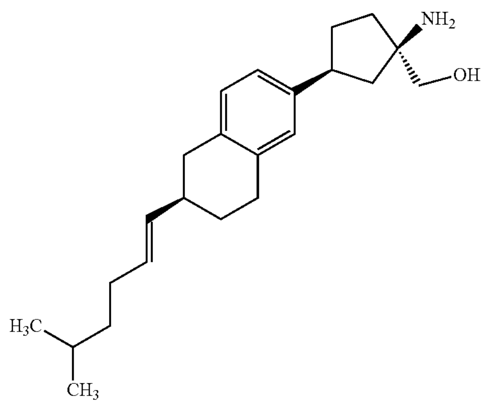 [SMILES: CC(C)CC/C=C/[C@@H]1CCc2cc([C@H]3CC[C@](N)(CO)C3)ccc2C1] | 341.5 | 9.05 | L | 342 |

The following olefins were made according to the method listed in the table.

TABLE 25

| Ex. No. | Structure | MW | HPLC ret. time (min.) | HPLC method | MS (M+1) | Method |
|---|---|---|---|---|---|---|
| 377 | 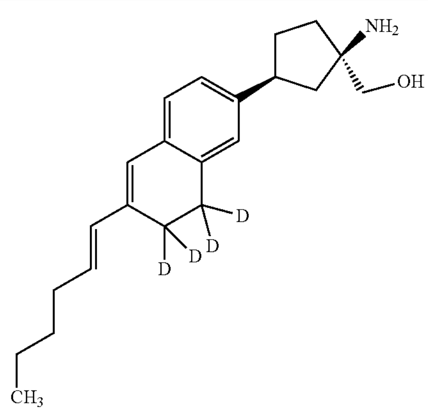 [SMILES: [2H]C1([2H])C(/C=C/CCCC)=Cc2ccc([C@H]3CC[C@](N)(CO)C3)cc2C1([2H])[2H]] | 329.5 | 8.23 | L | 330 | See method for Example 226 |

TABLE 25-continued

| Ex. No. | Structure | MW | HPLC ret. time (min.) | HPLC method | MS (M+1) | Method |
|---|---|---|---|---|---|---|
| 378 | 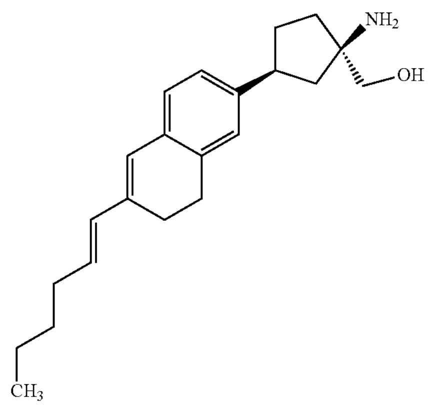 [SMILES: CCCC/C=C/C1=Cc2ccc([C@H]3CC[C@](N)(CO)C3)cc2CC1] | 325.5 | 8.26 | L | 326 | See method for Example 226 |
| 379 | 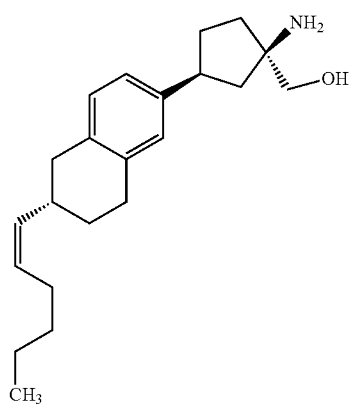 [SMILES: CCCC/C=C\[C@H]1CCc2cc([C@H]3CC[C@](N)(CO)C3)ccc2C1] | 327.5 | 8.37 | L | 328 | See method for alternative Preparation-2 of Example 679 |
| 380 | 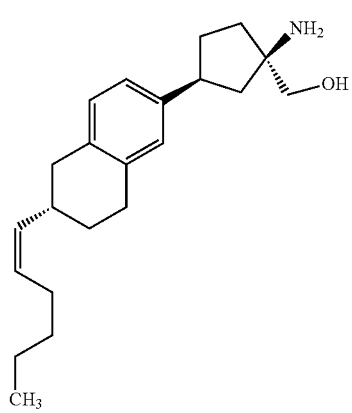 [SMILES: CCCC/C=C\[C@H]1CCc2cc([C@H]3CC[C@](N)(CO)C3)ccc2C1] | 327.5 | 8.75 | L | 328 | See method for alternative Preparation-2 of Example 679 |

Example 381

((1R,3S)-1-amino-3-((R)-6-((E)-hex-3-en-1-yl)-5,6,7,8-tetrahydronaphthalen-2-yl) cyclopentyl)methanol (381)

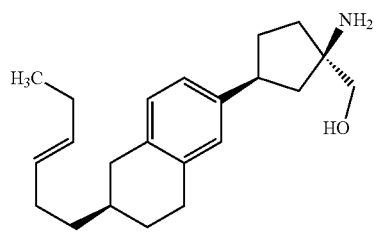

Preparation 381A: (5R,7S)-7-((R)-6-(hex-3-en-1-yl)-5,6,7,8-tetrahydronaphthalen-2-yl)-3-oxa-1-azaspiro[4.4]nonan-2-one

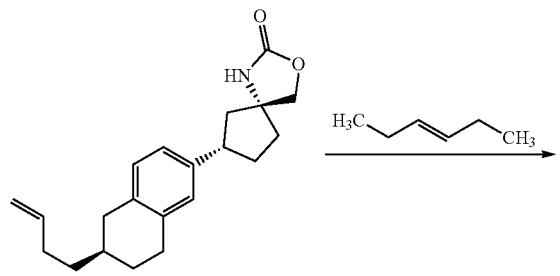

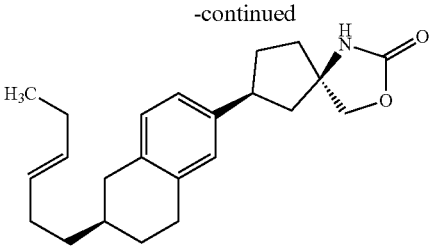

A mixture of trans-3-hexene (5.8 mL, 46.7 mmol), (5R,7S)-7-((R)-6-(but-3-en-1-yl)-5,6,7,8-tetrahydronaphthalen-2-yl)-3-oxa-1-azaspiro[4.4]nonan-2-one (1.5 g, 4.61 mmol) and dichloromethane (50 mL) was bubbled with nitrogen for 3 min at −78° C. before Grubbs catalyst 2nd generation (0.25 g, 0.294 mmol) was added. The bubbling was continued for 2 min. The mixture was then stirred under nitrogen at 40° C. for 3.5 h. The mixture was concentrated. Flash chromatography purification (24 g silica gel column, gradient elution from 0 to 40% of ethyl acetate in DCM) afforded (5R,7S)-7-((R)-6-(hex-3-en-1-yl)-5,6,7,8-tetrahydronaphthalen-2-yl)-3-oxa-1-azaspiro[4.4]nonan-2-one (1.2 g, 3.39 mmol) as a solid. SFC separation (20% MeOH in $CO_2$, ADH column; 40° C.; 140 bar BPR) gave PK1: (5R,7S)-7-((R)-6-((E)-hex-3-en-1-yl)-5,6,7,8-tetrahydronaphthalen-2-yl)-3-oxa-1-azaspiro[4.4]nonan-2-one (0.8 g, 2.263 mmol) (HPLC retention time=4.11 min (condition C); LC/MS $M^{+1}$=354); and PK2: (5R,7S)-7-((R)-6-((Z)-hex-3-en-1-yl)-5,6,7,8-tetrahydronaphthalen-2-yl)-3-oxa-1-azaspiro[4.4]nonan-2-one (0.1 g, 0.283 mmol) (HPLC retention time=4.08 min (condition C); LC/MS $M^{+1}$=354) as solids.

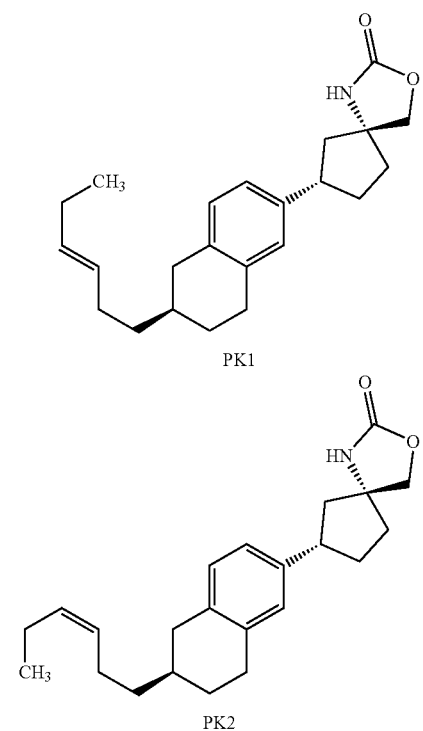

Example 381

A mixture of (5R,7S)-7-((R)-6-((E)-hex-3-en-1-yl)-5,6,7,8-tetrahydronaphthalen-2-yl)-3-oxa-1-azaspiro[4.4]nonan-2-one (0.41 g, 1.160 mmol), dioxane (5 mL), NaOH (0.928 g, 23.20 mmol), and water (7 mL) was stirred at 90° C. under nitrogen for 1.5 days. The mixture was extracted with ethyl acetate (4×4 mL). The combined ethyl acetate extracts were dried ($Na_2SO_4$) and concentrated. Purification using reverse phase HPLC (Phenomenex Luna 5μ 30×100 mm (Axia); gradient over 6 min from 40 to 100% of solvent B and holding @100% of solvent B for 6 min; solvent A: 10% MeOH: 90% $H_2O$: 0.1% TFA; solvent B: 90% MeOH, 10% $H_2O$, 0.1% TFA), concentration, basification with 2N aqueous NaOH, and extraction with ethyl acetate gave ((1R,3S)-1-amino-3-((R)-6-((E)-hex-3-en-1-yl)-5,6,7,8-tetrahydronaphthalen-2-yl)cyclopentyl)methanol (0.34 g, 1.027 mmol) as a solid. HPLC retention time=3.65 min (condition C); LC/MS $M^{+1}$=328. $^1$H NMR (400 MHz, CHLOROFORM-d) δ 7.05-6.93 (m, 3H), 5.56-5.36 (m, 2H), 3.53-3.40 (m, 2H), 3.09-2.96 (m, 1H), 2.88-2.74 (m, 3H), 2.38 (dd, J=16.4, 10.5 Hz, 1H), 2.28 (dd, J=13.3, 8.0 Hz, 1H), 2.15-1.85 (m, 8H), 1.83-1.62 (m, 2H), 1.52 (dd, J=13.2, 11.0 Hz, 1H), 1.46-1.32 (m, 3H), 0.97 (t, J=7.5 Hz, 3H).

The examples in Table 26 were prepared according to the general procedure of Example 381.

TABLE 26

| Ex. No. | Structure | MW | HPLC ret. time (min.) | HPLC method | MS (M+1) |
|---|---|---|---|---|---|
| 382 | 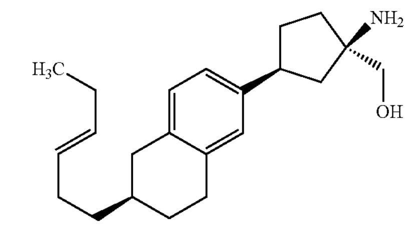 [SMILES: CC/C=C/CC[C@@H]1CCc2cc([C@H]3CC[C@](N)(CO)C3)ccc2C1] | 327.5 | 3.51 | C | 328 |
| 383 | 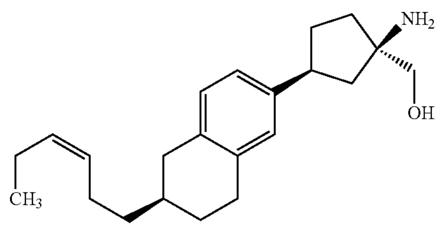 [SMILES: CC/C=C\CC[C@@H]1CCc2cc([C@H]3CC[C@](N)(CO)C3)ccc2C1] | 327.5 | 3.51 | C | 328 |
| 384 | 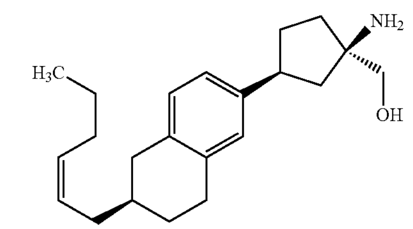 [SMILES: CCC/C=C\C[C@@H]1CCc2cc([C@H]3CC[C@](N)(CO)C3)ccc2C1] | 327.5 | 8.42 | L | 328 |
| 385 | 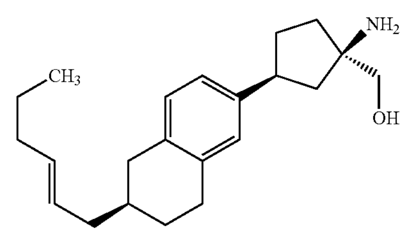 [SMILES: CCC/C=C/C[C@@H]1CCc2cc([C@H]3CC[C@](N)(CO)C3)ccc2C1] | 327.5 | 8.52 | L | 328 |
| 386 | 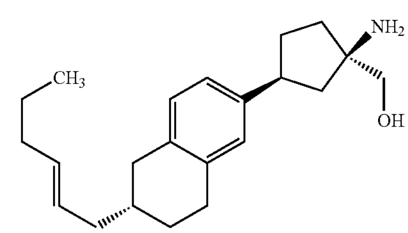 [SMILES: CCC/C=C/C[C@H]1CCc2cc([C@H]3CC[C@](N)(CO)C3)ccc2C1] | 327.5 | 9.51 | L | 328 |
| 387 | 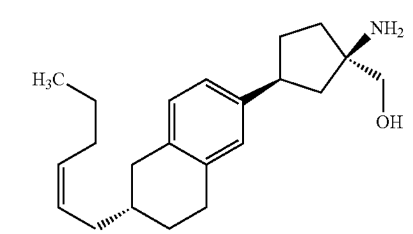 [SMILES: CCC/C=C\C[C@H]1CCc2cc([C@H]3CC[C@](N)(CO)C3)ccc2C1] | 327.5 | 3.61 | C | 328 |

TABLE 26-continued

| Ex. No. | Structure | MW | HPLC ret. time (min.) | HPLC method | MS (M$^{+1}$) |
|---|---|---|---|---|---|
| 388 | 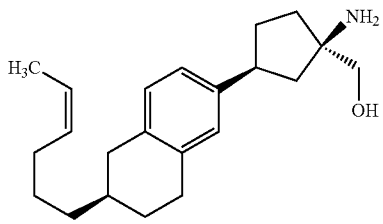 [SMILES: C/C=C\CCC[C@@H]1CCc2cc([C@H]3CC[C@](N)(CO)C3)ccc2C1] | 327.5 | 3.61 | C | 328 |
| 389 | 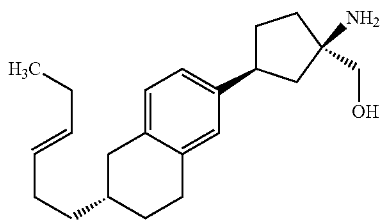 [SMILES: CC/C=C/CC[C@H]1CCc2cc([C@H]3CC[C@](N)(CO)C3)ccc2C1] | 327.5 | 3.64 | C | 328 |
| 390 | 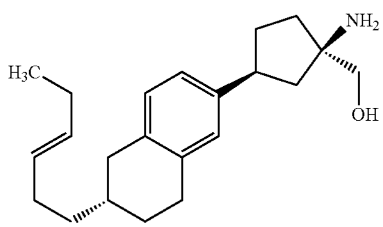 [SMILES: CC/C=C/CC[C@H]1CCc2cc([C@H]3CC[C@](N)(CO)C3)ccc2C1] | 327.5 | 3.54 | C | 328 |
| 391 | 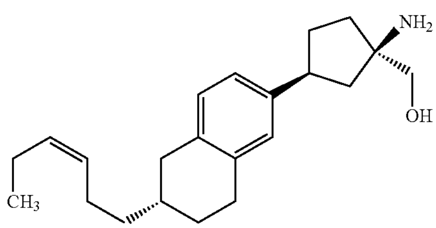 [SMILES: CC/C=C\CC[C@H]1CCc2cc([C@H]3CC[C@](N)(CO)C3)ccc2C1] | 327.5 | 10.11 | L | 328 |
| 392 | 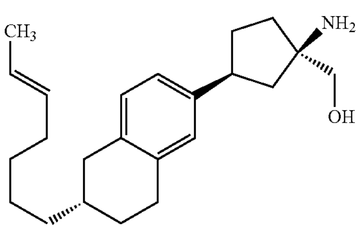 [SMILES: C/C=C/CCCC[C@H]1CCc2cc([C@H]3CC[C@](N)(CO)C3)ccc2C1] | 341.5 | 3.76 | C | 342 |
| 393 | 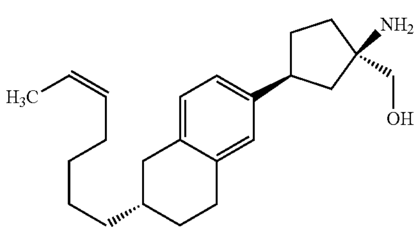 [SMILES: C/C=C\CCCC[C@H]1CCc2cc([C@H]3CC[C@](N)(CO)C3)ccc2C1] | 341.5 | 3.73 | C | 342 |

TABLE 26-continued
| Ex. No. | Structure | MW | HPLC ret. time (min.) | HPLC method | MS (M+1) |
|---|---|---|---|---|---|
| 394 | 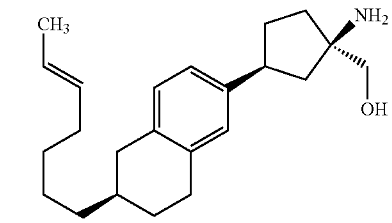 [SMILES: C/C=C/CCCC[C@@H]1CCc2cc([C@H]3CC[C@](N)(CO)C3)ccc2C1] | 341.5 | 3.71 | C | 342 |
| 395 | 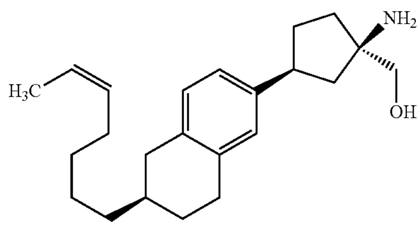 [SMILES: C/C=C\CCCC[C@@H]1CCc2cc([C@H]3CC[C@](N)(CO)C3)ccc2C1] | 341.5 | 3.66 | C | 342 |
| 396 | 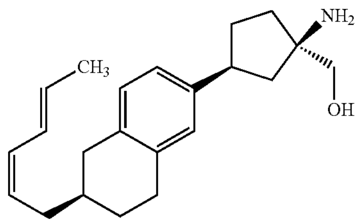 [SMILES: C/C=C/C=C\C[C@@H]1CCc2cc([C@H]3CC[C@](N)(CO)C3)ccc2C1] | 325.5 | 7.81 | L | 326 |
| 397 | 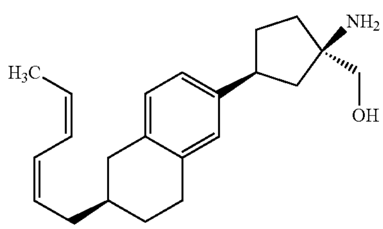 [SMILES: C/C=C\C=C/C[C@@H]1CCc2cc([C@H]3CC[C@](N)(CO)C3)ccc2C1] | 325.5 | 7.81 | L | 326 |
Examples 398 to 400
(E)-6-(3-amino-3-(hydroxymethyl)cyclopentyl)-3,4-dihydronaphthalen-1(2H)-one O-phenethyl oxime
Preparation 398A: Ethyl 1-((diphenylmethylene)amino)-4-(5-oxo-5,6,7,8-tetrahydronaphthalen-2-yl)cyclopent-2-en-ecarboxylate
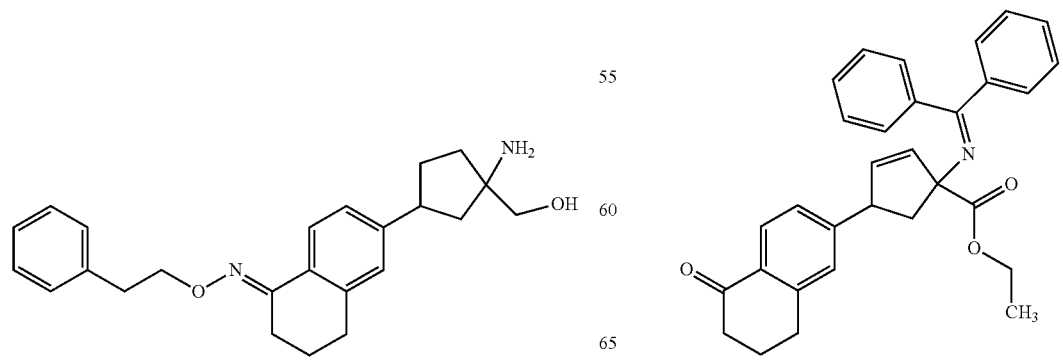
(398A)

A mixture was prepared by combining 6-bromo-3,4-dihydronaphthalen-1(2H)-one (200 mg, 0.889 mmol), ethyl 1-((diphenylmethylene)amino)cyclopent-3-enecarboxylate (426 mg, 1.333 mmol), Et$_3$N (0.248 mL, 1.777 mmol) and 1,1'-bis(di-tert-butylphosphino) ferrocene palladium dichloride (29.0 mg, 0.044 mmol) into DL-tocopherol methoxypolyethylene glycol succinate solution (2 wt % in H$_2$O) under nitrogen in a reaction vial. The vial was sealed and heated to 50° C. for 24 hours. The resulting mixture was poured into 200 ml ethyl acetate. The solution was washed with water. The organic layer was then concentrated and the crude materials were purified on a 24 g silica column (0-30% gradient ethyl acetate in hexane) to afford 260 mg of titled compound. LC-MS Ret. Time: 1.69. LC-MS M$^{+1}$=464.2. LC-MS Conditions: Column: Luna C18 4.6×30 mm 3 u A: 10:90 H$_2$O:ACN NH$_4$OAc/B: 10:90 H$_2$O:ACN NH$_4$OAc; 0%-95% B in 2 min; 4 mL/min flow. Product detected at 220 nm wavelength.

Preparation 398B: Ethyl 1-amino-3-(5-oxo-5,6,7,8-tetrahydronaphthalen-2-yl) cyclopentanecarboxylate

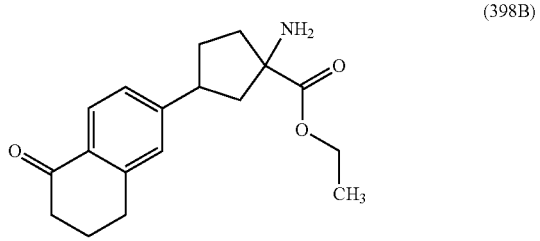 [SMILES: CCOC(=O)C1(N)CCC(c2ccc3c(c2)CCCC3=O)C1]

(398B)

To a solution of ethyl 1-((diphenylmethylene)amino)-4-(5-oxo-5,6,7,8-tetrahydronaphthalen-2-yl)cyclopent-2-enecarboxylate (290 mg, 0.626 mmol) in EtOH (3 mL) was added 1.5 ml of 4N HCl. The reaction mixture was allowed to stir at room temperature for 2 hours. LC-MS showed completed conversion. The mixture was poured into 50 ml of saturated NaHCO$_3$ and extracted with ethyl acetate twice. The organic layer were then dried over Na$_2$SO$_4$ and concentrated to provide 270 mg of crude materials as yellow oil. The above obtained material was dissolved into ethyl acetate. To the solution was added Pd/C (107 mg, 0.050 mmol) under N$_2$. The mixture was allowed to stir under H$_2$ for 1 hour. LC-MS showed the reaction was completed. The Pd catalyst was removed by filtration. Solvent was removed to provide 260 mg of material. The material was purified on a 40 g silica column (0%-30% gradient ethyl acetate in hexane in 10 mins) to afford 170 mg of titled compound as colorless oil. HPLC retention time=2.19 min (Condition K); LC/MS M$^{+1}$=302.

Preparation 398C: (E)-ethyl 1-amino-3-(5-(phenethoxyimino)-5,6,7,8-tetrahydronaphthalen-2-yl) cyclopentanecarboxylate

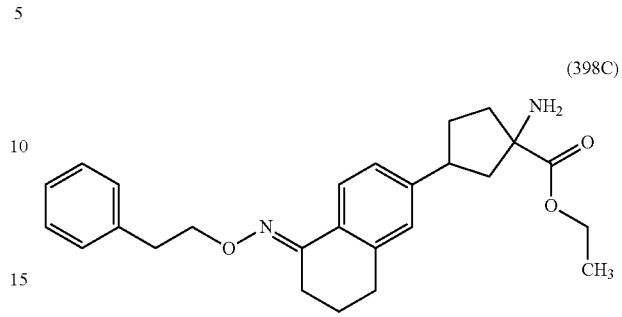

(398C)

Ethyl 1-amino-3-(5-oxo-5,6,7,8-tetrahydronaphthalen-2-yl) cyclopentanecarboxylate (160 mg, 0.531 mmol) was dissolved into ethanol (4 mL). Pyridine (0.129 mL, 1.593 mmol) was added followed by the addition of O-phenethylhydroxylamine (124 mg, 0.903 mmol). The mixture was allowed to stir at room temperature for 1 hour. LC-MS showed no reaction. The temperature was raised to 74° C. and the mixture was allowed to stir for 9 hours. LC-MS showed <10% conversion. The temperature was raised to 85° C. and allowed to stir for 18 hours. LC-MS showed 50% conversion. The heating was continued at 85° C. for 40 more hours. LC-MS showed >90% conversion. The reaction mixture was cooled down to room temperature and poured into 50 ml saturated NaHCO$_3$. It was extracted with ethyl acetate twice. The organic layers were then dried over Na$_2$SO$_4$ and concentrated to provide 290 mg of material having a HPLC purity of 75%. HPLC retention time=0.97 min (Condition G); LC/MS M$^{+1}$=421.

Examples 398 to 400

(E)-ethyl 1-amino-3-(5-(phenethoxyimino)-5,6,7,8-tetrahydronaphthalen-2-yl)cyclopentanecarboxylate (290 mg, 0.690 mmol) was dissolved into MeOH (6 mL). The mixture was cooled to 0° C. and NaBH$_4$ (117 mg, 3.10 mmol) was added in portions. The mixture was allowed to stir for 3 hours. LC-MS showed partial conversion. The reaction mixture was allowed to stir at room temperature for 18 more hours. LC-MS showed completed conversion. The reaction was quenched with 3 N HCl (aq.). The mixture was allowed to stir at room temperature for 30 mins. The crude material was purified on reverse phase HPLC to provide 155 mg of product as white solid (diastereoisomeric mixture). HPLC retention time=0.94 min (Condition G); LC/MS M$^{+1}$=379.

Chiral SFC Separation of isomers: Approximately 100 mg sample was resolved. The fractions ("Peak-1", "Peak-2", "Peak-3", and "Peak-4") were collected in MeOH w/0.1% DEA. The isomeric purity of each fraction was estimated to be greater than 95% based on the prep-SFC chromatograms. Experimental Details: Preparative Chromatographic Conditions: Instrument: Berger SFC MGII; Column: Phenomenex LUX Cellulose 2 25×3 cm ID, 5 μm; Flow rate: 85.0 mL/min; Mobile Phase: 65/35 CO$_2$/MeOH w/0.1% DEA; Detector Wavelength: 280 nm; Sample Prep and Inj. Volume: 500 μL of 100 mg dissolved in 4.5 mL MeOH.

Analytical Chromatographic Conditions: Instrument: Berger analytical SFC; Column: Phenomenex LUX Cellulose 2 250×4.6 mm ID, 5 μm; Flow rate: 2.0 mL/min; Mobile Phase: 65/35 CO2/MeOH w/0.1% DEA; Three fractions were isolated in a 1:10:10 ratio having one minor peak and two major peaks. Example 398: minor fraction, analytical SFC Retention Time: 12.58 min. Example 399: major fraction 1, analytical SFC Retention Time: 13.87 min; HPLC retention time=0.88 mins (Condition G) LC/MS $M^{+1}$=379. $^1$H NMR (400 MHz, METHANOL-$d_4$) δ 7.84 (d, J=8.1 Hz, 1H), 7.31-7.22 (m, 4H), 7.21-7.15 (m, 1H), 7.15-7.06 (m, 2H), 4.34 (t, J=6.8 Hz, 2H), 3.54-3.42 (m, 2H), 3.12-3.04 (m, 1H), 3.01 (t, J=6.8 Hz, 2H), 2.76-2.69 (m, 2H), 2.66 (t, J=6.6 Hz, 2H), 2.23 (dd, J=13.2, 7.7 Hz, 1H), 2.07-1.88 (m, 2H), 1.85-1.66 (m, 4H), 1.60-1.51 (m, 1H). Example 400: major Fraction 2, analytical SFC Retention Time: 15.56 min; HPLC retention time=0.88 mins (Condition G) LC/MS $M+^1$=379. $^1$H NMR (400 MHz, METHANOL-$d_4$) δ 7.83 (d, J=8.1 Hz, 1H), 7.30-7.22 (m, 4H), 7.20-7.15 (m, 1H), 7.13-7.03 (m, 2H), 4.33 (t, J=6.9 Hz, 2H), 3.53-3.42 (m, 2H), 3.10-3.03 (m, 1H), 3.02-2.97 (m, 2H), 2.71 (t, J=6.1 Hz, 2H), 2.65 (t, J=6.7 Hz, 2H), 2.23 (dd, J=13.2, 7.5 Hz, 1H), 2.05-1.87 (m, 2H), 1.85-1.66 (m, 4H), 1.55 (t, J=12.3 Hz, 1H).

Example 401

(E)-1-((R)-6-((1 S,3R)-3-amino-3-(hydroxymethyl)cyclopentyl)-1,2,3,4-tetrahydronaphthalen-2-yl)ethanone O-(2-methoxybenzyl) oxime (401)

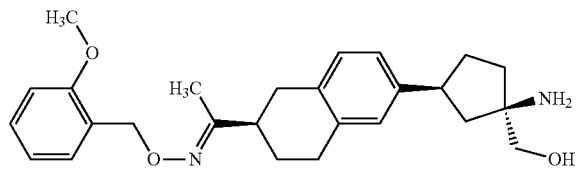

Preparation 401A: 1-((R)-6-((1S,3R)-3-amino-3-(hydroxymethyl)cyclopentyl)-1,2,3,4-tetrahydronaphthalen-2-yl)ethanone (401A)

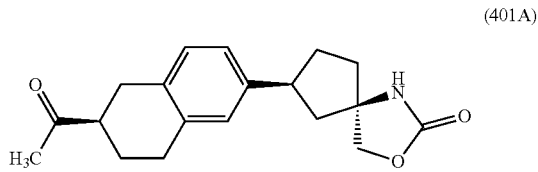 [SMILES: CC(=O)[C@@H]1CCc2cc([C@H]3CC[C@]4(COC(=O)N4)C3)ccc2C1]

A solution of (5R,7S)-7-((R)-6-acetyl-5,6,7,8-tetrahydronaphthalen-2-yl)-3-oxa-1-azaspiro[4.4]nonan-2-one (200 mg, 0.638 mmol) in DCM (5 ml) and lithium hydroxide hydrate (402 mg, 9.57 mmol) was mixed with THF (4 ml) and water (1 ml) and stirred at 100° C. for overnight. The mixture was purified with prep HPLC: Phenomenex Luna C 18 5 u (21.2×150 mm), Solvent A: 10% MeOH-90% $H_2O$-0.1% TFA; Solvent B: 90% MeOH-10% $H_2O$-0.1% TFA, Start B %=0, Final % B=100. Gradient time 15 min, stop time 22 min. (140 mg), LC/MS $M^{+1}$=288

Example 401

To a mixture of 1-((S)-6-((1S,3R)-3-amino-3-(hydroxymethyl)cyclopentyl)-1,2,3,4-tetrahydronaphthalen-2-yl)ethanone (15 mg, 0.052 mmol) and O-(2-methoxybenzyl)hydroxylamine (40.0 mg, 0.261 mmol) in EtOH (1.5 ml) was added 2 drops of 1N HCl. The mixture was stirred at room temperature for 2 h. LC-MS indicated the completion of conversion. The mixture was purified with prep HPLC: Phenomenex Luna C 18 5 u (21.2×150 mm), Solvent A: 10% MeOH-90% $H_2O$-0.1% TFA; Solvent B: 90% MeOH-10% $H_2O$-0.1% TFA, Start B %=0, Final % B=100. Gradient time 15 min, stop time 25 min. (15 mg as TFA salt). LC/MS $M^{+1}$=423. HPLC: Rt=7.50 min (condition L). $^1$H-NMR (400 MHz, METHANOL-$d_4$) δ 7.36-7.19 (m, 2H), 7.10-6.86 (m, 5H), 5.18-5.05 (m, 2H), 3.90-3.79 (m, 3H), 3.72-3.56 (m, 2H), 3.20-3.04 (m, 1H), 2.93-2.75 (m, 4H), 2.64-2.54 (m, 1H), 2.43 (dd, J=13.9, 6.6 Hz, 1H), 2.21-1.83 (m, 8H), 1.80-1.63 (m, 2H).

The examples in Table 27 were prepared according to the general procedure of Example 401

TABLE 27

| Ex. No. | Structure | MW | HPLC ret. time (min.) | HPLC method | MS ($M^{+1}$) |
|---|---|---|---|---|---|
| 402 | 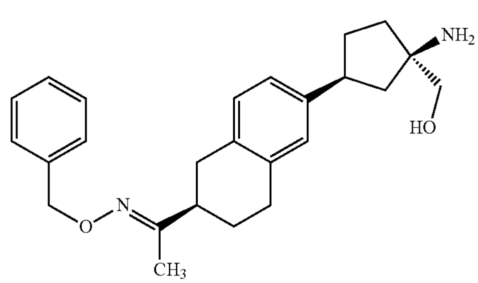 [SMILES: C/C(=N\OCc1ccccc1)[C@@H]1CCc2cc([C@H]3CC[C@](N)(CO)C3)ccc2C1] | 392.5 | 7.42 | L | 393 |

TABLE 27-continued

| Ex. No. | Structure | MW | HPLC ret. time (min.) | HPLC method | MS (M$^{+1}$) |
|---|---|---|---|---|---|
| 403 | 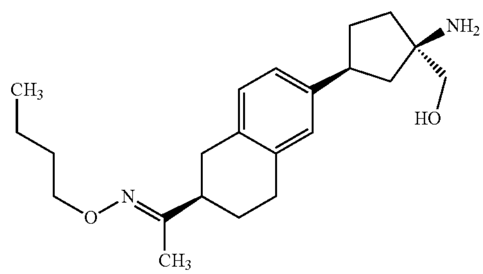 [SMILES: CCCCO/N=C(\C)[C@@H]1CCc2cc([C@H]3CC[C@](N)(CO)C3)ccc2C1] | 358.5 | 7.53 | L | 359 |
| 404 | 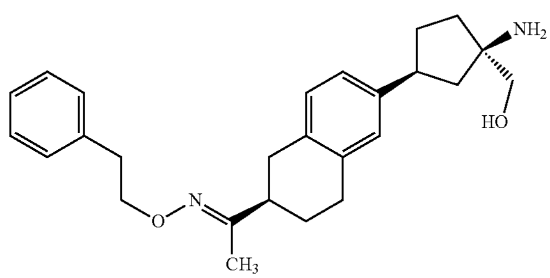 [SMILES: C/C(=N\OCCc1ccccc1)[C@@H]1CCc2cc([C@H]3CC[C@](N)(CO)C3)ccc2C1] | 406.6 | 7.72 | L | 407 |
| 405 | 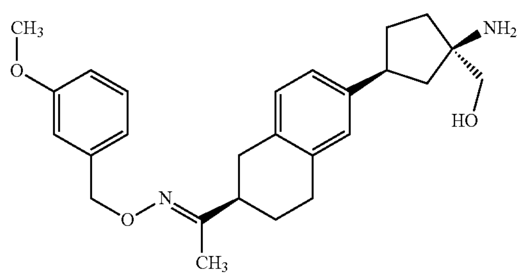 [SMILES: COc1cccc(CO/N=C(\C)[C@@H]2CCc3cc([C@H]4CC[C@](N)(CO)C4)ccc3C2)c1] | 422.6 | 7.39 | L | 423 |
| 406 | 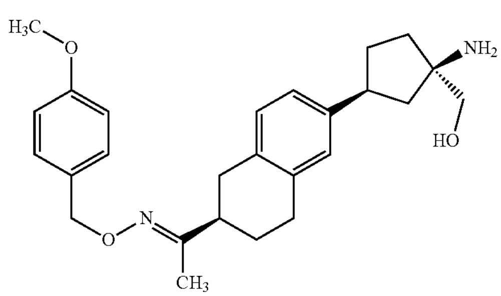 [SMILES: COc1ccc(CO/N=C(\C)[C@@H]2CCc3cc([C@H]4CC[C@](N)(CO)C4)ccc3C2)cc1] | 422.6 | 7.31 | L | 423 |
| 407 | 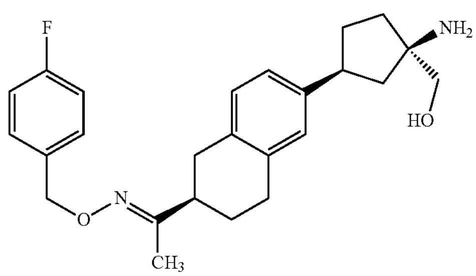 [SMILES: C/C(=N\OCc1ccc(F)cc1)[C@@H]1CCc2cc([C@H]3CC[C@](N)(CO)C3)ccc2C1] | 410.5 | 7.54 | L | 411 |

TABLE 27-continued

| Ex. No. | Structure | MW | HPLC ret. time (min.) | HPLC method | MS (M+1) |
|---|---|---|---|---|---|
| 408 | 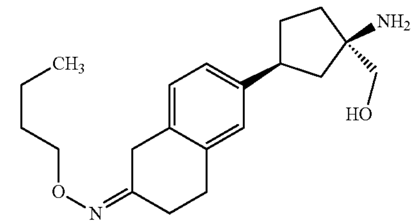 [SMILES: CCCCO/N=C1/CCc2cc([C@H]3CC[C@](N)(CO)C3)ccc2C1] | 330.4 | 7.51 | L | 331 |
| 409 | 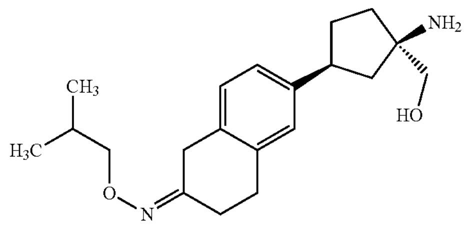 [SMILES: CC(C)CO/N=C1/CCc2cc([C@H]3CC[C@](N)(CO)C3)ccc2C1] | 330.5 | 7.49 | L | 331 |
| 410 | 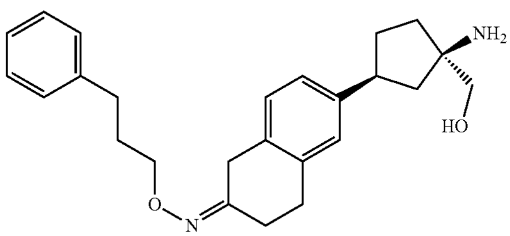 [SMILES: N[C@]1(CO)CC[C@H](c2ccc3c(c2)CC/C(=N/OCCCc2ccccc2)C3)C1] | 392.5 | 8.76 | L | 393 |
| 411 | 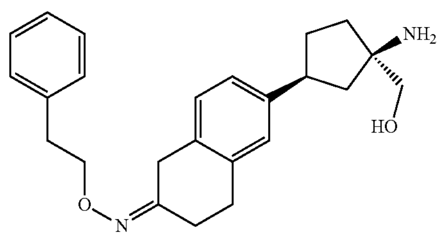 [SMILES: N[C@]1(CO)CC[C@H](c2ccc3c(c2)CC/C(=N/OCCc2ccccc2)C3)C1] | 378.5 | 8.06 | L | 379 |

PHOSPHORYLATED EXAMPLES

Example 412

((1R,3S)-1-amino-3-((R)-2-((pentyloxy)methyl)-2,3-dihydrobenzo[b][1,4]dioxin-6-yl)cyclopentyl)methyl dihydrogen phosphate

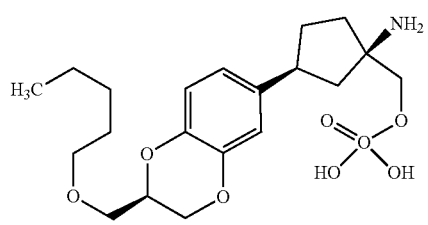

(412)

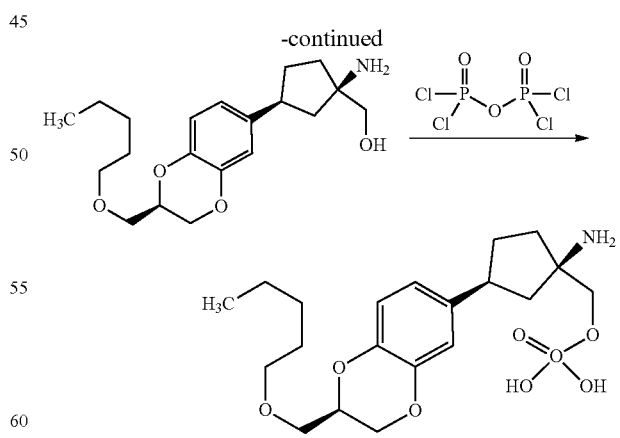

To a stirred solution of ((1R,3S)-1-amino-3-((R)-2-((pentyloxy)methyl)-2,3-dihydrobenzo[b][1,4]dioxin-6-yl)cyclopentyl)methanol (2.6 mg, 7.44 µmol) in anhydrous acetonitrile (1 mL) was added pyrophosphoryl chloride (0.011 mL, 0.082 mmol) at 0° C. under nitrogen. The clear solution obtained was stirred at the same temperature for 5 min and at room temperature for 2 hr. Additional pyrophosphoryl chloride (0.040 mL) was added and the mixture was stirred at room temperature for 3 hr before water (0.3 mL) was added. The mixture was stirred at room temperature overnight. Purification using reverse phase HPLC (Phenomenex AXIA 5 u 21.2×100 mm; gradient over 8 min from 20 to 100% of solvent B; solvent A: 0.1% TFA in water; solvent B: 0.1% TFA in acetonitrile), concentration, and lyophilization gave ((1R,3S)-1-amino-3-((R)-2-((pentyloxy)methyl)-2,3-dihydrobenzo[b][1,4]dioxin-6-yl)cyclopentyl)methyl dihydrogen phosphate (1.5 mg, 3.32 μmol) as a white solid. LC/MS $M^{+1}$=430. HPLC retention time=6.81 min (condition L) $^1$H NMR (500 MHz, METHANOL-$d_4$) δ 6.84-6.69 (m, 3H), 4.32-4.21 (m, 2H), 4.06-3.97 (m, 1H), 3.96-3.90 (m, 1H), 3.89-3.83 (m, 1H), 3.69-3.65 (m, 1H), 3.64-3.59 (m, 1H), 3.51 (t, J=6.5 Hz, 2H), 3.15-3.06 (m, 1H), 2.47 (dd, J=13.0, 6.7 Hz, 1H), 2.14-2.06 (m, 1H), 2.04-1.83 (m, 3H), 1.67 (t, J=12.8 Hz, 1H), 1.62-1.55 (m, 2H), 1.37-1.32 (m, 4H), 0.95-0.88 (m, 3H).

The phosphate ester examples ($R_1$ is —OP(O)(OH)$_2$) in Table 28 were prepared according to the general procedure for Example 412.

TABLE 28

| Example No. | Phosphate Ester of Example No. | MW | HPLC Retention Time (min.) | HPLC condition | MS ($M^{+1}$) |
|---|---|---|---|---|---|
| 413 | 2 | 429.5 | 6.75 | L | 430 |
| 414 | 5 | 415.4 | 2.55 | C | 416 |
| 415 | 6 | 415.4 | 2.55 | C | 416 |
| 416 | 8 | 424.5 | 6.09 | L | 425 |
| 417 | 10 | 424.5 | 6.08 | L | 425 |
| 418 | 14 | 411.5 | 7.09 | L | 412 |
| 419 | 15 | 411.5 | 3.53 | C | 412 |
| 420 | 16 | 411.5 | 3.53 | C | 412 |
| 421 | 19 | 411.5 | 3.37 | C | 412 |
| 422 | 20 | 411.5 | 3.50 | C | 412 |
| 423 | 21 | 411.5 | 3.56 | C | 412 |
| 424 | 22 | 411.5 | 3.56 | C | 412 |
| 425 | 23 | 411.5 | 3.66 | C | 412 |
| 426 | 24 | 411.5 | 3.38 | C | 412 |
| 427 | 25 | 411.5 | 3.38 | C | 412 |
| 428 | 26 | 425.5 | 9.97 | L | 426 |
| 429 | 27 | 425.5 | 9.97 | L | 426 |
| 430 | 28 | 411.5 | 7.08 | L | 412 |
| 431 | 29 | 411.5 | 7.09 | L | 412 |
| 432 | 31 | 439.5 | 0.94 | G | 440 |
| 433 | 32 | 411.0 | 0.82 | G | 412 |
| 434 | 33 | 411.0 | 0.82 | G | 412 |
| 435 | 34 | 425.5 | 8.82 | L | 426 |
| 436 | 37 | 397.4 | 0.77 | G | 398 |
| 437 | 38 | 423.4 | 3.51 | B | 424 |
| 438 | 39 | 423.4 | 3.32 | B | 424 |
| 439 | 41 | 423.5 | 7.19 | L | 424 |
| 440 | 42 | 437.5 | 3.79 | B | 438 |
| 441 | 45 | 431.5 | 6.63 | L | 432 |
| 442 | 46 | 461.8 | 6.59 | L | 462 |
| 443 | 47 | 461.8 | 6.59 | L | 462 |
| 444 | 48 | 475.5 | 7.07 | L | 476 |
| 445 | 50 | 445.5 | 8.18 | L | 446 |
| 446 | 52 | 411.5 | 7.02 | L | 412 |
| 447 | 53 | 411.5 | 7.03 | L | 412 |
| 448 | 54 | 425.5 | 8.81 | L | 426 |
| 449 | 57 | 449.5 | 7.34 | L | 450 |
| 450 | 63 | 495.6 | 12.57 | L | 496 |
| 451 | 64 | 465.5 | 8.20 | L | 466 |
| 452 | 65 | 409.5 | 6.51 | L | 410 |
| 453 | 66 | 423.5 | 7.04 | L | 424 |
| 454 | 67 | 423.5 | 7.20 | L | 424 |
| 455 | 68 | 423.5 | 7.11 | L | 424 |
| 456 | 69 | 423.5 | 7.07 | L | 424 |
| 457 | 70 | 425.5 | 3.40 | C | 426 |
| 458 | 71 | 427.5 | 5.44 | L | 428 |
| 459 | 72 | 431.4 | 8.28 | L | 432 |
| 460 | 73 | 473.5 | 7.77 | L | 474 |
| 461 | 74 | 437.5 | 7.61 | L | 438 |
| 462 | 75 | 437.5 | 7.69 | L | 438 |
| 463 | 76 | 439.4 | 6.38 | L | 440 |
| 464 | 77 | 439.5 | 3.53 | C | 440 |
| 465 | 78 | 441.5 | 5.84 | L | 442 |
| 466 | 79 | 445.4 | 7.59 | L | 446 |
| 467 | 80 | 445.4 | 8.93 | L | 446 |
| 468 | 81 | 445.4 | 8.85 | L | 446 |
| 469 | 82 | 445.4 | 8.85 | L | 446 |
| 470 | 83 | 445.4 | 8.78 | L | 446 |
| 471 | 84 | 449.5 | 6.00 | L | 450 |
| 472 | 85 | 451.5 | 6.78 | L | 452 |
| 473 | 86 | 451.5 | 6.68 | L | 452 |
| 474 | 88 | 459.5 | 7.47 | L | 460 |
| 475 | 89 | 461.5 | 2.97 | C | 462 |
| 476 | 90 | 461.5 | 3.13 | C | 462 |
| 477 | 91 | 462.4 | 3.93 | L | 463 |
| 478 | 94 | 473.5 | 8.52 | L | 474 |
| 479 | 95 | 473.5 | 8.61 | L | 474 |
| 480 | 96 | 475.5 | 0.80 | G | 476 |
| 481 | 97 | 475.5 | 7.02 | L | 476 |
| 482 | 99 | 475.5 | 6.95 | L | 476 |
| 483 | 100 | 475.5 | 7.05 | L | 476 |
| 484 | 102 | 479.4 | 8.24 | L | 480 |
| 485 | 103 | 479.4 | 7.12 | L | 480 |
| 486 | 104 | 479.4 | 7.04 | L | 480 |
| 487 | 105 | 479.4 | 7.54 | L | 480 |
| 488 | 107 | 479.6 | 7.70 | L | 480 |
| 489 | 108 | 479.6 | 7.79 | L | 480 |
| 490 | 109 | 488.5 | 4.29 | L | 489 |
| 491 | 110 | 491.5 | 2.89 | C | 492 |
| 492 | 112 | 493.6 | 3.87 | C | 494 |
| 493 | 113 | 495.9 | 8.84 | L | 496 |
| 494 | 117 | 497.5 | 3.20 | C | 498 |
| 495 | 118 | 502.5 | 5.75 | L | 503 |
| 496 | 119 | 503.5 | 8.20 | L | 504 |
| 497 | 120 | 515.5 | 8.27 | L | 516 |
| 498 | 122 | 517.6 | 3.82 | C | 518 |
| 499 | 123 | 519.5 | 7.89 | L | 520 |
| 500 | 124 | 544.6 | 6.91 | L | 545 |
| 501 | 125 | 530.6 | 6.97 | L | 531 |
| 502 | 142 | 413.5 | 8.73 | L | 414 |
| 503 | 143 | 413.5 | 8.76 | L | 414 |
| 504 | 144 | 427.5 | 3.42 | C | 428 |
| 505 | 145 | 427.5 | 0.88 | G | 428.1 |
| 506 | 146 | 427.5 | 0.89 | G | 428.1 |
| 507 | 147 | 447.5 | 0.86 | G | 448.1 |
| 508 | 148 | 447.5 | 0.86 | G | 448.1 |
| 509 | 149 | 427.5 | 3.42 | C | 428 |
| 510 | 150 | 441.6 | 3.61 | C | 442 |
| 511 | 151 | 441.6 | 3.60 | C | 442 |
| 512 | 152 | 441.6 | 3.64 | C | 442 |
| 513 | 153 | 441.6 | 3.65 | C | 442 |
| 514 | 154 | 441.6 | 3.57 | C | 442 |
| 515 | 155 | 441.6 | 3.59 | C | 442 |
| 516 | 156 | 448.5 | 2.35 | C | 449 |
| 517 | 157 | 448.5 | 1.64 | C | 449 |
| 518 | 158 | 455.6 | 3.69 | C | 456 |
| 519 | 159 | 455.6 | 3.72 | C | 456 |
| 520 | 160 | 461.6 | 3.55 | C | 462 |
| 521 | 163 | 475.6 | 3.51 | C | 476 |
| 522 | 164 | 475.6 | 3.51 | C | 476 |
| 523 | 165 | 475.6 | 3.79 | C | 476 |
| 524 | 166 | 476.6 | 1.84 | C | 477 |
| 525 | 167 | 476.6 | 1.88 | C | 477 |
| 526 | 169 | 477.6 | 2.60 | C | 478 |
| 527 | 170 | 477.6 | 3.16 | C | 478 |
| 528 | 171 | 477.6 | 3.34 | C | 478 |
| 529 | 172 | 477.6 | 3.32 | C | 478 |
| 530 | 173 | 489.6 | 3.75 | C | 490 |
| 531 | 175 | 507.6 | 3.10 | C | 508 |
| 532 | 177 | 413.5 | 3.22 | C | 414 |
| 533 | 178 | 413.5 | 3.24 | C | 414 |
| 534 | 179 | 427.5 | 9.13 | L | 428 |

TABLE 28-continued

| Example No. | Phosphate Ester of Example No. | MW | HPLC Retention Time (min.) | HPLC condition | MS (M$^{+1}$) |
|---|---|---|---|---|---|
| 535 | 180 | 427.5 | 9.22 | L | 428 |
| 536 | 181 | 427.5 | 3.41 | C | 428 |
| 537 | 182 | 427.5 | 3.44 | C | 428 |
| 538 | 183 | 441.6 | 3.56 | C | 442 |
| 539 | 176 | 441.6 | 3.55 | C | 442 |
| 540 | 186 | 383.4 | 0.67 | G | 384 |
| 541 | 187 | 397.5 | 0.98 | G | 398 |
| 542 | 191 | 425.5 | 8.40 | L | 426 |
| 543 | 192 | 425.5 | 8.36 | L | 426 |
| 544 | 193 | 475.5 | 7.47 | L | 476 |
| 545 | 194 | 475.5 | 7.48 | L | 476 |
| 546 | 195 | 459.5 | 8.58 | L | 460 |
| 547 | 196 | 459.5 | 3.61 | B | 460 |
| 548 | 197 | 459.5 | 8.83 | L | 460 |
| 549 | 198 | 459.5 | 8.83 | L | 460 |
| 550 | 199 | 459.5 | 0.81 | G | 460 |
| 551 | 200 | 459.5 | 7.71 | L | 460 |
| 552 | 201 | 459.5 | 0.84 | G | 460 |
| 553 | 202 | 475.5 | 0.77 | G | 476 |
| 554 | 203 | 463.4 | 7.12 | L | 464 |
| 555 | 204 | 407.5 | 8.26 | L | 408 |
| 556 | 205 | 421.5 | 8.73 | L | 422 |
| 557 | 206 | 451.5 | 7.12 | L | 452 |
| 558 | 207 | 437.5 | 6.57 | L | 438 |
| 559 | 208 | 473.5 | 8.05 | L | 474 |
| 560 | 209 | 473.5 | 8.01 | L | 474 |
| 561 | 211 | 438.5 | 4.06 | L | 439 |
| 562 | 213 | 500.6 | 0.93 | G | 501 |
| 563 | 214 | 473.5 | 8.40 | L | 474 |
| 564 | 215 | 473.5 | 8.19 | L | 474 |
| 565 | 216 | 445.5 | 0.85 | G | 446 |
| 566 | 217 | 445.5 | 0.83 | G | 446 |
| 567 | 221 | 445.5 | 0.83 | G | 446 |
| 568 | 223 | 445.5 | 0.82 | G | 446 |
| 569 | 226 | 401.4 | 0.80 | G | 402 |
| 570 | 227 | 401.4 | 0.81 | G | 402 |
| 571 | 228 | 415.5 | 7.32 | L | 416 |
| 572 | 229 | 415.5 | 7.31 | L | 416 |
| 573 | 230 | 429.5 | 0.89 | G | 430 |
| 574 | 233 | 402.4 | 0.46 | G | 403 |
| 575 | 234 | 395.5 | 0.93 | G | 396 |
| 576 | 235 | 395.5 | 0.94 | G | 396 |
| 577 | 236 | 381.5 | 0.88 | G | 396 |
| 578 | 237 | 381.5 | 0.88 | G | 396 |
| 579 | 238 | 425.5 | 2.46 | B | 426 |
| 580 | 240 | 453.5 | 7.54 | L | 454 |
| 581 | 243 | 475.5 | 7.75 | L | 476 |
| 582 | 244 | 461.5 | 6.62 | L | 462 |
| 583 | 245 | 461.5 | 6.61 | L | 462 |
| 584 | 246 | 439.5 | 5.96 | L | 440 |
| 585 | 247 | 467.5 | 6.80 | L | 468 |
| 586 | 250 | 455.5 | 6.95 | L | 456 |
| 587 | 251 | 455.5 | 6.86 | L | 456 |
| 588 | 255 | 481.5 | 6.28 | L | 482 |
| 589 | 260 | 481.5 | 6.28 | L | 482 |
| 590 | 265 | 475.5 | 7.08 | L | 476 |
| 591 | 266 | 441.5 | 7.50 | L | 442 |
| 592 | 267 | 441.5 | 7.50 | L | 442 |
| 593 | 268 | 459.5 | 0.88 | G | 456 |
| 594 | 269 | 459.5 | 0.88 | G | 456 |
| 595 | 270 | 397.5 | 0.72 | G | 398 |
| 596 | 272 | 411.5 | 0.80 | G | 412 |
| 597 | 274 | 439.5 | 0.86 | G | 440 |
| 598 | 275 | 425.5 | 1.01 | B | 426 |
| 599 | 277 | 425.5 | 1.01 | B | 426 |
| 600 | 278 | 425.5 | 8.39 | L | 426 |
| 601 | 281 | 423.5 | 0.80 | G | 424 |
| 602 | 282 | 425.5 | 8.45 | L | 426 |
| 603 | 284 | 443.5 | 0.80 | G | 444 |
| 604 | 289 | 480.5 | 0.60 | G | 481 |
| 605 | 290 | 480.5 | 0.60 | G | 481 |
| 606 | 292 | 430.5 | 0.64 | G | 431 |
| 607 | 299 | 477.5 | 0.93 | G | 478 |
| 608 | 300 | 477.5 | 1.12 | M | 478 |
| 609 | 305 | 477.5 | 1.14 | M | 478 |
| 610 | 315 | 439.5 | 0.86 | G | 440 |
| 611 | 316 | 439.5 | 1.10 | M | 440 |
| 612 | 318 | 410.5 | 0.74 | G | 411 |
| 613 | 327 | 444.5 | 5.64 | L | 445 |
| 614 | 328 | 444.5 | 5.61 | L | 445 |
| 615 | 332 | 472.5 | 6.00 | L | 473 |
| 616 | 334 | 424.5 | 5.60 | L | 425 |
| 617 | 335 | 424.5 | 1.32 | G | 425 |
| 618 | 337 | 479.5 | 6.98 | L | 480 |
| 620 | 343 | 535.4 | 10.58 | L | 536 |
| 621 | 345 | 444.0 | 0.81 | G | 445 |
| 622 | 346 | 423.5 | 10.11 | L | 424 |
| 623 | 347 | 439.5 | 0.83 | G | 440 |
| 624 | 348 | 467.5 | 0.89 | G | 468 |
| 625 | 351 | 440.5 | 0.70 | G | 441 |
| 626 | 352 | 468.5 | 0.79 | G | 469 |
| 627 | 353 | 445.5 | 0.75 | G | 446 |
| 628 | 354 | 454.5 | 0.74 | G | 455 |
| 629 | 355 | 438.5 | 0.67 | G | 439 |
| 630 | 357 | 451.5 | 0.90 | G | 453 |
| 631 | 358 | 451.5 | 0.89 | G | 453 |
| 632 | 359 | 451.5 | 0.89 | G | 453 |
| 633 | 360 | 451.5 | 0.90 | G | 453 |
| 634 | 361 | 395.4 | 0.67 | G | 396 |
| 635 | 364 | 395.4 | 0.75 | G | 396 |
| 636 | 367 | 407.5 | 8.46 | L | 408 |
| 637 | 368 | 407.5 | 8.45 | L | 408 |
| 638 | 369 | 423.5 | 6.62 | L | 424 |
| 639 | 370 | 405.5 | 6.35 | L | 406 |
| 640 | 371 | 423.5 | 6.63 | L | 424 |
| 641 | 372 | 457.5 | 7.56 | L | 458 |
| 642 | 373 | 435.5 | 6.34 | L | 436 |
| 643 | 374 | 457.5 | 8.79 | L | 458 |
| 644 | 375 | 441.5 | 8.11 | L | 442 |
| 645 | 376 | 421.5 | 9.01 | L | 422 |
| 646 | 377 | 409.5 | 8.16 | L | 410 |
| 647 | 378 | 405.5 | 8.16 | L | 406 |
| 648 | 379 | 407.5 | 8.53 | L | 408 |
| 649 | 380 | 407.5 | 8.53 | L | 408 |
| 650 | 381 | 407.5 | 3.71 | C | 408 |
| 651 | 383 | 407.5 | 3.68 | C | 408 |
| 652 | 384 | 327.5 | 8.28 | L | 328 |
| 653 | 385 | 327.5 | 8.42 | L | 328 |
| 654 | 386 | 327.5 | 8.52 | L | 328 |
| 655 | 387 | 327.5 | 9.51 | L | 328 |
| 656 | 388 | 407.5 | 3.70 | C | 408 |
| 657 | 389 | 407.5 | 3.76 | C | 408 |
| 658 | 390 | 407.5 | 3.72 | C | 408 |
| 659 | 392 | 421.5 | 10.28 | L | 422 |
| 660 | 393 | 421.5 | 10.13 | L | 422 |
| 661 | 395 | 421.5 | 10.60 | L | 422 |
| 662 | 399 | 458.5 | 0.83 | G | 459 |
| 663 | 400 | 458.5 | 0.83 | G | 459 |
| 664 | 402 | 472.5 | 7.37 | L | 473 |
| 665 | 403 | 438.5 | 7.45 | L | 439 |
| 666 | 409 | 410.4 | 6.36 | L | 411 |

Example 667

(((1R,3S)-1-amino-3-((6S)-6-((phenyl sulfinyl)methyl)-5,6,7,8-tetrahydronaphthalen-2-yl) cyclopentyl)methyl dihydrogen phosphate

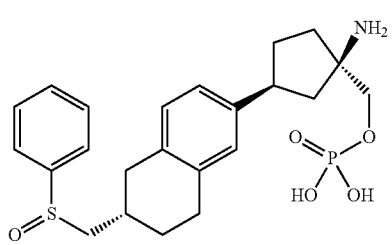
(667)

To a stirred clear solution of (((1R,3S)-1-amino-3-((S)-6-((phenylthio)methyl)-5,6,7,8-tetrahydronaphthalen-2-yl)cyclopentyl)methyl dihydrogen phosphate (4 mg, 8.94 mol), DMSO (0.013 mL, 0.179 mmol), and L-10-(-)-camphor sulfonic acid (10.38 mg, 0.045 mmol) in dichloromethane (0.5 mL) and methanol (0.2 mL) cooled with dry-ice was added 77% m-CPBA (2.003 mg, 8.94 μmol). The temperature was raised to 0° C. over 50 min. The mixture was stirred at 0° C. for 30 min and room temperature for 30 min. The mixture was concentrated. Purification using reverse phase HPLC (Waters Xbridge C18 19×100 mm; gradient over 8 min from 20 to 100% of solvent B; solvent A: 10% MeOH: 90% $H_2O$: 0.1% TFA; solvent B: 90% MeOH, 10% $H_2O$, 0.1% TFA), concentration, and lyophilization gave ((1R,3S)-1-amino-3-((6S)-6-((phenylsulfinyl)methyl)-5,6,7,8-tetrahydronaphthalen-2-yl)cyclopentyl)methyl dihydrogen phosphate (3.6 mg, 7.38 μmol) as a white solid. LC/MS $M^{+1}$=464. HPLC retention time=6.43 min (Condition L) $^1$H NMR (400 MHz, METHANOL-$d_4$) δ 7.73-7.67 (m, 2H), 7.63-7.56 (m, 3H), 7.08-6.96 (m, 3H), 3.99-3.87 (m, 2H), 3.18-3.09 (m, 1H), 3.02 (ddd, J=13.0, 7.3, 5.4 Hz, 1H), 2.96-2.79 (m, 3H), 2.73-2.56 (m, 1H), 2.49 (dd, J=13.4, 7.0 Hz, 1H), 2.41-2.11 (m, 3H), 2.07-1.89 (m, 4H), 1.78-1.58 (m, 2H).

The example in Table 29 was prepared according to the general procedure of Example 667.

Example 669

(((1R,3S)-1-amino-3-((S)-6-((phenylsulfonyl)methyl)-5,6,7,8-tetrahydronaphthalen-2-yl)cyclopentyl)methyl dihydrogen phosphate

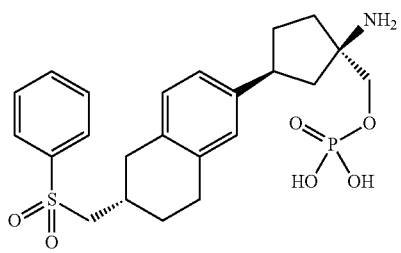
(669)

To a stirred clear solution of (((1R,3S)-1-amino-3-((S)-6-((phenylthio)methyl)-5,6,7,8-tetrahydronaphthalen-2-yl)cyclopentyl)methyl dihydrogen phosphate (4 mg, 8.94 mol) and L-10-(-)-camphor sulfonic acid (10.38 mg, 0.045 mmol) in dichloromethane (0.5 mL) and methanol (0.2 mL) was added 77% m-CPBA (4.01 mg, 0.018 mmol). The mixture was stirred at room temperature for 2 h before being concentrated. Purification using reverse phase HPLC (Waters Xbridge C18 19×100 mm; gradient over 8 min from 20 to 100% of solvent B; solvent A: 10% MeOH: 90% $H_2O$: 0.1% TFA; solvent B: 90% MeOH, 10% $H_2O$, 0.1% TFA), concentration, and lyophilization gave ((1R,3S)-1-amino-3-((S)-6-((phenyl sulfonyl)methyl)-5,6,7,8-tetrahydronaphthalen-2-yl)cyclopentyl)methyl dihydrogen phosphate (3.3 mg, 6.88 μmol) as a white solid. LC/MS $M^{+1}$=480. HPLC retention time=6.98 min (condition L $^1$H NMR (400 MHz, METHANOL-$d_4$) δ 7.98-7.92 (m, 2H), 7.77-7.72 (m, 1H), 7.68-7.59 (m, 2H), 6.99 (q, J=7.9 Hz, 3H), 3.98-3.84 (m, 2H), 3.25 (dd, J=6.4, 5.1 Hz, 2H), 3.03-2.95 (m, 1H), 2.84-2.76 (m, 2H), 2.60 (dd, J=16.6, 9.6 Hz, 1H), 2.48 (dd, J=13.1, 6.7 Hz, 1H), 2.37 (br. s., 1H), 2.18-1.87 (m, 6H), 1.76-1.56 (m, 2H).

TABLE 29

| Ex. No. | Structure | MW | HPLC ret. time (min.) | HPLC condition | MS (M + 1) |
|---|---|---|---|---|---|
| 668 | ![structure] | 443.5 | 2.20 | C | 444 |

Examples 672 and 673

((1R,3S)-1-amino-3-((S)-6-(5-methoxypentyl)-5,6,7,8-tetrahydronaphthalen-2-yl)cyclopentyl)methanol (672) and ((1R,3S)-1-amino-3-((R)-6-(5-methoxypentyl)-5,6,7,8-tetrahydronaphthalen-2-yl)cyclopentyl)methanol (673)

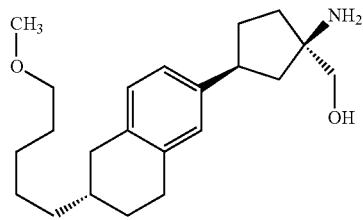
(672)

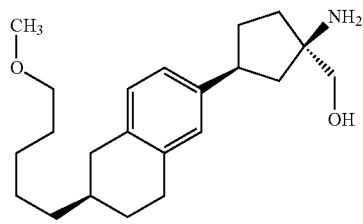
(673)

Preparation 672A: 5-methoxypent-1-yne

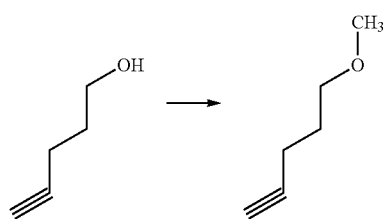
(672A)

To a mixture of pent-4-yn-1-ol (2 mL, 21.49 mmol) in THF (20 mL) was added sodium hydride (1032 mg, 25.8 mmol) portionwise over 15 minutes. The reaction mixture was stirred 30 minutes after addition and then methyl iodide (2.69 mL, 43.0 mmol) was added. The reaction mixture was heated at 40° C. for 6 h. An aliquot was removed, concentrated and checked by NMR. Reaction was incomplete. Additional sodium hydride (1032 mg, 25.8 mmol) and methyl iodide (2.69 mL, 43.0 mmol) were added and the reaction mixture was stirred overnight at 40° C. An aliquot check show reaction was complete. The reaction mixture was diluted with ethyl acetate and washed with H$_2$O. The organic layer was dried with MgSO$_4$, filtered and concentrated. The crude product was distilled at 90 to 100° C. to give 5-methoxypent-1-yne (950 mg, 9.68 mmol) as a clear liquid.

Preparation 672B: (5R,7S)-7-(6-(5-methoxypent-1-yn-1-yl)-7,8-dihydronaphthalen-2-yl)-3-oxa-1-azaspiro[4.4]nonan-2-one

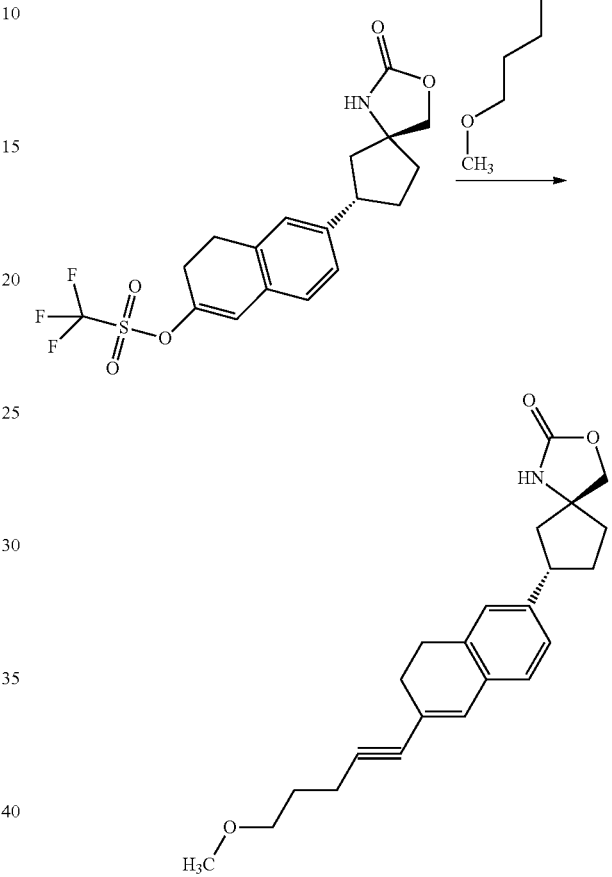
(672B)

To a mixture of 6-((5R,7S)-2-oxo-3-oxa-1-azaspiro[4.4]nonan-7-yl)-3,4-dihydronaphthalen-2-yl trifluoromethanesulfonate (1.35 g, 3.23 mmol), copper(I) iodide (0.062 g, 0.323 mmol), and bis(triphenylphosphine)palladium(II) chloride (0.227 g, 0.323 mmol) in TEA (3 mL) was added 5-methoxypent-1-yne (1.587 g, 16.17 mmol). The reaction mixture was heated at 60° C. for 1 hour. The reaction mixture was diluted with ethyl acetate and washed with 1M HCl. The organic layer was dried with MgSO$_4$, filtered and concentrated. The crude material was purified on a silica gel cartridge (40 g) using an EtOAc/Hex gradient (0-100% EtOAc over 12 CV). Fractions 28-33 were isolated, concentrated, and dried in vacuo to afford (5R,7S)-7-(6-(5-methoxypent-1-yn-1-yl)-7,8-dihydronaphthalen-2-yl)-3-oxa-1-azaspiro[4.4]nonan-2-one (1 g, 2.74 mmol). HPLC retention time=1.00 min (condition A); LC/MS M$^{+1}$=346; $^1$H NMR (400 MHz, CHLOROFORM-d) δ 7.08-6.89 (m, 3H), 6.69 (s, 1H), 5.62 (s, 1H), 4.44-4.22 (m, 2H), 3.52 (t, J=6.2 Hz, 2H), 3.39 (s, 3H), 3.14-2.97 (m, 1H), 2.83 (t, J=8.1 Hz, 2H), 2.50 (t, J=7.2 Hz, 2H), 2.46-2.39 (m, 2H), 2.33 (dd, J=13.2, 7.3 Hz, 1H), 2.21-2.09 (m, 2H), 2.03-1.92 (m, 2H), 1.85 (quin, J=6.7 Hz, 3H).

Preparations 672C and 673C: (5R,7S)-7-((S)-6-(5-methoxypentyl)-5,6,7,8-tetrahydronaphthalen-2-yl)-3-oxa-1-azaspiro[4.4]nonan-2-one (672C-Isomer 1) and (5R,7S)-7-((R)-6-(5-methoxypentyl)-5,6,7,8-tetrahydronaphthalen-2-yl)-3-oxa-1-azaspiro[4.4]nonan-2-one (673-Isomer 2)

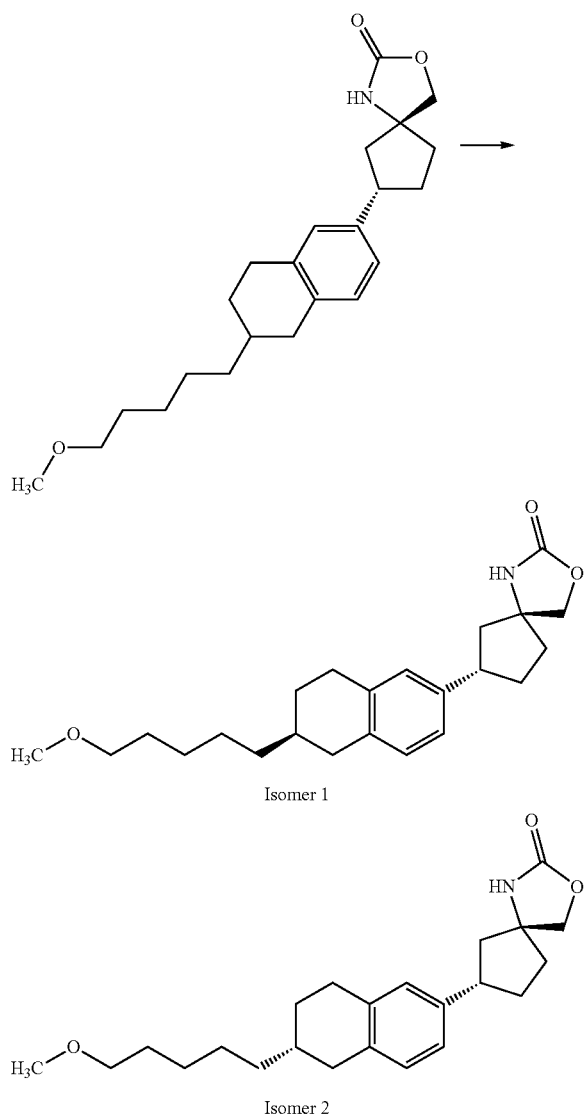

Isomer 1

Isomer 2

To a mixture of (5R,7S)-7-(6-(5-methoxypent-1-yn-1-yl)-7,8-dihydronaphthalen-2-yl)-3-oxa-1-azaspiro[4.4]nonan-2-one (105 mg, 0.287 mmol) in MeOH (10 mL) was added Pearlman's Catalyst (20.17 mg, 0.144 mmol). The reaction mixture was hydrogenated under a balloon of $H_2$ for 1 hour. LCMS show complete hydrogenation. The catalyst was removed by filtration. The mixture was concentrated in vacuo to afford 105 mg of desired product. The individual isomers were separated using a Chiral AD-H 25×3 cm ID, 5 um under SFC conditions (30% MeOH in $CO_2$). Two fractions were obtained and concentrated to dryness. Peak 1: recovered (5R,7S)-7-((S)-6-(5-methoxypentyl)-5,6,7,8-tetrahydronaphthalen-2-yl)-3-oxa-1-azaspiro[4.4]nonan-2-one (40 mg, 0.108 mmol). Peak 2: recovered (5R,7S)-7-((R)-6-(5-methoxypentyl)-5,6,7,8-tetrahydronaphthalen-2-yl)-3-oxa-1-azaspiro[4.4]nonan-2-one (38 mg, 0.102 mmol).

Example 672

To a mixture of (5R,7S)-7-((S)-6-(5-methoxypentyl)-5,6,7,8-tetrahydronaphthalen-2-yl)-3-oxa-1-azaspiro[4.4]nonan-2-one (40 mg, 0.108 mmol) in DMSO (0.5 mL) and MeOH (1 mL) was added 1N NaOH (0.5 mL). The reaction mixture was heated at 95° C. for 2 hours. Next, the mixture was cooled and then acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight. Recovered ((1R,3S)-1-amino-3-((S)-6-(5-methoxypentyl)-5,6,7,8-tetrahydronaphthalen-2-yl)cyclopentyl)methanol, TFA (32 mg, 0.067 mmol). HPLC retention time=8.15 min (condition L); LC/MS $M^{+1}$=346; $^1$H NMR in CD3OD (400 MHz, METHANOL-$d_4$) δ 7.05-6.94 (m, 3H), 3.72-3.56 (m, 2H), 3.42 (t, J=6.5 Hz, 2H), 3.34 (s, 3H), 3.19-3.03 (m, 1H), 2.91-2.70 (m, 3H), 2.50-2.28 (m, 2H), 2.20-2.04 (m, 1H), 2.03-1.86 (m, 4H), 1.79-1.65 (m, 2H), 1.61 (quin, J=7.0 Hz, 2H), 1.53-1.23 (m, 7H).

Example 673

To a mixture of (5R,7S)-7-((R)-6-(5-methoxypentyl)-5,6,7,8-tetrahydronaphthalen-2-yl)-3-oxa-1-azaspiro[4.4]nonan-2-one (40 mg, 0.108 mmol) in DMSO (0.5 mL) and MeOH (1 mL) was added 1N NaOH (0.5 mL). The reaction mixture was heated at 95° C. for 2 hours. The mixture was cooled and then acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight. Recovered ((1R,3S)-1-amino-3-((R)-6-(5-methoxypentyl)-5,6,7,8-tetrahydronaphthalen-2-yl)cyclopentyl)methanol, TFA (26 mg, 0.055 mmol). HPLC retention time=8.16 min (condition L); LC/MS $M^{+1}$=346; $^1$H NMR in CD3OD (400 MHz, METHANOL-$d_4$) δ 7.02-6.96 (m, 3H), 3.71-3.56 (m, 2H), 3.42 (t, J=6.6 Hz, 2H), 3.34 (s, 3H), 3.18-3.02 (m, 1H), 2.90-2.71 (m, 3H), 2.49-2.29 (m, 2H), 2.12 (d, J=2.9 Hz, 1H), 2.02-1.87 (m, 4H), 1.79-1.66 (m, 2H), 1.66-1.55 (m, 2H), 1.52-1.32 (m, 7H).

Examples 674 and 675

((1R,3R)-1-amino-3-(6-(5-methoxypentyl)-5,6,7,8-tetrahydronaphthalen-2-yl) cyclopentyl)methanol

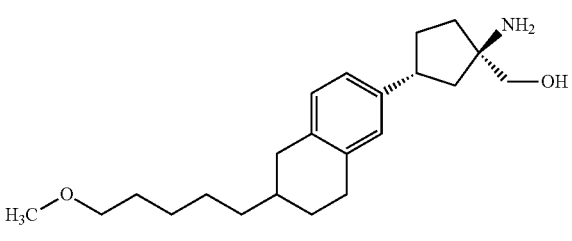 [SMILES: COCCCCCC1CCc2cc([C@@H]3CC[C@](N)(CO)C3)ccc2C1]

Preparation 674A: (5R,7R)-7-(6-(5-methoxypent-1-yn-1-yl)-7,8-dihydronaphthalen-2-yl)-3-oxa-1-azaspiro[4.4]nonan-2-one

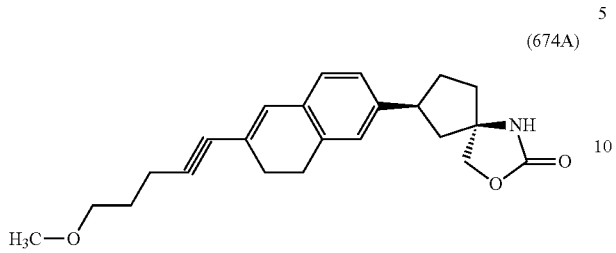
(674A)

To a mixture of 6-((5R,7R)-2-oxo-3-oxa-1-azaspiro[4.4]nonan-7-yl)-3,4-dihydronaphthalen-2-yl trifluoromethanesulfonate (130 mg, 0.311 mmol), copper(I) iodide (5.93 mg, 0.031 mmol), and bis(triphenylphosphine)palladium(II) chloride (21.86 mg, 0.031 mmol) in TEA (311 µl) was added 5-methoxypent-1-yne (153 mg, 1.557 mmol). The mixture was stirred at 60° C. for 1 hour. LCMS showed complete conversion. The reaction mixture was diluted with ethyl acetate and washed with 1M HCl. The organic layer was dried with MgSO₄, filtered and concentrated under reduced pressure. The crude material was purified on a silica gel cartridge (40 g) using an EtOAc/Hex gradient (0-100% EtOAc over 12 CV) giving access to (5R,7R)-7-(6-(5-methoxypent-1-yn-1-yl)-7,8-dihydronaphthalen-2-yl)-3-oxa-1-azaspiro[4.4]nonan-2-one (70 mg, 0.192 mmol). HPLC retention time=0.99 min (condition G) LC/MS M$^{+1}$=366.4. $^1$H NMR (400 MHz, METHANOL-d₄) δ 7.06-6.98 (m, 2H), 6.94 (d, J=7.7 Hz, 1H), 6.63 (s, 1H), 4.34 (dd, J=12.5, 7.9 Hz, 2H), 3.52 (t, J=6.3 Hz, 2H), 3.36 (s, 3H), 3.29-3.17 (m, 1H), 2.78 (t, J=8.1 Hz, 2H), 2.46 (t, J=7.0 Hz, 2H), 2.40-2.31 (m, 2H), 2.26 (dd, J=13.3, 7.4 Hz, 1H), 2.21-2.10 (m, 2H), 2.03-1.91 (m, 1H), 1.91-1.63 (m, 4H).

Preparation 674B: (5R,7R)-7-(6-(5-methoxypentyl)-5,6,7,8-tetrahydronaphthalen-2-yl)-3-oxa-1-azaspiro[4.4]nonan-2-one

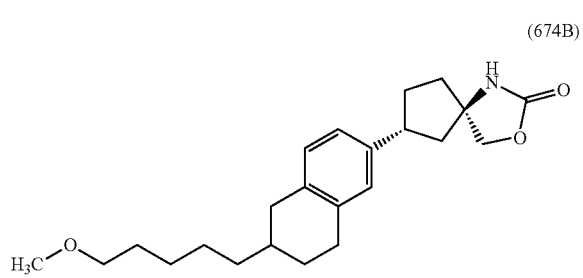 [SMILES: COCCCCCC1CCc2cc([C@@H]3CC[C@]4(COC(=O)N4)C3)ccc2C1]
(674B)

To a solution of (5R,7R)-7-(6-(5-methoxypent-1-yn-1-yl)-7,8-dihydronaphthalen-2-yl)-3-oxa-1-azaspiro[4.4]nonan-2-one (70 mg, 0.192 mmol) in EtOH (1596 µl) and EtOAc (319 µl) was added palladium hydroxide on carbon (26.9 mg, 0.038 mmol) at room temperature. The reaction mixture was purged with H₂ and stirred under H₂ overnight. LCMS showed complete conversion. The suspension was filtered through Celite and concentrated to provide (5R,7R)-7-(6-(5-methoxypentyl)-5,6,7,8-tetrahydronaphthalen-2-yl)-3-oxa-1-azaspiro[4.4]nonan-2-one (70 mg, 0.188 mmol) as a white solid. HPLC retention time=1.12 min (condition G) LC/MS M$^{+1}$=418.3. The individual isomers were separated using a Chiral OJ-H 25×3 cm ID, 5 um under SFC conditions (30% MeOH in CO₂). Two fractions were obtained and concentrated to dryness.

Examples 674 and 675: ((1R,3R)-1-amino-3-(6-(5-methoxypentyl)-5,6,7,8-tetrahydronaphthalen-2-yl)cyclopentyl)methanol

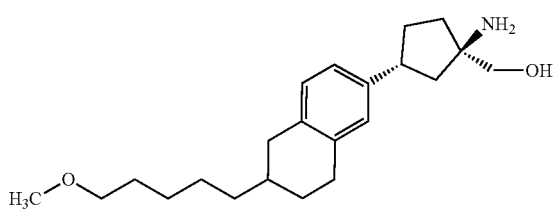 [SMILES: COCCCCCC1CCc2cc([C@@H]3CC[C@](N)(CO)C3)ccc2C1]

To a solution of (5R,7R)-7-(6-(5-methoxypentyl)-5,6,7,8-tetrahydronaphthalen-2-yl)-3-oxa-1-azaspiro[4.4]nonan-2-one (21 mg, 0.057 mmol) in dioxane (565 µl) was added NaOH (565 µl, 0.565 mmol). The temperature was elevated to 98° C. and LCMS showed complete conversion after 2 h. The reaction mixture was diluted with EtOAc and the aqueous layer was back-extracted with EtOAc. HPLC prep purification: HPLC: condition=2 mL injection, gradient time of 5 min, start B=20% to 100%, stop time of 15 min, Solvent A=0.1% TFA in water, Solvent B=0.1% TFA in MeCN, column=LUNA, wavelength of 220 nm. The product was then free base by extraction DCM/1N NaOH affording ((1R,3R)-1-amino-3-(6-(5-methoxypentyl)-5,6,7,8-tetrahydronaphthalen-2-yl)cyclopentyl)methanol (10 mg, 0.028 mmol).

Isomer 1. HPLC retention time=8.18 min (condition L); LC/MS M$^{+1}$=346.4. $^1$H NMR (400 MHz, METHANOL-d₄) δ 7.04-6.92 (m, 3H), 3.71-3.58 (m, 2H), 3.42 (t, J=6.5 Hz, 2H), 3.39 (s, 3H), 3.31-3.25 (m, 1H), 2.88-2.72 (m, 3H), 2.36 (dd, J=16.4, 10.5 Hz, 1H), 2.26-2.11 (m, 3H), 2.02-1.91 (m, 1H), 1.89-1.73 (m, 3H), 1.73-1.66 (m, 1H), 1.66-1.53 (m, 2H), 1.52-1.32 (m, 7H). Isomer 2: HPLC retention time=8.17 min (condition L); LC/MS M$^{+1}$=346.4; $^1$H NMR (400 MHz, METHANOL-d₄) δ 7.04-6.92 (m, 3H), 3.71-3.58 (m, 2H), 3.42 (t, J=6.5 Hz, 2H), 3.39 (s, 3H), 3.31-3.25 (m, 1H), 2.88-2.72 (m, 3H), 2.36 (dd, J=16.4, 10.5 Hz, 1H), 2.26-2.11 (m, 3H), 2.02-1.91 (m, 1H), 1.89-1.73 (m, 3H), 1.73-1.66 (m, 1H), 1.66-1.53 (m, 2H), 1.52-1.32 (m, 7H).

Examples 676 and 677

((1R,3S)-1-amino-3-((S)-6-(3-methoxyphenethyl)-5,6,7,8-tetrahydronaphthalen-2-yl)cyclopentyl)methanol (676) and ((1R,3S)-1-amino-3-((R)-6-(3-methoxyphenethyl)-5,6,7,8-tetrahydronaphthalen-2-yl)cyclopentyl)methanol (677)

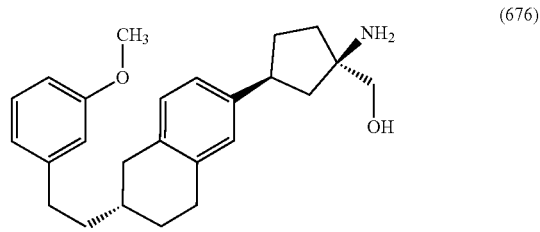
(676)

(677)

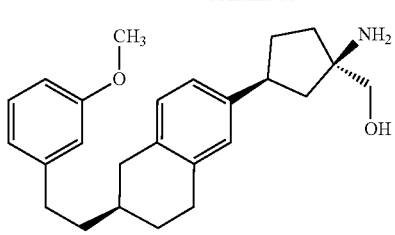

Preparation 676A: (5R,7S)-7-(6-((3-methoxyphenyl)ethynyl)-7,8-dihydronaphthalen-2-yl)-3-oxa-1-azaspiro[4.4]nonan-2-one (676A)

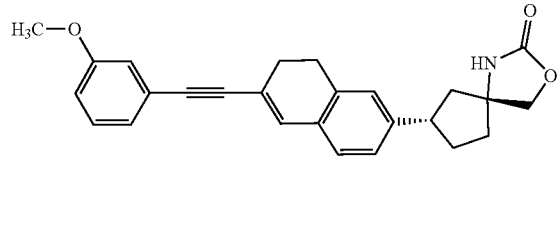

To a mixture of 6-((5R,7S)-2-oxo-3-oxa-1-azaspiro[4.4]nonan-7-yl)-3,4-dihydronaphthalen-2-yl trifluoromethanesulfonate (100 mg, 0.240 mmol), copper(I) iodide (4.56 mg, 0.024 mmol), and bis(triphenylphosphine)palladium(II) chloride (16.82 mg, 0.024 mmol) in TEA (3 mL) was added 1-ethynyl-3-methoxybenzene (0.091 mL, 0.719 mmol). The reaction mixture was heated at 60° C. for 1 hour. The reaction mixture was diluted with ethyl acetate and washed with 1M HCl. The organic layer was dried with $MgSO_4$, filtered and concentrated. The crude material was purified on a silica gel cartridge (12 g) using an EtOAc/Hex gradient (0-100% EtOAc over 20 CV). Fractions 15-17 were isolated, concentrated, and dried in vacuo to afford (5R,7S)-7-(6-((3-methoxyphenyl)ethynyl)-7,8-dihydronaphthalen-2-yl)-3-oxa-1-azaspiro[4.4]nonan-2-one (68 mg, 0.170 mmol). HPLC retention time=1.09 min (condition A) LC/MS $M^{+1}$=400; $^1H$ NMR (400 MHz, METHANOL-$d_4$) δ 7.30-7.22 (m, 1H), 7.14-6.97 (m, 5H), 6.92 (ddd, J=8.4, 2.6, 0.9 Hz, 1H), 6.83 (s, 1H), 6.42-6.01 (m, 1H), 4.84 (s, 3H), 4.41-4.25 (m, 2H), 3.33 (dt, J=3.2, 1.6 Hz, 2H), 3.06 (tt, J=11.0, 7.2 Hz, 1H), 2.86 (t, J=8.1 Hz, 2H), 2.49 (td, J=8.1, 1.3 Hz, 2H), 2.30 (dd, J=13.0, 7.3 Hz, 1H), 2.19-2.05 (m, 2H), 2.00-1.74 (m, 3H).

Preparations 676B and 677B: (5R,7S)-7-((R)-6-(3-methoxyphenethyl)-5,6,7,8-tetrahydronaphthalen-2-yl)-3-oxa-1-azaspiro[4.4]nonan-2-one (677B) and (5R,7S)-7-((S)-6-(3-methoxyphenethyl)-5,6,7,8-tetrahydronaphthalen-2-yl)-3-oxa-1-azaspiro[4.4]nonan-2-one (677B Isomer 1

(676B)

Isomer 2

(677B)

To a mixture of (5R,7S)-7-(6-((3-methoxyphenyl)ethynyl)-7,8-dihydronaphthalen-2-yl)-3-oxa-1-azaspiro[4.4]nonan-2-one (68 mg, 0.170 mmol) in MeOH (3 mL) and ethyl acetate (1 mL) was added Pearlman's Catalyst (23.90 mg, 0.170 mmol). The reaction mixture was hydrogenated under a balloon of $H_2$ for 1 hour. The mixture was filtered to remove the catalyst and concentrated in vacuo. The individual isomers were separated using a Chiral AS-H 25×3 cm ID, 5 um under SFC conditions (37% MeOH in $CO_2$). Two fractions which were obtained and concentrated to dryness. Isomer 1: recovered (5R,7S)-7-(6-(3-methoxyphenethyl)-5,6,7,8-tetrahydronaphthalen-2-yl)-3-oxa-1-azaspiro[4.4]nonan-2-one (17 mg, 0.042 mmol). Isomer 2; recovered (5R,7S)-7-(6-(3-methoxyphenethyl)-5,6,7,8-tetrahydronaphthalen-2-yl)-3-oxa-1-azaspiro[4.4]nonan-2-one (16 mg, 0.039 mmol).

Example 676

To a mixture of (5R,7S)-7-(6-(3-methoxyphenethyl)-5,6,7,8-tetrahydronaphthalen-2-yl)-3-oxa-1-azaspiro[4.4]nonan-2-one (Isomer 1, 17 mg, 0.042 mmol) in MeOH (1 mL) and DMSO (0.5 mL) was added 1N NaOH (1 mL). The reaction mixture was heated at 90° C. overnight, and then cooled and acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight. Recovered ((1R,3S)-1-amino-3-(6-(3-methoxyphenethyl)-5,6,7,8-tetrahydronaphthalen-2-yl)cyclopentyl)methanol, TFA (14 mg, 0.028 mmol). HPLC retention time=8.91 min (condition L) LC/MS M$^{+1}$=380. $^1$H NMR in CD$_3$OD (400 MHz, METHANOL-d$_4$) δ 7.18 (t, J=7.8 Hz, 1H), 7.05-6.96 (m, 3H), 6.85-6.76 (m, 2H), 6.74 (dd, J=8.3, 1.9 Hz, 1H), 3.79 (s, 3H), 3.71-3.56 (m, 2H), 3.19-3.02 (m, 1H), 2.89 (dd, J=16.4, 3.6 Hz, 1H), 2.83-2.75 (m, 2H), 2.75-2.68 (m, 2H), 2.50-2.35 (m, 2H), 2.20-2.06 (m, 1H), 2.06-1.87 (m, 4H), 1.82-1.61 (m, 4H), 1.53-1.36 (m, 1H).

Example 677

To a mixture of (5R,7S)-7-(6-(3-methoxyphenethyl)-5,6,7,8-tetrahydronaphthalen-2-yl)-3-oxa-1-azaspiro[4.4]nonan-2-one (Isomer 2, 16 mg, 0.042 mmol) in MeOH (1 mL) and DMSO (0.5 mL) was added 1N NaOH (1 mL). The reaction mixture was heated at 90° C. overnight, and then cooled and acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight. Recovered ((1R,3S)-1-amino-3-(6-(3-methoxyphenethyl)-5,6,7,8-tetrahydronaphthalen-2-yl)cyclopentyl)methanol, TFA (14 mg, 0.028 mmol). HPLC retention time=8.89 min (condition L) LC/MS M$^{+1}$=380; $^1$H NMR in CD3OD (400 MHz, METHANOL-d$_4$) δ 7.18 (t, J=7.8 Hz, 1H), 7.04-6.97 (m, 3H), 6.85-6.77 (m, 2H), 6.74 (dd, J=8.3, 1.9 Hz, 1H), 3.79 (s, 3H), 3.71-3.57 (m, 2H), 3.20-3.02 (m, 1H), 2.89 (dd, J=16.5, 3.3 Hz, 1H), 2.83-2.75 (m, 2H), 2.75-2.69 (m, 2H), 2.50-2.36 (m, 2H), 2.19-2.06 (m, 1H), 2.06-1.88 (m, 4H), 1.81-1.64 (m, 4H), 1.44 (dtd, J=12.8, 10.4, 5.9 Hz, 1H).

Examples 678 and 679

((1R,3S)-1-amino-3-((R)-6-(3-ethoxypropyl)-5,6,7,8-tetrahydronaphthalen-2-yl)cyclopentyl)methanol (678) and ((1R,3S)-1-amino-3-((S)-6-(3-ethoxypropyl)-5,6,7,8-tetrahydronaphthalen-2-yl)cyclopentyl)methanol (679)

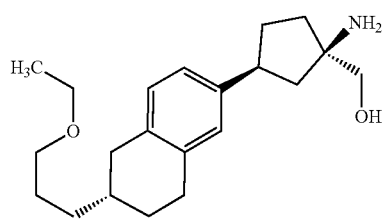

(678)

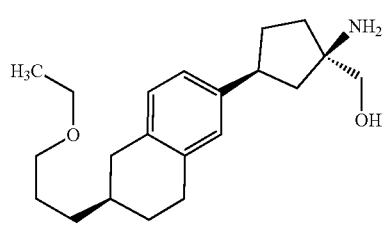

(679)

Preparation 678A: 3-(6-((5R,7S)-2-oxo-3-oxa-1-azaspiro[4.4]nonan-7-yl)-1,2,3,4-tetrahydronaphthalen-2-yl)propyl 4-methylbenzenesulfonate

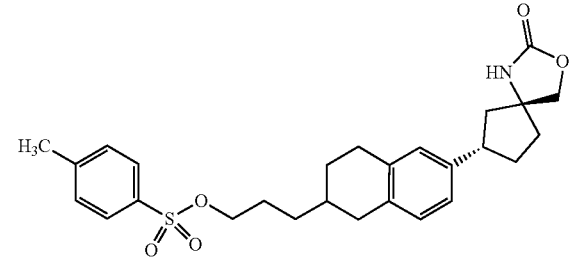

(678A)

To a mixture of 6-((5R,7S)-2-oxo-3-oxa-1-azaspiro[4.4]nonan-7-yl)-3,4-dihydronaphthalen-2-yl trifluoromethanesulfonate (330 mg, 0.791 mmol), copper(I) iodide (15.06 mg, 0.079 mmol), and bis(triphenylphosphine)palladium(II) chloride (55.5 mg, 0.079 mmol) in TEA (3 mL) was added benzyl propargyl ether (0.572 mL, 3.95 mmol). The reaction mixture was stirred at room temperature for 1 hour. The reaction mixture was diluted with ethyl acetate and washed with 1M HCl. The organic layer was dried with MgSO$_4$, filtered and concentrated. The crude material was purified on a silica gel cartridge (40 g) using an EtOAc/Hex gradient (0-100% EtOAc over 12 CV). Fractions 28-31 were isolated, concentrated, and dried in vacuo. The solid material was dissolved in MeOH (10 mL) and Pearlman's Catalyst (111 mg, 0.791 mmol) was added. The reaction mixture was hydrogenated under balloon pressure for 18 hours. The mixture was filtered to remove the catalyst and concentrated in vacuo. The solids were dissolved pyridine (5 mL) and then p-toluenesulfanonyl chloride (452 mg, 2.372 mmol) was added. After 2 hours, additional p-toluenesulfanonyl chloride (452 mg, 2.372 mmol) was added. The reaction mixture was diluted with ethyl acetate and washed with H$_2$O. The organic layer was dried with MgSO$_4$, filtered and concentrated. The crude material was purified on a silica gel cartridge (40 g) using an EtOAc/Hex gradient (0-100% EtOAc over 20 CV). Fractions 20-22 were concentrated and dried in vacuo to afford 3-(6-((5R,7S)-2-oxo-3-oxa-1-azaspiro[4.4]nonan-7-yl)-1,2,3,4-tetrahydronaphthalen-2-yl)propyl 4-methylbenzenesulfonate (200 mg, 0.414 mmol). $^1$H NMR (400 MHz, CHLOROFORM-d) δ 7.82 (d, J=8.1 Hz, 2H), 7.37 (d, J=7.9 Hz, 2H), 7.05-6.89 (m, 3H), 5.54 (s, 1H), 4.41-4.24 (m, 2H), 4.08 (t, J=6.5 Hz, 2H), 3.11-2.95 (m, 1H), 2.77 (td, J=10.0, 5.4 Hz, 3H), 2.47 (s, 3H), 2.40-2.26 (m, 2H), 2.21-2.08 (m, 2H), 2.03-1.73 (m, 6H), 1.70-1.55 (m, 2H), 1.48-1.32 (m, 2H).

Preparations 678B and 679B: (5R,7S)-7-((R)-6-(3-ethoxypropyl)-5,6,7,8-tetrahydronaphthalen-2-yl)-3-oxa-1-azaspiro[4.4]nonan-2-one (678B) and (5R,7S)-7-((R)-6-(3-ethoxypropyl)-5,6,7,8-tetrahydronaphthalen-2-yl)-3-oxa-1-azaspiro[4.4]nonan-2-one (679B Isomer 1

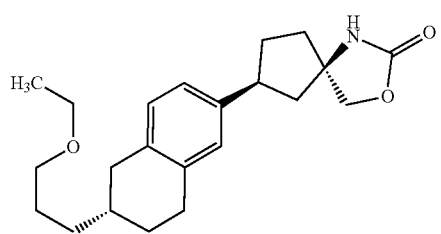

(678B)

Isomer 2

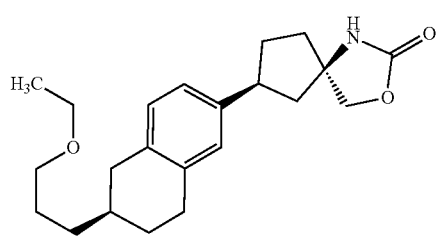

(679B)

To ethanol (0.5 mL, 0.248 mmol) was added sodium (114 mg, 4.96 mmol). The mixture was stirred until the sodium metal was consumed. A solution of 3-(6-((5R,7S)-2-oxo-3-oxa-1-azaspiro[4.4]nonan-7-yl)-1,2,3,4-tetrahydronaphthalen-2-yl)propyl 4-methylbenzenesulfonate (120 mg, 0.248 mmol) in DMF was added and the reaction mixture was stirred at room temperature. The reaction mixture was stirred for 12 hours. The reaction mixture was diluted with ethyl acetate and washed with saturated NaCl. The organic layer was dried with MgSO₄, filtered and concentrated. The crude material was purified on a silica gel cartridge (12 g) using an EtOAc/Hex gradient (0-100% EtOAc over 21 CV. Recovered 65 mg of a mixture of isomers. The individual isomers were separated using a Chiral AS-H 25×3 cm ID, 5 um under SFC conditions (27% MeOH in CO₂). Two fractions which were obtained and concentrated to dryness. Isomer 1: Recovered (5R,7S)-7-((R)-6-(3-ethoxypropyl)-5,6,7,8-tetrahydronaphthalen-2-yl)-3-oxa-1-azaspiro[4.4]nonan-2-one (30 mg, 0.084 mmol). Isomer 2: Recovered (5R,7S)-7-((S)-6-(3-ethoxypropyl)-5,6,7,8-tetrahydronaphthalen-2-yl)-3-oxa-1-azaspiro[4.4]nonan-2-one (31 mg, 0.087 mmol).

Example 678

To a mixture of (5R,7S)-7-((R)-6-(3-ethoxypropyl)-5,6,7,8-tetrahydronaphthalen-2-yl)-3-oxa-1-azaspiro[4.4]nonan-2-one (30 mg, 0.084 mmol) in DMSO (1 mL) and MeOH (1 mL) was added 1N NaOH. The reaction mixture was heated at 95° C. overnight. The mixture was cooled and acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with the correct mass were isolated and freeze-dried overnight. The material was poured into 1N NaOH (50 mL), stirred for 1 hour, and extracted with EtOAc. The organic layer was dried with MgSO₄, filtered, and concentrated to afford ((1R,3S)-1-amino-3-((R)-6-(3-ethoxypropyl)-5,6,7,8-tetrahydronaphthalen-2-yl)cyclopentyl)methanol (21 mg, 0.060 mmol). HPLC retention time=6.57 min (condition L); LC/MS M⁺¹=332; ¹H NMR in CD3OD (400 MHz, METHANOL-d₄) δ 7.10-6.78 (m, 3H), 3.61-3.40 (m, 6H), 3.02 (tt, J=11.2, 7.0 Hz, 1H), 2.90-2.70 (m, 3H), 2.37 (dd, J=16.3, 10.3 Hz, 1H), 2.23 (dd, J=13.1, 7.6 Hz, 1H), 2.09-1.85 (m, 3H), 1.85-1.64 (m, 5H), 1.61-1.51 (m, 1H), 1.49-1.31 (m, 3H), 1.21 (t, J=7.0 Hz, 3H).

Example 679

To a mixture of (5R,7S)-7-((S)-6-(3-ethoxypropyl)-5,6,7,8-tetrahydronaphthalen-2-yl)-3-oxa-1-azaspiro[4.4]nonan-2-one (30 mg, 0.084 mmol) in DMSO (1 mL) and MeOH (1 mL) was added 1N NaOH. The reaction mixture was heated at 95° C. overnight. The mixture was cooled, acidified with TFA, filtered, and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight. The material was poured into 1N NaOH (50 mL), stirred for 1 hour, and extracted with EtOAc (x). The organic layer was dried with MgSO₄, filtered, and concentrated to afford ((1R,3S)-1-amino-3-((S)-6-(3-ethoxypropyl)-5,6,7,8-tetrahydronaphthalen-2-yl)cyclopentyl) methanol (18 mg, 0.049 mmol). HPLC retention time=6.57 min (condition L); LC/MS M⁺¹=332; ¹H NMR in CD3OD (400 MHz, METHANOL-d₄) δ 7.20-6.76 (m, 3H), 3.59-3.43 (m, 6H), 3.03 (tt, J=11.2, 7.0 Hz, 1H), 2.90-2.67 (m, 3H), 2.36 (dd, J=16.2, 10.5 Hz, 1H), 2.26 (dd, J=12.8, 7.0 Hz, 1H), 2.09-1.88 (m, 3H), 1.88-1.74 (m, 2H), 1.74-1.64 (m, 3H), 1.59 (t, J=12.4 Hz, 1H), 1.50-1.28 (m, 3H), 1.20 (t, J=7.0 Hz, 3H).

Example 680

((1R,3R)-1-amino-3-((S)-6-(3-ethoxypropyl)-5,6,7,8-tetrahydronaphthalen-2-yl)cyclopentyl)methanol

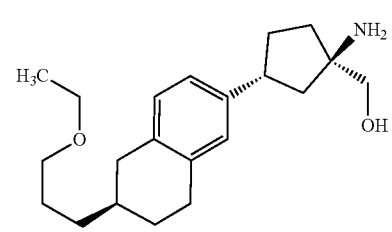

(680A)

Preparation 680A: (5R,7R)-7-((R)-6-(but-3-en-1-yl)-5,6,7,8-tetrahydronaphthalen-2-yl)-3-oxa-1-azaspiro[4.4]nonan-2-one

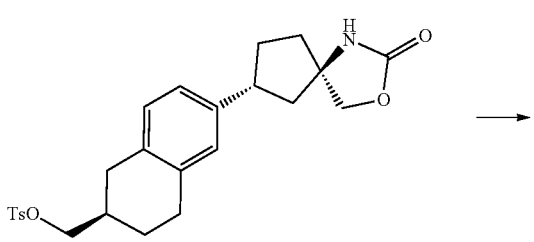

(680A)

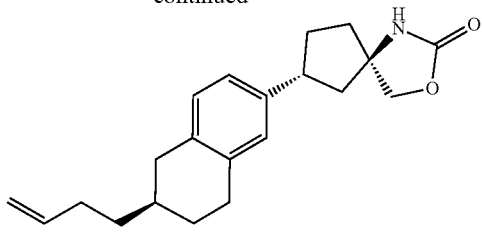

To a solution of ((R)-6-((5R,7R)-2-oxo-3-oxa-1-azaspiro[4.4]nonan-7-yl)-1,2,3,4-tetrahydronaphthalen-2-yl)methyl 4-methylbenzenesulfonate (250 mg, 0.549 mmol) and copper(I) bromide (157 mg, 1.098 mmol) in THF (5 mL) was added allylmagnesium bromide (1100 µl, 10.98 mmol) at room temperature and stirred at room temperature over 16 h. The reaction mixture was diluted with saturated NH₃Cl and water and extracted with EtOAc. The organic layer was collected, dried over Na₂SO₄, concentrated on the rotavapor to give (5R,7S)-7-((S)-6-(4-(dimethylamino)benzyl)-5,6,7,8-tetrahydronaphthalen-2-yl)-3-oxa-1-azaspiro[4.4]nonan-2-one, LC/MS $M^{+1}$=326.

Preparation 680B: 3-((S)-6-((5R,7R)-2-oxo-3-oxa-1-azaspiro[4.4]nonan-7-yl)-1,2,3,4-tetrahydronaphthalen-2-yl)propanal (680B)

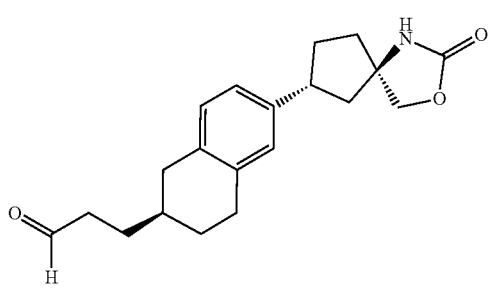

To a solution of (5R,7R)-7-((R)-6-(but-3-en-1-yl)-5,6,7,8-tetrahydronaphthalen-2-yl)-3-oxa-1-azaspiro[4.4]nonan-2-one (220 mg, 0.676 mmol) in THF (15 mL) was added NMO (158 mg, 1.352 mmol) and osmium tetroxide (6.37 µl, 0.020 mmol) at room temperature and stirred at room temperature over 16 h. Sodium periodate (578 mg, 2.70 mmol) in H₂O (1 mL) was added and precipitate formed. The mixture was stirred vigorously at room temperature under nitrogen for 30 min. The reaction mixture was diluted with saturated NH₄Cl and water and extracted with EtOAc. The organic layer was collected, dried over Na₂SO₄, concentrated on the rotavapor to give 3-((S)-6-((5R,7R)-2-oxo-3-oxa-1-azaspiro[4.4]nonan-7-yl)-1,2,3,4-tetrahydronaphthalen-2-yl)propanal, LC/MS $M^{+1}$=328.

Preparation 680C: (5R,7R)-7-((S)-6-(3-ethoxypropyl)-5,6,7,8-tetrahydronaphthalen-2-yl)-3-oxa-1-azaspiro[4.4]nonan-2-one (680C)

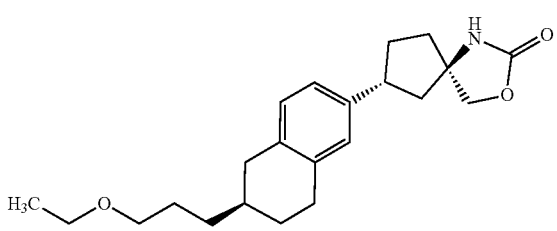

To a solution of 3-((S)-6-((5R,7R)-2-oxo-3-oxa-1-azaspiro[4.4]nonan-7-yl)-1,2,3,4-tetrahydronaphthalen-2-yl)propanal (200 mg, 0.611 mmol), ethoxytrimethylsilane (361 mg, 3.05 mmol), triethylsilane (355 mg, 3.05 mmol) in nitromethane (2 mL) was added iron(III) chloride (9.91 mg, 0.061 mmol) at 0° C., and stirred at room temperature for 16. The mixture was filtered and purified by prep HPLC to give (5R,7R)-7-((S)-6-(3-ethoxypropyl)-5,6,7,8-tetrahydronaphthalen-2-yl)-3-oxa-1-azaspiro[4.4]nonan-2-one, LC/MS $M^{+1}$=358.

Example 680

To a solution of the crude (5R,7R)-7-((S)-6-(3-ethoxypropyl)-5,6,7,8-tetrahydronaphthalen-2-yl)-3-oxa-1-azaspiro[4.4]nonan-2-one which was derived from previous step in dioxane (3 mL) and water (1 mL) was added LiOH (15.77 mg, 0.659 mmol), and stirred at 100° C. for 16 h. The reaction mixture was diluted with water, extracted with EtOAc. The organic layer was collected, dried over Na₂SO₄, and concentrated on the rotavapor to give the crude product which was purified with preparative HPLC: column Phenomenex Luna C18 5 u 21.2×100 mm. Solvent A: 10% MeOH-90% H₂O-0.1% TFA; Solvent B: 90% MeOH-10% H₂O-0.1% TFA. Gradient time=15 min. Start B=0%, Final B 100%. Stop time 25 min. ((1R,3S)-1-amino-3-((S)-6-((Z)-hex-2-en-1-yloxy)-5,6,7,8-tetrahydronaphthalen-2-yl)cyclopentyl)methanol, LC/MS $M^{+1}$=332. HPLC method: L; HPLC ret. time 6.86 (min.). ¹H NMR (400 MHz, METHANOL-d₄) δ 7.00-6.90 (m, 3H), 3.60-3.50 (m, 6H), 2.80-2.60 (m, 3H), 2.41-1.80 (m, 6H), 1.78-1.30 (m, 9H), 1.24 (t, J=7.0 Hz, 3H).

Examples 681 and 682

((1R,3S)-1-amino-3-((S)-6-(2-methoxyphenethyl)-5,6,7,8-tetrahydronaphthalen-2-yl)cyclopentyl)methanol (681) and ((1R,3S)-1-amino-3-((R)-6-(2-methoxyphenethyl)-5,6,7,8-tetrahydronaphthalen-2-yl)cyclopentyl)methanol (682)

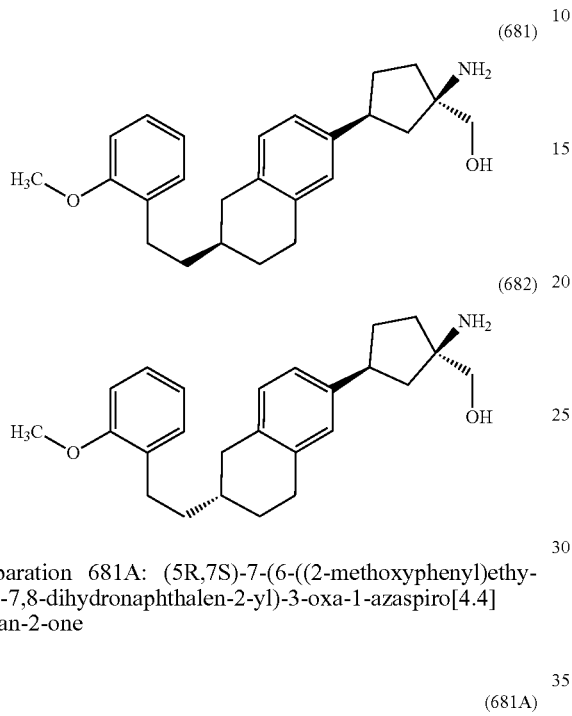

Preparation 681A: (5R,7S)-7-(6-((2-methoxyphenyl)ethynyl)-7,8-dihydronaphthalen-2-yl)-3-oxa-1-azaspiro[4.4]nonan-2-one To a mixture of 6-((5R,7S)-2-oxo-3-oxa-1-azaspiro[4.4]nonan-7-yl)-3,4-dihydronaphthalen-2-yl trifluoromethanesulfonate (64 mg, 0.153 mmol), copper(I) iodide (2.92 mg, 0.015 mmol), and bis(triphenylphosphine)palladium(II) chloride (10.76 mg, 0.015 mmol) in TEA (3 mL) was added 1-ethynyl-2-methoxybenzene (0.059 mL, 0.460 mmol). The reaction mixture was heated at 60° C. for 1 hour. The reaction mixture was diluted with ethyl acetate and washed with 1M HCl. The organic layer was dried with MgSO₄, filtered and concentrated. The crude material was purified on a silica gel cartridge (24 g) using an EtOAc/Hex gradient (0-100% EtOAc over 12 CV). Fractions 20-23 were isolated, concentrated, and dried in vacuo to afford (5R,7S)-7-(6-((2-methoxyphenyl)ethynyl)-7,8-dihydronaphthalen-2-yl)-3-oxa-1-azaspiro[4.4]nonan-2-one (45 mg, 0.113 mmol). HPLC retention time=1.07 min (condition A) LC/MS $M^{+1}=400$ Preparations 681B and 682B: (5R,7S)-7-(6-(2-methoxyphenethyl)-5,6,7,8-tetrahydronaphthalen-2-yl)-3-oxa-1-azaspiro[4.4]nonan-2-one

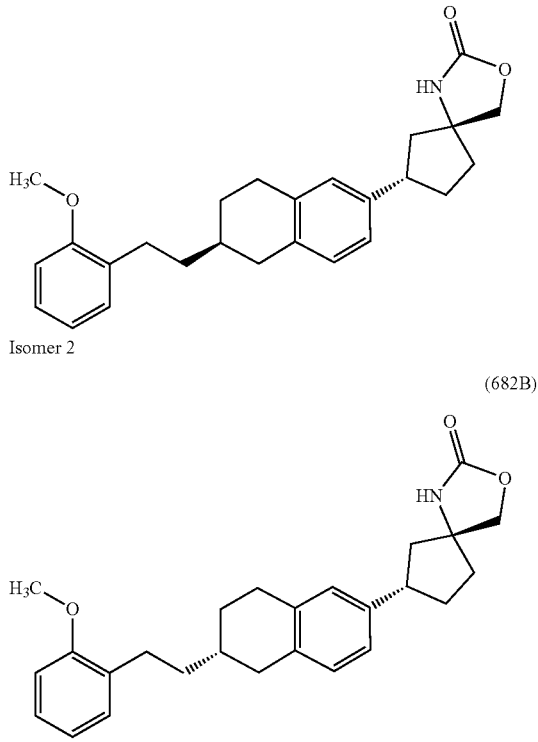

To a mixture of (5R,7S)-7-(6-((2-methoxyphenyl)ethynyl)-7,8-dihydronaphthalen-2-yl)-3-oxa-1-azaspiro[4.4]nonan-2-one (45 mg, 0.113 mmol) in MeOH (5 mL) was added Pearlman's Catalyst (15.82 mg, 0.113 mmol). The reaction mixture was hydrogenated under a balloon of $H_2$ overnight. The mixture was filtered to remove the catalyst and then concentrated in vacuo to afford 45 mg of a mixture of isomers. The individual isomers were separated using a Chiral OJ-H 25×3 cm ID, 5 um under SFC conditions (35% MeOH in $CO_2$). Two fractions which were obtained and concentrated to dryness. Isomer 1: Recovered (5R,7S)-7-(6-(2-methoxyphenethyl)-5,6,7,8-tetrahydronaphthalen-2-yl)-3-oxa-1-azaspiro[4.4]nonan-2-one (14 mg, 0.035 mmol). Isomer 2: Recovered (5R,7S)-7-(6-(2-methoxyphenethyl)-5,6,7,8-tetrahydronaphthalen-2-yl)-3-oxa-1-azaspiro[4.4]nonan-2-one (14 mg, 0.035 mmol).

Example 681

To a mixture of (5R,7S)-7-(6-(5-methoxypentyl)-5,6,7,8-tetrahydronaphthalen-2-yl)-3-oxa-1-azaspiro[4.4]nonan-2-one (40 mg, 0.108 mmol) in DMSO (0.5 mL) and MeOH (1 mL) was added 1N NaOH (0.5 mL). The reaction mixture was heated at 95° C. for 4 hours, cooled, and then acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with the correct mass were isolated and freeze-dried overnight to afford ((1R,3S)-1-amino-3-((R)-6-(2-methoxyphenethyl)-5,6,7,8-tetrahydronaphthalen-2-yl) cyclopentyl)methanol, TFA (26 mg, 0.055 mmol). HPLC retention time=8.87 min (condition L); LC/MS M$^{+1}$=380; $^1$H NMR in CD3OD (400 MHz, METHANOL-d$_4$) δ 7.21-7.10 (m, 2H), 7.05-6.96 (m, 3H), 6.91 (d, J=7.9 Hz, 1H), 6.86 (td, J=7.4, 1.0 Hz, 1H), 3.83 (s, 3H), 3.72-3.54 (m, 2H), 3.20-3.03 (m, 1H), 2.97-2.69 (m, 5H), 2.48-2.35 (m, 2H), 2.21-1.86 (m, 5H), 1.80-1.57 (m, 4H), 1.52-1.36 (m, 1H).

Example 682

To a mixture of (5R,7S)-7-(6-(5-methoxypentyl)-5,6,7,8-tetrahydronaphthalen-2-yl)-3-oxa-1-azaspiro[4.4]nonan-2-one (40 mg, 0.108 mmol) in DMSO (0.5 mL) and MeOH (1 mL) was added 1N NaOH (0.5 mL). The reaction mixture was heated at 95° C. for 4 hours, cooled, and then acidified with TFA. The mixture was filtered and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with the correct mass were isolated and freeze-dried overnight to afford ((1R,3S)-1-amino-3-((R)-6-(2-methoxyphenethyl)-5,6,7,8-tetrahydronaphthalen-2-yl)cyclopentyl)methanol, TFA (26 mg, 0.055 mmol). HPLC retention time=8.97 min (condition L); LC/MS M$^{+1}$=380; MS (m+1)=380; $^1$H NMR in CD$_3$OD (400 MHz, METHANOL-d$_4$) δ 7.21-7.10 (m, 2H), 7.04-6.97 (m, 3H), 6.91 (d, J=7.9 Hz, 1H), 6.86 (td, J=7.4, 1.1 Hz, 1H), 3.83 (s, 3H), 3.72-3.54 (m, 2H), 3.19-3.03 (m, 1H), 2.96-2.70 (m, 5H), 2.49-2.35 (m, 2H), 2.20-1.87 (m, 5H), 1.82-1.57 (m, 4H), 1.43 (dtd, J=12.8, 10.5, 6.1 Hz, 1H).

Example 683

((1R,3R)-1-amino-3-((S)-6-(2-methoxyphenethyl)-5,6,7,8-tetrahydronaphthalen-2-yl) cyclopentyl)methanol

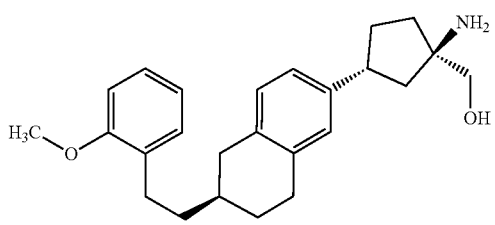

(683)

Preparation 683A: (5R,7R)-7-((S)-6-(2-methoxyphenethyl)-5,6,7,8-tetrahydronaphthalen-2-yl)-3-oxa-1-azaspiro[4.4]nonan-2-one

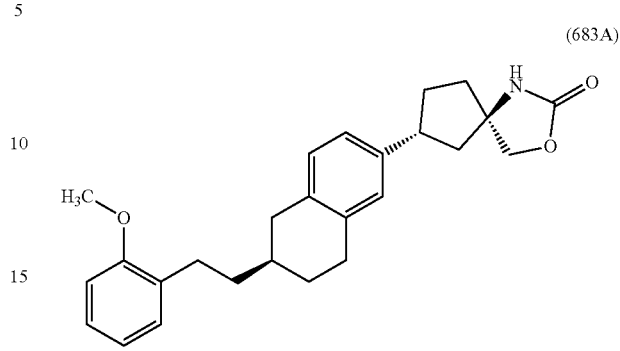

(683A)

The Grignard reagent (2-methoxybenzyl)magnesium chloride (2195 μl, 0.549 mmol) was added to a stirred mixture of ((R)-6-((5R,7R)-2-oxo-3-oxa-1-azaspiro[4.4]nonan-7-yl)-1,2,3,4-tetrahydronaphthalen-2-yl)methyl 4-methylbenzenesulfonate (50 mg, 0.110 mmol) and copper (I) bromide (31.5 mg, 0.220 mmol) in THF (10 ml) at −78° C. under nitrogen. The mixture was stirred at −78° C. and was slowly raised to room temperature and stirred for 2 days. The mixture was heated at 60° C. for another 6 h. The reaction mixture was cooled down to 0° C. Next, 1 ml of water was added and the mixture was mixed with EtOAc (30 ml) and water (20 ml). The organic phase was separated and washed with saturated NH$_4$Cl (2×20 ml) and brine (20 ml). The organic solution was dried over anhydrous sodium sulfate and concentrated. Flash chromatography purification using ISCO (24 g silica gel column, gradient elution from 0 to 60% of EtOAc in hexane) to provide (5R,7R)-7-((S)-6-(2-methoxyphenethyl)-5,6,7,8-tetrahydronaphthalen-2-yl)-3-oxa-1-azaspiro[4.4]nonan-2-one. LC/MS M$^{+1}$=406.

Preparation 683B: ((1R,3R)-1-amino-3-((S)-6-(2-methoxyphenethyl)-5,6,7,8-tetrahydronaphthalen-2-yl)cyclopentyl)methanol

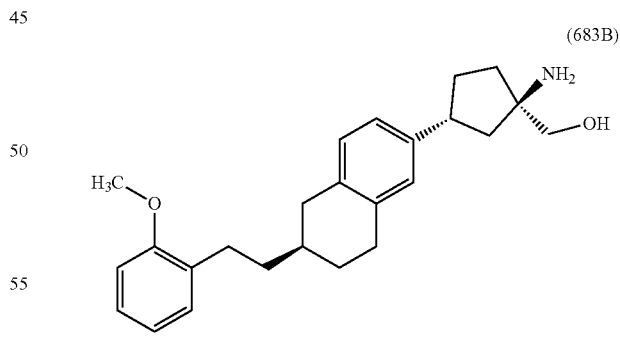

(683B)

(5R,7R)-7-((S)-6-(2-methoxyphenethyl)-5,6,7,8-tetrahydronaphthalen-2-yl)-3-oxa-1-azaspiro[4.4]nonan-2-one was mixed with 1,4-dioxane (2 ml), water (0.5 ml) and lithium hydroxide hydrate (69.1 mg, 1.646 mmol). The mixture was stirred at 100° C. overnight under N$_2$. The mixture was cooled and filtered, the filtrate was concentrated under vacuo and the residue was dissolved in DCM (20 ml), washed with water (5 ml), dried (Na$_2$SO$_4$) and concentrated under vacuo. The residue was freeze dried to afford ((1R,3R)-1-amino-3-

((S)-6-(2-methoxyphenethyl)-5,6,7,8-tetrahydronaphthalen-2-yl)cyclopentyl)methanol (25 mg over two steps). LC/MS M$^{+1}$=380. HPLC condition: L; HPLC ret. time 7.84 (min.). $^{1}$H NMR (400 MHz, METHANOL-d$_4$) δ 7.24-7.09 (m, 2H), 7.03-6.80 (m, 5H), 3.83 (s, 3H), 3.59-3.42 (m, 2H), 2.98-2.67 (m, 5H), 2.40 (dd, J=15.4, 10.6 Hz, 1H), 2.26-1.83 (m, 4H), 1.79-1.54 (m, 6H), 1.50-1.25 (m, 2H).

Example 684

((1R,3S)-1-amino-3-((R)-6-((3-methoxyphenoxy)methyl)-5,6,7,8-tetrahydronaphthalen-2-yl)cyclopentyl)methanol

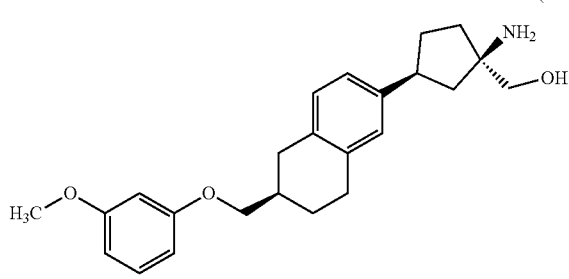

(684)

Preparation 684A: (5R,7S)-7-((R)-6-((3-methoxyphenoxy)methyl)-5,6,7,8-tetrahydronaphthalen-2-yl)-3-oxa-1-azaspiro[4.4]nonan-2-one

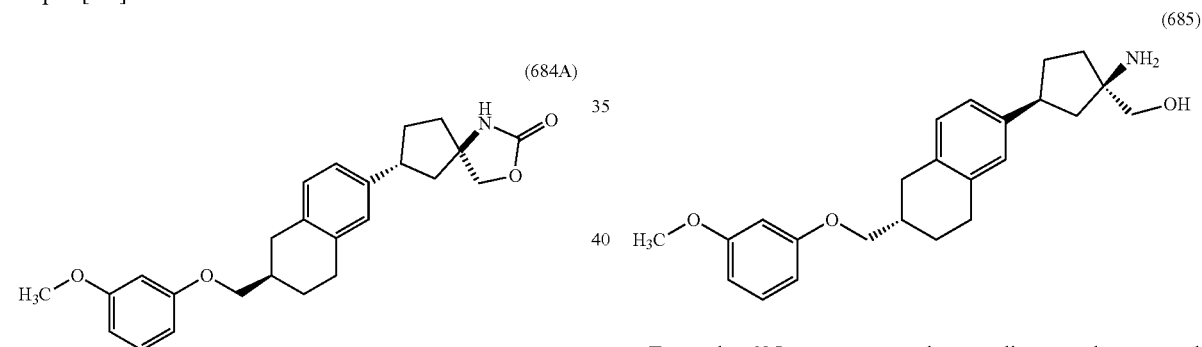

(684A)

To the mixture of 3-methoxyphenol (123 mg, 0.988 mmol) in dry DMF (3 ml), potassium tert-butoxide (790 μl, 0.790 mmol) in t-BuOH (1M) was added. After stirring at room temperature for 30 min, ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (90 mg, 0.198 mmol) in DMF (2 ml) was added and the mixture was stirred at 65° C. for 4 h. The reaction was quenched with water (5 ml) at 0° C. The mixture was taken up in EtOAc (30 ml), washed with saturated NaHCO$_3$(3×20 ml), dried (Na$_2$SO$_4$) and concentrated under vacuo. The residue was subject to flash chromatography purification (12 g silica gel column, gradient elution from 0 to 70% ethyl acetate in hexanes, gradient time=18 min, out at 45% EtOAc) to afford (5R,7S)-7-((R)-6-((3-methoxyphenoxy)methyl)-5,6,7,8-tetrahydronaphthalen-2-yl)-3-oxa-1-azaspiro[4.4]nonan-2-one (70 mg). LC/MS M$^{+1}$=408.

Example 684

(5R,7S)-7-((R)-6-((3-methoxyphenoxy)methyl)-5,6,7,8-tetrahydronaphthalen-2-yl)-3-oxa-1-azaspiro[4.4]nonan-2-one (25 mg, 0.061 mmol) in dioxane (2 ml) was mixed with water (0.5 ml) and was added lithium hydroxide hydrate (25.7 mg, 0.613 mmol), the mixture was stirred at 100° C. for 16 h under N$_2$. After cooling, the mixture was filtered and washed with MeOH, the combined solvents were evaporated and the residue was purified with preparative HPLC: column Phenomenex Luna C18 5 u 21.2×100 mm. Solvent A: 10% MeOH-90% H$_2$O-0.1% TFA; Solvent B: 90% MeOH-10% H$_2$O-0.1% TFA. Gradient time=15 min. Start B=0%, Final B 100%. Stop time 20 min. The collected fraction was basified with saturated NaHCO$_3$, concentrated under vacuo and the aqueous layer was extracted with DCM (3×20 ml) which was dried (Na$_2$SO$_4$) and concentrated under vacuo to give ((1R,3S)-1-amino-3-((R)-6-((3-methoxyphenoxy)methyl)-5,6,7,8-tetrahydronaphthalen-2-yl)cyclopentyl)methanol (15 mg) as white solid. LC/MS M$^{+1}$=382. HPLC retention time=7.19 minutes (Condition L)$^{1}$H NMR (400 MHz, METHANOL-d$_4$) δ 7.25-7.12 (m, 1H), 7.07-6.96 (m, 3H), 6.59-6.47 (m, 3H), 3.94 (d, J=6.4 Hz, 2H), 3.79 (s, 3H), 3.65-3.48 (m, 2H), 3.15-2.80 (m, 4H), 2.59 (dd, J=16.4, 10.5 Hz, 1H), 2.40-1.79 (m, 7H), 1.70-1.51 (m, 2H).

Example 685

((1R,3S)-1-amino-3-((S)-6-((3-methoxyphenoxy)methyl)-5,6,7,8-tetrahydronaphthalen-2-yl)cyclopentyl)methanol (685)

Example 685 was prepared according to the general procedure for Example 684 using (5R,7S)-7-((R)-6-((3-methoxyphenoxy)methyl)-5,6,7,8-tetrahydronaphthalen-2-yl)-3-oxa-1-azaspiro[4.4]nonan-2-one. MW 381.2; MS (M$^{+1}$)=382; HPLC method L, HPLC ret. time: 8.20 min.

Examples 686 and 687

((1R,3R)-1-amino-3-(6-((3-methoxyphenoxy)methyl)-5,6,7,8-tetrahydronaphthalen-2-yl)cyclopentyl)methanol

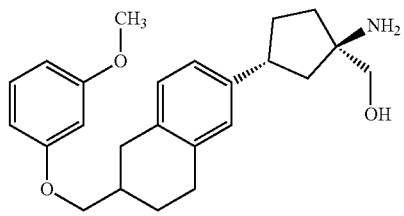 [SMILES: COc1cccc(OCC2CCc3cc([C@@H]4CC[C@](N)(CO)C4)ccc3C2)c1]

Preparation 686A: (E)-2-(4-((5R,7R)-2-oxo-3-oxa-1-azaspiro[4.4]nonan-7-yl)benzylidene) succinic acid

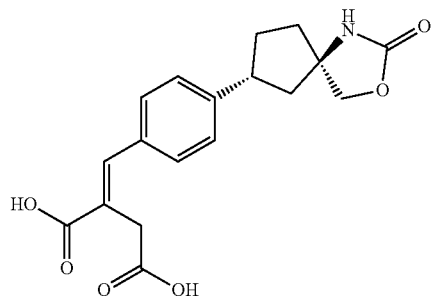

(686A)

To a mixture of K₂CO₃ (0.980 g, 7.09 mmol), (5R,7R)-7-(4-bromophenyl)-3-oxa-1-azaspiro[4.4]nonan-2-one (1.5 g, 5.06 mmol), and itaconic acid (0.857 g, 6.58 mmol) in acetonitrile (14.98 ml) was slowly added water (4.50 ml). The mixture was stirred until the evolution of $CO_2$ stopped and then bubbled with nitrogen for 5 min. Palladium(II) acetate (0.057 g, 0.253 mmol) and tri-o-tolylphosphine (0.154 g, 0.506 mmol) were then added. Nitrogen was bubbled through the reaction mixture for 10 more minutes. The reaction mixture was heated at 85° C. overnight with a reflux condenser. The reaction was complete according to LCMS. The reaction mixture was diluted with ethyl acetate and washed with 1N NaOH twice. The aqueous layers were combined and acidified with concentrated HCl to pH was 1-2. The aqueous layer was extracted with EtOAC several times. The organic layers were combined, dried with Na₂SO₄, filtered, and concentrated under reduced pressure to afford (E)-2-(4-((5R,7R)-2-oxo-3-oxa-1-azaspiro[4.4]nonan-7-yl)benzylidene)succinic acid (1.907 g, 5.52 mmol). HPLC retention time=0.63 min (condition G) LC/MS $M^{+1}$=346.3.

Preparation 686B: 2-(4-((5R,7R)-2-oxo-3-oxa-1-azaspiro[4.4]nonan-7-yl)benzyl)succinic acid

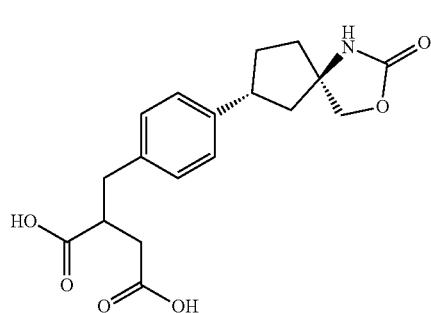

(686B)

To a mixture of (E)-2-(4-((5R,7R)-2-oxo-3-oxa-1-azaspiro[4.4]nonan-7-yl) benzylidene)succinic acid (1.75 g, 5.07 mmol) in MeOH (100 mL) was added Pearlman's Catalyst (0.356 g, 0.507 mmol). The reaction mixture was stirred under an atmosphere of H₂ overnight. LCMS showed complete conversion. The catalyst was removed by filtration through celite and 2-(4-((5R,7R)-2-oxo-3-oxa-1-azaspiro[4.4]nonan-7-yl)benzyl)succinic acid (2 g, 5.76 mmol) was obtained after concentration under reduced pressure. HPLC retention time=0.63 min (condition G) LC/MS $M^{+1}$=348.3.

Preparation 686C: Methyl 4-oxo-6-((5R,7R)-2-oxo-3-oxa-1-azaspiro[4.4]nonan-7-yl)-1,2,3,4-tetrahydronaphthalene-2-carboxylate

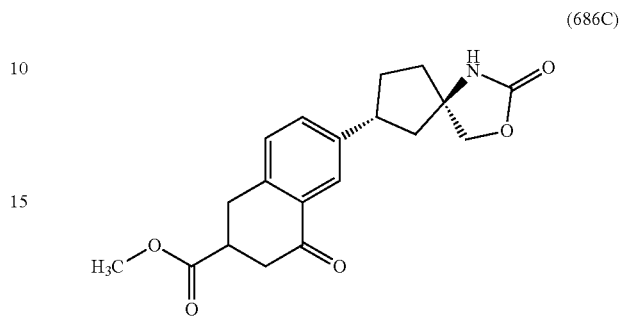

(686C)

To sulfuric acid (30 mL) was added 2-(4-((5R,7R)-2-oxo-3-oxa-1-azaspiro[4.4]nonan-7-yl)benzyl)succinic acid (1.761 g, 5.07 mmol). The solution was stirred overnight at room temperature. LCMS showed complete conversion. The solution was cooled to 0° C. followed by the dropwise addition of MeOH (25.4 ml). After 2 hours, the reaction was complete as judged by LCMS. The reaction mixture was poured onto ice and the aqueous layer was extracted with EtOAC several times until aqueous layer showed no desired product as judged by LCMS. The resulting solid was purified by ISCO using 100% hexanes to 100% EtOAc as eluent affording methyl 4-oxo-6-((5R,7R)-2-oxo-3-oxa-1-azaspiro[4.4]nonan-7-yl)-1,2,3,4-tetrahydronaphthalene-2-carboxylate (1.54 g, 4.48 mmol). HPLC retention time=0.74 min (condition G) LC/MS $M^{+1}$=344.3. ¹H NMR (400 MHz, CHLOROFORM-d) δ 7.89 (d, J=1.8 Hz, 1H), 7.38 (dd, J=7.9, 2.0 Hz, 1H), 7.26 (d, J=7.7 Hz, 1H), 6.48 (br. s., 1H), 4.45-4.32 (m, 3H), 3.79-3.71 (m, 3H), 3.37-3.16 (m, 4H), 3.05-2.91 (m, 1H), 2.91-2.81 (m, 1H), 2.43 (dd, J=13.6, 7.5 Hz, 1H), 2.35-2.22 (m, 1H), 2.22-2.14 (m, 1H), 2.11-2.00 (m, 1H), 1.94-1.82 (m, 1H), 1.82-1.70 (m, 1H).

Preparation 686D: Methyl 6-((5R,7R)-2-oxo-3-oxa-1-azaspiro[4.4]nonan-7-yl)-1,2,3,4-tetrahydronaphthalene-2-carboxylate

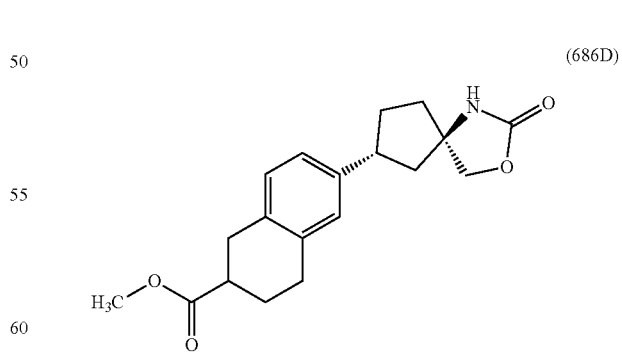

(686D)

To a solution of methyl 4-oxo-6-((5R,7R)-2-oxo-3-oxa-1-azaspiro[4.4]nonan-7-yl)-1,2,3,4-tetrahydronaphthalene-2-carboxylate (1.54 g, 4.48 mmol) in EtOH (44.8 ml) was added Pd(OH)₂ (0.630 g, 0.448 mmol). The reaction mixture was placed under a hydrogen atmosphere overnight. LCMS showed complete conversion. The mixture was filtered through celite to remove the catalyst and the solution was concentrated under reduced pressure to afford methyl 6-((5R,7R)-2-oxo-3-oxa-1-azaspiro[4.4]nonan-7-yl)-1,2,3,4-tetrahydronaphthalene-2-carboxylate (1.45 g, 4.40 mmol). HPLC retention time=0.87 min (condition G) LC/MS M$^{+1}$=330.3.

Preparation 686E: (5R,7R)-7-(6-(hydroxymethyl)-5,6,7,8-tetrahydronaphthalen-2-yl)-3-oxa-1-azaspiro[4.4]nonan-2-one

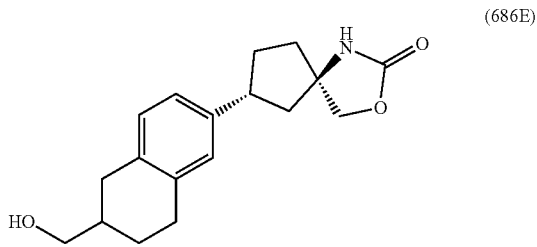 [SMILES: O=C1N[C@@]2(CC[C@@H](c3ccc4c(c3)CCC(CO)C4)C2)CO1]

(686E)

To a mixture of methyl 6-((5R,7R)-2-oxo-3-oxa-1-azaspiro[4.4]nonan-7-yl)-1,2,3,4-tetrahydronaphthalene-2-carboxylate (1.35 g, 4.10 mmol) in THF (100 mL) was added lithium borohydride in THF (4.10 ml, 8.20 mmol). The reaction mixture was heated at 60° C. overnight. The mixture was cooled and the reaction was quenched with water. The reaction mixture was diluted with ethyl acetate and washed with H$_2$O. The organic layer was dried with MgSO$_4$, filtered, and concentrated to afford (5R,7R)-7-(6-(hydroxymethyl)-5,6,7,8-tetrahydronaphthalen-2-yl)-3-oxa-1-azaspiro[4.4]nonan-2-one (1 g, 3.32 mmol). HPLC retention time=0.74 min (condition G) LC/MS M$^{+1}$=302.1; Separation of Isomers:
Instrument: Berger SFC MGIII; SFC Prep Conditions Column: ChiralPak AD-H 3×25 cm, 5 um; Column Temp. 40° C.; Flow rate: 200 ml/min; Mobile Phase: CO$_2$/MEOH=60/40; Injection Program: Stacked (2.5 min/Cycle); Sampler Conc. (mg/mL): 40 mg/mL; Detector Wavelength: 220 nm.
Isomer 1: HPLC retention time=0.74 min (condition G) LC/MS M$^{+1}$=302.1. $^1$H NMR (400 MHz, CHLOROFORM-d) δ 7.07 (d, J=7.7 Hz, 1H), 6.99-6.90 (m, 2H), 5.50 (br. s., 1H), 4.35 (q, J=8.5 Hz, 2H), 3.66 (dd, J=6.3, 1.7 Hz, 2H), 3.25-3.09 (m, 1H), 2.95-2.77 (m, 3H), 2.50 (dd, J=16.3, 10.8 Hz, 1H), 2.39 (dd, J=13.6, 7.5 Hz, 1H), 2.27-2.12 (m, 2H), 2.10-1.93 (m, 3H), 1.87 (dd, J=13.6, 11.0 Hz, 1H), 1.81-1.70 (m, 1H), 1.53-1.38 (m, 2H).
Isomer 2: HPLC retention time=0.74 min (condition G) LC/MS M$^{+1}$=302.1.
Preparations 686F and 687F: (6-((5R,7R)-2-oxo-3-oxa-1-azaspiro[4.4]nonan-7-yl)-1,2,3,4-tetrahydronaphthalen-2-yl)methyl 4-methylbenzenesulfonate

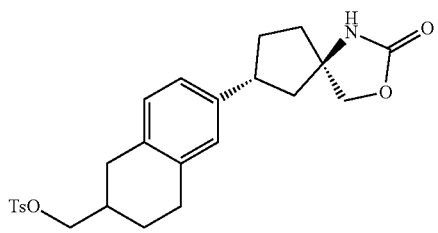 [SMILES: Cc1ccc(S(=O)(=O)OCC2CCc3cc([C@@H]4CC[C@]5(COC(=O)N5)C4)ccc3C2)cc1]

(5R,7R)-7-(6-(hydroxymethyl)-5,6,7,8-tetrahydronaphthalen-2-yl)-3-oxa-1-azaspiro[4.4]nonan-2-one (Isomer 1 of Preparation 686E, 410 mg, 1.360 mmol) was dissolved in dry pyridine (1360 μl) and p-toluenesulfonyl chloride (519 mg, 2.72 mmol) was added in one portion. The resulting mixture was reacted at room temperature for 3 h. The solvent was removed in vacuo. The residue was dissolved in DCM and loaded onto column with plenty DCM (to prevent product crystallization on column). Flash chromatography purification using ISCO (40 g silica gel column, 20->100% ethyl acetate in hexanes) afforded (6-((5R,7R)-2-oxo-3-oxa-1-azaspiro[4.4]nonan-7-yl)-1,2,3,4-tetrahydronaphthalen-2-yl)methyl 4-methylbenzenesulfonate (550 mg, 1.207 mmol).
Preparation 686F (Isomer 1): HPLC retention time=1.00 min (condition G) LC/MS M$^{+1}$=456.1.
Preparation 687F (Isomer 2): HPLC retention time=0.99 min (condition G) LC/MS M$^{+1}$=456.1. $^1$H NMR (400 MHz, CHLOROFORM-d) δ 7.88-7.78 (m, J=8.4 Hz, 2H), 7.43-7.33 (m, J=7.9 Hz, 2H), 7.07-6.98 (m, 1H), 6.94 (d, J=7.9 Hz, 1H), 6.90 (s, 1H), 5.20 (br. s., 1H), 4.41-4.25 (m, 2H), 4.02 (dd, J=6.6, 2.0 Hz, 2H), 3.23-3.07 (m, 1H), 2.92-2.73 (m, 3H), 2.48 (s, 3H), 2.48-2.28 (m, 2H), 2.28-2.10 (m, 3H), 2.06-1.92 (m, 2H), 1.85 (dd, J=13.6, 11.2 Hz, 1H), 1.78-1.65 (m, 1H), 1.60-1.55 (m, 1H), 1.50-1.36 (m, 1H).

Examples 686 and 687

To a suspension of (6-((5R,7R)-2-oxo-3-oxa-1-azaspiro[4.4]nonan-7-yl)-1,2,3,4-tetrahydronaphthalen-2-yl)methyl 4-methylbenzenesulfonate (Preparation 686F, 0.030 g, 0.066 mmol) in dioxane (0.5 mL) was added 3-methoxyphenol (0.108 ml, 0.988 mmol) followed by potassium tert-butoxide (0.074 g, 0.659 mmol) at room temperature. The mixture was then heated at 70° C. for 2 h when LCMS showed complete consumption of starting material. To this solution was added NaOH (0.5 mL, 0.500 mmol) at room temperature. The mixture was heated to 100° C. overnight. LCMS showed complete consumption of starting material. The solution was injected on the HPLC prep: condition=2 mL injection, gradient time of 5 min, start B=20% to 100%, stop time of 15 min, Solvent A=0.1% TFA in water, Solvent B=0.1% TFA in MeCN, column=LUNA, wavelength of 220 nm. ((1R,3R)-1-amino-3-(6-((3-methoxyphenoxy)methyl)-5,6,7,8-tetrahydronaphthalen-2-yl)cyclopentyl)methanol, TFA (21 mg, 0.040 mmol) was obtained as a white solid with >95% purity.
Example 687 was prepared from Preparation 687F according to the general procedure of Example 686.
Example 686 (Isomer 1): HPLC retention time=8.19 min (condition L) LC/MS M$^{+1}$=382.1; $^1$H NMR (400 MHz, METHANOL-d$_4$) δ 7.22-7.12 (m, 1H), 7.09-7.03 (m, 1H), 7.03-6.97 (m, 2H), 6.59-6.48 (m, 3H), 3.94 (d, J=6.4 Hz, 2H), 3.79 (s, 3H), 3.65 (dd, J=11.9, 6.4 Hz, 2H), 2.96 (dd, J=16.6, 5.0 Hz, 1H), 2.90-2.82 (m, 2H), 2.60 (dd, J=16.3, 10.3 Hz, 1H), 2.33-2.14 (m, 4H), 2.11 (s, 1H), 1.90-1.72 (m, 3H), 1.61 (s, 1H).
Example 687 (Isomer 2): HPLC retention time=8.17 min (condition L) LC/MS M$^{+1}$=382.1; $^1$H NMR (400 MHz, METHANOL-d$_4$) δ 7.22-7.12 (m, 1H), 7.09-7.03 (m, 1H), 7.03-6.97 (m, 2H), 6.59-6.48 (m, 3H), 3.94 (d, J=6.4 Hz, 2H), 3.79 (s, 3H), 3.65 (dd, J=11.9, 6.4 Hz, 2H), 2.96 (dd, J=16.6, 5.0 Hz, 1H), 2.90-2.82 (m, 2H), 2.60 (dd, J=16.3, 10.3 Hz, 1H), 2.33-2.14 (m, 4H), 2.11 (s, 1H), 1.90-1.72 (m, 3H), 1.61 (s, 1H).

PHOSPHORYLATED EXAMPLES

Example 688

((1R,3S)-1-amino-3-((R)-6-((3-methoxyphenoxy)methyl)-5,6,7,8-tetrahydronaphthalen-2-yl)cyclopentyl)methyl dihydrogen phosphate (688)

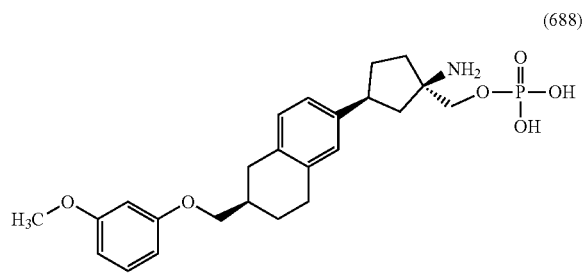 [SMILES: COc1cccc(OC[C@@H]2CCc3cc([C@H]4CC[C@](N)(COP(=O)(O)O)C4)ccc3C2)c1]

To a mixture of ((1R,3S)-1-amino-3-((R)-6-((3-methoxyphenoxy)methyl)-5,6,7,8-tetrahydronaphthalen-2-yl)cyclopentyl)methanol (1.5 mg, 3.93 μmol) in MeCN (1 ml) was added pyridine (15.90 μl, 0.197 mmol) and pyrophosphoryl chloride (14.85 mg, 0.059 mmol) at room temperature. The mixture was stirred at room temperature for 2 h. Water (0.5 ml) was added at 0° C. and the mixture was stirred at room temperature for 15 min. The mixture was purified with preparative (HPLC: column Phenomenex Luna C18 5 u 21.2×100 mm. Solvent A: 10% MeOH-90% $H_2O$-0.1% TFA; Solvent B: 90% MeOH-10% $H_2O$-0.1% TFA. Gradient time=15 min. Start B=0%, Final B 100%. Stop time 25 min.) to afford 1 mg of ((1R,3S)-1-amino-3-((R)-6-((3-methoxyphenoxy)methyl)-5,6,7,8-tetrahydronaphthalen-2-yl)cyclopentyl) methyl dihydrogen phosphate, LC/MS $M^{+1}$=462. HPLC Rt=7.07 min. (Condition L). $^1$H NMR (400 MHz, METHANOL-$d_4$) δ 7.17 (t, J=8.4 Hz, 1H), 7.04 (d, J=2.9 Hz, 3H), 6.60-6.46 (m, 3H), 4.04-3.86 (m, 4H), 3.79 (s, 3H), 3.15 (s, 1H), 3.00-2.81 (m, 2H), 2.66-2.48 (m, 2H), 2.33-1.90 (m, 8H), 1.82-1.68 (m, 1H).

The following compounds were prepared according to the general procedures of Example 688

| Ex. No. | Structure | MW | HPLC ret. time (min.) | HPLC condition | MS ($M^{+1}$) | Comment |
|---|---|---|---|---|---|---|
| 689 | 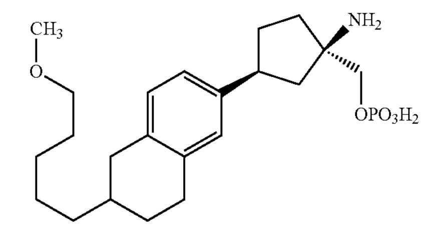 | 425.5 | 0.81 | G | 426 | (S) Isomer 1 |
| 690 | | 425.5 | 0.82 | G | 426 | (R) Isomer 2 |
| 691 | 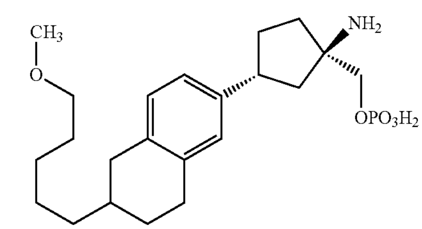 | 425.5 | 1.01 | B | 426 | Isomer 1 |
| 692 | | 425.5 | 1.01 | B | 426 | Isomer 2 |
| 693 | 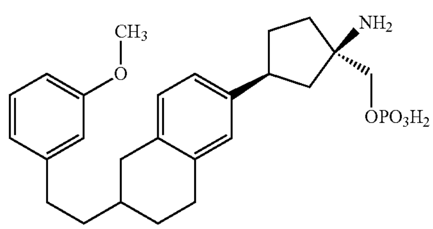 | 459.5 | 0.87 | G | 460 | (S) Isomer 1 |
| 694 | | 459.5 | 0.86 | G | 460 | (R) Isomer 2 |
| 695 | 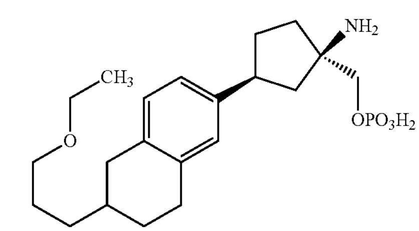 | 411.5 | 0.77 | G | 412 | (R) Isomer 1 |
| 696 | | 411.5 | 0.77 | G | 412 | (S) Isomer 2 |

| Ex. No. | Structure | MW | HPLC ret. time (min.) | HPLC condition | MS (M⁺¹) | Comment |
|---|---|---|---|---|---|---|
| 697 | 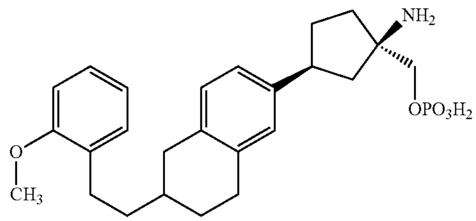 | 459.5 | 0.88 | G | 460 | (S) Isomer 1 |
| 698 | | 459.5 | 0.88 | G | 460 | (R) Isomer 2 |
| 699 | 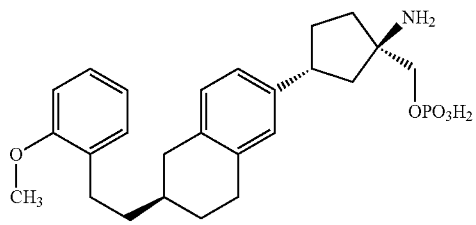 | 459.5 | 7.79 | L | 460 | (S) Isomer |
| 700 | 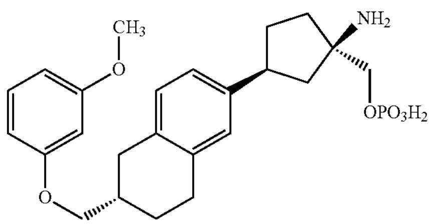 | 461.5 | 8.21 | L | 462 | (S) Isomer |
| 701 | 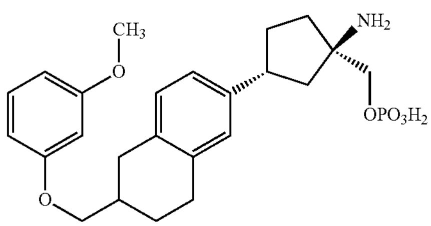 | 461.5 | 0.82 | G | 462 | Isomer 1 |
| 702 | | 461.5 | 0.82 | G | 462 | Isomer 2 |

Alternative Preparation of Example 672

To a stirred mixture of magnesium (1.814 g, 74.6 mmol) and anhydrous tetrahydrofuran (3 mL) was added several drops of 1,2-dibromoethane at room temperature under nitrogen. The mixture was stirred for 15 min before a solution of 1-bromo-4-methoxybutane (9.76 mL, 74.6 mmol) in anhydrous tetrahydrofuran (47 mL) was added dropwise to keep the reaction mixture warm but not boiling. After the addition, the mixture was stirred at 60° C. under nitrogen for 3 hr. The solution was separated and added to a stirred mixture of copper(I) bromide (1.071 g, 7.46 mmol), ((S)-6-((5R,7S)-2-oxo-3-oxa-1-azaspiro[4.4]nonan-7-yl)-1,2,3,4-tetrahydronaphthalen-2-yl)methyl 4-methylbenzenesulfonate (1.7 g, 3.73 mmol) and tetrahydrofuran (10 mL) at −78° C. under nitrogen. The mixture was stirred at −78° C. for 20 min before the temperature was slowly raised to room temperature. The mixture was stirred at room temperature for 16 hr. The reaction mixture was cooled to 0° C. and saturated aqueous NH₄Cl was added to quench the reaction. The reaction mixture was diluted with ethyl acetate and washed with saturated aqueous NH₄Cl. The organic layer was dried with MgSO₄, filtered and concentrated. The crude material was purified on a silica gel cartridge (40 g) using an EtOAc/Hex gradient (0-100% EtOAc over 20 CV) to afford (5R,7S)-7-((S)-6-(5-methoxypentyl)-5,6,7,8-tetrahydronaphthalen-2-yl)-3-oxa-1-azaspiro[4.4]nonan-2-one (1.3 g, 3.50 mmol). HPLC retention time=1.09 min (condition A); LC/MS M⁺¹=372.5.

To a mixture of (5R,7S)-7-((S)-6-(5-methoxypentyl)-5,6,7,8-tetrahydronaphthalen-2-yl)-3-oxa-1-azaspiro[4.4]nonan-2-one (680 mg, 1.830 mmol) in dioxane (20 mL) was added 1N NaOH (10 mL). The reaction mixture was heated at 95° C. After stirring two days, the reaction mixture was cooled, diluted with ethyl acetate, and washed with saturated NaCl. The organic layer was dried with MgSO₄, filtered and concentrated to afford 450 mg of Example 672 as a white solid. HPLC retention time=7.1 min (condition L); LC/MS M⁺¹=346.

Alternative Preparation of Example 677

To a mixture of ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (440 mg, 0.966 mmol) and copper(I) bromide (277 mg, 1.932 mmol) in THF (10 mL) at 0° C. was added (3-methoxybenzyl)magnesium chloride (35 ml, 8.75 mmol). The mixture was stirred at 0° C. and was slowly raised to room temperature and stirred overnight.

The reaction mixture was cooled down to 0° C., 1 ml of water was added and the mixture was mixed with EtOAc (80 ml) and water (20 ml). The organic phase was separated and washed with saturated NH$_4$Cl (3×30 ml) and brine (20 ml). The organic solution was dried over anhydrous sodium sulfate and concentrated. Flash chromatography purification using ISCO (40 g silica gel column, gradient elution from 0 to 100% of EtOAc/hexane for 13CV. Product containing fractions were isolated. Recovered (5R,7S)-7-((R)-6-(3-methoxyphenethyl)-5,6,7,8-tetrahydronaphthalen-2-yl)-3-oxa-1-azaspiro[4.4]nonan-2-one (370 mg, 0.912 mmol). HPLC retention time=1.14 min (condition A); LC/MS M$^{+1}$=406.

To a mixture of (5R,7S)-7-((R)-6-(3-methoxyphenethyl)-5,6,7,8-tetrahydronaphthalen-2-yl)-3-oxa-1-azaspiro[4.4]nonan-2-one (370 mg, 0.912 mmol) in dioxane (20 mL) was added 1N NaOH. The reaction mixture was heated at 95° C. overnight, cooled, diluted with ethyl acetate, and then washed with saturated NaCl. The organic layer was dried with MgSO$_4$, filtered and concentrated. The resulting solid was triturated in MeCN and allowed to stir overnight. The mixture was filtered and the resulting solid material was dried in vacuo to afford 255 mg of Example 677. HPLC retention time=7.73 min (condition L); LC/MS M$^{+1}$=380.
Alternative Preparation 1 of Example 679

A 1.0M THF solution of allylmagnesium bromide (8.78 mL, 8.78 mmol) was added to a stirred mixture of copper(I) bromide (126 mg, 0.878 mmol), ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (200 mg, 0.439 mmol) and anhydrous tetrahydrofuran (5 mL) at −78° C. under nitrogen. The mixture was stirred at −78° C. for 20 min before the temperature was raised to room temperature over 20 min. The mixture was stirred at room temperature for 5 hr. Saturated aqueous NH$_4$Cl solution (5 mL) was added slowly to quench the reaction. Hexanes (7 mL) and water (1 mL) were added. The aqueous layer was separated and extracted with ethyl acetate (2×3 mL). The combined organic solutions were dried over sodium sulfate and concentrated under reduced pressure. Flash chromatography purification using ISCO (4 g silica gel column, gradient elution from 0 to 100% of ethyl acetate in hexanes) afforded (5R,7S)-7-((R)-6-(but-3-en-1-yl)-5,6,7,8-tetrahydronaphthalen-2-yl)-3-oxa-1-azaspiro[4.4]nonan-2-one (90 mg, 0.277 mmol). HPLC retention time=1.14 min (condition A); LC/MS M$^{+1}$=326.

To a clear solution of (5R,7S)-7-((R)-6-(but-3-en-1-yl)-5,6,7,8-tetrahydronaphthalen-2-yl)-3-oxa-1-azaspiro[4.4]nonan-2-one (560 mg, 1.721 mmol) in THF (30 mL) were sequentially added 50% NMO (403 mg, 3.44 mmol) and osmium tetroxide in t-BuOH (0.647 mL, 0.052 mmol) at room temperature. The solution was vigorously stirred at room temperature overnight. Sodium periodate (1472 mg, 6.88 mmol) in H$_2$O (15 mL) was added. The mixture was stirred vigorously at room temperature under nitrogen for 30 min. The mixture was extracted with ethyl acetate (3×2 mL). The combined ethyl acetate extracts were dried (Na$_2$SO$_4$) and concentrated. Flash chromatography purification using ISCO (40 g silica gel column, gradient elution from 20 to 100% of ethyl acetate in hexanes) afforded 3-((S)-6-((5R,7S)-2-oxo-3-oxa-1-azaspiro[4.4]nonan-7-yl)-1,2,3,4-tetrahydronaphthalen-2-yl)propanal (440 mg, 1.344 mmol). NMR was consistent with desired product. HPLC retention time=0.91 min (condition A); LC/MS M$^{+1}$=328.

To a stirred solution of 3-((S)-6-((5R,7S)-2-oxo-3-oxa-1-azaspiro[4.4]nonan-7-yl)-1,2,3,4-tetrahydronaphthalen-2-yl)propanal (700 mg, 2.138 mmol), ethoxytrimethylsilane (1.670 mL, 10.69 mmol), and triethylsilane (1.707 mL, 10.69 mmol) in nitromethane (5 mL) was added ferric chloride (34.7 mg, 0.214 mmol) at 0° C. under nitrogen. The mixture was stirred at 0° C. for 15 min and at room temperature for 12 hours. The reaction mixture was diluted with ethyl acetate and washed with saturated NaCl. The organic layer was dried with MgSO$_4$, filtered and concentrated. The crude material was purified on a silica gel cartridge (40 g) using an EtOAc/Hex gradient (0-100% EtOAc over 12 CV). Recovered (5R,7S)-7-((S)-6-(3-ethoxypropyl)-5,6,7,8-tetrahydronaphthalen-2-yl)-3-oxa-1-azaspiro[4.4]nonan-2-one (660 mg, 1.846 mmol). HPLC retention time=1.06 min (condition A); LC/MS M$^{+1}$=356.

To a mixture of (5R,7S)-7-((S)-6-(3-ethoxypropyl)-5,6,7,8-tetrahydronaphthalen-2-yl)-3-oxa-1-azaspiro[4.4]nonan-2-one (250 mg, 0.699 mmol) in dioxane (10 mL) was added 1N NaOH. The reaction mixture was heated at reflux for 48 hrs. The mixture was cooled, diluted with ethyl acetate, and washed with saturated NaCl. The organic layer was dried with MgSO$_4$, filtered, and concentrated. Material was purified in batch by HPLC. HPLC conditions: Phenomenex Luna 5 micron C18 column (30×100 mm); MeCN (0.1% TFA)/water (0.1% TFA); 25%-100% gradient over 15 minutes; 30 mL/min. Fractions with correct mass were isolated, poured into 1N NaOH, extracted with EtOAc (2 times), and then the pooled EtOAc layers were washed with 1 N NaOH one more time. The solution was dried and concentrated in vacuo to afford ((1R,3S)-1-amino-3-((S)-6-(3-ethoxypropyl)-5,6,7,8-tetrahydronaphthalen-2-yl)cyclopentyl)methanol (186 mg, 0.554 mmol. HPLC retention time=7.08 min (condition L); LC/MS M$^{+1}$=332.
Alternative Preparation 2 of Example 679
Preparation of (5R,7S)-7-((R)-6-(hydroxymethyl)-5,6,7,8-tetrahydronaphthalen-2-yl)-3-oxa-1-azaspiro[4.4]nonan-2-one

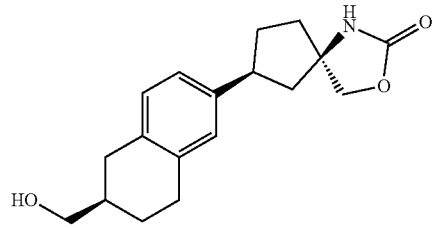 [SMILES: O=C1N[C@@]2(CC[C@H](c3ccc4c(c3)CC[C@@H](CO)C4)C2)CO1]

To a solution of (R)-methyl 6-((5R,7S)-2-oxo-3-oxa-1-azaspiro[4.4]nonan-7-yl)-1,2,3,4-tetrahydronaphthalene-2-carboxylate (40.9 g, 124 mmol) in THF (250 ml) was added a light suspension of calcium chloride (11.1 g, 100 mmol) in EtOH (250 ml) and the resulting solution was cooled to 0° C. Sodium borohydride (7.7 g, 199 mmol) was added and the mixture was stirred at 0° C. for 2.0 h. At this time, the mixture was allowed to warm up to room temperature and stirred for 36.5 h. Then, the mixture was cooled to 0° C. and quenched with phosphate buffer (1.5M KH$_2$PO$_4$+H$_3$PO$_4$ to pH 3, 500 mL, slow initial addition, gas evolution). The aqueous mixture was stirred at room temperature for 3.0 h and then mixed with CH$_2$Cl$_2$ (700 mL) in a separatory funnel. The pH of the aqueous layer was adjusted to 3 by addition of 6M HCl and the biphasic mixture was shaken. The organic layer was collected and the aqueous phase was extracted with CH$_2$Cl$_2$ (2×250 mL). The combined organic layers were dried (Na$_2$SO$_4$) and concentrated. The resulting solid was triturated with Et$_2$O and the suspension was filtered through a sintered funnel. The solid was rinsed with Et₂O, dried by suction, collected and dried under vacuum to afford (5R,7S)-7-((R)-6-(hydroxymethyl)-5,6,7,8-tetrahydronaphthalen-2-yl)-3-oxa-1-azaspiro[4.4]nonan-2-one (37.3 g) as a white solid. Analytical HPLC (Gemini method): RT=4.81 min, Area %: 100; LC/MS M⁺¹=302; ¹H NMR (400 MHz, CDCl₃) δ 7.04 (d, J=7.5 Hz, 1H), 6.96 (m, 2H), 5.12 (s, 1H), 4.35 (d, J=8.4 Hz, 1H), 4.30 (d, J=8.4 Hz, 1H), 3.66 (m, 2H), 3.05 (m, 1H), 2.86 (m, 3H), 2.51 (dd, J=16.3, 10.7 Hz, 1H), 2.33 (dd, J=13.3, 7.3 Hz, 1H), 2.15 (m, 2H), 2.00 (m, 4H) 1.84 (m, 1H), 1.52-1.36 (m, 2H).

Preparation of (R)-6-((5R,7S)-2-oxo-3-oxa-1-azaspiro[4.4]nonan-7-yl)-1,2,3,4-tetrahydronaphthalene-2-carbaldehyde

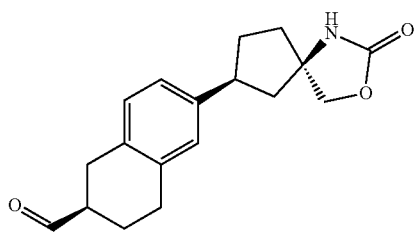 [SMILES: O=C[C@@H]1CCc2cc([C@H]3CC[C@]4(COC(=O)N4)C3)ccc2C1]

A 2M oxalyl chloride/CH₂Cl₂ solution (25.0 ml, 50.0 mmol) was diluted with CH₂Cl₂ (100 ml) and cooled to −78° C. while stirring. DMSO (7.1 ml, 100 mmol) was slowly added to the resulting solution and the mixture was stirred at −78° C. for 30 min. Then, a cloudy solution of (5R,7S)-7-((R)-6-(hydroxymethyl)-5,6,7,8-tetrahydronaphthalen-2-yl)-3-oxa-1-azaspiro[4.4]nonan-2-one (10.0 g, 33.3 mmol) in CH₂Cl₂ (50 ml) and DMSO (8.0 ml) was added over a 25 min period. After the addition was complete, stirring at −78° C. was continued for 30 min and after this time, triethylamine (14.0 ml, 100 mmol) was added dropwise over a 15 min period. The reaction mixture was stirred for 1.5 h at −78° C. and for 30 min while warming up to 0° C. The reaction was quenched at 0° C. with 1M KH₂PO₄ (150 mL). The biphasic mixture was shaken in a separatory funnel. The organic layer was washed with water (150 mL) and saturated NaCl (150 mL), dried (Na₂SO₄) and concentrated. Further drying under vacuum gave (R)-6-((5R,7S)-2-oxo-3-oxa-1-azaspiro[4.4]nonan-7-yl)-1,2,3,4-tetrahydronaphthalene-2-carbaldehyde (10.6 g, 31.5 mmol) as a colorless solid. Analytical HPLC (Gemini method): RT=5.77 min, Area %: 89; LC/MS M⁺¹=300; ¹H NMR (400 MHz, CDCl₃) 9.81 (d, J=1.1 Hz, 1H), 7.12 (d, J=7.9 Hz, 1H), 7.00 (dd, J=7.9, 1.6 Hz, 1H), 6.96 (s, 1H), 5.45 (s, 1H), 4.35 (d, J=8.4 Hz, 1H), 4.29 (d, J=8.4 Hz, 1H), 3.11-2.79 (m, 5H), 2.73 (m, 1H), 2.33 (dd, J=13.4, 7.4 Hz, 1H), 2.24 (m, 1H), 2.15 (m, 2H), 2.02-1.91 (m, 2H), 1.89-1.76 (m, 2H).

Preparation of (2-ethoxyethyl)triphenylphosphonium bromide

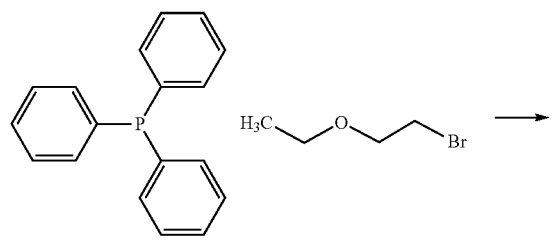

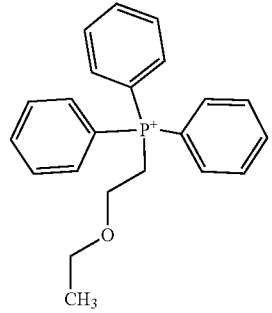

To a 3-necked round bottom flask equipped with a mechanic stirrer was charged with triphenylphosphine (41.7 g, 159 mmol) and toluene (550 mL). The solution was added 1-bromo-2-ethoxyethane (22.11 mL, 176 mmol) under N₂ at room temperature. The reaction mixture was heated to 95° C. for 18 hrs. The solid was formed during the reaction. After 18 hours, the reaction mixture was cooled down to room temperature and stirred for 30 minutes. The slurry was filtered, rinsed with toluene (2×100 ml) and dried under high vacuo to give (2-ethoxyethyl)triphenylphosphonium bromide (60.1 g, 145 mmol) as an off-white solid. LC/MS M⁺¹=336.

Preparation of (5R,7S)-7-((R)-6-((Z)-3-ethoxyprop-1-en-1-yl)-5,6,7,8-tetrahydronaphthalen-2-yl)-3-oxa-1-azaspiro[4.4]nonan-2-one

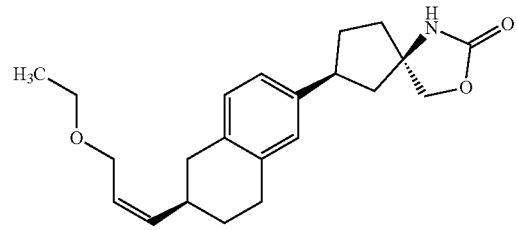 [SMILES: CCOC/C=C\[C@@H]1CCc2cc([C@H]3CC[C@]4(COC(=O)N4)C3)ccc2C1]

1M Potassium tert-butoxide (48.6 mL, 48.6 mmol) was added over a 20 min period to a suspension of (2-ethoxyethyl)triphenylphosphonium bromide (20.8 g, 50.1 mmol) in THF (205 mL) at −78° C. and under Ar. After the addition was complete, the mixture was stirred at −78° C. for 30 min and then, a solution of (R)-6-((5R,7S)-2-oxo-3-oxa-1-azaspiro[4.4]nonan-7-yl)-1,2,3,4-tetrahydronaphthalene-2-carbaldehyde (10.6 g, 31.5 mmol) in CH₂Cl₂ (69 ml) was added dropwise over a 40 min period. The mixture was stirred for 17.5 h while slowly warming up to 19° C. After cooling the reaction mixture to 0° C., 1M KH₂PO₄ (100 mL) was added. The resulting aqueous mixture was stirred at room temperature for 30 min and then extracted with EtOAc (300 mL). The organic extract was washed with water (100 mL) and saturated NaCl (100 mL), dried (Na₂SO₄) and concentrated. The crude was purified by chromatography (SiO₂ 750 g gold RediSep column, 0 to 40% acetone/hexanes) to afford (5R,7S)-7-((R)-6-((Z)-3-ethoxyprop-1-en-1-yl)-5,6,7,8-tetrahydronaphthalen-2-yl)-3-oxa-1-azaspiro[4.4]nonan-2-one (8.93 g) as a white solid. Analytical HPLC (Gemini method): RT=8.65 min, Area %: 97; LC/MS M⁺¹=356; ¹H NMR (400 MHz, CDCl₃) 7.04 (d, J=7.7 Hz, 1H), 6.97 (m, 2H), 5.59 (m, 2H), 5.10 (s, 1H), 4.35 (d, J=8.4 Hz, 1H), 4.30 (d, J=8.4 Hz, 1H), 4.09 (d, J=5.2 Hz, 2H), 3.52 (q, J=7.0 Hz, 2H), 3.05 (m, 1H), 2.85 (dd, J=8.3, 4.5 Hz, 2H), 2.83-2.71 (m, 2H), 2.57 (m, 1H), 2.34 (dd, J=13.4, 7.4 Hz, 1H), 2.21-2.08 (m, 2H), 2.05-1.77 (m, 2H), 1.61 (m, 1H), 1.24 (t, J=6.9 Hz, 3H).

Preparation of (5R,7S)-7-((S)-6-(3-ethoxypropyl)-5,6,7,8-tetrahydronaphthalen-2-yl)-3-oxa-1-azaspiro[4.4]nonan-2-one

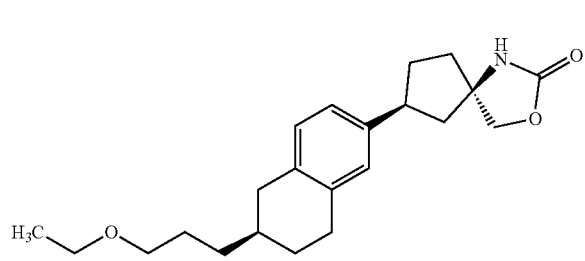 [SMILES: CCOCCC[C@@H]1CCc2cc([C@H]3CC[C@]4(COC(=O)N4)C3)ccc2C1]

To a stirred solution of (5R,7S)-7-((R)-6-((Z)-3-ethoxyprop-1-en-1-yl)-5,6,7,8-tetrahydronaphthalen-2-yl)-3-oxa-1-azaspiro[4.4]nonan-2-one (10.8 g, 28.9 mmol) in THF (275 ml) was added platinum(IV) oxide (0.408 g, 1.797 mmol). The resulting suspension was stirred under hydrogen (1 atm, balloon) for 10.0 h. The suspension was filtered through Celite and the filter cake was rinsed with $CH_2Cl_2$ (200 mL) and MeOH (80 mL). The filtrate and rinses were combined and evaporated to give crude (5R,7S)-7-((S)-6-(3-ethoxypropyl)-5,6,7,8-tetrahydronaphthalen-2-yl)-3-oxa-1-azaspiro[4.4]nonan-2-one (10.6 g) as a brownish solid. Analytical HPLC (Gemini method): RT=9.29 min, Area %: 92.

The above crude material was filtered through a short pad of $SiO_2$ (230-400 mesh) eluting with 4/1 to 7/3 $CH_2Cl_2$/EtOAc to obtain 10.0 g of a material that contained a hydrogenolysis byproduct and an epimeric impurity not resolved by the above HPLC conditions. This later material was purified by SFC to afford (5R,7S)-7-((S)-6-(3-ethoxypropyl)-5,6,7,8-tetrahydronaphthalen-2-yl)-3-oxa-1-azaspiro[4.4]nonan-2-one (7.3 g) as an off-white solid. Analytical HPLC (Gemini method): RT=9.39 min, Area %: 99; LC/MS $M^{+1}$=358.

Preparation of ((1R,3S)-1-amino-3-((S)-6-(3-ethoxypropyl)-5,6,7,8-tetrahydronaphthalen-2-yl)cyclopentyl)methanol

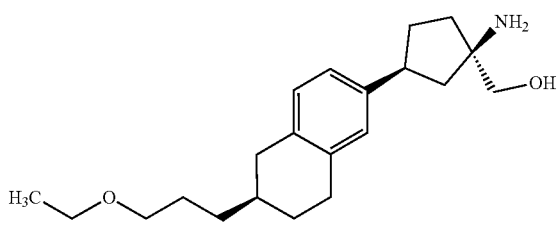 [SMILES: CCOCCC[C@@H]1CCc2cc([C@H]3CC[C@](N)(CO)C3)ccc2C1]

To a stirred solution of the (5R,7S)-7-((S)-6-(3-ethoxypropyl)-5,6,7,8-tetrahydronaphthalen-2-yl)-3-oxa-1-azaspiro[4.4]nonan-2-one (20.5 g, 56.8 mmol) in 2-methyltetrahydrofuran (60.0 ml) and EtOH (120 ml) was added a solution of lithium hydroxide (6.2 g, 254 mmol) in water (60.0 ml). The mixture was heated to 90° C. and stirred at this temperature for 16.0 h. Then, the reaction mixture was cooled to room temperature and filtered through a sintered funnel. The white solid remaining in the sintered funnel was triturated and rinsed with $CH_2Cl_2$ (200 mL), then water (150 mL) and finally with additional $CH_2Cl_2$ (200 mL). The filtrate and rinses were combined and transferred to a separatory funnel. The biphasic mixture was shaken and the layers separated. The organic layer was collected, dried ($Na_2SO_4$) and concentrated to give ((1R,3S)-1-amino-3-((S)-6-(3-ethoxypropyl)-5,6,7,8-tetrahydronaphthalen-2-yl)cyclopentyl)methanol (18.8 g) as a brownish foam: HPLC (Gemini method): RT=4.74 min, Area %: 99; LC/MS $M^{+1}$=332.

Preparation of ((1R,3S)-1-amino-3-((S)-6-(3-ethoxypropyl)-5,6,7,8-tetrahydronaphthalen-2-yl)cyclopentyl)methanol, hydrochloride

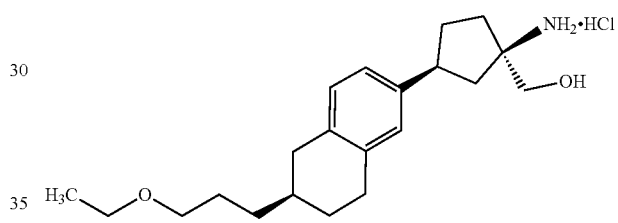

To a stirred solution of the ((1R,3S)-1-amino-3-((S)-6-(3-ethoxypropyl)-5,6,7,8-tetrahydronaphthalen-2-yl)cyclopentyl)methanol (17.0 g, 50.8 mmol) in EtOH (115 ml) at room temperature was added 1.25M HCl/EtOH (50.0 ml, 62.4 mmol). The resulting solution was stirred for 2.4 h and became a suspension. The solid that formed was collected by filtration, rinsed with diethyl ether, then dissolved in MeOH and filtered through the sintered funnel. The methanolic solution was evaporated and dried under vacuum to obtain 13.9 g of a white solid. The filtered solution and ether rinses were combined and evaporated in vacuo until precipitation was observed. The solid that formed was isolated as described above to give an additional 2.33 g of white solid. The above solids were combined to afford ((1R,3S)-1-amino-3-((S)-6-(3-ethoxypropyl)-5,6,7,8-tetrahydronaphthalen-2-yl)cyclopentyl)methanol, hydrochloride (16.2 g) as a white solid: HPLC (Gemini method): RT=4.77 min, Area %: 99; LC/MS $M^{+1}$=332; $^1$H NMR (500 MHz, $CD_3OD$) δ 7.00 (m, 3H), 3.66 (d, J=11.6 Hz, 1H), 3.60 (t, J=11.6 Hz, 1H), 3.52 (q, J=7.0 Hz, 2H), 3.49 (t, J=6.6 Hz, 2H), 3.11 (m, 1H), 2.90-2.71 (m, 3H), 2.40 (m, 2H), 2.11 (m, 1H), 2.02-1.86 (m, 4H), 1.77-1.64 (m, 4H), 1.50-1.33 (m, 3H), 1.21 (t, J=7.1 Hz, 3H).

Alternative Preparation-1 of Example 681

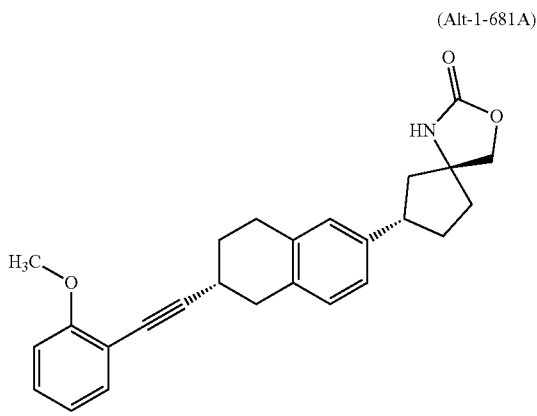 [SMILES: COc1ccccc1C#C[C@@H]1CCc2cc([C@H]3CC[C@]4(COC(=O)N4)C3)ccc2C1]

(Alt-1-681A)

To a mixture of bis(di-tert-butyl(4-dimethylaminophenyl) phosphine) dichloropalladium(II) (23.97 mg, 0.034 mmol), cesium carbonate (331 mg, 1.016 mmol), and (5R,7S)-7-((R)-6-ethynyl-5,6,7,8-tetrahydronaphthalen-2-yl)-3-oxa-1-azaspiro[4.4]nonan-2-one (100 mg, 0.339 mmol) in acetonitrile (10 mL) was added 1-iodo-2-methoxybenzene (0.132 mL, 1.016 mmol). The reaction mixture was sparged with nitrogen for 5 minutes then heated at 70° C. overnight. The reaction mixture was diluted with ethyl acetate and washed with saturated NaCl. The organic layer was dried with $MgSO_4$, filtered and concentrated. The crude material was purified on a silica gel cartridge (24 g) using an EtOAc/hexane gradient (0-100% EtOAc over 20 CV). Isolated fractions 14-15 were concentrated and dried in vacuo to afford (5R,7S)-7-((R)-6-((2-methoxyphenyl)ethynyl)-5,6,7,8-tetrahydronaphthalen-2-yl)-3-oxa-1-azaspiro[4.4]nonan-2-one (70 mg, 0.174 mmol). HPLC retention time=1.07 min (condition A); LC/MS $M^{+1}$=402.

To a mixture of (5R,7S)-7-((R)-6-((2-methoxyphenyl)ethynyl)-5,6,7,8-tetrahydronaphthalen-2-yl)-3-oxa-1-azaspiro[4.4]nonan-2-one (65 mg, 0.162 mmol) in MeOH (5 mL) was added Pearlman's Catalyst (5 mg, 0.036 mmol). The reaction mixture was hydrogenated under a balloon of $H_2$ for 1 hour. The mixture was filtered to remove catalyst. Next, 1 N NaOH (5 mL) was added and the mixture was heated at 95° C. overnight. The reaction mixture was diluted with ethyl acetate and washed with $H_2O$. The organic layer was dried with $MgSO_4$, filtered and concentrated. Purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were pooled, then washed with 1N NaOH and extracted with EtOAc. EtOAc layer was washed two more times and then back extracted the aqueous layer once. The organic layer was dried with $MgSO_4$, filtered, concentrated, and freeze dried from MeCN/water to afford ((1R,3S)-1-amino-3-((S)-6-(2-methoxyphenethyl)-5,6,7,8-tetrahydronaphthalen-2-yl)cyclopentyl)methanol (55 mg, 0.138 mmol). HPLC retention time=8.26 min (condition L); LC/MS $M^{+1}$=380.

Alternative Preparation-2 of Example 681

To a mixture of ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (1 g, 2.195 mmol) and potassium carbonate (0.910 g, 6.59 mmol) in DMF (10) was added 1-phenyl-1H-tetrazole-5-thiol (0.782 g, 4.39 mmol). The reaction mixture was heated at 80° C. overnight. The reaction mixture was diluted with ethyl acetate and washed with saturated NaCl. The organic layer was dried with $MgSO_4$, filtered and concentrated. The crude material was purified on a silica gel cartridge (40 g) using an EtOAc/Hex gradient (0-100% EtOAc over 13 CV) to afford (5R,7S)-7-((R)-6-(((1-phenyl-1H-tetrazol-5-yl)thio)methyl)-5,6,7,8-tetrahydronaphthalen-2-yl)-3-oxa-1-azaspiro[4.4]nonan-2-one (0.94 g, 2.036 mmol). HPLC retention time=1.02 min (condition A); LC/MS $M^{+1}$=462.

To hydrogen peroxide (8.32 mL, 81 mmol) at 0° C. was added ammonium molybdate tetrahydrate (0.503 g, 0.407 mmol). The resulting solution was added to a mixture of (5R,7S)-7-((R)-6-(((1-phenyl-1H-tetrazol-5-yl)thio)methyl)-5,6,7,8-tetrahydronaphthalen-2-yl)-3-oxa-1-azaspiro[4.4]nonan-2-one (0.94 g, 2.036 mmol) in THF (15 mL) at 0° C. The reaction mixture was stirred overnight. The reaction mixture was diluted with ethyl acetate and washed with saturated NaCl. The organic layer was dried with $MgSO_4$, filtered and concentrated to afford (5R,7S)-7-((R)-6-(((1-phenyl-1H-tetrazol-5-yl)sulfonyl)methyl)-5,6,7,8-tetrahydronaphthalen-2-yl)-3-oxa-1-azaspiro[4.4]nonan-2-one (1 g, 2.026 mmol). HPLC retention time=0.96 min (condition A); LC/MS $M^{+1}$=494.

To a mixture of 2-methoxybenzaldehyde (497 mg, 3.65 mmol) and (5R,7S)-7-((R)-6-(((1-phenyl-1H-tetrazol-5-yl)sulfonyl)methyl)-5,6,7,8-tetrahydronaphthalen-2-yl)-3-oxa-1-azaspiro[4.4]nonan-2-one (600 mg, 1.216 mmol) in THF was added KHMDS (4.86 mL, 4.86 mmol). After stirring at room temperature for 1 hour, the reaction was quenched with MeOH. The mixture was purified by HPLC. The crude material was purified on a silica gel cartridge (24 g) using an EtOAc/Hex gradient (0-100% EtOAc over 12 CV). Isolated fractions 18-20 were concentrated and dried in vacuo to afford (5R,7S)-7-((R)-6-((E)-2-methoxystyryl)-5,6,7,8-tetrahydronaphthalen-2-yl)-3-oxa-1-azaspiro[4.4]nonan-2-one (182 mg, 0.451 mmol). HPLC retention time=1.13 min (condition A); LC/MS $M^{+1}$=404.

To a mixture of (5R,7S)-7-((R)-6-((E)-2-methoxystyryl)-5,6,7,8-tetrahydronaphthalen-2-yl)-3-oxa-1-azaspiro[4.4]nonan-2-one (182 mg, 0.451 mmol) in MeOH (10 mL) was added Pearlman's Catalyst (5 mg, 0.036 mmol). The reaction mixture was hydrogenated under a balloon of $H_2$ for 1 hour. The mixture was filtered to remove the catalyst, and 1 N NaOH (5 mL) was added. The reaction mixture was heated at 95° C. overnight. The mixture was cooled, diluted with ethyl acetate, and washed with $H_2O$. The organic layer was dried with $MgSO_4$, filtered and concentrated. The solid material was triturated in MeCN and stirred overnight. Solids were collected by filtration and dried to afford ((1R,3S)-1-amino-3-((S)-6-(2-methoxyphenethyl)-5,6,7,8-tetrahydronaphthalen-2-yl)cyclopentyl)methanol (90 mg, 0.235 mmol). HPLC retention time=7.93 min (condition L); LC/MS $M^{+1}$=380.

Alternative Preparation-3 of Example 681

To a solution of ((R)-6-((5R,7S)-2-oxo-3-oxa-1-azaspiro[4.4]nonan-7-yl)-1,2,3,4-tetrahydronaphthalen-2-yl)methyl 4-methylbenzenesulfonate (700 mg, 1.537 mmol) and copper(I) bromide-dimethyl sulfide complex (948 mg, 4.61 mmol) in $Et_2O$ (50 mL) was added (2-methoxybenzyl)magnesium chloride (58 ml, 14.50 mmol) at room temperature. The reaction mixture was stirred for 16 h. The reaction mixture was diluted with saturated $NH_3Cl$ and water, and extracted with EtOAc. The organic layer was collected, dried over Na₂SO₄, concentrated to give 580 mg of desired product, M+H=406. This material was dissolved in dioxane (10 mL) and 1N NaOH was added (10 mL). The mixture was heated at 100° C. overnight. The mixture was cooled, diluted with water, and extracted with EtOAc (2×). The combined organic layer was washed with saturated NaCl, then dried over MgSO₄, and concentrated on the rotavapor. The solid material was triturated in MeCN (10 mL) and then stirred for several hours. The solid material was collected by filtration and dried in vacuo to give ((1R,3S)-1-amino-3-((S)-6-(2-methoxyphenethyl)-5,6,7,8-tetrahydronaphthalen-2-yl)cyclopentyl)methanol (350 mg, 0.876 mmol). MS (m+1)=380; HPLC Peak RT=9.06 min (Condition L)Purity=97%.

Alternative Preparation-4 of Example 681

Preparation of
5-((2-methoxybenzyl)thio)-1-phenyl-1H-tetrazole

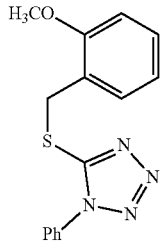 [SMILES: COc1ccccc1CSc1nnnn1-c1ccccc1]

Sodium carbonate (135 g, 1277 mmol) was added portionwise to a solution of 1-(chloromethyl)-2-methoxybenzene (200 g, 639 mmol) and 1-phenyl-1H-tetrazole-5-thiol (125 g, 702 mmol) in anhydrous DMF (639 ml). The reaction mixture was allowed to stir at room temperature under a nitrogen atmosphere for 2 days before diluting with water (1000 ml) and extracting with ethyl acetate (3×300 ml). The combined organics were then washed with water (500 mL), brine (500 mL) and then dried (MgSO₄). The solvent was evaporated in vacuo and the crude purified by column chromatography using ethyl acetate hexane as eluent to give 5-((2-methoxybenzyl)thio)-1-phenyl-1H-tetrazole (167 g, 88%) as a white solid. HPLC retention time (Sunfire C18 5 um 4.6×50 (4 min grad.) Solvent A=10% MeOH-90% H₂O-0.2% H₃PO₄; Solvent B=90% MeOH-10% H₂O-0.2% H₃PO₄)=3.34 min. ¹H NMR (400 MHz, DMSO-d₆) δ 7.73-7.48 (m, 5H), 7.37 (dd, J=7.5, 1.8 Hz, 1H), 7.29 (td, J=7.8, 1.8 Hz, 1H), 6.99 (d, J=8.1 Hz, 1H), 6.88 (td, J=7.5, 0.9 Hz, 1H), 4.53 (s, 2H), 3.76 (s, 3H).

5-((2-methoxybenzyl)sulfonyl)-1-phenyl-1H-tetrazole

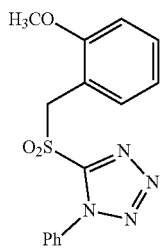 [SMILES: COc1ccccc1CS(=O)(=O)c1nnnn1-c1ccccc1]

To a 500 mL, 3 neck round bottom flask was added hydrogen peroxide (0.274 L, 2681 mmol). The contents of the flask were cooled to 0-5° C. Ammonium molybdate tetrahydrate (66.3 g, 53.6 mmol) was added portionwise over 10 minutes while maintaining the temperature below 5° C. To a separate 5 L, 3 neck round bottom flask with a mechanical stirrer was added 5-((2-methoxybenzyl)thio)-1-phenyl-1H-tetrazole (80 g, 268 mmol) in acetonitrile (2 L). The peroxide solution was added slowly while maintaining the temperature below 30° C. during the addition. A yellow suspension formed. The reaction mixture was stirred at room temperature for 18 h. The reaction mixture was cooled with an ice bath to 5° C. and diluted with water (2.7 L) and stirred for 1 h. The suspension was filtered and washed with water and dried by vacuum suction to give a mixture of sulfone and sulfoxide (~80 g) which was re-subjected to the oxidation conditions described above to give the crude product (~80 g) which was then purified by column chromatography using ethyl acetate hexane as eluent to give 5-((2-methoxybenzyl)sulfonyl)-1-phenyl-1H-tetrazole (71 g, 215 mmol) as a white crystalline solid. HPLC retention time (BEH C18 2.1×50 mm 1.7 um, 2 min grad., Solvent Name A: 100% H₂O w/0.05% TFA; Solvent Name B: 100% ACN w/0.05% TFA) 0.91 min. ¹H NMR (400 MHz, CHLOROFORM-d) δ 7.62-7.54 (m, 1H), 7.54-7.45 (m, 2H), 7.41 (ddd, J=8.3, 7.5, 1.8 Hz, 1H), 7.37-7.30 (m, 3H), 6.96 (td, J=7.5, 1.0 Hz, 1H), 6.91 (d, J=8.4 Hz, 1H), 5.02 (s, 2H), 3.74 (s, 3H).

(5R,7S)-7-((R)-6-((E)-2-methoxystyryl)-5,6,7,8-tetrahydronaphthalen-2-yl)-3-oxa-1-azaspiro[4.4]nonan-2-one

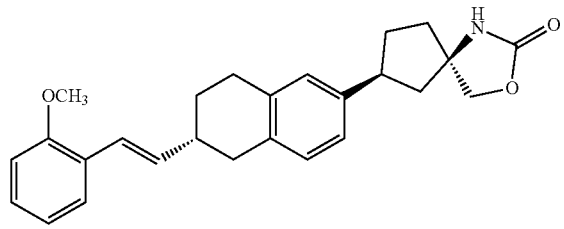 [SMILES: COc1ccccc1/C=C/[C@@H]1CCc2cc([C@H]3CC[C@]4(COC(=O)N4)C3)ccc2C1]

LiHMDS (46.8 ml, 70.1 mmol) was added dropwise to a solution of 5-((2-methoxybenzyl)sulfonyl)-1-phenyl-1H-tetrazole (23.17 g, 70.1 mmol) in anhydrous THF (84 ml) and DMF (55.9 ml) at −78° C. under a nitrogen atmosphere. The addition took ~5 min and the temperature of the reaction mixture did not rise above −60° C. The resulting solution was colored orange. The reaction mixture was allowed to stir at −78° C. for 30 min before the dropwise addition of (R)-6-((5R,7S)-2-oxo-3-oxa-1-azaspiro[4.4]nonan-7-yl)-1,2,3,4-tetrahydronaphthalene-2-carbaldehyde (10 g, 33.4 mmol) in anhydrous DMF (39.9 ml) [as 14 mL+6 mL washing]. The temperature did not rise above −70° C. during the addition. The reaction mixture was allowed to warm slowly to room temperature overnight. HPLC indicated desired product. The reaction mixture was cooled to −78° C. before the reaction was quenched with water (20 mL). The mixture was allowed to warm to room temperature. The reaction mixture was partitioned between water and ethyl acetate, and the aqueous layer was extracted with ethyl acetate (2×). The combined organics were then washed with water, brine, and dried (MgSO₄). The evaporated organic layer was then purified by column chromatography using ethyl acetate:hexane as eluent to give (5R,7S)-7-((R)-6-((E)-

2-methoxystyryl)-5,6,7,8-tetrahydronaphthalen-2-yl)-3-oxa-1-azaspiro[4.4]nonan-2-one (12.1 g, 90%) as a white solid. HPLC retention time (BEH C18 2.1×50 mm 1.7 um, 2 min grad., Solvent Name A: 100% H$_2$O w/0.05% TFA; Solvent Name B: 100% ACN w/0.05% TFA): 1.27 and 1.28 min, as a 1:2 mixture of double bond isomers. $^1$H NMR (400 MHz, CHLOROFORM-d) δ 7.48 (dd, J=7.7, 1.5 Hz, 1H), 7.33-7.18 (m, 5H), 7.13-7.02 (m, 2H), 7.01-6.87 (m, 6H), 6.83 (d, J=16.1 Hz, 1H), 6.56 (d, J=11.7 Hz, 1H), 6.29 (dd, J=16.1, 6.8 Hz, 1H), 5.69 (dd, J=11.7, 9.9 Hz, 1H), 5.15 (br. s., 1H), 4.40-4.25 (m, 3H), 3.87 (d, J=4.0 Hz, 5H), 3.13-2.78 (m, 7H), 2.76-2.58 (m, 3H), 2.41-2.27 (m, 2H), 2.22-2.05 (m, 4H), 2.04-1.91 (m, 4H), 1.89-1.75 (m, 2H), 1.74-1.60 (m, 2H), 1.57 (s, 4H).

(5R,7S)-7-((S)-6-(2-methoxyphenethyl)-5,6,7,8-tetrahydronaphthalen-2-yl)-3-oxa-1-azaspiro[4.4]nonan-2-one

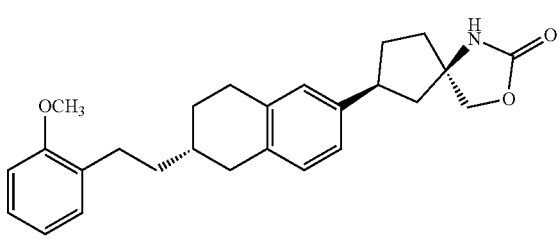 [SMILES: COc1ccccc1CC[C@@H]1CCc2cc([C@H]3CC[C@]4(COC(=O)N4)C3)ccc2C1]

(5R,7S)-7-((R)-6-((E)-2-methoxystyryl)-5,6,7,8-tetrahydronaphthalen-2-yl)-3-oxa-1-azaspiro[4.4]nonan-2-one (24 g, 59.5 mmol) was dissolved in dichloromethane (297 ml) and MeOH (297 ml). Nitrogen gas was bubbled through the solution for about 10 minutes. Next, Pd/C (6.33 g, 5.95 mmol) was added in one portion. A hydrogen filled balloon was placed on the reaction flask before evacuating the flask for ~2 minutes. Hydrogen was then introduced and this process was repeated 2 more times. After stirring at room temperature overnight, HPLC indicated conversion to the desired product but with significant starting material remained. The reaction mixture was filtered through Celite, washed with 1:1 MeOH:DCM and the filtrate was evaporated in vacuo. The residue was set up as described above and resubjected to the hydrogenation overnight. HPLC still shows starting material remaining. A third hydrogenation gave complete conversion to the desired product. The reaction mixture was filtered through Celite and evaporated. SFC was performed to remove a minor undesired isomer and gave (5R,7S)-7-((S)-6-(2-methoxyphenethyl)-5,6,7,8-tetrahydronaphthalen-2-yl)-3-oxa-1-azaspiro[4.4]nonan-2-one (24.67 g, 60.8 mmol) as a white solid. HPLC retention time (Sunfire C18 5 um 4.6×50 (4 min grad.) Solvent A=10% MeOH-90% H$_2$O-0.2% H$_3$PO$_4$; Solvent B=90% MeOH-10% H$_2$O-0.2% H$_3$PO$_4$)=4.15 min.

((1R,3S)-1-amino-3-((S)-6-(2-methoxyphenethyl)-5,6,7,8-tetrahydronaphthalen-2-yl)cyclopentyl)methanol

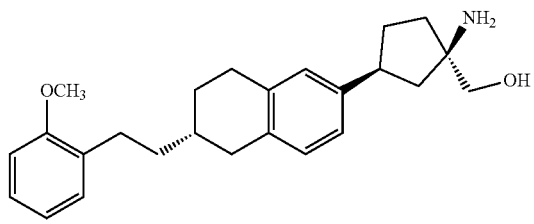 [SMILES: COc1ccccc1CC[C@@H]1CCc2cc([C@H]3CC[C@](N)(CO)C3)ccc2C1]

LiOH (21.91 g, 915 mmol) was added in one portion to a solution of (5R,7S)-7-((S)-6-(2-methoxyphenethyl)-5,6,7,8-tetrahydronaphthalen-2-yl)-3-oxa-1-azaspiro[4.4]nonan-2-one (53 g, 131 mmol) in dioxane (523 ml) and H$_2$O (131 ml). The reaction mixture was allowed to reflux under a nitrogen atmosphere for 72 hours. The reaction mixture was allowed to cool to room temperature before diluting with water (300 ml) and extracting with ethyl acetate (3×300 ml). The combined organics were then dried (MgSO$_4$) and evaporated in vacuo. The residue was recrystallized from IPA to give a white solid (27 g). The remainder of the material formed a chelate with the drying agent. This material was treated with hot ethanol and the resulting slurry filtered to remove the drying agent. The filtrate was evaporated in vacuo and taken up in ethyl acetate (300 ml) before washing with 1N sodium hydroxide solution (200 ml). The organic layer was dried (Na$_2$SO$_4$) and evaporated to give a residue which was recrystallized from IPA to give a white solid (13 g). The remainder of the material (filtrates from the above two manipulations) was purified by SFC to give 10 g of a white solid. HPLC retention time (Sunfire C18 5 um 4.6×50 (4 min grad.) Solvent A=10% MeOH-90% H$_2$O-0.2% H$_3$PO$_4$; Solvent B=90% MeOH-10% H$_2$O-0.2% H$_3$PO$_4$)=3.21 min.

Comparative Compound 703

(1R,3R)-1-Amino-3-(6-(pentyloxy)naphthalen-2-yl)cyclopentyl)methanol (703)

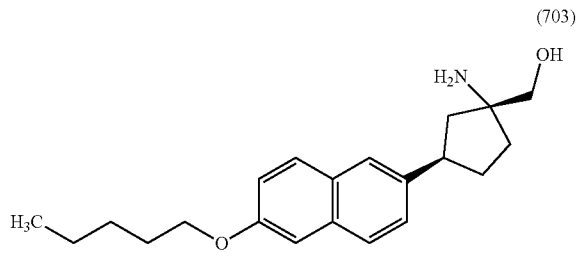 [SMILES: CCCCCOc1ccc2cc([C@@H]3CC[C@](N)(CO)C3)ccc2c1]

Comparative Compound 703 was disclosed in WO 2008/079382, Example Q.1.

Intermediate 703A: (5R,7R)-7-(6-(Pentyloxy)naphthalen-2-yl)-3-oxa-1-azaspiro[4.4]nonan-2-one (I-703A)

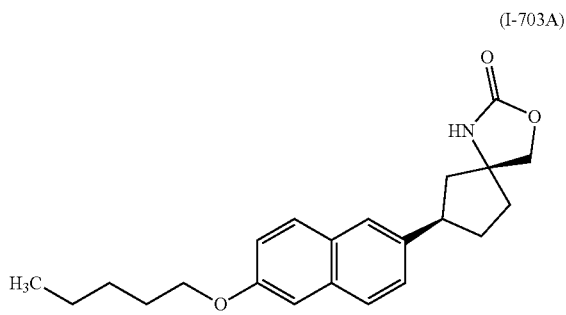 [SMILES: CCCCCOc1ccc2cc([C@@H]3CC[C@]4(COC(=O)N4)C3)ccc2c1]

A mixture of 1-pentanol (6.13 mL, 56.4 mmol), p-toluenesulfonic acid monohydrate (4.60 mg, 0.024 mmol), and trimethoxymethane (0.353 mL, 3.22 mmol) was stirred at 100° C. for 3 hr with a slow air stream flowing over the mixture to remove methanol and some pentanol. The obtained residual liquid was mixed with (5R,7R)-7-(6-oxo-5,6,7,8-tetrahydronaphthalen-2-yl)-3-oxa-1-azaspiro[4.4]nonan-2-one (Int. 7, 230 mg, 0.806 mmol) and stirred at 100° C. under nitrogen for 2.5 hr. The solution was allowed to cool down to room temperature before palladium on carbon (172 mg, 0.081 mmol) was added, followed by ethyl acetate (4 mL). The mixture was left to stir under a balloon-pressure of hydrogen at room temperature overnight. The resulting mixtures were filtered through a membrane filter and the filtrate was concentrated. Flash chromatography purification (24 g silica gel column, 0% to 70% ethyl acetate in hexanes) afforded 180 mg of material that required additional purification. Supercritical Fluid Chromatographic separation afforded a major fraction by UV analysis identified as (5R,7R)-7-(6-(pentyloxy)naphthalen-2-yl)-3-oxa-1-azaspiro[4.4]nonan-2-one (36 mg) as a solid. Instrument: Thar 350 Thar Analytical SFC-MS; Conditions: Analytical Conditions: Analytical Column: AD-H (0.46×25 cm, 5 µm); BPR pressure: 100 bars; Temperature: 45° C.; Flow rate: 3.0 mL/min; Mobile Phase: $CO_2$/MeOH (70/30); Detector Wavelength: UV 200-400 nm. Preparative Conditions: Preparative Column: AD-H (3×25 cm, 5 µm); BPR pressure: 100 bars; Temperature: 35° C.; Flow rate: 120 mL/min; Mobile Phase: $CO_2$/MeOH (70/30); Detector Wavelength: 220 nm; Separation program: Stack injection; Injection: 2.5 mL with cycle time 480 sec. (Analytical SFC ret. time=11.68 min, purity >99.5%) HPLC retention time=1.11 min (Condition G); LC/MS $M^{+1}$=354. $^1$H NMR (400 MHz, chloroform-d) δ 7.68 (d, J=8.4 Hz, 2H), 7.55 (s, 1H), 7.30 (s, 1H), 7.21-7.04 (m, 2H), 6.48 (br. s., 1H), 4.50-4.28 (m, 2H), 4.07 (t, J=6.6 Hz, 2H), 3.49-3.31 (m, 1H), 2.46 (dd, J=13.3, 7.6 Hz, 1H), 2.39-2.24 (m, 1H), 2.24-2.12 (m, 1H), 2.12-2.00 (m, 1H), 2.00-1.90 (m, 1H), 1.90-1.76 (m, 3H), 1.58-1.30 (m, 4H), 0.96 (t, J=7.0 Hz, 3H).

Comparative Compound 703

To a solution of (5R,7R)-7-(6-(pentyloxy)naphthalen-2-yl)-3-oxa-1-azaspiro[4.4]nonan-2-one (36 mg, 0.102 mmol) in dioxane (2 mL) and water (0.8 mL) was added LiOH (36.6 mg, 1.528 mmol). The solution was heated to 90° C. and allowed to stir for 15 hours. The reaction mixture was cooled to room temperature and was poured into ethyl acetate and washed with water. The crude material was then purified on reverse phase HPLC [Column: Luna Axia 30*100 mm; Gradient time: 10 min; Flow rate=40 ml/min; Solvent A=10% MeOH-90% Water-0.1% TFA; Solvent B=90% MeOH-10% water-0.1% TFA; Start % B=20; Final % B=100]. The product containing fractions were collected and dried under high vacuum to provide ((1R,3R)-1-amino-3-(6-(pentyloxy)naphthalen-2-yl)cyclopentyl)methanol, TFA (31 mg) as a solid. HPLC retention time=0.90 min (Condition G); LC/MS $M^{+1}$=328. $^1$H NMR (400 MHz, methanol-$d_4$) δ 7.75-7.66 (m, 2H), 7.66-7.59 (m, 1H), 7.40-7.33 (m, 1H), 7.17 (d, J=2.6 Hz, 1H), 7.14-7.08 (m, 1H), 4.07 (t, J=6.5 Hz, 2H), 3.74-3.60 (m, 2H), 3.59-3.41 (m, 1H), 2.39-2.22 (m, 3H), 2.04-1.80 (m, 5H), 1.55-1.34 (m, 4H), 1.01-0.89 (m, 3H).

Biological Assays

The compounds of Formulas (Ia), (IIa), (IIIa), (IVa), and (Va) or salts thereof engage their biological targets (e.g. S1P1) after bioactivation through phosphorylation of the alcohol to provide an active phosphate ester compound of Formulas (Ib), (IIb), (IIIb), (IVb), and (Vb), or salts thereof. In vitro characterization of biological activity of the examples was conducted on synthetically prepared samples of the phosphorylated compounds.

S1P$_1$ Binding Assay:

Membranes were prepared from CHO cells expressing human S1P$_1$. Cells pellets ($1 \times 10^9$ cells/pellet) were suspended in buffer containing 20 mM HEPES (4-(2-hydroxyethyl)-1-piperazineethanesulfonic acid), pH 7.5, 50 mM NaCl, 2 mM EDTA (Ethylenediaminetetraacetic acid) and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM $MgCl_2$, 2 mM EDTA and stored in aliquots at −80° C. after protein concentration determination.

Membranes (2 µg/well) and 0.03 nM final concentration of $^{33}$P-S1P ligand (1 mCi/ml, Perkin elmer or American Radiolabeled Chemicals) diluted in assay buffer (50 mM HEPES, pH7.4, 5 mM $MgCl_2$, 1 mM $CaCl_2$, 0.5% fatty acid free BSA (bovine serum albumin), 1 mM NaF) were added to the compound plates (384 Falcon v-bottom plate (0.5 l/well in a 11 point, 3-fold dilution). Binding was performed for 45 minutes at room temperature, terminated by collecting the membranes onto 384-well Millipore FB filter plates, and radioactivity was measured by TOPCOUNT®. The competition data of the test compounds over a range of concentrations was plotted as percentage inhibition of radioligand specific binding. The IC$_{50}$ is defined as the concentration of competing ligand needed to reduce specific binding by 50%. The IC$_{50}$ for Example 689 was determined to be 1.7 nM.

TABLE A

| Ex. No. | S1P$_1$ Binding IC$_{50}$ (nM) |
|---|---|
| 689 | 1.7 |
| 690 | 3.0 |
| 692 | 2.3 |
| 693 | 5.2 |
| 695 | 118.9 |
| 698 | 69.4 |

TABLE A-continued

| Ex. No. | S1P$_1$ Binding IC$_{50}$ (nM) |
|---|---|
| 699 | 183.4 |
| 701 | 48.7 |
| 702 | 151.1 |

Receptor [$^{35}$S] GTPγS Binding Assays: (S1P$_1$ GTPγS/S1P$_3$ GTPγS)

Compounds were loaded in a 384 Falcon v-bottom plate (0.5 μl/well in a 11 point, 3-fold dilution). Membranes prepared from S1P$_1$/CHO cells or EDG3-Gal5-bla HEK293T cells (EDG3 equivalent S1P$_3$) were added to the compound plate (40 l/well, final protein 3 μg/well) with MULTIDROP®. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA (ethylene glycol tetraacetic acid), 1 mM DTT (Dithiothreitol), 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to Millipore 384-well FB filter plates via the VELOCITY11® Vprep liquid handler. The filter plate was washed with water 4 times by using the manifold Embla plate washer and dried at 60° C. for 45 min. MicroScint 20 scintillation fluid (30 μl) was added to each well for counting on the Packard TOPCOUNT®. EC$_{50}$ is defined as the agonist concentration that corresponds to 50% of the Ymax (maximal response) obtained for each individual compound tested. The EC$_{50}$ for Example 689 was determined to be 5.7 nM in the assay utilizing membranes prepared from S1P$_1$/CHO cells. The EC$_{50}$ for Example 689 was determined to be >2000 nM in the assay utilizing membranes prepared from EDG3-Gal5-bla HEK293T cells.

A smaller value for GTPγS S1P$_1$ EC$_{50}$ value indicated greater activity for the compound in the GTPγS S1P$_1$ binding assay. A larger value for the GTPγS S1P$_3$ EC$_{50}$ value indicated less activity in the GTPγS S1P$_3$ binding assay. Example 689, which is the phosphate ester of Example 672, possessed activity as an agonist of S1P$_1$ and is selective over S1P$_3$. Example 697, which is the phosphate ester of Example 681, possessed activity as an agonist of S1P$_1$ and is selective over S1P$_3$. Thus the compounds of the present invention may be used in treating, preventing, or curing various S1P$_1$ receptor-related conditions while reducing or minimizing the side effects due to S1P$_3$ activity. The selectivity of the compounds of the present invention indicate their potential use in treating, preventing, or curing autoimmune and inflammatory diseases such as multiple sclerosis, rheumatoid arthritis, inflammatory bowel disease, lupus, psoriasis, or vascular diseases, while reducing or minimizing possible side effects due to S1P$_3$ activity. Other potential uses of the compounds of the present invention include minimizing or reducing rejection of transplanted organs, while reducing or minimizing side effects due to S1P$_3$ activity.

TABLE B

| Ex. No. | GTPγS S1P$_1$ EC$_{50}$ (nM) | GTPγS S1P$_3$ EC$_{50}$ (nM) |
|---|---|---|
| 689 | 5.7 | >2000 |
| 690 | 21.4 | >625 |
| 692 | 4.4 | >625 |

TABLE B-continued

| Ex. No. | GTPγS S1P$_1$ EC$_{50}$ (nM) | GTPγS S1P$_3$ EC$_{50}$ (nM) |
|---|---|---|
| 693 | 19.2 | >4162 |
| 694 | 38.6 | >1250 |
| 695 | 49.0 | >625 |
| 696 | 1.2 | >1000 |
| 697 | 0.6 | >1000 |
| 698 | 8.9 | >625 |
| 699 | 82.6 | >625 |
| 701 | 133.4 | >1250 |
| 702 | 120.2 | >625 | hS1P$_1$ ERK Phosphorylation (S1P$_1$ pERK)

hS1P$_1$/CHO cells were plated into BD Amine 384-well plates the day before the assay. On the day of the assay, growth medium was removed and replaced with serum-free medium (Ham's F-12 Invitrogen) and incubated for 2 hours. Test compounds pre-diluted in HBSS (Gibco)/20 mM HEPES (Gibco) were transferred to the cell plates and incubated for 7 minutes at 37° C. Cells were lysed in lysis buffer (Perkin Elmer) and phospho-ERK was measured using the SureFire pERK kit (Perkin Elmer) as described by the manufacturer. Data was plotted as percentage activation of the test compound relative to the efficacy of 10 μM S1P. The EC$_{50}$ is defined as the concentration of test compound which produces 50% of the maximal response and was quantified using the 4 parameter logistic equation to fit the data. Data for phosphate examples in this assay are shown in Table I.

Blood Lymphocyte Reduction (BLR) Assay in Rodent:

Lewis rats or BALB/c mice were dosed orally with vehicle alone (polyethylene glycol 300, "PEG300") or with test compounds. Compounds were dosed as a solution or suspension in the vehicle, adjusted to reflect the free amount of test article in the event that salt forms are utilized. Blood was drawn at 24 hr and blood lymphocyte counts were determined on an ADVIA 120 Hematology Analyzer (Siemens Healthcare Diagnostics). The results were measured as a reduction in the percentage of circulating lymphocytes as compared to the vehicle treated group at the time of measurement. The results represent the average results of all animals within each treatment group (n=2-4). The results of the Blood Lymphocyte Reduction assay (BLR) in rat described hereinabove are shown in Table C.

The stereochemical orientation of the compounds in the present invention was found to influence the activity in the rodent BLR assay. For example, the diastereomeric set of compounds Examples 672, 673, 674, and 675 were evaluated at the same dosage level of 0.1 mg/kg and the resulting lymphocyte reduction at 24 hours post-dose was found to range from 30% for Example 674 to 63% for Example 675. The diastereomeric compounds Examples 678 and 679 were each evaluated at 0.1 mg/kg and the resulting lymphocyte reduction was found to be 16% and 65% respectively. Likewise, diastereomeric compounds Examples 681 and 682 were each evaluated at 0.1 mg/kg and the resulting lymphocyte reduction was found to be 53% and 17%, respectively.

TABLE C-1

| Ex. No. | Dosage (mg/kg) | Percent reduction vs. control at 24 hr post-dose |
|---|---|---|
| 672 | 0.1 | 47% |
| 673 | 0.1 | 62% |

TABLE C-1-continued

| Ex. No. | Dosage (mg/kg) | Percent reduction vs. control at 24 hr post-dose |
| --- | --- | --- |
| 674 | 0.1 | 30% |
|  | 0.3 | 73% |
| 675 | 0.1 | 63% |
| 676 | 0.1 | 63% |
| 677 | 0.05 | 49% |
| 678 | 0.1 | 16% |
|  | 0.3 | 53% |
| 679 | 0.1 | 65% |
| 681 | 0.1 | 53% |
| 682 | 0.1 | 17% |
|  | 2.0 | 83% |
| 684 | 0.05 | 72% |
| 685 | 0.1 | 55% |

The compounds of the present invention, as exemplified by Examples 679, 681, and 684, have been compared to Comparative Compound 703, disclosed in WO 2008/079382, and have been found to be advantageous. As shown in Table C-2, Examples 679, 681, and 684 administered to mice at a dose of 0.5 mg/kg, showed lymphocyte reductions of 59%, 85%, and 79%, respectively, at 24 hours post dose in this study. In comparison, Comparative Compound 703 administered a dose of 1.0 mg/kg, showed a lymphocyte reduction of 52% at 24 hours post dose.

TABLE C-2

| Example or Compound No | Dosage (mg/kg) | Mouse Blood Lymphocyte Reduction Assay at 24 hr post-dose Percent reduction vs. control |
| --- | --- | --- |
| 679 | 0.5 | 59% |
| 681 | 0.5 | 85% |
| 684 | 0.5 | 79% |
| 703 | 1.0 | 52% |

The compounds of the present invention possess activity as agonists of the $S1P_1$ receptor, leading to the reduction of circulating blood lymphocytes, and thus may be used in treating, preventing, or curing various $S1P_1$ receptor-related conditions. The surprising selectivity of the compounds of the present invention indicate their potential use in treating, preventing, or curing autoimmune and inflammatory diseases such as multiple sclerosis, rheumatoid arthritis, inflammatory bowel diseases, lupus, psoriasis, or vascular diseases. Other potential uses of the compounds of the present invention include minimizing or reducing rejection of transplanted organs.

Rat Adjuvant Induced Arthritis Assay (AA)

The rat adjuvant-induced arthritis model is an animal model for human rheumatoid arthritis.

Male Lewis rats (150-175 g; Harlan, n=8 treatment group) were immunized at the base of the tail with 100 μl of 10 mg/ml freshly ground *Mycobacterium butyricum* (Difco Laboratories) in incomplete Freund's adjuvant (sigma). Animals were dosed once daily with the test article (as a solution or suspension in the vehicle) or vehicle alone (polyethylene glycol 300, "PEG300") starting from the day of immunization. The volumes of their hind paws were measured in a water displacement plethysmometer (Ugo Basile, Italy). The baseline paw measurements were taken before onset of the disease (between day 7 to day 10). The paw measurements were then taken three times a week until the end of the study on day 20 to 21. All procedures involving animals were reviewed and approved by the Institutional Animal Care Use Committee.

Example 672 of the present invention was tested in rat AA assay described hereinabove and the results are shown in Table D. The compounds of this invention, as exemplified by Example 672, in the reported test, showed inhibiton of disease progression as measured by reduced paw swelling in the Lewis rat using a prophylactic oral dosing regimen.

TABLE D

| Group | | paw swelling (mL) on day 20 |
| --- | --- | --- |
| Vehicle | Mean | 2.63 |
|  | SEM* | 0.14 |
| Example 672 | Mean | 2.60 |
| (0.1 mg/kg) | SEM | 0.36 |
| Example 672 | Mean | 1.46 |
| (0.3 mg/kg) | SEM | 0.34 |
| Example 672 | Mean | 0.17 |
| (1.0 mg/kg) | SEM | 0.08 |

*SEM: standard error of the mean

Example 679 was tested in the rat AA assay described hereinabove and the results are shown in Table E. The compounds of this invention, as exemplified by Example 679 in the reported test, showed inhibition of disease progression as measured by reduced paw swelling in the Lewis rat using a prophylactic oral dosing regimen.

TABLE E

| Group | | paw swelling (mL) on day 22 |
| --- | --- | --- |
| Vehicle | Mean | 1.62 |
|  | SEM | 0.24 |
| Example 679 | Mean | 1.55 |
| (0.1 mg/kg) | SEM | 0.22 |
| Example 679 | Mean | 0.36 |
| (0.5 mg/kg) | SEM | 0.19 |
| Example 679 | Mean | 0.00 |
| (2.50 mg/kg) | SEM | 0.05 |

Mouse Experimental Autoimmune Encephalomyelitis Assay (EAE)

Mice (C57BL/6 female, 6-8 weeks of age, Charles River, n=10 treatment group) were immunized subcutaneously with 150 μg MOG35-55 emulsified 1:1 with incomplete Freund's adjuvant (sigma) supplemented with 150 μg *Mycobacterium tuberculosis* H37RA (Difco Laboratories). 400 ng of pertussis toxin (CalBiochem) was injected intraperitoneally on the day of immunization and 2 day later. Clinical scoring and body weight were taken 3 times per week. Clinical scoring system: 0.5: partial tail weakness; 1: limp tail or waddling gait with tail tonicity; 1.5: waddling gait with partial tail weakness; 2: waddling gait with limp tail (ataxia); 2.5: ataxia with partial limb paralysis; 3: full paralysis of one limb; 3.5: full paralysis of one limbs with partial paralysis of a second limb; 4: full paralysis of two limbs; 4.5: moribund; 5: death. Mean clinical score was calculated by averaging the scores of all mice in each group. All procedures involving animals were reviewed and approved by the Institutional Animal Care Use Committee.

Example 681 of the present invention was tested in the mouse EAE assay described herein above and the results are shown in Table F. The compounds of this invention, as exemplified by Example 681, in the reported test, showed inhibition of disease progression as measured by clinical scores in $C_{57}Bl/6$ mice using a prophylactic oral dosing regimen.

TABLE F

| Group | | Clinical scores on day 22 |
|---|---|---|
| Vehicle | Mean | 4.1 |
| | SEM | 0.03 |
| Example 681 | Mean | 3.1 |
| (0.1 mg/kg) | SEM | 0.16 |
| Example 681 | Mean | 1.1 |
| (0.5 mg/kg) | SEM | 0.1 |
| Example 681 | Mean | 0.8 |
| (2 mg/kg) | SEM | 0.12 |

Example 679 of the present invention was tested in the mouse EAE assay described herein above and the results are shown in Table G. The compound of this invention, as exemplified by Example 679, in the reported test, showed inhibition of disease progression as measured by clinical scores in C57Bl/6 mice using a prophylactic oral dosing regimen.

TABLE G

| Group | | Clinical scores on day 21 |
|---|---|---|
| Vehicle | Mean | 4.1 |
| | SEM | 0.03 |
| Example 679 | Mean | 2.9 |
| (0.6 mg/kg) | SEM | 0.14 |
| Example 679 | Mean | 1.8 |
| (3 mg/kg) | SEM | 0.14 |
| Example 679 | Mean | 1.3 |
| (15 mg/kg) | SEM | 0.08 |

In the mouse experimental autoimmune encephalomyelitis (EAE) model, an animal model for multiple sclerosis, Examples 679 and 681 inhibit disease progression as determined by the clinical scores in C57Bl/6 mice using a prophylactic oral dosing regimen.

Rat Experimental Autoimmune Encephalomyelitis (EAE):

Female Lewis rats (150-200 g; Harlan) were immunized at the base of the tail with 0.1 ml of a complete Freund's adjuvant emulsion containing 0.5 mg/mL guinea pig myelin basic protein (Genemed Synthesis) and 2 mg/mL *Mycobacterium butyricum* (Difco). Beginning on Day 7, rats (n=11/group) were scored individually at least 3x/wk according to the following scheme:

| Score | Clinical presentation |
|---|---|
| 0.25 | paralysis in the distal tail |
| 0.5 | limp tail |
| 1 | ataxia (waddling gait with limp tail) |
| 2 | hind-leg paresis |
| 3 | full hind-leg paralysis |
| 4 | Moribund |
| 5 | Death |

Average clinical scores were calculated for each treatment group on each day of assessment.

Example 679 of the present invention was tested in rat EAE assay described hereinabove and the results are shown in Table H. The compound of this invention, as exemplified by Example 679, in the reported test, showed inhibition of disease progression as measured by reduced clinical scores in the Lewis rat using a prophylactic oral dosing regimen.

TABLE H

| Group | | Clinical Score on Day 11 |
|---|---|---|
| Vehicle | Mean | 2.18 |
| | SEM | 0.07 |
| Example 679 | Mean | 0.36 |
| (0.3 mg/kg) | SEM | 0.08 |
| Example 679 | Mean | 0.09 |
| (1.0 mg/kg) | SEM | 0.01 |
| Example 679 | Mean | 0.02 |
| (3.0 mg/kg) | SEM | 0.01 |

MRL/lpr Lupus Model:

MRL/lpr is a spontaneous model of lupus. Male MRL/lpr mice (Jackson Laboratory) at the age of 12-14 weeks were enrolled for the study (N=12). Mice were dosed p.o. daily with vehicle (18.4% (w/v) hydroxypropyl-b-cyclodextrin in 13.8 mM citric acid) or with Example 681 at 0.06, 0.3, 1.5 mg/kg. Mice were bled every other week for anti-dsDNA antibodies measured by ELISA using pooled serum from diseased MRL/lpr mice as a positive comparator in each assay. The data were expressed in arbitrary units as a ratio of the titer of the test serum to the titer of the pooled MRL/lpr immune serum.

At the end of study, one kidney was collected into 10% neutral buffered formalin and ZincTris fixatives. Fixed tissues were processed into paraffin blocks, sectioned at 3 μm, and stained with H&E or PASH. Kidney sections were graded using following criteria: Glomerular Damage: 1. Mesangial matrix thickening, cell proliferation, 2. Crescent formation, cellular deposits/casts in Bowman's space, 3. Cellular infiltration, mononuclear cells in glomerular tufts, 4. Fibrosis of Bowman's capsule. Tubular damage: 1. Infiltration of mononuclear cells, 2. Severity of tubular damage, 3. Protein casts. Tubulo-interstitial damage: 1. Fibrosis, 2. Infiltration of mononuclear cells. Each subcategory was assigned a score from 0-4, with the scores for glomerular indices representing the mean from 20 glomeruli per kidney. The total score for each mouse was the sum of the above 9 subcategories, with the highest possible score=36.

Example 681 was tested in MRL/lpr lupus model described herein above and the results are shown in Table I-1 for anti-dsDNA antibody titers and Table I-2 for kidney histological analysis. Compounds of this invention, as exemplified by Example 681, in the reported test, showed inhibition of disease progression as measured by anti-dsDNA titers and kidney histology.

TABLE I-1

| Group | | Anti-dsDNA antibody titers (23 weeks of age) |
|---|---|---|
| Vehicle | Mean | 3.328 |
| | SEM | 0.660 |
| Example 681 | Mean | 1.861 |
| (0.06 mg/kg) | SEM | 0.581 |
| Example 681 | Mean | 0.978 |

TABLE I-1-continued

| Group | | Anti-dsDNA antibody titers (23 weeks of age) |
|---|---|---|
| (0.3 mg/kg) | SEM | 0.179 |
| Example 681 | Mean | 1.023 |
| (1.5 mg/kg) | SEM | 0.179 |

TABLE I-2

| Group | | Kidney Histology (nephritis) 23 weeks of age |
|---|---|---|
| Vehicle | Mean | 20.13 |
|  | SEM | 3.182 |

TABLE I-2-continued

| Group | | Kidney Histology (nephritis) 23 weeks of age |
|---|---|---|
| Example 681 | Mean | 10.13 |
| (0.06 mg/kg) | SEM | 5.793 |
| Example 681 | Mean | 10.00 |
| (0.3 mg/kg) | SEM | 3.295 |
| Example 681 | Mean | 12.63 |
| (1.5 mg/kg) | SEM | 4.719 |

In Table J, in vitro activity data determined by one or more of the following assays: $S1P_1$ binding assay, receptor [$^{35}$S] GTPγS binding assays ($S1P_1$ GTPγS/$S1P_3$GTPγS), or $hS1P_1$ ERK Phosphorylation assay ($S1P_1$ pERK) are shown for representative phosphate examples of this invention.

TABLE J

| Ex. No. | $S1P_1$ Binding<br>A = (<10 nM)<br>B = (10-100 nM)<br>C = (100-1000 nM)<br>D = (1000-10000 nM) | $S1P_1$ GTPγS<br>A = (<10 nM)<br>B = (10-100 nM)<br>C = (100-1000 nM)<br>D = (1000-10000 nM) | $S1P_1$ pERK<br>A = (<10 nM)<br>B = (10-100 nM)<br>C = (100-1000 nM)<br>D = (1000-10000 nM) | $S1P_3$ GTPγS<br>I = (>625 nM)<br>II = (>100 nM)<br>III = (>50 nM) |
|---|---|---|---|---|
| 412 | A | A | A | I |
| 414 | A | B | D | I |
| 415 | B | B | B | I |
| 416 | D | — | — | I |
| 417 | B | C | A | I |
| 419 | — | — | B | I |
| 420 | B | B | D | I |
| 421 | A | A | A | I |
| 423 | C | C | B | I |
| 424 | B | B | A | I |
| 425 | A | A | A | I |
| 426 | B | A | A | I |
| 427 | B | A | A | I |
| 428 | A | A | B | I |
| 429 | A | A | B | I |
| 430 | B | B | A | I |
| 431 | B | C | A | I |
| 432 | A | A | B | II |
| 433 | B | C | A | I |
| 434 | A | B | A | I |
| 435 | B | — | — | I |
| 436 | A | B | A | I |
| 437 | A | A | A | I |
| 438 | A | B | A | I |
| 439 | A | B | A | I |
| 440 | A | A | A | I |
| 441 | B | A | A | I |
| 442 | A | A | A | I |
| 444 | A | A | A | I |
| 445 | B | B | B | I |
| 446 | B | C | A | I |
| 447 | B | C | A | I |
| 448 | A | A | A | I |
| 449 | A | B | B | I |
| 450 | A | A | B | I |
| 451 | A | A | B | I |
| 452 | A | A | A | I |
| 453 | B | B | A | I |
| 454 | A | B | A | I |
| 455 | A | A | A | I |
| 456 | B | A | A | I |
| 457 | A | B | A | I |
| 458 | A | B | A | I |
| 459 | A | B | A | I |
| 460 | A | A | A | I |
| 461 | A | A | A | I |
| 462 | A | A | A | III |
| 464 | A | A | B | I |
| 465 | A | B | A | I |
| 466 | B | B | B | I |
| 467 | B | B | B | I |
| 468 | A | B | B | I |
| 469 | B | B | A | I |
| 470 | C | B | A | I |
| 471 | C | — | B | I |

TABLE J-continued

| Ex. No. | S1P$_1$ Binding<br>A = (<10 nM)<br>B = (10-100 nM)<br>C = (100-1000 nM)<br>D = (1000-10000 nM) | S1P$_1$ GTPγS<br>A = (<10 nM)<br>B = (10-100 nM)<br>C = (100-1000 nM)<br>D = (1000-10000 nM) | S1P$_1$ pERK<br>A = (<10 nM)<br>B = (10-100 nM)<br>C = (100-1000 nM)<br>D = (1000-10000 nM) | S1P$_3$ GTPγS<br>I = (>625 nM)<br>II = (>100 nM)<br>III = (>50 nM) |
|---|---|---|---|---|
| 472 | C | C | A | I |
| 473 | A | — | B | I |
| 474 | A | B | A | I |
| 475 | A | B | A | I |
| 476 | B | B | B | I |
| 477 | A | B | A | I |
| 478 | B | B | B | I |
| 479 | C | B | B | I |
| 480 | D | A | C | I |
| 481 | A | A | A | I |
| 482 | C | B | B | I |
| 484 | C | B | B | I |
| 485 | B | B | B | I |
| 486 | — | A | B | I |
| 488 | A | B | A | — |
| 489 | A | B | A | I |
| 490 | A | C | B | I |
| 491 | A | A | B | I |
| 493 | A | A | B | I |
| 494 | B | B | B | I |
| 495 | B | B | A | I |
| 496 | A | A | A | I |
| 497 | B | A | A | I |
| 498 | B | C | B | I |
| 499 | A | B | B | I |
| 500 | — | A | A | I |
| 501 | — | A | A | I |
| 502 | A | B | A | I |
| 503 | A | A | A | I |
| 504 | A | B | A | I |
| 505 | B | B | B | I |
| 506 | A | A | A | I |
| 507 | C | C | B | I |
| 508 | B | C | B | I |
| 509 | B | B | A | I |
| 510 | A | B | A | I |
| 511 | A | B | A | I |
| 512 | A | A | B | I |
| 513 | A | B | A | I |
| 514 | A | B | B | I |
| 515 | B | B | A | I |
| 516 | B | B | A | I |
| 517 | B | B | A | I |
| 518 | A | A | A | I |
| 519 | A | A | A | I |
| 520 | B | B | B | I |
| 521 | A | A | B | III |
| 522 | A | B | B | I |
| 523 | B | C | B | I |
| 524 | B | A | A | I |
| 525 | A | B | A | I |
| 526 | B | B | A | I |
| 527 | A | A | A | I |
| 528 | B | C | B | I |
| 529 | A | B | A | I |
| 530 | B | A | B | I |
| 531 | B | B | B | I |
| 532 | A | A | A | I |
| 533 | A | A | A | I |
| 534 | A | A | B | I |
| 535 | A | A | A | I |
| 536 | A | B | A | I |
| 537 | A | A | A | I |
| 538 | A | A | A | I |
| 539 | A | A | A | I |
| 540 | A | C | A | I |
| 541 | A | B | A | I |
| 542 | — | A | A | I |
| 543 | — | A | A | I |
| 544 | B | C | A | I |
| 545 | B | B | A | I |
| 546 | C | C | B | I |
| 547 | A | B | B | I |
| 548 | B | B | A | I |

TABLE J-continued

| Ex. No. | S1P₁ Binding<br>A = (<10 nM)<br>B = (10-100 nM)<br>C = (100-1000 nM)<br>D = (1000-10000 nM) | S1P₁ GTPγS<br>A = (<10 nM)<br>B = (10-100 nM)<br>C = (100-1000 nM)<br>D = (1000-10000 nM) | S1P₁ pERK<br>A = (<10 nM)<br>B = (10-100 nM)<br>C = (100-1000 nM)<br>D = (1000-10000 nM) | S1P₃ GTPγS<br>I = (>625 nM)<br>II = (>100 nM)<br>III = (>50 nM) |
|---|---|---|---|---|
| 549 | C | C | A | I |
| 550 | B | B | A | I |
| 551 | B | B | B | I |
| 552 | A | B | B | I |
| 553 | C | C | A | I |
| 554 | — | B | B | I |
| 555 | A | B | B | I |
| 556 | D | A | A | I |
| 557 | B | B | B | I |
| 558 | A | A | A | I |
| 559 | C | C | B | I |
| 560 | B | A | A | I |
| 561 | C | C | B | I |
| 562 | C | C | B | I |
| 563 | C | C | C | I |
| 564 | B | B | B | I |
| 565 | A | B | A | I |
| 566 | A | A | A | I |
| 567 | A | A | B | I |
| 568 | B | A | A | I |
| 569 | A | B | A | I |
| 570 | B | B | A | I |
| 571 | B | B | B | I |
| 572 | A | A | B | I |
| 573 | B | B | B | I |
| 574 | C | — | B | I |
| 575 | B | B | A | I |
| 576 | B | C | B | I |
| 577 | A | A | A | I |
| 578 | A | B | A | I |
| 579 | C | C | B | I |
| 580 | B | B | — | I |
| 581 | A | A | — | I |
| 582 | A | B | A | I |
| 583 | — | A | A | II |
| 584 | A | A | — | I |
| 585 | — | B | — | I |
| 586 | A | B | A | I |
| 587 | A | B | A | I |
| 589 | A | B | A | II |
| 591 | B | B | A | I |
| 592 | A | B | A | I |
| 593 | A | B | B | I |
| 594 | B | B | C | I |
| 595 | A | B | A | I |
| 596 | A | B | A | I |
| 597 | A | A | B | I |
| 598 | B | B | A | I |
| 599 | A | A | A | I |
| 600 | B | A | A | I |
| 601 | A | C | A | II |
| 602 | A | A | A | I |
| 604 | C | C | B | I |
| 605 | A | A | A | I |
| 606 | B | B | A | I |
| 607 | C | C | B | I |
| 608 | A | A | A | I |
| 609 | B | B | A | I |
| 610 | B | A | A | II |
| 611 | A | A | A | I |
| 612 | D | B | — | I |
| 613 | D | — | C | I |
| 614 | D | C | — | I |
| 615 | C | C | — | I |
| 617 | C | — | — | I |
| 618 | C | C | A | I |
| 620 | B | A | — | I |
| 622 | A | A | — | I |
| 623 | A | A | — | I |
| 624 | D | A | C | I |
| 625 | — | C | B | I |
| 626 | B | B | A | I |
| 628 | — | A | A | I |
| 629 | C | C | A | I |

TABLE J-continued

| Ex. No. | S1P₁ Binding<br>A = (<10 nM)<br>B = (10-100 nM)<br>C = (100-1000 nM)<br>D = (1000-10000 nM) | S1P₁ GTPγS<br>A = (<10 nM)<br>B = (10-100 nM)<br>C = (100-1000 nM)<br>D = (1000-10000 nM) | S1P₁ pERK<br>A = (<10 nM)<br>B = (10-100 nM)<br>C = (100-1000 nM)<br>D = (1000-10000 nM) | S1P₃ GTPγS<br>I = (>625 nM)<br>II = (>100 nM)<br>III = (>50 nM) |
|---|---|---|---|---|
| 630 | A | — | C | I |
| 632 | B | B | A | I |
| 633 | B | C | A | I |
| 634 | B | — | B | I |
| 635 | A | B | A | I |
| 636 | B | B | B | I |
| 637 | A | B | B | I |
| 638 | A | B | A | II |
| 639 | B | B | B | I |
| 640 | A | A | A | I |
| 641 | C | B | B | I |
| 642 | B | A | A | I |
| 643 | A | B | B | I |
| 644 | C | B | C | I |
| 645 | C | B | B | I |
| 646 | B | C | B | I |
| 647 | — | C | B | I |
| 648 | B | B | B | I |
| 649 | B | C | B | I |
| 650 | B | C | B | I |
| 651 | B | B | B | I |
| 652 | B | B | B | I |
| 653 | A | A | A | I |
| 654 | A | A | A | I |
| 655 | A | B | B | I |
| 656 | B | B | B | I |
| 657 | A | A | B | I |
| 658 | A | B | A | I |
| 659 | A | A | B | I |
| 660 | A | A | B | I |
| 661 | A | A | A | I |
| 664 | A | A | A | I |
| 665 | A | A | B | I |
| 666 | C | C | — | I |
| 667 | C | C | C | I |
| 668 | A | A | B | I |

What is claimed is:

1. A compound of Formula (V):

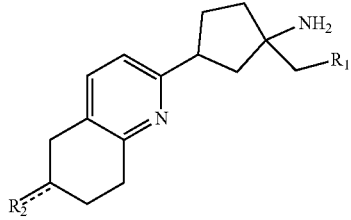

(V)

or a salt thereof, wherein:
$R_1$ is —OH or —OP(O)(OH)$_2$;
$R_2$ is $R_{2a}$;
---- represents a single bond to $R_{2a}$; and
$R_{2a}$ is —(CH$_2$)$_3$CH$_3$ or —(CH$_2$)$_{5-6}$CH$_3$.

2. The compound according to claim 1 having the structure of Formula (Vc):

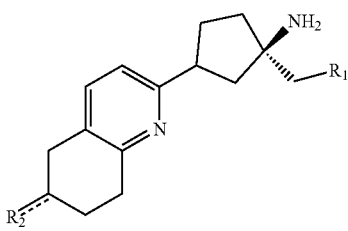

(Vc)

or a salt thereof.

3. The compound according to claim 1, wherein said compound is:

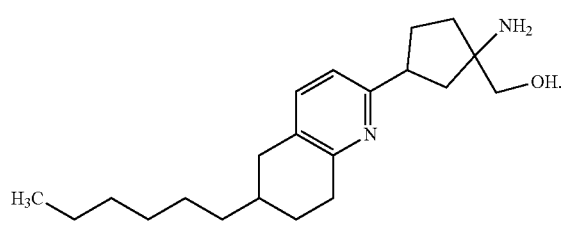 [SMILES: CCCCCCC1CCc2nc(C3CCC(N)(CO)C3)ccc2C1]

4. A pharmaceutical composition comprising a compound according to claim 1 or a pharmaceutically acceptable salt thereof; and a pharmaceutically acceptable carrier, wherein $R_1$ is —OH.

* * * * *